US012060408B2

United States Patent
Pfleger et al.

(10) Patent No.: US 12,060,408 B2
(45) Date of Patent: Aug. 13, 2024

(54) SCREENING ASSAYS, MODULATORS AND MODULATION OF ACTIVATION OF RECEPTOR FOR ADVANCED GLYCATION END-PRODUCTS (RAGE)

(71) Applicants: Monash University, Clayton (AU); The University of Western Australia, Nedlands (AU)

(72) Inventors: Kevin Donald George Pfleger, Nedlands (AU); Merlin Christopher Thomas, Ashburton (AU); Raelene Jane Pickering, Cheltenham (AU); Carlos Rosado, Sunshine (AU); Christos Tikellis, Oakleigh (AU)

(73) Assignees: Monash University, Clayton (AU); The University of Western Australia, Crawley (AU)

( * ) Notice: Subject to any disclaimer, the term of this patent is extended or adjusted under 35 U.S.C. 154(b) by 788 days.

(21) Appl. No.: 16/641,174

(22) PCT Filed: Aug. 21, 2018

(86) PCT No.: PCT/AU2018/050883
§ 371 (c)(1),
(2) Date: Feb. 21, 2020

(87) PCT Pub. No.: WO2019/036753
PCT Pub. Date: Feb. 28, 2019

(65) Prior Publication Data
US 2020/0207836 A1    Jul. 2, 2020

(30) Foreign Application Priority Data

Aug. 22, 2017 (AU) ................................ 2017903381
Jun. 26, 2018 (AU) ................................ 2018902298

(51) Int. Cl.
| | |
|---|---|
| C07K 14/72 | (2006.01) |
| A61K 38/00 | (2006.01) |
| A61P 29/00 | (2006.01) |
| C07K 14/705 | (2006.01) |

(52) U.S. Cl.
CPC ............ *C07K 14/723* (2013.01); *A61P 29/00* (2018.01); *C07K 14/70503* (2013.01); *A61K 38/00* (2013.01); *C07K 2319/03* (2013.01); *C07K 2319/10* (2013.01); *C07K 2319/60* (2013.01)

(58) Field of Classification Search
None
See application file for complete search history.

(56) References Cited

U.S. PATENT DOCUMENTS

2009/0220484 A1    9/2009 Schmidt et al.

OTHER PUBLICATIONS

Ichiki, T., et al., "Modulation of leukotriene B4 receptor I signaling by receptor for advanced glycation end products (RAGE)", The FASEB Journal, 2016, vol. 30, pp. 1811-1822 Figures 1 and 3.*
Greene T.W. et al. Protective groups in organic synthesis, 1991, Wiley, New York, Second Edition, 248 pages.
Petersen, H. & Myren, J. (1974) Secretin dose-response in health and chronic pancreatic inflammatory disease. Scandinavian journal of gastroenterology, 10, 851-861.
Yang J, Yan R, Roy A, Xu D, Poisson J, Zhang Y. The I-TASSER Suite: Protein structure and function prediction, Nature Methods, 2015, 12: 7-8.
Ichiki et al., "Modulation of leukotriene B4 receptor 1 signaling by receptor for advanced glycation end products (RAGE)", The FASEB Journal, May 2016, vol. 30, pp. 1811-1822.
Slowik et al., "Involvement of formyl peptide receptors in receptor for advanced glycation end products (RAGE)—and amyloid beta 1-42-induced signal transduction in glial cells", Molecular Neurodegeneration, 2012, pp. 1-18, vol. 7, Article 55.
Zhu, W., et al., "Interaction of β1-adrenoceptor with RAGE mediates cardiomyopathy via CaMKII signaling", JCI Insight, Jan. 21, 2016, vol. 1, e84969, pp. 1-12.
Kew, R.R., et al., "The IKKα-Dependent NF-KB p52/ReIB Noncanonical Pathway Is Essential To Sustain a CXCL12 Autocrine Loop in Cells Migrating in Response to HMGB1", The Journal of Immunology, Jan. 27, 2012, Article 1102454, pp. 1-7.
Patent Cooperation Treaty, "International Search Report and Written Opinion", dated Oct. 18, 2018, 15 pages.
Calderón-Garcidueñas, L., Kavanaugh, M., Block, M., D'Angiulli, A., Delgado-Chávez, R., Torres-Jardón, R., Gonzalez-Maciel, A., Reynoso-Robles, R., Osnaya, N. & Villarreal-Calderon, R. (2012) Neuroinflammation, hyperphosphorylated tau, diffuse amyloid plaques, and down-regulation of the cellular prion protein in air pollution exposed children and young adults. Journal of Alzheimer's Disease, 28, 93-107.
Calonge, M., de Salamanca, A.E., Siemasko, K.F., Diebold, Y., Gao, J., Juarez-Campo, M. & Stern, M.E. (2005) Variation in the Expression of Inflammatory Markers and Neuroreceptors in Human Conjunctival Epithelial Cells. The Ocular Surface, 3, S-145-S-148.

(Continued)

*Primary Examiner* — Christian L Fronda
(74) *Attorney, Agent, or Firm* — Nyemaster Goode P.C.

(57) ABSTRACT

A method of screening candidate agents for their ability to modulate RAGE activity where such RAGE activity is induced by an active co-located GPCR, the method comprising the steps of: contacting a RAGE polypeptide with a GPCR polypeptide in the presence of a candidate agent where the GPCR polypeptide is constitutively active and/or is activated by addition of an agonist, partial agonist or allosteric modulator of that GPCR; and detecting whether the candidate agent is a modulator of RAGE ligand-independent activation of RAGE by activated co-located GPCR by detecting an effect indicative of modulation of RAGE activation by the presence of the candidate agent and/or by detecting RAGE-dependent signalling that is modulated by the presence of the candidate agent.

26 Claims, 100 Drawing Sheets
Specification includes a Sequence Listing.

(56) References Cited

OTHER PUBLICATIONS

Caminschi, I., Vandenabeele, S., Sofi, M., Mcknight, A.J., Ward, N., Brodnicki, T.C., Toy, T., Lahoud, M., Maraskovsky, E. & Shortman, K. (2006) Gene structure and transcript analysis of the human and mouse EGF-TM7 molecule, FIRE: Full Length Research Paper. DNA Sequence, 17, 8-14.

Candido, R., et al. (2002) Prevention of accelerated atherosclerosis by angiotensin-converting enzyme inhibition in diabetic apolipoprotein E-deficient mice. Circulation, 106: 246-253.

Candido, R., et al. (2004) Irbesartan but not amlodipine suppresses diabetes-associated atherosclerosis. Circulation, 109: 1536-1542.

Cani, P.D., Possemiers, S., Van de Wiele, T., Guiot, Y., Everard, A., Rottier, O., Geurts, L., Naslain, D., Neyrinck, A. & Lambert, D.M. (2009) Changes in gut microbiota control inflammation in obese mice through a mechanism involving GLP-2-driven improvement of gut permeability. Gut, 58, 1091-1103.

Cantagrel, V., Lossi, A., Boulanger, S., Depetris, D., Mattei, M., Gecz, J., Schwartz, C., Van Maldergem, L. & Villard, L. (2004) Disruption of a new X linked gene highly expressed in brain in a family with two mentally retarded males. Journal of medical genetics, 41, 736-742.

Cantarella, G., Scollo, M., Lempereur, L., Saccani-Jotti, G., Basile, F. & Bernardini, R. (2011) Endocannabinoids inhibit release of nerve growth factor by inflammation-activated mast cells. Biochemical pharmacology, 82, 380-388.

Capra, V., Ravasi, S., Accomazzo, M.R., Citro, S., Grimoldi, M., Abbracchio, M.P. & Rovati, G.E. (2005) CysLT1 receptor is a target for extracellular nucleotide-induced heterologous desensitization: a possible feedback mechanism In inflammation. Journal of Cell Science, 118, 5625-5636.

Caronti, B., Calderaro, C., Passarelli, F., Palladini, G. & Pontieri, F.E. (1998) Dopamine receptor mRNAs in the rat lymphocytes. Life sciences, 62, 1919-1925.

Carrillo-Vico, A., García, S., Calvo, J.R. & Guerrero, J.M. (2003) Melatonin counteracts the inhibitory effect of PGE2 on IL-2 production in human lymphocytes via its mt1 membrane receptor. The FASEB Journal, 17, 755-757.

Caruso, C., Durand, D., Schioth, H.B., Rey, R., Seilicovich, A. & Lasaga, M. (2007) Activation of melanocortin 4 receptors reduces the inflammatory response and prevents apoptosis induced by lipopolysaccharide and interferon-gamma in astrocytes. Endocrinology, 148, 4918-4926.

Charo, I.F. & Ransohoff, R.M. (2006) The many roles of chemokines and chemokine receptors in inflammation. N Engl J Med, 354, 610-621.

Chen, A., Dong, L., Leffler, N.R., Asch, A.S., Witte, O.N. & Yang, L.V. (2011) Activation of GPR4 by acidosis increases endothelial cell adhesion through the cAMP/Epac pathway. PloS one, 6, e27586.

Chen, H.F., Jeung, E.B., Stephenson, M. & Leung, P.C. (1999) Human peripheral blood mononuclear cells express gonadotropin-releasing hormone (GnRH), GnRH receptor, and interleukin-2 receptor gamma-chain messenger ribonucleic acids that are regulated by GnRH in vitro. The Journal of clinical endocrinology and metabolism, 84, 743-750.

Chen, T.-Y., Hwang, T.-L., Lin, C.-Y., Lin, T.-N., Lai, H.-Y., Tsai, W.-P. & Lin, H.-H. (2011) EMR2 receptor ligation modulates cytokine secretion profiles and cell survival of lipopolysaccharide-treated neutrophils. Chang Gung Med J, 34, 468-477.

Chen, Y., Corriden, R., Inoue, Y., Yip, L., Hashiguchi, N., Zinkernagel, A., Nizet, V., Insel, P.A. & Junger, W.G. (2006) ATP release guides neutrophil chemotaxis via P2Y2 and A3 receptors. Science, 314, 1792-1795.

Chen, Z.J. & Minneman, K.P. (2005) Recent progress in alpha1-adrenergic receptor research. Acta Pharmacol Sin, 26, 1281-1287.

Chhajlani, V. (1996) Distribution of cDNA for melanocortin receptor subtypes in human tissues. Biochemistry and molecular biology international, 38, 73-80.

Chhuon, C., Pranke, I., Borot, F., Tondelier, D., Lipecka, J., Fritsch, J., Chanson, M., Edelman, A., Ollero, M. & Guerrera, I. (2016) Changes in lipid raft proteome upon TNF-α stimulation of cystic fibrosis cells. Journal of Proteomics, 145, 246-253.

Chuah, Y.K., Basir, R., Talib, H., Tie, T.H. & Nordin, N. Receptor for advanced glycation end products and its Involvement in inflammatory diseases. International journal of inflammation, 2013, 2013: 403460.

Consortium, I.G.o.A.S. (2013) Identification of multiple risk variants for ankylosing spondylitis through high-density genotyping of immune-related loci. Nature genetics, 45, 730-738.

Cook, I.H., Evans, J., Maldonado-Perez, D., Critchley, H.O., Sales, K.J. & Jabbour, H.N. (2010) Prokineticin (PROK1) modulates interleukin (IL)-11 expression via prokineticin receptor 1 (PROKR1) and the calcineurin/NFAT signalling pathway. Molecular human reproduction, 16, 158-169.

Costa, A., Toschi, A., Murfuni, I., et al. Local Overexpression of V1a-Vasopressin Receptor Enhances Regeneration in Tumor Necrosis Factor-Induced Muscle Atrophy. BioMed Research International, 2014, Article ID 235426, doi:10.1155/2014/235426.

Cuddihy, R.M., Dutton, C.M. & Bahn, R.S. (1995) A polymorphism in the extracellular domain of the thyrotropin receptor is highly associated with autoimmune thyroid disease in females. Thyroid, 5, 89-95.

Cunningham, M. A., E. Rondeau, X. Chen, S. R. Coughlin, S. R. Holdsworth, and P. G. Tipping. Protease-activated receptor 1 mediates thrombin-dependent, cell-mediated renal inflammation in crescentic glomerulonephritis. J Exp Med, 2000, 191:455-62.

Czepielewski, R.S., Porto, B.N., Rizzo, L.B., Roesler, R., Abujamra, A.L., Pinto, L.G., Schwartsmann, G., de Queiroz Cunha, F. & Bonorino, C. (2012) Gastrin-releasing peptide receptor (GRPR) mediates chemotaxis in neutrophils. Proceedings of the National Academy of Sciences, 109, 547-552.

Czerwinski, M., Kern, J., Grodecka, M., Paprocka, M., Krop-Watorek, A. & Wasniowska, K. (2007) Mutational analysis of the N-glycosylation sites of Duffy antigen/receptor for chemokines. Biochem Biophys Res Commun, 356, 816-821.

D'Andrea, G., Terrazzino, S., Fortin, D., Farruggio, A., Rinaldi, L. & Leon, A. (2003) HPLC electrochemical detection of trace amines in human plasma and platelets and expression of mRNA transcripts of trace amine receptors in circulating leukocytes. Neuroscience letters, 346, 89-92.

D'Amato, M., Bruce, S., Bresso, F., Zucchelli, M., Ezer, S., Pulkkinen, V., Lindgren, C., Astegiano, M., Rizzetto, M. & Gionchetti, P. (2007) Neuropeptide s receptor 1 gene polymorphism is associated with susceptibility to inflammatory bowel disease. Gastroenterology, 133, 808-817.

D'Andrea, G., D'Arrigo, A., Facchinetti, F., Del Giudice, E., Colavito, D., Bernardini, D. & Leon, A. (2012) Octopamine, unlike other trace amines, inhibits responses of astroglia-enriched cultures to lipopolysaccharide via a β-adrenoreceptor-mediated mechanism. Neuroscience letters, 517, 36-40.

Da Silveira, K.D., Coelho, F.M., Vieira, A.T., Sachs, D., Barroso, L.C., Costa, V.V., Bretas, T.L.B., Bader, M., de Sousa, L.P. & da Silva, T.A. (2010) Anti-inflammatory effects of the activation of the angiotensin-(1-7) receptor, MAS, in experimental models of arthritis. The Journal of Immunology, 185, 5569-5576.

Daffu, G., et al. Radical roles for RAGE in the pathogenesis of oxidative stress in cardiovascular diseases and beyond. International journal of molecular sciences, 2013, 14: 19891-19910.

Daugherty, A., Manning, M.W. & Cassis, L.A. (2000) Angiotensin II promotes atherosclerotic lesions and aneurysms in apolipoprotein E-deficient mice. J Clin Invest, 105: 1605-1612.

Davidson, C., Asaduzzaman, M., Arizmendi, N., Polley, D., Wu, Y., Gordon, J., Hollenberg, M., Cameron, L. & Vliagoftis, H. (2013) Proteinase-activated receptor-2 activation participates in allergic sensitization to house dust mite allergens in a murine model. Clinical & Experimental Allergy, 43, 1274-1285.

Dawson, J., Miltz, W., Mir, A.K., & Wiessner, C. (2003) Targeting monocyte chemoattractant protein-1 signalling in disease. Expert Opin Ther Targets, 7: 35-48.

(56) References Cited

OTHER PUBLICATIONS

De Martino, M.C., Hofland, L.J. & Lamberts, S.W. (2010) Somatostatin and somatostatin receptors: from basic concepts to clinical applications. Prog Brain Res, 182, 255-280.

Deng, J., Fujimoto, J., Ye, X.-F., Men, T.-Y., Van Pelt, C.S., Chen, Y.-L., Lin, X.-F., Kadara, H., Tao, Q. & Lotan, D. (2010) Knockout of the tumor suppressor gene Gprc5a in mice leads to NF-κB activation in airway epithelium and promotes lung inflammation and tumorigenesis. Cancer prevention research, 3, 424-437.

Dijksterhuis, J., Petersen, J. & Schulte, G. (2014) WNT/Frizzled signalling: receptor-ligand selectivity with focus on FZD-G protein signalling and its physiological relevance: IUPHAR Review 3. British journal of pharmacology, 171, 1195-1209.

Dixit, V.D., Schaffer, E.M., Pyle, R.S., Collins, G.D., Sakthivel, S.K., Palaniappan, R., Lillard, J.W. & Taub, D.D. (2004) Ghrelin inhibits leptin-and activation-induced proinflammatory cytokine expression by human monocytes and T cells. The Journal of clinical investigation, 114, 57-66.

Doi, Y., T. Minami, M. Nishizawa, T. Mabuchi, H. Mori, and S. Ito. Central nociceptive role of prostacyclin (IP) receptor induced by peripheral inflammation. Neuroreport, 2002, 13:93-6.

Donoghue, M., et al. A novel angiotensin-converting enzyme-related carboxypeptidase (ACE2) converts angiotensin I to angiotensin 1-9. Circulation research, 2000, 87: E1-9.

Dorsch, M., Qiu, Y., Soler, D., Frank, N., Duong, T., Goodearl, A., O'Neil, S., Lora, J. & Fraser, C.C. (2005) PK1/EG-VEGF induces monocyte differentiation and activation. Journal of Leukocyte Biology, 78, 426-434.

Drazen, D.L. & Nelson, R.J. (2001) Melatonin receptor subtype MT2 (Mel 1b) and not mt1 (Mel 1a) is associated with melatonin-induced enhancement of cell-mediated and humoral immunity. Neuroendocrinology, 74, 178-184.

Duchene, J., and A. Ahluwalia. The kinin B(1) receptor and inflammation: new therapeutic target for cardiovascular disease. Curr Opin Pharmacol, 2009, 9:125-31.

Duffy, R. A. Potential therapeutic targets for neurokinin-1 receptor antagonists. Expert Opin Emerg Drugs, 2004, 9:9-21.

Ehrenfeld, P., Millan, C., Matus, C., Figueroa, J., Burgos, R., Nualart, F., Bhoola, K. & Figueroa, C. (2006) Activation of kinin B1 receptors induces chemotaxis of human neutrophils. Journal of leukocyte biology, 80, 117-124.

Ekholm, M., Kahan, T., Jorneskog, G., Broijersen, A. & Wallen, N.H. (2009) Angiotensin II infusion in man is proinflammatory but has no short-term effects on thrombin generation in vivo. Thromb Res, 124: 110-115.

Elliott, S.E., Parchim, N.F., Kellems, R.E., Xia, Y., Soffici, A.R. & Daugherty, P.S. (2016) A pre-eclampsia-associated Epstein-Barr virus antibody cross-reacts with placental GPR50. Clinical Immunology, 168, 64-71.

Elsasser, T.H. & Kahl, S. (2002) Adrenomedullin has multiple roles in disease stress: development and remission of the inflammatory response. Microscopy research and technique, 57, 120-129.

Engel, K.M., Schrock, K., Teupser, D., Holdt, L.M., Tönjes, A., Kern, M., Dietrich, K., Kovacs, P., Krugel, U. & Scheidt, H.A. (2011) Reduced food intake and body weight in mice deficient for the G protein-coupled receptor GPR82. PLoS One, 6, e29400.

English, D., A. T. Kovala, Z. Welch, K. A. Harvey, R. A. Siddiqui, and D. N. Brindley. Induction of endothelial cell chemotaxis by sphingosine 1-phosphate and stabilization of endothelial monolayer barrier function by lysophosphatidic acid, potential mediators of hematopoietic angiogenesis. J Hematother Stem Cell Res, 1999, 8:627-34.

Evankovich, J., Lear, T., Mckelvey, A., Dunn, S., Londino, J., Liu, Y., Chen, B.B., Mallampalli, R.K. (2017) Receptor for advanced glycation end products is targeted by FBXO10 for ubiquitination and degradation. FASEB J. doi: 10.1096/j.201700031R.

Fallarino, F., Volpi, C., Fazio, F., Notartomaso, S., Vacca, C., Busceti, C., Bicciato, S., Battaglia, G., Bruno, V. & Puccetti, P. (2010) Metabotropic glutamate receptor-4 modulates adaptive immunity and restrains neuroinflammation. Nature medicine, 16, 897-902.

Farzan, M., Choe, H., Martin, K., Marcon, L., Hofmann, W., Karlsson, G., Sun, Y., Barrett, P., Marchand, N. & Sullivan, N. (1997) Two orphan seven-transmembrane segment receptors which are expressed in CD4-positive cells support simian immunodeficiency virus infection. The Journal of experimental medicine, 186, 405-411.

Feingold, E.A., Penny, L.A., Nienhuis, A.W. & Forget, B.G. (1999) An olfactory receptor gene is located in the extended human β-globin gene cluster and is expressed in erythroid cells. Genomics, 61, 15-23.

Ferrario, C.M. & Strawn, W.B. (2006) Role of the renin-angiotensin-aldosterone system and proinflammatory mediators in cardiovascular disease. Am J Cardiol, 98: 121-128.

Ferre, S., Baler, R., Bouvier, M., Caron, M.G., Devi, L.A., Durroux, T., Fuxe, K., George, S.R., Javitch, J.A., Lohse, M. J., Mackie, K., Milligan, G., Pfleger, K.D.G., Pin, J.P., Volkow, N., Waldhoer, M., Woods, A.S. and Franco R. (2009) Building a new conceptual framework for receptor heteromers. Nat Chem Biol, 5: 131-134.

Ferreira, M., Barcelos, L.S., Campos, P.P., Vasconcelos, A.C., Teixeira, M.M. & Andrade, S.P. (2004) Sponge-induced angiogenesis and inflammation in PAF receptor-deficient mice (PAFR-KO). British journal of pharmacology, 141, 1185-1192.

Ferrier L, Serradeil-Le Gal C, Schulte AM, Vasina V, Gaultier E, Schroedel S, Ursino MG, Chaumaz G, Pascal M, De Ponti F, Bueno L. Proinflammatory role of vasopressin through V1b receptors in hapten-induced experimental colitis in rodents: implication in IBD. Am J Physiol Gastrointest Liver Physiol, 2010, 299: G1298-307.

Finch, A.M., Sarramegna, V. & Graham, R.M. (2006) Ligand Binding, Activation, and Agonist Trafficking. In Perez, D. M. (ed) The Adrenergic Receptors: In the 21st Century. Humana Press, Totowa, NJ, pp. 25-85.

Fischer, A., Schmid, B., Ellinghaus, D., Nothnagel, M., Gaede, K.I., Schürmann, M., Lipinski, S., Rosenstiel, P., Zissel, G. & Höhne, K. (2012) A novel sarcoidosis risk locus for Europeans on chromosome 11q13. 1. American journal of respiratory and critical care medicine, 186, 877-885.

Flegel, C., Manteniotis, S., Osthold, S., Hatt, H. & Gisselmann, G. (2013) Expression Profile of Ectopic Olfactory Receptors Determined by Deep Sequencing. PLoS One, 8, e55368.

Fleischmann, A., Läderach, U., Friess, H., Buechler, M.W. & Reubi, J.C. (2000) Bombesin receptors in distinct tissue compartments of human pancreatic diseases. Laboratory investigation, 80, 1807-1817.

Fornari, T.A., Donate, P.B., Macedo, C., Sakamoto-Hojo, E.T., Donadi, E.A. & Passos, G.A. (2011) Development of type 1 diabetes mellitus in nonobese diabetic mice follows changes in thymocyte and peripheral T lymphocyte transcriptional activity. Clinical and Developmental Immunology, 2011.

Foster, H.R., Fuerst, E., Branchett, W., Lee, T.H., Cousins, D.J. & Woszczek, G. (2016) Leukotriene E4 is a full functional agonist for human cysteinyl leukotriene type 1 receptor-dependent gene expression. Scientific reports, 6.

Frasch, S.C., Berry, K.Z., Fernandez-Boyanapalli, R., Jin, H.-S., Leslie, C., Henson, P.M., Murphy, R.C. & Bratton, D.L. (2008) NADPH oxidase-dependent generation of lysophosphatidylserine enhances clearance of activated and dying neutrophils via G2A. Journal of Biological Chemistry, 283, 33736-33749.

Fredholm, B.B., AP, I.J., Jacobson, K.A., Linden, J. & Muller, C.E. (2011) International Union of Basic and Clinical Pharmacology. LXXXI. Nomenclature and classification of adenosine receptors—an update. Pharmacol Rev, 63, 1-34.

Freire-Garabal, M., Nunez, M., Balboa, J., López-Delgado, P., Gallego, R., Garcia-Caballero, T., Fernández-Roel, M., Brenlla, J. & Rey-Mendez, M. (2003) Serotonin upregulates the activity of phagocytosis through 5-HT1A receptors. British journal of pharmacology, 139, 457-463.

Fujita, T., Matsuoka, T., Honda, T., Kabashima, K., Hirata, T. & Narumiya, S. (2011) A GPR40 agonist GW9508 suppresses CCL5,

(56) References Cited

OTHER PUBLICATIONS

CCL17, and CXCL10 induction in keratinocytes and attenuates cutaneous immune inflammation. Journal of Investigative Dermatology, 131, 1660-1667.

Fujita, T., Tozaki-Saitoh, H. & Inoue, K. (2009) P2Y1 receptor signalling enhances neuroprotection by astrocytes against oxidative stress via IL-6 release in hippocampal cultures. Glia, 57, 244-257.

Fukami K, Ueda S, Yamagishi S, Kato S, Inagaki Y, Takeuchi M, Motomiya Y, Bucala R, Iida S, Tamaki K, Imaizumi T, Cooper ME, Okuda S. (2004) AGEs activate mesangial TGF-β-Smad signalling via an angiotensin II type I receptor Interaction. Kidney Int, 66: 2137-2147.

Fukami, K., Taguchi, K., Yamagishi, S. & Okuda, S. Receptor for advanced glycation endproducts and progressive kidney disease. Current opinion in nephrology and hypertension, 2015, 24: 54-60.

Galiegue, S., Mary, S., Marchand, J., Dussossoy, D., Carrière, D., Carayon, P., Bouaboula, M., Shire, D., Le Fur, G. & Casellas, P. (1995) Expression of Central and Peripheral Cannabinoid Receptors in Human Immune Tissues and Leukocyte Subpopulations. European Journal of Biochemistry, 232, 54-61.

Galle, J., Sittig, D., Hanisch, I., Wobus, M., Wandel, E., Loeffler, M. & Aust, G. (2006) Individual cell-based models of tumor-environment interactions: Multiple effects of CD97 on tumor invasion. Am J Pathol, 169, 1802-1811.

Gantz, I., Muraoka, A., Yang, Y.-K., Samuelson, L.C., Zimmerman, E.M., Cook, H. & Yamada, T. (1997) Cloning and chromosomal localization of a gene (GPR18) encoding a novel seven transmembrane receptor highly expressed in spleen and testis. Genomics, 42, 462-466.

Gao, Z.-G., Ding, Y. & Jacobson, K.A. (2010) P2Y 13 receptor is responsible for ADP-mediated degranulation in RBL-2H3 rat mast cells. Pharmacological research, 62, 500-505.

Garcia-Vivas, J.M., Galaviz-Hernandez, C., Fernandez-Retana, J., Pedroza-Torres, A., Perez-Plasencia, C., Lopez-Camarillo, C. & Marchat, L.A. (2016) Transcriptomic Profiling of Adipose Tissue in Obese Women in Response to Acupuncture Catgut Embedding Therapy with Moxibustion. The Journal of Alternative and Complementary Medicine, 22, 658-668.

Garcia, J. G., A. Siflinger-Birnboim, R. Bizios, P. J. Del Vecchio, J. W. Fenton, 2nd, and A. B. Malik. Thrombin-induced increase in albumin permeability across the endothelium. J Cell Physiol, 1986, 128:96-104.

Garg, D. & Merhi, Z. Advanced Glycation End Products: Link between Diet and Ovulatory Dysfunction in PCOS? Nutrients, 2015, 7: 10129-10144.

Gatto, D., Wood, K. & Brink, R. (2011) EBI2 operates independently of but in cooperation with CXCR5 and CCR7 to direct B cell migration and organization in follicles and the germinal center. The Journal of Immunology, 187, 4621-4628.

Gaveriaux, C., Peluso, J., Simonin, F., Laforet, J. & Kieffer, B. (1995) Identification of kappa- and delta-opioid receptor transcripts in immune cells. FEBS Lett, 369, 272-276.

Gazel, A., Rosdy, M., Bertino, B., Tornier, C., Sahuc, F. & Blumenberg, M. (2006) A characteristic subset of psoriasis-associated genes is induced by oncostatin-M in reconstituted epidermis. Journal of investigative dermatology, 126, 2647-2657.

Gervais, F.G., Cruz, R.P., Chateauneuf, A., Gale, S., Sawyer, N., Nantel, F., Metters, K.M. & O'Neill, G.P. (2001) Selective modulation of chemokinesis, degranulation, and apoptosis in eosinophils through the PGD 2 receptors CRTH2 and DP. Journal of Allergy and Clinical Immunology, 108, 982-988.

Getting, S.J., Gibbs, L., Clark, A.J., Flower, R.J. & Perretti, M. (1999) POMC gene-derived peptides activate melanocortin type 3 receptor on murine macrophages, suppress cytokine release, and inhibit neutrophil migration in acute experimental inflammation. The Journal of Immunology, 162, 7446-7453.

Giannini, E., Lattanzi, R., Nicotra, A., Campese, A.F., Grazioli, P., Screpanti, I., Balboni, G., Salvadori, S., Sacerdote, P. & Negri, L. (2009) The chemokine Bv8/prokineticin 2 is up-regulated in inflammatory granulocytes and modulates Inflammatory pain. Proceedings of the National Academy of Sciences, 106, 14646-14651.

Goldin, A., Beckman, J.A., Schmidt, A.M., and CreAGER, M.A. (2006) Advanced glycation end products: sparking the development of diabetic vascular injury Circulation, 114: 597-605.

Grafe, M., et al. (1997) Angiotensin Il-induced leukocyte adhesion on human coronary endothelial cells is mediated by E-selectin. Circ Res, 81: 804-811.

Granados-Soto, V., Arguelles, C.F., Rocha-González, H.I., Godinez-Chaparro, B., Flores-Murrieta, F.J. & Villalón, C.M. (2010) The role of peripheral 5-HT1A, 5-HT1B, 5-HT1D, 5-HT1E and 5-HT1F serotonergic receptors in the reduction of nociception in rats. Neuroscience, 165, 561-568.

Grantham, R. (1974) Amino acid difference formula to help explain protein evolution. Science, 185: 862-864.

Grassel, S., Opolka, A., Anders, S., Straub, R.H., Grifka, J., Luger, T.A. & Böhm, M. (2009) The melanocortin system in articular chondrocytes: Melanocortin receptors, pro-opiomelanocortin, precursor proteases, and a regulatory effect of a-melanocyte-stimulating hormone on proinflammatory cytokines and extracellular matrix components. Arthritis & Rheumatism, 60, 3017-3027.

Gregory, M.A., Phang, T.L., Neviani, P., Alvarez-Calderon, F., Eide, C.A., O'Hare, T., Zaberezhnyy, V., Williams, R.T., Druker, B.J. & Perrotti, D. (2010) Wnt/Ca 2+/NFAT signalling maintains survival of Ph+ leukemia cells upon inhibition of Bcr-Abl. Cancer cell, 18, 74-87.

Guénard, F., Lamontagne, M., Bosse, Y., Deshaies, Y., Cianflone, K., Kral, J.G., Marceau, P. & Vohl, M.-C. (2015) Influences of Gestational Obesity on Associations between Genotypes and Gene Expression Levels in Offspring following Maternal Gastrointestinal Bypass Surgery for Obesity. PloS one, 10, e0117011.

Gugliucci, A. & Menini, T. The axis AGE-RAGE-soluble RAGE and oxidative stress in chronic kidney disease. Advances in experimental medicine and biology, 2014, 824: 191-208.

Guo, W.A., Knight, P.R. & Raghavendran, K. The receptor for advanced glycation end products and acute lung injury/acute respiratory distress syndrome. Intensive care medicine¬¬, 2012, 38: 1588-1598.

Haga, K., Kruse, A.C., Asada, H., Yurugi-Kobayashi, T., Shiroishi, M., Zhang, C., Weis, W.I., Okada, T., Kobilka, B.K., Haga, T. & Kobayashi, T. (2012) Structure of the human M2 muscarinic acetylcholine receptor bound to an antagonist. Nature, 482, 547-551.

Tagner, S., Stahl, U., Knoblauch, B., McGregor, G. & Lang, R. (2002) Calcitonin receptor-like receptor: identification and distribution in human peripheral tissues. Cell and tissue research, 310, 41-50.

Han, Y.T., et al. Fine tuning of 4,6-bisphenyl-2-(3-alkoxyanilino)pyrimidine focusing on the activity-sensitive aminoalkoxy moiety for a therapeutically useful inhibitor of receptor for advanced glycation end products (RAGE). Bioorganic & medicinal chemistry, 2015, 23: 579-587.

Riichiro Abe et al., AGE-RAGE System and Carcinogenesis, Current Pharmaceutical Design, (2008), pp. 940-945, vol. 14, No. 10.

Ahmad, A., Bhattacharya, S., Sridhar, A., Iqbal, A.M. & Mariani, T.J. (Jun. 2016) Recurrent copy number variants associated with bronchopulmonary dysplasia. Pediatric research, 79, 940-945.

Aho, V., Ollila, H.M., Rantanen, V., Kronholm, E., Surakka, I., van Leeuwen, W.M.A., Lehto, M., Matikainen, S., Ripatti, S., Härmä, M., Sallinen, M., Salomaa, V., Jauhiainen, M., Alenius, H., Paunio, T. & Porkka-Heiskanen, T. (Oct. 23, 2013) Partial Sleep Restriction Activates Immune Response-Related Gene Expression Pathways: Experimental and Epidemiological Studies in Humans. PLoS One, 8, e77184, 12 pages.

Alexander, S., Mathie, A. & Peter, J. (Nov. 2011) Guide to Receptors and Channels (GRAC), 5th edition. Br. J. Pharmacol., 164, pp. S1-S324.

Allen, S. et al. Chemokine: Receptor Structure, Interactions and Antagonism. Annual Review Immunology, Jan. 2007, 25: pp. 787-820.

Allende, M.L., Bektas, M., Lee, B.G., Bonifacino, E., Kang, J., Tuymetova, G., Chen, W., Saba, J.D. & Proia, R.L. (Mar. 4, 2011) Sphingosine-1-phosphate lyase deficiency produces a pro-

(56) References Cited

OTHER PUBLICATIONS inflammatory response while impairing neutrophil trafficking. Journal of Biological Chemistry, 286, pp. 7348-7358.
An, S., Bleu, T., Hallmark, O.G. & Goetzl, E.J. (Apr. 3, 1998) Characterization of a novel subtype of human G protein-coupled receptor for lysophosphatidic acid. Journal of Biological Chemistry, 273, pp. 7906-7910.
Anders HJ et al. (2010) Questions about Chemokine and Chemokine Receptor Antagonism in Renal Inflammation, Nephron Exp Nephrol, 114: pp. e33-e38.
Angelopoulou, E., Piperi, C., Adamopoulos, C. & Papavassiliou, A.G. (2016) Pivotal role of high-mobility group box 1 (HMGB1) signalling pathways in glioma development and progression. Journal of molecular medicine, doi: 10.1007/s00109-016-1435-y, pp. 867-874.
Antoniak, S., Owens, A.P., Baunacke, M., Williams, J.C., Lee, R.D., Weithäuser, A., Sheridan, P.A., Malz, R., Luyendyk, J.P. & Esserman, D.A. (Mar. 2013) PAR-1 contributes to the innate immune response during viral Infection. The Journal of clinical investigation, 123, pp. 1310-1322.
Arita, M., Ohira, T., Sun, Y.-P., Elangovan, S., Chiang, N. & Serhan, C.N. (2007) Resolvin E1 selectively interacts with leukotriene B4 receptor BLT1 and ChemR23 to regulate inflammation. The Journal of Immunology, 178, pp. 3912-3917.
Awojoodu, A.O., Ogle, M.E., Sefcik, L.S., Bowers, D.T., Martin, K., Brayman, K.L., Lynch, K.R., Peirce-Cottler, S.M. & Botchwey, E. (2013) Sphingosine 1-phosphate receptor 3 regulates recruitment of anti-inflammatory monocytes to microvessels during implant arteriogenesis. Proceedings of the National Academy of Sciences, 110, pp. 13785-13790.
Ayer, L.M., Wilson, S.M., Traves, S.L., Proud, D. & Giembycz, M.A. (2008) 4,5-Dihydro-1H-imidazol-2-yl)-[4-(4-sopropoxy-benzyl)-phenyl]-amine (RO1138452) is a selective, pseudo-irreversible orthosteric antagonist at the prostacyclin (IP)-receptor expressed by human airway epithelial cells: IP-receptor-mediated inhibition of CXCL9 and CXCL 10 release. Journal of Pharmacology and Experimental Therapeutics, 324, pp. 815-826.
Babusyte, A., Kotthoff, M., Fiedler, J. & Krautwurst, D. (Mar. 2013) Biogenic amines activate blood leukocytes via trace amine-associated receptors TAAR1 and TAAR2. Journal of leukocyte biology, 93, pp. 387-394.
Bader, M., Alenina, N., Andrade-Navarro, M.A. & Santos, R.A. (2014) MAS and its related G protein-coupled receptors, Mrgprs. Pharmacol. Rev., 66, pp. 1080-1105.
Ballatore C., Huryn D.M. and Smith A.B. Carboxylic Acid (Bio)Isosteres in Drug Design. ChemMedChem, 2013, 8: pp. 385-395.
Ballinger, M.L., et al. Glycated and carboxy-methylated proteins do not directly activate human vascular smooth muscle cells. Kidney Int, 2005, 68: pp. 2756-2765.
Bandyopadhyay, S., Jeong, K.H., Hansen, J.T., Vassilev, P.M., Brown, E.M. & Chattopadhyay, N. (2007) Calcium-sensing receptor stimulates secretion of an interferon-γ-induced monokine (CXCL10) and monocyte chemoattractant protein-3 in immortalized GnRH neurons. Journal of neuroscience research, 85, pp. 882-895.
Barile, G.R. & Schmidt, A.M. (2007) RAGE and its ligands in retinal disease. Current molecular medicine, 7: pp. 758-765.
Baroni, A., Perfetto, B., Canozo, N., Braca, A., Farina, E., Melito, A., De Maria, S. & Carteni, M. (2008) Bombesin: A possible role in wound repair. Peptides, 29, pp. 1157-1166.
Bathgate, R., Halls, M., Van Der Westhuizen, E., Callander, G., Kocan, M. & Summers, R. (2013) Relaxin family peptides and their receptors. Physiological reviews, 93, pp. 405-480.
Batkulwar KB, Bansode SB, Patil GV, Godbole RK, Kazi RS, Chinnathambi S, Shanmugam D, Kulkarni MJ (2015) Investigation of phosphoproteome in RAGE signalling. Proteomics, 15, pp. 245-259.
Beaulieu, J.M. & Gainetdinov, R.R. (2011) The physiology, signalling, and pharmacology of dopamine receptors. Pharmacol Rev, 63, pp. 182-217.

Benigni A, Corna D, Zoja C, et al. (2009) Disruption of the angiotensin II type 1 receptor promotes longevity in mice. J Clin Invest, 119: pp. 524-530.
Benigni, A., Cassis, P. and Remuzzi, G. (2010) Angiotensin II revisited: new roles in inflammation, immunology and aging. EMBO Mol Med, 2: pp. 247-257.
Benya, R.V., Matkowskyj, K.A., Danilkovich, A. & Hecht, G. (1998) Galanin Causes Cl-Secretion in the Human Colon: Potential Significance of Inflammation-Associated NF-κB Activation on Galanin-1 Receptor Expression and Function. Annals of the New York Academy of Sciences, 863, pp. 64-77.
Bernardi, S., Candido, R., Toffoli, B., Carretta, R. & Fabris, B. (2011) Prevention of accelerated atherosclerosis by AT1 receptor blockade in experimental renal failure. Nephrology, dialysis, transplantation : official publication of the European Dialysis and Transplant Association—European Renal Association, 26: pp. 832-838.
Bhave, G., Karim, F., Carlton, S. & Gereau Iv, R. (2001) Peripheral group I metabotropic glutamate receptors modulate nociception in mice. Nature neuroscience, 4, pp. 417-423.
Bierhaus, A., et al. (2001) Diabetes-associated sustained activation of the transcription factor nuclear factor-kappaB. Diabetes, 50: pp. 2792-2808.
Billings, E.A., Lee, C.S., Owen, K.A., D'Souza, R.S., Ravichandran, K.S. & Casanova, J.E. (2016) The adhesion GPCR BAI1 mediates macrophage ROS production and microbicidal activity against Gram-negative bacteria. Sci. Signal., 9, ra14-ra14.
Blaes, N. & Girolami, J.-P. (2013) Targeting the 'Janus face' of the B2-bradykinin receptor. Expert Opinion on Therapeutic Targets, 17, 1145-1166.
Body, J.-J., Glibert, F., Nejai, S., Fernandez, G., Van Langendonck, A. & Borkowski, A. (1990) Calcitonin Receptors on Circulating Normal Human Lymphocytes*. The Journal of Clinical Endocrinology & Metabolism, 71, 675-681.
Boie, Y., N. Sawyer, D. M. Slipetz, K. M. Metters, and M. Abramovitz. Molecular cloning and characterization of the human prostanoid DP receptor. J Biol Chem, 1995, 270:18910-6.
Boie, Y., T. H. Rushmore, A. Darmon-Goodwin, R. Grygorczyk, D. M. Slipetz, and K. M. Metters. Cloning and expression of a cDNA for the human prostanoid IP receptor. J Biol Chem, 1994, 269:12173-8.
Boisvert, W.A. (2004) Modulation of atherogenesis by chemokines. Trends in Cardiovascular Medicine, 14: 161-165.
Bossard, C., Souazé, F., Jarry, A., Bezieau, S., Mosnier, J.-F., Forgez, P. & Laboisse, C.L. (2007) Over-expression of neurotensin high-affinity receptor 1 (NTS1) in relation with its ligand neurotensin (NT) and nuclear ß-catenin in Inflammatory bowel disease-related oncogenesis. Peptides, 28, 2030-2035.
Boulay, F., M. Tardif, L. Brouchon, and P. Vignais. The human N-formylpeptide receptor: characterization of two cDNA solates and evidence for a new subfamily of G-protein-coupled receptors. Biochemistry, 1990, 29:11123-33.
Boxall, S., Berthele, A., Laurie, D., Sommer, B., Zieglgänsberger, W., Urban, L. & Tolle, T. (1997) Enhanced expression of metabotropic glutamate receptor 3 messenger RNA in the rat spinal cord during ultraviolet irradiation induced peripheral inflammation. Neuroscience, 82, 591-602.
Boyd, J.H., Holmes, C.L., Wang, Y., Roberts, H. & Walley, K.R. (2008) Vasopressin decreases sepsis-induced pulmonary inflammation through the V2R. Resuscitation, 79, 325-331.
Braley A., Kwak T., Jules J., Harja E., Landgraf R., Hudson B.I. (2016) Regulation of Receptor for Advanced Glycation End Products (RAGE) Ectodomain Shedding and Its Role in Cell Function. J Biol Chem. 291, 12057-73.
Brauner-Osborne, H., Jensen, A.A., Sheppard, P.O., Brodin, B., Krogsgaard-Larsen, P. & O'Hara, P. (2001) Cloning and characterization of a human orphan family C G-protein coupled receptor GPRC5D. Biochimica et Biophysica Acta (BBA)-Gene Structure and Expression, 1518, 237-248.
Breyer, R. M., C. K. Bagdassarian, S. A. Myers, and M. D. Breyer. Prostanoid receptors: subtypes and signalling. Annu Rev Pharmacol Toxicol, 2001, 41:661-90.
Brezillon, S., Lannoy, V., Franssen, J.-D., Le Poul, E., Dupriez, V., Lucchetti, J., Detheux, M. & Parmentier, M. (2003) Identification of

(56) References Cited

OTHER PUBLICATIONS natural ligands for the orphan G protein-coupled receptors GPR7 and GPR8. Journal of Biological Chemistry, 278, 776-783.

Briscoe, C.P., Tadayyon, M., Andrews, J.L., Benson, W.G., Chambers, J.K., Eilert, M.M., Ellis, C., Elshourbagy, N.A., Goetz, A.S. & Minnick, D.T. (2003) The orphan G protein-coupled receptor GPR40 is activated by medium and long chain fatty acids. Journal of Biological chemistry, 278, 11303-11311.

Brothers, S.P. & Wahlestedt, C. (2010) Therapeutic potential of neuropeptide Y (NPY) receptor ligands. EMBO Mol Med, 2, 429-439.

Brown, A.J., Goldsworthy, S.M., Barnes, A.A., Eilert, M.M., Tcheang, L., Daniels, D., Muir, A.I., Wigglesworth, M.J., Kinghorn, I. & Fraser, N.J. (2003) The Orphan G protein-coupled receptors GPR41 and GPR43 are activated by propionate and other short chain carboxylic acids. Journal of Biological Chemistry, 278, 11312-11319.

Bucher, M., Hobbhahn, J., Taeger, K. & Kurtz, A. (2002) Cytokine-mediated downregulation of vasopressin V1A receptors during acute endotoxemia in rats. American Journal of Physiology-Regulatory, Integrative and Comparative Physiology, 282, R979-R984.

Buler, M., Aatsinki, S.-M., Skoumal, R., Komka, Z., Tóth, M., Kerkelä, R., Georgiadi, A., Kersten, S. & Hakkola, J. (2012) Energy-sensing Factors Coactivator Peroxisome Proliferator-activated Receptor γ Coactivator 1-α (PGC-1α) and AMP-activated Protein Kinase Control Expression of Inflammatory Mediators in Liver Induction of Interleukin 1 Receptor Antagonist. Journal of Biological Chemistry, 287, 1847-1860.

Burgess, G. M., M. N. Perkins, H. P. Rang, E. A. Campbell, M. C. Brown, and P. Mcintyre. Bradyzide, a potent non-peptide B(2) bradykinin receptor antagonist with long-lasting oral activity in animal models of inflammatory hyperalgesia. Br J Pharmacol, 2000, 129:77-86.

Cai, Z., et al. Role of RAGE in Alzheimer's Disease. Cellular and molecular neurobiology, 2016, 36: 483-495.

Theodoropoulou, M. & Stalla, G.K. (2013) Somatostatin receptors: from signalling to clinical practice. Front Neuroendocrinol, 34, 228-252.

Thoene-Reineke, C., Rumschussel, K., Schmerbach, K. et al., Prevention and intervention studies with telmisartan, ramipril and their combination in different rat stroke models. PloS One, 2011, 6: e23646, 10 pages.

Thomas, M.C., Pickering, R.J., Tsorotes, D., Koitka, A., Sheehy, K., Bernardi, S., Toffoli B., Nguyen-Huu, T.P., Head, G.A., Fu, Y., Chin-Dusting, J., Cooper, M.E., Tikellis C. (2010) Genetic Ace2 deficiency accentuates vascular Inflammation and atherosclerosis in the ApoE knockout mouse. Circulation Research, 107: 888-97.

Thomas, M.C., Tikellis, C., Burns, W.M., et al., Interactions between renin angiotensin system and advanced glycation in the kidney, Journal of the American Society of Nephrology, 2005, 16: 2976-2984.

Thompson, S. W., A. Dray, and L. Urban. Injury-induced plasticity of spinal reflex activity: NK1 neurokinin receptor activation and enhanced A- and C-fiber mediated responses in the rat spinal cord in vitro. J Neurosci, 1994, 14:3672-87.

Tichelaar, J.W., Wesselkamper, S.C., Chowdhury, S., Yin, H., Berclaz, P.-Y., Sartor, M.A., Leikauf, G.D. & Whitsett, J. A. (2007) Duration-dependent cytoprotective versus inflammatory effects of lung epithelial fibroblast growth factor-7 expression. Experimental lung research, 33, 385-417.

Tikellis, C, Wookey, P.J., Candido, R., Thomas, M.C. (2004) Improved islet morphology after blockade of the renin-angiotensin system in the ZDF rat, Diabetes, 53: 989-997.

Tikellis, C., Pickering, R.J., Tsorotes, D., Huet, O., Chin-Dusting, J., Cooper, M.E., and Thomas, M.C. (2012) Activation of the Renin-Angiotensin system mediates the effects of dietary salt intake on atherogenesis in the apolipoprotein E knockout mouse, Hypertension, 60: 98-105.

Tiruppathi, C., R. D. Minshall, B. C. Paria, S. M. Vogel, and A. B. Malik. Role of Ca2+signalling in the regulation of endothelial permeability. Vascul Pharmacol, 2002, 39:173-85.

Tiulpakov A, White CW, Abhayawardana RS, See HB, Chan AS, Seeber RM, Heng JI, Dedov I, Pavlos NJ, Pfleger KDG, Mutations of vasopressin receptor 2 including novel L312S have differential effects on trafficking, Mol Endocrinol, 2016, 30: 889-904.

Tong, L., Lan, W., Lim, R.R. & Chaurasia, S.S. S100A proteins as molecular targets in the ocular surface inflammatory diseases. The ocular surface, 2014, 12: 23-31.

Torres, R., S. D. Croll, J. Vercollone, J. Reinhardt, J. Griffiths, and S. Zabski. Mice genetically deficient in neuromedin J receptor 2, but not neuromedin U receptor 1, have impaired nociceptive responses. Pain, 2007, 130:267-78.

Tsatsanis, C., Androulidaki, A., Dermitzaki, E., Gravanis, A. & Margioris, A.N. (2007) Corticotropin releasing factor receptor 1 (CRF1) and CRF2 agonists exert an anti-inflammatory effect during the early phase of inflammation suppressing LPS-induced TNFα release from macrophages via induction of COX-2 and PGE2. Journal of cellular physiology, 210, 774-783.

Uhlén, M., FAGERberg, L., Hallstrom, B.M., Lindskog, C., Oksvold, P., Mardinoglu, A., Sivertsson, A., Kampf, C., Sjöstedt, E. & Asplund, A. (2015) Tissue-based map of the human proteome. Science, 347, 1260419.

Vaughan, K.R., Stokes, L., Prince, L.R., Marriott, H.M., Meis, S., Kassack, M.U., Bingle, C.D., Sabroe, I., Surprenant, A. & Whyte, M.K. (2007) Inhibition of neutrophil apoptosis by ATP is mediated by the P2Y11 receptor. The Journal of Immunology, 179, 8544-8553.

Venkataraman, C. & Kuo, F. (2005) The G-protein coupled receptor, GPR84 regulates IL-4 production by T lymphocytes in response to CD3 crosslinking. Immunology letters, 101, 144-153.

Voice, J.K., Grinninger, C., Kong, Y., Bangale, Y., Paul, S. & Goetzl, E.J. (2003) Roles of vasoactive intestinal peptide (VIP) in the expression of different immune phenotypes by wild-type mice and T cell-targeted type II VIP receptor transgenic mice. The Journal of Immunology, 170, 308-314.

Volpi, C., Fazio, F. & Fallarino, F. (2012) Targeting metabotropic glutamate receptors in neuroimmune communication. Neuropharmacology, 63, 501-506.

Volz, H.C., Kaya, Z., Katus, H.A. & Andrassy, M. (2010) The role of HMGB1/RAGE in inflammatory cardiomyopathy. Seminars in thrombosis and hemostasis, 36: 185-194.

Vu, T. K., D. T. Hung, V. I. Wheaton, and S. R. Coughlin. Molecular cloning of a functional thrombin receptor reveals a novel proteolytic mechanism of receptor activation. Cell, 1991, 64:1057-68.

Wacker, D., Wang, C., Katritch, V., Han, G.W., Huang, X.P., Vardy, E., McCorvy, J.D., Jiang, Y., Chu, M., Siu, F.Y., Liu, W., Xu, H.E., Cherezov, V., Roth, B.L. & Stevens, R.C. (2013) Structural features for functional selectivity at serotonin receptors. Science, 340, 615-619.

Nada, N., Hashinaga, T., Otabe, S., Yuan, X., Kurita, Y., Kakino, S., Ohoki, T., Nakayama, H., Fukutani, T. & Tajiri, Y. (2013) Selective modulation of Wnt ligands and their receptors in adipose tissue by chronic hyperadiponectinemia. PloS one, 8, e67712, 11 pages.

Wan, W., et al. The Emerging Role of HMGB1 in Neuropathic Pain: A Potential Therapeutic Target for Neuroinflammation. Journal of immunology research, 2016, 2016: 6430423.

Wang, D.B., Dayton, R.D., Zweig, R.M. & Klein, R.L. (2010) Transcriptome analysis of a tau overexpression model in rats implicates an early pro-inflammatory response. Experimental neurology, 224, 197-206.

Wang, J., Simonavicius, N., Wu, X., Swaminath, G., Reagan, J., Tian, H. & Ling, L. (2006) Kynurenic acid as a ligand for orphan G protein-coupled receptor GPR35. Journal of Biological Chemistry, 281, 22021-22028.

Warny, M., Aboudola, S., Robson, S.C., Sevigny, J., Communi, D., Soltoff, S.P. & Kelly, C.P. (2001) P2Y6 nucleotide receptor mediates monocyte interleukin-8 production in response to UDP or lipopolysaccharide. Journal of Biological Chemistry, 276, 26051-26056.

Watanabe, T., Tomioka, N.H., Doshi, M., Watanabe, S., Tsuchiya, M. & Hosoyamada, M. (2013) Macrophage migration inhibitory

(56) References Cited

OTHER PUBLICATIONS factor is a possible candidate for the induction of microalbuminuria in diabetic db/db mice. Biological and Pharmaceutical Bulletin, 36, 741-747.

Waters, K.M., Tan, R., Genetos, D.C., Verma, S., Yellowley, C.E. & Karin, N.J. (2007) DNA microarray analysis reveals a role for lysophosphatidic acid in the regulation of anti-inflammatory genes in MC3T3-E1 cells. Bone, 41, 833-841.

Wellendorph, P. & Brauner-Osborne, H. (2004) Molecular cloning, expression, and sequence analysis of GPRC6A, a novel family C G-protein-coupled receptor. Gene, 335, 37-46.

Wensman, H., Kamgari, N., Johansson, A., Grujic, M., Calounova, G., Lundequist, A., Rönnberg, E. & Pejler, G. (2012) Tumor-mast cell interactions: Induction of pro-tumorigenic genes and anti-tumorigenic 4-1BB in MCs in response to Lewis Lung Carcinoma. Molecular immunology, 50, 210-219.

Wess, J., Eglen, R.M. & Gautam, D. (2007) Muscarinic acetylcholine receptors: mutant mice provide new insights for drug development. Nat Rev Drug Discov, 6, 721-733.

White, J.F., Noinaj, N., Shibata, Y., Love, J., Kloss, B., Xu, F., Gvozdenovic-Jeremic, J., Shah, P., Shiloach, J., Tate, C.G. & Grisshammer, R. (2012) Structure of the agonist-bound neurotensin receptor. Nature, 490, 508-513.

White, J.H., Chiano, M., Wigglesworth, M., Geske, R., Riley, J., White, N., Hall, S., Zhu, G., Maurio, F. & Savage, T. (2008) Identification of a novel asthma susceptibility gene on chromosome 1qter and its functional evaluation. Human molecular genetics, 17, 1890-1903.

Wright, D.H., Ford-Hutchinson, A.W., Chadee, K. & Metters, K.M. (2000) The human prostanoid DP receptor stimulates mucin secretion in LS174T cells. British journal of pharmacology, 131, 1537-1545.

Wu, B., Chien, E.Y., Mol, C.D., Fenalti, G., Liu, W., Katritch, V., Abagyan, R., Brooun, A., Wells, P., Bi, F.C., Hamel, D. J., Kuhn, P., Handel, T.M., Cherezov, V. & Stevens, R.C. (2010) Structures of the CXCR4 chemokine GPCR with small-molecule and cyclic peptide antagonists. Science, 330, 1066-1071.

Wu, Q.-L., Zierold, C. & Ranheim, E.A. (2009) Dysregulation of Frizzled 6 is a critical component of B-cell eukemogenesis in a mouse model of chronic lymphocytic leukemia. Blood, 113, 3031-3039.

Xia, W., Han, J., Huang, G. & Ying, W. Inflammation in ischaemic brain injury: current advances and future perspectives. Clinical and experimental pharmacology & physiology, 2010, 37: 253-258.

Xie, J., Mendez, J.D., Mendez-Valenzuela, V. & Aguilar-Hernandez, M.M. Cellular signalling of the receptor for advanced glycation end products (RAGE). Cellular signalling, 2013, 25: 2185-2197.

Xiong, X., White, R.E., Xu, L., Yang, L., Sun, X., Zou, B., Pascual, C., Sakurai, T., Giffard, R.G. & Xie, X.S. (2013) Mitigation of murine focal cerebral ischemia by the hypocretin/orexin system is associated with reduced inflammation. Stroke, 44, 764-770.

Xue J., Manigrasso M., Scalabrin M., Rai V., Reverdatto S., Burz D.S., Fabris D., Schmidt A.M., Shekhtman A. (2016) Change in the Molecular Dimension of a RAGE-Ligand Complex Triggers RAGE Signaling. Structure. 24, 1509-22.

Yadav, M., Huang, M.-C. & Goetzl, E.J. (2011) VPAC1 (vasoactive intestinal peptide (VIP) receptor type 1) G protein-coupled receptor mediation of VIP enhancement of murine experimental colitis. Cellular immunology, 267, 124-132.

Yamagishi, S. & Matsui, T. Role of receptor for advanced glycation end products (RAGE) in liver disease. European journal of medical research, 2015, 20: 15.

Yan, S.F., Ramasamy, R., Schmidt, A.M., The RAGE axis: A fundamental mechanism signalling danger to the vulnerable vasculature. Circ Res, 2010, 106: 842-853.

Yang, D., Chen, Q., Gertz, B., He, R., Phulsuksombati, M., Ye, R.D. & Oppenheim, J.J. (2002) Human dendritic cells express functional formyl peptide receptor-like-2 (FPRL2) throughout maturation. J Leukoc Biol, 72, 598-607.

Yang, H.-Y. & Iadarola, M. (2003) Activation of spinal neuropeptide FF and the neuropeptide FF receptor 2 during inflammatory hyperalgesia in rats. Neuroscience, 118, 179-187.

Ye, R. D., F. Boulay, J. M. Wang, C. Dahlgren, C. Gerard, and M. Parmentier. International Union of Basic and Clinical Pharmacology. LXXIII. Nomenclature for the formyl peptide receptor (FPR) family. Pharmacol Rev, 2009, 61:119-61.

Yi, T., Lee, D.-S., Jeon, M.-S., Kwon, S.W. & Song, S.U. (2012) Gene expression profile reveals that STAT2 is involved in the immunosuppressive function of human bone marrow-derived mesenchymal stem cells. Gene, 497, 131-139.

Yin, J., Babaoglu, K., Brautigam, C.A., Clark, L., Shao, Z., Scheuermann, T.H., Harrell, C.M., Gotter, A.L., Roecker, A. J., Winrow, C.J., Renger, J.J., Coleman, P.J. & Rosenbaum, D.M. (2016) Structure and ligand-binding mechanism of the human OX1 and OX2 orexin receptors. Nat Struct Mol Biol, 23, 293-299.

Yin, J., Mobarec, J.C., Kolb, P. & Rosenbaum, D.M. (2015) Crystal structure of the human OX2 orexin receptor bound to the insomnia drug suvorexant. Nature, 519, 247-250.

Yin, X., Cheng, H., Lin, Y., Fan, X., Cui, Y., Zhou, F., Shen, C., Zuo, X., Zheng, X. & Zhang, W. (2014) Five regulatory genes detected by matching signatures of eQTL and GWAS in psoriasis. Journal of dermatological science, 76, 139-142.

Yokomizo, T., Kato, K., Terawaki, K., Izumi, T. & Shimizu, T. (2000) A Second Leukotriene B4 Receptor, BIt2 A New Therapeutic Target in Inflammation and Immunological Disorders. The Journal of experimental medicine, 192, 421-432.

Yost, C. C., A. S. Weyrich, and G. A. Zimmerman. The platelet activating factor (PAF) signalling cascade in systemic inflammatory responses. Biochimie, 2010, 92:692-7.

You, J., Nguyen, A.V., Albers, C.G., Lin, F. & Holcombe, R.F. (2008) Wnt pathway-related gene expression in inflammatory bowel disease. Digestive diseases and sciences, 53, 1013-1019.

Zammataro, M., Chiechio, S., Montana, M.C., Traficante, A., Copani, A., Nicoletti, F. & Gereau, R.W. (2011) mGlu2 metabotropic glutamate receptors restrain inflammatory pain and mediate the analgesic activity of dual mGlu2/mGlu3 receptor agonists. Molecular pain, 7, 1, 5 pages.

Zeng, H., A. GrAGERov, J. G. Hohmann, M. N. Pavlova, B. A. Schimpf, and H. Xu. Neuromedin U receptor 2-deficient mice display differential responses in sensory perception, stress, and feeding. Mol Cell Biol, 2006, 26:9352-63.

Zhang Y. I-Tasser server for protein 3D structure prediction. BMC Bioinformatics, 2008, 9: 40, 8 pages.

Zhang, F., Wu, R., Qiang, X., Zhou, M. & Wang, P. (2010a) Antagonism of α2A-adrenoceptor: a novel approach to inhibit inflammatory responses in sepsis. Journal of Molecular Medicine, 88, 289-296.

Zhang, H., Unal, H., Gati, C., Won Han, G., Liu, W., Zatsepin, N.A., James, D., Want, D., Nelson, G., Weierstall, U., Sawaya, M.R., Xu, Q., Messerschmidt, M., Williams, G.J., Boutet, S., Yefanov, O.M., White, T.,A., Wang, C., Ishchenko, A., Tirupula, K.C., Desnoyer, et al., Structure of the Angiotensin Receptor Revealed by Serial Femtosecond Crystallography, Cell, 2015, 161: 4, 833-844.

Zhang, X., Schmudde, I., Laumonnier, Y., Pandey, M., Clark, J., Konig, P., Gerard, N., Gerard, C., Wills-Karp, M. & Kohl, J. (2010b) A critical role for C5L2 in the pathogenesis of experimental allergic asthma. Journal of immunology (Baltimore, Md.: 1950), 185, 6741-6752.

Zhao, W., Ho, L., Varghese, M., Yemul, S., Dams-O'Connor, K., Gordon, W., Knable, L., Freire, D., Haroutunian, V. & Pasinetti, G.M. (2013) Decreased level of olfactory receptors in blood cells following traumatic brain injury and potential association with tauopathy. Journal of Alzheimer's Disease, 34, 417-429.

Zhao, Z., Lee, C.C., Baldini, A. & Caskey, C.T. (1995) A Human Homologue of the *Drosophila* Polarity Gene frizzled Has Been Identified and Mapped to 17q21.1. Genomics, 27, 370-373.

Zheng, Y., Qin, L., Zacarias, N.V., de Vries, H., Han, G.W., Gustavsson, M., Dabros, M., Zhao, C., Cherney, R.J., Carter, P., Stamos, D., Abagyan, R., Cherezov, V., Stevens, R.C., AP, I.J., Heitman, L.H., Tebben, A., Kufareva, I. & Handel, T.M. (2016) Structure of CC chemokine receptor 2 with orthosteric and allosteric antagonists. Nature, 540, 458-461.

(56) References Cited

OTHER PUBLICATIONS

Zhong, H., Shlykov, S.G., Molina, J.G., Sanborn, B.M., Jacobson, M.A., Tilley, S.L. & Blackburn, M.R. (2003) Activation of murine lung mast cells by the adenosine A3 receptor. The Journal of Immunology, 171, 338-345.
Zhou, N., Fan, X., Mukhtar, M., Fang, J., Patel, C.A., DuBois, G.C. & Pomerantz, R.J. (2003) Cell-cell fusion and internalization of the CNS-based, HIV-1 co-receptor, APJ. Virology, 307, 22-36.
Zhou, Z., et al. Receptor for AGE (RAGE) mediates neointimal formation in response to arterial injury. Circulation, 2003, 107: 2238-2243.
Zhu, P., Sun, W., Zhang, C., Song, Z. & Lin, S. (2016) The role of neuropeptide Y in the pathophysiology of atherosclerotic cardiovascular disease. International Journal of Cardiology, 220, 235-241.
Ziogas, D.C., Gras-Miralles, B., Mustafa, S., Geiger, B.M., Najarian, R.M., Nagel, J.M., Flier, S.N., Popov, Y., Tseng, Y.-H. & Kokkotou, E. (2013) Anti-melanin-concentrating hormone treatment attenuates chronic experimental colitis and fibrosis. American Journal of Physiology—Gastrointestinal and Liver Physiology, 304, G876-G884.
Zlotnik, A., and O. Yoshie. (2000) Chemokines: a new classification system and their role in immunity. Immunity, 12:121-7.
Horton, J., Yamamoto, S. & Bryant-Greenwood, G. (2012) Relaxin augments the inflammatory IL6 response in the choriodecidua. Placenta, 33, 399-407.
European Patent Office, "Extended European Search Report", issued in connection with corresponding European patent application, EP 18849151.8, dated May 11, 2021, 11 pages.
Patent Cooperation Treaty, "International Preliminary Report on Patentability", issued in connection with PCT/AU2018/050883, dated Feb. 25, 2020, 9 pages.
Ma, T.K., Kam, K.K., Yan, B.P., Lam, Y.Y., Renin-angiotensin-aldosterone system blockade for cardiovascular diseases: current status, Br J Pharmacol, 2010, 160: 1273-1292.
Maekawa, A., Balestrieri, B., Austen, K.F. & Kanaoka, Y. (2009) GPR17 is a negative regulator of the cysteinyl eukotriene 1 receptor response to leukotriene D4. Proceedings of the National Academy of Sciences, 106, 11685-11690.
Malik, P., Chaudhry, N., Mittal, R. & Mukherjee, T.K. (2015) Role of receptor for advanced glycation end products in the complication and progression of various types of cancers. Biochimica et biophysica acta, 1850: 1898-1904.
Malki, A., Fiedler, J., Fricke, K., Ballweg, I., Pfaffl, M.W. & Krautwurst, D. (2015) Class I odorant receptors, TAS1R and TAS2R taste receptors, are markers for subpopulations of circulating leukocytes. Journal of leukocyte biology, 97, 533-545.
Manigrasso, M.B., et al. (2016) Small Molecule Inhibition of Ligand-Stimulated RAGE-DIAPH1 Signal Transduction. Scientific reports, 6: 22450, 13 pages.
Manning, M., Stoev, S., Chini, B., Durroux, T., Mouillac, B. & Guillon, G. (2008) Peptide and non-peptide agonists and antagonists for the vasopressin and oxytocin V1a, V1b, V2 and OT receptors: research tools and potential therapeutic agents. Prog Brain Res, 170, 473-512.
Mao, Y., Zhang, M., Tuma, R.F. & Kunapuli, S.P. (2010) Deficiency of PAR4 attenuates cerebral ischemia/reperfusion injury in mice. Journal of Cerebral Blood Flow & Metabolism, 30, 1044-1052.
Marazziti, D., Ori, M., Nardini, M., Rossi, A., Nardi, I. & Cassano, G.B. (2001) mRNA expression of serotonin receptors of type 2C and 5A in human resting lymphocytes. Neuropsychobiology, 43, 123-126.
Marinakis, E., Bagkos, G., Piperi, C., Roussou, P. & Diamanti-Kandarakis, E. (2014) Critical role of RAGE in lung physiology and tumorigenesis: a potential target of therapeutic intervention? Clinical chemistry and laboratory medicine, 52: 189-200.
Martinez, C., Abad, C., Delgado, M., Arranz, A., Juarranz, M.G., Rodriguez-Henche, N., Brabet, P., Leceta, J. & Gomariz, R.P. (2002) Anti-inflammatory role in septic shock of pituitary adenylate cyclase-activating polypeptide receptor. Proceedings of the National Academy of Sciences, 99, 1053-1058.

Martinez, F.O., Gordon, S., Locati, M. & Mantovani, A. (2006) Transcriptional profiling of the human monocyte-to-macrophage differentiation and polarization: new molecules and patterns of gene expression. The Journal of Immunology, 177, 7303-7311.
Marvar, P.J., et al. (2010) Central and peripheral mechanisms of T-lymphocyte activation and vascular inflammation produced by angiotensin II-induced hypertension. Circ Res, 107: 263-270.
Mas, V., Maluf, D., Archer, K.J., Potter, A., Suh, J., Gehrau, R., Descalzi, V. & Villamil, F. (2011) Transcriptome at the time of hepatitis C virus recurrence may predict the severity of fibrosis progression after liver transplantation. Liver Transplantation, 17, 824-835.
Maslowski, K.M., Vieira, A.T., Ng, A., Kranich, J., Sierro, F., Yu, D., Schilter, H.C., Rolph, M.S., Mackay, F. & Artis, D. (2009) Regulation of inflammatory responses by gut microbiota and chemoattractant receptor GPR43. Nature, 461, 1282-1286.
Masters, S.L., Dunne, A., Subramanian, S.L., Hull, R.L., Tannahill, G.M., Sharp, F.A., Becker, C., Franchi, L., Yoshihara, E. & Chen, Z. (2010) Activation of the NLRP3 inflammasome by islet amyloid polypeptide provides a mechanism for enhanced IL-1 [beta] in type 2 diabetes. Nature immunology, 11, 897-904.
Matavelli, L.C., Huang, J. & Siragy, H.M. (2011) Angiotensin AT2 receptor stimulation inhibits early renal inflammation in renovascular hypertension. Hypertension, 57, 308-313.
Matloubian, M., Lo, C.G., Cinamon, G., Lesneski, M.J., Xu, Y., Brinkmann, V., Allende, M.L., Proia, R.L. & Cyster, J.G. (2004) Lymphocyte egress from thymus and peripheral lymphoid organs is dependent on S1P receptor 1. Nature, 427, 355-360.
Matsumoto, M., Saito, T., Takasaki, J., Kamohara, M., Sugimoto, T., Kobayashi, M., Tadokoro, M., Matsumoto, S.-i., Ohishi, T. & Furuichi, K. (2000) An evolutionarily conserved G-protein coupled receptor family, SREB, expressed in the central nervous system. Biochemical and biophysical research communications, 272, 576-582.
Matsumura, T., Oyama, M., Kozuka-Hata, H., Ishikawa, K., Inoue, T., Muta, T., Semba, K. & Inoue, J.-i. (2010) Identification of BCAP-L as a negative regulator of the TLR signalling-induced production of IL-6 and IL-10 in macrophages by tyrosine phosphoproteomics. Biochemical and Biophysical Research Communications, 400, 265-270.
Matsuoka, T., M. Hirata, H. Tanaka, Y. Takahashi, T. Murata, and K. Kabashima. Prostaglandin D2 as a mediator of allergic asthma. Science, 2000, 287:2013-7.
Matteucci, C., Minutolo, A., Sinibaldi-Vallebona, P., Palamara, A.T., Rasi, G., Mastino, A. & Garaci, E. (2010) Transcription profile of human lymphocytes following in vitro treatment with thymosin alpha-1. Annals of the New York Academy of Sciences, 1194, 6-19.
McPherson, J.A., Barringhaus, K.G., Bishop, G.G., Sanders, J.M., Rieger, J.M., Hesselbacher, S.E., Gimple, L.W., Powers, E.R., Macdonald, T. & Sullivan, G. (2001) Adenosine A2A receptor stimulation reduces inflammation and neointimal growth in a murine carotid ligation model. Arteriosclerosis, Thrombosis, and Vascular Biology, 21, 791-796.
McQuiston, T., Luberto, C. & Del Poeta, M. (2011) Role of sphingosine-1-phosphate (S1P) and S1P receptor 2 in the phagocytosis of Cryptococcus neoformans by alveolar macrophages. Microbiology, 157, 1416-1427.
McVerry, B. J., X. Peng, P. M. Hassoun, S. Sammani, B. A. Simon, and J. G. Garcia. Sphingosine 1-phosphate reduces vascular leak in murine and canine models of acute lung injury. Am J Respir Crit Care Med, 2004, 170:987-993.
Mehta, D., M. Konstantoulaki, G. U. Ahmmed, and A. B. Malik. Sphingosine 1-phosphate-induced mobilization of intracellular Ca2+ mediates rac activation and adherens junction assembly in endothelial cells. J Biol Chem, 2005, 280:17320-17328.
Mellado, M., Fernandez-Agullo, T., Rodríguez-Frade, J.M., Garcia San Frutos, M., de la Peña, P., Martinez-A, C. & Montoya, E. (1999) Expression analysis of the thyrotropin-releasing hormone receptor (TRHR) in the immune system using agonist anti-TRHR monoclonal antibodies. FEBS Letters, 451, 308-314.
Michel, M.C., Beck-Sickinger, A., Cox, H., Doods, H.N., Herzog, H., Larhammar, D., Quirion, R., Schwartz, T. & Westfall, T. (1998) XVI. International Union of Pharmacology recommendations for

(56) References Cited

OTHER PUBLICATIONS the nomenclature of neuropeptide Y, peptide YY, and pancreatic polypeptide receptors. Pharmacol Rev, 50, 143-150.
Minami, T., H. Nakano, T. Kobayashi, Y. Sugimoto, F. Ushikubi, and A. Ichikawa. Characterization of EP receptor subtypes responsible for prostaglandin E2-induced pain responses by use of EP1 and EP3 receptor knockout mice. Br J Pharmacol, 2001, 133:438-444.
Mitić, K., Stanojević, S., Kutrimović, N., Vujić, V. & Dimitrijević, M. (2011) Neuropeptide Y modulates functions of inflammatory cells in the rat: Distinct role for Y1, Y2 and Y5 receptors. Peptides, 32, 1626-1633.
Mitsuhashi, M., Mitsuhashi, T. & Payan, D. (1989) Multiple signalling pathways of histamine H2 receptors. Identification of an H2 receptor-dependent Ca2+ mobilization pathway in human HL-60 promyelocytic leukemia cells. Journal of Biological Chemistry, 264, 18356-18362.
Mo, J., Yang, A., Chen, Z., Shao, T., Zhang, Y. & Chen, Q. (2013) Neuronostatin ameliorates sodium taurocholate-induced acute pancreatitis in rats. Digestive diseases and sciences, 58, 2903-2907.
Moore, D.J., Chambers, J.K., Wahlin, J.-P., Tan, K.B., Moore, G.B., Jenkins, O., Emson, P.C. & Murdock, P.R. (2001) Expression pattern of human P2Y receptor subtypes: a quantitative reverse transcription-polymerase chain reaction study. Biochimica et Biophysica Acta (BBA)-Gene Structure and Expression, 1521, 107-119.
Moriyama, M., Sato, T., Inoue, H., Fukuyama, S., Teranishi, H., Kangawa, K., Kano, T., Yoshimura, A. & Kojima, M. (2005) The neuropeptide neuromedin U promotes inflammation by direct activation of mast cells. The Journal of experimental medicine, 202, 217-224.
Morooka H, Iwanaga Y, Tamaki Y, Takase T, Akahoshi Y, Nakano Y, Fujiki H, Miyazaki S. Chronic administration of pral vasopressin type 2 receptor antagonist tolvaptan exerts both myocardial and renal protective effects in rats with hypertensive heart failure. Circ Heart Fail, 2012, 5: 484-92.
Muir, A.I., Chamberlain, L., Elshourbagy, N.A., Michalovich, D., Moore, D.J., Calamari, A., Szekeres, P.G., Sarau, H. M., Chambers, J.K. & Murdock, P. (2001) AXOR12, a novel human G protein-coupled receptor, activated by the peptide KiSS-1. Journal of Biological Chemistry, 276, 28969-28975.
Murata, T., F. Ushikubi, T. Matsuoka, M. Hirata, A. Yamasaki, and Y. Sugimoto. Altered pain perception and inflammatory response in mice lacking prostacyclin receptor. Nature, 1997, 388:678-82.
Murphy, P. M., M. Baggiolini, I. F. Charo, C. A. Hebert, R. Horuk, and K. Matsushima. (2000) International Union of Pharmacology. XXII. Nomenclature for chemokine receptors. Pharmacol Rev, 52:145-176.
Mustafa, S., Ayoub, M.A. and Pfleger, K.D.G., (2010) Uncovering GPCR heteromer-biased ligands. Drug Discov Today Technol, 7: e77-e85.
Mustafa, S., See, H.B., Seeber, R.M., Armstrong, S.P., White, C.W., Ventura, S., Ayoub, M.A., and Pfleger, K.D., Identification and profiling of novel alpha1A-adrenoceptor-CXC chemokine receptor 2 heteromer, J Biol Chem, 2012, 287: 12952-12965.
Nagamachi, M., Sakata, D., Kabashima, K., Furuyashiki, T., Murata, T., Segi-Nishida, E., Soontrapa, K., Matsuoka, T., Miyachi, Y. & Narumiya, S. (2007) Facilitation of Th1-mediated immune response by prostaglandin E receptor EP1. The Journal of experimental medicine, 204, 2865-2874.
Neeper, M., Schmidt, A.M., Brett, J., Yan, S.D., Wang, F., Pan, Y.C., Elliston, K., Stern, D., Shaw, A., Cloning and expression of a cell surface receptor for advanced glycosylation end products of proteins, J Biol Chem, 1992, 268;21, 14998-5004.
Németh, Z.H., Lutz, C.S., Csóka, B., Deitch, E.A., Leibovich, S.J., Gause, W.C., Tone, M., Pacher, P., Vizi, E.S. & Haskó, G. (2005) Adenosine augments IL-10 production by macrophages through an A2B receptor-mediated posttranscriptional mechanism. The Journal of Immunology, 175, 8260-8270.
Neumann, J., Schaale, K., Farhat, K., Endermann, T., Ulmer, A.J., Ehlers, S. & Reiling, N. (2010) Frizzled1 is a marker of inflammatory macrophages, and its ligand Wnt3a is involved in reprogramming *Mycobacterium tuberculosis*-infected macrophages. The FASEB Journal, 24, 4599-4612.
Nichols, D.E. & Nichols, C.D. (2008) Serotonin receptors. Chem Rev, 108, 1614-1641.
Nie, Y., Ma, R.C., Chan, J.C., Xu, H. & Xu, G. (2012) Glucose-dependent insulinotropic peptide impairs insulin signalling via inducing adipocyte inflammation in glucose-dependent insulinotropic peptide receptor-overexpressing adipocytes. The FASEB Journal, 26, 2383-2393.
Niedernberg, A., Tunaru, S., Blaukat, A., Ardati, A. & Kostenis, E. (2003) Sphingosine 1-phosphate and dioleoylphosphatidic acid are low affinity agonists for the orphan receptor GPR63. Cellular Signalling, 15, 435-446.
Nijmeijer, S., Vischer, H.F. & Leurs, R. (2016) Adhesion GPCRs in immunology. Biochemical pharmacology, 88-102.
Nishio, R., Matsumori, A., Shioi, T., Wang, W., Yamada, T., Ono, K. & Sasayama, S. (1998) Denopamine, a β1-adrenergic agonist, prolongs survival in a murine model of congestive heart failure induced by viral myocarditis: suppression of tumor necrosis factor-α production in the heart. Journal of the American College of Cardiology, 32, 808-815.
Sarkar, C., Das, S., Chakroborty, D., Chowdhury, U.R., Basu, B., Dasgupta, P.S. & Basu, S. (2006) Cutting edge: stimulation of dopamine D4 receptors induce T cell quiescence by up-regulating Krüppel-like factor-2 expression through Inhibition of ERK1/ERK2 phosphorylation. The Journal of Immunology, 177, 7525-7529.
Sasaki, Y., Hoshi, M., Akazawa, C., Nakamura, Y., Tsuzuki, H., Inoue, K. & Kohsaka, S. (2003) Selective expression of Gi/o-coupled ATP receptor P2Y12 in microglia in rat brain. Glia, 44, 242-250.
Sato, K.Z., Fujii, T., Watanabe, Y., Yamada, S., Ando, T., Kazuko, F. & Kawashima, K. (1999) Diversity of mRNA expression for muscarinic acetylcholine receptor subtypes and neuronal nicotinic acetylcholine receptor subunits in human mononuclear leukocytes and leukemic cell lines. Neuroscience letters, 266, 17-20.
Satoh, A., Shimosegawa, T., Satoh, K., Ito, H., Kohno, Y., Masamune, A., Fujita, M. & Toyota, T. (2000) Activation of adenosine A1-receptor pathway induces edema formation in the pancreas of rats. Gastroenterology, 119, 829-836.
Schaub, A., Futterer, A. & Pfeffer, K. (2001) PUMA-G, an IFN-gamma-inducible gene in macrophages is a novel member of the seven transmembrane spanning receptor superfamily. Eur J Immunol, 31, 3714-3725.
Schiffmann, E., Corcoran, B.A. & Wahl, S.M. (1975) N-formylmethionyl peptides as chemoattractants for leucocytes. Proceedings of the National Academy of Sciences, 72, 1059-1062.
Schmidhuber, S.M., Rauch, I., Kofler, B. & Brain, S.D. (2009) Evidence that the modulatory effect of galanin on inflammatory edema formation is mediated by the galanin receptor 3 in the murine microvasculature. Journal of molecular neuroscience : MN, 37, 177-181.
Schmidt, A.M., Yan, S.D., Wautier, J.L. & Stern, D. (1999) Activation of receptor for advanced glycation end products: a mechanism for chronic vascular dysfunction in diabetic vasculopathy and atherosclerosis. Circ Res, 84: 489-497.
Schmitz, F., Schrader, H., Otte, J.-M., Schmitz, H., Stuber, E., Herzig, K.-H. & Schmidt, W.E. (2001) Identification of CCK-B/gastrin receptor splice variants in human peripheral blood mononuclear cells. Regulatory peptides, 101, 25-33.
Schuelert, N. & McDougall, J.J. (2011) The abnormal cannabidiol analogue O-1602 reduces nociception in a rat model of acute arthritis via the putative cannabinoid receptor GPR55. Neuroscience letters, 500, 72-76.
Schwarze, S.R., Hruska, K.A., Dowdy, S.F. (2000) Protein transduction: unrestricted delivery into all cells? Trends Cell Biol, 10: 290-295.
Shen, Z.-J., Hu, J., Esnault, S., Dozmorov, I. & Malter, U.S. (2015) RNA Seq profiling reveals a novel expression pattern of TGF-β target genes in human blood eosinophils. Immunology letters, 167, 1-10.

(56) References Cited

OTHER PUBLICATIONS

Shen. J., Huang. Y.M., Wang. M., et al. (2016) Renin-angiotensin system blockade for the risk of cancer and death. J Renin Angiotensin Aldosterone Syst. 8, 17(3), 14 pages.

Shihoya, W., Nishizawa, T., Okuta, A., Tani, K., Dohmae, N., Fujiyoshi, Y., Nureki, O. & Doi, T. (2016) Activation mechanism of endothelin ETB receptor by endothelin-1. Nature, 537, 363-368.

Sima, C., Cheng, Q., Rautava, J., Levesque, C., Sherman, P. & Glogauer, M. (2015) Identification of quantitative trait oci influencing inflammation-mediated alveolar bone loss: insights into polygenic inheritance of host-biofilm disequilibria in periodontitis. Journal of periodontal research, 237-249.

Sjolander S and Urbaniczky C. Integrated fluid handling system for biomolecular interaction analysis. Anal. Chem., 1991, 63: 2338-2345.

Sohn, S.-H., Chung, H.-S., Ko, E., Jeong, H.-j., Kim, S.-H., Jeong, J.-H., Kim, Y., Shin, M., Hong, M. & Bae, H. (2009) The genome-wide expression profile of Nelumbinis semen on lipopolysaccharide-stimulated BV-2 microglial cells. Biological and Pharmaceutical Bulletin, 32, 1012-1020.

Solinski, H.J., Petermann, F., Rothe, K., Boekhoff, I., Gudermann, T. & Breit, A. (2013) Human Mas-Related G Protein-Coupled Receptors-X1 Induce Chemokine Receptor 2 Expression in Rat Dorsal Root Ganglia Neurons and Release of Chemokine Ligand 2 from the Human LAD-2 Mast Cell Line. PLoS One, 8, e58756, 15 pages.

Sonobe, Y., Nakane, H., Watanabe, T. & Nakano, K. (2004) Regulation of Con A-dependent cytokine production from CD4+ and CD8+ T lymphocytes by autosecretion of histamine. Inflammation Research, 53, 87-92.

Sonoda, N., Katabuchi, H., Tashiro, H., Ohba, T., Nishimura, R., Minegishi, T. & Okamura, H. (2005) Expression of variant luteinizing hormone/chorionic gonadotropin receptors and degradation of chorionic gonadotropin in human chorionic villous macrophages. Placenta, 26, 298-307.

Soro-Paavonen, A., Watson, AM., Thomas, M.C., et al. (2008) Receptor for advanced glycation end products (RAGE) deficiency attenuates the development of atherosclerosis in diabetes, Diabetes, 57:2461-2469.

Souza, D.G., Lomez, E.S.L., Pinho, V., Pesquero, J.B., Bader, M., Pesquero, J.L. & Teixeira, M.M. (2004) Role of Bradykinin B2 and B1 Receptors in the Local, Remote, and Systemic Inflammatory Responses That Follow Intestinal Ischemia and Reperfusion Injury. The Journal of Immunology, 172, 2542-2548.

Sparvero, L.J., et al. (2009) RAGE (Receptor for Advanced Glycation Endproducts), RAGE ligands, and their role in cancer and inflammation. Journal of translational medicine, 7: 17, 21 pages.

Stacey, M., Lin, H.-H., Hilyard, K.L., Gordon, S. & McKnight, A.J. (2001) Human epidermal growth factor (EGF) module-containing mucin-like hormone receptor 3 is a new member of the EGF-TM7 family that recognizes a ligand on human macrophages and activated neutrophils. Journal of Biological Chemistry, 276, 18863-18870.

Stefulj, J., Jernej, B., Cicin-Sain, L., Rinner, I. & Schauenstein, K. (2000) mRNA expression of serotonin receptors in cells of the immune tissues of the rat. Brain, behavior, and immunity, 14, 219-224.

Stockhammer, O.W., Rauwerda, H., Wittink, F.R., Breit, T.M., Meijer, A.H. & Spaink, H.P. (2010) Transcriptome analysis of Traf6 function in the innate immune response of zebrafish embryos. Molecular immunology, 48, 179-190.

Stoddart LA, Johnstone EKM, Wheal AJ, Goulding J, Robers MB, Machleidt T, Wood KV, Hill SJ and Pfleger KDG. Application of BRET to monitor ligand binding to GPCRs. Nat Methods, 2015, 12: 661-663.

Su P.C., Berger B.W. (2013) A novel assay for assessing juxtamembrane and transmembrane domain interactions important for receptor heterodimerization. J Mol Biol. 425, 4652-4658.

Subramanian, H., Gupta, K., Guo, Q., Price, R. & Ali, H. (2011) Mas-related Gene X2 (MrgX2) Is a Novel G Protein-coupled Receptor for the Antimicrobial Peptide LL-37 in Human Mast Cells Resistance To Receptor Phosphorylation, Desensitization, and Internalization. Journal of Biological Chemistry, 286, 44739-44749.

Sugimoto, T., Saito, M., Mochizuki, S., Watanabe, Y., Hashimoto, S. & Kawashima, H. (1994) Molecular cloning and functional expression of a cDNA encoding the human V1b vasopressin receptor. Journal of Biological Chemistry, 269, 27088-27092.

Sugimoto, Y. & Narumiya, S. (2007) Prostaglandin E receptors. J Biol Chem, 282, 11613-11617.

Sugo, T., Tachimoto, H., Chikatsu, T., Murakami, Y., Kikukawa, Y., Sato, S., Kikuchi, K., Nagi, T., Harada, M. & Ogi, K. (2006) Identification of a lysophosphatidylserine receptor on mast cells. Biochemical and biophysical research communications, 341, 1078-1087.

Sukkar, M.B., et al. RAGE: a new frontier in chronic airways disease. British Journal of Pharmacology, 2012, 167: 1161-1176.

Sunuwar, L., Medini, M., Cohen, L., Sekler, I. & Hershfinkel, M. (2016) The zinc sensing receptor, ZnR/GPR39, triggers metabotropic calcium signalling in colonocytes and regulates occludin recovery in experimental colitis. Phil. Trans. R. Soc. B, 371, Apr. 20, 2015, 12 pages.

Suzuki, T., Won, K.-J., Horiguchi, K., Kinoshita, K., Hori, M., Torihashi, S., Momotani, E., Itoh, K., Hirayama, K. & Ward, S.M. (2004) Muscularis inflammation and the loss of interstitial cells of Cajal in the endothelin ETB receptor null at. American Journal of Physiology—Gastrointestinal and Liver Physiology, 287, G638-G646.

Swan, C., Duroudier, N.P., Campbell, E., Zaitoun, A., Hastings, M., Dukes, G.E., Cox, J., Kelly, F.M., Wilde, J. & Lennon, M.G. (2013) Identifying and testing candidate genetic polymorphisms in the irritable bowel syndrome (IBS): association with TNFSF15 and TNFα. Gut, 62, 985-994.

Swaney, J., Chapman, C., Correa, L., Stebbins, K., Bundey, R., Prodanovich, P., Fagan, P., Baccei, C., Santini, A. & Hutchinson, J. (2010) A novel, orally active LPA1 receptor antagonist inhibits lung fibrosis in the mouse bleomycin model. British journal of pharmacology, 160, 1699-1713.

Szabo, A., Stolz, L. and Granzow, R. Surface plasmon resonance and its use in biomolecular interaction analysis (BIA). Curr Opin Struct Biol, 1995, 5: 699-705.

Taguchi, A., et al. (2000) Blockade of RAGE-amphoterin signalling suppresses tumour growth and metastases. Nature, 405: 354-360.

Takayama, K., Yuhki, K., Ono, K., Fujino, T., Hara, A., Yamada, T., Kuriyama, S., Karibe, H., Okada, Y., Takahata, O., Taniguchi, T., Iijima, T., Iwasaki, H., Narumiya, S. & Ushikubi, F. (2005) Thromboxane A2 and prostaglandin F2alpha mediate inflammatory tachycardia. Nat Med, 11, 562-566.

Takenouchi, R., Inoue, K., Kambe, Y. & Miyata, A. (2012) N-arachidonoyl glycine induces macrophage apoptosis via GPR18. Biochemical and biophysical research communications, 418, 366-371.

Tan, Q., Zhu, Y., Li, J., Chen, Z., Han, G.W., Kufareva, I., Li, T., Ma, L., Fenalti, G., Li, J., Zhang, W., Xie, X., Yang, H., Jiang, H., Cherezov, V., Liu, H., Stevens, R.C., Zhao, Q. & Wu, B. (2013) Structure of the CCR5 chemokine receptor-HIV entry inhibitor maraviroc complex. Science, 341, 1387-1390.

Taniyama, Y., Suzuki, T., Mikami, Y., Moriya, T., Satomi, S. & Sasano, H. (2005) Systemic distribution of somatostatin receptor subtypes in human: an immunohistochemical study. Endocrine journal, 52, 605-611.

Taquet, N., Philippe, C., Reimund, J.-M. & Muller, C.D. (2012) Inflammatory Bowel Disease G-Protein Coupled Receptors (GPCRs) Expression Profiling with Microfluidic Cards, 59-86.

Taub, D.D., Eisenstein, T.K., Geller, E.B., Adler, M.W. & Rogers, T.J. (1991) Immunomodulatory activity of mu-and kappa-selective opioid agonists. Proceedings of the National Academy of Sciences, 88, 360-364.

Tayebati, S., Bronzetti, E., Morra Di Cella, S., Mulatero, P., Ricci, A., Rossodivita, I., Schena, M., Schiavone, D., Veglio, F. & Amenta, F. (2000) In situ hybridization and immunocytochemistry of alpha1-adrenoceptors in human peripheral blood lymphocytes. Journal of autonomic pharmacology, 20, 305-312.

(56) References Cited

OTHER PUBLICATIONS

Ter Beek, W.P., Muller, E.S., Van Den Berg, M., Meijer, M.J., Biemond, I. & Lamers, C.B. (2008) Motilin receptor expression in smooth muscle, myenteric plexus, and mucosa of human inflamed and noninflamed intestine. Inflammatory bowel diseases, 14, 612-619.

Tesch, G.H. (2008) MCP-1/CCL2: a new diagnostic marker and therapeutic target for progressive renal injury in diabetic nephropathy. Am J Physiol Renal Physiol, 294: 697-701.

Teuscher, C., Subramanian, M., Noubade, R., Gao, J.F., Offner, H., Zachary, J.F. & Blankenhorn, E.P. (2007) Central histamine H3 receptor signalling negatively regulates susceptibility to autoimmune inflammatory disease of the CNS. Proceedings of the National Academy of Sciences, 104, 10146-10151.

Thal, D.M., Sun, B., Feng, D., Nawaratne, V., Leach, K., Felder, C.C., Bures, M.G., Evans, D.A., Weis, W.I., Bachhawat, P., Kobilka, T.S., Sexton, P.M., Kobilka, B.K. & Christopoulos, A. (2016) Crystal structures of the M1 and M4 muscarinic acetylcholine receptors. Nature, 531, 335-340.

Obinata, H. and Hla, T., Sphingosine 1-phosphate in coagulation and inflammation, Semin Immunopathol, 2012, 34: 73-91.

Ohshima, S., Yamaguchi, N., Nishioka, K., Mima, T., Ishii, T., Umeshita-Sasai, M., Kobayashi, H., Shimizu, M., Katada, Y. & Wakitani, S. (2002) Enhanced local production of osteopontin in rheumatoid joints. The Journal of Rheumatology, 29, 2061-2067.

Okamoto, K., Imbe, H., Morikawa, Y., Itoh, M., Sekimoto, M., Nemoto, K. & Senba, E. (2002) 5-HT2A receptor subtype in the peripheral branch of sensory fibers is involved in the potentiation of inflammatory pain in rats. Pain, 99, 133-143.

Osborn, O., McNelis, J., Sanchez-Alavez, M., Talukdar, S., Lu, M., Li, P., Thiede, L., Morinaga, H., Kim, J.J. & Heinrichsdorff, J. (2012) G protein-coupled receptor 21 deletion improves insulin sensitivity in diet-induced obese mice. The Journal of clinical investigation, 122, 2444-2453.

Othman, M.A., Grygalewicz, B., Pienkowska-Grela, B., Rincic, M., Rittscher, K., Melo, J.B., Carreira, I.M., Meyer, B., Marzena, W. & Liehr, T. (2015) Novel Cryptic Rearrangements in Adult B-Cell Precursor Acute Lymphoblastic Leukemia Involving the MLL Gene. Journal of Histochemistry & Cytochemistry, 0022155415576201, pp. 384-390.

Ott, C., et al. Role of advanced glycation end products in cellular signalling. Redox biology, 2014, 2: 411-429.

Paavonen, A., Watson, A.M., Li J., Paavonen, K., Koitka, A., Calkin, A.C., Barit, D., Coughlan, M.T., Drew, B.G., Lancaster, G.I., Thomas, M., Forbes, J.M., Nawroth, P.P., Bierhaus A., Cooper M.E., and Jandeleit-Dahm K.A. Receptor for advanced glycation end products (RAGE) deficiency attenuates the development of atherosclerosis in diabetes. Diabetes. 2008, 57: 2461-2469.

Panula, P., Chazot, P.L., Cowart, M., Gutzmer, R., Leurs, R., Liu, W.L., Stark, H., Thurmond, R.L. & Haas, H.L. (2015) International Union of Basic and Clinical Pharmacology. XCVIII. Histamine Receptors. Pharmacol Rev, 67, 601-655.

Park J et al. (2008) MCP-1/CCR2 system is involved in high glucose-induced fibronectin and type IV collagen expression in cultured mesangial cells, Am J Physiol Renal Physiol, 295: F749-F757.

Park, L., et al. (1998) Suppression of accelerated diabetic atherosclerosis by the soluble receptor for advanced glycation endproducts. Nature medicine, 4: 1025-1031.

Parker, H., Habib, A., Rogers, G., Gribble, F. & Reimann, F. (2009) Nutrient-dependent secretion of glucose-dependent insulinotropic polypeptide from primary murine K cells. Diabetologia, 52, 289-298.

Pasternack, S.M., von Kugelgen, I., Al Aboud, K., Lee, Y.-A., Ruschendorf, F., Voss, K., Hillmer, A.M., Molderings, G. J., Franz, T. & Ramirez, A. (2008) G protein-coupled receptor P2Y5 and its ligand LPA are involved in maintenance of human hair growth. Nature genetics, 40, 329-334.

Patel, Y.C. (1999) Somatostatin and its receptor family. Front Neuroendocrinol, 20, 157-198.

Peluso, J., LaForge, K.S., Matthes, H.W., Kreek, M.J., Kieffer, B.L. & Gaveriaux-Ruff, C. (1998) Distribution of nociceptin/orphanin FQ receptor transcript in human central nervous system and immune cells. Journal of neuroimmunology, 81, 184-192.

Peng, Y.-M., van de Garde, M.D., Cheng, K.-F., Baars, P.A., Remmerswaal, E.B., van Lier, R.A., Mackay, C.R., Lin, H.-H. & Hamann, J. (2011) Specific expression of GPR56 by human cytotoxic lymphocytes. Journal of leukocyte biology, 90, 735-740.

Perret, G., Valensi, P., Hugues, J.N., Vassy, R. & Uzzan, B. (1988) Use of a pharmacokinetic model to characterize the thyrotropin (TSH) and prolactin (PRL) response to thyrotropin-releasing hormone (THR) in man. Methods and findings in experimental and clinical pharmacology, 10, 387-391.

Pfleger, K.D. & Eidne, K.A. (2006) Illuminating insights into protein-protein interactions using bioluminescence resonance energy transfer (BRET). Nat Methods 3, 165-174.

Piirainen, H., Ashok, Y., Nanekar, R.T. & Jaakola, V.P. (2011) Structural features of adenosine receptors: from crystal to function. Biochim Biophys Acta, 1808, 1233-1244.

Pillai, S.G., Cousens, D.J., Barnes, A.A., Buckley, P.T., Chiano, M.N., Hosking, L.K., Cameron, L.-A., Fling, M.E., Foley, J.J. & Green, A. (2004) A coding polymorphism in the CYSLT2 receptor with reduced affinity to LTD4 is associated with asthma. Pharmacogenetics and Genomics, 14, 627-633.

Piomelli, D., A. Giuffrida, A. Calignano, and F. Rodriguez de Fonseca. The endocannabinoid system as a target for therapeutic drugs. Trends Pharmacol Sci, 2000, 21:218-24.

Poloso, N.J., Urquhart, P., Nicolaou, A., Wang, J. & Woodward, D.F. (2013) PGE 2 differentially regulates monocyte-derived dendritic cell cytokine responses depending on receptor usage (EP 2/EP 4). Molecular immunology, 54, 284-295.

Powell, W.S. & Rokach, J. (2013) The eosinophil chemoattractant 5-oxo-ETE and the OXE receptor. Progress in lipid research, 52, 651-665.

Putranto EW, Murata H, Yamamoto K, Kataoka K, Yamada H, Futami J, Sakaguchi M, Huh NH (2013) Inhibition of RAGE signalling through the intracellular delivery of inhibitor peptides by PEI cationization. Int J Mol Med., 32, 938-944.

Qin, L., Kufareva, I., Holden, L.G., Wang, C., Zheng, Y., Zhao, C., Fenalti, G., Wu, H., Han, G.W., Cherezov, V., Abagyan, R., Stevens, R.C. & Handel, T.M. (2015) Structural biology. Crystal structure of the chemokine receptor CXCR4 in complex with a viral chemokine. Science, 347, 1117-1122.

Qu, L., Fan, N., Ma, C., Wang, T., Han, L., Fu, K., Wang, Y., Shimada, S.G., Dong, X. & LaMotte, R.H. (2014) Enhanced excitability of MRGPRA3-and MRGPRD-positive nociceptors in a model of inflammatory itch and pain. Brain, 137, 1039-1050.

Quigley, D.A., To, M.D., Pérez-Losada, J., Pelorosso, F.G., Mao, J.-H., Nagase, H., Ginzinger, D.G. & Balmain, A. (2009) Genetic architecture of mouse skin inflammation and tumour susceptibility. Nature, 458, 505-508.

Raether H. Surface plasmons on smooth and rough surfaces and on gratings, in Series Springer Tracts in Modern Physics, 1988, Springer-Verlag Berlin Heidelberg, 143 pages.

Rai V, Maldonado AY, Burz DS, Reverdatto S, Schmidt AM and Shekhtman A; Signal Transduction in Receptor for Advanced Glycation End Products (Rage), J Biol Chem, 2012, 287: 5133-5144.

Rajagopalan, S., Kurz, S., Munzel, T., Tarpey, M., Freeman, B.A., Griendling, K.K. and Harrison, D.G., (1996) Angiotensin II-mediated hypertension in the rat increases vascular superoxide production via membrane NADH/NADPH oxidase activation. Contribution to alterations of vasomotor tone, J Clin Invest., 97: 1916-1923.

Ramasamy R, Shekhtman A, Schmidt AM, The multiple faces of RAGE—opportunities for therapeutic intervention in aging and chronic disease. Expert Opin Ther Targets, 2016, 20: 431-446.

Ramasamy, R. & Schmidt, A.M. Receptor for advanced glycation end products (RAGE) and implications for the pathophysiology of heart failure. Current heart failure reports, 2012, 9: 107-116.

Rao V et al. (2006) Role for Macrophage Metalloelastase in Glomerular Basement Membrane Damage Associated with Alport Syndrome, American Journal of Pathology, 169: 32-46.

(56) References Cited

OTHER PUBLICATIONS

Rao, S., Garrett-Sinha, L.A., Yoon, J. & Simon, M.C. (1999) The Ets Factors PU. 1 and Spi-B Regulate the Transcriptionin Vivo of P2Y10, a Lymphoid Restricted Heptahelical Receptor. Journal of Biological Chemistry, 274, 34245-34252.

Ray, R., Juranek, J.K. & Rai, V. RAGE axis in neuroinflammation, neurodegeneration and its emerging role in the pathogenesis of amyotrophic lateral sclerosis. Neuroscience and biobehavioral reviews, 2016, 62: 48-55.

Rebeck, G.W., Maynard, K.I., Hyman, B.T. & Moskowitz, M.A. (1994) Selective 5-HT1D alpha serotonin receptor gene expression in trigeminal ganglia: implications for antimigraine drug development. Proceedings of the National Academy of Sciences, 91, 3666-3669.

Rees, S., den Daas, I., Foord, S., Goodson, S., Bull, D., Kilpatrick, G. & Lee, M. (1994) Cloning and characterisation of the human 5-HT5A serotonin receptor. FEBS letters, 355, 242-246.

Robinson, L.J., Tourkova, I., Wang, Y., Sharrow, A.C., Landau, M.S., Yaroslavskiy, B.B., Sun, L., Zaidi, M. & Blair, H. C. (2010) FSH-receptor isoforms and FSH-dependent gene transcription in human monocytes and osteoclasts. Biochemical and biophysical research communications, 394, 12-17.

Rollins, B.J. (1996) Monocyte chemoattractant protein 1: a potential regulator of monocyte recruitment in inflammatory disease. Mol. Med. Today, 2: 198-204.

Rompler, H., Schulz, A., Pitra, C., Coop, G., Przeworski, M., Paabo, S. & Schoneberg, T. (2005) The rise and fall of the chemoattractant receptor GPR33. Journal of Biological Chemistry, pp. 31068-31075.

Rosen, H., Gonzalez-Cabrera, P.J., Sanna, M.G. & Brown, S. (2009) Sphingosine 1-phosphate receptor signalling. Annu Rev Biochem, 78, 743-768.

Rossi, L., Lemoli, R.M. & Goodell, M.A. (2013) Gpr171, a putative P2Y-like receptor, negatively regulates myeloid differentiation in murine hematopoietic progenitors. Experimental hematology, 41, 102-112.

Roy A, Kucukural A, Zhang Y. I-Tasser: a unified platform for automated protein structure and function prediction. Nature Protocols, 2010, 5: 725-738.

Rubic, T., Lametschwandtner, G., Jost, S., Hinteregger, S., Kund, J., Carballido-Perrig, N., Schwarzler, C., Junt, T., Voshol, H. & Meingassner, J.G. (2008) Triggering the succinate receptor GPR91 on dendritic cells enhances immunity. Nature immunology, 9, 1261-1269.

Russo, I. & Frangogiannis, N.G. Diabetes-associated cardiac fibrosis: Cellular effectors, molecular mechanisms and therapeutic opportunities. Journal of molecular and cellular cardiology, 2016, 90: 84-93.

Saban, R., Saban, M.R., Nguyen, N.-B., Lu, B., Gerard, C., Gerard, N.P. & Hammond, T.G. (2000) Neurokinin-1 (NK-1) receptor is required in antigen-induced cystitis. The American journal of pathology, 156, 775-780.

Sakaguchi M, Murata H, Yamamoto K, Ono T, Sakaguchi Y, Motoyama A, Hibino T, Kataoka K, Huh NH. (2011) TIRAP, an adaptor protein for TLR2/4, transduces a signal from RAGE phosphorylated upon ligand binding. PLoS One, 6: e23132, 10 pages.

Sakamoto, Y., Inoue, H., Kawakami, S., Miyawaki, K., Miyamoto, T., Mizuta, K. & Itakura, M. (2006) Expression and distribution of Gpr119 in the pancreatic islets of mice and rats: predominant localization in pancreatic polypeptide-secreting PP-cells. Biochemical and biophysical research communications, 351, 474-480.

Salmon, A.-M., Damaj, M.I., Marubio, L.M., Epping-Jordan, M.P., Merlo-Pich, E. & Changeux, J.-P. (2001) Altered neuroadaptation in opiate dependence and neurogenic inflammatory nociception in aCGRP-deficient mice. Nature neuroscience, 4, 357-358.

Sampaio, A.L., Rae, G.A. & Maria das Graças, M. (2004) Effects of endothelin ETA receptor antagonism on granulocyte and lymphocyte accumulation in LPS-induced inflammation. Journal of leukocyte biology, 76, 210-216.

Keermann, M., Koks, S., Reimann, E., Prans, E., Abram, K. & Kingo, K. (2015) Transcriptional landscape of psoriasis identifies the involvement of IL36 and IL36RN. BMC genomics, 16, 1, 11 pages.

Khasar, S. G., M. S. Gold, and J. D. Levine. A tetrodotoxin-resistant sodium current mediates inflammatory pain in the rat. Neurosci Lett, 1998, 256:17-20.

Kim, S.V., Xiang, W.V., Kwak, C., Yang, Y., Lin, X.W., Ota, M., Sarpel, U., Rifkin, D.B., Xu, R. & Littman, D.R. (2013) GPR15-mediated homing controls immune homeostasis in the large intestine mucosa. Science, 340, 1456-1459.

Kim, Y.-J., Sano, T., Nabetani, T., Asano, Y. & Hirabayashi, Y. (2012) GPRC5B activates obesity-associated Inflammatory signalling in adipocytes. Sci. Signal., 5, ra85-ra85.

Kitagawa K et al. (2004) Blockade of CCR2 Ameliorates Progressive Fibrosis in Kidney, American Journal of Pathology, 165: 237-246.

Knowles, J.W., et al. (2000) Enhanced atherosclerosis and kidney dysfunction in eNOS(-/-) ApoE(-/-) mice are ameliorated by enalapril treatment. J Clin Invest, 105: 451-458.

Kodera, R., Shikata, K., Kataoka, H., Takatsuka, T., Miyamoto, S., Sasaki, M., Kajitani, N., Nishishita, S., Sarai, K. & Hirota, D. (2011) Glucagon-like peptide-1 receptor agonist ameliorates renal injury through its anti-inflammatory action without lowering blood glucose level in a rat model of type 1 diabetes. Diabetologia, 54, 965-978.

Kononikhin, A., Fedorchenko, K.Y., Ryabokon, A., Starodubtseva, N., Popov, I., Zavialova, M., Anaev, E., Chuchalin, A., Varfolomeev, S. & Nikolaev, E. (2016) Proteomic analysis of exhaled breath condensate for diagnostics of respiratory system diseases. Biochemistry (Moscow) Supplement Series B: Biomedical Chemistry, 10, 230-234.

Kottyan, L.C., Collier, A.R., Cao, K.H., Niese, K.A., Hedgebeth, M., Radu, C.G., Witte, O.N., Hershey, G.K.K., Rothenberg, M.E. & Zimmermann, N. (2009) Eosinophil viability is increased by acidic pH in a cAMP-and GPR65-dependent manner. Blood, 114, 2774-2782.

Krishnamoorthy, S., Recchiuti, A., Chiang, N., Fredman, G. & Serhan, C.N. (2012) Resolvin D1 receptor stereoselectivity and regulation of inflammation and proresolving microRNAs. The American journal of pathology, 180, 2018-2027.

Krishnamoorthy, S., Recchiuti, A., Chiang, N., Yacoubian, S., Lee, C.-H., Yang, R., Petasis, N.A. & Serhan, C.N. (2010) Resolvin D1 binds human phagocytes with evidence for proresolving receptors. Proceedings of the National Academy of Sciences, 107, 1660-1665.

Kruse, A.C., Ring, A.M., Manglik, A., Hu, J., Hu, K., Eitel, K., Hubner, H., Pardon, E., Valant, C., Sexton, P.M., Christopoulos, A., Felder, C.C., Gmeiner, P., Steyaert, J., Weis, W.I., Garcia, K.C., Wess, J. & Kobilka, B.K. (2013) Activation and allosteric modulation of a muscarinic acetylcholine receptor. Nature, 504, 101-106.

Kuduk, S. D., and M. G. Bock. Bradykinin B1 receptor antagonists as novel analgesics: a retrospective of selected medicinal chemistry developments. Curr Top Med Chem, 2008, 8:1420-30.

Kufareva, I., Salanga, C.L. & Handel, T.M. (2015) Chemokine and chemokine receptor structure and interactions: implications for therapeutic strategies. Immunol Cell Biol, 93, 372-383.

Kunikata, T., Yamane, H., Segi, E., Matsuoka, T., Sugimoto, Y., Tanaka, S., Tanaka, H., Nagai, H., Ichikawa, A. & Narumiya, S. (2005) Suppression of allergic inflammation by the prostaglandin E receptor subtype EP3. Nature Immunology, 6, 524-531.

Kupp, L.I., Kosco, M.H., Schenkein, H.A. & Tew, J.G. (1991) Chemotaxis of germinal centers B cells in response to C5a. European journal of immunology, 21, 2697-2701.

Kwon, J.Y., Park, M.K., Seo, Y.R. & Song, J.-J. (2014) Genomic-based identification of novel potential biomarkers and molecular signalling networks in response to diesel exhaust particles in human middle ear epithelial cells. Molecular & Cellular Toxicology, 10, 95-105.

Lafrance, M., Roussy, G., Belleville, K., Maeno, H., Beaudet, N., Wada, K. & Sarret, P. (2010) Involvement of NTS2 receptors in stress-induced analgesia. Neuroscience, 166, 639-652.

(56) References Cited

OTHER PUBLICATIONS

Laird, J.M., Olivar, T., Lopez-Garcia, J.A., Maggi, C.A. & Cervero, F. (2001) Responses of rat spinal neurons to distension of inflamed colon: role of tachykinin NK2 receptors. Neuropharmacology, 40, 696-701.

Lamas, O., Martinez, J.A. & Marti, A. (2003) Effects of a β3-adrenergic agonist on the immune response in diet-induced (cafeteria) obese animals. Journal of Physiology and Biochemistry, 59, 183-191.

Lattin, J.E., Schroder, K., Su, A.I., Walker, J.R., Zhang, J., Wiltshire, T., Saijo, K., Glass, C.K., Hume, D.A. & Kellie, S. (2008) Expression analysis of G Protein-Coupled Receptors in mouse macrophages. Immunome research, 4, 1, 13 pages.

Laukova, M., Vargovic, P., Krizanova, O. & Kvetnansky, R. (2010) Repeated Stress Down-Regulates β2- and α2C-Adrenergic Receptors and Up-Regulates Gene Expression of IL-6 in the Rat Spleen. Cellular and Molecular Neurobiology, 30, 1077-1087.

Lazennec, G. & Richmond, A. (2010) Chemokines and chemokine receptors: new insights into cancer-related Inflammation. Trends in molecular medicine, 16, 133-144.

Leeb-Lundberg, L.M., Marceau, F., Muller-Esterl, W., Pettibone, D.J. & Zuraw, B.L. (2005) International union of pharmacology. XLV. Classification of the kinin receptor family: from molecular mechanisms to pathophysiological consequences. Pharmacol Rev, 57, 27-77.

Le Poul, E., Loison, C., Struyf, S., Springael, J.-Y., Lannoy, V., Decobecq, M.-E., Brezillon, S., Dupriez, V., Vassart, G. & Van Damme, J. (2003) Functional characterization of human receptors for short chain fatty acids and their role in polymorphonuclear cell activation. Journal of Biological Chemistry, 278, 25481-25489.

Le, Y., Gong, W., Li, B., Dunlop, N.M., Shen, W., Su, S.B., Richard, D.Y. & Wang, J.M. (1999) Utilization of two seven-transmembrane, G protein-coupled receptors, formyl peptide receptor-like 1 and formyl peptide receptor, by the synthetic hexapeptide WKYMVm for human phagocyte activation. The Journal of Immunology, 163, 6777-6784.

Leclerc E, Fritz G, Weibel M, Heizmann CW, Galichet A. (2007) S100B and S100A6 differentially modulate cell survival by interacting with distinct RAGE (receptor for advanced glycation end products) immunoglobulin domains. J Biol Chem, 282: 31317-31331.

Leclerc, E. & Vetter, S.W. (2015) The role of S100 proteins and their receptor RAGE in pancreatic cancer. Biochimica et biophysica acta, 1852: 2706-2711.

Lee, B.-C., Cheng, T., Adams, G.B., Attar, E.C., Miura, N., Lee, S.B., Saito, Y., Olszak, I., Dombkowski, D. & Olson, D. P. (2003) P2Y-like receptor, GPR105 (P2Y14), identifies and mediates chemotaxis of bone-marrowhematopoietic stem cells. Genes & development, 17, 1592-1604.

Lee, B.-Y., Cho, S., Shin, D.H. & Kim, H. (2011) Genome-wide association study of copy No. variations associated with pulmonary function measures in Korea Associated Resource (KARE) cohorts. Genomics, 97, 101-105.

Lee, J.E., Hong, E.J., Nam, H.Y., Kim, J.W., Han, B.G. & Jeon, J.P. (2011) MicroRNA signatures associated with Immortalization of EBV-transformed lymphoblastoid cell lines and their clinical traits. Cell proliferation, 44, 59-66.

Lee, M.A., Bohm, M., Paul, M., and Ganten, D. (1993) Tissue renin-angiotensin systems. Their role in cardiovascular disease. Circulation, 87: IV7-13, 15 pages.

Leeb-Lundberg, L. M., F. Marceau, W. Muller-Esterl, D. J. Pettibone, and B. L. Zuraw. (2005) International Union of Pharmacology. XLV. Classification of the kinin receptor family: from molecular mechanisms to pathophysiological consequences. Pharmacol Rev, 57:27-77.

Levite, M., Chowers, Y., Ganor, Y., Besser, M., Hershkovits, R. & Cahalon, L. (2001) Dopamine interacts directly with its D3 and D2 receptors on normal human T cells, and activates β1 integrin function. European journal of immunology, 31, 3504-3512.

Li C., Pazgier M., Li J., Li C., Liu M., Zou G., Li Z., Chen J., Tarasov S.G., Lu W.Y., Lu W. Limitations of peptide retro-inverso isomerization in molecular mimicry. J Biol Chem, 2010, 285: 19572-19581.

Li X.C., and Zhuo J,L. (2008) Nuclear factor-kappaB as a hormonal intracellular signalling molecule: focus on angiotensin II-induced cardiovascular and renal injury. Current opinion in nephrology and hypertension. 17: 37-43.

Li, X. & Tai, H.H. (2013) Activation of thromboxane A2 receptor (TP) increases the expression of monocyte chemoattractant protein-1 (MCP-1)/chemokine (C-C motif) ligand 2 (CCL2) and recruits macrophages to promote invasion of lung cancer cells. PLoS One, 8, e54073, 11 pages.

Liang, M., Niu, J., Zhang, L., Deng, H., Ma, J., Zhou, W., Duan, D., Zhou, Y., Xu, H. & Chen, L. (2016) Gene expression profiling reveals different molecular patterns in G-protein coupled receptor signalling pathways between early-and late-onset preeclampsia. Placenta, 40, 52-59.

Lin, C.-I., Chen, C.-N., Lin, P.-W., Chang, K.-J., Hsieh, F.-J. & Lee, H. (2007) Lysophosphatidic acid regulates Inflammation-related genes in human endothelial cells through LPA 1 and LPA 3. Biochemical and biophysical research communications, 363, 1001-1008.

Lin, E.-J.D., Sainsbury, A., Lee, N.J., Boey, D., Couzens, M., Enriquez, R., Slack, K., Bland, R., During, M.J. & Herzog, H. (2006) Combined deletion of Y1, Y2, and Y4 receptors prevents hypothalamic neuropeptide Y overexpression-induced hyperinsulinemia despite persistence of hyperphagia and obesity. Endocrinology, 147, 5094-5101.

Lin, H.H., Faunce, D.E., Stacey, M., Terajewicz, A., Nakamura, T., Zhang-Hoover, J., Kerley, M., Mucenski, M.L., Gordon, S. & Stein-Streilein, J. (2005) The macrophage F4/80 receptor is required for the induction of antigen-specific efferent regulatory T cells in peripheral tolerance. J Exp Med, 201, 1615-1625.

Ling, P., Ngo, K., Nguyen, S., Thurmond, R.L., Edwards, J.P., Karlsson, L. & Fung-Leung, W.P. (2004) Histamine H4 receptor mediates eosinophil chemotaxis with cell shape change and adhesion molecule upregulation. British journal of pharmacology, 142, 161-171.

Liu, C., Kuei, C., Sutton, S., Chen, J., Bonaventure, P., Wu, J., Nepomuceno, D., Kamme, F., Tran, D.-T. & Zhu, J. (2005) INSL5 is a high affinity specific agonist for GPCR142 (GPR100). Journal of Biological Chemistry, 280, 292-300.

Liu, J., Escher, A., Improved assay sensitivity of an engineered secreted Renilla luciferase, Gene, 1999, 237 (1): 153-9.

Liu, S., Qian, Y., Li, L., Wei, G., Guan, Y., Pan, H., Guan, X., Zhang, L., Lu, X. & Zhao, Y. (2013) Lgr4 gene deficiency increases susceptibility and severity of dextran sodium sulfate-induced inflammatory bowel disease in mice. Journal of Biological Chemistry, 288, 8794-8803.

Liu, W., Wacker, D., Gati, C., Han, G.W., James, D., Wang, D., Nelson, G., Weierstall, U., Katritch, V., Barty, A., Zatsepin, N.A., Li, D., Messerschmidt, M., Boutet, S., Williams, G.J., Koglin, J.E., Seibert, M.M., Wang, C., Shah, S.T., Basu, S., Fromme, R., Kupitz, C., Rendek, K.N., Grotjohann, I., Fromme, P., Kirian, R.A., Beyerlein, K.R., White, T.A., Chapman, H.N., Caffrey, M., Spence, J.C., Stevens, R.C. & Cherezov, V. (2013) Serial femtosecond crystallography of G protein-coupled receptors. Science, 342, 1521-1524.

Logsdon, C.D., Fuentes, M.K., Huang, E.H. & Arumugam, T. (2007) RAGE and RAGE ligands in cancer. Current molecular medicine, 7: 777-789.

Lu, D., Zhao, Y., Tawatao, R., Cottam, H.B., Sen, M., Leoni, L.M., Kipps, T.J., Corr, M. & Carson, D.A. (2004) Activation of the Wnt signalling pathway in chronic lymphocytic leukemia. Proceedings of the National Academy of Sciences of the United States of America, 101, 3118-3123.

Lu, M.C., Lai, N.S., Yu, H.C., Huang, H.B., Hsieh, S.C. & Yu, C.L. (2010) Anti-citrullinated protein antibodies bind surface-expressed citrullinated Grp78 on monocyte/macrophages and stimulate tumor necrosis factor α production. Arthritis & Rheumatism, 62, 1213-1223.

(56) References Cited

OTHER PUBLICATIONS

Lundequist, A. & Boyce, J.A. (2011) LPA5 is abundantly expressed by human mast cells and important for lysophosphatidic acid induced MIP-1β release. PLoS One, 6, e18192.

Han, Y.T., et al. Ligand-based design, synthesis, and biological evaluation of 2-aminopyrimidines, a novel series of receptor for advanced glycation end products (RAGE) inhibitors. Journal of medicinal chemistry, 2012, 55: 9120-9135.

Han, Y.T., et al. Pyrazole-5-carboxamides, novel inhibitors of receptor for advanced glycation end products (RAGE). European journal of medicinal chemistry, 2014, 79: 128-142.

Handley, D. A., C. M. Arbeeny, M. L. Lee, R. G. Van Valen, and R. N. Saunders. Effect of platelet activating factor on endothelial permeability to plasma macromolecules. Immunopharmacology, 1984, 8:137-42.

Hansen, W., Westendorf, A., Toepfer, T., Mauel, S., Geffers, R., Gruber, A. & Buer, J. (2010) Inflammation in vivo is modulated by GPR83 isoform-4 but not GPR83 isoform-1 expression in regulatory T cells. Genes and immunity, 11, 357-361.

Hanson, M.A., Roth, C.B., Jo, E., Griffith, M.T., Scott, F.L., Reinhart, G., Desale, H., Clemons, B., Cahalan, S.M., Schuerer, S.C., Sanna, M.G., Han, G.W., Kuhn, P., Rosen, H. & Stevens, R.C. (2012) Crystal structure of a lipid G protein-coupled receptor. Science, 335, 851-855.

Hartmann, K., Henz, B.M., Kruger-Krasagakes, S., Köhl, J., Burger, R., Guhl, S., Haase, I., Lippert, U. & Zuberbier, T. (1997) C3a and C5a stimulate chemotaxis of human mast cells. Blood, 89, 2863-2870.

Hartmeyer, M., Scholzen, T., Becher, E., Bhardwaj, R., Schwarz, T. & Luger, T. (1997) Human dermal microvascular endothelial cells express the melanocortin receptor type 1 and produce increased levels of IL-8 upon stimulation with alpha-melanocyte-stimulating hormone. The Journal of Immunology, 159, 1930-1937.

Harvey, R.C., Mullighan, C.G., Wang, X., Dobbin, K.K., Davidson, G.S., Bedrick, E.J., Chen, I.-M., Atlas, S.R., Kang, H. & Ar, K. (2010) Identification of novel cluster groups in pediatric high-risk B-precursor acute lymphoblastic leukemia with gene expression profiling: correlation with genome-wide DNA copy number alterations, clinical characteristics, and outcome. Blood, 116, 4874-4884.

Hata, A. N., and R. M. Breyer. Pharmacology and signalling of prostaglandin receptors: multiple roles in inflammation and immune modulation. Pharmacol Ther, 2004, 103:147-66.

Haworth, O., Cernadas, M. & Levy, B.D. (2011) NK cells are effectors for resolvin E1 in the timely resolution of allergic airway inflammation. The Journal of Immunology, 186, 6129-6135.

Hess B, Kutzner C, Van Der Spoel D, Lindahl E. GROMACS 4: Algorithms for highly efficient, load-balanced, and scalable molecular simulation. J Chem Theory Comput, 2008, 4: 435.

Heublein, S., Lenhard, M., Vrekoussis, T., Schoepfer, J., Kuhn, C., Friese, K., Makrigiannakis, A., Mayr, D. & Jeschke, U. (2012) The G-protein-coupled estrogen receptor (GPER) is expressed in normal human ovaries and is upregulated in ovarian endometriosis and pelvic inflammatory disease involving the ovary. Reproductive Sciences, 19, 1197-1204.

Hill, J., Duckworth, M., Murdock, P., Rennie, G., Sabido-David, C., Ames, R.S., Szekeres, P., Wilson, S., Bergsma, D. J. & Gloger, I.S. (2001) Molecular cloning and functional characterization of MCH2, a novel human MCH receptor. Journal of Biological Chemistry, 276, 20125-20129.

Hohenhaus, D.M., Schaale, K., Le Cao, K.-A., Seow, V., Iyer, A., Fairlie, D.P. & Sweet, M.J. (2013) An mRNA atlas of G protein-coupled receptor expression during primary human monocyte/macrophage differentiation and ipopolysaccharide-mediated activation identifies targetable candidate regulators of inflammation. Immunobiology, 218, 1345-1353.

Hollenberg, A.N. (2008) The role of the thyrotropin-releasing hormone (TRH) neuron as a metabolic sensor. Thyroid, 18, 131-139.

Hong, K.W., Shin, M.S., Ahn, Y.B., Lee, H.J. & Kim, H.D. (2015) Genomewide association study on chronic periodontitis in Korean population: results from the Yangpyeong health cohort. Journal of clinical pe riodontology, 42, 703-710.

Hoque, R., Farooq, A., Ghani, A., Gorelick, F. & Mehal, W.Z. (2014) Lactate reduces liver and pancreatic injury in Toll-like receptor-and inflammasome-mediated inflammation via GPR81-mediated suppression of innate immunity. Gastroenterology, 146, 1763-1774.

Horinouchi, T., Terada, K., Higashi, T. & Miwa, S. (2013) Endothelin receptor signalling: new insight into its regulatory mechanisms. J Pharmacol Sci, 123, 85-101.

Horne, K. & Woolley, I.J. (2009) Shedding light on DARC: the role of the Duffy antigen/receptor for chemokines in inflammation, infection and malignancy. Inflamm Res, 58, 431-435.167.

Hsu, S.Y., Nakabayashi, K., Nishi, S., Kumagai, J., Kudo, M., Sherwood, O.D. & Hsueh, A.J. (2002) Activation of orphan receptors by the hormone relaxin. Science, 295, 671-674.

Ichimonji, I., Tomura, H., Mogi, C., Sato, K., Aoki, H., Hisada, T., Dobashi, K., Ishizuka, T., Mori, M. & Okajima, F. (2010) Extracellular acidification stimulates IL-6 production and Ca2+ mobilization through proton-sensing OGR1 receptors in human airway smooth muscle cells. American Journal of Physiology—Lung Cellular and Molecular Physiology, 299, L567-L577.

Ignatov, A., Robert, J., Gregory-Evans, C. & Schaller, H. (2006) RANTES stimulates Ca2+ mobilization and inositol trisphosphate (IP3) formation in cells transfected with G protein-coupled receptor 75. British journal of pharmacology, 149, 490-497.

Improta, G., Carpino, F., Petrozza, V., Guglietta, A., Tabacco, A. & Broccardo, M. (2003) Central effects of selective NK 1 and NK 3 tachykinin receptor agonists on two models of experimentally-induced colitis in rats. Peptides, 24, 903-911.

Inbe, H., Watanabe, S., Miyawaki, M., Tanabe, E. & Encinas, J.A. (2004) Identification and characterization of a cell-surface receptor, P2Y15, for AMP and adenosine. Journal of Biological Chemistry, 279, 19790-19799.

Yukayama-Tomobe, Y., Tanaka, H., Yokomizo, T., Hashidate-Yoshida, T., Yanagisawa, M. & Sakurai, T. (2009) Aromatic D-amino acids act as chemoattractant factors for human leukocytes through a G protein-coupled receptor, GPR109B. Proceedings of the National Academy of Sciences, 106, 3930-3934.

Işeri, S.Ö., Şener, G., Sağlam, B., Gedik, N., Ercan, F. & Yeğen, B.Ç. (2005) Oxytocin ameliorates oxidative colonic inflammation by a neutrophil-dependent mechanism. Peptides, 26, 483-491.

Ishihara, H., Connolly, A.J., Zeng, D., Kahn, M.L., Zheng, Y.W., Timmons, C., Tram, T. & Coughlin, S.R. (1997) Protease-activated receptor 3 is a second thrombin receptor in humans, pp. 502-506.

Ito, Y., Banno, R., Shibata, M., Adachi, K., Hagimoto, S., Hagiwara, D., Ozawa, Y., Goto, M., Suga, H. & Sugimura, Y. (2013) GABA type B receptor signalling in proopiomelanocortin neurons protects against obesity, insulin resistance, and hypothalamic inflammation in male mice on a high-fat diet. The Journal of Neuroscience, 33, 17166-17173.

Iwasa, T., Matsuzaki, T., Tungalagsuvd, A., Munkhzaya, M., Kawami, T., Niki, H., Kato, T., Kuwahara, A., Uemura, H., Yasui, T. & Irahara, M. (2014) Hypothalamic Kiss1 and RFRP gene expressions are changed by a high dose of lipopolysaccharide in female rats. Hormones and Behavior, 66, 309-316.

Izeboud, C.A., Vermeulen, R.M., Zwart, A., Voss, H.-P., van Miert, A.S.J.P.A.M. & Witkamp, R.F. (2000) Stereoselectivity at the β2-adrenoceptor on macrophages is a major determinant of the anti-inflammatory effects of β2-agonists. Naunyn-Schmiedeberg's Archives of Pharmacology, 362, 184-189.

Jacoby, D.S., and Rader, D.J. (2003) Renin-angiotensin system and atherothrombotic disease: from genes to treatment. Arch Intern Med, 163: 1155-64.

Jaeger, W.C., Armstrong, S.P., Hill, S.J. and Pfleger, K.D.G., Biophysical detection of diversity and bias in GPCR function. Front Endocrinol, 2014, 5: 26.

Jaffre, F., Bonnin, P., Callebert, J., Debbabi, H., Setola, V., Doly, S., Monassier, L., Mettauer, B., Blaxall, B.C. & Launay, J.-M. (2009) Serotonin and angiotensin receptors in cardiac fibroblasts coregulate adrenergic-dependent cardiac hypertrophy. Circulation research, 104, 113-123.

(56) References Cited

OTHER PUBLICATIONS

Jahnsen, J., Falch, J., Mowinckel, P. & Aadland, E. (2002) Vitamin D status, parathyroid hormone and bone mineral density in patients with inflammatory bowel disease. Scandinavian journal of gastroenterology, 37, 192-199.

Jenne, C.N., Enders, A., Rivera, R., Watson, S.R., Bankovich, A.J., Pereira, J.P., Xu, Y., Roots, C.M., Beilke, J.N. & Banerjee, A. (2009) T-bet-dependent S1P5 expression in NK cells promotes egress from lymph nodes and bone marrow. The Journal of experimental medicine, 206, 2469-2481.

Jia, R.-Z., Zhang, X., Hu, P., Liu, X.-M., Hua, X.-D., Wang, X. & Ding, H.-J. (2012) Screening for differential methylation status in human placenta in preeclampsia using a CpG island plus promoter microarray. International journal of molecular medicine, 30, 133.

Jimenez-Andrade, J.M., Zhou, S., Du, J., Yamani, A., Grady, J.J., Castañeda-Hernandez, G. & Carlton, S.M. (2004) Pro-nociceptive role of peripheral galanin in inflammatory pain. Pain, 110, 10-21.

Johns, D.G., Ao, Z., Naselsky, D., Herold, C.L., Maniscalco, K., Sarov-Blat, L., Steplewski, K., Aiyar, N. & Douglas, S. A. (2004) Urotensin-II-mediated cardiomyocyte hypertrophy: effect of receptor antagonism and role of inflammatory mediators. Naunyn-Schmiedeberg's archives of pharmacology, 370, 238-250.

Jossart, C., Mulumba, M., Granata, R., Gallo, D., Ghigo, E., Marleau, S., Servant, M.J. & Ong, H. (2013) Pyroglutamylated RF-amide peptide (QRFP) gene is regulated by metabolic endotoxemia. Molecular Endocrinology, 28, 65-79.

Jules J, Maiguel D, Hudson BI, Alternative Splicing of the RAGE Cytoplasmic Domain Regulates Cell Signalling and Function. PLoS One, 2013, 8: e78267.

Jurisic, G., Sundberg, J., Bleich, A., Leiter, E., Broman, K., Buechler, G., Alley, L., Vestweber, D. & Detmar, M. (2010) Quantitative lymphatic vessel trait analysis suggests Vcam1 as candidate modifier gene of inflammatory bowel disease. Genes and immunity, 11, 219-231.

Kabashima, K., Saji, T., Murata, T., Nagamachi, M., Matsuoka, T., Segi, E., Tsuboi, K., Sugimoto, Y., Kobayashi, T. & Miyachi, Y. (2002) The prostaglandin receptor EP4 suppresses colitis, mucosal damage and CD4 cell activation in the gut. The Journal of clinical investigation, 109, 883-893.

Kable, J.W., Murrin, L.C. & Bylund, D.B. (2000) In vivo gene modification elucidates subtype-specific functions of alpha (2)-adrenergic receptors. J Pharmacol Exp Ther, 293, 1-7.

Kahn, M. L., Y. W. Zheng, W. Huang, V. Bigornia, D. Zeng, and S. Moff. A dual thrombin receptor system for platelet activation. Nature, 1998, 394:690-4.

Kalbe, B., Knobloch, J., Schulz, V.M., Wecker, C., Schlimm, M., Scholz, P., Jansen, F., Stoelben, E., Philippou, S., Hecker, E., Lubbert, H., Koch, A., Hatt, H. & Osterloh, S. (2016) Olfactory Receptors Modulate Physiological Processes in Human Airway Smooth Muscle Cells. Frontiers in Physiology, 7, 15 pages.

Kaminski, N. E. Immune regulation by cannabinoid compounds through the inhibition of the cyclic AMP signalling cascade and altered gene expression. Biochem Pharmacol, 1996, 52:1133-40.

Kanazawa, M., Watanabe, S., Tana, C., Komuro, H., Aoki, M. & Fukudo, S. (2011) Effect of 5-HT4 receptor agonist mosapride citrate on rectosigmoid sensorimotor function in patients with irritable bowel syndrome. Neurogastroenterology & Motility, 23, 754-e332.

Kang, Y.S et al. (2010) CCR2 antagonism improves insulin resistance, lipid metabolism, and diabetic nephropathy in type 2 diabetic mice. Kidney International, 78: 883-894.

Kawamata, Y., Fujii, R., Hosoya, M., Harada, M., Yoshida, H., Miwa, M., Fukusumi, S., Habata, Y., Itoh, T. & Shintani, Y. (2003) AG protein-coupled receptor responsive to bile acids. Journal of Biological Chemistry, 278, 9435-9440.

Kazemian, P., Kazemi-Bajestani, S.M., Alherbish, A., Steed, J. & Oudit, G.Y. (2012) The use of ω-3 poly-unsaturated fatty acids in heart failure: a preferential role in patients with diabetes. Cardiovascular drugs and therapy, 26, 311-320.

\* cited by examiner

Example 1

(i)

(ii)

(i)

(ii)

(iii)

Example 2

(i)

(ii)

(i)

(ii)

(iii)

(i)

(ii)

(iii)

Example 3

(i)

(ii)

Example 4

(i)

(ii)

(iii)

Example 5

(i)

(ii)

(iii)

Example 6

Example 7

Example 8

Example 9

Example 10

Example 11
Figure 11A

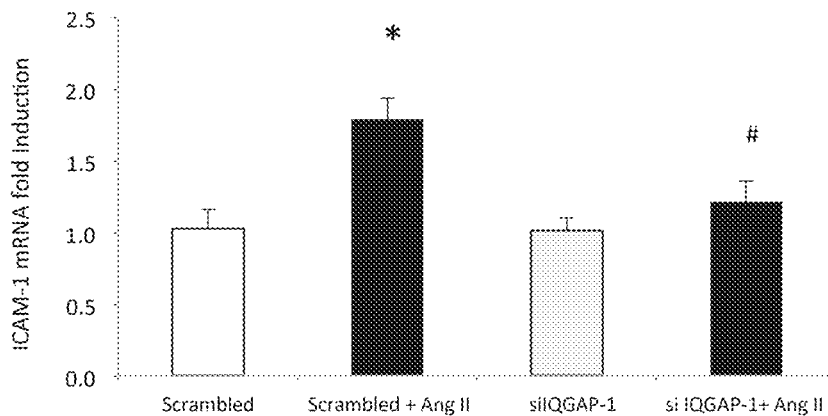

Figure 11B

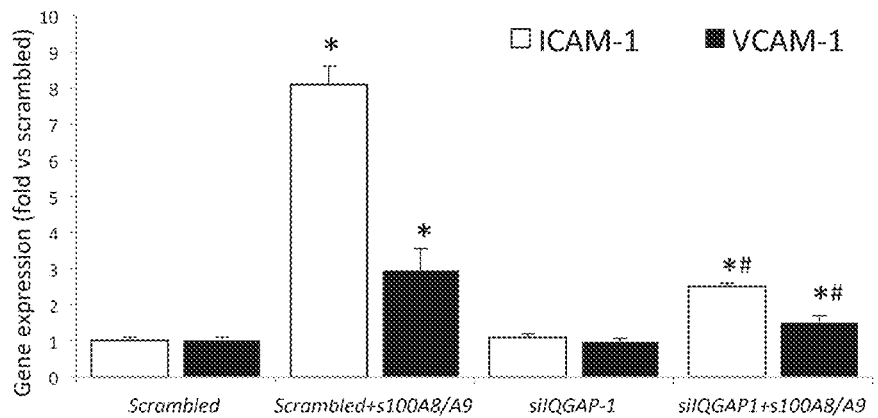

Figure 11C

| | |
|---|---|
| 1. | G3ICI3 - Olfactory receptor 2T2 |
| 2. | G3H777 - ADP/ATP translocase 2 |
| 3. | G3GXU1 - Protein phosphatase 1G |
| 4. | Q9ERF7 - Intercellular adhesion molecule 1 |
| 5. | G3IEU2 - Protein DJ-1 (PARK7) |
| 6. | G3I4M4 - Calponin-3 |
| 7. | G3H170 – Drebrin |
| 8. | G3HFM4 – Filamin B |
| 9. | G3IF62 - Ras GTPase-activating-like protein IQGAP-1 |
| 10. | G3HC04 - Ras-related protein Rab-13 |
| 11. | G3HFP1 – Radixin/Ezrin/Moesin |
| 12. | G3HNB8 - Proteolipid protein 2 |
| 13. | G3I3Z5 – Coronin |
| 14. | G3HUU6 - Protein S100 A11 |
| 15. | G3HQ05 - Succinyl-CoA ligase [GDP-forming] subunit alpha |
| 16. | G3I539 - Hsc70-interacting protein |
| 17. | G3IH34 - Apoptosis Inhibitor 5 |

Example 12

| RAGE379-390 | Q | E | E | E | E | E | R | - | - | A | E | L | N | Q |
|---|---|---|---|---|---|---|---|---|---|---|---|---|---|---|
| Streptomyces | K | E | E | E | E | E | R | A | F | A | E | L | N | K |
| Prevotella albensis | Q | E | E | E | E | E | R | - | - | A | E | G | N | Q |
| Nafulsella turpanensis | K | E | E | E | E | E | R | - | - | A | S | L | N | |
| Proteobacteria bacterium | | E | E | E | E | E | R | - | - | A | E | L | N | |

Example 13

(i)

(ii)

Example 14

Example 15

Example 16

Example 17

Example 18

Example 19
Figure 19A: Adenosine 1A receptor + RAGE/Rluc8 + Venus-tagged KRAS or Rabs Adenosine at $10^{-5}$ M
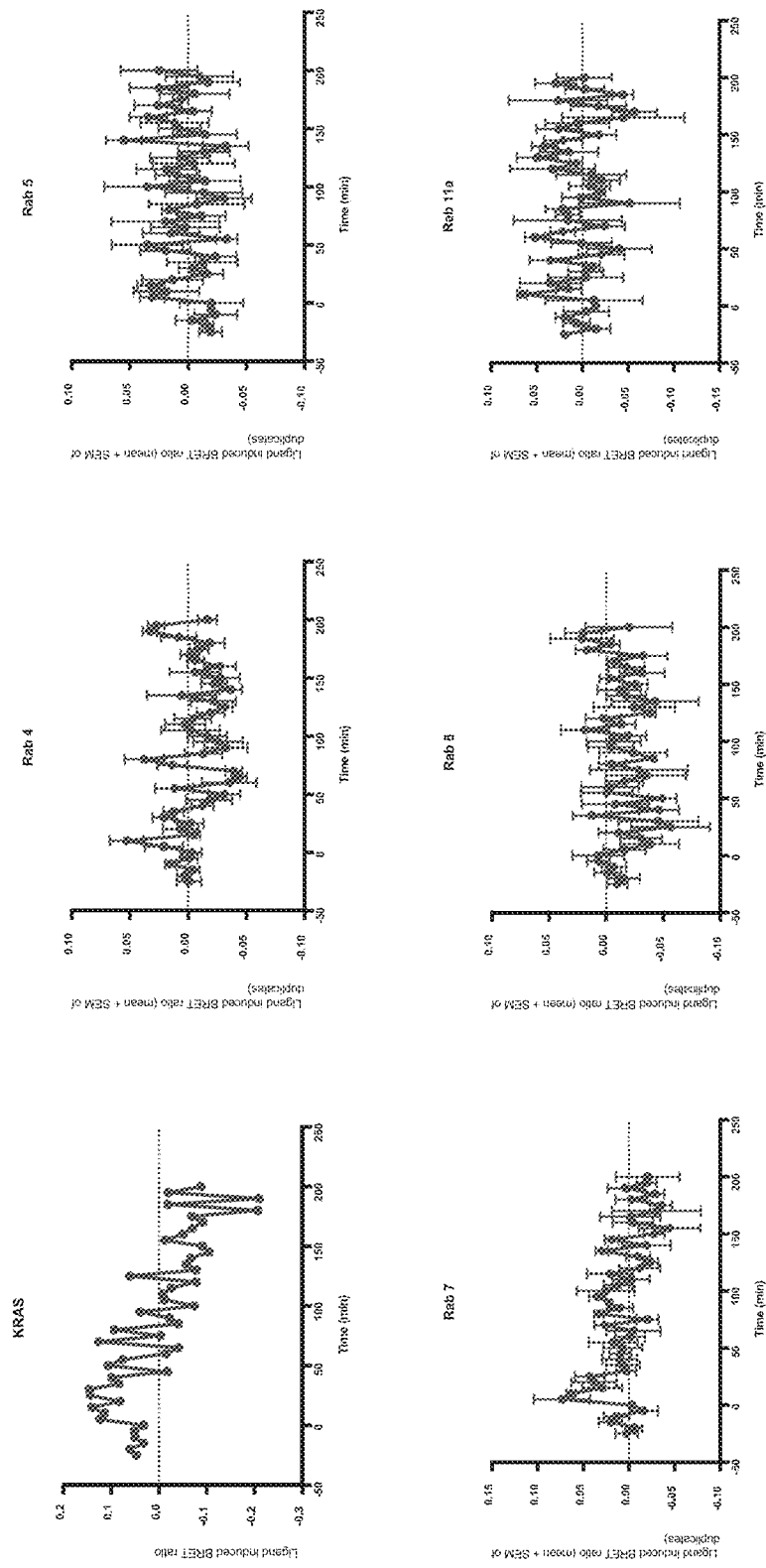

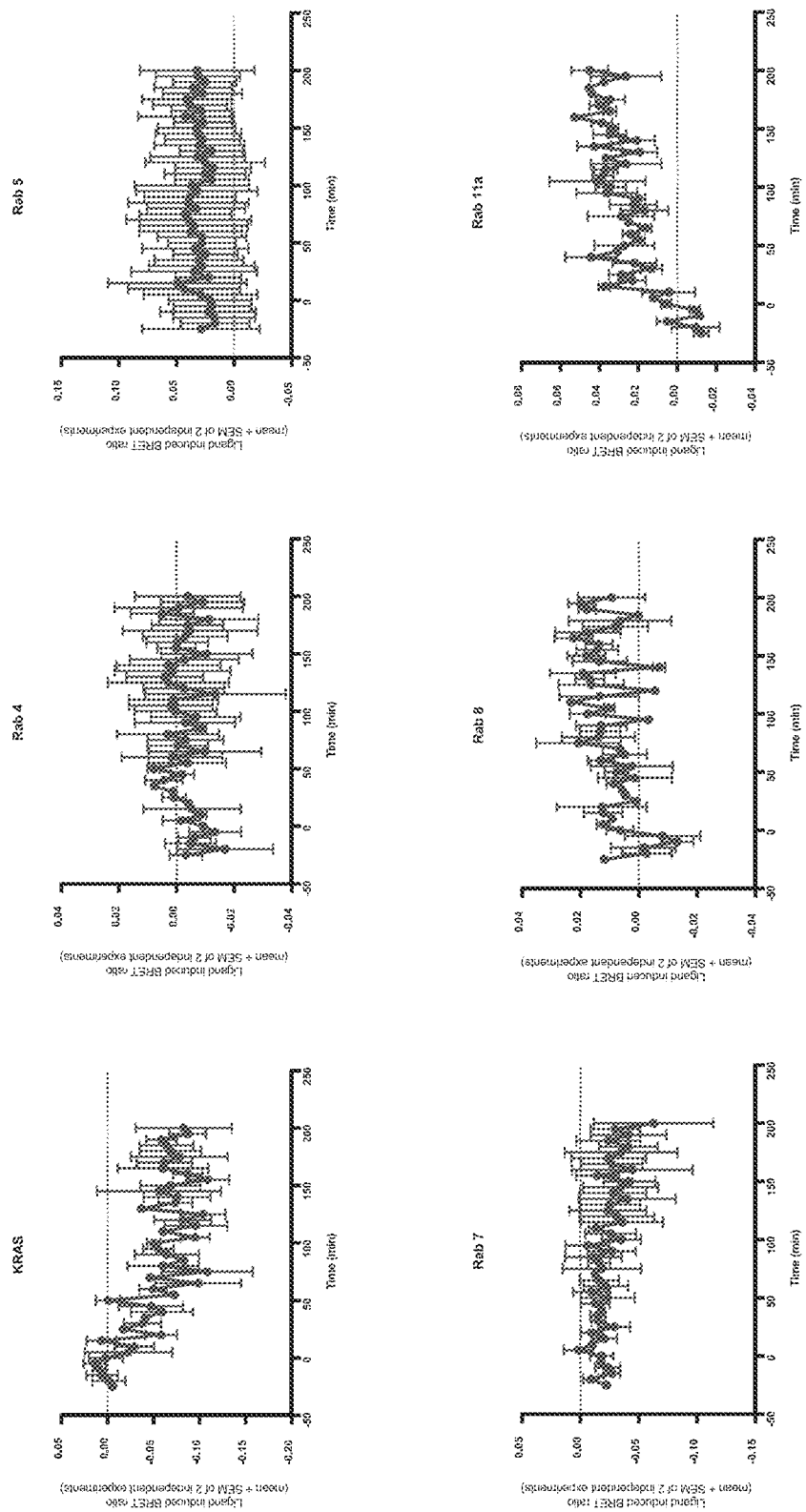
Figure 19B: Adrenergic α1A receptor + RAGE/Rluc8 + Venus-tagged KRAS or Rabs Noradrenaline at $10^{-5}$ M

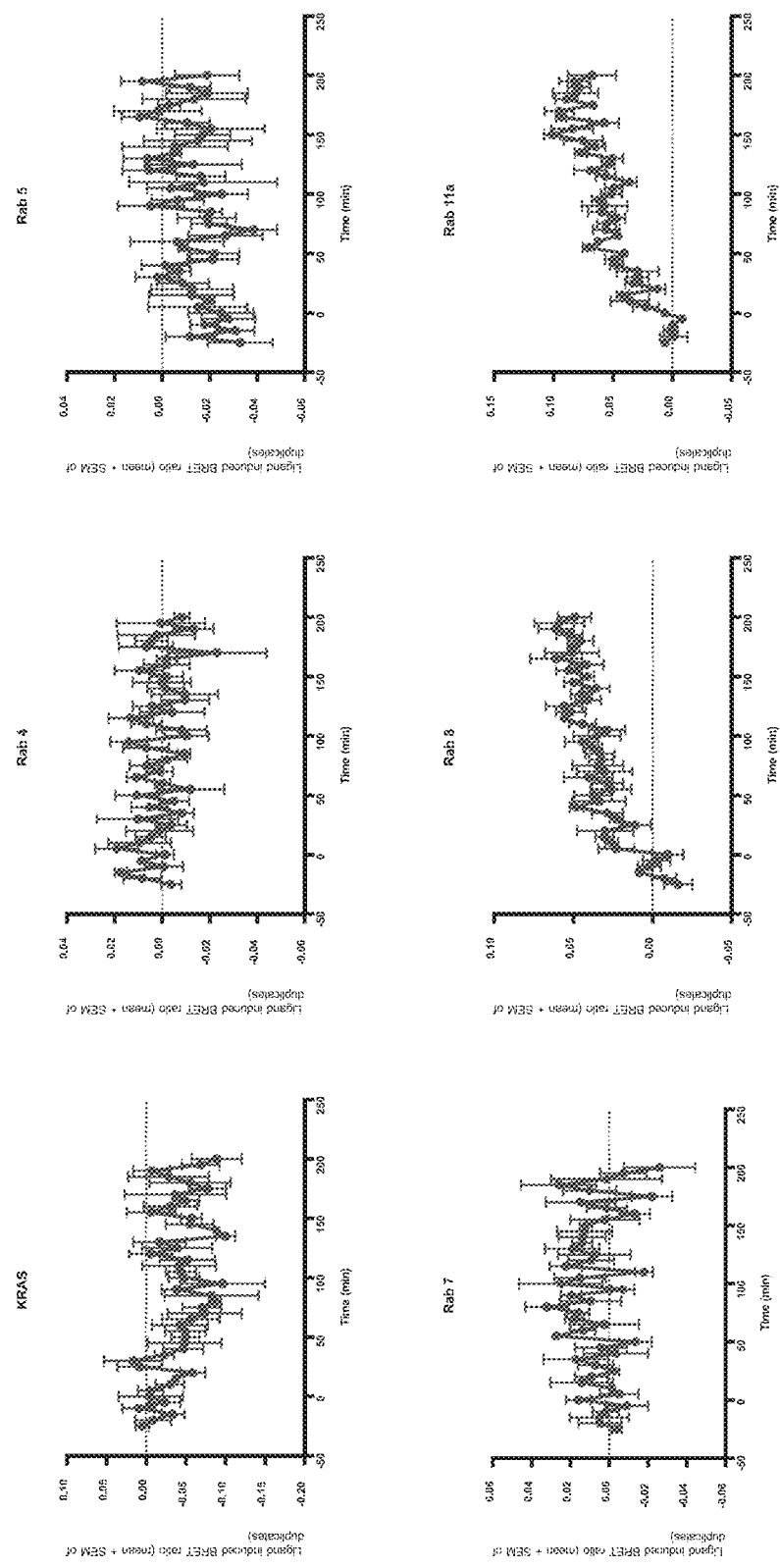
Figure 19C: Adrenergic α1B receptor + RAGE/Rluc8 + Venus-tagged KRAS or Rabs Noradrenaline at $10^{-5}$ M

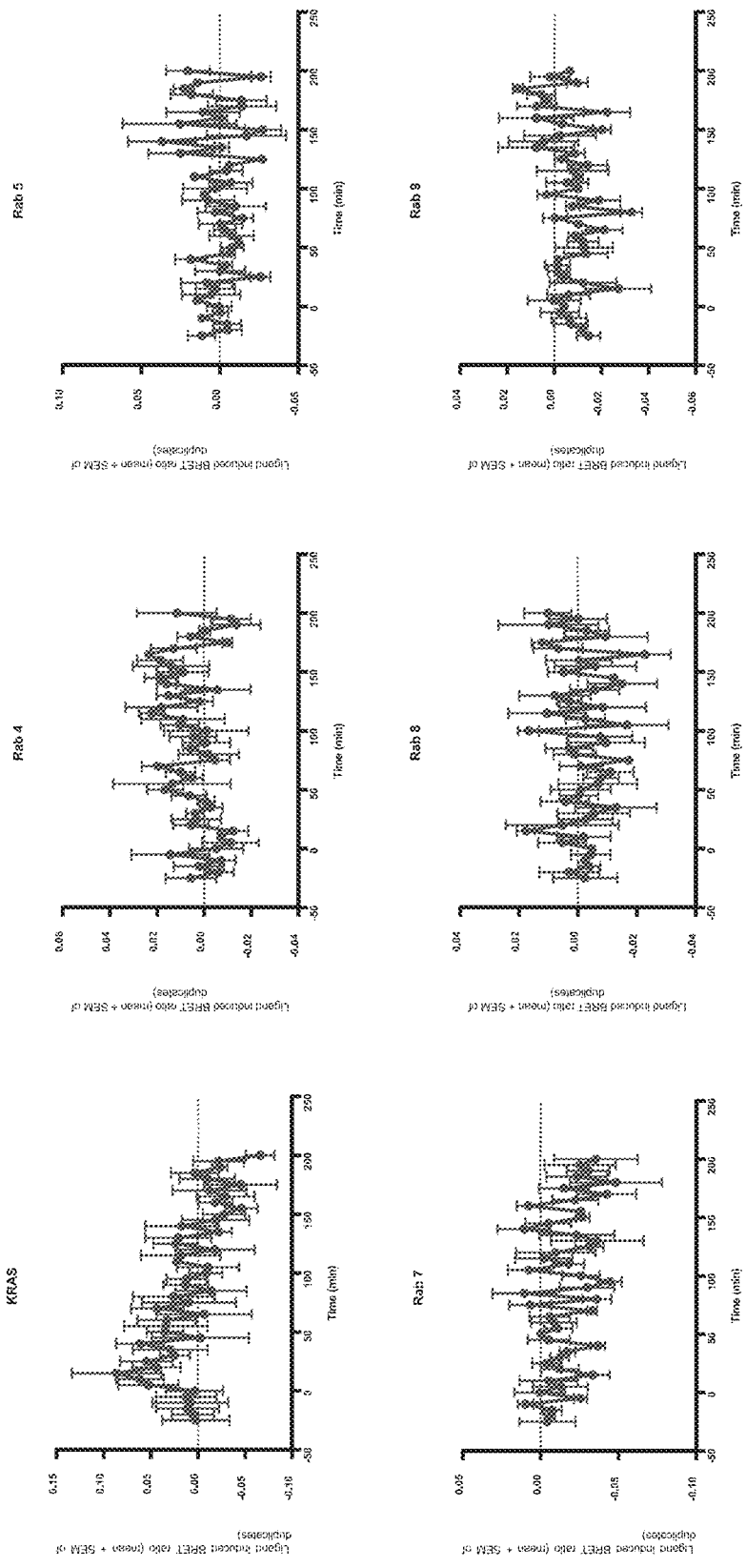
Figure 19D: Adrenergic α2B receptor + RAGE/Rluc8 + Venus-tagged KRAS or Rabs Noradrenaline at $10^{-5}$ M

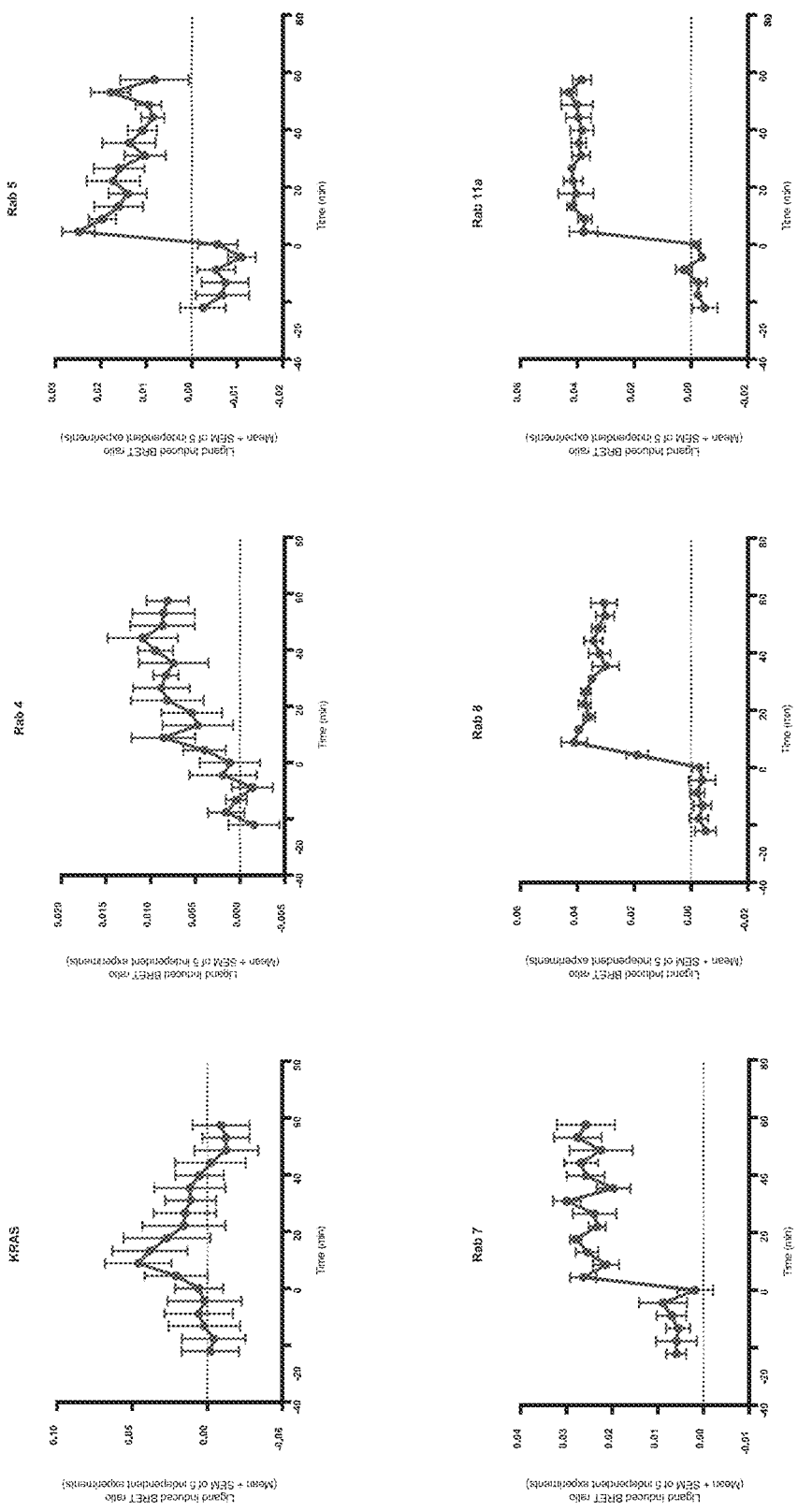
Figure 19E: Angiotensin II type 1 receptor + RAGE/Rluc8 + Venus-tagged KRAS or Rabs
Angiotensin II at $10^{-6}$ M

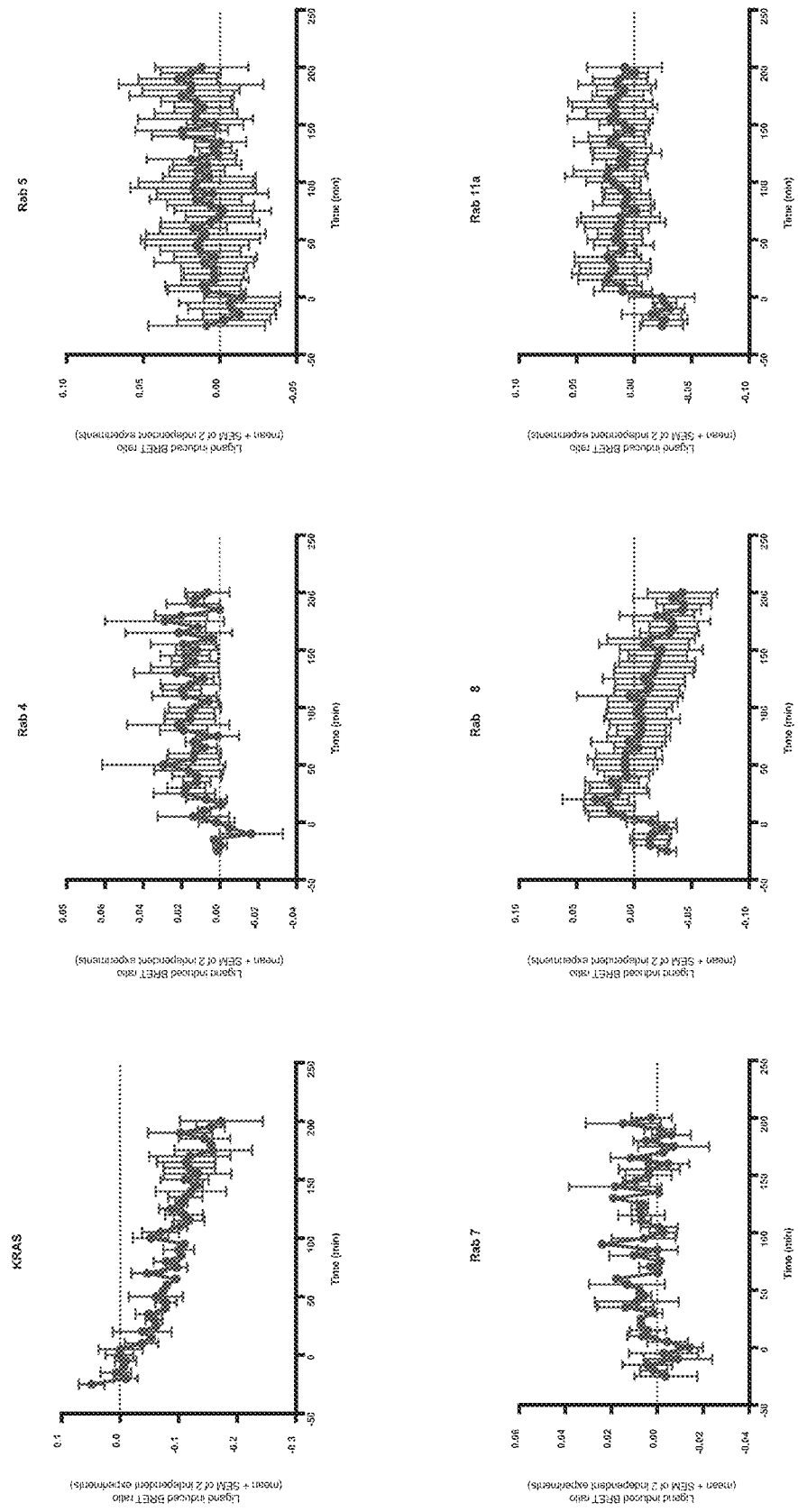
Figure 19F: Bradykinin type 2 receptor + RAGE/Rluc8 + Venus-tagged KRAS or Rabs Bradykinin at at $10^{-5}$ M

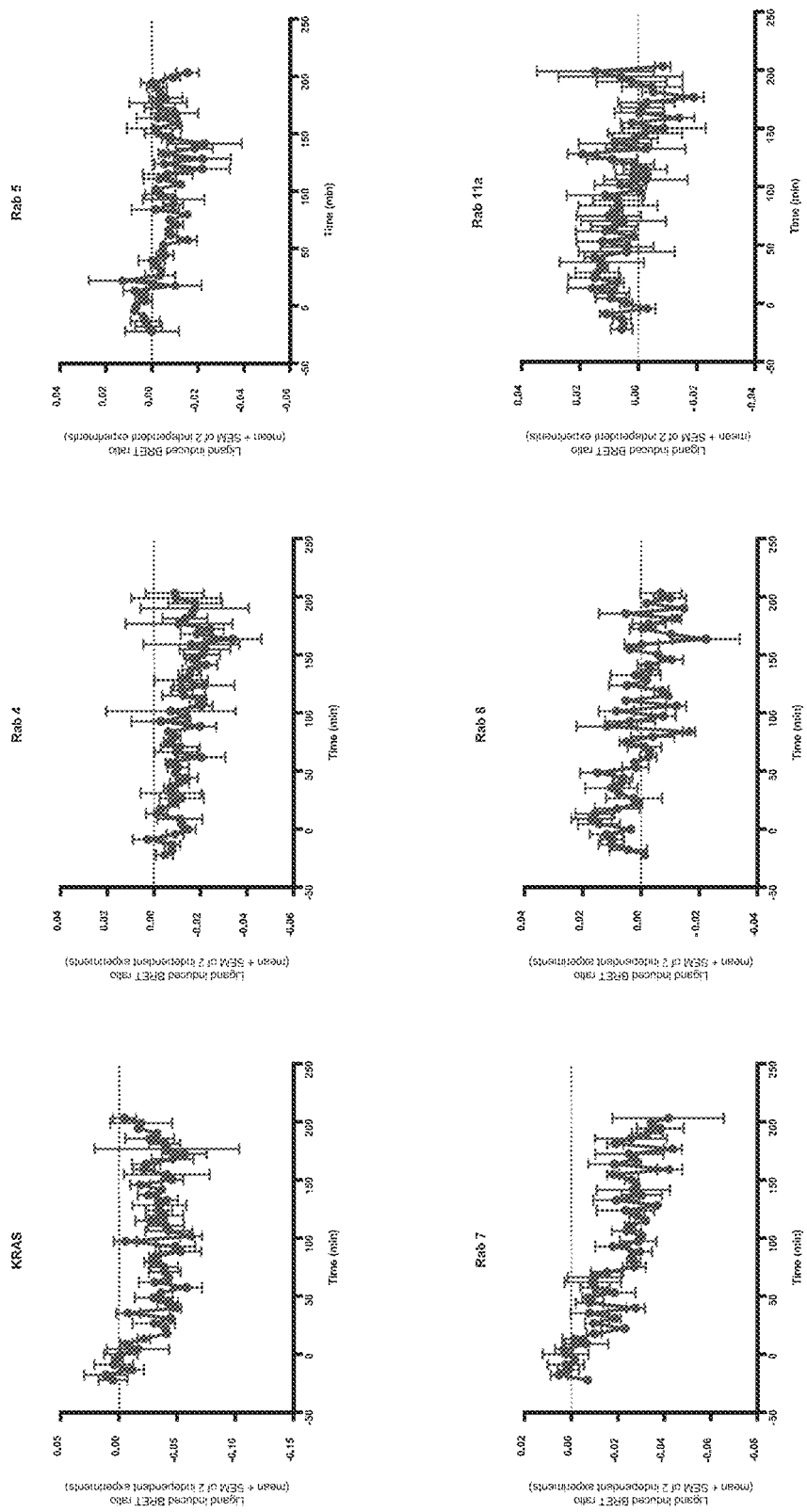
Figure 19G: CCR1 + RAGE/Rluc8 + Venus-tagged KRAS or Rabs CCL3 at $10^{-7}$ M

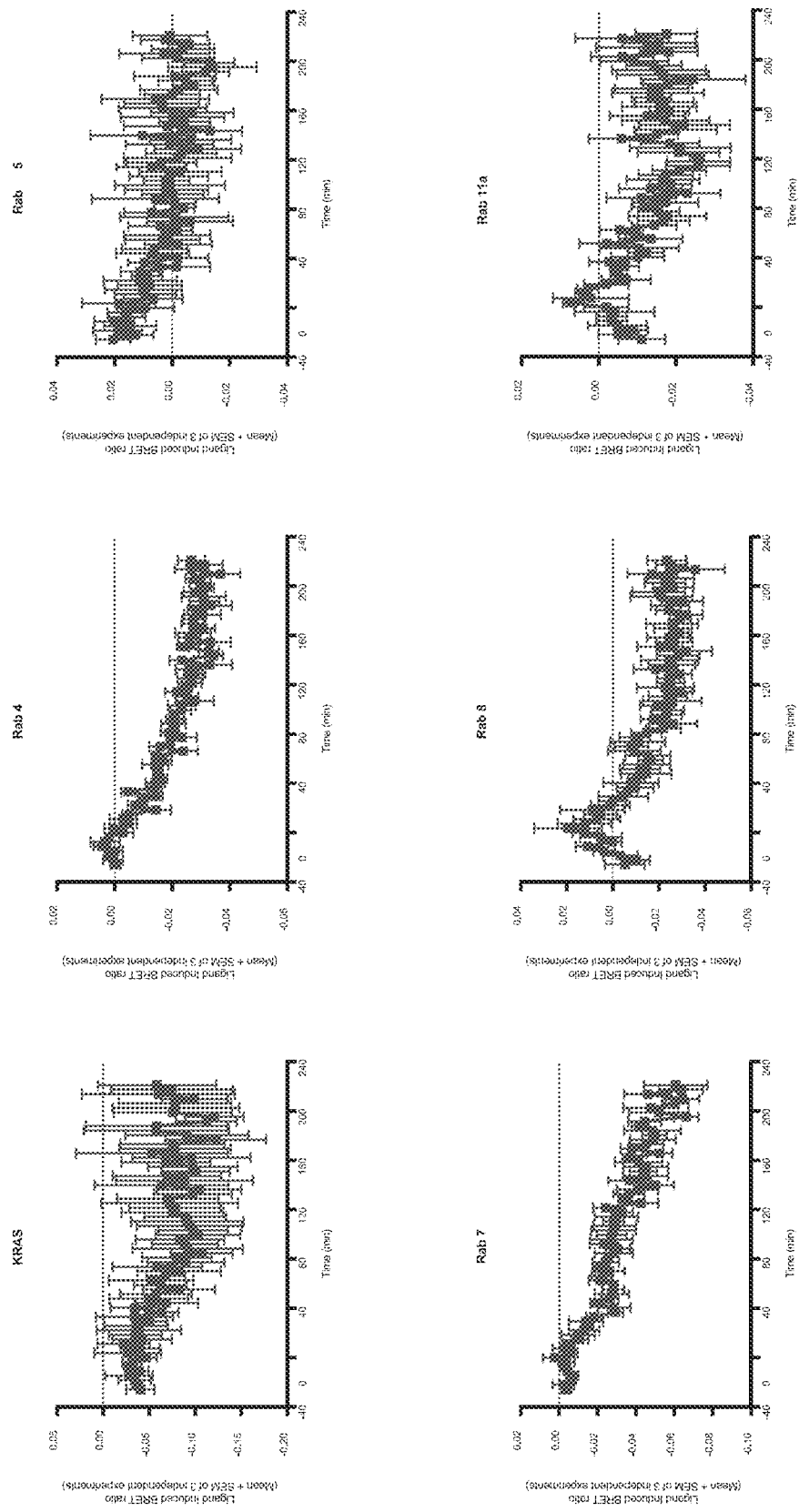
Figure 19H: CCR2 + RAGE/Rluc8 + Venus-tagged KRAS or Rabs CCL2 at $10^{-7}$ M

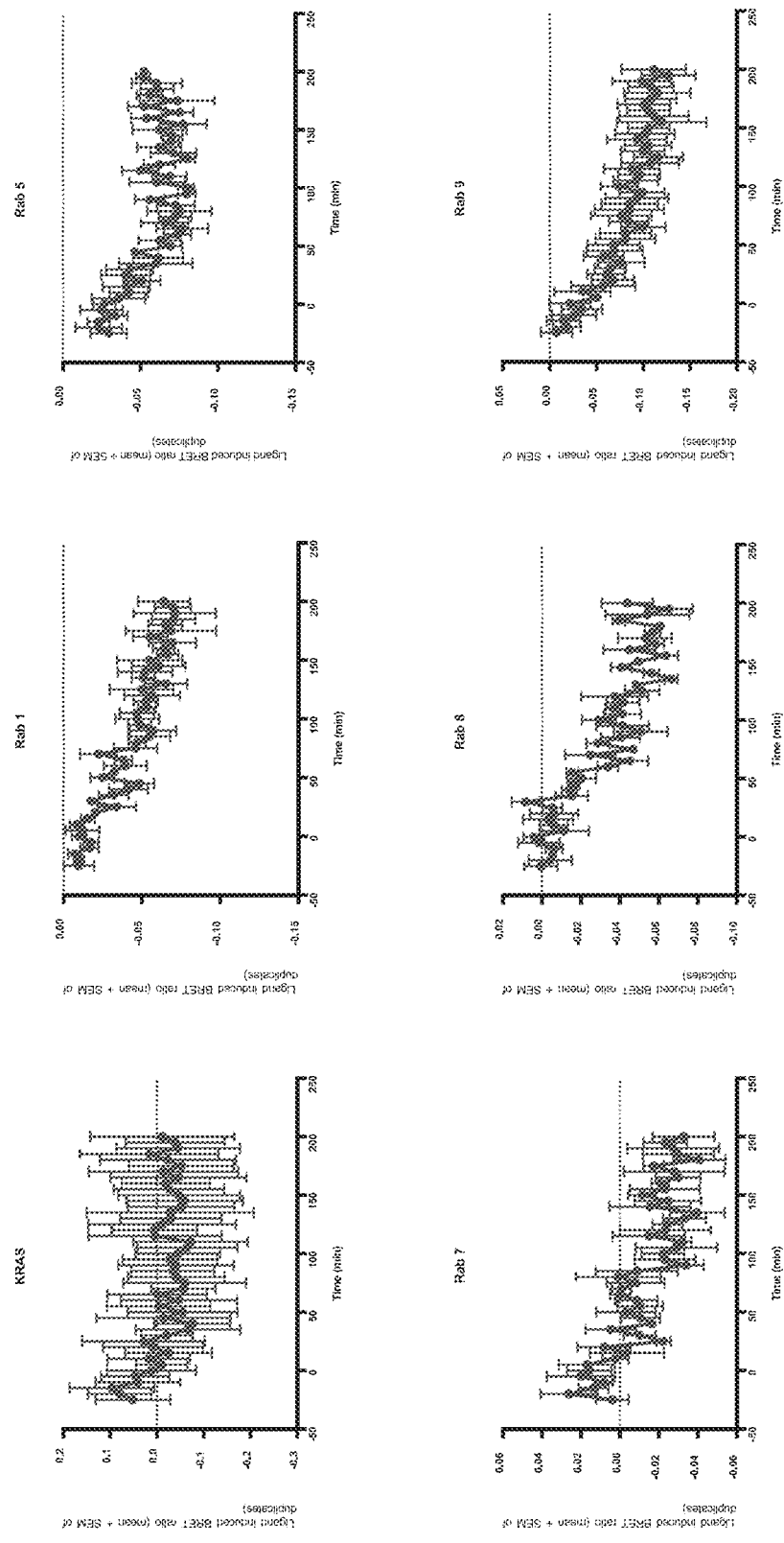
Figure 191: CCR3 + RAGE/Rluc8 + Venus-tagged KRAS or Rabs CCL13 at $10^{-7}$ M

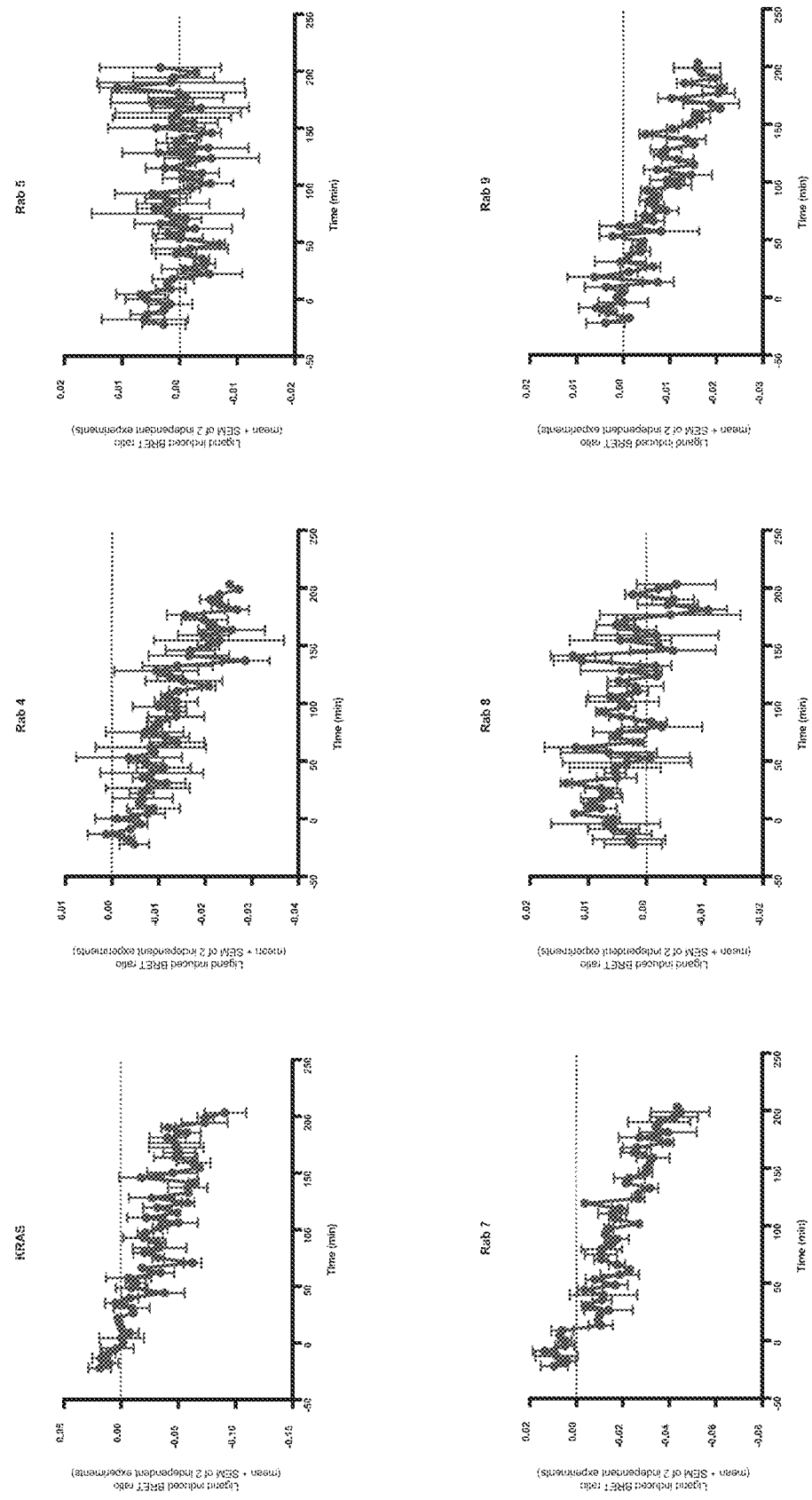
Figure 19.l: CCR4 + RAGE/Rluc8 + Venus-tagged KRAS or Rabs CCL2 at $10^{-7}$ M

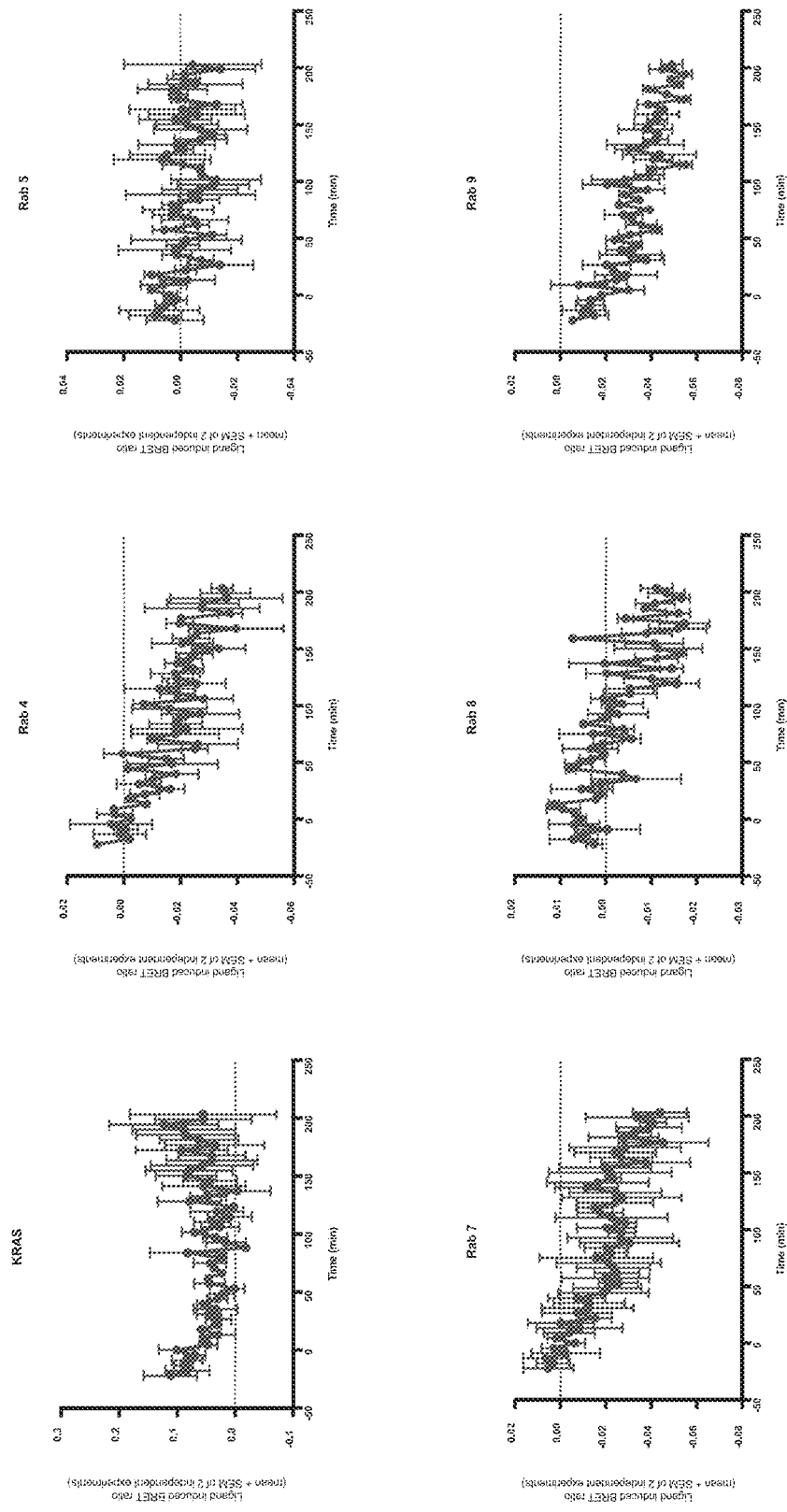
Figure 19K: CCR5 + RAGE/Rluc8 + Venus-tagged KRAS or Rabs CCL4 at $10^{-7}$ M

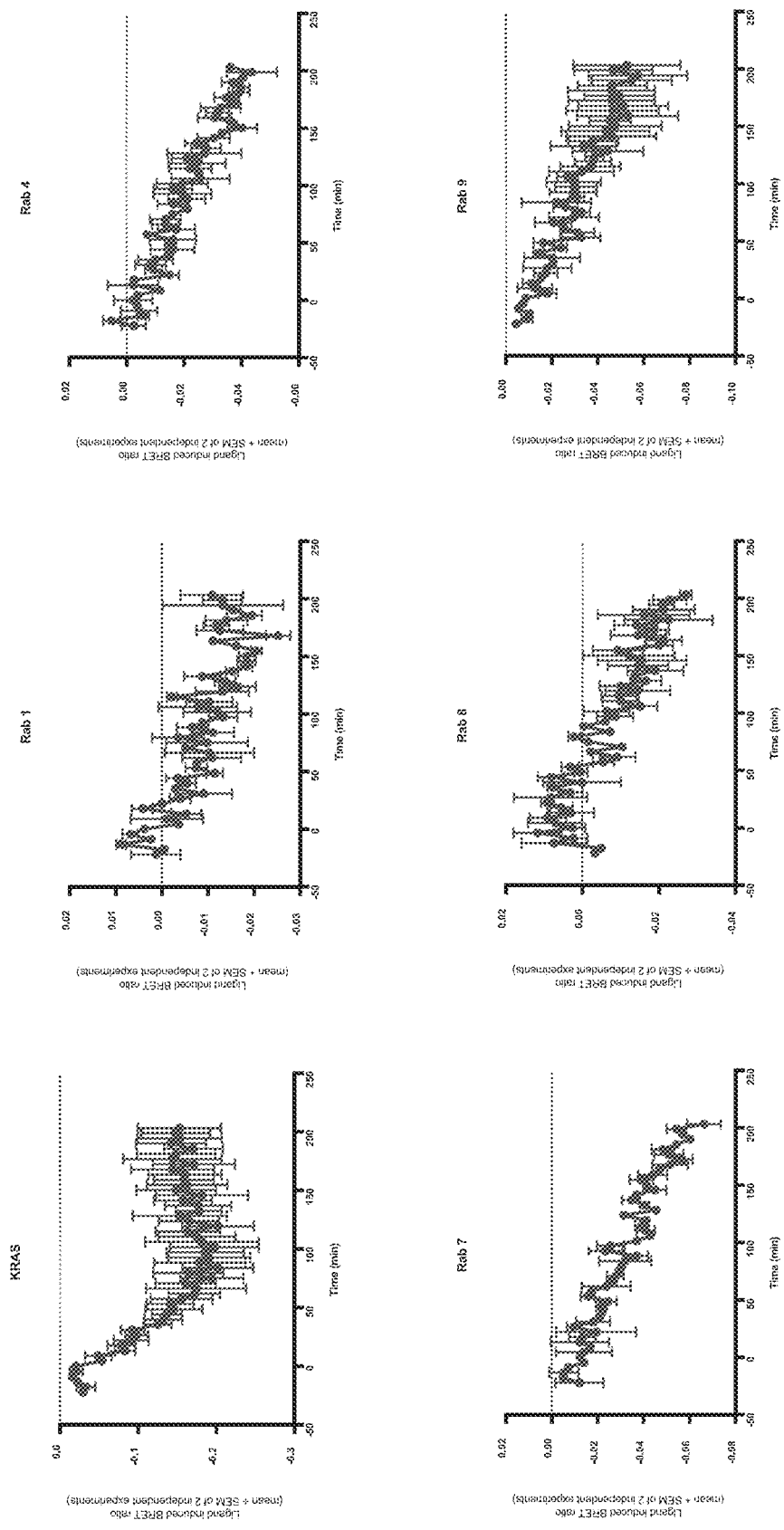
Figure 19L. CCR6 + RAGE/Rluc8 + Venus-tagged KRAS or Rabs CCL20 at $10^{-7}$ M

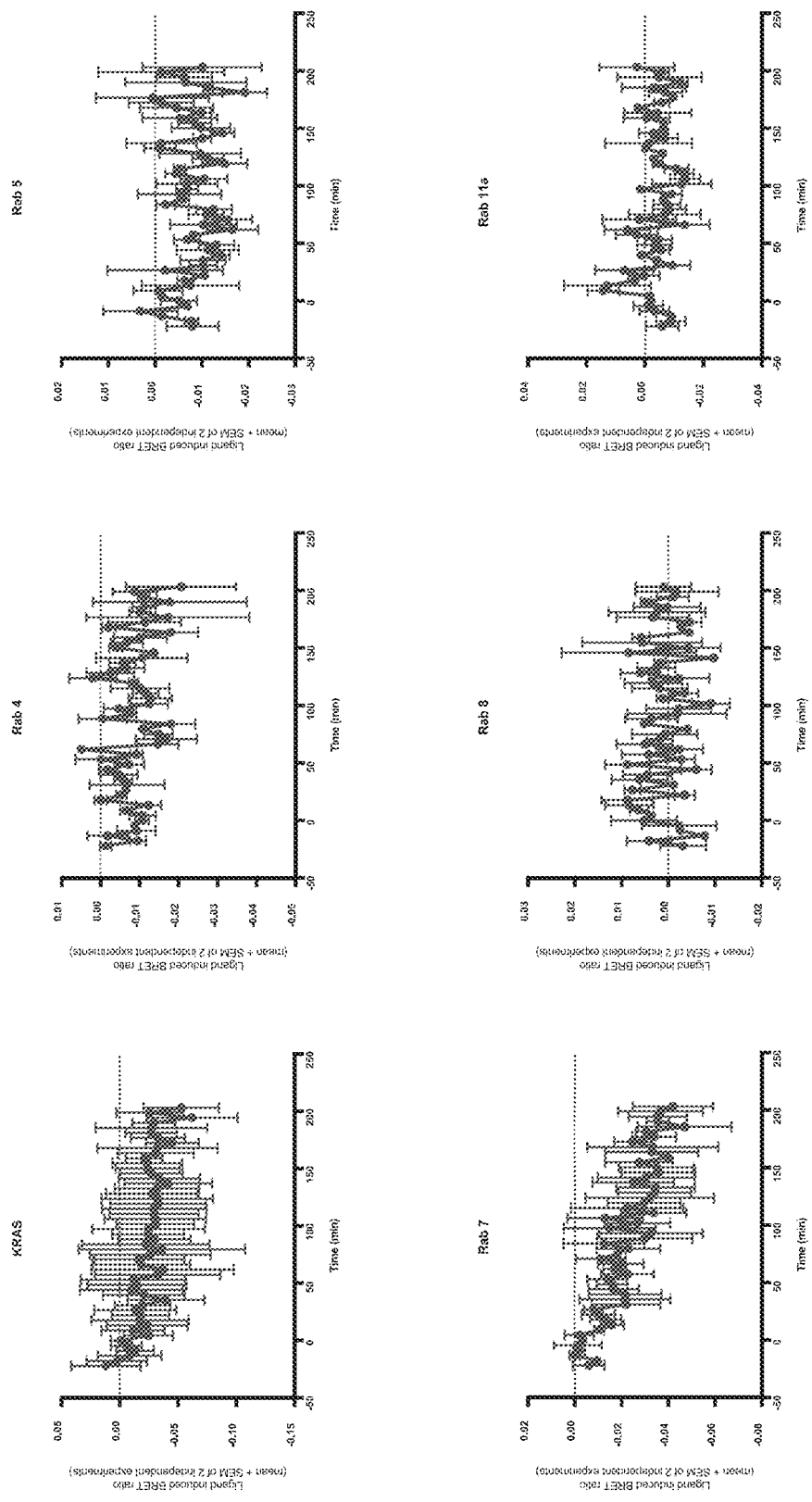
Figure 19M: CCR7 + RAGE/Rluc8 + Venus-tagged KRAS or Rabs CCL19 at 10⁻⁷ M

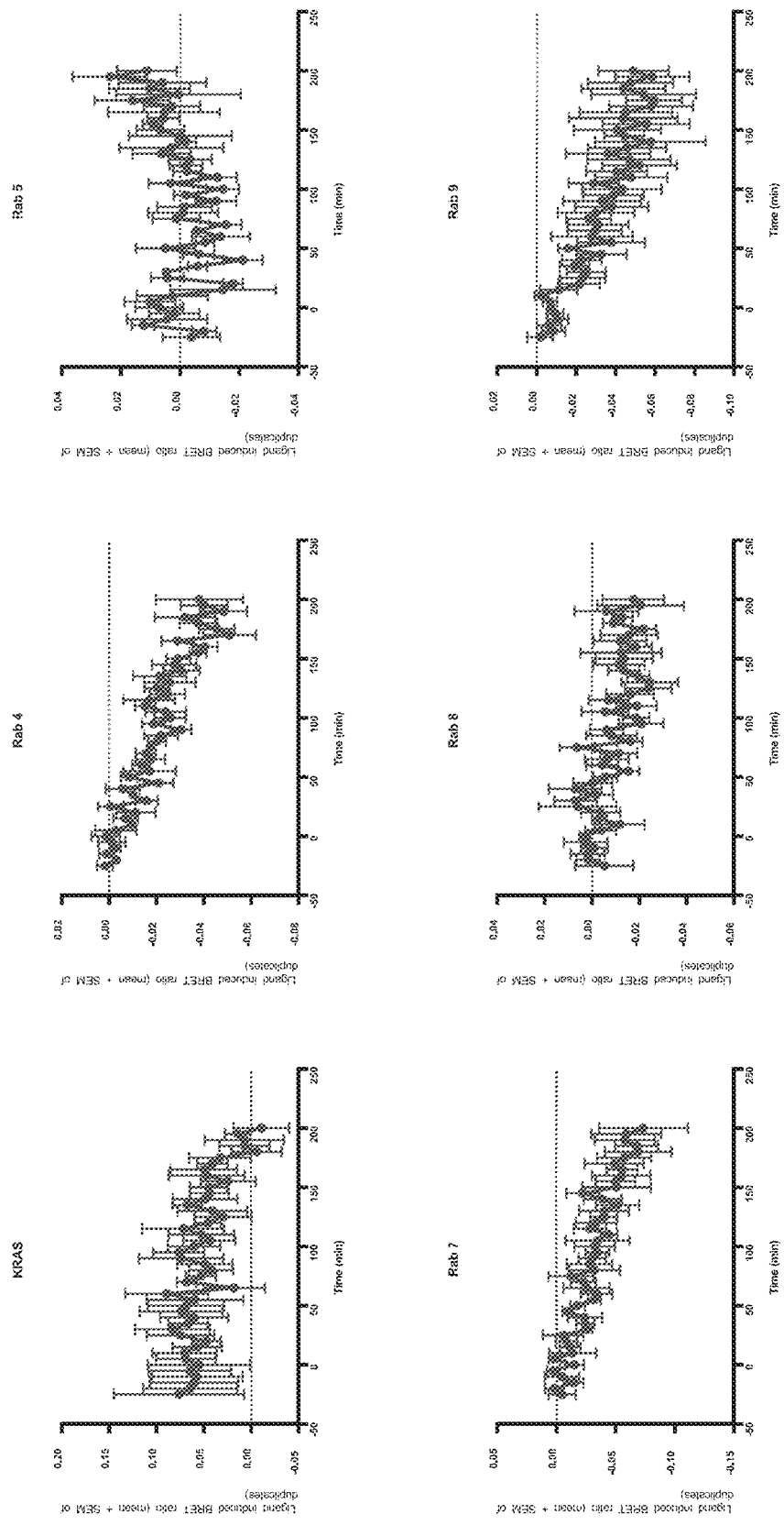
Figure 19N: CCR9 + RAGE/Rluc8 + Venus-tagged KRAS or Rabs CCL25 at $10^{-7}$ M

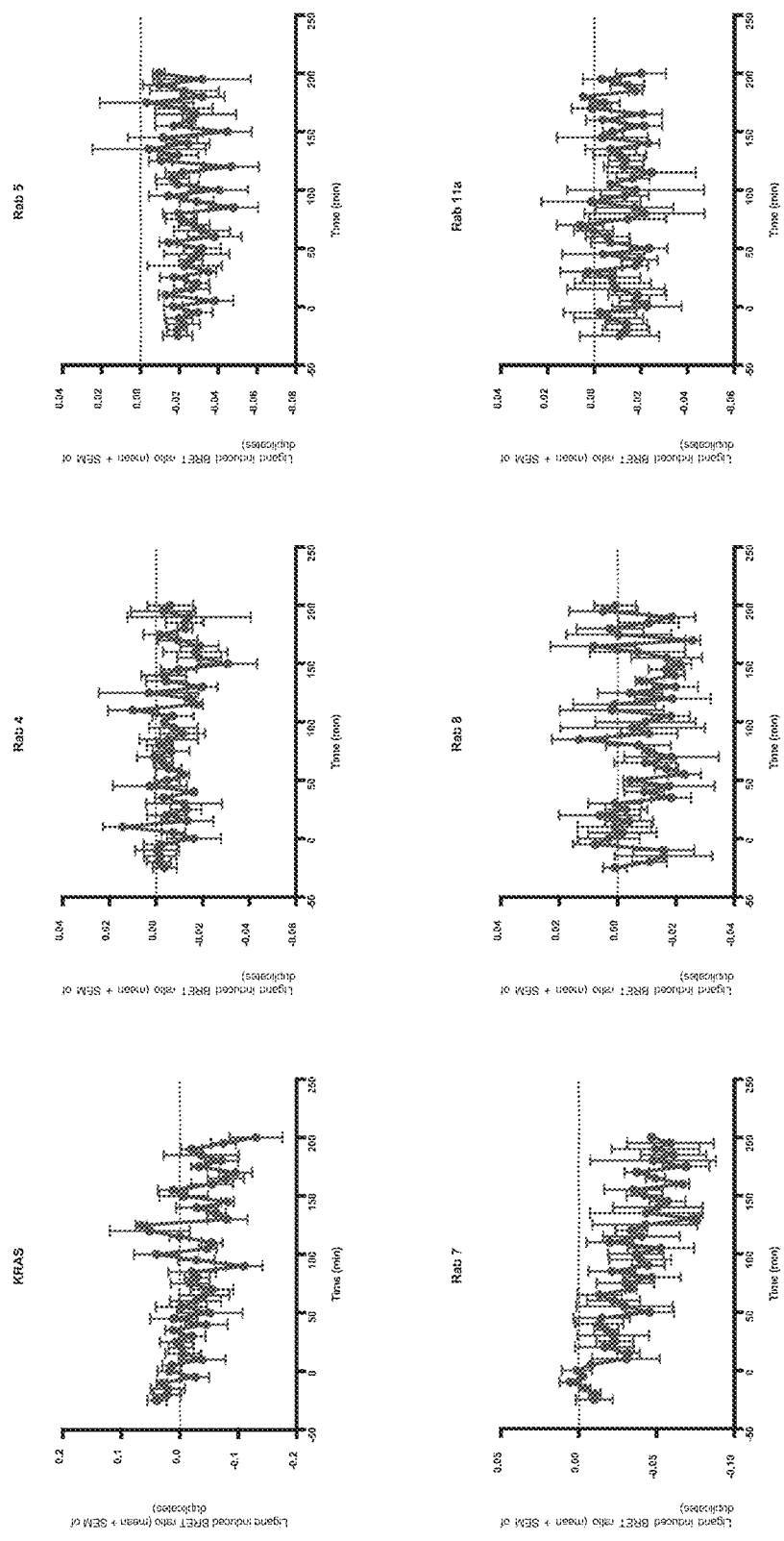
Figure 19O: CXCR2 + RAGE/Rluc8 + Venus-tagged KRAS or Rabs CXCL8 at $10^{-7}$ M

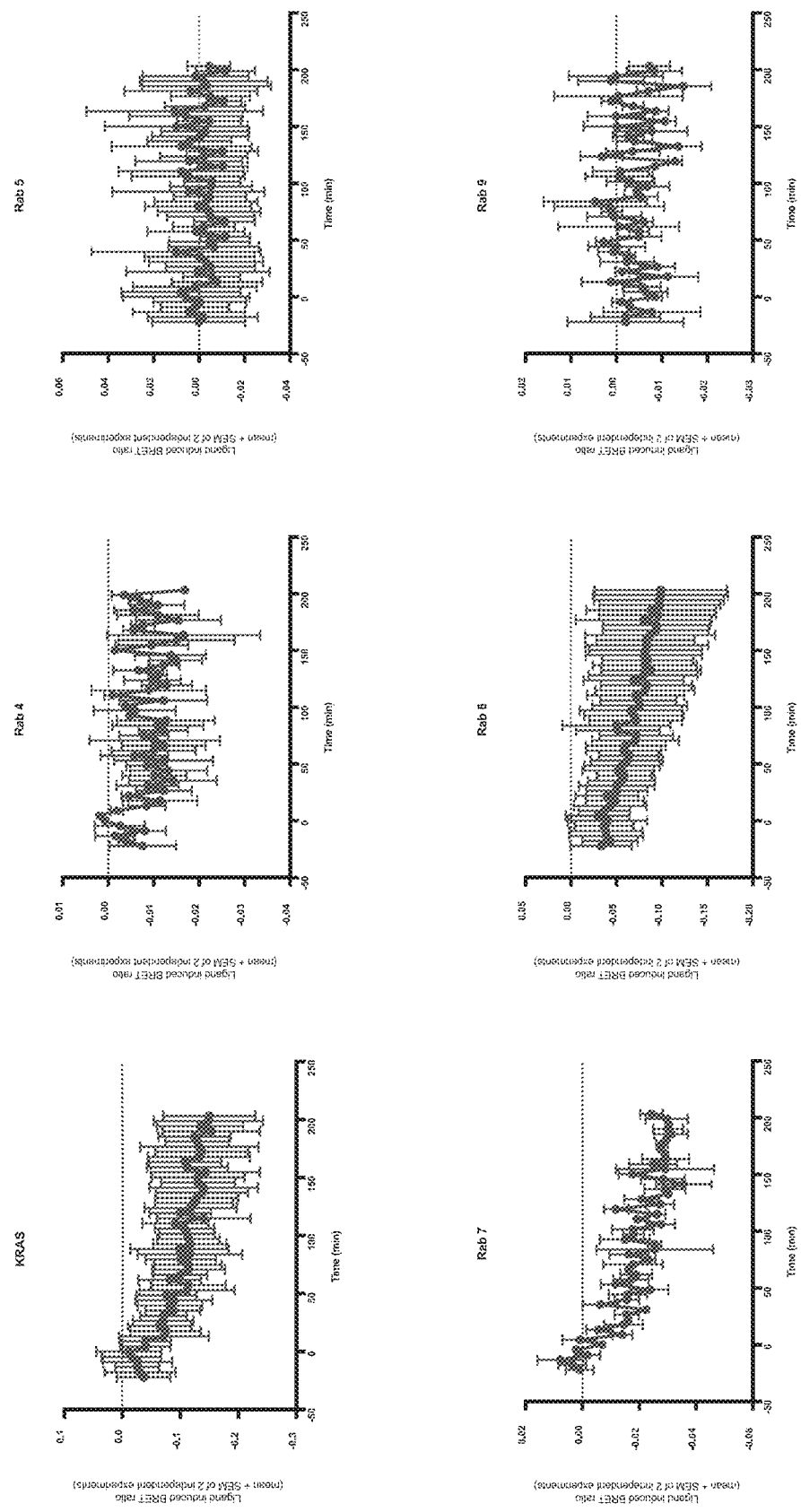
Figure 19P: CXCR4 + RAGE/Rluc8 + Venus-tagged KRAS or Rabs CXCL12 at $10^{-7}$ M

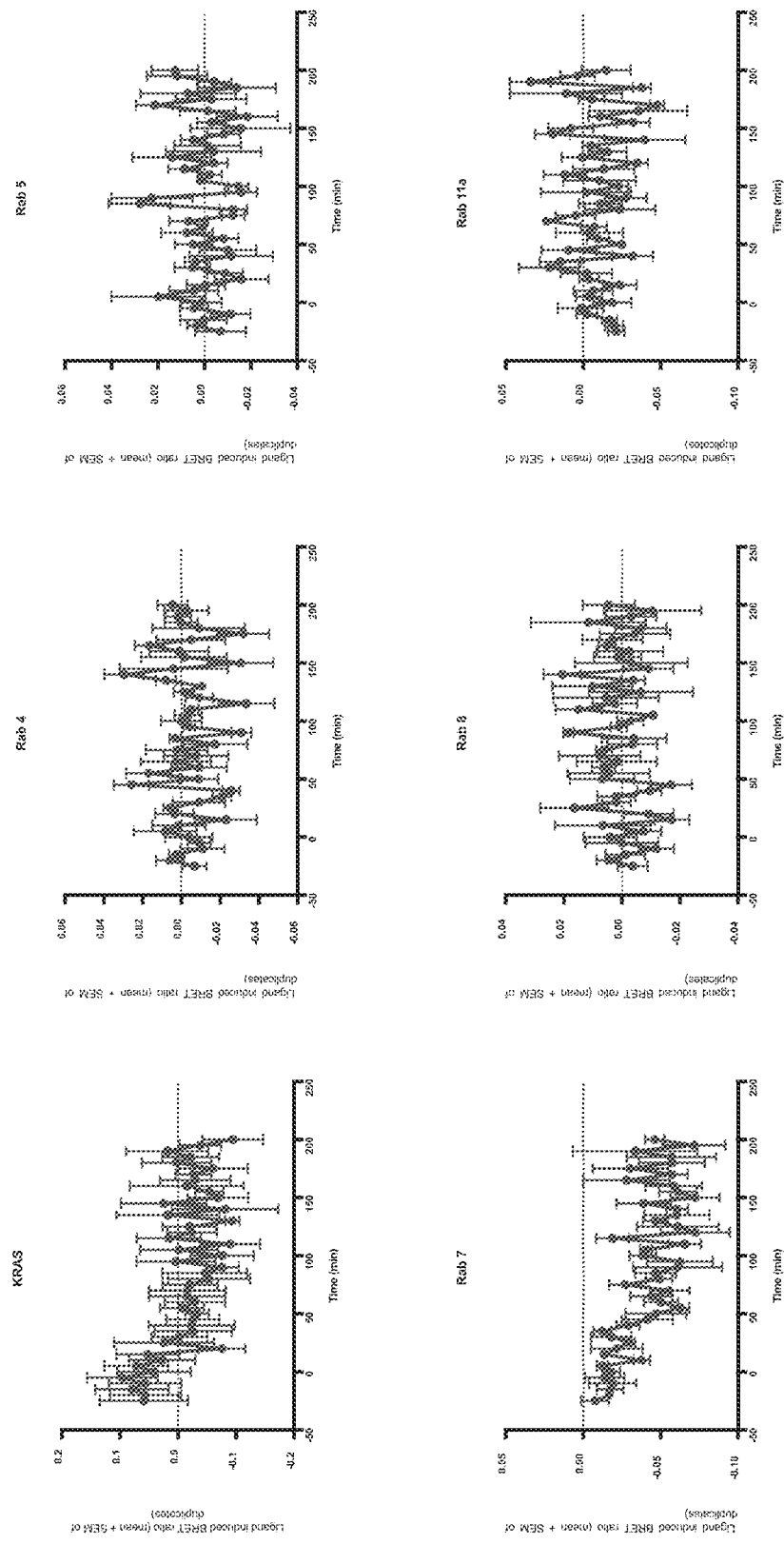
Figure 19Q: CXCR5 + RAGE/Rluc8 + Venus-tagged KRAS or Rabs CXCL13 at $10^{-7}$ M

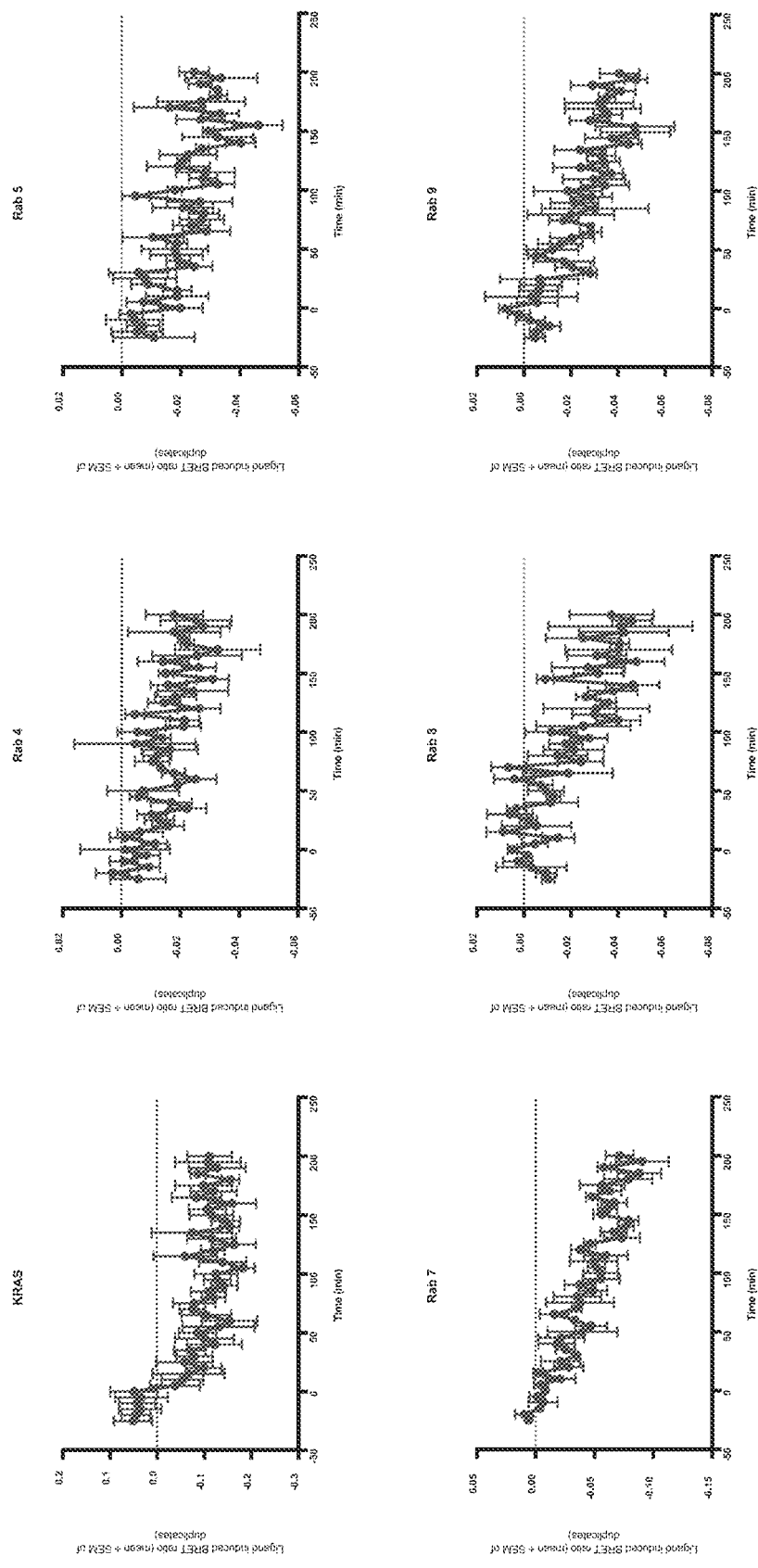
Figure 19R: Dopamine receptor 1 + RAGE/Rluc8 + Venus-tagged KRAS or Rabs Dopamine at $10^{-5}$ M

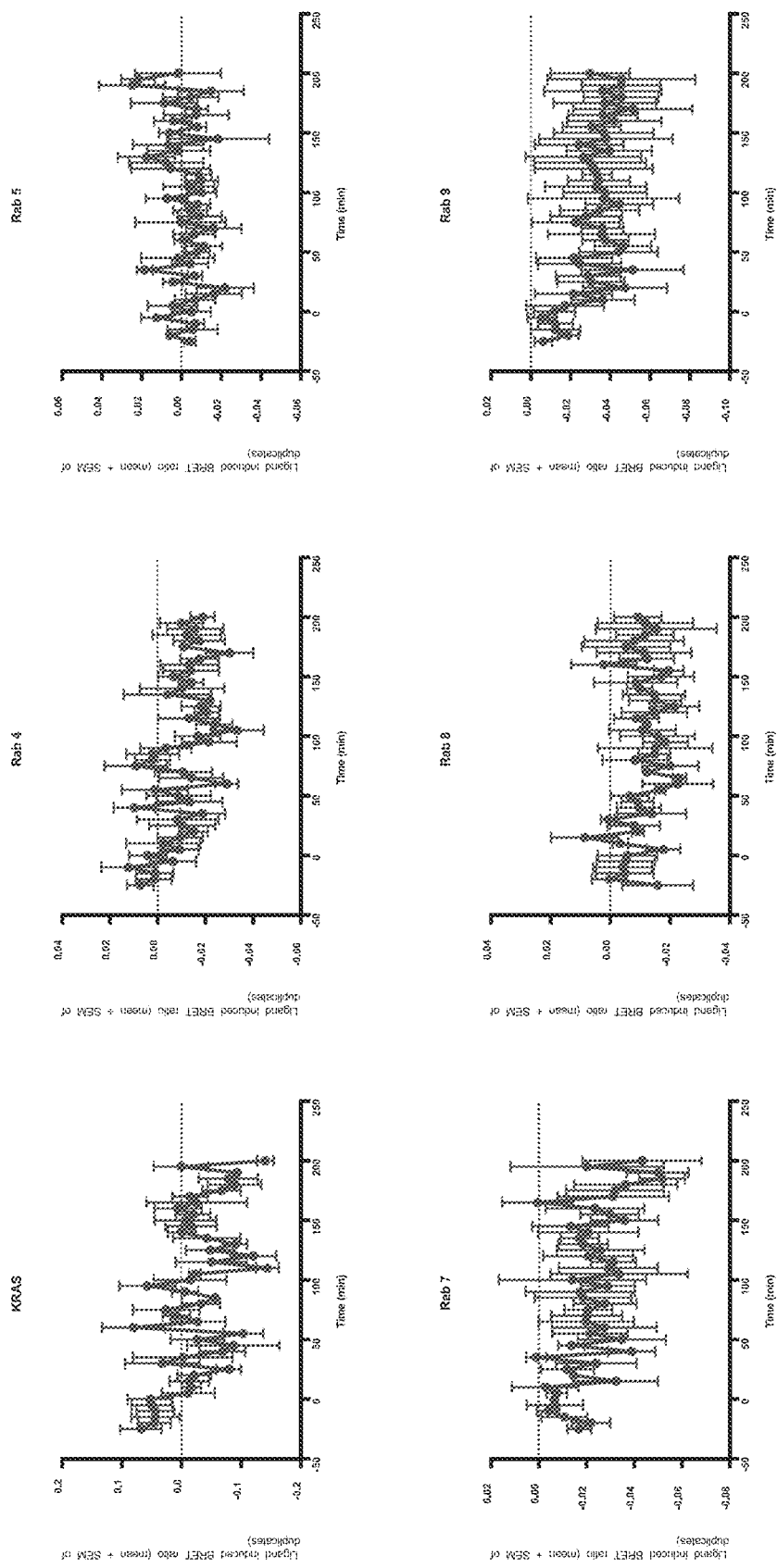

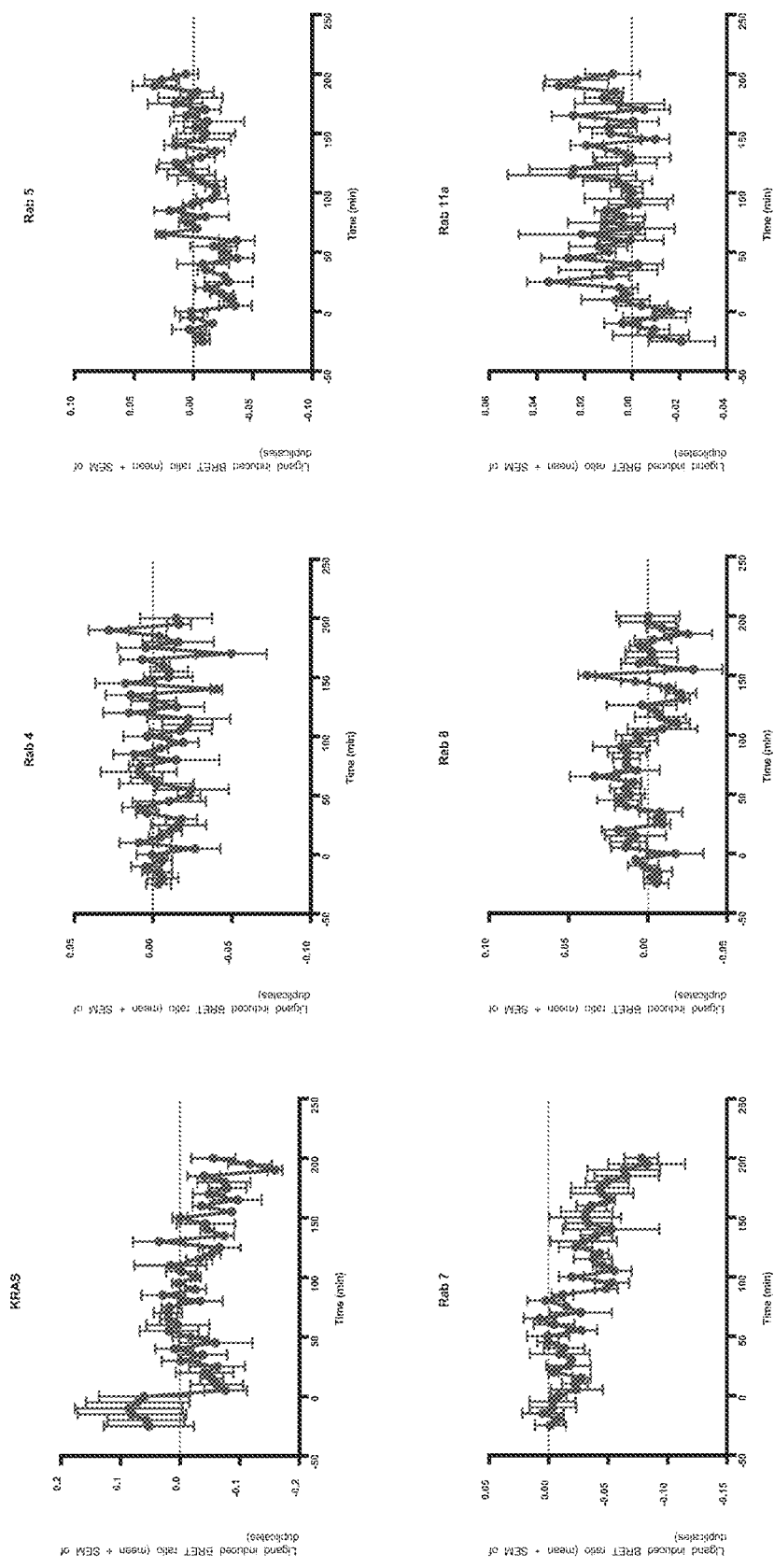
Figure 19T: Endothelin receptor type B + RAGE/Rluc8 + Venus-tagged KRAS or Rabs Endothelin at $10^{-6}$ M

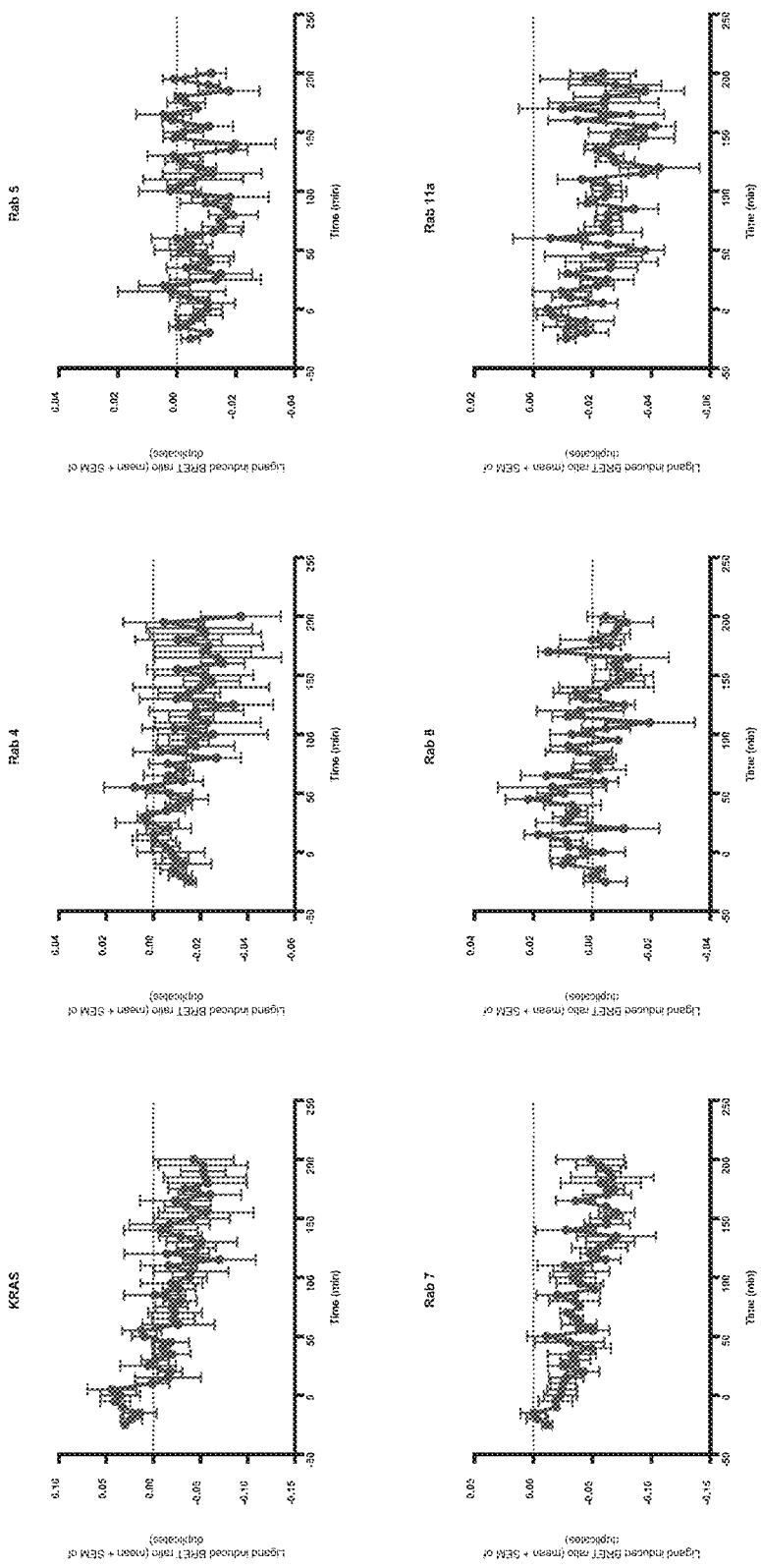
Figure 19U: Histamine receptor 3 + RAGE/Rluc8 + Venus-tagged KRAS or Rabs R-α methylhistamine at $10^{-5}$ M

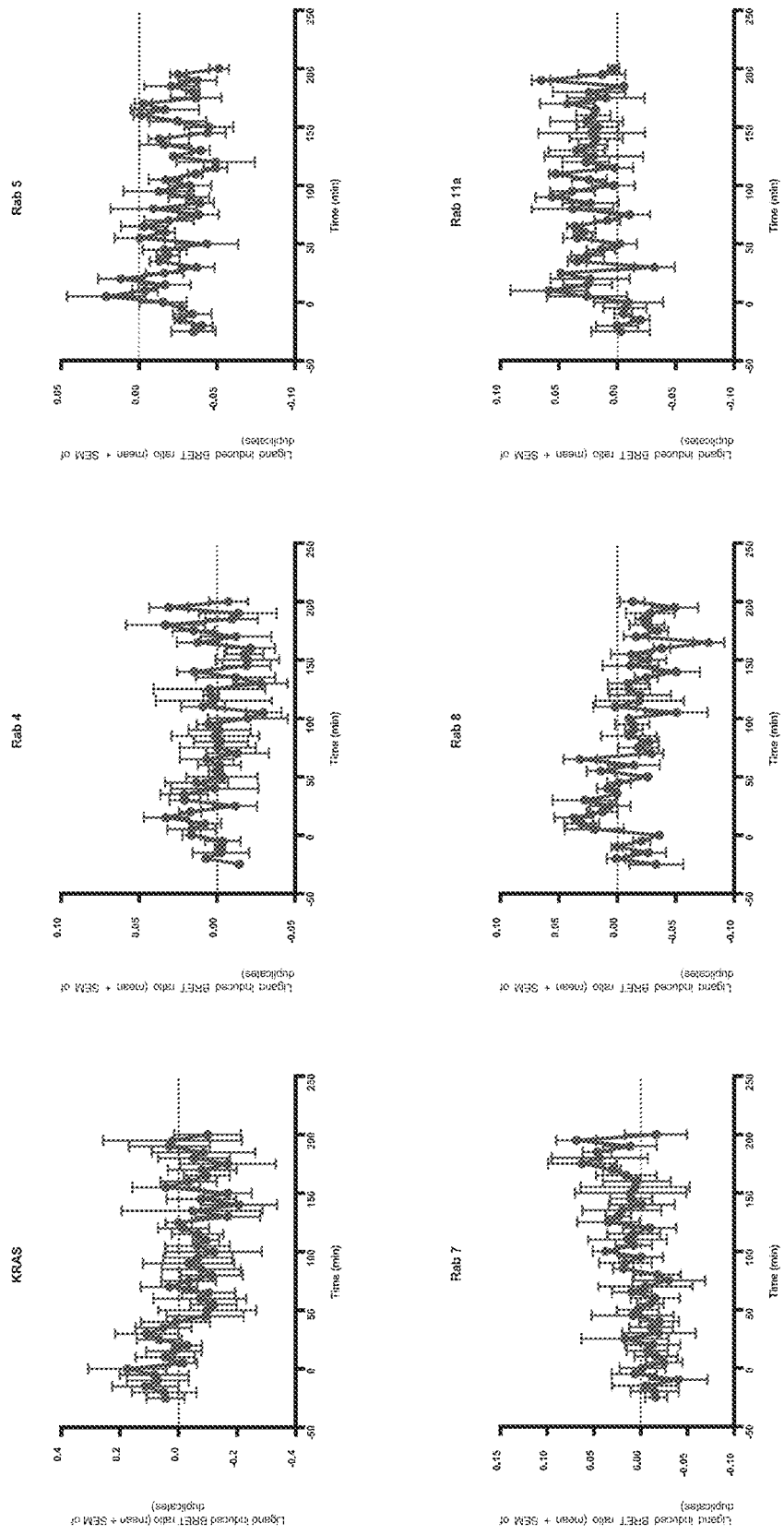

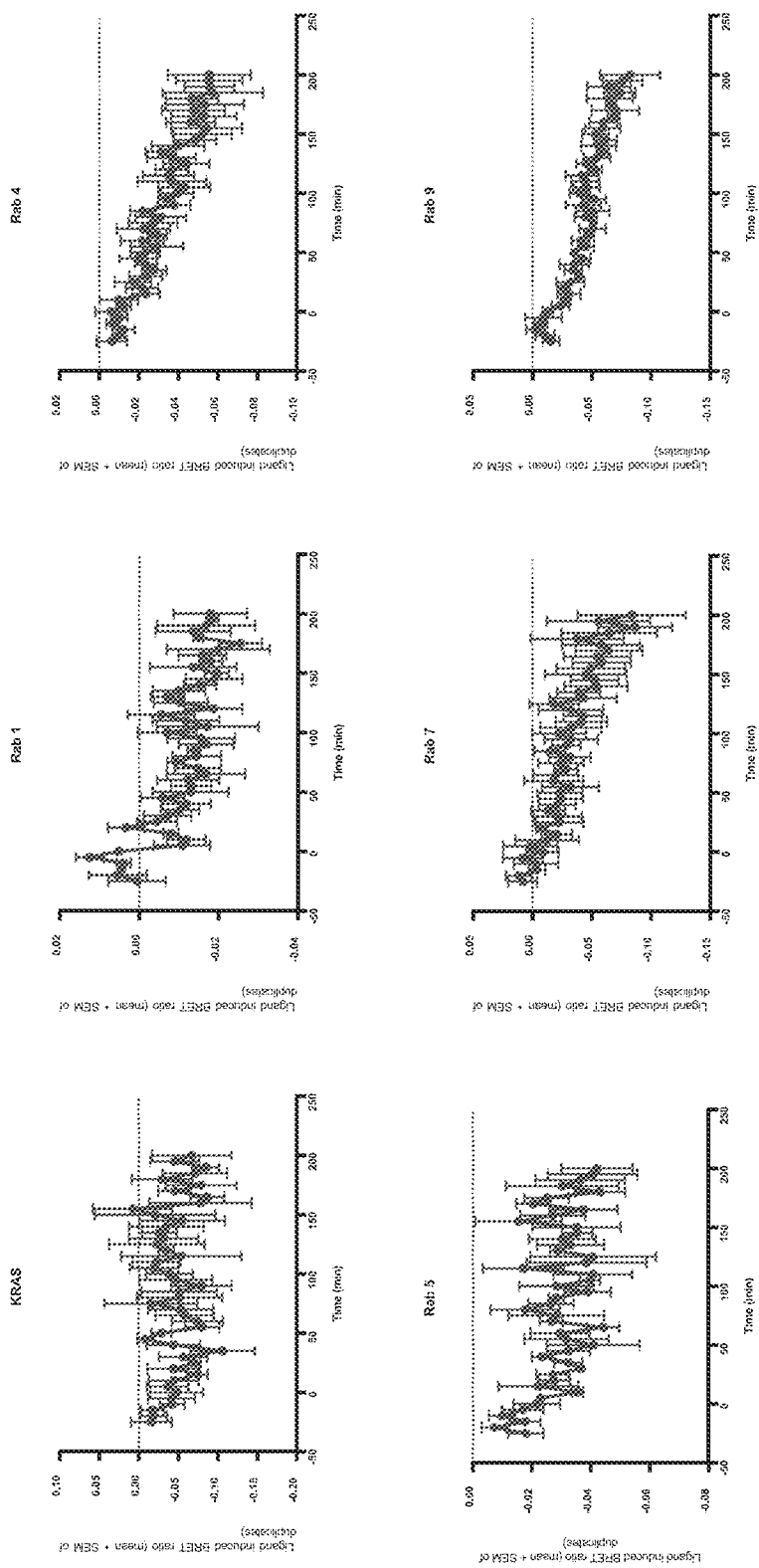
Figure 19W. Muscarinic receptor 2 + RAGE/Rluc8 + Venus-tagged KRAS or Rabs Acetylcholine at $10^{-5}$ M

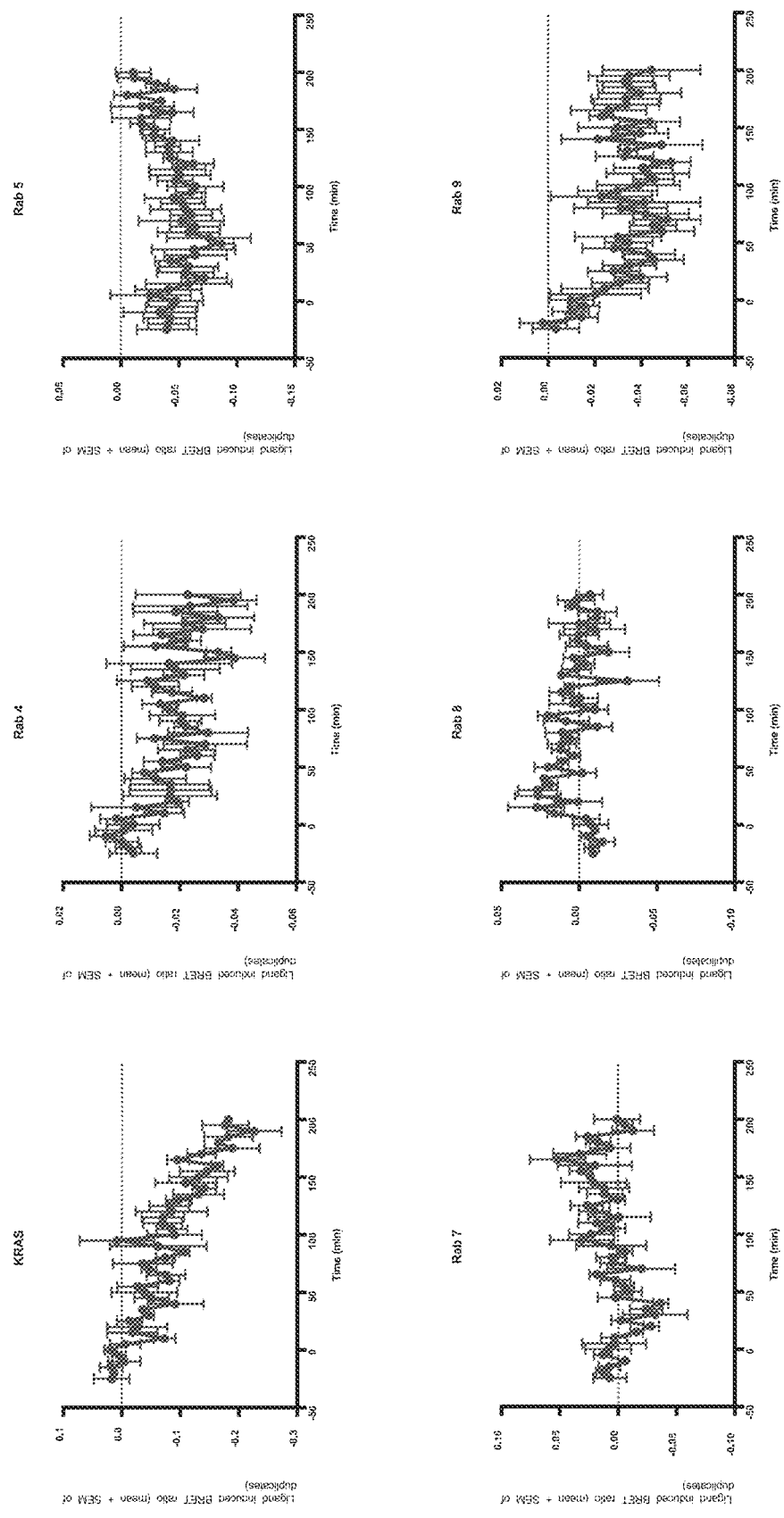
Figure 19X: Muscarinic receptor 3 + RAGE/Rluc8 + Venus-tagged KRAS or Rabs Acetylcholine at $10^{-5}$ M

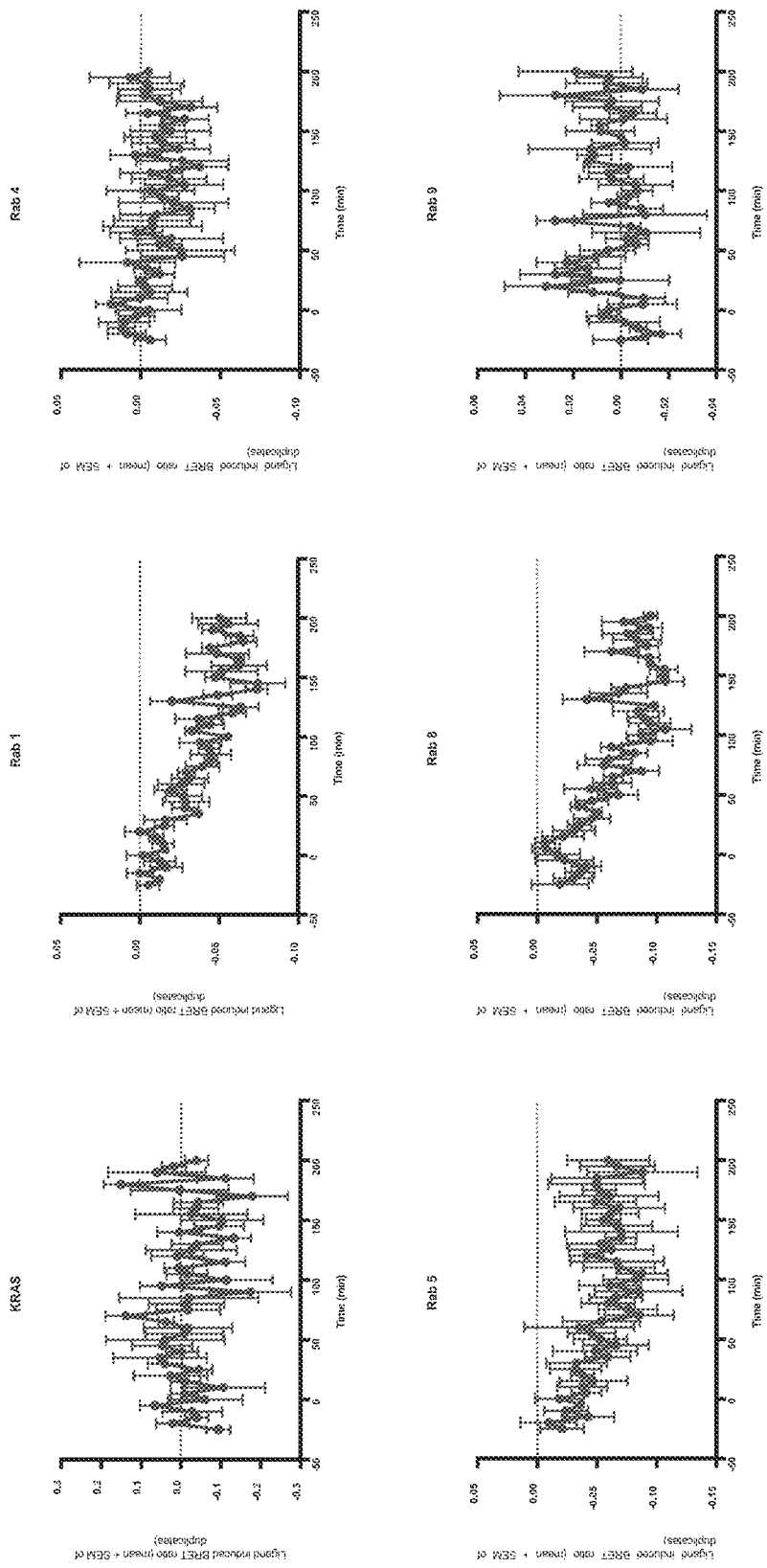

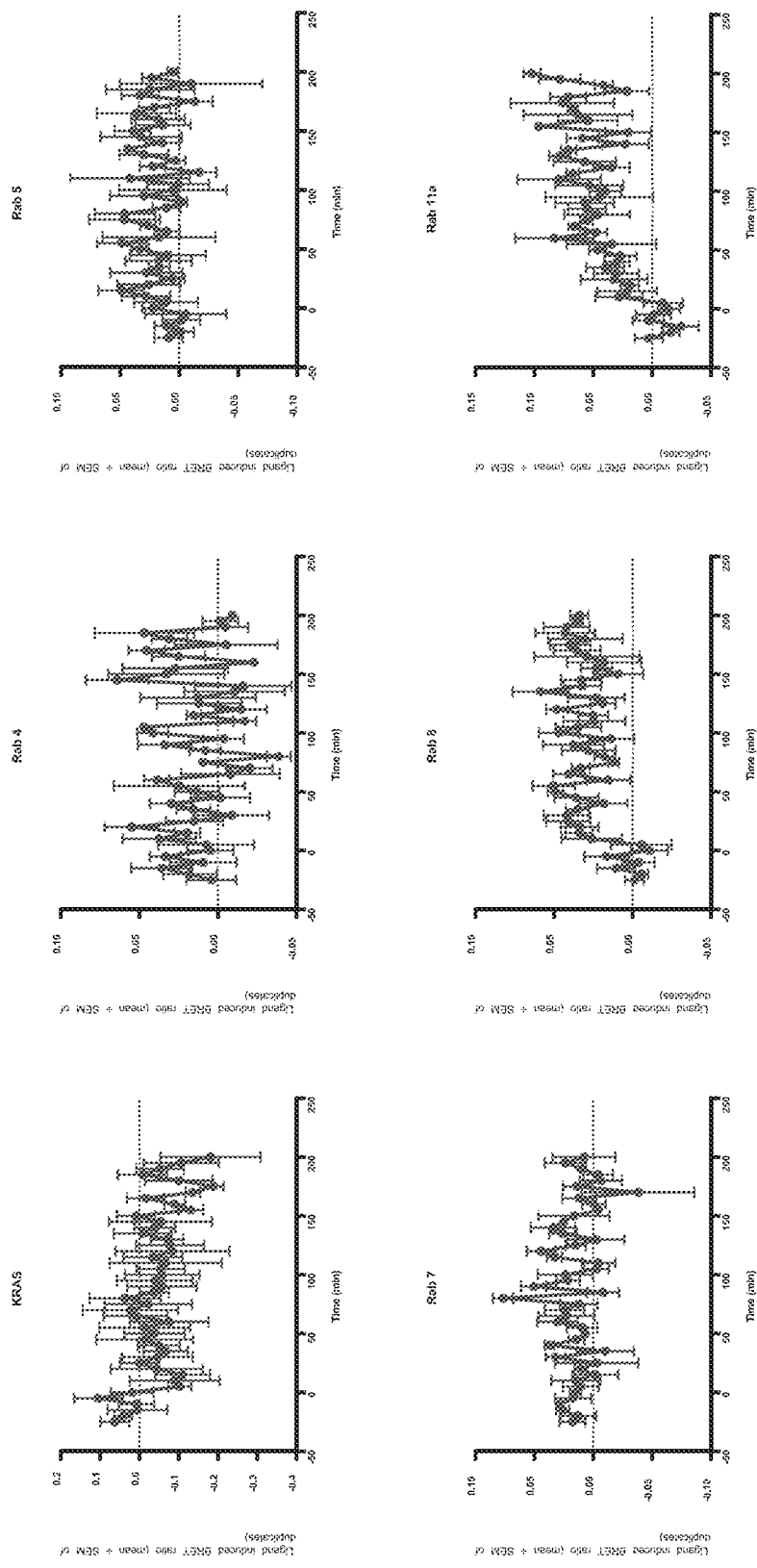
Figure 19Z: Neurotensin 1 receptor + RAGE/Rluc8 + Venus-tagged KRAS or Rabs Neurotensin at $10^{-7}$ M

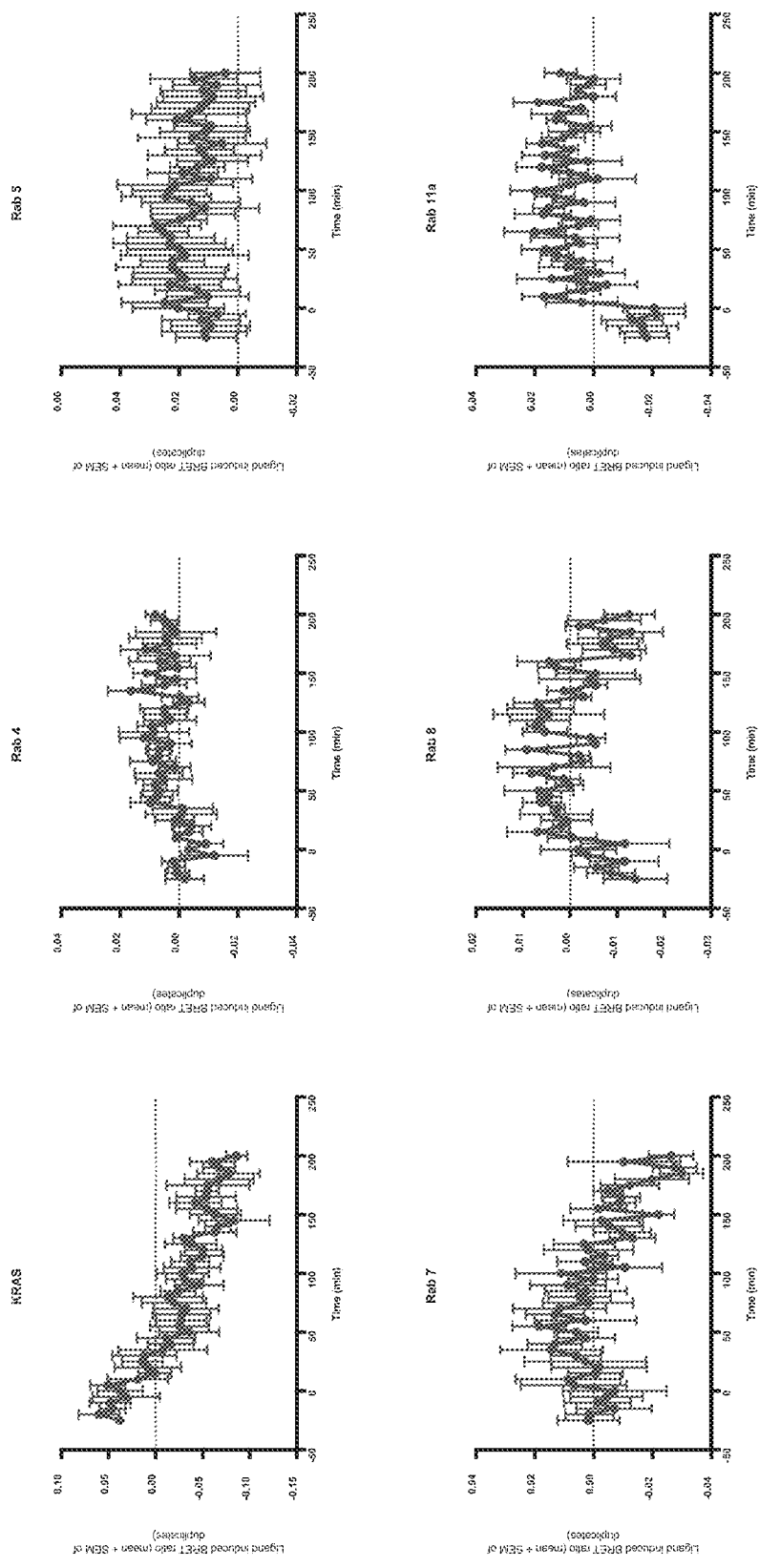
Figure 19AA: Orexin receptor 1 + RAGE/Rluc8 + Venus-tagged KRAS or Rabs Orexin A at $10^{-6}$ M

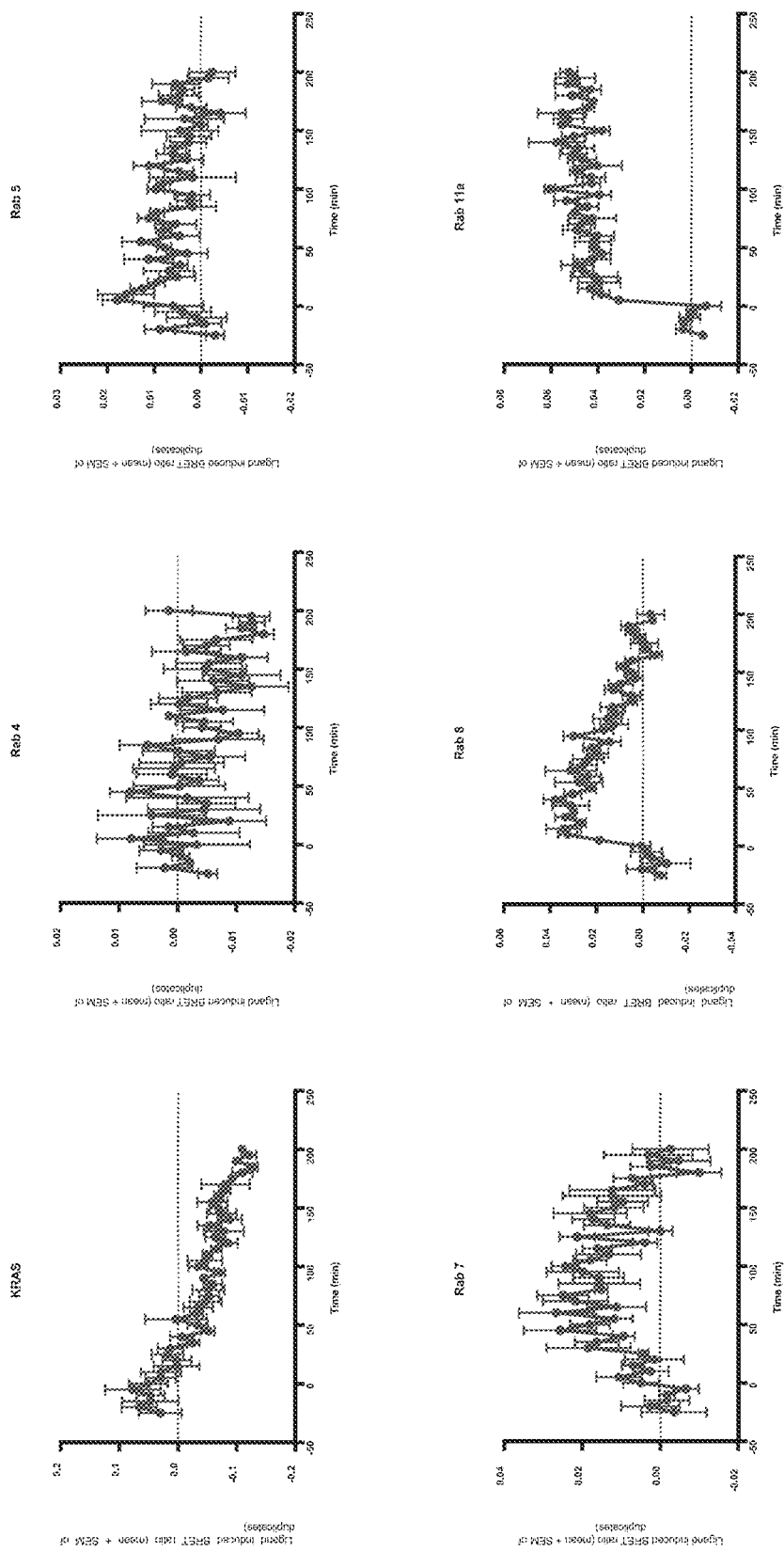

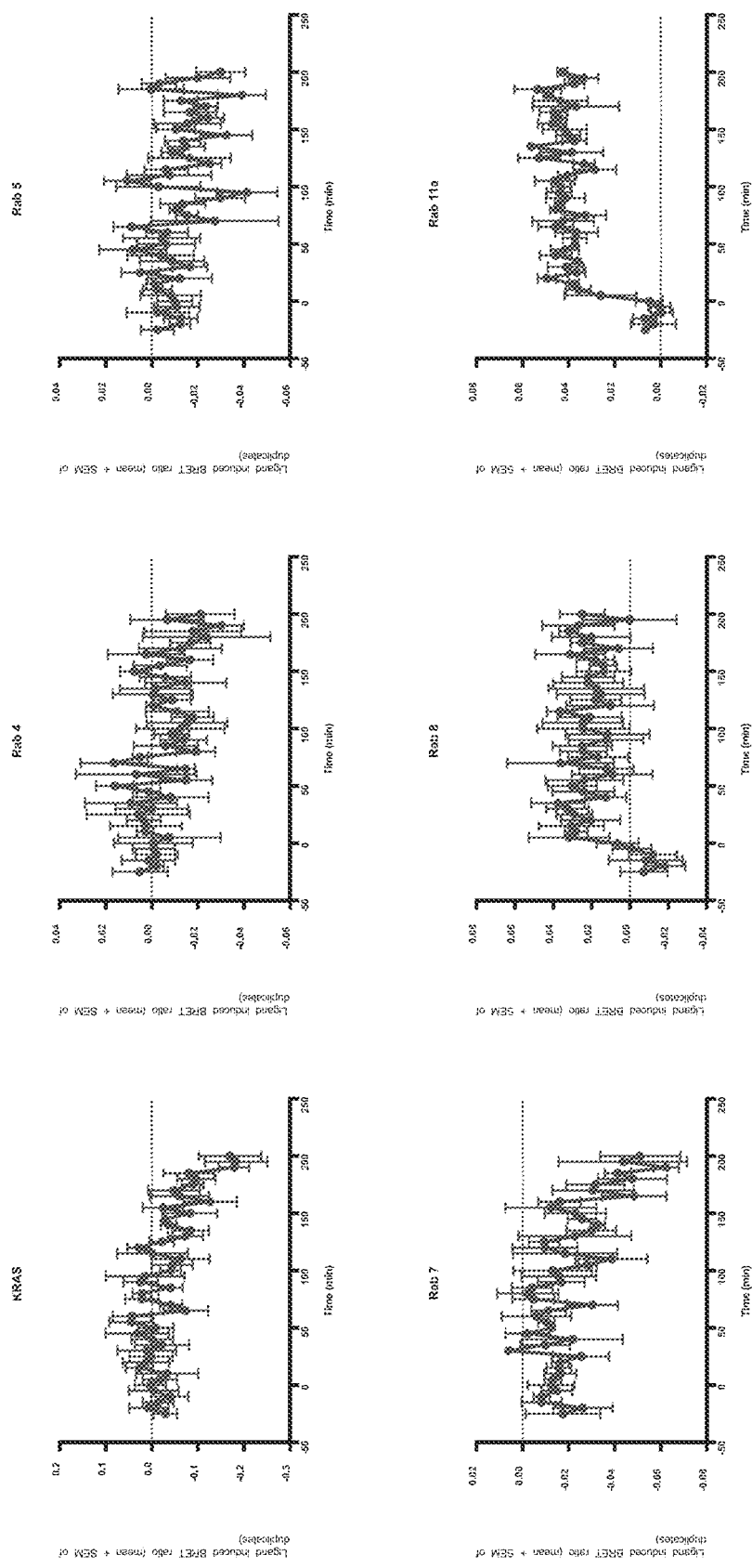
Figure 19CC: Prostaglandin E1 receptor + RAGE/Rluc8 + Venus-tagged KRAS or Rabs
Prostaglandin E2 at $10^{-7}$ M

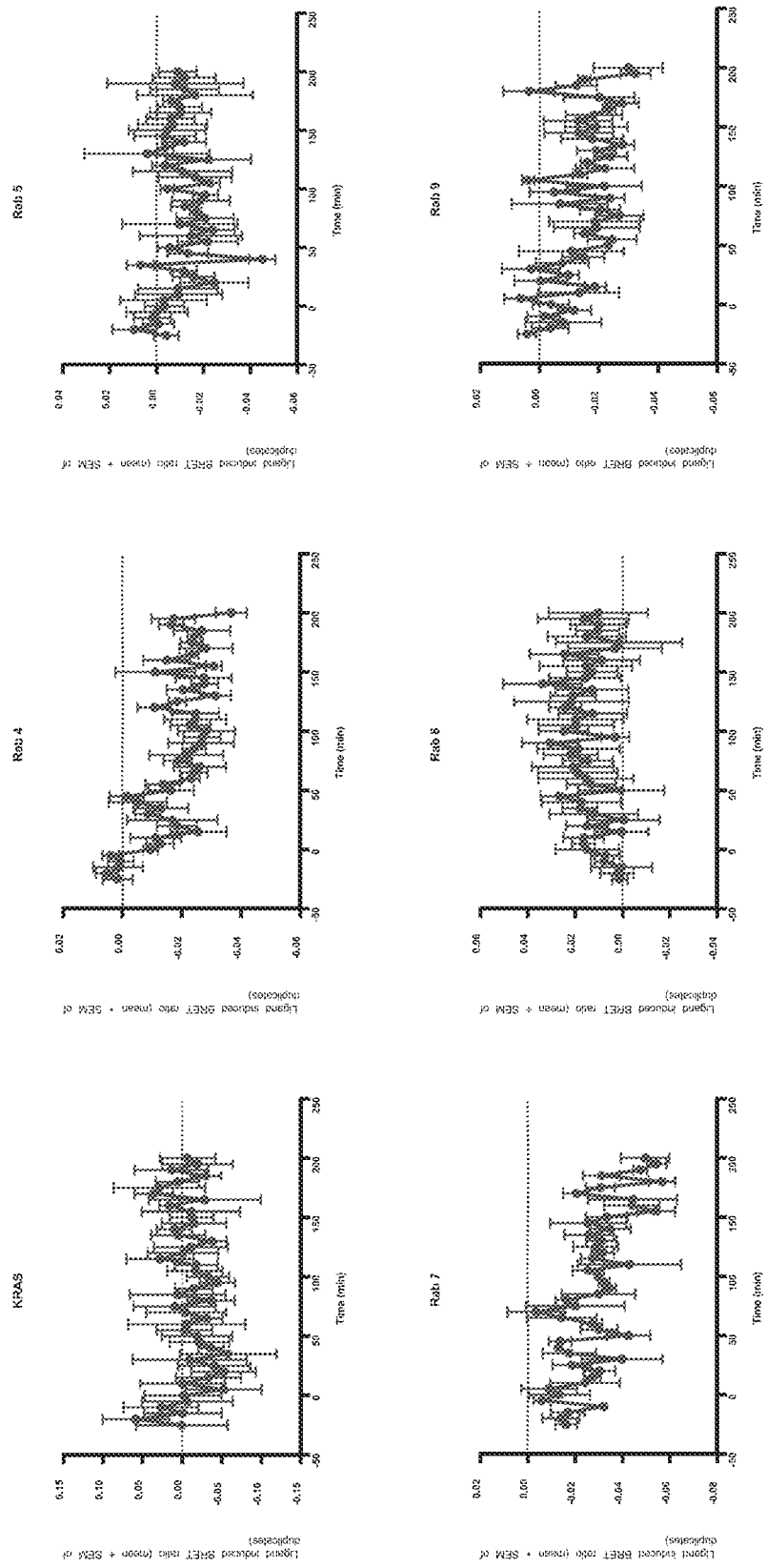

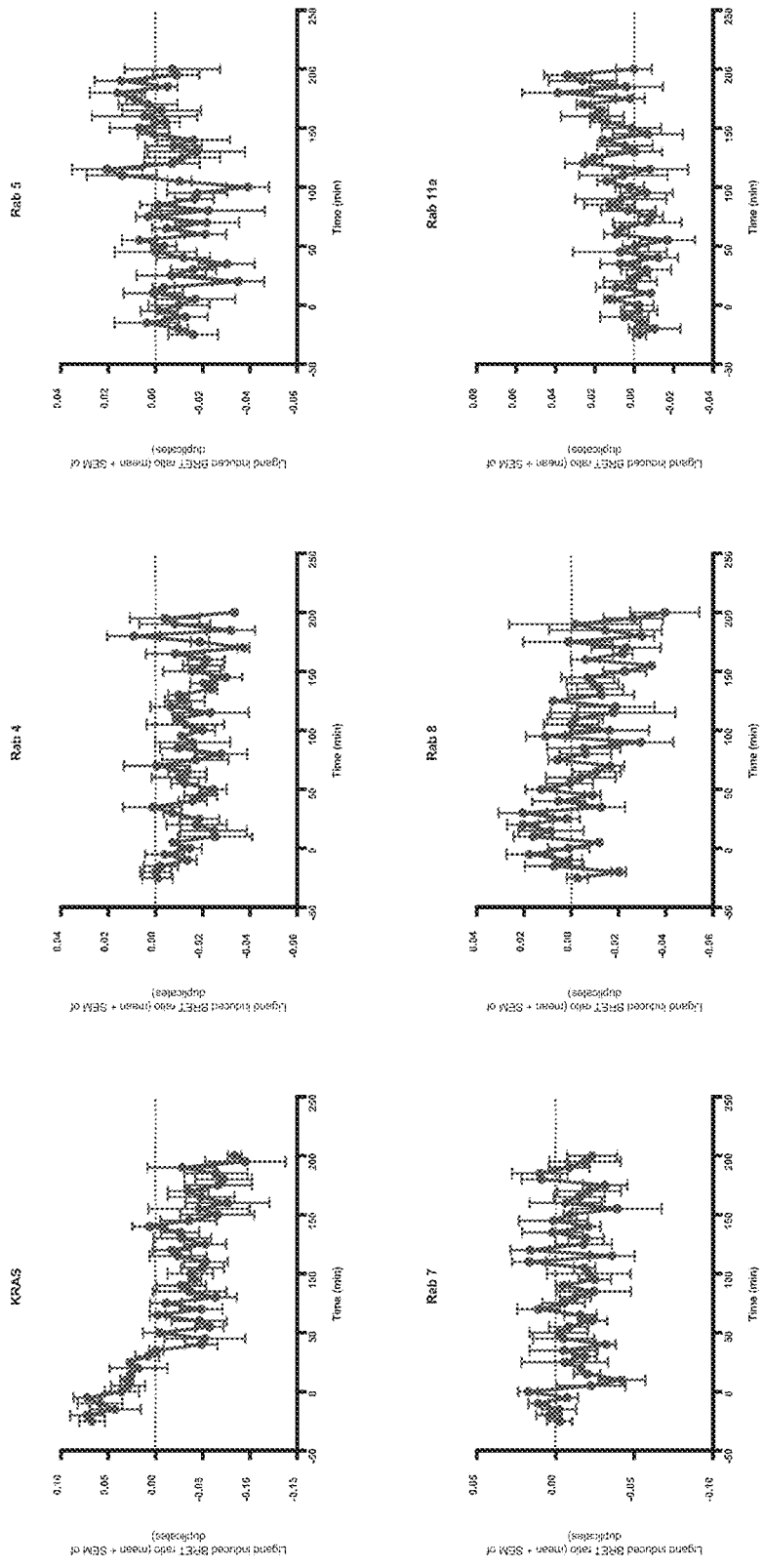

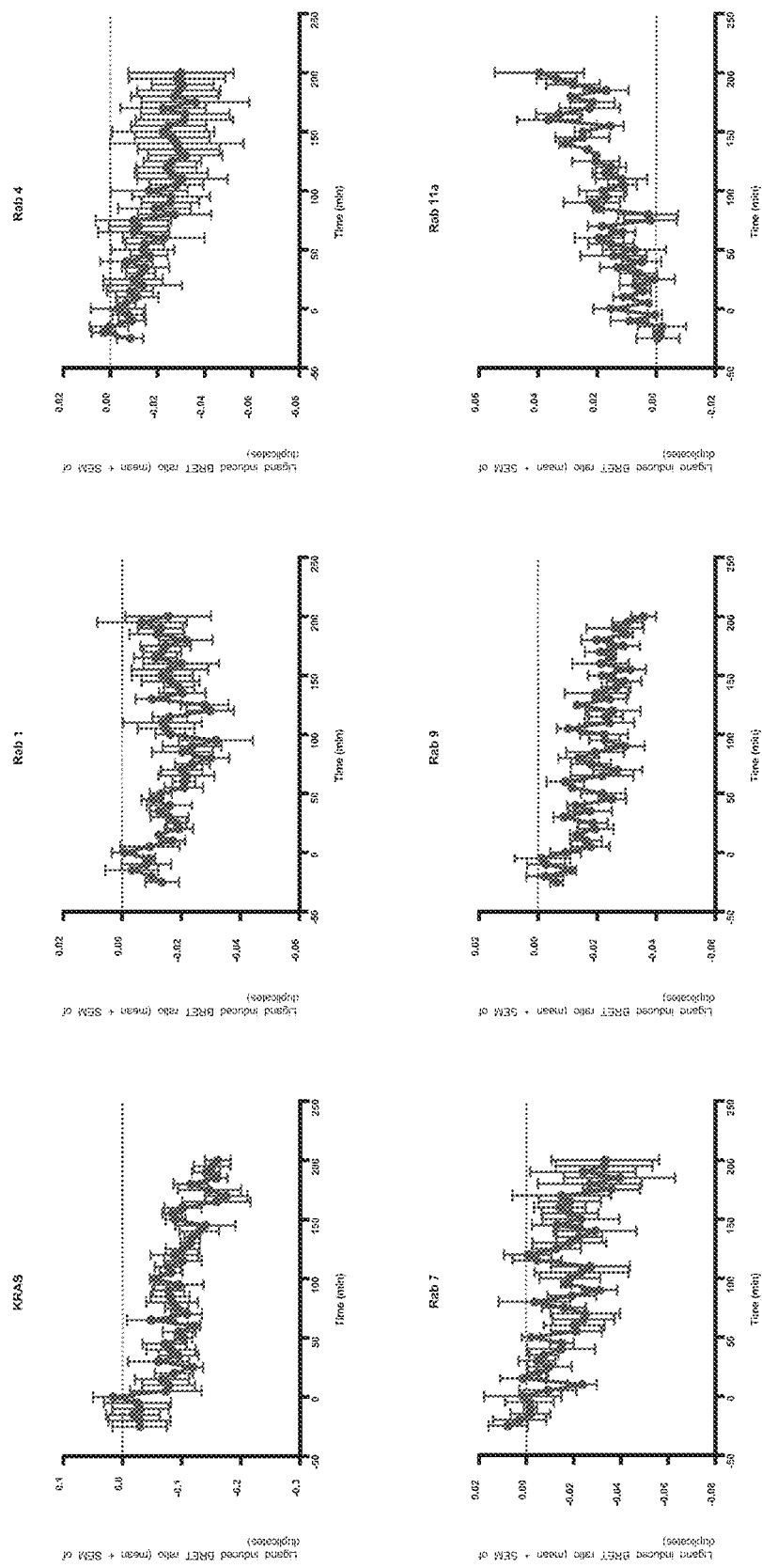

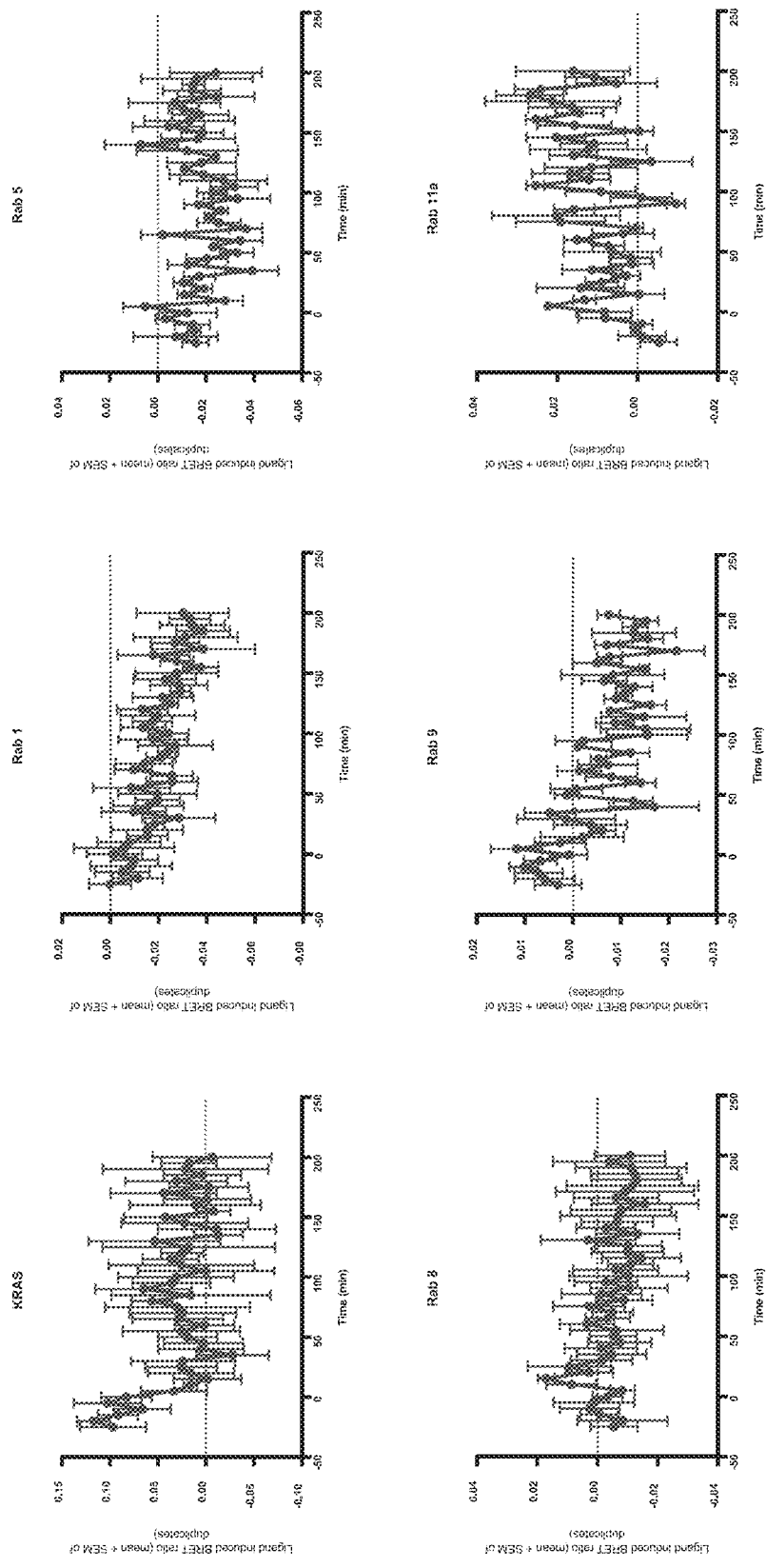
Figure 19GG: Serotonin 2C receptor + RAGE/Rluc8 + Venus-tagged KRAS or Rabs Serotonin at $10^{-5}$ M

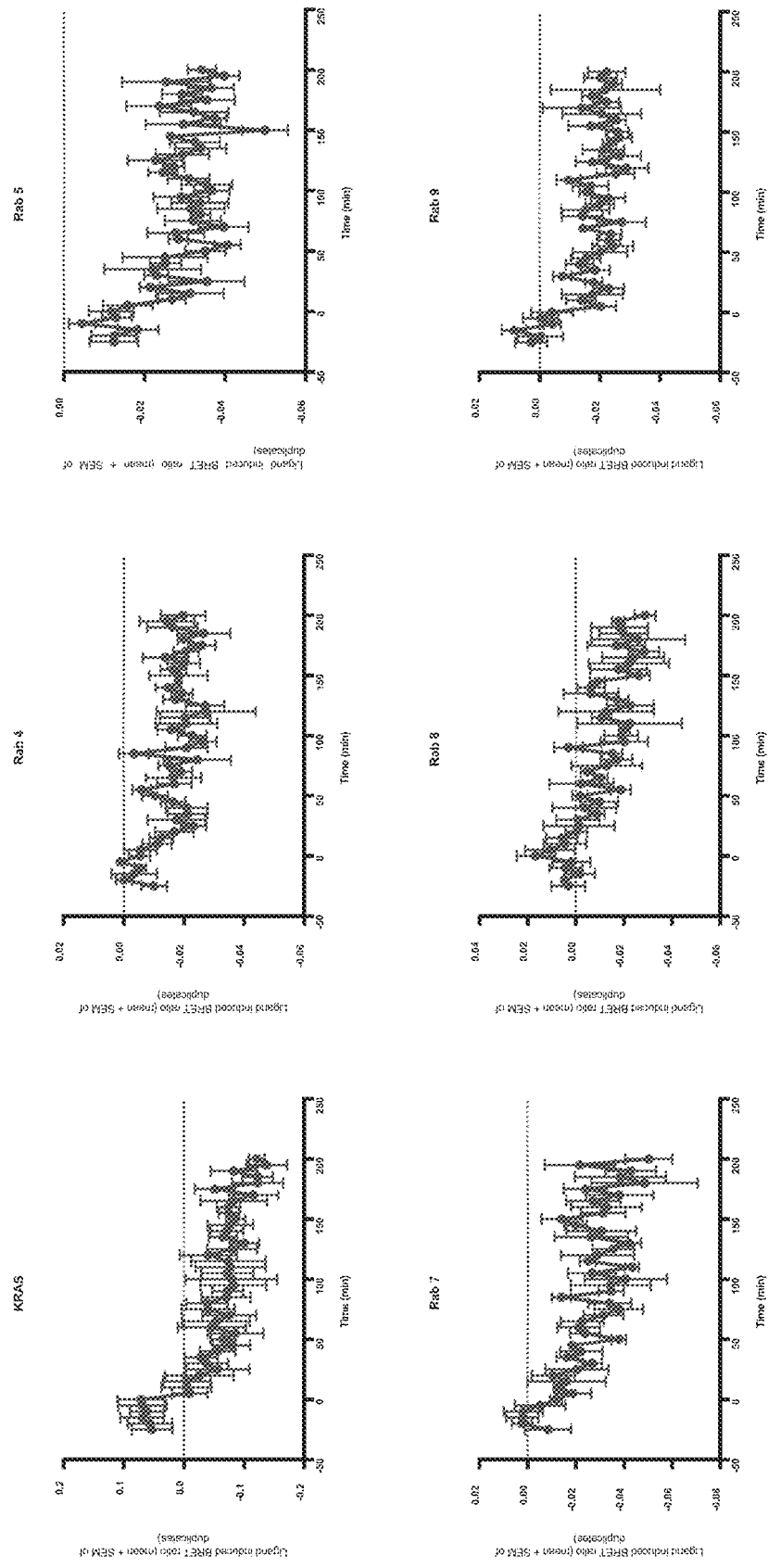

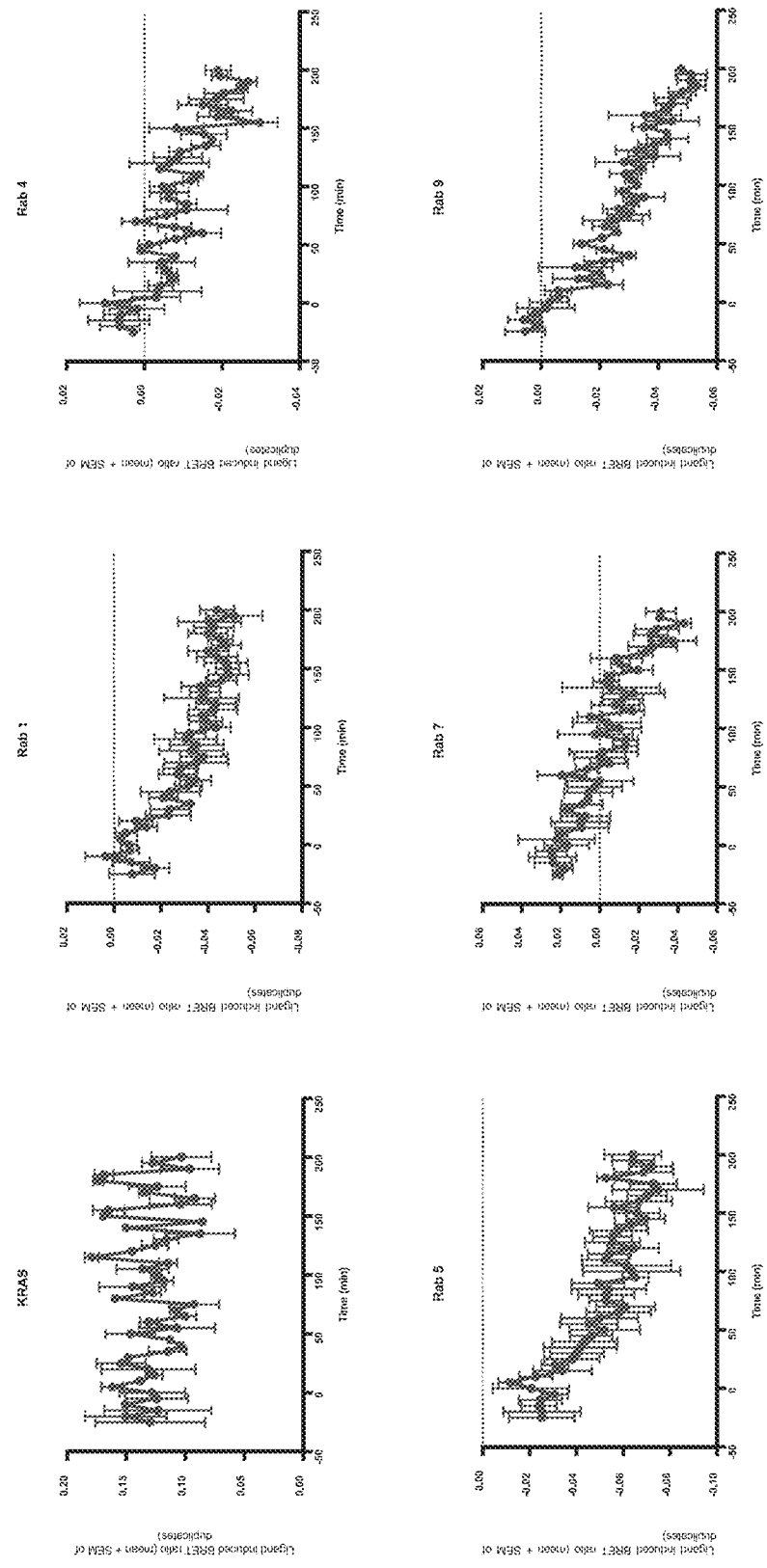
Figure 19ll: Somatostatin receptor 2 + RAGE/Rluc8 + Venus-tagged KRAS or Rabs Somatostatin at $10^{-6}$ M

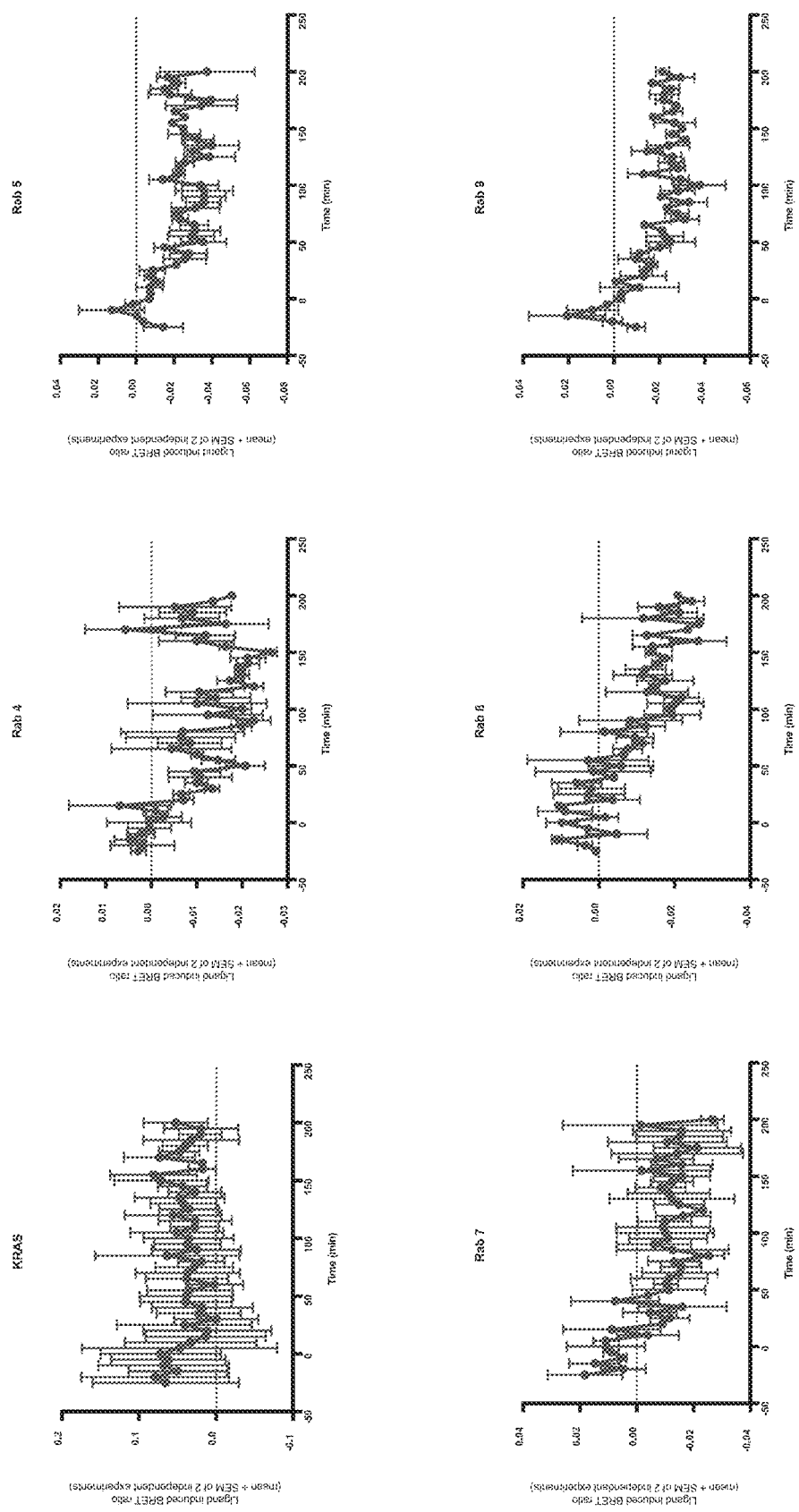
Figure 19.J: S1P receptor 1 + RAGE/Rluc8 + Venus-tagged KRAS or Rabs Sphingosine-1-phosphate at $10^{-6}$ M

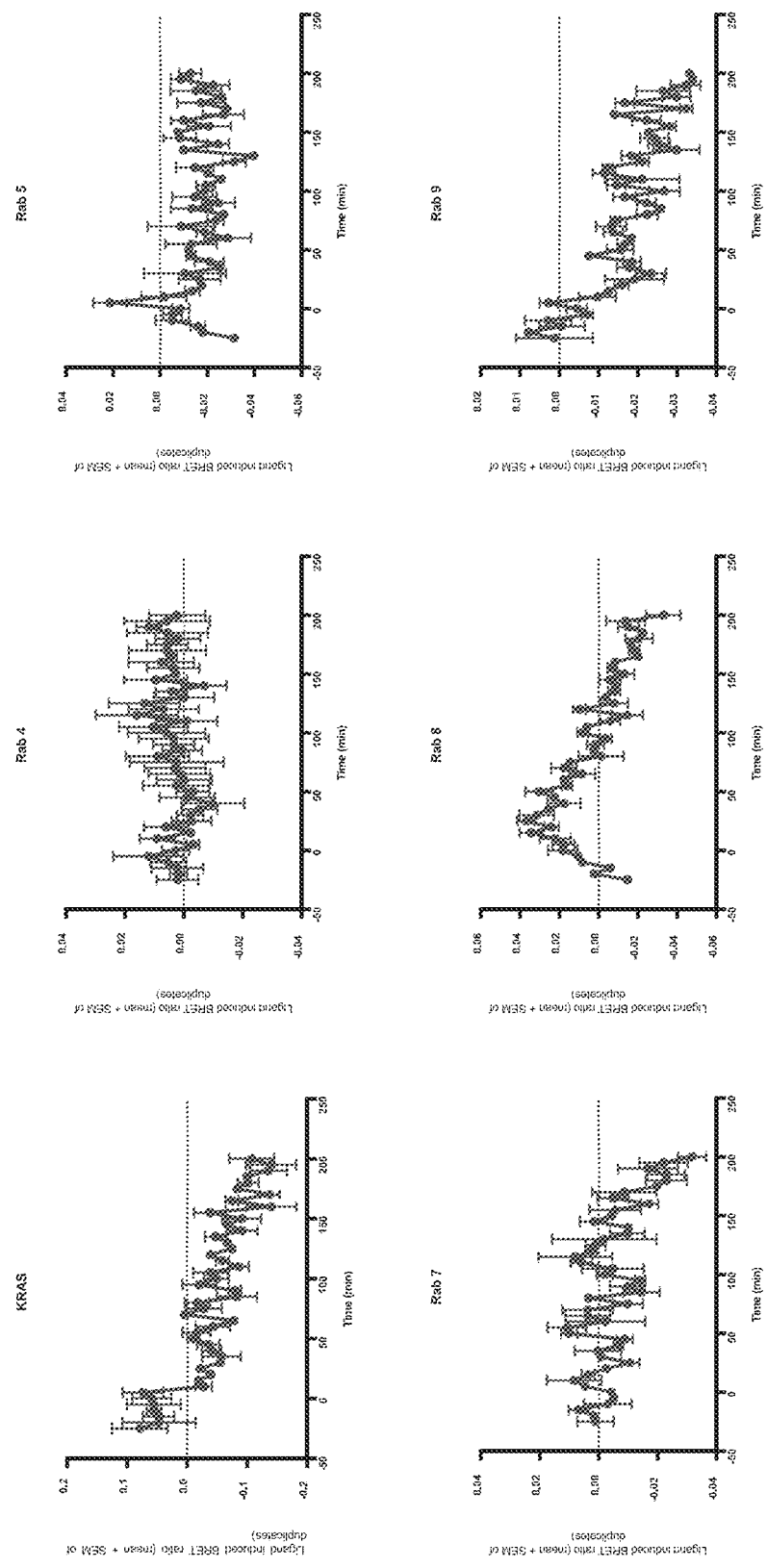
Figure 19KK: S1P receptor 3 + RAGE/Rluc8 + Venus-tagged KRAS or Rabs Sphingosine-1-phosphate at $10^{-6}$ M Thyrotropin-releasing hormone receptor 1 + RAGE/Rluc8 + Venus-tagged KRAS or Rabs
Thyrotropin-releasing hormone at $10^{-5}$ M

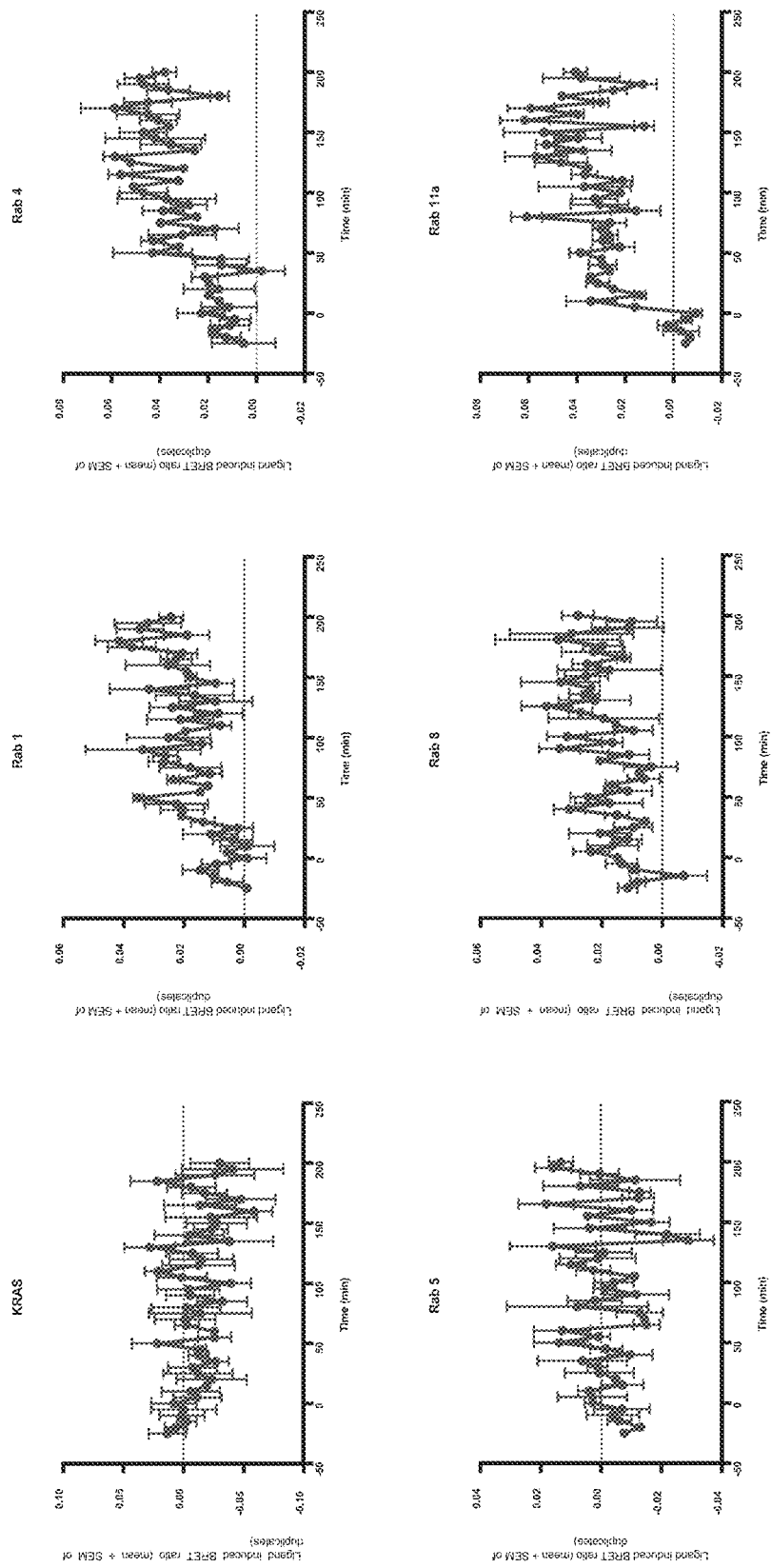

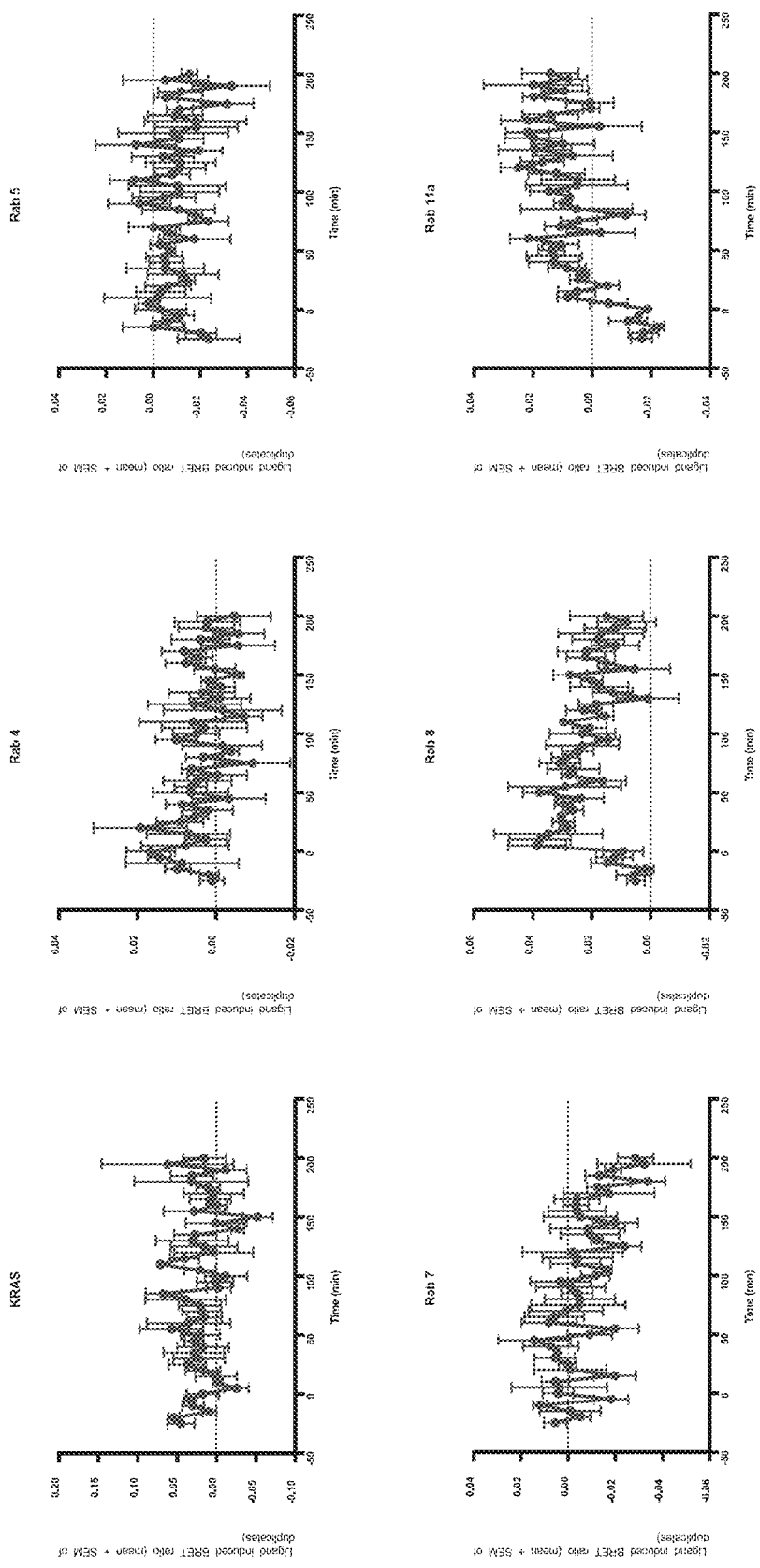
Figure 19NN: Vasopressin receptor type 1B + RAGE/Rluc8 + Venus-tagged KRAS or Rabs
Arginine vasopressin 10⁻⁶ M

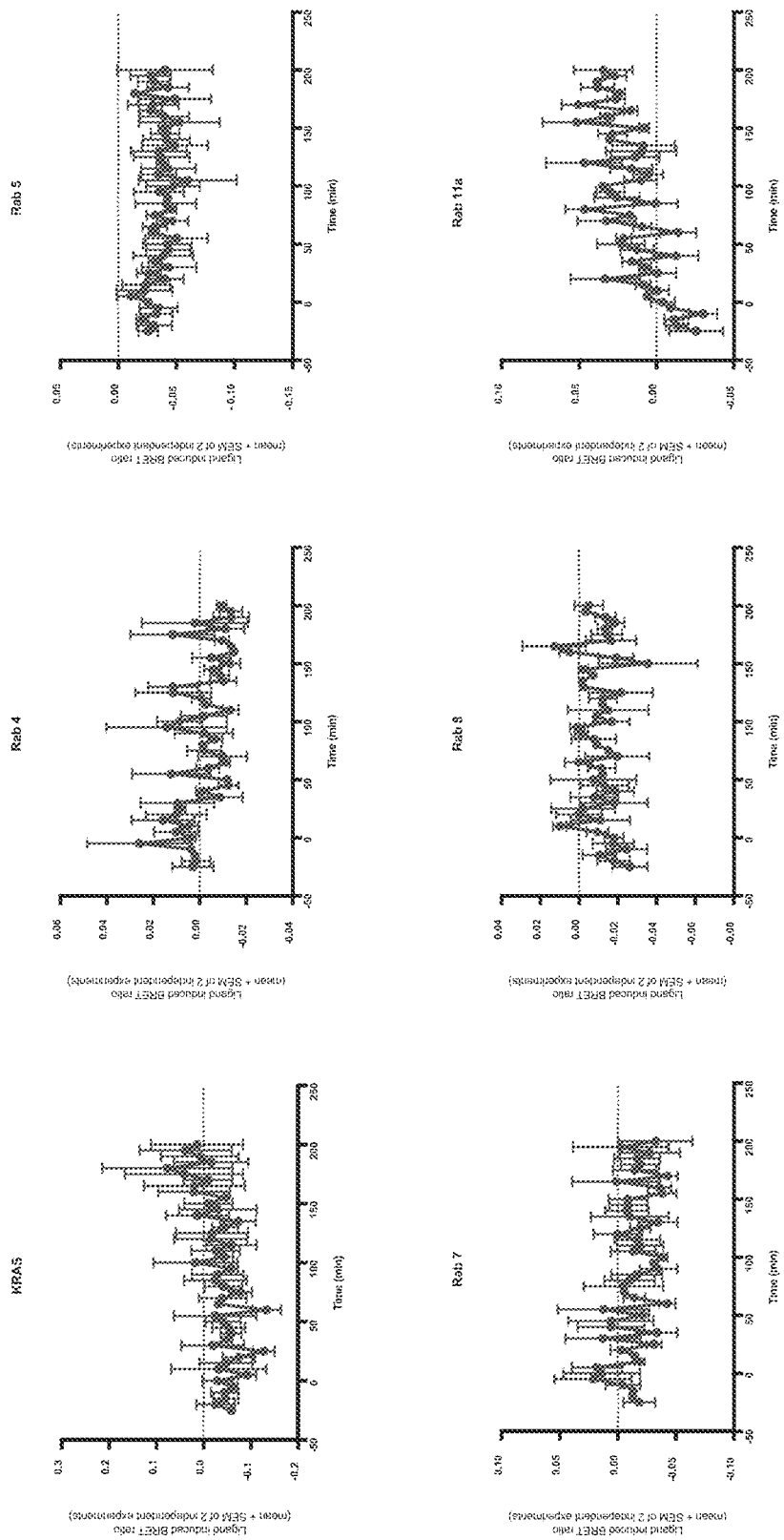
Figure 19OO: Vasopressin receptor type 2 + RAGE/Rluc8 + Venus-tagged KRAS or Rabs
Arginine vasopressin $10^{-6}$ M Example 20

Example 21

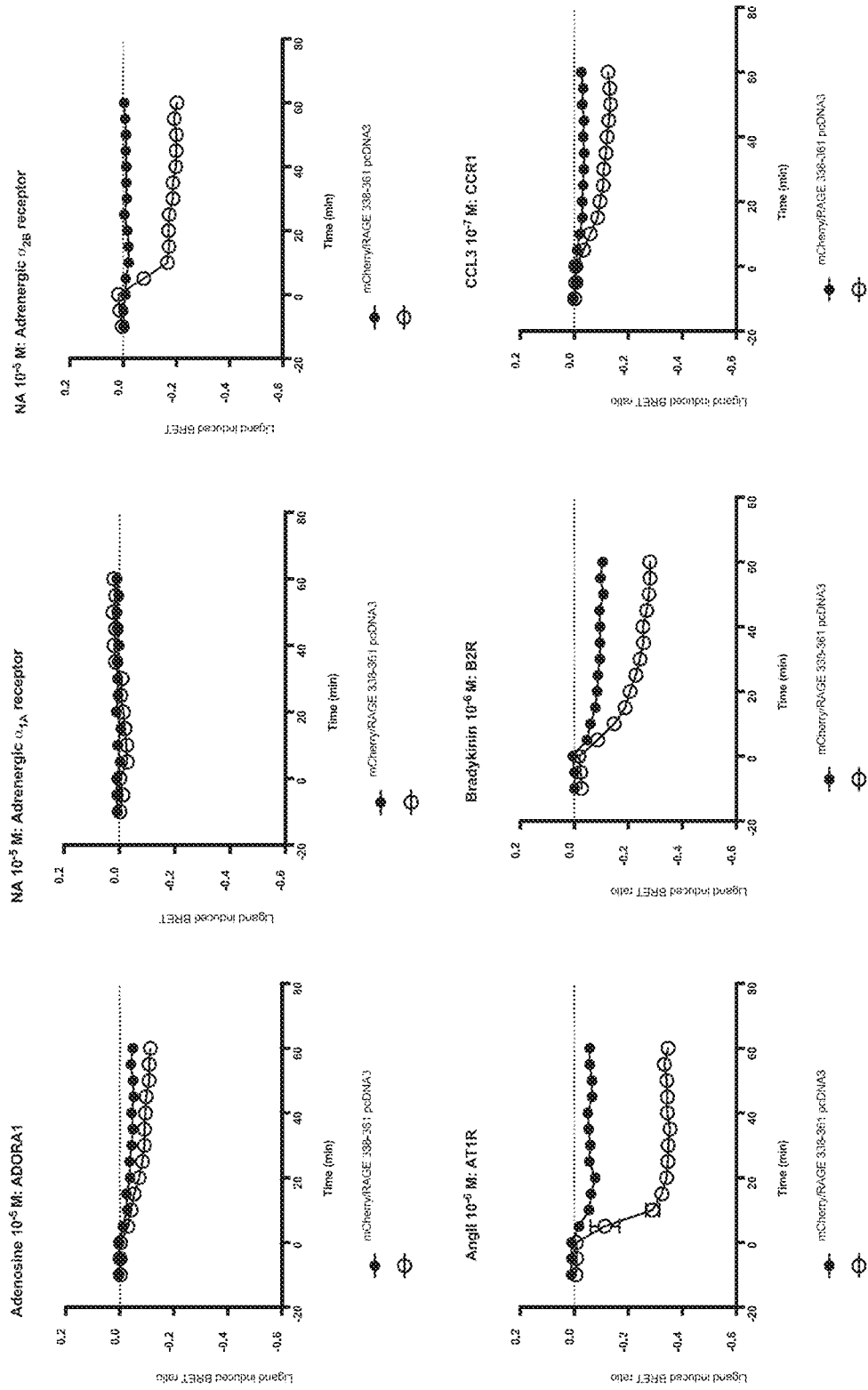

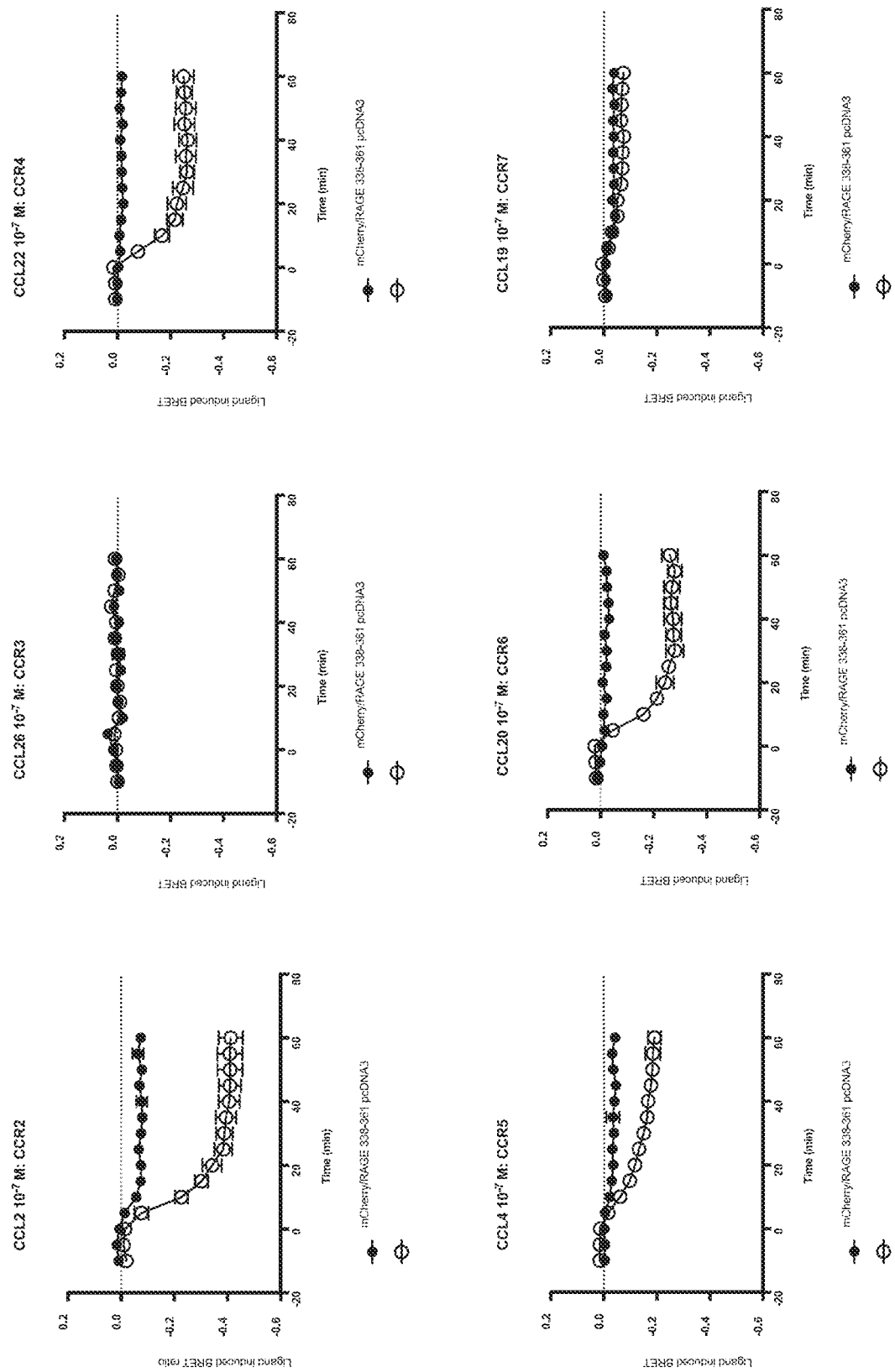

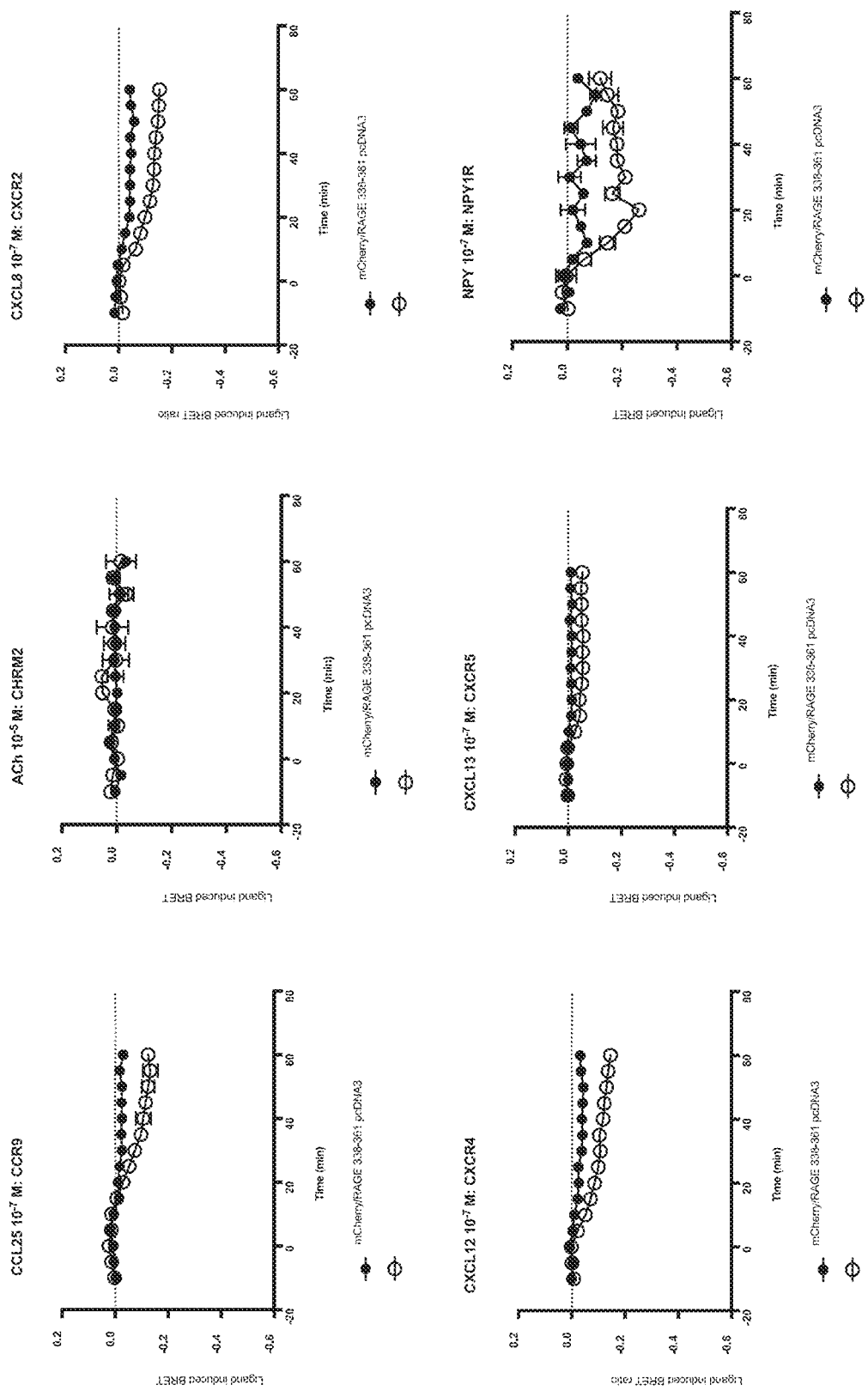

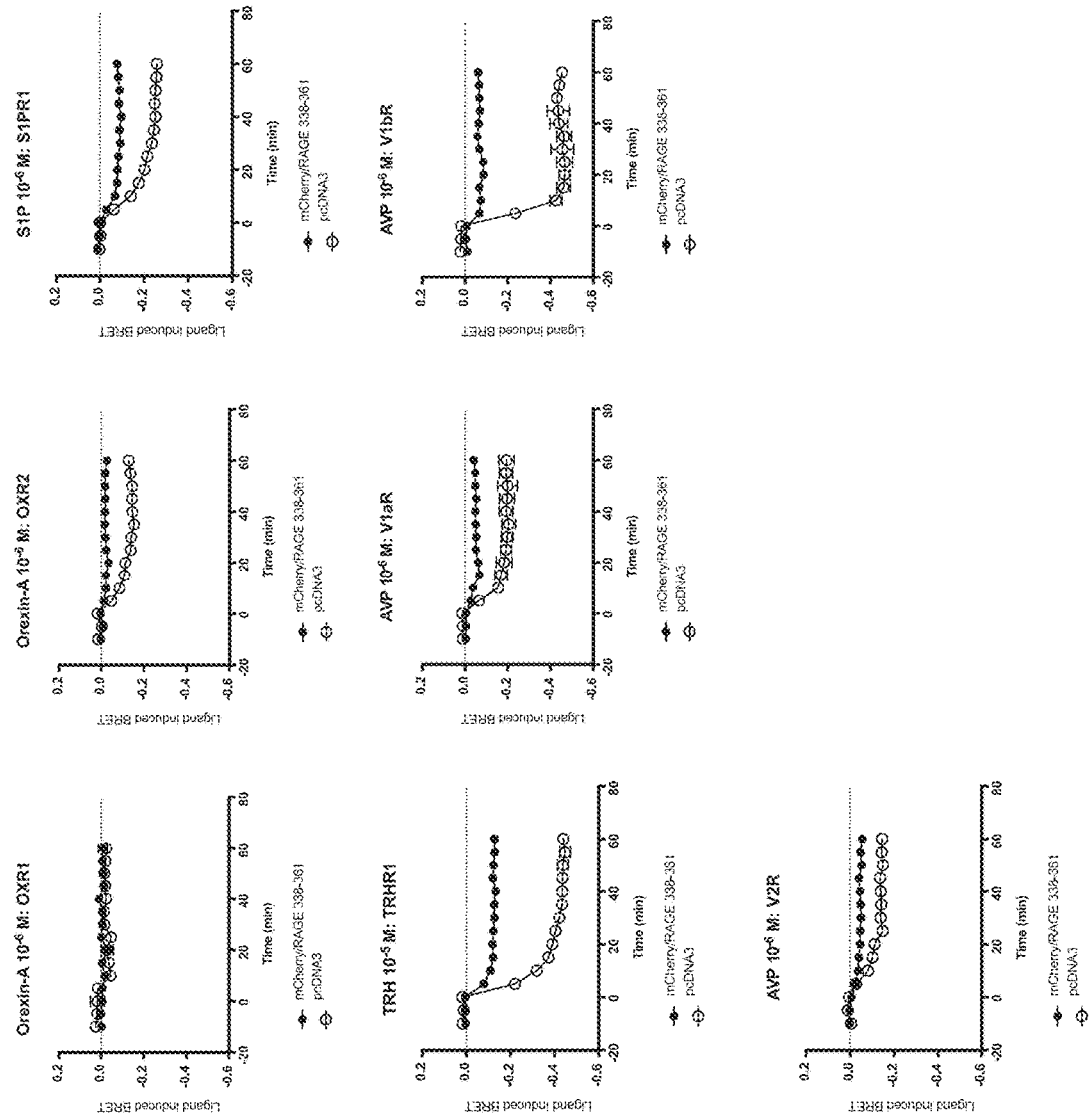

SEQUENCE LISTING

```
<160> NUMBER OF SEQ ID NOS: 61

<210> SEQ ID NO 1
<211> LENGTH: 43
<212> TYPE: PRT
<213> ORGANISM: Homo sapiens

<400> SEQUENCE: 1

Leu Trp Gln Arg Arg Gln Arg Arg Gly Glu Glu Arg Lys Ala Pro Glu
1               5                   10                  15

Asn Gln Glu Glu Glu Glu Glu Arg Ala Glu Leu Asn Gln Ser Glu Glu
            20                  25                  30

Pro Glu Ala Gly Glu Ser Ser Thr Gly Gly Pro
        35                  40

<210> SEQ ID NO 2
<211> LENGTH: 43
<212> TYPE: PRT
<213> ORGANISM: Homo sapiens

<400> SEQUENCE: 2

Leu Trp Gln Arg Arg Gln Arg Arg Gly Glu Glu Arg Lys Ala Pro Glu
1               5                   10                  15

Asn Gln Glu Glu Glu Glu Glu Arg Ala Glu Leu Asn Gln Ala Glu Glu
            20                  25                  30

Pro Glu Ala Gly Glu Ser Ser Thr Gly Gly Pro
        35                  40

<210> SEQ ID NO 3
<211> LENGTH: 24
<212> TYPE: PRT
<213> ORGANISM: Homo sapiens

<400> SEQUENCE: 3
```

```
Leu Gly Thr Leu Ala Leu Ala Leu Gly Ile Leu Gly Gly Leu Gly Thr
1               5                   10                  15

Ala Ala Leu Leu Ile Gly Val Ile
            20
```

<210> SEQ ID NO 4
<211> LENGTH: 11
<212> TYPE: PRT
<213> ORGANISM: Homo sapiens

<400> SEQUENCE: 4

```
Tyr Gly Arg Lys Lys Arg Arg Gln Arg Arg Arg
1               5                   10
```

<210> SEQ ID NO 5
<211> LENGTH: 21
<212> TYPE: PRT
<213> ORGANISM: Homo sapiens

<400> SEQUENCE: 5

```
Gly Glu Glu Arg Lys Ala Pro Glu Asn Gln Glu Glu Glu Glu Glu Arg
1               5                   10                  15

Ala Glu Leu Asn Gln
            20
```

<210> SEQ ID NO 6
<211> LENGTH: 12
<212> TYPE: PRT
<213> ORGANISM: Homo sapiens

<400> SEQUENCE: 6

```
Gln Glu Glu Glu Glu Glu Arg Ala Glu Leu Asn Gln
1               5                   10
```

<210> SEQ ID NO 7
<211> LENGTH: 30
<212> TYPE: PRT
<213> ORGANISM: Homo sapiens

<400> SEQUENCE: 7

```
Leu Trp Gln Arg Arg Gln Arg Arg Gly Glu Glu Arg Lys Ala Pro Glu
1               5                   10                  15

Asn Gln Glu Glu Glu Glu Glu Arg Ala Glu Leu Asn Gln Ala
            20                  25                  30
```

<210> SEQ ID NO 8
<211> LENGTH: 29
<212> TYPE: PRT
<213> ORGANISM: Homo sapiens

<400> SEQUENCE: 8

```
Leu Trp Gln Arg Arg Gln Arg Arg Gly Glu Glu Arg Lys Ala Pro Glu
1               5                   10                  15

Asn Gln Glu Glu Glu Glu Glu Arg Ala Glu Leu Asn Gln
            20                  25
```

<210> SEQ ID NO 9
<211> LENGTH: 12
<212> TYPE: PRT
<213> ORGANISM: Homo sapiens

<400> SEQUENCE: 9

Gln Glu Glu Glu Glu Glu Arg Ala Glu Leu Asn Arg
1               5                   10

<210> SEQ ID NO 10
<211> LENGTH: 12
<212> TYPE: PRT
<213> ORGANISM: Homo sapiens

<400> SEQUENCE: 10

Gln Glu Glu Glu Glu Glu Arg Ala Glu Leu Asn Lys
1               5                   10

<210> SEQ ID NO 11
<211> LENGTH: 12
<212> TYPE: PRT
<213> ORGANISM: Homo sapiens

<400> SEQUENCE: 11

Lys Glu Glu Glu Glu Glu Arg Ala Glu Leu Asn Gln
1               5                   10

<210> SEQ ID NO 12
<211> LENGTH: 12
<212> TYPE: PRT
<213> ORGANISM: Homo sapiens

<400> SEQUENCE: 12

Lys Glu Glu Glu Glu Glu Arg Ala Glu Leu Asn Lys
1               5                   10

<210> SEQ ID NO 13
<211> LENGTH: 12
<212> TYPE: PRT
<213> ORGANISM: Homo sapiens

<400> SEQUENCE: 13

Lys Glu Glu Glu Glu Glu Arg Ala Glu Leu Asn Arg
1               5                   10

<210> SEQ ID NO 14
<211> LENGTH: 404
<212> TYPE: PRT
<213> ORGANISM: Homo sapiens

<400> SEQUENCE: 14

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

```
Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Gly Leu Gly
            340                 345                 350

Thr Ala Ala Leu Leu Ile Gly Val Ile Leu Trp Gln Arg Arg Gln Arg
        355                 360                 365

Arg Gly Glu Glu Arg Lys Ala Pro Glu Asn Gln Glu Glu Glu Glu Glu
    370                 375                 380

Arg Ala Glu Leu Asn Gln Ser Glu Glu Pro Glu Ala Gly Glu Ser Ser
385                 390                 395                 400

Thr Gly Gly Pro

<210> SEQ ID NO 15
<211> LENGTH: 1704
<212> TYPE: DNA
<213> ORGANISM: Homo sapiens

<400> SEQUENCE: 15
tcatcttaaa ccaatagaat cgctcggtgg acgagagtgt ctgactcaga tatctacctc      60
ggagggagtt tctgctactt tagggaatta ttgactgggc tttggggttg aacttttttt     120
tttttaaaga aagaaaaaga aaccctggga tccatctatt tttttttgttg ttgttggttt     180 ttgttgttgg tggtggtggt ggtggtggtg gttcttaatt tttaatttag tttggggaag     240
tagcttgttt tttttttttat aaatatgttg atttcttgtc tttttttttt atttcttact     300
ttcccatatt agggtagcc atgaaagggg tactggtaag agaaaggggg acaaacagaa     360
ctggtaaaga ggccccctg gctccaggcc tgtccatcag gaagtaaatt ttacagggca     420
ccaagctttg ccccctaaaa tcccttaggt gttctttgtt catgcaggca ggtttctgcc     480
gcatttgatg tggaggcagt gaagggcttg ccctgctggc ctctcatccc ccttcttccc     540
```

```
acaacccttg ggcagggctg gactcagtaa ttttgaggaa attgaagatg ccatcttccc      600
ctgtgagtga catgtcttta atttttaaa aaactactat ttgaaaattg gagggggaag      660
aatgggaagg gagttattgc caaatatgtt aaatatgggt tggggtgctt gtatatgtat      720
cttcctcaat ttccccataa atgaggtatc ttttgtcac accaaaatca aggggtaggg      780
agagggagga ggttgcaaaa agccagatgt gggggaaaag taacatcaac actgtcccat      840
cctcagccct gaactagcta ccatctgatc ccctcagaca ttctcaggat tttacaagac      900
tgtcagagtg gggaacccct cccattaaag atccgggcag gactgggaca ggttggaagt      960
gtgatgggtg ggggggtggg aggcatgggc cggggggcagt tctctcctca cttgtaaact     1020
tgtgtagttt cacagaaaaa aaacaaaatg cagttttaaa taaagaaatt tctttttttc     1080
cctgggttta gttgagaatt tttttcaaaa aacatgagaa accccagaaa aaaaatgatt     1140
ttctttcacg aagttccaaa caggtttctc tcctgttccc cagccttgcc ttcatgatgc     1200
aggcccaatt gcaccettgc agacaacagt ctggcctgaa ccctattgat gcaactttgc     1260
gcaatcaaga tggggctcca gtgggtcacc aggcagccct gatggactga tggaataaat     1320
aggatcgggg gctctgaggg aatgagaccc tagagggtac actccccatc ccccagggaa     1380
gtgactgtac ccagaggctg gtagtaccca ggggtgggt gataattatt tctctagtac     1440
ctgaaggact cttgtcccaa aggcatgaat tcctagcatt ccctgtgaca agacgactga     1500
aagatggggg ctggagagag ggtgcaggcc ccacctaggg cggaggccac agcagggaga     1560
ggggcagaca gagccaggac cctggaagga agcaggatgg cagccggaac agcagttgga     1620
gcctgggtgc tggtcctcag tcttggggtg agccactccc tcaacccccac tgaccctccc     1680
tgcagaaagc actttaaccc caca                                              1704
```

<210> SEQ ID NO 16
<211> LENGTH: 359
<212> TYPE: PRT
<213> ORGANISM: Homo sapiens

<400> SEQUENCE: 16

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Val Gly Ile Phe Gly Asn Ser Leu
            35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn

```
                    165                 170                 175
Ile Thr Val Cys Ala Phe His Tyr Glu Ser Gln Asn Ser Thr Leu Pro
                180                 185                 190

Ile Gly Leu Gly Leu Thr Lys Asn Ile Leu Gly Phe Leu Phe Pro Phe
            195                 200                 205

Leu Ile Ile Leu Thr Ser Tyr Thr Leu Ile Trp Lys Ala Leu Lys Lys
        210                 215                 220

Ala Tyr Glu Ile Gln Lys Asn Lys Pro Arg Asn Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
                260                 265                 270

Asp Cys Arg Ile Ala Asp Ile Val Asp Thr Ala Met Pro Ile Thr Ile
            275                 280                 285

Cys Ile Ala Tyr Phe Asn Asn Cys Leu Asn Pro Leu Phe Tyr Gly Phe
        290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
            340                 345                 350

Ala Pro Cys Phe Glu Val Glu
        355

<210> SEQ ID NO 17
<211> LENGTH: 326
<212> TYPE: PRT
<213> ORGANISM: Homo sapiens

<400> SEQUENCE: 17

Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
                20                  25                  30

Ala Val Lys Val Asn Gln Ala Leu Arg Asp Ala Thr Phe Cys Phe Ile
            35                  40                  45

Val Ser Leu Ala Val Ala Asp Val Ala Val Gly Ala Leu Val Ile Pro
        50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
                85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Val Ala Ile
            115                 120                 125

Ala Gly Cys Trp Ile Leu Ser Phe Val Val Gly Leu Thr Pro Met Phe
        130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
                165                 170                 175
```

```
Met Glu Tyr Met Val Tyr Phe Asn Phe Val Trp Val Leu Pro Pro
            180                 185                 190

Leu Leu Leu Met Val Leu Ile Tyr Leu Glu Val Phe Tyr Leu Ile Arg
            195                 200                 205

Lys Gln Leu Asn Lys Lys Val Ser Ala Ser Ser Gly Asp Pro Gln Lys
210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
            245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
            275                 280                 285

Ala Phe Arg Ile Gln Lys Phe Arg Val Thr Phe Leu Lys Ile Trp Asn
            290                 295                 300

Asp His Phe Arg Cys Gln Pro Ala Pro Pro Ile Asp Glu Asp Leu Pro
305                 310                 315                 320

Glu Glu Arg Pro Asp Asp
                325

<210> SEQ ID NO 18
<211> LENGTH: 427
<212> TYPE: PRT
<213> ORGANISM: Homo sapiens

<400> SEQUENCE: 18

Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
            35                  40                  45

Leu Ser Val Ala Cys His Arg His Leu His Ser Val Thr His Tyr Tyr
50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
            85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
            115                 120                 125

Ser Tyr Pro Leu Arg Tyr Pro Thr Ile Val Thr Gln Arg Arg Gly Leu
130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
            165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
            195                 200                 205

Val Val Ala Lys Arg Glu Ser Arg Gly Leu Lys Ser Gly Leu Lys Thr
            210                 215                 220
```

```
Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
            245                 250                 255

Phe Ser Val Arg Leu Leu Lys Phe Ser Arg Glu Lys Lys Ala Ala Lys
        260                 265                 270

Thr Leu Gly Ile Val Gly Cys Phe Val Leu Cys Trp Leu Pro Phe
    275                 280                 285

Phe Leu Val Met Pro Ile Gly Ser Phe Phe Pro Asp Phe Lys Pro Ser
290                 295                 300

Glu Thr Val Phe Lys Ile Val Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Cys Arg Lys Gln Ser Ser
            340                 345                 350

Lys His Ala Leu Gly Tyr Thr Leu His Pro Pro Ser Gln Ala Val Glu
        355                 360                 365

Gly Gln His Lys Asp Met Val Arg Ile Pro Val Gly Ser Arg Glu Thr
    370                 375                 380

Phe Tyr Arg Ile Ser Lys Thr Asp Gly Val Cys Glu Trp Lys Phe Phe
385                 390                 395                 400

Ser Ser Met Pro Arg Gly Ser Ala Arg Ile Thr Val Ser Lys Asp Gln
                405                 410                 415

Ser Ser Cys Thr Thr Ala Arg Ser Ser Gly Phe
            420                 425

<210> SEQ ID NO 19
<211> LENGTH: 520
<212> TYPE: PRT
<213> ORGANISM: Homo sapiens

<400> SEQUENCE: 19

Met Asn Pro Asp Leu Asp Thr Gly His Asn Thr Ser Ala Pro Ala His
1               5                   10                  15

Trp Gly Glu Leu Lys Asn Ala Asn Phe Thr Gly Pro Asn Gln Thr Ser
            20                  25                  30

Ser Asn Ser Thr Leu Pro Gln Leu Asp Ile Thr Arg Ala Ile Ser Val
        35                  40                  45

Gly Leu Val Leu Gly Ala Phe Ile Leu Phe Ala Ile Val Gly Asn Ile
    50                  55                  60

Leu Val Ile Leu Ser Val Ala Cys Asn Arg His Leu Arg Thr Pro Thr
65                  70                  75                  80

Asn Tyr Phe Ile Val Asn Leu Ala Met Ala Asp Leu Leu Leu Ser Phe
                85                  90                  95

Thr Val Leu Pro Phe Ser Ala Ala Leu Glu Val Leu Gly Tyr Trp Val
            100                 105                 110

Leu Gly Arg Ile Phe Cys Asp Ile Trp Ala Ala Val Asp Val Leu Cys
        115                 120                 125

Cys Thr Ala Ser Ile Leu Ser Leu Cys Ala Ile Ser Ile Asp Arg Tyr
    130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
```

165                 170                 175
Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Val Arg Ile Leu Gly Cys Gln Cys Arg
        355                 360                 365

Gly Arg Gly Arg Arg Arg Arg Arg Arg Arg Arg Leu Gly Gly Cys
    370                 375                 380

Ala Tyr Thr Tyr Arg Pro Trp Thr Arg Gly Gly Ser Leu Glu Arg Ser
385                 390                 395                 400

Gln Ser Arg Lys Asp Ser Leu Asp Asp Ser Gly Ser Cys Leu Ser Gly
                405                 410                 415

Ser Gln Arg Thr Leu Pro Ser Ala Ser Pro Ser Pro Gly Tyr Leu Gly
            420                 425                 430

Arg Gly Ala Pro Pro Val Glu Leu Cys Ala Phe Pro Glu Trp Lys
        435                 440                 445

Ala Pro Gly Ala Leu Leu Ser Leu Pro Ala Pro Glu Pro Pro Gly Arg
    450                 455                 460

Arg Gly Arg His Asp Ser Gly Pro Leu Phe Thr Phe Lys Leu Leu Thr
465                 470                 475                 480

Glu Pro Glu Ser Pro Gly Thr Asp Gly Gly Ala Ser Asn Gly Gly Cys
                485                 490                 495

Glu Ala Ala Ala Asp Val Ala Asn Gly Gln Pro Gly Phe Lys Ser Asn
            500                 505                 510

Met Pro Leu Ala Pro Gly Gln Phe
        515                 520

<210> SEQ ID NO 20
<211> LENGTH: 450
<212> TYPE: PRT
<213> ORGANISM: Homo sapiens

<400> SEQUENCE: 20

Met Asp His Gln Asp Pro Tyr Ser Val Gln Ala Thr Ala Ala Ile Ala
1               5                   10                  15

```
Ala Ala Ile Thr Phe Leu Ile Leu Phe Thr Ile Phe Gly Asn Ala Leu
             20                  25                  30

Val Ile Leu Ala Val Leu Thr Ser Arg Ser Leu Arg Ala Pro Gln Asn
         35                  40                  45

Leu Phe Leu Val Ser Leu Ala Ala Asp Ile Leu Val Ala Thr Leu
 50                  55                  60

Ile Ile Pro Phe Ser Leu Ala Asn Glu Leu Leu Gly Tyr Trp Tyr Phe
 65              70                  75                  80

Arg Arg Thr Trp Cys Glu Val Tyr Leu Ala Leu Asp Val Leu Phe Cys
                 85                  90                  95

Thr Ser Ser Ile Val His Leu Cys Ala Ile Ser Leu Asp Arg Tyr Trp
                100                 105                 110

Ala Val Ser Arg Ala Leu Glu Tyr Asn Ser Lys Arg Thr Pro Arg Arg
            115                 120                 125

Ile Lys Cys Ile Ile Leu Thr Val Trp Leu Ile Ala Ala Val Ile Ser
130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Ala Pro Cys Leu Ile Met Ile Leu Val Tyr
            180                 185                 190

Leu Arg Ile Tyr Leu Ile Ala Lys Arg Ser Asn Arg Arg Gly Pro Arg
        195                 200                 205

Ala Lys Gly Gly Pro Gly Gln Gly Glu Ser Lys Gln Pro Arg Pro Asp
210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
        275                 280                 285

Cys Gly Ala Ser Pro Glu Asp Glu Ala Glu Glu Glu Glu Glu Glu
290                 295                 300

Glu Glu Glu Glu Glu Cys Glu Pro Gln Ala Val Pro Val Ser Pro Ala
305                 310                 315                 320

Ser Ala Cys Ser Pro Pro Leu Gln Gln Pro Gln Gly Ser Arg Val Leu
                325                 330                 335

Ala Thr Leu Arg Gly Gln Val Leu Leu Gly Arg Gly Val Gly Ala Ile
            340                 345                 350

Gly Gly Gln Trp Trp Arg Arg Arg Ala Gln Leu Thr Arg Glu Lys Arg
        355                 360                 365

Phe Thr Phe Val Leu Ala Val Val Ile Gly Val Phe Val Leu Cys Trp
370                 375                 380

Phe Pro Phe Phe Phe Ser Tyr Ser Leu Gly Ala Ile Cys Pro Lys His
385                 390                 395                 400

Cys Lys Val Pro His Gly Leu Phe Gln Phe Phe Phe Trp Ile Gly Tyr
                405                 410                 415

Cys Asn Ser Ser Leu Asn Pro Val Ile Tyr Thr Ile Phe Asn Gln Asp
            420                 425                 430

Phe Arg Arg Ala Phe Arg Arg Ile Leu Cys Arg Pro Trp Thr Gln Thr
```

Ala Trp
    450

<210> SEQ ID NO 21
<211> LENGTH: 391
<212> TYPE: PRT
<213> ORGANISM: Homo sapiens

<400> SEQUENCE: 21

Met Phe Ser Pro Trp Lys Ile Ser Met Phe Leu Ser Val Arg Glu Asp
1               5                   10                  15

Ser Val Pro Thr Thr Ala Ser Phe Ser Ala Asp Met Leu Asn Val Thr
            20                  25                  30

Leu Gln Gly Pro Thr Leu Asn Gly Thr Phe Ala Gln Ser Lys Cys Pro
        35                  40                  45

Gln Val Glu Trp Leu Gly Trp Leu Asn Thr Ile Gln Pro Pro Phe Leu
    50                  55                  60

Trp Val Leu Phe Val Leu Ala Thr Leu Glu Asn Ile Phe Val Leu Ser
65                  70                  75                  80

Val Phe Cys Leu His Lys Ser Ser Cys Thr Val Ala Glu Ile Tyr Leu
                85                  90                  95

Gly Asn Leu Ala Ala Ala Asp Leu Ile Leu Ala Cys Gly Leu Pro Phe
            100                 105                 110

Trp Ala Ile Thr Ile Ser Asn Asn Phe Asp Trp Leu Phe Gly Glu Thr
        115                 120                 125

Leu Cys Arg Val Val Asn Ala Ile Ile Ser Met Asn Leu Tyr Ser Ser
    130                 135                 140

Ile Cys Phe Leu Met Leu Val Ser Ile Asp Arg Tyr Leu Ala Leu Val
145                 150                 155                 160

Lys Thr Met Ser Met Gly Arg Met Arg Gly Val Arg Trp Ala Lys Leu
                165                 170                 175

Tyr Ser Leu Val Ile Trp Gly Cys Thr Leu Leu Leu Ser Ser Pro Met
            180                 185                 190

Leu Val Phe Arg Thr Met Lys Glu Tyr Ser Asp Glu Gly His Asn Val
        195                 200                 205

Thr Ala Cys Val Ile Ser Tyr Pro Ser Leu Ile Trp Glu Val Phe Thr
    210                 215                 220

Asn Met Leu Leu Asn Val Val Gly Phe Leu Leu Pro Leu Ser Val Ile
225                 230                 235                 240

Thr Phe Cys Thr Met Gln Ile Met Gln Val Leu Arg Asn Asn Glu Met
                245                 250                 255

Gln Lys Phe Lys Glu Ile Gln Thr Glu Arg Arg Ala Thr Val Leu Val
            260                 265                 270

Leu Val Val Leu Leu Leu Phe Ile Ile Cys Trp Leu Pro Phe Gln Ile
        275                 280                 285

Ser Thr Phe Leu Asp Thr Leu His Arg Leu Gly Ile Leu Ser Ser Cys
    290                 295                 300

Gln Asp Glu Arg Ile Ile Asp Val Ile Thr Gln Ile Ala Ser Phe Met
305                 310                 315                 320

Ala Tyr Ser Asn Ser Cys Leu Asn Pro Leu Val Tyr Val Ile Val Gly
                325                 330                 335

Lys Arg Phe Arg Lys Lys Ser Trp Glu Val Tyr Gln Gly Val Cys Gln
            340                 345                 350

Lys Gly Gly Cys Arg Ser Glu Pro Ile Gln Met Glu Asn Ser Met Gly
            355                 360                 365

Thr Leu Arg Thr Ser Ile Ser Val Glu Arg Gln Ile His Lys Leu Gln
    370                 375                 380

Asp Trp Ala Gly Ser Arg Gln
385                 390

<210> SEQ ID NO 22
<211> LENGTH: 355
<212> TYPE: PRT
<213> ORGANISM: Homo sapiens

<400> SEQUENCE: 22

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

```
Glu Arg Val Ser Ser Thr Ser Pro Ser Thr Gly Glu His Glu Leu Ser
                340                 345                 350
Ala Gly Phe
        355

<210> SEQ ID NO 23
<211> LENGTH: 374
<212> TYPE: PRT
<213> ORGANISM: Homo sapiens

<400> SEQUENCE: 23

Met Leu Ser Thr Ser Arg Ser Arg Phe Ile Arg Asn Thr Asn Glu Ser
1               5                   10                  15
Gly Glu Glu Val Thr Thr Phe Phe Asp Tyr Asp Tyr Gly Ala Pro Cys
                20                  25                  30
His Lys Phe Asp Val Lys Gln Ile Gly Ala Gln Leu Leu Pro Pro Leu
            35                  40                  45
Tyr Ser Leu Val Phe Ile Phe Gly Phe Val Gly Asn Met Leu Val Val
        50                  55                  60
Leu Ile Leu Ile Asn Cys Lys Lys Leu Lys Cys Leu Thr Asp Ile Tyr
65                  70                  75                  80
Leu Leu Asn Leu Ala Ile Ser Asp Leu Leu Phe Leu Ile Thr Leu Pro
                85                  90                  95
Leu Trp Ala His Ser Ala Ala Asn Glu Trp Val Phe Gly Asn Ala Met
            100                 105                 110
Cys Lys Leu Phe Thr Gly Leu Tyr His Ile Gly Tyr Phe Gly Gly Ile
        115                 120                 125
Phe Phe Ile Ile Leu Leu Thr Ile Asp Arg Tyr Leu Ala Ile Val His
    130                 135                 140
Ala Val Phe Ala Leu Lys Ala Arg Thr Val Thr Phe Gly Val Val Thr
145                 150                 155                 160
Ser Val Ile Thr Trp Leu Val Ala Val Phe Ala Ser Val Pro Gly Ile
                165                 170                 175
Ile Phe Thr Lys Cys Gln Lys Glu Asp Ser Val Tyr Val Cys Gly Pro
            180                 185                 190
Tyr Phe Pro Arg Gly Trp Asn Asn Phe His Thr Ile Met Arg Asn Ile
        195                 200                 205
Leu Gly Leu Val Leu Pro Leu Leu Ile Met Val Ile Cys Tyr Ser Gly
    210                 215                 220
Ile Leu Lys Thr Leu Leu Arg Cys Arg Asn Glu Lys Lys Arg His Arg
225                 230                 235                 240
Ala Val Arg Val Ile Phe Thr Ile Met Ile Val Tyr Phe Leu Phe Trp
                245                 250                 255
Thr Pro Tyr Asn Ile Val Ile Leu Leu Asn Thr Phe Gln Glu Phe Phe
            260                 265                 270
Gly Leu Ser Asn Cys Glu Ser Thr Ser Gln Leu Asp Gln Ala Thr Gln
        275                 280                 285
Val Thr Glu Thr Leu Gly Met Thr His Cys Cys Ile Asn Pro Ile Ile
    290                 295                 300
Tyr Ala Phe Val Gly Glu Lys Phe Arg Ser Leu Phe His Ile Ala Leu
305                 310                 315                 320
Gly Cys Arg Ile Ala Pro Leu Gln Lys Pro Val Cys Gly Gly Pro Gly
                325                 330                 335
Val Arg Pro Gly Lys Asn Val Lys Val Thr Thr Gln Gly Leu Leu Asp
```

340                 345                 350
Gly Arg Gly Lys Gly Lys Ser Ile Gly Arg Ala Pro Glu Ala Ser Leu
                355                 360                 365
Gln Asp Lys Glu Gly Ala
    370

<210> SEQ ID NO 24
<211> LENGTH: 355
<212> TYPE: PRT
<213> ORGANISM: Homo sapiens

<400> SEQUENCE: 24

Met Thr Thr Ser Leu Asp Thr Val Glu Thr Phe Gly Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Val Pro Pro Leu Tyr Ser Leu Val Phe Thr Val Gly
            35                  40                  45

Leu Leu Gly Asn Val Val Val Val Met Ile Leu Ile Lys Tyr Arg Arg
        50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
                100                 105                 110

Tyr His Thr Gly Leu Tyr Ser Glu Ile Phe Phe Ile Ile Leu Leu Thr
                115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Phe Cys Leu
                195                 200                 205

Val Leu Pro Leu Leu Val Met Ala Ile Cys Tyr Thr Gly Ile Ile Lys
                210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
                260                 265                 270

Cys Glu Arg Ser Lys His Leu Asp Leu Val Met Leu Val Thr Glu Val
                275                 280                 285

Ile Ala Tyr Ser His Cys Cys Met Asn Pro Val Ile Tyr Ala Phe Val
                290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

```
Glu Arg Thr Ser Ser Val Ser Pro Thr Ala Glu Pro Glu Leu Ser
                340                 345                 350

Ile Val Phe
        355

<210> SEQ ID NO 25
<211> LENGTH: 360
<212> TYPE: PRT
<213> ORGANISM: Homo sapiens

<400> SEQUENCE: 25

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Tyr Thr Gln Ser Thr Met
            340                 345                 350
```

```
Asp His Asp Leu His Asp Ala Leu
        355                 360

<210> SEQ ID NO 26
<211> LENGTH: 352
<212> TYPE: PRT
<213> ORGANISM: Homo sapiens

<400> SEQUENCE: 26

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
            35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
            275                 280                 285

His Cys Cys Ile Asn Pro Ile Ile Tyr Ala Phe Val Gly Glu Lys Phe
            290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
            325                 330                 335

Ser Val Tyr Thr Arg Ser Thr Gly Glu Gln Glu Ile Ser Val Gly Leu
            340                 345                 350
```

```
<210> SEQ ID NO 27
<211> LENGTH: 374
<212> TYPE: PRT
<213> ORGANISM: Homo sapiens

<400> SEQUENCE: 27

Met Ser Gly Glu Ser Met Asn Phe Ser Asp Val Phe Asp Ser Glu
1               5                   10                  15

Asp Tyr Phe Val Ser Val Asn Thr Ser Tyr Tyr Ser Val Asp Ser Glu
                20                  25                  30

Met Leu Leu Cys Ser Leu Gln Glu Val Arg Gln Phe Ser Arg Leu Phe
                35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
                100                 105                 110

Phe Ser Asn Ala Thr Cys Lys Leu Leu Lys Gly Ile Tyr Ala Ile Asn
                115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
                180                 185                 190

Gly Ser Asp Val Cys Glu Pro Lys Tyr Gln Thr Val Ser Glu Pro Ile
                195                 200                 205

Arg Trp Lys Leu Leu Met Leu Gly Leu Glu Leu Leu Phe Gly Phe Phe
    210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
                260                 265                 270

Val Leu Leu Val Thr Ala Ala Asn Leu Gly Lys Met Asn Arg Ser Cys
                275                 280                 285

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
                355                 360                 365

Ala Ser Ser Phe Thr Met
    370
```

<210> SEQ ID NO 28
<211> LENGTH: 378
<212> TYPE: PRT
<213> ORGANISM: Homo sapiens

<400> SEQUENCE: 28

```
Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp
                20                  25                  30

Ile Gly Asp Asn Thr Thr Val Asp Tyr Thr Leu Phe Glu Ser Leu Cys
                35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                    85                  90                  95

Leu Leu Asn Leu Ala Val Ala Asp Ile Leu Phe Leu Leu Thr Leu Pro
                100                 105                 110

Phe Trp Ala Tyr Ser Ala Ala Lys Ser Trp Val Phe Gly Val His Phe
                115                 120                 125

Cys Lys Leu Ile Phe Ala Ile Tyr Lys Met Ser Phe Phe Ser Gly Met
                130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
                180                 185                 190

Glu Leu Leu Tyr Ser Asp Leu Gln Arg Ser Ser Ser Glu Gln Ala Met
                195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
                260                 265                 270

Ile Val Phe Gln Leu Pro Tyr Asn Gly Val Val Leu Ala Gln Thr Val
    275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
                370                 375
```

<210> SEQ ID NO 29
<211> LENGTH: 369
<212> TYPE: PRT
<213> ORGANISM: Homo sapiens

<400> SEQUENCE: 29

```
Met Thr Pro Thr Asp Phe Thr Ser Pro Ile Pro Asn Met Ala Asp Asp
1               5                   10                  15
Tyr Gly Ser Glu Ser Thr Ser Ser Met Glu Asp Tyr Val Asn Phe Asn
                20                  25                  30
Phe Thr Asp Phe Tyr Cys Glu Lys Asn Asn Val Arg Gln Phe Ala Ser
            35                  40                  45
His Phe Leu Pro Pro Leu Tyr Trp Leu Val Phe Ile Val Gly Ala Leu
        50                  55                  60
Gly Asn Ser Leu Val Ile Leu Val Tyr Trp Tyr Cys Thr Arg Val Lys
65                  70                  75                  80
Thr Met Thr Asp Met Phe Leu Leu Asn Leu Ala Ile Ala Asp Leu Leu
                85                  90                  95
Phe Leu Val Thr Leu Pro Phe Trp Ala Ile Ala Ala Asp Gln Trp
            100                 105                 110
Lys Phe Gln Thr Phe Met Cys Lys Val Val Asn Ser Met Tyr Lys Met
        115                 120                 125
Asn Phe Tyr Ser Cys Val Leu Leu Ile Met Cys Ile Ser Val Asp Arg
130                 135                 140
Tyr Ile Ala Ile Ala Gln Ala Met Arg Ala His Thr Trp Arg Glu Lys
145                 150                 155                 160
Arg Leu Leu Tyr Ser Lys Met Val Cys Phe Thr Ile Trp Val Leu Ala
                165                 170                 175
Ala Ala Leu Cys Ile Pro Glu Ile Leu Tyr Ser Gln Ile Lys Glu Glu
            180                 185                 190
Ser Gly Ile Ala Ile Cys Thr Met Val Tyr Pro Ser Asp Glu Ser Thr
        195                 200                 205
Lys Leu Lys Ser Ala Val Leu Thr Leu Lys Val Ile Leu Gly Phe Phe
210                 215                 220
Leu Pro Phe Val Val Met Ala Cys Cys Tyr Thr Ile Ile His Thr
225                 230                 235                 240
Leu Ile Gln Ala Lys Lys Ser Lys His Lys Ala Leu Lys Val Thr
                245                 250                 255
Ile Thr Val Leu Thr Val Phe Val Leu Ser Gln Phe Pro Tyr Asn Cys
            260                 265                 270
Ile Leu Leu Val Gln Thr Ile Asp Ala Tyr Ala Met Phe Ile Ser Asn
        275                 280                 285
Cys Ala Val Ser Thr Asn Ile Asp Ile Cys Phe Gln Val Thr Gln Thr
290                 295                 300
Ile Ala Phe Phe His Ser Cys Leu Asn Pro Val Leu Tyr Val Phe Val
305                 310                 315                 320
Gly Glu Arg Phe Arg Arg Asp Leu Val Lys Thr Leu Lys Asn Leu Gly
                325                 330                 335
Cys Ile Ser Gln Ala Gln Trp Val Ser Phe Thr Arg Arg Glu Gly Ser
            340                 345                 350
Leu Lys Leu Ser Ser Met Leu Leu Glu Thr Thr Ser Gly Ala Leu Ser
        355                 360                 365
Leu
```

<210> SEQ ID NO 30
<211> LENGTH: 360
<212> TYPE: PRT
<213> ORGANISM: Homo sapiens

<400> SEQUENCE: 30

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 31
<211> LENGTH: 352
<212> TYPE: PRT
<213> ORGANISM: Homo sapiens

<400> SEQUENCE: 31

Met Glu Gly Ile Ser Ile Tyr Thr Ser Asp Asn Tyr Thr Glu Met
1               5                   10                  15

Gly Ser Gly Asp Tyr Asp Ser Met Lys Glu Pro Cys Phe Arg Glu
                20                  25                  30

Asn Ala Asn Phe Asn Lys Ile Phe Leu Pro Thr Ile Tyr Ser Ile
                35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Phe Gln Phe Gln His Ile Met Val Gly Leu
    195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 32
<211> LENGTH: 372
<212> TYPE: PRT
<213> ORGANISM: Homo sapiens

```
<400> SEQUENCE: 32

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 33
<211> LENGTH: 342
<212> TYPE: PRT
<213> ORGANISM: Homo sapiens
```

<400> SEQUENCE: 33

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
                20                  25                  30

Phe Leu Pro Cys Met Tyr Leu Val Phe Val Cys Gly Leu Val Gly
            35                  40                  45

Asn Ser Leu Val Leu Val Ile Ser Ile Phe Tyr His Lys Leu Gln Ser
        50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
                100                 105                 110

Phe Tyr Thr Ser Met Leu Ile Leu Thr Cys Ile Thr Val Asp Arg Phe
            115                 120                 125

Ile Val Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 34
<211> LENGTH: 362
<212> TYPE: PRT
<213> ORGANISM: Homo sapiens

<400> SEQUENCE: 34

Met Asp Leu His Leu Phe Asp Tyr Ser Glu Pro Gly Asn Phe Ser Asp
1               5                   10                  15

```
Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 35
<211> LENGTH: 446
<212> TYPE: PRT
<213> ORGANISM: Homo sapiens

<400> SEQUENCE: 35

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
```

-continued

```
                20                  25                  30
Leu Ile Leu Ser Thr Leu Leu Gly Asn Thr Leu Val Cys Ala Ala Val
             35                  40                  45
Ile Arg Phe Arg His Leu Arg Ser Lys Val Thr Asn Phe Val Ile
 50                  55                  60
Ser Leu Ala Val Ser Asp Leu Leu Val Ala Val Leu Val Met Pro Trp
 65                  70                  75                  80
Lys Ala Val Ala Glu Ile Ala Gly Phe Trp Pro Phe Gly Ser Phe Cys
                 85                  90                  95
Asn Ile Trp Val Ala Phe Asp Ile Met Cys Ser Thr Ala Ser Ile Leu
             100                 105                 110
Asn Leu Cys Val Ile Ser Val Asp Arg Tyr Trp Ala Ile Ser Ser Pro
             115                 120                 125
Phe Arg Tyr Glu Arg Lys Met Thr Pro Lys Ala Ala Phe Ile Leu Ile
             130                 135                 140
Ser Val Ala Trp Thr Leu Ser Val Leu Ile Ser Phe Ile Pro Val Gln
145                 150                 155                 160
Leu Ser Trp His Lys Ala Lys Pro Thr Ser Pro Ser Asp Gly Asn Ala
             165                 170                 175
Thr Ser Leu Ala Glu Thr Ile Asp Asn Cys Asp Ser Ser Leu Ser Arg
             180                 185                 190
Thr Tyr Ala Ile Ser Ser Ser Val Ile Ser Phe Tyr Ile Pro Val Ala
             195                 200                 205
Ile Met Ile Val Thr Tyr Thr Arg Ile Tyr Arg Ile Ala Gln Lys Gln
             210                 215                 220
Ile Arg Arg Ile Ala Ala Leu Glu Arg Ala Ala Val His Ala Lys Asn
225                 230                 235                 240
Cys Gln Thr Thr Thr Gly Asn Gly Lys Pro Val Glu Cys Ser Gln Pro
             245                 250                 255
Glu Ser Ser Phe Lys Met Ser Phe Lys Arg Glu Thr Lys Val Leu Lys
             260                 265                 270
Thr Leu Ser Val Ile Met Gly Val Phe Val Cys Cys Trp Leu Pro Phe
             275                 280                 285
Phe Ile Leu Asn Cys Ile Leu Pro Phe Cys Gly Ser Gly Glu Thr Gln
             290                 295                 300
Pro Phe Cys Ile Asp Ser Asn Thr Phe Asp Val Phe Val Trp Phe Gly
305                 310                 315                 320
Trp Ala Asn Ser Ser Leu Asn Pro Ile Ile Tyr Ala Phe Asn Ala Asp
             325                 330                 335
Phe Arg Lys Ala Phe Ser Thr Leu Leu Gly Cys Tyr Arg Leu Cys Pro
             340                 345                 350
Ala Thr Asn Asn Ala Ile Glu Thr Val Ser Ile Asn Asn Asn Gly Ala
             355                 360                 365
Ala Met Phe Ser Ser His His Glu Pro Arg Gly Ser Ile Ser Lys Glu
             370                 375                 380
Cys Asn Leu Val Tyr Leu Ile Pro His Ala Val Gly Ser Ser Glu Asp
385                 390                 395                 400
Leu Lys Lys Glu Glu Ala Ala Gly Ile Ala Arg Pro Leu Glu Lys Leu
             405                 410                 415
Ser Pro Ala Leu Ser Val Ile Leu Asp Tyr Asp Thr Asp Val Ser Leu
             420                 425                 430
Glu Lys Ile Gln Pro Ile Thr Gln Asn Gly Gln His Pro Thr
             435                 440                 445
```

<210> SEQ ID NO 36
<211> LENGTH: 427
<212> TYPE: PRT
<213> ORGANISM: Homo sapiens

<400> SEQUENCE: 36

```
Met Glu Thr Leu Cys Leu Arg Ala Ser Phe Trp Leu Ala Leu Val Gly
1               5                   10                  15

Cys Val Ile Ser Asp Asn Pro Glu Arg Tyr Ser Thr Asn Leu Ser Asn
                20                  25                  30

His Val Asp Asp Phe Thr Thr Phe Arg Gly Thr Glu Leu Ser Phe Leu
            35                  40                  45

Val Thr Thr His Gln Pro Thr Asn Leu Val Leu Pro Ser Asn Gly Ser
        50                  55                  60

Met His Asn Tyr Cys Pro Gln Gln Thr Lys Ile Thr Ser Ala Phe Lys
65                  70                  75                  80

Tyr Ile Asn Thr Val Ile Ser Cys Thr Ile Phe Ile Val Gly Met Val
                85                  90                  95

Gly Asn Ala Thr Leu Leu Arg Ile Ile Tyr Gln Asn Lys Cys Met Arg
                100                 105                 110

Asn Gly Pro Asn Ala Leu Ile Ala Ser Leu Ala Leu Gly Asp Leu Ile
            115                 120                 125

Tyr Val Val Ile Asp Leu Pro Ile Asn Val Phe Lys Leu Leu Ala Gly
        130                 135                 140

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
                180                 185                 190

Val Gln Gly Ile Gly Ile Pro Leu Val Thr Ala Ile Glu Ile Val Ser
            195                 200                 205

Ile Trp Ile Leu Ser Phe Ile Leu Ala Ile Pro Glu Ala Ile Gly Phe
        210                 215                 220

Val Met Val Pro Phe Glu Tyr Arg Gly Glu Gln His Lys Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
                260                 265                 270

Ile Phe Tyr Thr Leu Met Thr Cys Glu Met Leu Asn Arg Arg Asn Gly
            275                 280                 285

Ser Leu Arg Ile Ala Leu Ser Glu His Leu Lys Gln Arg Arg Glu Val
        290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asn Glu Met
                325                 330                 335

Asp Lys Asn Arg Cys Glu Leu Leu Ser Phe Leu Leu Leu Met Asp Tyr
                340                 345                 350

Ile Gly Ile Asn Leu Ala Thr Met Asn Ser Cys Ile Asn Pro Ile Ala
            355                 360                 365

Leu Tyr Phe Val Ser Lys Lys Phe Lys Asn Cys Phe Gln Ser Cys Leu
```

370                 375                 380
Cys Cys Cys Cys Tyr Gln Ser Lys Ser Leu Met Thr Ser Val Pro Met
385                 390                 395                 400

Asn Gly Thr Ser Ile Gln Trp Lys Asn His Asp Gln Asn Asn His Asn
                    405                 410                 415

Thr Asp Arg Ser Ser His Lys Asp Ser Met Asn
                420                 425

<210> SEQ ID NO 37
<211> LENGTH: 442
<212> TYPE: PRT
<213> ORGANISM: Homo sapiens

<400> SEQUENCE: 37

Met Gln Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
                20                  25                  30

Pro Asp Arg Ala Thr Pro Leu Leu Gln Thr Ala Glu Ile Met Thr Pro
            35                  40                  45

Pro Thr Lys Thr Leu Trp Pro Lys Gly Ser Asn Ala Ser Leu Ala Arg
50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
                100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
            260                 265                 270

Lys Asp Trp Trp Leu Phe Ser Phe Tyr Phe Cys Leu Pro Leu Ala Ile
            275                 280                 285

Thr Ala Phe Phe Tyr Thr Leu Met Thr Cys Glu Met Leu Arg Lys Lys
            290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
            325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
            355                 360                 365

Tyr Ile Gly Ile Asn Met Ala Ser Leu Asn Ser Cys Ile Asn Pro Ile
        370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
            420                 425                 430

Phe Arg Ser Ser Asn Lys Tyr Ser Ser Ser
            435                 440

<210> SEQ ID NO 38
<211> LENGTH: 445
<212> TYPE: PRT
<213> ORGANISM: Homo sapiens

<400> SEQUENCE: 38

Met Glu Arg Ala Pro Pro Asp Gly Pro Leu Asn Ala Ser Gly Ala Leu
1               5                   10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
            35                  40                  45

Val Leu Gly Asn Ala Leu Val Met Leu Ala Phe Val Ala Asp Ser Ser
        50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
            115                 120                 125

Ser Tyr Asp Arg Phe Leu Ser Val Thr Arg Ala Val Ser Tyr Arg Ala
        130                 135                 140

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
            210                 215                 220

Ile Gln Arg Arg Thr Arg Leu Arg Leu Asp Gly Ala Arg Glu Ala Ala
225                 230                 235                 240

Gly Pro Glu Pro Pro Pro Glu Ala Gln Pro Ser Pro Pro Pro Pro
                245                 250                 255

```
Gly Cys Trp Gly Cys Trp Gln Lys Gly His Gly Glu Ala Met Pro Leu
            260                 265                 270

His Arg Tyr Gly Val Gly Glu Ala Val Gly Ala Glu Ala Gly Glu
            275                 280                 285

Ala Thr Leu Gly Gly Gly Gly Gly Ser Val Ala Ser Pro Thr
290                 295                 300

Ser Ser Ser Gly Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
            325                 330                 335

Met Lys Met Val Ser Gln Ser Phe Thr Gln Arg Phe Arg Leu Ser Arg
            340                 345                 350

Asp Arg Lys Val Ala Lys Ser Leu Ala Val Ile Val Ser Ile Phe Gly
            355                 360                 365

Leu Cys Trp Ala Pro Tyr Thr Leu Leu Met Ile Ile Arg Ala Ala Cys
370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
            405                 410                 415

His Ser Phe Arg Arg Ala Phe Thr Lys Leu Leu Cys Pro Gln Lys Leu
            420                 425                 430

Lys Ile Gln Pro His Ser Ser Leu Glu His Cys Trp Lys
            435                 440                 445

<210> SEQ ID NO 39
<211> LENGTH: 460
<212> TYPE: PRT
<213> ORGANISM: Homo sapiens

<400> SEQUENCE: 39

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
            35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
```

```
              180                 185                 190
Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
                260                 265                 270

Ser Trp Lys Glu Glu Glu Glu Asp Glu Gly Ser Met Glu Ser Leu
    275                 280                 285

Thr Ser Ser Glu Gly Glu Glu Pro Gly Ser Glu Val Val Ile Lys Met
        290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Gly Arg Asp Arg
                325                 330                 335

Ala Gly Lys Gly Gln Lys Pro Arg Gly Lys Glu Gln Leu Ala Lys Arg
                340                 345                 350

Lys Thr Phe Ser Leu Val Lys Glu Lys Ala Ala Arg Thr Leu Ser
                355                 360                 365

Ala Ile Leu Leu Ala Phe Ile Leu Thr Trp Thr Pro Tyr Asn Ile Met
        370                 375                 380

Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Ile Asn Pro Met
                405                 410                 415

Cys Tyr Ala Leu Cys Asn Lys Ala Phe Arg Asp Thr Phe Arg Leu Leu
                420                 425                 430

Leu Leu Cys Arg Trp Asp Lys Arg Arg Trp Arg Lys Ile Pro Lys Arg
                435                 440                 445

Pro Gly Ser Val His Arg Thr Pro Ser Arg Gln Cys
                450                 455                 460

<210> SEQ ID NO 40
<211> LENGTH: 466
<212> TYPE: PRT
<213> ORGANISM: Homo sapiens

<400> SEQUENCE: 40

Met Asn Ser Thr Asn Ser Ser Asn Ser Leu Ala Leu Thr Ser
1               5                   10                  15

Pro Tyr Lys Thr Phe Glu Val Val Phe Ile Val Leu Val Ala Gly Ser
                20                  25                  30

Leu Ser Leu Val Thr Ile Ile Gly Asn Ile Leu Val Met Val Ser Ile
            35                  40                  45

Lys Val Asn Arg His Leu Gln Thr Val Asn Asn Tyr Phe Leu Phe Ser
    50                  55                  60

Leu Ala Cys Ala Asp Leu Ile Ile Gly Val Phe Ser Met Asn Leu Tyr
65                  70                  75                  80

Thr Leu Tyr Thr Val Ile Gly Tyr Trp Pro Leu Gly Pro Val Val Cys
                85                  90                  95
```

```
Asp Leu Trp Leu Ala Leu Asp Tyr Val Val Ser Asn Ala Ser Val Met
            100                 105                 110

Asn Leu Leu Ile Ile Ser Phe Asp Arg Tyr Phe Cys Val Thr Lys Pro
        115                 120                 125

Leu Thr Tyr Pro Val Lys Arg Thr Thr Lys Met Ala Gly Met Met Ile
    130                 135                 140

Ala Ala Ala Trp Val Leu Ser Phe Ile Leu Trp Ala Pro Ala Ile Leu
145                 150                 155                 160

Phe Trp Gln Phe Ile Val Gly Val Arg Thr Val Glu Asp Gly Glu Cys
                165                 170                 175

Tyr Ile Gln Phe Phe Ser Asn Ala Ala Val Thr Phe Gly Thr Ala Ile
            180                 185                 190

Ala Ala Phe Tyr Leu Pro Val Ile Ile Met Thr Val Leu Tyr Trp His
        195                 200                 205

Ile Ser Arg Ala Ser Lys Ser Arg Ile Lys Lys Asp Lys Lys Glu Pro
    210                 215                 220

Val Ala Asn Gln Asp Pro Val Ser Pro Ser Leu Val Gln Gly Arg Ile
225                 230                 235                 240

Val Lys Pro Asn Asn Asn Met Pro Ser Ser Asp Asp Gly Leu Glu
                245                 250                 255

His Asn Lys Ile Gln Asn Gly Lys Ala Pro Arg Asp Pro Val Thr Glu
            260                 265                 270

Asn Cys Val Gln Gly Glu Lys Glu Ser Ser Asn Asp Ser Thr Ser
                275                 280                 285

Val Ser Ala Val Ala Ser Asn Met Arg Asp Asp Glu Ile Thr Gln Asp
290                 295                 300

Glu Asn Thr Val Ser Thr Ser Leu Gly His Ser Lys Asp Glu Asn Ser
305                 310                 315                 320

Lys Gln Thr Cys Ile Arg Ile Gly Thr Lys Thr Pro Lys Ser Asp Ser
                325                 330                 335

Cys Thr Pro Thr Asn Thr Thr Val Glu Val Val Gly Ser Ser Gly Gln
            340                 345                 350

Asn Gly Asp Glu Lys Gln Asn Ile Val Ala Arg Lys Ile Val Lys Met
            355                 360                 365

Thr Lys Gln Pro Ala Lys Lys Lys Pro Pro Ser Arg Glu Lys Lys
    370                 375                 380

Val Thr Arg Thr Ile Leu Ala Ile Leu Leu Ala Phe Ile Ile Thr Trp
385                 390                 395                 400

Ala Pro Tyr Asn Val Met Val Leu Ile Asn Thr Phe Cys Ala Pro Cys
                405                 410                 415

Ile Pro Asn Thr Val Trp Thr Ile Gly Tyr Trp Leu Cys Tyr Ile Asn
            420                 425                 430

Ser Thr Ile Asn Pro Ala Cys Tyr Ala Leu Cys Asn Ala Thr Phe Lys
        435                 440                 445

Lys Thr Phe Lys His Leu Leu Met Cys His Tyr Lys Asn Ile Gly Ala
    450                 455                 460

Thr Arg
465

<210> SEQ ID NO 41
<211> LENGTH: 590
<212> TYPE: PRT
<213> ORGANISM: Homo sapiens

<400> SEQUENCE: 41
```

```
Met Thr Leu His Asn Asn Ser Thr Thr Ser Pro Leu Phe Pro Asn Ile
1               5                   10                  15

Ser Ser Ser Trp Ile His Ser Pro Ser Asp Ala Gly Leu Pro Pro Gly
            20                  25                  30

Thr Val Thr His Phe Gly Ser Tyr Asn Val Ser Arg Ala Ala Gly Asn
        35                  40                  45

Phe Ser Ser Pro Asp Gly Thr Thr Asp Asp Pro Leu Gly Gly His Thr
    50                  55                  60

Val Trp Gln Val Val Phe Ile Ala Phe Leu Thr Gly Ile Leu Ala Leu
65                  70                  75                  80

Val Thr Ile Ile Gly Asn Ile Leu Val Ile Val Ser Phe Lys Val Asn
                85                  90                  95

Lys Gln Leu Lys Thr Val Asn Asn Tyr Phe Leu Leu Ser Leu Ala Cys
                100                 105                 110

Ala Asp Leu Ile Ile Gly Val Ile Ser Met Asn Leu Phe Thr Thr Tyr
            115                 120                 125

Ile Ile Met Asn Arg Trp Ala Leu Gly Asn Leu Ala Cys Asp Leu Trp
        130                 135                 140

Leu Ala Ile Asp Tyr Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
                180                 185                 190

Trp Val Ile Ser Phe Val Leu Trp Ala Pro Ala Ile Leu Phe Trp Gln
            195                 200                 205

Tyr Phe Val Gly Lys Arg Thr Val Pro Pro Gly Glu Cys Phe Ile Gln
210                 215                 220

Phe Leu Ser Glu Pro Thr Ile Thr Phe Gly Thr Ala Ile Ala Ala Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
                260                 265                 270

Thr Glu Ala Glu Thr Glu Asn Phe Val His Pro Thr Gly Ser Ser Arg
            275                 280                 285

Ser Cys Ser Ser Tyr Glu Leu Gln Gln Gln Ser Met Lys Arg Ser Asn
            290                 295                 300

Arg Arg Lys Tyr Gly Arg Cys His Phe Trp Phe Thr Thr Lys Ser Trp
305                 310                 315                 320

Lys Pro Ser Ser Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
                340                 345                 350

Asp Glu Glu Asp Ile Gly Ser Glu Thr Arg Ala Ile Tyr Ser Ile Val
            355                 360                 365

Leu Lys Leu Pro Gly His Ser Thr Ile Leu Asn Ser Thr Lys Leu Pro
370                 375                 380

Ser Ser Asp Asn Leu Gln Val Pro Glu Glu Glu Leu Gly Met Val Asp
385                 390                 395                 400

Leu Glu Arg Lys Ala Asp Lys Leu Gln Ala Gln Lys Ser Val Asp Asp
                405                 410                 415
```

```
Gly Gly Ser Phe Pro Lys Ser Phe Lys Leu Pro Ile Gln Leu Glu
            420             425             430

Ser Ala Val Asp Thr Ala Lys Thr Ser Asp Val Asn Ser Ser Val Gly
        435                 440                 445

Lys Ser Thr Ala Thr Leu Pro Leu Ser Phe Lys Glu Ala Thr Leu Ala
    450                 455                 460

Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495

Leu Leu Ala Phe Ile Ile Thr Trp Thr Pro Tyr Asn Ile Met Val Leu
            500                 505                 510

Val Asn Thr Phe Cys Asp Ser Cys Ile Pro Lys Thr Phe Trp Asn Leu
        515                 520                 525

Gly Tyr Trp Leu Cys Tyr Ile Asn Ser Thr Val Asn Pro Val Cys Tyr
    530                 535                 540

Ala Leu Cys Asn Lys Thr Phe Arg Thr Thr Phe Lys Met Leu Leu Leu
545                 550                 555                 560

Cys Gln Cys Asp Lys Lys Arg Arg Lys Gln Gln Tyr Gln Gln Arg
                565                 570                 575

Gln Ser Val Ile Phe His Lys Arg Ala Pro Glu Gln Ala Leu
            580                 585                 590

<210> SEQ ID NO 42
<211> LENGTH: 384
<212> TYPE: PRT
<213> ORGANISM: Homo sapiens

<400> SEQUENCE: 42

Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
                100                 105                 110

Cys Lys Leu Asn Pro Phe Val Gln Cys Val Ser Ile Thr Val Ser Ile
            115                 120                 125

Phe Ser Leu Val Leu Ile Ala Val Glu Arg His Gln Leu Ile Ile Asn
        130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
                180                 185                 190

Lys Asp Lys Tyr Val Cys Phe Asp Gln Phe Pro Ser Asp Ser His Arg
            195                 200                 205
```

```
Leu Ser Tyr Thr Thr Leu Leu Leu Val Leu Gln Tyr Phe Gly Pro Leu
    210                 215                 220
Cys Phe Ile Phe Ile Cys Tyr Phe Lys Ile Tyr Ile Arg Leu Lys Arg
225                 230                 235                 240
Arg Asn Asn Met Met Asp Lys Met Arg Asp Asn Lys Tyr Arg Ser Ser
                245                 250                 255
Glu Thr Lys Arg Ile Asn Ile Met Leu Leu Ser Ile Val Val Ala Phe
            260                 265                 270
Ala Val Cys Trp Leu Pro Leu Thr Ile Phe Asn Thr Val Phe Asp Trp
        275                 280                 285
Asn His Gln Ile Ile Ala Thr Cys Asn His Asn Leu Leu Phe Leu Leu
    290                 295                 300
Cys His Leu Thr Ala Met Ile Ser Thr Cys Val Asn Pro Ile Phe Tyr
305                 310                 315                 320
Gly Phe Leu Asn Lys Asn Phe Gln Arg Asp Leu Gln Phe Phe Phe Asn
                325                 330                 335
Phe Cys Asp Phe Arg Ser Arg Asp Asp Tyr Glu Thr Ile Ala Met
                340                 345                 350
Ser Thr Met His Thr Asp Val Ser Lys Thr Ser Leu Lys Gln Ala Ser
            355                 360                 365
Pro Val Ala Phe Lys Lys Ile Asn Asn Asn Asp Asp Asn Glu Lys Ile
        370                 375                 380

<210> SEQ ID NO 43
<211> LENGTH: 418
<212> TYPE: PRT
<213> ORGANISM: Homo sapiens

<400> SEQUENCE: 43

Met Arg Leu Asn Ser Ser Ala Pro Gly Thr Pro Gly Thr Pro Ala Ala
1               5                   10                  15
Asp Pro Phe Gln Arg Ala Gln Ala Gly Leu Glu Glu Ala Leu Leu Ala
            20                  25                  30
Pro Gly Phe Gly Asn Ala Ser Gly Asn Ala Ser Glu Arg Val Leu Ala
        35                  40                  45
Ala Pro Ser Ser Glu Leu Asp Val Asn Thr Asp Ile Tyr Ser Lys Val
    50                  55                  60
Leu Val Thr Ala Val Tyr Leu Ala Leu Phe Val Val Gly Thr Val Gly
65                  70                  75                  80
Asn Thr Val Thr Ala Phe Thr Leu Ala Arg Lys Lys Ser Leu Gln Ser
                85                  90                  95
Leu Gln Ser Thr Val His Tyr His Leu Gly Ser Leu Ala Leu Ser Asp
            100                 105                 110
Leu Leu Thr Leu Leu Leu Ala Met Pro Val Glu Leu Tyr Asn Phe Ile
        115                 120                 125
Trp Val His His Pro Trp Ala Phe Gly Asp Ala Gly Cys Arg Gly Tyr
    130                 135                 140
Tyr Phe Leu Arg Asp Ala Cys Thr Tyr Ala Thr Ala Leu Asn Val Ala
145                 150                 155                 160
Ser Leu Ser Val Glu Arg Tyr Leu Ala Ile Cys His Pro Phe Lys Ala
                165                 170                 175
Lys Thr Leu Met Ser Arg Ser Arg Thr Lys Lys Phe Ile Ser Ala Ile
            180                 185                 190
Trp Leu Ala Ser Ala Leu Leu Ala Val Pro Met Leu Phe Thr Met Gly
```

```
                195                 200                 205
Glu Gln Asn Arg Ser Ala Asp Gly Gln His Ala Gly Gly Leu Val Cys
210                 215                 220

Thr Pro Thr Ile His Thr Ala Thr Val Lys Val Ile Gln Val Asn
225                 230                 235                 240

Thr Phe Met Ser Phe Ile Phe Pro Met Val Val Ile Ser Val Leu Asn
                245                 250                 255

Thr Ile Ile Ala Asn Lys Leu Thr Val Met Val Arg Gln Ala Ala Glu
                260                 265                 270

Gln Gly Gln Val Cys Thr Val Gly Gly Glu His Ser Thr Phe Ser Met
                275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335

Phe Leu Tyr Asp Phe Tyr His Tyr Phe Tyr Met Val Thr Asn Ala Leu
                340                 345                 350

Phe Tyr Val Ser Ser Thr Ile Asn Pro Ile Leu Tyr Asn Leu Val Ser
                355                 360                 365

Ala Asn Phe Arg His Ile Phe Leu Ala Thr Leu Ala Cys Leu Cys Pro
370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr

<210> SEQ ID NO 44
<211> LENGTH: 425
<212> TYPE: PRT
<213> ORGANISM: Homo sapiens

<400> SEQUENCE: 44

Met Glu Pro Ser Ala Thr Pro Gly Ala Gln Met Gly Val Pro Pro Gly
1               5                   10                  15

Ser Arg Glu Pro Ser Pro Val Pro Pro Asp Tyr Glu Asp Glu Phe Leu
                20                  25                  30

Arg Tyr Leu Trp Arg Asp Tyr Leu Tyr Pro Lys Gln Tyr Glu Trp Val
            35                  40                  45

Leu Ile Ala Ala Tyr Val Ala Val Phe Val Val Ala Leu Val Gly Asn
50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
                100                 105                 110

Leu Phe Gly His Ala Leu Cys Lys Val Ile Pro Tyr Leu Gln Ala Val
            115                 120                 125

Ser Val Ser Val Ala Val Leu Thr Leu Ser Phe Ile Ala Leu Asp Arg
130                 135                 140

Trp Tyr Ala Ile Cys His Pro Leu Leu Phe Lys Ser Thr Ala Arg Arg
```

```
145                 150                 155                 160
Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
                180                 185                 190

Ala Asn Arg Thr Arg Leu Phe Ser Val Cys Asp Glu Arg Trp Ala Asp
                195                 200                 205

Asp Leu Tyr Pro Lys Ile Tyr His Ser Cys Phe Phe Ile Val Thr Tyr
210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
                245                 250                 255

Asn Trp Lys Arg Pro Ser Asp Gln Leu Gly Asp Leu Glu Gln Gly Leu
                260                 265                 270

Ser Gly Glu Pro Gln Pro Arg Ala Arg Ala Phe Leu Ala Glu Val Lys
                275                 280                 285

Gln Met Arg Ala Arg Arg Lys Thr Ala Lys Met Leu Met Val Val Leu
    290                 295                 300

Leu Val Phe Ala Leu Cys Tyr Leu Pro Ile Ser Val Leu Asn Val Leu
305                 310                 315                 320

Lys Arg Val Phe Gly Met Phe Arg Gln Ala Ser Asp Arg Glu Ala Val
                325                 330                 335

Tyr Ala Cys Phe Thr Phe Ser His Trp Leu Val Tyr Ala Asn Ser Ala
                340                 345                 350

Ala Asn Pro Ile Ile Tyr Asn Phe Leu Ser Gly Lys Phe Arg Glu Gln
                355                 360                 365

Phe Lys Ala Ala Phe Ser Cys Cys Leu Pro Gly Leu Gly Pro Cys Gly
370                 375                 380

Ser Leu Lys Ala Pro Ser Pro Arg Ser Ser Ala Ser His Lys Ser Leu
385                 390                 395                 400

Ser Leu Gln Ser Arg Cys Ser Ile Ser Lys Ile Ser Glu His Val Val
                405                 410                 415

Leu Thr Ser Val Thr Thr Val Leu Pro
                420                 425

<210> SEQ ID NO 45
<211> LENGTH: 444
<212> TYPE: PRT
<213> ORGANISM: Homo sapiens

<400> SEQUENCE: 45

Met Ser Gly Thr Lys Leu Glu Asp Ser Pro Pro Cys Arg Asn Trp Ser
1               5                   10                  15

Ser Ala Ser Glu Leu Asn Glu Thr Gln Glu Pro Phe Leu Asn Pro Thr
                20                  25                  30

Asp Tyr Asp Asp Glu Glu Phe Leu Arg Tyr Leu Trp Arg Glu Tyr Leu
            35                  40                  45

His Pro Lys Glu Tyr Glu Trp Val Leu Ile Ala Gly Tyr Ile Ile Val
        50                  55                  60

Phe Val Val Ala Leu Ile Gly Asn Val Leu Val Cys Val Ala Val Trp
65                  70                  75                  80

Lys Asn His His Met Arg Thr Val Thr Asn Tyr Phe Ile Val Asn Leu
                85                  90                  95
```

```
Ser Leu Ala Asp Val Leu Val Thr Ile Thr Cys Leu Pro Ala Thr Leu
                100                 105                 110

Val Val Asp Ile Thr Glu Thr Trp Phe Phe Gly Gln Ser Leu Cys Lys
            115                 120                 125

Val Ile Pro Tyr Leu Gln Thr Val Ser Val Ser Val Ser Val Leu Thr
        130                 135                 140

Leu Ser Cys Ile Ala Leu Asp Arg Trp Tyr Ala Ile Cys His Pro Leu
145                 150                 155                 160

Met Phe Lys Ser Thr Ala Lys Arg Ala Arg Asn Ser Ile Val Ile Ile
                165                 170                 175

Trp Ile Val Ser Cys Ile Ile Met Ile Pro Gln Ala Ile Val Met Glu
            180                 185                 190

Cys Ser Thr Val Phe Pro Gly Leu Ala Asn Lys Thr Thr Leu Phe Thr
        195                 200                 205

Val Cys Asp Glu Arg Trp Gly Glu Ile Tyr Pro Lys Met Tyr His
        210                 215                 220

Ile Cys Phe Phe Leu Val Thr Tyr Met Ala Pro Leu Cys Leu Met Val
225                 230                 235                 240

Leu Ala Tyr Leu Gln Ile Phe Arg Lys Leu Trp Cys Arg Gln Ile Pro
                245                 250                 255

Gly Thr Ser Ser Val Val Gln Arg Lys Trp Lys Pro Leu Gln Pro Val
            260                 265                 270

Ser Gln Pro Arg Gly Pro Gly Gln Pro Thr Lys Ser Arg Met Ser Ala
        275                 280                 285

Val Ala Ala Glu Ile Lys Gln Ile Arg Ala Arg Arg Lys Thr Ala Arg
        290                 295                 300

Met Leu Met Ile Val Leu Leu Val Phe Ala Ile Cys Tyr Leu Pro Ile
305                 310                 315                 320

Ser Ile Leu Asn Val Leu Lys Arg Val Phe Gly Met Phe Ala His Thr
                325                 330                 335

Glu Asp Arg Glu Thr Val Tyr Ala Trp Phe Thr Phe Ser His Trp Leu
            340                 345                 350

Val Tyr Ala Asn Ser Ala Ala Asn Pro Ile Ile Tyr Asn Phe Leu Ser
        355                 360                 365

Gly Lys Phe Arg Glu Glu Phe Lys Ala Ala Phe Ser Cys Cys Cys Leu
        370                 375                 380

Gly Val His His Arg Gln Glu Asp Arg Leu Thr Arg Gly Arg Thr Ser
385                 390                 395                 400

Thr Glu Ser Arg Lys Ser Leu Thr Thr Gln Ile Ser Asn Phe Asp Asn
                405                 410                 415

Ile Ser Lys Leu Ser Glu Gln Val Val Leu Thr Ser Ile Ser Thr Leu
            420                 425                 430

Pro Ala Ala Asn Gly Ala Gly Pro Leu Gln Asn Trp
        435                 440

<210> SEQ ID NO 46
<211> LENGTH: 402
<212> TYPE: PRT
<213> ORGANISM: Homo sapiens

<400> SEQUENCE: 46

Met Ser Pro Cys Gly Pro Leu Asn Leu Ser Leu Ala Gly Glu Ala Thr
1               5                   10                  15

Thr Cys Ala Ala Pro Trp Val Pro Asn Thr Ser Ala Val Pro Pro Ser
            20                  25                  30
```

Gly Ala Ser Pro Ala Leu Pro Ile Phe Ser Met Thr Leu Gly Ala Val
        35                  40                  45

Ser Asn Leu Leu Ala Leu Ala Leu Leu Ala Gln Ala Ala Gly Arg Leu
 50                  55                  60

Arg Arg Arg Arg Ser Ala Ala Thr Phe Leu Leu Phe Val Ala Ser Leu
 65                  70                  75                  80

Leu Ala Thr Asp Leu Ala Gly His Val Ile Pro Gly Ala Leu Val Leu
                 85                  90                  95

Arg Leu Tyr Thr Ala Gly Arg Ala Pro Ala Gly Ala Cys His Phe
                100                 105                 110

Leu Gly Gly Cys Met Val Phe Phe Gly Leu Cys Pro Leu Leu Leu Gly
             115                 120                 125

Cys Gly Met Ala Val Glu Arg Cys Val Gly Val Thr Arg Pro Leu Leu
             130                 135                 140

His Ala Ala Arg Val Ser Val Ala Arg Ala Arg Leu Ala Leu Ala Ala
145                 150                 155                 160

Val Ala Ala Val Ala Leu Ala Val Ala Leu Leu Pro Leu Ala Arg Val
                 165                 170                 175

Gly Arg Tyr Glu Leu Gln Tyr Pro Gly Thr Trp Cys Phe Ile Gly Leu
                 180                 185                 190

Gly Pro Pro Gly Gly Trp Arg Gln Ala Leu Leu Ala Gly Leu Phe Ala
             195                 200                 205

Ser Leu Gly Leu Val Ala Leu Leu Ala Ala Leu Val Cys Asn Thr Leu
             210                 215                 220

Ser Gly Leu Ala Leu Leu Arg Ala Arg Trp Arg Arg Ser Arg Arg
225                 230                 235                 240

Pro Pro Pro Ala Ser Gly Pro Asp Ser Arg Arg Trp Gly Ala His
                 245                 250                 255

Gly Pro Arg Ser Ala Ser Ala Ser Ser Ala Ser Ser Ile Ala Ser Ala
             260                 265                 270

Ser Thr Phe Phe Gly Gly Ser Arg Ser Ser Gly Ser Ala Arg Arg Ala
             275                 280                 285

Arg Ala His Asp Val Glu Met Val Gly Gln Leu Val Gly Ile Met Val
             290                 295                 300

Val Ser Cys Ile Cys Trp Ser Pro Met Leu Val Leu Val Ala Leu Ala
305                 310                 315                 320

Val Gly Gly Trp Ser Ser Thr Ser Leu Gln Arg Pro Leu Phe Leu Ala
                 325                 330                 335

Val Arg Leu Ala Ser Trp Asn Gln Ile Leu Asp Pro Trp Val Tyr Ile
             340                 345                 350

Leu Leu Arg Gln Ala Val Leu Arg Gln Leu Leu Arg Leu Leu Pro Pro
             355                 360                 365

Arg Ala Gly Ala Lys Gly Gly Pro Ala Gly Leu Gly Leu Thr Pro Ser
 370                 375                 380

Ala Trp Glu Ala Ser Ser Leu Arg Ser Ser Arg His Ser Gly Leu Ser
385                 390                 395                 400

His Phe

<210> SEQ ID NO 47
<211> LENGTH: 422
<212> TYPE: PRT
<213> ORGANISM: Homo sapiens

<400> SEQUENCE: 47

```
Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Gly Thr Leu Ile Phe
        35                  40                  45

Cys Ala Val Leu Gly Asn Ala Cys Val Val Ala Ala Ile Ala Leu Glu
        50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
        130                 135                 140

Val Asn Lys Arg Thr Pro Arg Arg Ala Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
        290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
        355                 360                 365

Pro Phe Cys Glu Ser Ser Cys His Met Pro Thr Leu Leu Gly Ala Ile
        370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415
```

```
Cys Lys Phe Cys Arg Gln
            420
```

<210> SEQ ID NO 48
<211> LENGTH: 471
<212> TYPE: PRT
<213> ORGANISM: Homo sapiens

<400> SEQUENCE: 48

```
Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
                20                  25                  30

Asn Ser Gly Glu Ala Asn Thr Ser Asp Ala Phe Asn Trp Thr Val Asp
            35                  40                  45

Ser Glu Asn Arg Thr Asn Leu Ser Cys Glu Gly Cys Leu Ser Pro Ser
        50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
            115                 120                 125

Pro Val Ser Met Leu Thr Ile Leu Tyr Gly Tyr Arg Trp Pro Leu Pro
        130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
                180                 185                 190

Phe Leu Lys Ile Ile Ala Val Trp Thr Ile Ser Val Gly Ile Ser Met
            195                 200                 205

Pro Ile Pro Val Phe Gly Leu Gln Asp Asp Ser Lys Val Phe Lys Glu
        210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
                260                 265                 270

Gly Thr Arg Ala Lys Leu Ala Ser Phe Ser Phe Leu Pro Gln Ser Ser
            275                 280                 285

Leu Ser Ser Glu Lys Leu Phe Gln Arg Ser Ile His Arg Glu Pro Gly
        290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
                340                 345                 350

Cys Asn Glu Asp Val Ile Gly Ala Leu Leu Asn Val Phe Val Trp Ile
            355                 360                 365
```

```
Gly Tyr Leu Ser Ser Ala Val Asn Pro Leu Val Tyr Thr Leu Phe Asn
        370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln His Ser Glu Glu Ala Ser Lys Asp Asn Ser Asp Gly Val
    450                 455                 460

Asn Glu Lys Val Ser Cys Val
465                 470

<210> SEQ ID NO 49
<211> LENGTH: 481
<212> TYPE: PRT
<213> ORGANISM: Homo sapiens

<400> SEQUENCE: 49

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
            20                  25                  30

Gly Leu Gln Thr Glu Ser Ile Pro Glu Met Lys Gln Ile Val Glu
        35                  40                  45

Glu Gln Gly Asn Lys Leu His Trp Ala Ala Leu Leu Ile Leu Met Val
    50                  55                  60

Ile Ile Pro Thr Ile Gly Gly Asn Thr Leu Val Ile Leu Ala Val Ser
65                  70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
            100                 105                 110

Leu Thr Ile Met Phe Glu Ala Met Trp Pro Leu Pro Leu Val Leu Cys
        115                 120                 125

Pro Ala Trp Leu Phe Leu Asp Val Leu Phe Ser Thr Ala Ser Ile Met
    130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
```

```
                    260                 265                 270
Thr Pro Cys Ser Ser Pro Glu Lys Val Ala Met Leu Asp Gly Ser Arg
            275                 280                 285
Lys Asp Lys Ala Leu Pro Asn Ser Gly Asp Glu Thr Leu Met Arg Arg
        290                 295                 300
Thr Ser Thr Ile Gly Lys Lys Ser Val Gln Thr Ile Ser Asn Glu Gln
305                 310                 315                 320
Arg Ala Ser Lys Val Leu Gly Ile Val Phe Leu Phe Leu Phe Leu Met
                325                 330                 335
Trp Cys Pro Phe Phe Ile Thr Asn Ile Thr Leu Val Leu Cys Asp Ser
            340                 345                 350
Cys Asn Gln Thr Thr Leu Gln Met Leu Leu Glu Ile Phe Val Trp Ile
        355                 360                 365
Gly Tyr Val Ser Ser Gly Val Asn Pro Leu Val Tyr Thr Leu Phe Asn
    370                 375                 380
Lys Thr Phe Arg Asp Ala Phe Gly Arg Tyr Ile Thr Cys Asn Tyr Arg
385                 390                 395                 400
Ala Thr Lys Ser Val Lys Thr Leu Arg Lys Arg Ser Ser Lys Ile Tyr
                405                 410                 415
Phe Arg Asn Pro Met Ala Glu Asn Ser Lys Phe Phe Lys Lys His Gly
            420                 425                 430
Ile Arg Asn Gly Ile Asn Pro Ala Met Tyr Gln Ser Pro Met Arg Leu
        435                 440                 445
Arg Ser Ser Thr Ile Gln Ser Ser Ser Ile Ile Leu Leu Asp Thr Leu
    450                 455                 460
Leu Leu Thr Glu Asn Glu Gly Asp Lys Thr Glu Glu Gln Val Ser Tyr
465                 470                 475                 480
Val

<210> SEQ ID NO 50
<211> LENGTH: 457
<212> TYPE: PRT
<213> ORGANISM: Homo sapiens

<400> SEQUENCE: 50

Met Val Asn Leu Arg Asn Ala Val His Ser Phe Leu Val His Leu Ile
1               5                   10                  15
Gly Leu Leu Val Trp Gln Cys Asp Ile Ser Val Ser Pro Val Ala Ala
                20                  25                  30
Ile Val Thr Asp Ile Phe Asn Thr Ser Asp Gly Gly Arg Phe Lys Phe
            35                  40                  45
Pro Asp Gly Val Gln Asn Trp Pro Ala Leu Ser Ile Val Ile Ile Ile
        50                  55                  60
Ile Met Thr Ile Gly Gly Asn Ile Leu Val Ile Met Ala Val Ser Met
65                  70                  75                  80
Glu Lys Lys Leu His Asn Ala Thr Asn Tyr Phe Leu Met Ser Leu Ala
                85                  90                  95
Ile Ala Asp Met Leu Val Gly Leu Leu Val Met Pro Leu Ser Leu Leu
            100                 105                 110
Ala Ile Leu Tyr Asp Tyr Val Trp Leu Pro Arg Tyr Leu Cys Pro Val
        115                 120                 125
Trp Ile Ser Leu Asp Val Leu Phe Ser Thr Ala Ser Ile Met His Leu
    130                 135                 140
Cys Ala Ile Ser Leu Asp Arg Tyr Val Ala Ile Arg Asn Pro Ile Glu
```

```
            145                 150                 155                 160
His Ser Arg Phe Asn Ser Arg Thr Lys Ala Ile Met Lys Ile Ala Ile
                165                 170                 175

Val Trp Ala Ile Ser Ile Gly Val Ser Val Pro Ile Pro Val Ile Gly
            180                 185                 190

Leu Arg Asp Glu Glu Lys Val Phe Val Asn Asn Thr Thr Cys Val Leu
                195                 200                 205

Asn Asp Pro Asn Phe Val Leu Ile Gly Ser Phe Val Ala Phe Phe Ile
            210                 215                 220

Pro Leu Thr Ile Met Val Ile Thr Tyr Cys Leu Thr Ile Tyr Val Leu
225                 230                 235                 240

Arg Arg Gln Ala Leu Met Leu Leu His Gly His Thr Glu Glu Pro Pro
                    245                 250                 255

Gly Leu Ser Leu Asp Phe Leu Lys Cys Cys Lys Arg Asn Thr Ala Glu
            260                 265                 270

Glu Glu Asn Ser Ala Asn Pro Asn Gln Asp Gln Asn Ala Arg Arg Arg
                275                 280                 285

Lys Lys Lys Glu Arg Arg Pro Arg Gly Thr Met Gln Ala Ile Asn Asn
            290                 295                 300

Glu Arg Lys Ala Ser Lys Val Leu Gly Ile Val Phe Phe Val Phe Leu
305                 310                 315                 320

Ile Met Trp Cys Pro Phe Phe Ile Thr Asn Ile Leu Ser Val Leu Cys
                    325                 330                 335

Glu Lys Ser Cys Asn Gln Lys Leu Met Glu Lys Leu Leu Asn Val Phe
            340                 345                 350

Val Trp Ile Gly Tyr Val Cys Ser Gly Ile Asn Pro Leu Val Tyr Thr
            355                 360                 365

Leu Phe Asn Lys Ile Tyr Arg Arg Ala Phe Ser Asn Tyr Leu Arg Cys
            370                 375                 380

Asn Tyr Lys Val Glu Lys Lys Pro Pro Val Arg Gln Ile Pro Arg Val
385                 390                 395                 400

Ala Ala Thr Ala Leu Ser Gly Arg Glu Leu Asn Val Asn Ile Tyr Arg
                    405                 410                 415

His Thr Asn Glu Pro Val Ile Glu Lys Ala Ser Asp Asn Glu Pro Gly
            420                 425                 430

Ile Glu Met Gln Val Glu Asn Leu Glu Leu Pro Val Asn Pro Ser Ser
                435                 440                 445

Val Val Ser Glu Arg Ile Ser Ser Val
            450                 455

<210> SEQ ID NO 51
<211> LENGTH: 388
<212> TYPE: PRT
<213> ORGANISM: Homo sapiens

<400> SEQUENCE: 51

Met Asp Lys Leu Asp Ala Asn Val Ser Ser Glu Glu Gly Phe Gly Ser
1               5                   10                  15

Val Glu Lys Val Val Leu Leu Thr Phe Leu Ser Thr Val Ile Leu Met
                20                  25                  30

Ala Ile Leu Gly Asn Leu Leu Val Met Val Ala Val Cys Trp Asp Arg
            35                  40                  45

Gln Leu Arg Lys Ile Lys Thr Asn Tyr Phe Ile Val Ser Leu Ala Phe
        50                  55                  60
```

Ala Asp Leu Leu Val Ser Val Leu Val Met Pro Phe Gly Ala Ile Glu
65                  70                  75                  80

Leu Val Gln Asp Ile Trp Ile Tyr Gly Glu Val Phe Cys Leu Val Arg
            85                  90                  95

Thr Ser Leu Asp Val Leu Leu Thr Thr Ala Ser Ile Phe His Leu Cys
        100                 105                 110

Cys Ile Ser Leu Asp Arg Tyr Tyr Ala Ile Cys Cys Gln Pro Leu Val
    115                 120                 125

Tyr Arg Asn Lys Met Thr Pro Leu Arg Ile Ala Leu Met Leu Gly Gly
130                 135                 140

Cys Trp Val Ile Pro Thr Phe Ile Ser Phe Leu Pro Ile Met Gln Gly
145                 150                 155                 160

Trp Asn Asn Ile Gly Ile Ile Asp Leu Ile Glu Lys Arg Lys Phe Asn
                165                 170                 175

Gln Asn Ser Asn Ser Thr Tyr Cys Val Phe Met Val Asn Lys Pro Tyr
            180                 185                 190

Ala Ile Thr Cys Ser Val Val Ala Phe Tyr Ile Pro Phe Leu Leu Met
        195                 200                 205

Val Leu Ala Tyr Tyr Arg Ile Tyr Val Thr Ala Lys Glu His Ala His
210                 215                 220

Gln Ile Gln Met Leu Gln Arg Ala Gly Ala Ser Ser Glu Ser Arg Pro
225                 230                 235                 240

Gln Ser Ala Asp Gln His Ser Thr His Arg Met Arg Thr Glu Thr Lys
                245                 250                 255

Ala Ala Lys Thr Leu Cys Ile Ile Met Gly Cys Phe Cys Leu Cys Trp
            260                 265                 270

Ala Pro Phe Phe Val Thr Asn Ile Val Asp Pro Phe Ile Asp Tyr Thr
        275                 280                 285

Val Pro Gly Gln Val Trp Thr Ala Phe Leu Trp Leu Gly Tyr Ile Asn
290                 295                 300

Ser Gly Leu Asn Pro Phe Leu Tyr Ala Phe Leu Asn Lys Ser Phe Arg
305                 310                 315                 320

Arg Ala Phe Leu Ile Ile Leu Cys Cys Asp Asp Glu Arg Tyr Arg Arg
                325                 330                 335

Pro Ser Ile Leu Gly Gln Thr Val Pro Cys Ser Thr Thr Thr Ile Asn
        340                 345                 350

Gly Ser Thr His Val Leu Arg Asp Ala Val Glu Cys Gly Gly Gln Trp
            355                 360                 365

Glu Ser Gln Cys His Pro Pro Ala Thr Ser Pro Leu Val Ala Ala Gln
    370                 375                 380

Pro Ser Asp Thr
385

<210> SEQ ID NO 52
<211> LENGTH: 369
<212> TYPE: PRT
<213> ORGANISM: Homo sapiens

<400> SEQUENCE: 52

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45

```
Ile Tyr Phe Val Val Cys Ile Ile Gly Leu Cys Gly Asn Thr Leu Val
            50                  55                  60

Ile Tyr Val Ile Leu Arg Tyr Ala Lys Met Lys Thr Ile Thr Asn Ile
 65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
               100                 105                 110

Ala Ile Cys Arg Val Val Met Thr Val Asp Gly Ile Asn Gln Phe Thr
               115                 120                 125

Ser Ile Phe Cys Leu Thr Val Met Ser Ile Asp Arg Tyr Leu Ala Val
               130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
               165                 170                 175

Ile Met Ile Tyr Ala Gly Leu Arg Ser Asn Gln Trp Gly Arg Ser Ser
               180                 185                 190

Cys Thr Ile Asn Trp Pro Gly Glu Ser Gly Ala Trp Tyr Thr Gly Phe
               195                 200                 205

Ile Ile Tyr Thr Phe Ile Leu Gly Phe Leu Val Pro Leu Thr Ile Ile
               210                 215                 220

Cys Leu Cys Tyr Leu Phe Ile Ile Lys Val Lys Ser Ser Gly Ile
225                 230                 235                 240

Arg Val Gly Ser Ser Lys Arg Lys Lys Ser Glu Lys Lys Val Thr Arg
               245                 250                 255

Met Val Ser Ile Val Val Ala Val Phe Ile Phe Cys Trp Leu Pro Phe
               260                 265                 270

Tyr Ile Phe Asn Val Ser Ser Val Ser Met Ala Ile Ser Pro Thr Pro
               275                 280                 285

Ala Leu Lys Gly Met Phe Asp Phe Val Val Val Leu Thr Tyr Ala Asn
               290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
               325                 330                 335

Asp Gly Glu Arg Ser Asp Ser Lys Gln Asp Lys Ser Arg Leu Asn Glu
               340                 345                 350

Thr Thr Glu Thr Gln Arg Thr Leu Leu Asn Gly Asp Leu Gln Thr Ser
               355                 360                 365

Ile

<210> SEQ ID NO 53
<211> LENGTH: 382
<212> TYPE: PRT
<213> ORGANISM: Homo sapiens

<400> SEQUENCE: 53

Met Gly Pro Thr Ser Val Pro Leu Val Lys Ala His Arg Ser Ser Val
 1               5                  10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
                35                  40                  45
```

```
Ser Val Val Phe Ile Leu Ile Cys Cys Phe Ile Ile Leu Glu Asn Ile
 50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
                 85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
            115                 120                 125

Ser Ala Ser Val Phe Ser Leu Leu Ala Ile Ala Ile Glu Arg Tyr Ile
130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
            195                 200                 205

Val Phe Thr Leu Leu Leu Ser Ile Val Ile Leu Tyr Cys Arg Ile
210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
            275                 280                 285

Ile Leu Phe Arg Ala Glu Tyr Phe Leu Val Leu Ala Val Leu Asn Ser
290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
            355                 360                 365

Pro Glu Thr Ile Met Ser Ser Gly Asn Val Asn Ser Ser Ser
370                 375                 380

<210> SEQ ID NO 54
<211> LENGTH: 378
<212> TYPE: PRT
<213> ORGANISM: Homo sapiens

<400> SEQUENCE: 54

Met Ala Thr Ala Leu Pro Pro Arg Leu Gln Pro Val Arg Gly Asn Glu
 1               5                  10                  15

Thr Leu Arg Glu His Tyr Gln Tyr Val Gly Lys Leu Ala Gly Arg Leu
                20                  25                  30

Lys Glu Ala Ser Glu Gly Ser Thr Leu Thr Thr Val Leu Phe Leu Val
```

```
            35                  40                  45
Ile Cys Ser Phe Ile Val Leu Glu Asn Leu Met Val Leu Ile Ala Ile
 50                  55                  60

Trp Lys Asn Asn Lys Phe His Asn Arg Met Tyr Phe Phe Ile Gly Asn
 65                  70                  75                  80

Leu Ala Leu Cys Asp Leu Leu Ala Gly Ile Ala Tyr Lys Val Asn Ile
                 85                  90                  95

Leu Met Ser Gly Lys Lys Thr Phe Ser Leu Ser Pro Thr Val Trp Phe
                100                 105                 110

Leu Arg Glu Gly Ser Met Phe Val Ala Leu Gly Ala Ser Thr Cys Ser
                115                 120                 125

Leu Leu Ala Ile Ala Ile Glu Arg His Leu Thr Met Ile Lys Met Arg
                130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
                180                 185                 190

Ser Lys Lys Tyr Ile Ala Phe Cys Ile Ser Ile Phe Thr Ala Ile Leu
                195                 200                 205

Val Thr Ile Val Ile Leu Tyr Ala Arg Ile Tyr Phe Leu Val Lys Ser
210                 215                 220

Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
                260                 265                 270

Ala Cys Pro Ile Leu Phe Lys Ala Gln Trp Phe Ile Val Leu Ala Val
                275                 280                 285

Leu Asn Ser Ala Met Asn Pro Val Ile Tyr Thr Leu Ala Ser Lys Glu
                290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Asn Asn Ser Ser His Ser Pro Lys Val Lys
                340                 345                 350

Glu Asp Leu Pro His Thr Ala Pro Ser Ser Cys Ile Met Asp Lys Asn
                355                 360                 365

Ala Ala Leu Gln Asn Gly Ile Phe Cys Asn
                370                 375

<210> SEQ ID NO 55
<211> LENGTH: 398
<212> TYPE: PRT
<213> ORGANISM: Homo sapiens

<400> SEQUENCE: 55

Met Glu Asn Glu Thr Val Ser Glu Leu Asn Gln Thr Gln Leu Gln Pro
 1               5                  10                  15

Arg Ala Val Val Ala Leu Glu Tyr Gln Val Val Thr Ile Leu Leu Val
                20                  25                  30
```

```
Leu Ile Ile Cys Gly Leu Gly Ile Val Gly Asn Ile Met Val Val Leu
         35                  40                  45

Val Val Met Arg Thr Lys His Met Arg Thr Pro Thr Asn Cys Tyr Leu
 50                  55                  60

Val Ser Leu Ala Val Ala Asp Leu Met Val Leu Val Ala Ala Gly Leu
 65                  70                  75                  80

Pro Asn Ile Thr Asp Ser Ile Tyr Gly Ser Trp Val Tyr Gly Tyr Val
                 85                  90                  95

Gly Cys Leu Cys Ile Thr Tyr Leu Gln Tyr Leu Gly Ile Asn Ala Ser
             100                 105                 110

Ser Cys Ser Ile Thr Ala Phe Thr Ile Glu Arg Tyr Ile Ala Ile Cys
         115                 120                 125

His Pro Ile Lys Ala Gln Phe Leu Cys Thr Phe Ser Arg Ala Lys Lys
     130                 135                 140

Ile Ile Ile Phe Val Trp Ala Phe Thr Ser Leu Tyr Cys Met Leu Trp
145                 150                 155                 160

Phe Phe Leu Leu Asp Leu Asn Ile Ser Thr Tyr Lys Asp Ala Ile Val
                 165                 170                 175

Ile Ser Cys Gly Tyr Lys Ile Ser Arg Asn Tyr Tyr Ser Pro Ile Tyr
             180                 185                 190

Leu Met Asp Phe Gly Val Phe Tyr Val Val Pro Met Ile Leu Ala Thr
         195                 200                 205

Val Leu Tyr Gly Phe Ile Ala Arg Ile Leu Phe Leu Asn Pro Ile Pro
     210                 215                 220

Ser Asp Pro Lys Glu Asn Ser Lys Thr Trp Lys Asn Asp Ser Thr His
225                 230                 235                 240

Gln Asn Thr Asn Leu Asn Val Asn Thr Ser Asn Arg Cys Phe Asn Ser
                 245                 250                 255

Thr Val Ser Ser Arg Lys Gln Val Thr Lys Met Leu Ala Val Val Val
             260                 265                 270

Ile Leu Phe Ala Leu Leu Trp Met Pro Tyr Arg Thr Leu Val Val Val
         275                 280                 285

Asn Ser Phe Leu Ser Ser Pro Phe Gln Glu Asn Trp Phe Leu Leu Phe
     290                 295                 300

Cys Arg Ile Cys Ile Tyr Leu Asn Ser Ala Ile Asn Pro Val Ile Tyr
305                 310                 315                 320

Asn Leu Met Ser Gln Lys Phe Arg Ala Ala Phe Arg Lys Leu Cys Asn
                 325                 330                 335

Cys Lys Gln Lys Pro Thr Glu Lys Pro Ala Asn Tyr Ser Val Ala Leu
             340                 345                 350

Asn Tyr Ser Val Ile Lys Glu Ser Asp His Phe Ser Thr Glu Leu Asp
         355                 360                 365

Asp Ile Thr Val Thr Asp Thr Tyr Leu Ser Ala Thr Lys Val Ser Phe
     370                 375                 380

Asp Asp Thr Cys Leu Ala Ser Glu Val Ser Phe Ser Gln Ser
385                 390                 395

<210> SEQ ID NO 56
<211> LENGTH: 418
<212> TYPE: PRT
<213> ORGANISM: Homo sapiens

<400> SEQUENCE: 56

Met Arg Leu Ser Ala Gly Pro Asp Ala Gly Pro Ser Gly Asn Ser Ser
 1               5                  10                  15
```

```
Pro Trp Trp Pro Leu Ala Thr Gly Ala Gly Asn Thr Ser Arg Glu Ala
            20                  25                  30

Glu Ala Leu Gly Glu Gly Asn Gly Pro Pro Arg Asp Val Arg Asn Glu
         35                  40                  45

Glu Leu Ala Lys Leu Glu Ile Ala Val Leu Ala Val Thr Phe Ala Val
50                  55                  60

Ala Val Leu Gly Asn Ser Ser Val Leu Ala Leu His Arg Thr Pro
65                  70                  75                  80

Arg Lys Thr Ser Arg Met His Leu Phe Ile Arg His Leu Ser Leu Ala
                85                  90                  95

Asp Leu Ala Val Ala Phe Phe Gln Val Leu Pro Gln Met Cys Trp Asp
             100                 105                 110

Ile Thr Tyr Arg Phe Arg Gly Pro Asp Trp Leu Cys Arg Val Val Lys
             115                 120                 125

His Leu Gln Val Phe Gly Met Phe Ala Ser Ala Tyr Met Leu Val Val
         130                 135                 140

Met Thr Ala Asp Arg Tyr Ile Ala Val Cys His Pro Leu Lys Thr Leu
145                 150                 155                 160

Gln Gln Pro Ala Arg Arg Ser Arg Leu Met Ile Ala Ala Trp Val
                 165                 170                 175

Leu Ser Phe Val Leu Ser Thr Pro Gln Tyr Phe Val Phe Ser Met Ile
             180                 185                 190

Glu Val Asn Asn Val Thr Lys Ala Arg Asp Cys Trp Ala Thr Phe Ile
         195                 200                 205

Gln Pro Trp Gly Ser Arg Ala Tyr Val Thr Trp Met Thr Gly Gly Ile
210                 215                 220

Phe Val Ala Pro Val Val Ile Leu Gly Thr Cys Tyr Gly Phe Ile Cys
225                 230                 235                 240

Tyr Asn Ile Trp Cys Asn Val Arg Gly Lys Thr Ala Ser Arg Gln Ser
             245                 250                 255

Lys Gly Ala Glu Gln Ala Gly Val Ala Phe Gln Lys Gly Phe Leu Leu
         260                 265                 270

Ala Pro Cys Val Ser Ser Val Lys Ser Ile Ser Arg Ala Lys Ile Arg
         275                 280                 285

Thr Val Lys Met Thr Phe Val Ile Val Thr Ala Tyr Ile Val Cys Trp
         290                 295                 300

Ala Pro Phe Phe Ile Ile Gln Met Trp Ser Val Trp Asp Pro Met Ser
305                 310                 315                 320

Val Trp Thr Glu Ser Glu Asn Pro Thr Ile Thr Ile Thr Ala Leu Leu
             325                 330                 335

Gly Ser Leu Asn Ser Cys Cys Asn Pro Trp Ile Tyr Met Phe Phe Ser
         340                 345                 350

Gly His Leu Leu Gln Asp Cys Val Gln Ser Phe Pro Cys Cys Gln Asn
         355                 360                 365

Met Lys Glu Lys Phe Asn Lys Glu Asp Thr Asp Ser Met Ser Arg Arg
         370                 375                 380

Gln Thr Phe Tyr Ser Asn Asn Arg Ser Pro Thr Asn Ser Thr Gly Met
385                 390                 395                 400

Trp Lys Asp Ser Pro Lys Ser Ser Lys Ser Ile Lys Phe Ile Pro Val
                 405                 410                 415

Ser Thr
```

```
<210> SEQ ID NO 57
<211> LENGTH: 424
<212> TYPE: PRT
<213> ORGANISM: Homo sapiens

<400> SEQUENCE: 57

Met Asp Ser Gly Pro Leu Trp Asp Ala Asn Pro Thr Pro Arg Gly Thr
1               5                   10                  15

Leu Ser Ala Pro Asn Ala Thr Thr Pro Trp Leu Gly Arg Asp Glu Glu
            20                  25                  30

Leu Ala Lys Val Glu Ile Gly Val Leu Ala Thr Val Leu Val Leu Ala
        35                  40                  45

Thr Gly Gly Asn Leu Ala Val Leu Leu Thr Leu Gly Gln Leu Gly Arg
    50                  55                  60

Lys Arg Ser Arg Met His Leu Phe Val Leu His Leu Ala Leu Thr Asp
65                  70                  75                  80

Leu Ala Val Ala Leu Phe Gln Val Leu Pro Gln Leu Leu Trp Asp Ile
            85                  90                  95

Thr Tyr Arg Phe Gln Gly Pro Asp Leu Leu Cys Arg Ala Val Lys Tyr
            100                 105                 110

Leu Gln Val Leu Ser Met Phe Ala Ser Thr Tyr Met Leu Leu Ala Met
        115                 120                 125

Thr Leu Asp Arg Tyr Leu Ala Val Cys His Pro Leu Arg Ser Leu Gln
    130                 135                 140

Gln Pro Gly Gln Ser Thr Tyr Leu Leu Ile Ala Ala Pro Trp Leu Leu
145                 150                 155                 160

Ala Ala Ile Phe Ser Leu Pro Gln Val Phe Ile Phe Ser Leu Arg Glu
            165                 170                 175

Val Ile Gln Gly Ser Gly Val Leu Asp Cys Trp Ala Asp Phe Gly Phe
            180                 185                 190

Pro Trp Gly Pro Arg Ala Tyr Leu Thr Trp Thr Thr Leu Ala Ile Phe
        195                 200                 205

Val Leu Pro Val Thr Met Leu Thr Ala Cys Tyr Ser Leu Ile Cys His
    210                 215                 220

Glu Ile Cys Lys Asn Leu Lys Val Lys Thr Gln Ala Trp Arg Val Gly
225                 230                 235                 240

Gly Gly Gly Trp Arg Thr Trp Asp Arg Pro Ser Pro Ser Thr Leu Ala
            245                 250                 255

Ala Thr Thr Arg Gly Leu Pro Ser Arg Val Ser Ser Ile Asn Thr Ile
            260                 265                 270

Ser Arg Ala Lys Ile Arg Thr Val Lys Met Thr Phe Val Ile Val Leu
        275                 280                 285

Ala Tyr Ile Ala Cys Trp Ala Pro Phe Phe Ser Val Gln Met Trp Ser
    290                 295                 300

Val Trp Asp Lys Asn Ala Pro Asp Glu Asp Ser Thr Asn Val Ala Phe
305                 310                 315                 320

Thr Ile Ser Met Leu Leu Gly Asn Leu Asn Ser Cys Cys Asn Pro Trp
            325                 330                 335

Ile Tyr Met Gly Phe Asn Ser His Leu Leu Pro Arg Pro Leu Arg His
            340                 345                 350

Leu Ala Cys Cys Gly Gly Pro Gln Pro Arg Met Arg Arg Arg Leu Ser
        355                 360                 365

Asp Gly Ser Leu Ser Ser Arg His Thr Thr Leu Leu Thr Arg Ser Ser
    370                 375                 380
```

```
Cys Pro Ala Thr Leu Ser Leu Ser Leu Ser Leu Thr Leu Ser Gly Arg
385                 390                 395                 400

Pro Arg Pro Glu Glu Ser Pro Arg Asp Leu Glu Leu Ala Asp Gly Glu
                405                 410                 415

Gly Thr Ala Glu Thr Ile Ile Phe
            420

<210> SEQ ID NO 58
<211> LENGTH: 371
<212> TYPE: PRT
<213> ORGANISM: Homo sapiens

<400> SEQUENCE: 58

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
                20                  25                  30

Asp Pro Leu Leu Ala Arg Ala Glu Leu Ala Leu Leu Ser Ile Val Phe
            35                  40                  45

Val Ala Val Ala Leu Ser Asn Gly Leu Val Leu Ala Ala Leu Ala Arg
50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
            115                 120                 125

Met Ile Leu Ala Met Thr Leu Asp Arg His Arg Ala Ile Cys Arg Pro
130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
            195                 200                 205

Ile Ala Leu Met Val Phe Val Ala Pro Thr Leu Gly Ile Ala Ala Cys
210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Ala Val Ala Lys Thr Val Arg Met
            260                 265                 270

Thr Leu Val Ile Val Val Val Tyr Val Leu Cys Trp Ala Pro Phe Phe
            275                 280                 285

Leu Val Gln Leu Trp Ala Ala Trp Asp Pro Glu Ala Pro Leu Glu Gly
            290                 295                 300

Ala Pro Phe Val Leu Leu Met Leu Leu Ala Ser Leu Asn Ser Cys Thr
305                 310                 315                 320

Asn Pro Trp Ile Tyr Ala Ser Phe Ser Ser Ser Val Ser Ser Glu Leu
                325                 330                 335
```

```
Arg Ser Leu Leu Cys Cys Ala Arg Gly Arg Thr Pro Pro Ser Leu Gly
                340                 345                 350

Pro Gln Asp Glu Ser Cys Thr Thr Ala Ser Ser Ser Leu Ala Lys Asp
            355                 360                 365

Thr Ser Ser
    370

<210> SEQ ID NO 59
<211> LENGTH: 311
<212> TYPE: PRT
<213> ORGANISM: Homo sapiens

<400> SEQUENCE: 59

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 60
<211> LENGTH: 311
<212> TYPE: PRT
<213> ORGANISM: Homo sapiens

<400> SEQUENCE: 60

```
Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 61
<211> LENGTH: 311
<212> TYPE: PRT
<213> ORGANISM: Homo sapiens

<400> SEQUENCE: 61

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
```

```
                    20                  25                  30
Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
50                      55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
        130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310
```

SCREENING ASSAYS, MODULATORS AND MODULATION OF ACTIVATION OF RECEPTOR FOR ADVANCED GLYCATION END-PRODUCTS (RAGE)

CROSS-REFERENCE TO RELATED APPLICATIONS

This application is a National Stage Entry of International Patent Application No. PCT/AU2018/050883, filed on Aug. 21, 2018, entitled "Screening Assays, Modulators and Modulation of Activation of Receptor for Advanced Glycation End-Products (RAGE)", which claims priority to Australian Patent Application No. 2018902298, filed on Jun. 26, 2018, entitled "Screening Assays, Modulators and Modulation of Activation of Receptor for Advanced Glycation End-Products (RAGE)" and Australian Patent Application No. 2017903381, filed on Aug. 22, 2017, entitled "Screening Assays, Modulators and Modulation of Activation of Receptor for Advanced Glycation End-Products (RAGE)." The disclosures of all of the above applications are hereby incorporated herein by reference in their entirety.

REFERENCE TO A SEQUENCE LISTING SUBMITTED IN A COMPUTER READABLE FORMAT

The application includes an electronic sequence listing in a filed named 264950_RAGE_GPCR_Prov_ST25.TXT, created on Jun. 26, 2018 and containing 169,425 bytes, which is here by incorporated by reference in its entirety for all purposes.

FIELD OF THE INVENTION

This invention relates generally to screening assays for identifying modulators of activation of receptors associated with certain diseases and/or conditions, to such modulators, and to methods of treatment comprising administration of such modulators. More specifically, the invention relates to modulators of activation of the Receptor for Advanced Glycation End-products (RAGE) via RAGE ligand-independent mechanisms by certain co-located, activated G Protein-Coupled Receptors (GPCRs) (also known as RAGE ligand-independent transactivation of RAGE), including activated type 1 angiotensin receptor ($AT_1R$) and activated CC chemokine receptor 2 (CCR2), with or without also modulating activation of RAGE by RAGE ligands, including S100A8/A9, advanced glycation end products (AGEs) and HMGB1. This invention also relates to screening assays for identifying such modulators, and to methods of treatment of RAGE-related disorders using said modulators.

BACKGROUND OF THE INVENTION

The Receptor for Advanced Glycation End-products (RAGE) is a multivalent type I transmembrane glycoprotein belonging to the immunoglobulin (Ig) superfamily (Neeper et al., 1992). The 50-55 kDa glycosylated RAGE protein is constitutively expressed in a limited range of cells (e.g. vascular endothelium, type II pneumocytes, leukocytes), although RAGE expression may be induced in most cell types and tissues following injury and inflammation (Ballinger et al., 2005). RAGE expression is markedly upregulated in important inflammatory and metabolic disorders including but not limited to cardiovascular disease (CVD), cancer, diabetes, chronic kidney disease (CKD), ischaemic injury and Alzheimer's disease (Yan et al., 2010).

It has previously been demonstrated that genetic deletion of the AGER gene coding for RAGE results in protection from a number of diseases and disease processes in mice, including some cancers (Malik et al., 2015) and inflammatory disorders (Chuah et al., 2013) including atherosclerosis and diabetic complications. For example, in apolipoprotein E (apoE) knock-out (KO) mice deletion of RAGE results in less plaque accumulation with age and attenuates diabetes-accelerated atherosclerosis (Soro-Paavonen et al., 2008). Similarly, deletion of AGER is able to attenuate renal injury in diabetic mice without affecting glucose control (Thomas et al., 2005).

Polymorphisms in the AGER gene have been associated with a number of diseases and disease processes in humans, including but not limited to arthritis, atherosclerosis and diabetic complications, cancer risk, obesity, epilepsy, and cognitive impairment including Alzheimer's disease.

Binding to the ectodomain of RAGE by Advanced Glycation End-products (AGEs) and non-AGE ligands (including members of the S100 calgranulin family of proteins, HMGB1, amyloid and Mac-1) activates a range of signal transduction cascades implicated in inflammation, injury and dysfunction, including nuclear factor kappa B (NFκB) and the renin-angiotensin aldosterone system (RAAS).

In experimental models, inhibition of ligand-mediated activation of RAGE using a soluble decoy receptor attenuates atherogenesis and vascular injury (Schmidt et al. 1999), implying that the pathological actions of RAGE are partly mediated by ligand-mediated activation of RAGE in these settings.

The precise molecular mechanisms by which RAGE is activated and asserts all its biological effects are poorly understood, and thus the ability to target these clinically important signalling pathways has not yet occurred in a clinical setting.

The renin-angiotensin aldosterone system (RAAS) is a key homeostatic pathway that is also implicated in the development and progression of many common diseases and disease processes. Inhibition of the renin-angiotensin aldosterone system (RAAS) with angiotensin-converting enzyme (ACE) inhibitors, or angiotensin II receptor type 1 ($AT_1R$) blockers (inhibitors) is widely used for the management of many diseases and/or conditions including hypertension, cardiovascular disease (CVD), heart failure, chronic kidney disease (CKD), and diabetic complications. RAAS inhibition has also been shown to have benefits in preventing diabetes (Tikellis et al., 2004), in neuroprotection (Thoene-Reineke et al., 2011), modifying the growth of certain cancers (Shen et al., 2016) and even in ageing, with genetic deletion of $AT_1R$ conferring longevity in mice (Benigni et al., 2009).

These actions of RAAS blockers are additional to and independent of blood pressure lowering conferred by RAAS blockers, as comparable lowering of the blood pressure with other agents does not confer the same benefits (Lee et al., 1993). Specifically, activation of the $AT_1R$ by angiotensin II (Ang II) triggers induction of oxidative stress, activation of Nuclear Factor κB (NFκB) and inflammation through pathways that are distinct from those that cause vasoconstriction.

Activation of the renin-angiotensin aldosterone system (RAAS) is known to be an important mediator of atherosclerosis (Lee et al., 1993; and Jacoby et al., 2003). Atherogenesis is increased following an infusion of angiotensin (Ang) II and in experimental models is associated with physiological RAAS activation, including a low salt diet (Tikellis et al., 2012), diabetes (Goldin et al., 2006; and Soro-Paavonen et al., 2008) and genetic deletion of angiotensin converting enzyme 2 (Ace2) (Thomas et al., 2010), independent of its effects on blood pressure homeostasis. Similarly, inhibition of the RAAS has anti-atherosclerotic actions that are additional to and independent of lowering systemic blood pressure (Candido et al., 2002; Candido et al., 2004; and Knowles et al., 2000). Ang II has a number of direct pro-atherosclerotic effects (Daugherty et al., 2000; Ferrario et al., 2006; and Ekholm et al., 2009), including the induction of oxidative stress (Rajagopalan et al., 1996), vascular adhesion (Grafe et al., 1997) and inflammation (Marvar et al., 2010).

These pro-atherosclerotic actions are thought to be primarily mediated by activation of the type 1 angiotensin receptor ($AT_1R$) and subsequent induction of reactive oxygen species (ROS) and activation of NFκB signalling (Li et al., 2008). However, the signalling mechanisms that underlie these actions are poorly understood, including their relative independence from conventional vasoconstrictor signalling via the $AT_1R$.

The pathogenesis of atherosclerosis has also been shown to involve certain chemokine signalling pathways, with the infiltration of macrophages into arterial lesions directly contributing to this aberrant inflammatory disorder (Boisvert et al., 2004). Indeed, all known CC and CXC chemokine receptors, as well as CX3CR1 and XCR1, have been implicated in inflammation (Murphy et al. 2000; Zlotnik and Yoshie 2000). The primary physiological function of chemokine ligands (CCLs) is the regulation of "cell migration during routine immune surveillance, inflammation and development". (Allen et al., 2007). CCLs are released in response to pro-inflammatory cytokines and selectively bind to a large family of G protein-coupled receptors, which mediate the physiological responses to chemokines. Chemokines were originally referred to as chemotactic cytokines.

Animal model studies of chronic inflammatory diseases have demonstrated that inhibition of binding between MCP-1 (monocyte chemotactic protein-1, also known as monocyte chemoattractant protein-1, monocyte chemotactic and activating factor (MCAF) and chemokine (C-C motif) ligand 2 (CCL2)) and CCR2 (chemokine (C-C motif) receptor 2) by an antagonist suppresses the inflammatory response. The interaction between MCP-1 and its cognate receptor CCR2 has been implicated (Rollins, 1996; Dawson et al., 2003) in inflammatory disease pathologies such as uveitis, atherosclerosis, rheumatoid arthritis, multiple sclerosis, Crohn's Disease, nephritis, organ allograft rejection, fibroid lung, renal insufficiency, diabetes and diabetic complications, diabetic nephropathy, diabetic retinopathy, diabetic retinitis, diabetic microangiopathy, tuberculosis, sarcoidosis, invasive staphylococcal infection, inflammation after cataract surgery, allergic rhinitis, allergic conjunctivitis, chronic urticaria, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumours and cancers, chronic lymphocytic leukaemia, chronic myeloid leukaemia, multiple myeloma, malignant myeloma, Hodgkin's disease, and carcinomas of the bladder, breast, cervix, colon, lung, prostate, or stomach.

Both MCP-1 and CCR2 KO mice have demonstrated that monocyte infiltration into inflammatory lesions is significantly decreased in the absence of these signalling pathways. In addition, such KO mice are resistant to the development of experimental allergic encephalomyelitis (EAE, a model of human Multiple Sclerosis), cockroach allergen-induced asthma, atherosclerosis, and uveitis. Rheumatoid arthritis and Crohn's Disease patients have improved during treatment with TNFα antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e. to up-regulate) the expression of MCP-1 and other chemokines in the nasal mucosa of people with allergic rhinitis, suggesting the presence of a positive feedback loop in such patients.

Kidney disease is associated with chronic inflammation characterised by the accumulation of kidney macrophages. The production of monocyte chemoattractant protein-1 (MCP-1/CCL2) by diabetic kidneys has been identified as a major factor influencing macrophage accumulation in the kidney disease arising from diabetic nephropathy (Tesch et al., 2008). In various animal models inhibition of CCR2 and/or inhibition of specific CCR2 pathways and/or inhibition of the CCR2 ligand MCP-1 has been shown to reduce kidney damage (Tesch et al., 2008; Rao V et a., 2006; Kang et al., 2010; Kitagawa et al., 2004; Park J et al., 2008).

Tesch (2008) notes that selective targeting of MCP-1 has been proven to be an effective treatment in suppressing animal models of kidney disease that include diabetic nephropathy. Treatments including small molecular antagonists of CCR2 (INCB3344, propagermanium, RS-504393) have been shown to suppress inflammation in mouse models of multiple sclerosis, renal ischemia-reperfusion injury, ureteric obstruction, and diabetic nephropathy and in a rat model of arthritis. Engineered biological antagonists of CCR2 have also proven effective. Subcutaneous infusion of cells transfected with a vector expressing a truncated inactive form of MCP-1 has been found to suppress the development of renal inflammation in a mouse model of lupus nephritis. Similarly, muscle transfection with 7ND (a mutant of MCP-1) reduces renal inflammation in mouse models of renal ischemia-reperfusion injury, lupus nephritis, and diabetic nephropathy. Human trials of chemokine monotherapies for inflammatory diseases, to date, have not led to drug approvals. Anders H J et al. considers reasons why single chemokine antagonist treatments have not been effective in disease treatments and discuss possible explanations including redundancy of single chemokine mediators and variable expression patterns of chemokine receptors (Anders H J et al. 2010). Therefore, there exists a need in the art for an effective treatment of diseases that are caused through activation of CCR2 pathways.

It is important to note that the concept that RAGE can be activated in a RAGE ligand-independent manner via an activated, co-located GPCR that is the subject of this invention has implications for a number of GPCRs, particularly those associated with inflammation and cellular proliferation.

It is against this background that the novel functional interactions between certain activated co-located GPCRs, including the $AT_1R$ and CCR2, and RAGE in a RAGE ligand-independent manner, are described.

SUMMARY OF THE INVENTION

It is known that RAGE signalling, the renin angiotensin aldosterone system (RAAS) and certain chemokine signalling pathways interact functionally in pathways implicated in the development and progression of vascular complications. For example, binding of RAGE ligands to RAGE is able to induce pro-inflammatory signalling, which can be reduced by antagonists (inhibitors) of the $AT_1R$ (e.g. Fukami et al. 2004). Equally, activation of the $AT_1R$ receptor by Ang II increases the formation and release of RAGE ligands, and inhibition of RAGE ligand-binding to RAGE or interventions to reduce RAGE ligands are able to attenuate Ang II-$AT_1R$ induced injury (e.g. Thomas et al. 2005). Some of the downstream signalling pathways and mediators induced following activation of RAGE by RAGE ligands, especially those that lead to inflammation, are also similar to those signalling pathways and mediators induced following activation of $AT_1R$ by Ang II (e.g. NFκB activation).

This prior art does not suggest or disclose any evidence for complexing between RAGE and a GPCR, such as an angiotensin receptor, such as $AT_1R$, or certain chemokine receptors, such as CCR2. Nor does it anticipate that activation of a co-located GPCR by that GPCR's cognate ligand, such as an angiotensin receptor by Ang II or CCR2 by MCP-1, would directly result in activation of RAGE, in particular the cytosolic tail of RAGE, nor the subsequent induction of signalling via RAGE, in the absence of any RAGE ligand, or indeed without requiring the presence of the RAGE ligand-binding ectodomain of RAGE. Consequently, it could not be anticipated that modulation of RAGE ligand-independent activation of the cytosolic tail of RAGE would involve modulation of signalling induced following activation of a certain co-located GPCR, such as by binding of Ang II to the $AT_1R$ or MCP-1 to CCR2.

One of the salient features of RAGE is its activation by multiple ligands at multiple sites on its ectodomain, rather than a single ligand and a single binding site amenable to inhibition. RAGE may be activated by Advanced Glycation End-products (AGEs) and other non-AGE ligands including high mobility group box-1 (HMGB-1), S-100/calgranulins, SAA, Aβ, C3a, heat shock protein 70 (HSP70), the matricellular injury-related glycoprotein secreted protein acidic and rich in cysteine (SPARC), the β2-integrin Mac-1 (CD11b), phosphatidylserine (PS), double-stranded DNA (dsDNA), double stranded RNA (dsRNA), lipopolysaccharides (LPS) and advanced oxidation protein products.

Activation of the ectodomain of RAGE by RAGE ligands triggers the activation of NFκB and subsequent NFκB-driven gene expression leading to inflammation, oxidative stress, fibrogenesis and cellular proliferation (Bierhaus et al., 2001).

RAGE ligand-induced signalling also triggers a positive feedback loop in which RAGE ligand-receptor interaction increases expression of RAGE via NFκB activation, thereby augmenting subsequent RAGE-induced cellular activation. In fact, the only means the inventors know to strongly downregulate RAGE expression is to reduce activation of RAGE. This situation contrasts with other receptors, such as the low-density lipoprotein (LDL) receptor, in which increased levels of ligand decrease expression of the receptor.

Importantly, the inventors have shown that following activation of certain co-located GPCRs, such as $AT_1R$ by Ang II or CCR2 by MCP-1, the cytosolic tail of RAGE is activated, independently of any RAGE ligand or the ectodomain of RAGE, initiating downstream signalling leading to activation of NFκB, a key transcription factor implicated in inflammation, oxidative stress, fibrogenesis, cellular proliferation and cellular survival. The absence of RAGE expression, and specifically the absence of expression of a key domain in the RAGE cytosolic tail, independent of expression of the RAGE ectodomain, prevents the induction of NFκB activation following activation of the co-located GPCR, such as $AT_1R$ by Ang II or CCR2 by MCP-1. Without wishing to be bound by theory, the inventors believe that RAGE ligand-independent activation of RAGE cytosolic tail by certain co-located activated GPCRs, including $AT_1R$ and CCR2, is a dominant pathway by which RAGE is activated. Moreover, and again without wishing to be bound by theory, the inventors believe the de novo expression of RAGE in cells subjected to injury, stress or hypoxia for example, provides a conduit for pro-inflammatory signalling to occur via activation of established GPCR signalling.

The inventors have shown that RAGE ligand-independent activation of the RAGE cytosolic tail following activation of certain co-located GPCRs, such as $AT_1R$ by Ang II or CCR2 by MCP-1, also triggers signalling to increase RAGE expression.

RAGE has been implicated in many aspects of tumour biology including growth, migration and invasion of tumour cells (Malik et al., 2015; Abe et al., 2008). Many cancers have higher levels of RAGE (illustrative examples are breast, colon, kidney and stomach cancer; Taguchi et al., 2000). The exception is lung cancer in which RAGE expression is reduced as RAGE is a normal part of lung function and is lost as lung cells differentiate and become more malignant (Marinakis et al., 2014). In C6 glioma cells, tumour volume is markedly diminished in tumours comprised of cells in which RAGE was blocked. In contrast, tumours overexpressing RAGE grew rapidly and invaded the surrounding tissue very efficiently (Taguchi et al., 2000). Calls for therapeutics to block RAGE signalling as a cancer treatment have been made for many common cancers including but not limited to: glioma/medulloblastoma multiforme (Taguchi et al., 2000); pancreatic cancer (Malik et al., 2015; Leclerc et al., 2015); melanoma (Malik et al., 2015); prostate cancer (Malik et al., 2015); breast cancer (Malik et al., 2015); liver cancer/hepatoma (Logsdon et al., 2007; Volz et al., 2010); and colon cancer (Sparvero et al., 2009).

RAGE has been implicated in a range of brain disorders including but not limited to Alzheimer's Disease in which preclinical and clinical studies have supported that RAGE inhibitors could be useful in its treatment (Cai et al., 2016). Other brain conditions in which RAGE signalling is implicated include but are not limited to: amylotrophic lateral sclerosis (Ray et al 2016); Huntington's Disease (Ray et al 2016); Creutzfeld-Jakob's disease (Ray et al 2016); neurodegenerative conditions such as diabetic neuropathy, familial amyloid polyneuropathy, Charcot neuroarthropathy and vasculitic neuropathy (Ray et al 2016); neuropathic pain (Wan et al., 2016); glioma development and progression (Angelopoulou et al., 2016); and ischaemic brain injury/stroke (Xia et al 2010).

Under healthy conditions, the lungs' expression of RAGE is the highest of all tissues. However, RAGE expression in the lung is normally only seen in type 1 pneumocytes. Upregulation of RAGE signalling in the lung in other cells and at other sites has been implicated in a range of lung disorders including but not limited to: chronic obstructive pulmonary disease (COPD)/emphysema (Sukkar et al., 2012); asthma (Sukkar et al., 2012); injury due to cigarette smoking/pollution; acute lung injury/Acute Respiratory Distress Syndrome (ARDS) (Guo et al., 2012); and pulmonary fibrosis.

RAGE is critically involved in a number of inflammatory conditions and is consequently a potential therapeutic target for their treatment. Such conditions include but are not limited to: inflammatory arthritis (Sparvero et al., 2009; Chuah et al., 2013); osteoarthritis (Xie et al., 2013); retinal disease (Barile. et al., 2007); atherosclerosis (Soro-Paavonen et al., 2008; Schmidt et al., 1999; Park et al., 1998; Zhou et al., 2003; Yan et al., 2010); vascular calcification (Ott et al., 2014); cardiomyopathy (Volz et al., 2010; Russo et al., 2016); ischaemic cardiac disease/cardiac remodelling/fibrosis (Yan et al., 2010; Ramasamy et al., 2012); heart failure (Ramasamy et al., 2012); diabetic and non-diabetic kidney disease (Fukami et al., 2015; Gugliucci et al., 2014); inflammatory bowel disease (Ott et al., 2014); pre-eclampsia (Daffu et al., 2013); polycystic ovarian syndrome (Garg et al., 2015); hepatic steatosis, fibrosis, ischemic and non-ischemic liver injury (Yamagishi et al., 2015); spinal cord injury (Yamagishi et al., 2015); skin inflammation and ageing (Tong et al., 2014); and keratitis (Tong et al., 2014).

The present invention arises in part from the determination by the inventors that RAGE forms a receptor heteromer complex in the cell membrane with certain co-located GPCRs, including $AT_1R$ and CCR2.

Furthermore, the present invention arises in part from a recognition by the inventors that activation of certain co-located GPCRs, such as the angiotensin receptor, in the form of $AT_1R$, in this case with Ang II, or certain chemokine receptors such as CCR2 in this case with MCP-1, triggers RAGE ligand-independent activation of the cytosolic tail of RAGE.

The inventors have shown that activation of certain co-located GPCRs, such as the $AT_1R$ by Ang II or CCR2 by MCP-1, results in the activation of a domain of the cytosolic tail of RAGE through a common mechanism. This pathway of transactivation does not require the liberation of RAGE ligands or require their binding to the ectodomain of RAGE (i.e. it is RAGE ligand-independent activation of RAGE).

Even though there are published data suggesting that the cytosolic tail of RAGE is phosphorylated (Sakaguchi et al., 2011), the inventors have shown that RAGE ligand-independent signalling induced following activation of certain co-located GPCRs, such as the $AT_1R$ receptor by Ang II, does not require the cytosolic tail of RAGE to be phosphorylated at Serine391 or any other site in the cytosolic tail of RAGE. Furthermore, the inventors have shown that RAGE ligand-dependent signalling induced following RAGE ligand (e.g. S100A8/A9) binding to the ectodomain of RAGE also does not necessarily require the cytosolic tail of RAGE to be phosphorylated at Serine391 or any other site in the cytosolic tail, as RAGE homologs from other mammals and RAGE mutants devoid of any residues capable of sustaining phosphorylation are still able to be activated and induce signalling in response to RAGE ligand-dependent and RAGE ligand-independent activation of RAGE. Furthermore, the inhibitory functions of N-truncated constructs of RAGE (e.g. S391A-$RAGE_{362-404}$) are maintained in the absence of targets for RAGE phosphorylation, confirming that the modulatory effects of the RAGE constructs described by the inventors are independent of phosphorylation of RAGE.

Prior art demonstrates that inhibitors of PKCζ inhibit RAGE ligand-dependent (e.g. s100-induced) signalling via RAGE, as well as many other PKCζ-dependent pathways. In humans and animals severe illness results from genetic deletion of PKCζ. The investigators have shown that inhibitors of PKCζ also inhibit RAGE ligand-independent (i.e. transactivation-induced) signalling via full-length RAGE. However, the modulatory functions of N-truncated constructs of RAGE (e.g. $RAGE_{362-404}$) are not affected by inhibition of PKCζ, confirming that the modulatory effects of the RAGE constructs described by the inventors are independent of PKCζ.

Inhibitors of the shared pathways induced subsequent to RAGE activation (e.g. myD88, TIRAP, interleukin-1 receptor-associated kinase 4 (IRAK4) or NFκB) non-specifically block both RAGE ligand-dependent (e.g. s100-induced) and RAGE ligand-independent (i.e. transactivation-induced) signalling via RAGE. As other receptors (e.g. TLRs) also use these signalling molecules/pathways, inhibition of any of these mediators would not be specific to RAGE signalling and impact on the many other functions of these signalling mediators, which may be deleterious to human health (e.g. genetic deletion of myD88, TIRAP, IRAK4 or NFκB are harmful to humans and animals, unlike RAGE deletion).

The inventors have further shown that selective modulation, such as inhibition, of RAGE ligand-independent signalling can be achieved by selectively targeting signalling mediated through the cytosolic tail of RAGE, and the inventors' assays and modulators identified therefrom, act upon this transactivation (RAGE ligand-independent activation of RAGE) process.

The inventors have further shown that dual inhibition of RAGE ligand-dependent activation of RAGE and RAGE ligand-independent transactivation of RAGE signalling can also be achieved through selectively targeting signalling mediated through the cytosolic tail of RAGE, and the inventors' assays and modulators identified therefrom are able to act simultaneously upon both modalities of RAGE activation due to shared mediators. This is in direct distinction to soluble $RAGE_{22-331}$, RAGE neutralising antibodies and small molecules that selectively bind to the ectodomain of RAGE and can only potentially inhibit RAGE ligand-dependent activation of RAGE.

The inventors have further shown that modulation of RAGE ligand-dependent signalling and/or RAGE ligand-independent transactivation of RAGE signalling by selectively targeting signalling mediated through the cytosolic tail of RAGE can be achieved without modulation of the interaction of RAGE and Diaphanous-1 (Diaph1), that prior art suggests is potentially a modulator of ligand-dependent RAGE activation (Manigrasso, M. B., et al 2016). Furthermore, the modulatory functions of N-truncated constructs of RAGE (e.g. $RAGE_{362-404}$) are maintained in the absence of Diaph1, confirming that the modulatory effects of the RAGE constructs described by the inventors are independent of Diaph1

Sakaguchi and co-workers found that common pro-inflammatory adaptor proteins TIRAP, MyD88 and IRAK were co-precipitated with overexpressed RAGE in HEK293 cells predominantly when the cells were treated with RAGE ligands, S100A11, S100A12, HMGB1 or AGEs, resulting in the RAGE ligand-dependent activation of RAGE. These interactions are not specific to RAGE, as TIRAP, MyD88 and IRAK also function as adaptor proteins for all toll-like receptors (TLRs) except TLR-3, to activate the transcription of NFκB.

Following this work, the same group published research proposing S391E-$RAGE_{387-395}$ (RAGE(E)-I) as an inhibitor of particular aspects of RAGE ligand-dependent signalling (namely inhibition of apoptosis, cell migration and invasion) through mimicking the phosphorylated state of RAGE and sequestering the adaptor protein TIRAP, and thereby preventing endogenous RAGE signalling (Putranto et al., 2013). However, the inventors have shown that phosphorylation is not required for RAGE activation. Moreover, sequestering these common adaptor proteins will also impact on signalling through TLRs (e.g. TLR-2 and TLR-4), some of which may also be activated by RAGE ligands (e.g. s100 proteins) which likely explains the findings of Puranto et al. In the same experiments, they also argued that S391A-RAGE$_{387-395}$ was not a suitable inhibitor as it did not show any appreciable binding to TIRAP and did not attenuate apoptosis induced by RAGE ligand S100B (Putranto et al., 2013). They also noted that S391E-RAGE$_{387-395}$ did not inhibit all RAGE-ligand induced signalling pathways, as the growth of U-87MG cells was not significantly affected as assessed by determining intracellular adenosine triphosphate content (Putranto et al., 2013). Therefore, the RAGE ligand-dependent pathway putatively inhibited by Putranto and co-workers and the fragment of RAGE cytosolic tail that they utilised are demonstrably distinct from the RAGE ligand-independent activation of RAGE by co-located activated GPCR and the modulators that are the subject of this invention. Indeed, their negative findings with S391A-RAGE$_{387-395}$ teach away from the current invention. At no point in this publication did Putranto et al contemplate RAGE ligand-independent activation of the cytosolic tail of RAGE by co-located GPCRs.

EP 1 415 997-A1 details the identification and use of polypeptides to bind directly or indirectly to the cytosolic tail of RAGE and thereby inhibit or augment the signal transduction arising from binding of a ligand to RAGE and subsequent activation of NFκB and downstream pathways arising from its activation. The present invention is distinct from this teaching in a number of ways. Firstly, this teaching does not contemplate RAGE ligand-independent signalling via RAGE or dual inhibition of RAGE ligand-dependent and RAGE ligand-independent signalling via RAGE. Secondly, claims in EP 1 415 997 A1 relate to use of polypeptides to bind to unidentified elements in the cytosolic tail of RAGE. By contrast, the present inventors have demonstrated that a polypeptide coding for the cytosolic tail of RAGE, and mutated forms of such, can be used to selectively bind signalling molecules associated with RAGE ligand-independent signalling via RAGE or RAGE ligand-dependent and RAGE ligand-independent signalling via RAGE leading to the modulation of the subsequent activation of NFκB and downstream pathways arising from its activation. Thirdly, the inventors have demonstrated the ability to modulate RAGE ligand-independent signalling via RAGE using selectively modified polypeptides containing key elements of the RAGE cytosolic tail. Fourthly, no modulation of RAGE ligand-dependent signalling via RAGE is shown in EP 1 415 997-A1. Moreover, the only polypeptide capable of modulating RAGE ligand-dependent signalling specifically identified in EP 1 415 997-A1 is PKCζ, a well-known binding partner and signalling mediator of full length RAGE. The present inventors show that PKCζ is not required for the actions of their modulators.

RAGE is mono-ubiquitinated by the F-box protein, FBXO10, at cytosolic residue K374 following binding of CpG-DNA, triggering its endocytosis and lysosomal-mediated degradation (Evankovich et al. 2017). Endocytosis and/or RAGE ubiquitination has not been observed with other pro-inflammatory RAGE ligands.

Ubiquitination of RAGE is partly dependent on S391, such that S391A-RAGE mutants are partly resistant to ubiquitination and subsequent degradation following FBXO10 overexpression.

These data suggest that K374R and S391A-RAGE mutants may have resistance to ubiquitination in certain circumstances, potentially allowing them to accumulate in higher levels than wild-type RAGE. However, this potentially increased stability/resistance to degradation cannot explain the rapid modulation of RAGE ligand-independent activation of RAGE following activation of a co-located GPCR, as well as inhibition of RAGE ligand-independent activation of RAGE signalling achieved by S391A-RAGE mutants even in the presence of wild-type RAGE delivered in 1000-fold excess, detailed below, nor that this modulation occurs similarly in the presence and absence of K374.

Without limiting the generality of the following description of the invention, the inventors have demonstrated that activation of certain co-located GPCRs such as the AT$_1$R, such as by Ang II, or CCR2, such as by MCP-1, triggers activation of co-located cytosolic tail of RAGE. This activation is able to take place in the absence of the ectodomain of RAGE and therefore is entirely independent of RAGE ligands or their interaction with the ectodomain of RAGE. Without wishing to be bound by theory, the inventors believe that this transactivation of RAGE by certain co-located GPCRs represents the major mechanism of RAGE activation. Consistent with this premise, the inventors demonstrate that selective restoration of RAGE ligand-independent RAGE signalling in AGER apoE double KO (DKO) mice restores atherogenesis to levels not significantly different from that observed in apoE KO mice replete in RAGE, even though RAGE-ligand-dependent signalling remains completely absent.

Many of the adverse signalling events induced by AT$_1$R activation are attenuated when RAGE expression is absent (e.g. genetic deletion or silencing, or in healthy cells not expressing RAGE, or when RAGE ligand-independent activation of RAGE by activated AT$_1$R is prevented or inhibited).

At the same time, RAGE-independent AT$_1$R signalling pathways, such as the Gq signalling pathway induced by AT$_1$R activation leading to the induction of inositol phosphate and calcium influx, which are inhibited by AT$_1$R antagonists, are unaffected by RAGE deletion, silencing of RAGE expression or inhibition of RAGE function.

As such, modulation, in particular inhibition, of RAGE ligand-independent activation of RAGE by certain activated co-located GPCRs, such as AT$_1$R or CCR2, provides particular advantages for therapeutic interventions targeting pathogenic signalling induced via RAGE following activation of the co-located GPCR. For example, such modulators, in specific embodiments, allow aggressive targeting of the adverse effects of AT$_1$R without compromising blood pressure regulation or inducing feedback "escape" from AT$_1$R inhibition, such as occurs following AT$_1$R inhibition, that limits the use of RAAS inhibitors. Such modulators would also only affect cells and tissues in which this transactivation pathway was constitutively active (e.g. leukocytes, endothelial cells) or induced (e.g. sites of inflammation and injury), leaving the RAAS and other GPCR-mediated signalling unaffected in cells not also expressing RAGE (e.g. healthy smooth muscle cells).

Activation of AT$_1$R has both hemodynamic and non-hemodynamic effects. Hemodynamic effects are those that lead to changes in blood flow, and include changes in blood volume, blood pressure, flow rate or velocity, resistance, cardiac output, turbulence and wall tension. AT$_1$R blockers (inhibitors) can exhibit both hemodynamic (e.g. lower the blood pressure, alter resistance and cardiac output) as well as non-hemodynamic effects (e.g. trigger oxidative stress and inflammation). In states in which the RAAS is activated (e.g. heart disease, kidney disease, hypertension) both hemodynamic and non-hemodynamic pathways are activated.

RAGE ligand-independent activation of RAGE by activated $AT_1R$ is a mediator only of the non-hemodynamic (non-blood flow effects) of $AT_1R$ activation. The inventors have observed that total genetic deletion of RAGE has no direct hemodynamic effect (e.g. no effect on blood pressure, vessel resistance or flow, blood volume) and does not modify the hemodynamic effects of $AT_1R$ activation or inhibition. The key advantage of targeting RAGE ligand-independent activation of RAGE by activated $AT_1R$ is that it is therefore not limited by the constraints of blood pressure regulation, which limit how much blood pressure lowering is possible before adverse hemodynamic effects render said treatment unsafe.

Moreover, changes in blood flow automatically trigger feedback (homeostatic) responses to maintain blood flow at a constant level. These feedback responses act to offset or escape the hemodynamic effects of inhibition of the RAAS by $AT_1R$ inhibition or inhibition of Angiotensin Converting Enzyme (ACE). By contrast, selective inhibition of non-hemodynamic pathways induced following activation of the RAAS achieved through inhibiting RAGE ligand-independent activation of RAGE by activated angiotensin receptor, such as $AT_1R$, is not associated with feedback/escape responses. The absence of such feedback responses supports the durability and efficacy of such inhibition.

Modulators of RAGE Ligand-Independent Activation of RAGE by Activated Co-Located GPCRs In one form, the present invention comprises modulators of RAGE activity where such RAGE activity is induced by certain active co-located GPCRs.

In one form, the present invention comprises modulators of RAGE ligand-independent activation of RAGE by certain activated co-located GPCRs.

In one form, the present invention comprises modulators wherein the modulators are modulators of RAGE-dependent signalling induced by certain activated co-located GPCRs.

In one form of the present invention, the modulators of RAGE ligand-independent activation of RAGE by certain activated co-located GPCRs act in the absence of any RAGE ligand.

In one form of the present invention, the modulators of RAGE ligand-independent activation of RAGE by certain activated co-located GPCRs act in the presence of a truncated ectodomain of RAGE.

In one form of the present invention, the modulators of RAGE ligand-independent activation of RAGE by certain activated co-located GPCRs act in the presence of a truncated ectodomain of RAGE which is not greater than 40, not greater than 20, not greater than 10 or not greater than 5 amino acids in length.

In one form of the present invention, the modulators of RAGE ligand-independent activation of RAGE by certain activated co-located GPCRs, contain the entire ectodomain of RAGE conjugated to an analogue, fragment or derivative of the transmembrane domain of RAGE which is greater than 5, greater than 10, or greater than 20 amino acids in length.

In one form of the present invention, the modulators of RAGE ligand-independent activation of RAGE by certain activated co-located GPCRs act in the absence of the RAGE ligand-binding ectodomain of RAGE.

In one form of the present invention, the modulators of RAGE ligand-independent activation of RAGE by certain activated co-located GPCRs do not contain the ectodomain of RAGE.

In one form of the present invention, the modulators of RAGE ligand-independent activation of RAGE by certain activated co-located GPCRs do not contain an analogue, fragment or derivative of the ectodomain of RAGE.

In one form of the present invention, the modulators of RAGE ligand-independent activation of RAGE by certain activated co-located GPCRs contain a fragment of the ectodomain of RAGE.

In one form of the present invention, the modulators of RAGE ligand-independent activation of RAGE by certain activated co-located GPCRs contain a fragment of the ectodomain of RAGE, which is not greater than 40, not greater than 20, not greater than 10 or not greater than 5 amino acids in length.

In one form of the present invention, the modulators of RAGE ligand-independent activation of RAGE by certain activated co-located GPCRs do not bind to the ectodomain of RAGE.

In one form of the present invention, the modulators of RAGE ligand-independent activation of RAGE by certain activated co-located GPCRs inhibit or facilitate signalling that occurs through the C-terminal cytosolic tail of RAGE induced by an activated co-located GPCR.

In one form of the present invention, the modulators of RAGE ligand-independent activation of RAGE by certain activated co-located GPCRs inhibit binding that occurs to the C-terminal cytosolic tail of RAGE.

In one form of the present invention, the modulators of RAGE ligand-independent activation of RAGE by certain activated co-located GPCRs inhibit or facilitate the interaction between the transmembrane domain of RAGE and certain GPCRs.

In one form of the present invention, the modulators of RAGE ligand-independent activation of RAGE by certain activated co-located GPCRs inhibit the interaction between the transmembrane domain of RAGE and certain GPCRs.

In one form of the present invention, the modulators of RAGE ligand-independent activation of RAGE by certain activated co-located GPCRs inhibit or facilitate the capacity of an activated GPCR to modulate RAGE-dependent signalling that is dependent upon proximity of the transmembrane domains of RAGE and the certain GPCR.

In one form of the present invention, the modulators of RAGE ligand-independent activation of RAGE by certain activated co-located GPCRs inhibit the capacity of an activated GPCR to modulate RAGE-dependent signalling that is dependent upon proximity of the transmembrane domains of RAGE and the certain GPCR.

In one form of the present invention, the modulators of RAGE ligand-independent activation of RAGE by certain activated co-located GPCRs inhibit or facilitate the capacity of an activated GPCR to modulate RAGE-dependent signalling that is dependent upon proximity of the transmembrane domains of RAGE and the certain GPCR and inhibit or facilitate signalling that occurs through the C-terminal cytosolic tail of RAGE induced by an activated co-located GPCR.

In one form of the present invention, the modulators of RAGE ligand-independent activation of RAGE by certain activated co-located GPCRs inhibit the capacity of an activated GPCR to modulate RAGE-dependent signalling that is dependent upon proximity of the transmembrane domains of RAGE and the certain GPCR and inhibit signalling that occurs through the C-terminal cytosolic tail of RAGE induced by an activated co-located GPCR.

Throughout this specification, unless the context requires otherwise, a co-located GPCR means a member of the G protein-coupled receptor superfamily (GPCR; also known as seven-transmembrane domain receptors, 7TM receptors, hepta-helical receptors, serpentine receptors, and G protein-linked receptors; some other 7TM proteins have been classified as being members of the G protein-coupled receptor superfamily, including GPR107, GPR137, OR51E1, TPRA1, GPR143 and GPR157) that is co-expressed in the same cell as RAGE, either endogenously or as a result of transfection. Note that not all members of this superfamily couple to G proteins and the term GPCR in this context includes members of the superfamily that do not couple to G protein. Co-expression in the same cell may be demonstrated by a number of techniques known to those skilled in the art, including co-immunoprecipitation, bioluminescence resonance energy transfer (BRET), fluorescence resonance energy transfer (FRET) and microscopy. A co-located GPCR is preferably a GPCR that is sufficiently proximal to RAGE that functional interaction occurs between the GPCR and RAGE. Even more preferably, a co-located GPCR is a GPCR that is sufficiently proximal to RAGE that a suitable proximity assay is able to detect this proximity. Examples of suitable proximity assays are BRET, FRET, enzyme fragment complementation, split luciferase complementation, split fluorophore complementation, TANGO assay, Nano-Luc Binary Technology (NanoBIT) assay, proximity ligation assay (PLA) or any other proximity assay that is able to detect the proximity of two proteins regardless of whether one or more of these proteins is labelled or tagged to facilitate the use of the assay. Such proximity assays can be configured in different ways, and the Receptor-Heteromer Investigation Technology (Receptor-HIT) configuration, and derivations thereof, are preferred configurations of such proximity assays (WO2008/055313; Jaeger et al., 2014).

Throughout this specification, unless the context requires otherwise, an activated GPCR means a GPCR that is in an active state that may result from the binding of an agonist, partial agonist and/or allosteric modulator, and/or as a consequence of constitutive activity that does not necessitate ligand binding.

Throughout this specification, unless the context requires otherwise, the certain activated co-located GPCRs of the invention are GPCRs that are expressed in the same cell as RAGE and for which an effect on RAGE, indicative of modulation of RAGE activation and/or modulation of induction of RAGE-dependent signalling, is detected upon activation by cognate ligands of the certain co-located GPCRs or when the GPCRs are constitutively active.

In one embodiment, an effect on RAGE indicative of modulation of RAGE activation is a change in intracellular trafficking such as that detected by a change in proximity of luciferase-conjugated RAGE (such as RAGE/Rluc8) to intracellular compartment markers such as fluorophore-labelled Rabs, such as Rab1, Rab4, Rab5, Rab6, Rab7, Rab8, Rab9 and/or Rab11 (such as Venus-Rab1, Venus-Rab4, Venus-Rab5, Venus-Rab6, Venus-Rab7, Venus-Rab8, Venus-Rab9 and/or Venus-Rab11), and/or a plasma membrane marker, such as a fluorophore-conjugated fragment of K-ras (such as Venus-K-ras) using bioluminescence resonance energy transfer (BRET) upon addition of a cognate ligand for the co-located GPCR (Tiulpakov et al., 2016).

In another embodiment, an effect on RAGE is a change in RAGE-dependent signalling, such as detected by a change in proximity of luciferase-conjugated RAGE (such as RAGE-Rluc8) to a RAGE-interacting group, such as fluorophore-labelled proteins interacting with the cytosolic tail of RAGE, such as IQGAP-1, protein kinase C zeta (PKCζ), Dock7, MyD88, TIRAP, ERK1/2, (Jules et al., 2013; Ramasamy et al., 2016), olfactory receptor 2T2, ADP/ATP translocase 2, Protein phosphatase 1G, Intercellular adhesion molecule 1, Protein DJ-1 (PARK7), Calponin-3, Drebrin, Filamin B, Ras-related protein Rab-13, Radixin/Ezrin/Moesin, Proteolipid protein 2, Coronin, S100 A11, Succinyl-CoA ligase [GDP-forming] subunit alpha, Hsc70-interacting protein, Apoptosis Inhibitor 5, neuropilin, cleavage stimulation factor, growth factor receptor-bound protein 2, sec61 beta subunit, or Nck1.

In another embodiment, an effect on RAGE is a change in RAGE-dependent signalling, such as detected by a change in canonical activation of NFκB upon activation of the certain co-located GPCRs by their cognate ligands as measured by one or more of the following:

Activity of IkB kinase (IKK) by monitoring in vitro phosphorylation of a substrate, such as GST-IκBα;

Detection of IKB Degradation Dynamics, including phosphorylation/ubiquitination and/or degradation of IκB and/or IκB-α;

Detection of p65(Rel-A) phosphorylation/ubiquitination, such as by using antibodies, gel-shift, EMSA, and/or mass spectroscopy;

Detection of cytosolic to nuclear shuttling/translocation of NFκB components/subunits, such as p65/phospho-p65;

Detection of NFκB subunit dimerization/complexation;

Detection of active NFκB components/subunits by binding to immobilized DNA sequence/oligonucleotide containing the NFκB response element/consensus NFκB binding motif, such as by using electrophoretic mobility shift assay or gel shift assay, SELEX, protein-binding microarray, or sequencing-based approaches;

Chromatin-immunoprecipitation (ChIP) assays to detect NFκB in situ binding to DNA to the promoters and enhancers of specific genes;

In vitro kinase assay for NFκB kinase activity;

Measurement of NFκB transcriptional activity using NFκB reporter assays via transgene expression of reporter constructs, such as LacZ Fluc, eGFP SEAP, and NF-gluc, using such approaches as plasmid transfection, reporter cell lines, mini-circles, retrovirus, or lentivirus;

Measuring changes in expression of downstream targets of NFκB, such as cytokines, growth factors, adhesion molecules and mitochondrial anti-apoptotic genes, by real-time PCR, protein, or functional assays (Note the pleiotropic nature of NFκB is reflected in its transcriptional targets that presently number approximately 500 (see http://www.bu.edu/nf-kb/gene-resources/target-genes/ as at 2 Aug. 2017); and Measuring changes in function or structure induced by NFκB-dependent signalling, such as POLKADOTS in T-cells, adhesion in endothelial cells, activation in leucocytes, or oncogenicity.

In another embodiment, an effect on RAGE is a change in RAGE signalling, such as detected by a change in non-canonical activation of NFκB by measuring one or more of the following:

Detection of NIK (NFκB-Inducing Kinase);

Detecting IKKα Activation/phosphorylation;

Detection of NIK kinase activity by ability to autophosphorylate or to phosphorylate a substrate by performing a kinase assay;

Generation of p52-containing NFκB dimers, such as p52/RelB;

Detection of Phospho-NFκB2 p100(Ser866/870);

Detection of partial degradation (called processing) of the precursor p100 into p52;

Detecting p52/RelB translocation into the nucleus;

Detecting p52/RelB binding to NFκB sites;

Measurement of NFκB transcriptional activity using NFκB reporter assays via transgene expression of reporter constructs, such as LacZ Fluc, eGFP SEAP, NF-gluc, using such approaches as plasmid transfection, reporter cell lines, mini-circles, retrovirus, or lentivirus; and Measuring changes in expression of downstream targets of non-canonical signalling of NFκB, such as CXCL12, by real-time PCR, protein expression or by functional assays.

Co-Located GPCRs

In one embodiment, the certain activated co-located GPCRs of the invention are those GPCRs that are expressed in the same cell as RAGE and are associated with RAGE-related disorders.

In one embodiment, the certain activated co-located GPCRs of the invention are those GPCRs that are expressed in the same cell as RAGE, are associated with RAGE-related disorder(s), and upon their removal and/or inhibition result in reduction or alleviation of the RAGE-related disorder(s).

In one embodiment, the certain activated co-located GPCRs of the invention are those GPCRs that are implicated in inflammation.

In one embodiment, the certain activated co-located GPCRs of the invention are those GPCRs that are implicated in inflammation, and upon their removal and/or inhibition result in reduction or alleviation of the inflammation.

In one embodiment, the certain activated co-located GPCRs of the invention are those GPCRs that are implicated in cell proliferation.

In one embodiment, the certain activated co-located GPCRs of the invention are those GPCRs that are implicated in cell proliferation, and upon their removal and/or inhibition result in reduction or alleviation of the cell proliferation.

Indeed there is evidence for many GPCRs being involved in inflammation to some degree, and these levels can be differentiated according to the level of evidence:

1—No evidence found to date;
2—Receptor structure, or motif within receptor is similar to known inflammatory/immunological receptor or motif involved in an inflammatory/immunological process;
3—Receptor binds a ligand that mediates an inflammatory/immunological process;
4—Receptor is associated with/involved in an inflammatory/immunological disease;
5—At least one paper describing direct involvement of receptor in Inflammatory/immunological process;
6—Receptor is expressed in inflammatory/Immune cells; and
7—Receptor's involvement in inflammatory/Immunological processes is well characterised (as described in http://www.guidetopharmacology.org database).

Family A GPCRs (except olfactory, vomeronasal, opsins) and the current level of evidence for their involvement in inflammation (see key above):

| Type | Subtype | Level of Evidence | Reference |
| --- | --- | --- | --- |
| 5-Hydroxytryptamine receptors | 5-HT1A receptor | 7 | (Freire-Garabal et al., 2003) |
| 5-Hydroxytryptamine receptors | 5-HT1B receptor | 6 | (Stefulj et al., 2000) |
| 5-Hydroxytryptamine receptors | 5-HT1D receptor | 5 | (Rebeck et al., 1994) |
| 5-Hydroxytryptamine receptors | 5-HT1E receptor | 5 | (Granados-Soto et al., 2010) |
| 5-Hydroxytryptamine receptors | 5-HT1F receptor | 6 | (Stefulj et al., 2000) |
| 5-Hydroxytryptamine receptors | 5-HT2A receptor | 7 | (Okamoto et al., 2002) |
| 5-Hydroxytryptamine receptors | 5-HT2B receptor | 6 | (Stefulj et al., 2000) |
| 5-Hydroxytryptamine receptors | 5-HT2C receptor | 6 | (Marazziti et al., 2001) |
| 5-Hydroxytryptamine receptors | 5-HT4 receptor | 4 | (Kanazawa et al., 2011) |
| 5-Hydroxytryptamine receptors | 5-HT5A receptor | 6 | (Marazziti et al., 2001) |
| 5-Hydroxytryptamine receptors | 5-HT5B receptor | 1 | (Rees et al., 1994)-Not expressed in humans due to internal stop codon in gene |
| 5-Hydroxytryptamine receptors | 5-HT6 receptor | 6 | (Stefulj et al., 2000) |
| 5-Hydroxytryptamine receptors | 5-HT7 receptor | 6 | (Stefulj et al., 2000) |
| Acetylcholine receptors (muscarinic) | M1 receptor | 6 | (Sato et al., 1999) |
| Acetylcholine receptors (muscarinic) | M2 receptor | 6 | (Sato et al., 1999) |
| Acetylcholine receptors (muscarinic) | M3 receptor | 6 | (Sato et al., 1999) |
| Acetylcholine receptors (muscarinic) | M4 receptor | 6 | (Sato et al., 1999) |
| Acetylcholine receptors (muscarinic) | M5 receptor | 6 | (Sato et al., 1999) |
| Adenosine receptors | A1 receptor | 7 | (Satoh et al., 2000) |

-continued

| Type | Subtype | Level of Evidence | Reference |
|---|---|---|---|
| Adenosine receptors | A2A receptor | 7 | (McPherson et al., 2001) |
| Adenosine receptors | A2B receptor | 7 | (Németh et al., 2005) |
| Adenosine receptors | A3 receptor | 7 | (Zhong et al., 2003) |
| Adrenoceptors | α1A-adrenoceptor | 6 | (Tayebati et al., 2000) |
| Adrenoceptors | α1B-adrenoceptor | 6 | (Tayebati et al., 2000) |
| Adrenoceptors | α1D-adrenoceptor | 6 | (Tayebati et al., 2000) |
| Adrenoceptors | α2A-adrenoceptor | 5 | (Zhang et al., 2010a) |
| Adrenoceptors | α2B-adrenoceptor | 5 | (Calonge et al., 2005) |
| Adrenoceptors | α2C-adrenoceptor | 5 | (Laukova et al., 2010) |
| Adrenoceptors | β1-adrenoceptor | 5 | (Nishio et al., 1998) |
| Adrenoceptors | β2-adrenoceptor | 7 | (Izeboud et al., 2000) |
| Adrenoceptors | β3-adrenoceptor | 5 | (Lamas et al., 2003) |
| Complement peptide receptors | C3a receptor | 7 | (Hartmann et al., 1997) |
| Complement peptide receptors | C5a1 receptor | 7 | (Kupp et al., 1991) |
| Complement peptide receptors | C5a2 receptor | 7 | (Zhang et al., 2010b) |
| Angiotensin receptors | $AT_1$ receptor | 7 | (Jaffré et al., 2009) |
| Angiotensin receptors | $AT_2$ receptor | 5 | (Matavelli et al., 2011) |
| Apelin receptor | apelin receptor | 7 | (Zhou et al., 2003) |
| Bile acid receptor | GPBA receptor | 6 | (Kawamata et al., 2003) |
| Bombesin receptors | BB1 receptor | 5 | (Baroni et al., 2008) |
| Bombesin receptors | BB2 (GRP) receptor | 7 | (Czepielewski et al., 2012) |
| Bombesin receptors | BB3 receptor | 5 | (Fleischmann et al., 2000) |
| Bradykinin receptors | B1 receptor | 7 | (Ehrenfeld et al., 2006) |
| Bradykinin receptors | B2 receptor | 7 | (Souza et al., 2004) |
| Cannabinoid receptors | CB1 receptor | 6 | (Galiègue et al., 1995) |
| Cannabinoid receptors | CB2 receptor | 6 | (Galiègue et al., 1995) |
| Chemokine receptors | CCR1 | 7 | (Lazennec & Richmond, 2010) |
| Chemokine receptors | CCR2 | 7 | (Lazennec & Richmond, 2010) |
| Chemokine receptors | CCR3 | 7 | (Lazennec & Richmond, 2010) |
| Chemokine receptors | CCR4 | 7 | (Lazennec & Richmond, 2010) |
| Chemokine receptors | CCR5 | 7 | (Lazennec & Richmond, 2010) |
| Chemokine receptors | CCR6 | 7 | (Lazennec & Richmond, 2010) |
| Chemokine receptors | CCR7 | 7 | (Lazennec & Richmond, 2010) |
| Chemokine receptors | CCR8 | 7 | (Lazennec & Richmond, 2010) |
| Chemokine receptors | CCR9 | 7 | (Lazennec & Richmond, 2010) |
| Chemokine receptors | CCR10 | 7 | (Lazennec & Richmond, 2010) |
| Chemokine receptors | CXCR1 | 7 | (Lazennec & Richmond, 2010) |
| Chemokine receptors | CXCR2 | 7 | (Lazennec & Richmond, 2010) |
| Chemokine receptors | CXCR3 | 7 | (Lazennec & Richmond, 2010) |
| Chemokine receptors | CXCR4 | 7 | (Lazennec & Richmond, 2010) |
| Chemokine receptors | CXCR5 | 7 | (Lazennec & Richmond, 2010) |
| Chemokine receptors | CXCR6 | 7 | (Lazennec & Richmond, 2010) |
| Chemokine receptors | CX3CR1 | 7 | (Lazennec & Richmond, 2010) |

-continued

| Type | Subtype | Level of Evidence | Reference |
|---|---|---|---|
| Chemokine receptors | XCR1 | 7 | (Lazennec & Richmond, 2010) |
| Chemokine receptors | ACKR1 | 7 | (Lazennec & Richmond, 2010) |
| Chemokine receptors | ACKR2 | 7 | (Lazennec & Richmond, 2010) |
| Chemokine receptors | ACKR3 | 7 | (Lazennec & Richmond, 2010) |
| Chemokine receptors | ACKR4 | 7 | (Lazennec & Richmond, 2010) |
| Chemokine receptors | CCRL2 | 7 | (Lazennec & Richmond, 2010) |
| Cholecystokinin receptors | CCK1 receptor | 6 | (Schmitz et al., 2001) |
| Cholecystokinin receptors | CCK2 receptor | 6 | (Schmitz et al., 2001) |
| Dopamine receptors | D1 receptor | 6 | (Caronti et al., 1998) |
| Dopamine receptors | D2 receptor | 6 | (Levite et al., 2001) |
| Dopamine receptors | D3 receptor | 6 | (Levite et al., 2001) |
| Dopamine receptors | D4 receptor | 6 | (Sarkar et al., 2006) |
| Dopamine receptors | D5 receptor | 6 | (Caronti et al., 1998) |
| Endothelin receptors | ETA receptor | 5 | (Sampaio et al., 2004) |
| Endothelin receptors | ETB receptor | 5 | (Suzuki et al., 2004) |
| G protein-coupled estrogen receptor | GPER | 5 | (Heublein et al., 2012) |
| Formylpeptide receptors | FPR1 | 7 | (Schiffmann et al., 1975) |
| Formylpeptide receptors | FPR2/ALX | 7 | (Le et al., 1999) |
| Formylpeptide receptors | FPR3 | 7 | (Yang et al., 2002) |
| Free fatty acid receptors | FFA1 receptor | 6 | (Briscoe et al., 2003) |
| Free fatty acid receptors | FFA2 receptor | 7 | (Maslowski et al., 2009) |
| Free fatty acid receptors | FFA3 receptor | 6 | (Le Poul et al., 2003) |
| Free fatty acid receptors | FFA4 receptor | 7 | (Kazemian et al., 2012) |
| Free fatty acid receptors | GPR42 | 1 | (Brown et al., 2003)- may be a pseudogene |
| Galanin receptors | GAL1 receptor | 5 | (Benya et al., 1998) |
| Galanin receptors | GAL2 receptor | 7 | (Jimenez-Andrade et al., 2004) |
| Galanin receptors | GAL3 receptor | 7 | (Schmidhuber et al., 2009) |
| Ghrelin receptor | ghrelin receptor | 7 | (Dixit et al., 2004) |
| Glycoprotein hormone receptors | FSH receptor | 6 | (Robinson et al., 2010) |
| Glycoprotein hormone receptors | LH receptor | 6 | (Sonoda et al., 2005) |
| Glycoprotein hormone receptors | TSH receptor | 5 | (Cuddihy et al., 1995) |
| Gonadotrophin-releasing hormone receptors | GnRH1 receptor | 6 | (Chen et al., 1999) |
| Gonadotrophin-releasing hormone receptors | GnRH2 receptor | 5 | (Stockhammer et al., 2010) |
| Histamine receptors | H1 receptor | 7 | (Sonobe et al., 2004) |
| Histamine receptors | H2 receptor | 7 | (Mitsuhashi et al., 1989) |
| Histamine receptors | H3 receptor | 5 | (Teuscher et al., 2007) |
| Histamine receptors | H4 receptor | 7 | (Ling et al., 2004) |
| Kisspeptin receptor | kisspeptin receptor | 6 | (Muir et al., 2001) |
| Leukotriene receptors | BLT1 receptor | 7 | (Arita et al., 2007) |
| Leukotriene receptors | BLT2 receptor | 7 | (Yokomizo et al., 2000) |
| Leukotriene receptors | CysLT1 receptor | 7 | (Capra et al., 2005) |
| Leukotriene receptors | CysLT2 receptor | 7 | (Pillai et al., 2004) |
| Leukotriene receptors | OXE receptor | 7 | (Powell & Rokach, 2013) |
| Leukotriene receptors | FPR2/ALX | 7 | (Krishnamoorthy et al., 2012) |
| Lysophospholipid (LPA) receptors | LPA1 receptor | 5 | (Swaney et al., 2010) |
| Lysophospholipid (LPA) receptors | LPA2 receptor | 6 | (An et al., 1998) |
| Lysophospholipid (LPA) receptors | LPA3 receptor | 5 | (Lin et al., 2007) |
| Lysophospholipid (LPA) receptors | LPA4 receptor | 5 | (Waters et al., 2007) |
| Lysophospholipid (LPA) receptors | LPA5 receptor | 7 | (Lundequist & Boyce, 2011) |
| Lysophospholipid (LPA) receptors | LPA6 receptor | 6 | (Pasternack et al., 2008) |
| Melanin-concentrating hormone receptors | MCH1 receptor | 7 | (Ziogas et al., 2013) |

-continued

| Type | Subtype | Level of Evidence | Reference |
|---|---|---|---|
| Melanin-concentrating hormone receptors | MCH2 receptor | 6 | (Hill et al., 2001) |
| Melanocortin receptors | MC1 receptor | 7 | (Hartmeyer et al., 1997) |
| Melanocortin receptors | MC2 receptor | 5 | (Grässel et al., 2009) |
| Melanocortin receptors | MC3 receptor | 6 | (Getting et al., 1999) |
| Melanocortin receptors | MC4 receptor | 5 | (Caruso et al., 2007) |
| Melanocortin receptors | MC5 receptor | 6 | (Chhajlani, 1996) |
| Melatonin receptors | MT1 receptor | 7 | (Carrillo-Vico et al., 2003) |
| Melatonin receptors | MT2 receptor | 7 | (Drazen & Nelson, 2001) |
| Motilin receptor | motilin receptor | 5 | (Ter Beek et al., 2008) |
| Neuromedin U receptors | NMU1 receptor | 7 | (Moriyama et al., 2005) |
| Neuromedin U receptors | NMU2 receptor | 3 | (Moriyama et al., 2005) |
| Neuropeptide FF/neuropeptide AF receptors | NPFF1 receptor | 5 | (Iwasa et al., 2014) |
| Neuropeptide FF/neuropeptide AF receptors | NPFF2 receptor | 5 | (Yang & Iadarola, 2003) |
| Neuropeptide S receptor | NPS receptor | 5 | (D'Amato et al., 2007) |
| Neuropeptide W/neuropeptide B receptors | NPBW1 receptor | 6 | (Brezillon et al., 2003) |
| Neuropeptide W/neuropeptide B receptors | NPBW2 receptor | 6 | (Brezillon et al., 2003) |
| Neuropeptide Y receptors | Y1 receptor | 6 | (Mitić et al., 2011) |
| Neuropeptide Y receptors | Y2 receptor | 6 | (Mitić et al., 2011) |
| Neuropeptide Y receptors | Y4 receptor | 4 | (Lin et al., 2006) |
| Neuropeptide Y receptors | Y5 receptor | 6 | (Mitić et al., 2011) |
| Neuropeptide Y receptors | y6 receptor | 3 | (Zhu et al., 2016) |
| Neurotensin receptors | NTS1 receptor | 5 | (Bossard et al., 2007) |
| Neurotensin receptors | NTS2 receptor | 4 | (Lafrance et al., 2010) |
| Hydroxycarboxylic acid receptors | HCA1 receptor | 5 | (Hoque et al., 2014) |
| Hydroxycarboxylic acid receptors | HCA2 receptor | 6 | (Schaub et al., 2001) |
| Hydroxycarboxylic acid receptors | HCA3 receptor | 6 | (Irukayama-Tomobe et al., 2009) |
| Opioid receptors | δ receptor | 6 | (Gaveriaux et al., 1995) |
| Opioid receptors | κ receptor | 7 | (Taub et al., 1991) |
| Opioid receptors | μ receptor | 7 | (Taub et al., 1991) |
| Opioid receptors | NOP receptor | 6 | (Peluso et al., 1998) |
| Orexin receptors | OX1 receptor | 3 or 4-currently unclear which receptor subtype is mediating response | (Xiong et al., 2013) |
| Orexin receptors | OX2 receptor | 3 or 4-currently unclear which receptor subtype is mediating response | (Xiong et al., 2013) |
| P2Y receptors | P2Y1 receptor | 7 | (Fujita et al., 2009) |
| P2Y receptors | P2Y2 receptor | 7 | (Chen et al., 2006) |
| P2Y receptors | P2Y4 receptor | 6 | (Moore et al., 2001) |
| P2Y receptors | P2Y6 receptor | 7 | (Warny et al., 2001) |
| P2Y receptors | P2Y11 receptor | 7 | (Vaughan et al., 2007) |
| P2Y receptors | P2Y12 receptor | 6 | (Sasaki et al., 2003) |
| P2Y receptors | P2Y13 receptor | 7 | (Gao et al., 2010) |
| P2Y receptors | P2Y14 receptor | 7 | (Lee et al., 2003) |
| QRFP receptor | QRFP receptor | 6 | (Jossart et al., 2013) |
| Platelet-activating factor receptor | PAF receptor | 7 | (Ferreira et al., 2004) |
| Prokineticin receptors | PKR1 | 7 | (Cook et al., 2010) |
| Prokineticin receptors | PKR2 | 7 | (Giannini et al., 2009) |
| Prolactin-releasing peptide receptor | PrRP receptor | 6 | (Dorsch et al., 2005) |
| Prostanoid receptors | DP1 receptor | 7 | (Wright et al., 2000) |
| Prostanoid receptors | DP2 receptor | 7 | (Gervais et al., 2001) |
| Prostanoid receptors | EP1 receptor | 7 | (Nagamachi et al., 2007) |
| Prostanoid receptors | EP2 receptor | 7 | (Poloso et al., 2013) |
| Prostanoid receptors | EP3 receptor | 7 | (Kunikata et al., 2005) |
| Prostanoid receptors | EP4 receptor | 7 | (Kabashima et al., 2002) |
| Prostanoid receptors | FP receptor | 7 | (Takayama et al., 2005) |
| Prostanoid receptors | IP receptor | 7 | (Ayer et al., 2008) |
| Prostanoid receptors | TP receptor | 7 | (Li & Tai, 2013) |

-continued

| Type | Subtype | Level of Evidence | Reference |
|---|---|---|---|
| Proteinase-activated receptors | PAR1 | 7 | (Antoniak et al., 2013) |
| Proteinase-activated receptors | PAR2 | 7 | (Davidson et al., 2013) |
| Proteinase-activated receptors | PAR3 | 7 | (Ishihara et al., 1997) |
| Proteinase-activated receptors | PAR4 | 7 | (Mao et al., 2010) |
| Relaxin family peptide receptors | RXFP1 receptor | 5 | (Horton et al., 2012) |
| Relaxin family peptide receptors | RXFP2 receptor | 6 | (Hsu et al., 2002) |
| Relaxin family peptide receptors | RXFP3 receptor | 1 | (Bathgate et al., 2013) |
| Relaxin family peptide receptors | RXFP4 receptor | 6 | (Liu et al., 2005) |
| Somatostatin receptors | sst1 receptor | 6 | (Taniyama et al., 2005) |
| Somatostatin receptors | sst2 receptor | 6 | (Taniyama et al., 2005) |
| Somatostatin receptors | sst3 receptor | 6 | (Taniyama et al., 2005) |
| Somatostatin receptors | sst4 receptor | 6 | (Taniyama et al., 2005) |
| Somatostatin receptors | sst5 receptor | 6 | (Taniyama et al., 2005) |
| Tachykinin receptors | NK1 receptor | 7 | (Saban et al., 2000) |
| Tachykinin receptors | NK2 receptor | 5 | (Laird et al., 2001) |
| Tachykinin receptors | NK3 receptor | 7 | (Improta et al., 2003) |
| Thyrotropin-releasing hormone receptors | TRH1 receptor | 6 | (Mellado et al., 1999) |
| Thyrotropin-releasing hormone receptors | TRH2 receptor | 1 | (Alexander et al., 2011)- not found in humans |
| Trace amine receptor | TA1 receptor | 6 | (D'Andrea et al., 2003) |
| Urotensin receptor | UT receptor | 5 | (Johns et al., 2004) |
| Vasopressin and oxytocin receptors | V1A receptor | 5 | (Bucher et al., 2002) |
| Vasopressin and oxytocin receptors | V1B receptor | 3 | (Sugimoto et al., 1994) |
| Vasopressin and oxytocin receptors | V2 receptor | 5 | (Boyd et al., 2008) |
| Vasopressin and oxytocin receptors | OT receptor | 5 | ((işeri et al., 2005) |
| GPR18, GPR55 and GPR119 | GPR18 | 7 | (Takenouchi et al., 2012) |
| GPR18, GPR55 and GPR119 | GPR55 | 7 | (Cantarella et al., 2011) |
| GPR18, GPR55 and GPR119 | GPR119 | 4 | (Sakamoto et al., 2006) |
| Lysophospholipid (S1P) receptors | S1P1 receptor | 7 | (Matloubian et al., 2004) |
| Lysophospholipid (S1P) receptors | S1P2 receptor | 7 | (McQuiston et al., 2011) |
| Lysophospholipid (S1P) receptors | S1P3 receptor | 7 | (Awojoodu et al., 2013) |
| Lysophospholipid (S1P) receptors | S1P4 receptor | 7 | (Allende et al., 2011) |
| Lysophospholipid (S1P) receptors | S1P5 receptor | 7 | (Jenne et al., 2009) |
| Chemerin receptor | chemerin receptor | 7 | (Haworth et al., 2011) |
| Succinate receptor | succinate receptor | 7 | (Rubic et al., 2008) |
| Oxoglutarate receptor | oxoglutarate receptor | 6 | (Inbe et al., 2004) |
| Taste 2 receptors | TAS2R1 | 6 | (Malki et al., 2015) |
| Taste 2 receptors | TAS2R3 | 6 | (Malki et al., 2015) |
| Taste 2 receptors | TAS2R4 | 6 | (Malki et al., 2015) |
| Taste 2 receptors | TAS2R5 | 6 | (Malki et al., 2015) |
| Taste 2 receptors | TAS2R7 | 6 | (Malki et al., 2015) |
| Taste 2 receptors | TAS2R8 | 6 | (Malki et al., 2015) |
| Taste 2 receptors | TAS2R9 | 6 | (Malki et al., 2015) |
| Taste 2 receptors | TAS2R10 | 6 | (Malki et al., 2015) |
| Taste 2 receptors | TAS2R13 | 6 | (Malki et al., 2015) |
| Taste 2 receptors | TAS2R14 | 6 | (Malki et al., 2015) |
| Taste 2 receptors | TAS2R16 | 6 | (Malki et al., 2015) |
| Taste 2 receptors | TAS2R19 | 6 | (Malki et al., 2015) |
| Taste 2 receptors | TAS2R20 | 6 | (Malki et al., 2015) |
| Taste 2 receptors | TAS2R30 | 6 | (Malki et al., 2015) |
| Taste 2 receptors | TAS2R31 | 6 | (Malki et al., 2015) |
| Taste 2 receptors | TAS2R38 | 6 | (Malki et al., 2015) |
| Taste 2 receptors | TAS2R39 | 6 | (Malki et al., 2015) |
| Taste 2 receptors | TAS2R40 | 6 | (Malki et al., 2015) |

-continued

| Type | Subtype | Level of Evidence | Reference |
|---|---|---|---|
| Taste 2 receptors | TAS2R41 | 6 | (Malki et al., 2015) |
| Taste 2 receptors | TAS2R42 | 6 | (Malki et al., 2015) |
| Taste 2 receptors | TAS2R43 | 6 | (Malki et al., 2015) |
| Taste 2 receptors | TAS2R45 | 6 | (Malki et al., 2015) |
| Taste 2 receptors | TAS2R46 | 6 | (Malki et al., 2015) |
| Taste 2 receptors | TAS2R50 | 6 | (Malki et al., 2015) |
| Taste 2 receptors | TAS2R60 | 6 | (Malki et al., 2015) |
| Class A Orphans | GPR1 | 6 | (Farzan et al., 1997) |
| Class A Orphans | GPR3 | 6 | (Uhlén et al., 2015) |
| Class A Orphans | GPR4 | 7 | (Chen et al., 2011) |
| Class A Orphans | GPR42 | 1 | (Brown et al., 2003)-RT-PCR detected no signal for GPR42 mRNA in samples of normal human tissues |
| Class A Orphans | GPR6 | 6 | (Taquet et al., 2012) |
| Class A Orphans | GPR12 | 6 | (Fornari et al., 2011) |
| Class A Orphans | GPR15 | 7 | (Kim et al., 2013) |
| Class A Orphans | GPR17 | 6 | (Maekawa et al., 2009) |
| Class A Orphans | GPR18 | 6 | (Gantz et al., 1997) |
| Class A Orphans | GPR19 | 4 | (Gazel et al., 2006) |
| Class A Orphans | GPR20 | 6 | (Taquet et al., 2012) |
| Class A Orphans | GPR21 | 7 | (Osborn et al., 2012) |
| Class A Orphans | GPR22 | 6 | (Matteucci et al., 2010) |
| Class A Orphans | GPR25 | 4 | (Consortium, 2013) |
| Class A Orphans | GPR26 | 6 | (Matteucci et al., 2010) |
| Class A Orphans | GPR27 | 6 | (Matsumoto et al., 2000) |
| Class A Orphans | GPR31 | 7 | (Schaub et al., 2001) |
| Class A Orphans | GPR32 | 7 | (Krishnamoorthy et al., 2010) |
| Class A Orphans | GPR33 | 6 | (Rompler et al., 2005) |
| Class A Orphans | GPR34 | 7 | (Sugo et al., 2006) |
| Class A Orphans | GPR35 | 6 | (Wang et al., 2006) |
| Class A Orphans | GPR37 | 4 | (Consortium, 2013) |
| Class A Orphans | GPR37L1 | 4 | (Mas et al., 2011) |
| Class A Orphans | GPR39 | 5 | (Sunuwar et al., 2016) |
| Class A Orphans | GPR45 | 5 | (Fujita et al., 2011) |
| Class A Orphans | GPR50 | 4 | (Elliott et al., 2016) |
| Class A Orphans | GPR52 | 1 | |
| Class A Orphans | GPR55 | 7 | (Schuelert & McDougall, 2011) |
| Class A Orphans | GPR61 | 6 | (Matsumura et al., 2010) |
| Class A Orphans | GPR62 | 4 | (Kwon et al., 2014) |
| Class A Orphans | GPR63 | 3 | (Niedernberg et al., 2003) |
| Class A Orphans | GPR65 | 7 | (Kottyan et al., 2009) |
| Class A Orphans | GPR68 | 7 | (Ichimonji et al., 2010) |
| Class A Orphans | GPR75 | 3 | (Ignatov et al., 2006) |
| Class A Orphans | GPR78 | 6 | (Lu et al., 2010) |
| Class A Orphans | GPR79 | 1 | |
| Class A Orphans | GPR82 | 6 | (Engel et al., 2011) |
| Class A Orphans | GPR83 | 6 | (Hansen et al., 2010) |
| Class A Orphans | GPR84 | 6 | (Venkataraman & Kuo, 2005) |
| Class A Orphans | GPR85 | 6 | (Lattin et al., 2008) |
| Class A Orphans | GPR87 | 6 | (Martinez et al., 2006) |
| Class A Orphans | GPR88 | 5 | (Jurisic et al., 2010) |
| Class A Orphans | GPR101 | 4 | (Watanabe et al., 2013) |
| Class A Orphans | GPR119 | 6 | (Parker et al., 2009) |
| Class A Orphans | GPR132 | 7 | (Frasch et al., 2008) |
| Class A Orphans | GPR135 | 4 | (Kwon et al., 2014) |
| Class A Orphans | GPR139 | 5 | (Tichelaar et al., 2007) |
| Class A Orphans | GPR141 | 4 | (Hong et al., 2015) |
| Class A Orphans | GPR142 | 6 | (Taquet et al., 2012) |
| Class A Orphans | GPR146 | 6 | (Lattin et al., 2008) |
| Class A Orphans | GPR148 | 6 | (Taquet et al., 2012) |
| Class A Orphans | GPR149 | 4 | (Sohn et al., 2009) |
| Class A Orphans | GPR150 | 4 | (Yin et al., 2014) |
| Class A Orphans | GPR151 | 4 | (Keermann et al., 2015) |
| Class A Orphans | GPR152 | 4 | (Ahmad et al., 2016) |
| Class A Orphans | GPR153 | 6 | (Shen et al., 2015) |
| Class A Orphans | GPR160 | 6 | (Lee et al., 2011) |
| Class A Orphans | GPR161 | 5 | (Swan et al., 2013) |
| Class A Orphans | GPR162 | 6 | (Lattin et al., 2008) |
| Class A Orphans | GPR171 | 5 | (Rossi et al., 2013) |
| Class A Orphans | GPR173 | 6 | (Fornari et al., 2011) |
| Class A Orphans | GPR174 | 6 | (Shen et al., 2015) |
| Class A Orphans | GPR176 | 6 | (Wensman et al., 2012) |
| Class A Orphans | GPR182 | 6 | (Matteucci et al., 2010) |
| Class A Orphans | GPR183 | 7 | (Gatto et al., 2011) |

-continued

| Type | Subtype | Level of Evidence | Reference |
|---|---|---|---|
| Class A Orphans | LGR4 | 6 | (Liu et al., 2013) |
| Class A Orphans | LGR5 | 4 | (Quigley et al., 2009) |
| Class A Orphans | LGR6 | 6 | (Aho et al., 2013) |
| Class A Orphans | MAS1 | 7 | (da Silveira et al., 2010) |
| Class A Orphans | MAS1L | 6 | (Foster et al., 2016) |
| Class A Orphans | MRGPRD | 5 | (Qu et al., 2014) |
| Class A Orphans | MRGPRE | 4 | (Kwon et al., 2014) |
| Class A Orphans | MRGPRF | 4 | (Liang et al., 2016) |
| Class A Orphans | MRGPRG | 6 | (Othman et al., 2015) |
| Class A Orphans | MRGPRX1 | 5 | (Solinski et al., 2013) |
| Class A Orphans | MRGPRX2 | 7 | (Subramanian et al., 2011) |
| Class A Orphans | MRGPRX3 | 5 | (Yi et al., 2012) |
| Class A Orphans | MRGPRX4 | 1 | (Bader et al., 2014) |
| Class A Orphans | OPN3 | 6 | (White et al., 2008) |
| Class A Orphans | OPN4 | 4 | (Wang et al., 2010) |
| Class A Orphans | OPN5 | 3 | (Ohshima et al., 2002) |
| Class A Orphans | P2RY8 | 6 | (Cantagrel et al., 2004) |
| Class A Orphans | P2RY10 | 6 | (Rao et al., 1999) |
| Class A Orphans | TAAR2 | 6 | (Babusyte et al., 2013) |
| Class A Orphans | TAAR3 | 4 | (D'Andrea et al., 2012) |
| Class A Orphans | TAAR4P | 1 | |
| Class A Orphans | TAAR5 | 6 | (Taquet et al., 2012) |
| Class A Orphans | TAAR6 | 6 | (D'Andrea et al., 2012) |
| Class A Orphans | TAAR8 | 6 | (D'Andrea et al., 2012) |
| Class A Orphans | TAAR9 | 6 | (Taquet et al., 2012) |

Family A olfactory GPCRs and the current level of evidence for their involvement in inflammation (see key above):

| Family ID | Sub Family | Symbol | Level of Evidence | Reference |
|---|---|---|---|---|
| 1 | C | OR1C1 | 1 | |
| 1 | F | OR1F12 | 1 | |
| 1 | J | OR1J1 | 1 | |
| 1 | J | OR1J2 | 1 | |
| 1 | J | OR1J4 | 1 | |
| 1 | N | OR1N1 | 1 | |
| 1 | N | OR1N2 | 1 | |
| 1 | L | OR1L8 | 1 | |
| 1 | Q | OR1Q1 | 1 | |
| 1 | B | OR1B1 | 1 | |
| 1 | L | OR1L1 | 4 | (Garcia-Vivas et al., 2016) |
| 1 | L | OR1L3 | 1 | |
| 1 | L | OR1L4 | 1 | |
| 1 | L | OR1L6 | 1 | |
| 1 | K | OR1K1 | 1 | |
| 1 | S | OR1S2 | 4 | (Lee et al., 2011) |
| 1 | S | OR1S1 | 4 | (Lee et al., 2011) |
| 1 | F | OR1F1 | 1 | |
| 1 | D | OR1D5 | 1 | |
| 1 | D | OR1D2 | 5 | (Kalbe et al., 2016) |
| 1 | G | OR1G1 | 1 | |
| 1 | A | OR1A2 | 4 | (Garcia-Vivas et al., 2016) |
| 1 | A | OR1A1 | 1 | |
| 1 | D | OR1D4 | 1 | |
| 1 | E | OR1E1 | 1 | |
| 1 | E | OR1E2 | 1 | |
| 1 | M | OR1M1 | 1 | |
| 1 | I | OR1I1 | 1 | |
| 2 | B | OR2B11 | 6 | (Flegel et al., 2013) |
| 2 | W | OR2W5 | 1 | |
| 2 | C | OR2C3 | 6 | (Flegel et al., 2013) |
| 2 | G | OR2G2 | 1 | |
| 2 | G | OR2G3 | 1 | |
| 2 | W | OR2W3 | 6 | (Flegel et al., 2013) |
| 2 | T | OR2T8 | 1 | |
| 2 | AJ | OR2AJ1 | 1 | |
| 2 | L | OR2L8 | 1 | |
| 2 | AK | OR2AK2 | 4 | (Garcia-Vivas et al., 2016) |
| 2 | L | OR2L5 | 1 | |
| 2 | L | OR2L2 | 1 | |
| 2 | L | OR2L3 | 1 | |
| 2 | L | OR2L13 | 6 | (Flegel et al., 2013) |
| 2 | M | OR2M5 | 1 | |
| 2 | M | OR2M2 | 1 | |
| 2 | M | OR2M3 | 1 | |
| 2 | M | OR2M4 | 1 | |
| 2 | T | OR2T33 | 1 | |
| 2 | T | OR2T12 | 1 | |
| 2 | M | OR2M7 | 1 | |
| 2 | T | OR2T4 | 1 | |
| 2 | T | OR2T6 | 1 | |
| 2 | T | OR2T1 | 1 | |
| 2 | T | OR2T7 | 1 | |
| 2 | T | OR2T2 | 1 | |
| 2 | T | OR2T3 | 1 | |
| 2 | T | OR2T5 | 1 | |
| 2 | G | OR2G6 | 1 | |
| 2 | T | OR2T29 | 1 | |
| 2 | T | OR2T34 | 6 | (Flegel et al., 2013) |
| 2 | T | OR2T10 | 1 | |
| 2 | T | OR2T11 | 6 | (Flegel et al., 2013) |
| 2 | T | OR2T35 | 1 | |
| 2 | T | OR2T27 | 1 | |
| 2 | Y | OR2Y1 | 1 | |
| 2 | V | OR2V1 | 1 | |
| 2 | V | OR2V2 | 1 | |
| 2 | B | OR2B2 | 1 | |
| 2 | B | OR2B6 | 6 | (Flegel et al., 2013) |
| 2 | W | OR2W1 | 1 | |
| 2 | B | OR2B3 | 1 | |
| 2 | J | OR2J3 | 6 | (Zhao et al., 2013) |
| 2 | J | OR2J2 | 1 | |
| 2 | H | OR2H1 | 1 | |
| 2 | H | OR2H2 | 1 | |
| 2 | A | OR2A4 | 6 | (Flegel et al., 2013) |
| 2 | AE | OR2AE1 | 1 | |
| 2 | F | OR2F2 | 1 | |
| 2 | F | OR2F1 | 1 | |
| 2 | A | OR2A5 | 1 | |
| 2 | A | OR2A25 | 1 | |
| 2 | A | OR2A12 | 1 | |
| 2 | A | OR2A2 | 6 | (Flegel et al., 2013) |

| Family ID | Sub Family | Symbol | Level of Evidence | Reference |
|---|---|---|---|---|
| 2 | A | OR2A14 | 1 | |
| 2 | A | OR2A42 | 6 | (Flegel et al., 2013) |
| 2 | A | OR2A7 | 6 | (Flegel et al., 2013) |
| 2 | A | OR2A1 | 6 | (Flegel et al., 2013) |
| 2 | S | OR2S2 | 1 | |
| 2 | K | OR2K2 | 1 | |
| 2 | AG | OR2AG2 | 1 | |
| 2 | AG | OR2AG1 | 5 | (Kalbe et al., 2016) |
| 2 | D | OR2D2 | 4 | (Lee et al., 2011) |
| 2 | D | OR2D3 | 4 | (Lee et al., 2011) |
| 2 | AT | OR2AT4 | 1 | |
| 2 | AP | OR2AP1 | 1 | |
| 2 | C | OR2C1 | 6 | (Flegel et al., 2013) |
| 2 | Z | OR2Z1 | 1 | |
| 3 | A | OR3A2 | 1 | |
| 3 | A | OR3A1 | 1 | |
| 3 | A | OR3A4 | 1 | |
| 3 | A | OR3A3 | 6 | (Flegel et al., 2013) |
| 4 | F | OR4F5 | 1 | |
| 4 | F | OR4F29 | 1 | |
| 4 | F | OR4F16 | 1 | |
| 4 | F | OR4F3 | 1 | |
| 4 | F | OR4F21 | 1 | |
| 4 | B | OR4B1 | 1 | |
| 4 | X | OR4X2 | 1 | |
| 4 | X | OR4X1 | 1 | |
| 4 | S | OR4S1 | 1 | |
| 4 | C | OR4C3 | 1 | |
| 4 | C | OR4C5 | 1 | |
| 4 | A | OR4A47 | 1 | |
| 4 | C | OR4C13 | 4 | (Lee et al., 2011) |
| 4 | C | OR4C12 | 4 | (Garcia-Vivas et al., 2016) |
| 4 | A | OR4A5 | 1 | |
| 4 | C | OR4C46 | 1 | |
| 4 | A | OR4A16 | 1 | |
| 4 | A | OR4A15 | 4 | (Garcia-Vivas et al., 2016) |
| 4 | C | OR4C15 | 4 | (Lee et al., 2011) |
| 4 | C | OR4C16 | 4 | (Lee et al., 2011) |
| 4 | C | OR4C11 | 4 | (Lee et al., 2011) |
| 4 | P | OR4P4 | 1 | |
| 4 | S | OR4S2 | 1 | |
| 4 | C | OR4C6 | 1 | |
| 4 | D | OR4D6 | 1 | |
| 4 | D | OR4D10 | 6 | (Zhao et al., 2013) |
| 4 | D | OR4D11 | 1 | |
| 4 | D | OR4D9 | 1 | |
| 4 | D | OR4D5 | 1 | |
| 4 | Q | OR4Q3 | 6 | (Zhao et al., 2013) |
| 4 | M | OR4M1 | 6 | (Zhao et al., 2013) |
| 4 | N | OR4N2 | 1 | |
| 4 | K | OR4K2 | 1 | |
| 4 | K | OR4K5 | 1 | |
| 4 | K | OR4K1 | 1 | |
| 4 | K | OR4K15 | 4 | (Lee et al., 2011) |
| 4 | K | OR4K14 | 4 | (Lee et al., 2011) |
| 4 | K | OR4K13 | 4 | (Garcia-Vivas et al., 2016) |
| 4 | L | OR4L1 | 1 | |
| 4 | K | OR4K17 | 4 | (Garcia-Vivas et al., 2016) |
| 4 | N | OR4N5 | 4 | (Lee et al., 2011) |
| 4 | E | OR4E2 | 1 | |
| 4 | M | OR4M2 | 1 | |
| 4 | N | OR4N4 | 1 | |
| 4 | F | OR4F6 | 1 | |
| 4 | F | OR4F15 | 1 | |
| 4 | F | OR4F4 | 1 | |
| 4 | D | OR4D1 | 1 | |
| 4 | D | OR4D2 | 1 | |
| 4 | F | OR4F17 | 1 | |
| 4 | C | OR4C45 | 1 | |
| 5 | AC | OR5AC2 | 4 | (Lee et al., 2011) |
| 5 | H | OR5H1 | 1 | |
| 5 | H | OR5H14 | 1 | |
| 5 | H | OR5H15 | 1 | |
| 5 | H | OR5H6 | 1 | |
| 5 | H | OR5H2 | 1 | |
| 5 | K | OR5K4 | 1 | |
| 5 | K | OR5K3 | 4 | (Garcia-Vivas et al., 2016) |
| 5 | K | OR5K1 | 1 | |
| 5 | K | OR5K2 | 1 | |
| 5 | V | OR5V1 | 1 | |
| 5 | C | OR5C1 | 1 | |
| 5 | P | OR5P2 | 1 | |
| 5 | P | OR5P3 | 1 | |
| 5 | D | OR5D13 | 4 | (Lee et al., 2011) |
| 5 | D | OR5D14 | 4 | (Lee et al., 2011) |
| 5 | L | OR5L1 | 4 | (Lee et al., 2011) |
| 5 | D | OR5D18 | 4 | (Lee et al., 2011) |
| 5 | L | OR5L2 | 4 | (Lee et al., 2011) |
| 5 | D | OR5D16 | 4 | (Lee et al., 2011) |
| 5 | W | OR5W2 | 4 | (Lee et al., 2011) |
| 5 | I | OR5I1 | 4 | (Garcia-Vivas et al., 2016) |
| 5 | F | OR5F1 | 4 | (Lee et al., 2011) |
| 5 | AS | OR5AS1 | 4 | (Lee et al., 2011) |
| 5 | J | OR5J2 | 4 | (Lee et al., 2011) |
| 5 | T | OR5T2 | 4 | (Garcia-Vivas et al., 2016) |
| 5 | T | OR5T3 | 4 | (Garcia-Vivas et al., 2016) |
| 5 | T | OR5T1 | 4 | (Lee et al., 2011) |
| 5 | R | OR5R1 | 4 | (Lee et al., 2011) |
| 5 | M | OR5M9 | 4 | (Lee et al., 2011) |
| 5 | M | OR5M3 | 4 | (Lee et al., 2011) |
| 5 | M | OR5M8 | 4 | (Lee et al., 2011) |
| 5 | M | OR5M11 | 4 | (Lee et al., 2011) |
| 5 | M | OR5M10 | 4 | (Lee et al., 2011) |
| 5 | M | OR5M1 | 4 | (Lee et al., 2011) |
| 5 | AP | OR5AP2 | 4 | (Lee et al., 2011) |
| 5 | AR | OR5AR1 | 4 | (Lee et al., 2011) |
| 5 | AK | OR5AK2 | 4 | (Garcia-Vivas et al., 2016) |
| 5 | B | OR5B17 | 4 | (Garcia-Vivas et al., 2016) |
| 5 | B | OR5B3 | 4 | (Garcia-Vivas et al., 2016) |
| 5 | B | OR5B2 | 4 | (Lee et al., 2011) |
| 5 | B | OR5B12 | 4 | (Lee et al., 2011) |
| 5 | B | OR5B21 | 4 | (Lee et al., 2011) |
| 5 | AN | OR5AN1 | 1 | |
| 5 | A | OR5A2 | 1 | |
| 5 | A | OR5A1 | 1 | |
| 5 | AU | OR5AU1 | 1 | |
| 6 | Y | OR6Y1 | 1 | |
| 6 | P | OR6P1 | 1 | |
| 6 | K | OR6K2 | 1 | |
| 6 | K | OR6K3 | 1 | |
| 6 | K | OR6K6 | 4 | (Garcia-Vivas et al., 2016) |
| 6 | N | OR6N1 | 1 | |
| 6 | N | OR6N2 | 1 | |
| 6 | F | OR6F1 | 1 | |
| 6 | B | OR6B2 | 1 | |
| 6 | B | OR6B3 | 1 | |
| 6 | V | OR6V1 | 6 | (Feingold et al., 1999) |
| 6 | B | OR6B1 | 1 | |
| 6 | A | OR6A2 | 1 | |
| 6 | Q | OR6Q1 | 4 | (Lee et al., 2011) |
| 6 | X | OR6X1 | 4 | (Lee et al., 2011) |
| 6 | M | OR6M1 | 4 | (Lee et al., 2011) |
| 6 | T | OR6T1 | 1 | |
| 6 | C | OR6C74 | 4 | (Garcia-Vivas et al., 2016) |
| 6 | C | OR6C6 | 1 | |
| 6 | C | OR6C1 | 1 | |
| 6 | C | OR6C3 | 1 | |
| 6 | C | OR6C75 | 1 | |
| 6 | C | OR6C65 | 1 | |
| 6 | C | OR6C76 | 1 | |
| 6 | C | OR6C2 | 1 | |
| 6 | C | OR6C70 | 1 | |
| 6 | C | OR6C68 | 1 | |
| 6 | C | OR6C4 | 1 | |
| 6 | S | OR6S1 | 1 | |
| 6 | J | OR6J1 | 1 | |
| 7 | G | OR7G2 | 1 | |
| 7 | G | OR7G1 | 1 | |
| 7 | G | OR7G3 | 1 | |
| 7 | D | OR7D2 | 6 | (Flegel et al., 2013) |
| 7 | D | OR7D4 | 1 | |
| 7 | E | OR7E24 | 1 | |

| Family ID | Sub Family | Symbol | Level of Evidence | Reference |
|---|---|---|---|---|
| 7 | C | OR7C1 | 1 | |
| 7 | A | OR7A5 | 1 | |
| 7 | A | OR7A10 | 1 | |
| 7 | A | OR7A17 | 1 | |
| 7 | C | OR7C2 | 1 | |
| 8 | I | OR8I2 | 1 | |
| 8 | H | OR8H2 | 4 | (Lee et al., 2011) |
| 8 | H | OR8H3 | 4 | (Lee et al., 2011) |
| 8 | J | OR8J3 | 4 | (Lee et al., 2011) |
| 8 | K | OR8K5 | 4 | (Lee et al., 2011) |
| 8 | H | OR8H1 | 4 | (Lee et al., 2011) |
| 8 | K | OR8K3 | 4 | (Lee et al., 2011) |
| 8 | K | OR8K1 | 4 | (Lee et al., 2011) |
| 8 | J | OR8J1 | 4 | (Lee et al., 2011) |
| 8 | U | OR8U1 | 4 | (Lee et al., 2011) |
| 8 | D | OR8D4 | 1 | |
| 8 | G | OR8G1 | 1 | |
| 8 | G | OR8G5 | 1 | |
| 8 | D | OR8D1 | 1 | |
| 8 | D | OR8D2 | 1 | |
| 8 | B | OR8B2 | 1 | |
| 8 | B | OR8B3 | 1 | |
| 8 | B | OR8B4 | 1 | |
| 8 | B | OR8B8 | 1 | |
| 8 | B | OR8B12 | 1 | |
| 8 | A | OR8A1 | 1 | |
| 8 | S | OR8S1 | 1 | |
| 8 | U | OR8U8 | 4 | (Lee et al., 2011) |
| 8 | U | OR8U9 | 1 | |
| 9 | A | OR9A4 | 4 | (Lee et al., 2011) |
| 9 | A | OR9A2 | 6 | (Malki et al., 2015) |
| 9 | G | OR9G1 | 4 | (Lee et al., 2011) |
| 9 | G | OR9G4 | 4 | (Lee et al., 2011) |
| 9 | I | OR9I1 | 1 | |
| 9 | Q | OR9Q1 | 1 | |
| 9 | Q | OR9Q2 | 4 | (Lee et al., 2011) |
| 9 | K | OR9K2 | 1 | |
| 9 | G | OR9G9 | 4 | (Lee et al., 2011) |
| 10 | T | OR10T2 | 1 | |
| 10 | K | OR10K2 | 1 | |
| 10 | K | OR10K1 | 1 | |
| 10 | R | OR10R2 | 1 | |
| 10 | X | OR10X1 | 1 | |
| 10 | Z | OR10Z1 | 1 | |
| 10 | J | OR10J3 | 1 | |
| 10 | J | OR10J1 | 1 | |
| 10 | J | OR10J5 | 1 | |
| 10 | C | OR10C1 | 1 | |
| 10 | A | OR10A5 | 1 | |
| 10 | A | OR10A2 | 1 | |
| 10 | A | OR10A4 | 1 | |
| 10 | A | OR10A6 | 1 | |
| 10 | A | OR10A3 | 1 | |
| 10 | AG | OR10AG1 | 4 | (Lee et al., 2011) |
| 10 | Q | OR10Q1 | 4 | (Lee et al., 2011) |
| 10 | W | OR10W1 | 4 | (Lee et al., 2011) |
| 10 | V | OR10V1 | 1 | |
| 10 | S | OR10S1 | 1 | |
| 10 | G | OR10G6 | 1 | |
| 10 | G | OR10G4 | 1 | |
| 10 | G | OR10G9 | 1 | |
| 10 | G | OR10G8 | 1 | |
| 10 | G | OR10G7 | 1 | |
| 10 | D | OR10D3 | 1 | |
| 10 | AD | OR10AD1 | 1 | |
| 10 | A | OR10A7 | 4 | (Garcia-Vivas et al., 2016) |
| 10 | P | OR10P1 | 1 | |
| 10 | G | OR10G3 | 1 | |
| 10 | G | OR10G2 | 1 | |
| 10 | H | OR10H2 | 1 | |
| 10 | H | OR10H3 | 1 | |
| 10 | H | OR10N5 | 1 | |
| 10 | H | OR10H1 | 1 | |
| 10 | H | OR10H4 | 1 | |
| 11 | L | OR11L1 | 1 | |
| 11 | A | OR11A1 | 1 | |
| 11 | H | OR11H12 | 1 | |
| 11 | H | OR11H2 | 1 | |
| 11 | G | OR11G2 | 1 | |
| 11 | H | OR11H6 | 1 | |
| 11 | H | OR11H4 | 1 | |
| 11 | H | OR11H1 | 6 | (Zhao et al., 2013) |
| 12 | D | OR12D3 | 4 | (Garcia-Vivas et al., 2016) |
| 12 | D | OR12D2 | 1 | |
| 13 | G | OR13G1 | 4 | (Garcia-Vivas et al., 2016) |
| 13 | J | OR13J1 | 1 | |
| 13 | F | OR13F1 | 4 | (Lee et al., 2011) |
| 13 | C | OR13C4 | 4 | (Garcia-Vivas et al., 2016) |
| 13 | C | OR13C3 | 4 | (Lee et al., 2011) |
| 13 | C | OR13C8 | 4 | (Lee et al., 2011) |
| 13 | C | OR13C5 | 4 | (Lee et al., 2011) |
| 13 | C | OR13C2 | 4 | (Lee et al., 2011) |
| 13 | C | OR13C9 | 1 | |
| 13 | D | OR13D1 | 1 | |
| 13 | A | OR13A1 | 1 | |
| 13 | H | OR13H1 | 1 | |
| 14 | A | OR14A2 | 1 | |
| 14 | K | OR14K1 | 1 | |
| 14 | A | OR14A16 | 1 | |
| 14 | C | OR14C36 | 1 | |
| 14 | I | OR14I1 | 1 | |
| 14 | J | OR14J1 | 1 | |
| 51 | D | OR51D1 | 6 | (Malki et al., 2015) |
| 51 | E | OR51E1 | 6 | (Malki et al., 2015) |
| 51 | E | OR51E2 | 6 | (Malki et al., 2015) |
| 51 | F | OR51F1 | 6 | (Malki et al., 2015) |
| 51 | F | OR51F2 | 6 | (Malki et al., 2015) |
| 51 | S | OR51S1 | 6 | (Malki et al., 2015) |
| 51 | T | OR51T1 | 6 | (Malki et al., 2015) |
| 51 | A | OR51A7 | 6 | (Malki et al., 2015) |
| 51 | G | OR51G2 | 6 | (Malki et al., 2015) |
| 51 | G | OR51G1 | 6 | (Malki et al., 2015) |
| 51 | A | OR51A4 | 6 | (Malki et al., 2015) |
| 51 | A | OR51A2 | 6 | (Malki et al., 2015) |
| 51 | L | OR51L1 | 6 | (Malki et al., 2015) |
| 51 | V | OR51V1 | 6 | (Malki et al., 2015) |
| 51 | B | OR51B4 | 6 | (Malki et al., 2015) |
| 51 | B | OR51B2 | 6 | (Malki et al., 2015) |
| 51 | B | OR51B5 | 6 | (Malki et al., 2015) |
| 51 | B | OR51B6 | 6 | (Malki et al., 2015) |
| 51 | M | OR51M1 | 6 | (Malki et al., 2015) |
| 51 | J | OR51J1 | 6 | (Malki et al., 2015) |
| 51 | Q | OR51Q1 | 6 | (Malki et al., 2015) |
| 51 | I | OR51I1 | 6 | (Malki et al., 2015) |
| 51 | I | OR51I2 | 6 | (Malki et al., 2015) |
| 52 | B | OR52B4 | 6 | (Malki et al., 2015) |
| 52 | K | OR52K2 | 6 | (Malki et al., 2015) |
| 52 | K | OR52K1 | 6 | (Malki et al., 2015) |
| 52 | M | OR52M1 | 6 | (Malki et al., 2015) |
| 52 | I | OR52I2 | 6 | (Malki et al., 2015) |
| 52 | I | OR52I1 | 6 | (Malki et al., 2015) |
| 52 | R | OR52R1 | 6 | (Malki et al., 2015) |
| 52 | J | OR52J3 | 6 | (Malki et al., 2015) |
| 52 | E | OR52E2 | 6 | (Malki et al., 2015) |
| 52 | A | OR52A4 | 6 | (Malki et al., 2015) |
| 52 | A | OR52A5 | 6 | (Malki et al., 2015) |
| 52 | A | OR52A1 | 6 | (Malki et al., 2015) |
| 52 | D | OR52D1 | 6 | (Malki et al., 2015) |
| 52 | H | OR52H1 | 6 | (Malki et al., 2015) |
| 52 | B | OR52B6 | 6 | (Malki et al., 2015) |
| 52 | N | OR52N4 | 6 | (Flegel et al., 2013) |
| 52 | N | OR52N5 | 6 | (Zhao et al., 2013) |
| 52 | N | OR52N1 | 6 | (Malki et al., 2015) |
| 52 | N | OR52N2 | 6 | (Malki et al., 2015) |
| 52 | E | OR52E6 | 6 | (Malki et al., 2015) |
| 52 | E | OR52E8 | 6 | (Malki et al., 2015) |
| 52 | E | OR52E4 | 6 | (Malki et al., 2015) |
| 52 | E | OR52E5 | 6 | (Malki et al., 2015) |
| 52 | L | OR52L1 | 6 | (Malki et al., 2015) |
| 52 | B | OR52B2 | 6 | (Malki et al., 2015) |
| 52 | W | OR52W1 | 6 | (Malki et al., 2015) |
| 56 | B | OR56B1 | 6 | (Malki et al., 2015) |

-continued

| Family ID | Sub Family | Symbol | Level of Evidence | Reference |
|---|---|---|---|---|
| 56 | A | OR56A3 | 6 | (Malki et al., 2015) |
| 56 | A | OR56A5 | 6 | (Malki et al., 2015) |
| 56 | A | OR56A4 | 6 | (Malki et al., 2015) |
| 56 | A | OR56A1 | 6 | (Malki et al., 2015) |
| 56 | B | OR56B4 | 6 | (Malki et al., 2015) |

Family A vomeronasal and opsin GPCRs and the current level of evidence for their involvement in inflammation (see key above):

| Type | Subtype | Symbol | Level of Evidence | Reference |
|---|---|---|---|---|
| Vomeronasal | vomeronasal 1 receptor 1 | VN1R1 | 1 | |
| Vomeronasal | vomeronasal 1 receptor 2 | VN1R2 | 1 | |
| Vomeronasal | vomeronasal 1 receptor 3 (gene/pseudogene) | VN1R3 | 1 | |
| Vomeronasal | vomeronasal 1 receptor 4 | VN1R4 | 1 | |
| Vomeronasal | vomeronasal 1 receptor 5 (gene/pseudogene) | VN1R5 | 1 | |
| Opsin | opsin 1 (cone pigments) | OPN1LW | 1 | |
| Opsin | opsin 1 (cone pigments) | OPN1MW | 1 | |
| Opsin | opsin 1 (cone pigments) | OPN1MW2 | 1 | |
| Opsin | opsin 1 (cone pigments) | OPN1MW3 | 1 | |
| Opsin | opsin 1 (cone pigments) | OPN1SW | 1 | |
| Opsin | opsin 3 | OPN3 | 1 | |
| Opsin | opsin 4 | OPN4 | 4 | (Lee et al., 2011) |
| Opsin | opsin 5 | OPN5 | 1 | |
| Opsin | retinal G protein coupled receptor | RGR | 1 | |
| Opsin | rhodopsin | RHO | 1 | |
| Opsin | retinal pigment epithelium-derived rhodopsin homolog | RRH | 1 | |

Family B GPCRs and the current level of evidence for their involvement in inflammation (see key above):

| Type | Subtype | Level of Evidence | Reference |
|---|---|---|---|
| Calcitonin receptors | CT receptor | 6 | (Body et al., 1990) |
| Calcitonin receptors | AMY1 receptor | 3-currently unknown which AMY receptor subtype mediates this | (Masters et al., 2010) |
| Calcitonin receptors | AMY2 receptor | 3-currently unknown which AMY receptor subtype mediates this | (Masters et al., 2010) |
| Calcitonin receptors | AMY3 receptor | 3-currently unknown which AMY receptor subtype mediates this | (Masters et al., 2010) |
| Calcitonin receptors | calcitonin receptor-like receptor | 6 | (Hagner et al., 2002) |
| Calcitonin receptors | CGRP receptor | 5 | (Salmon et al., 2001) |
| Calcitonin receptors | AM1 receptor | 3-currently unknown which AM receptor subtype mediates this | (Elsasser & Kahl, 2002) |
| Calcitonin receptors | AM2 receptor | 3-currently unknown which AM receptor subtype mediates this | (Elsasser & Kahl, 2002) |
| Corticotropin-releasing factor receptors | CRF1 receptor | 5 | (Tsatsanis et al., 2007) |
| Corticotropin-releasing factor receptors | CRF2 receptor | 5 | (Tsatsanis et al., 2007) |
| Glucagon receptor family | GHRH receptor | 6 | (Chen et al., 1999) |
| Glucagon receptor family | GIP receptor | 5 | (Nie et al., 2012) |
| Glucagon receptor family | GLP-1 receptor | 5 | (Kodera et al., 2011) |
| Glucagon receptor family | GLP-2 receptor | 5 | (Cani et al., 2009) |
| Glucagon receptor family | glucagon receptor | 5 | (Buler et al., 2012) |
| Glucagon receptor family | secretin receptor | 5 | (Petersen & Myren, 1974) |
| Parathyroid hormone receptors | PTH1 receptor | 3-currently unknown which PTH receptor subtype mediates this | (Jahnsen et al., 2002) |
| Parathyroid hormone receptors | PTH2 receptor | 3-currently unknown which PTH receptor subtype mediates this | (Jahnsen et al., 2002) |
| VIP and PACAP receptors | PAC1 receptor | 5 | (Martinez et al., 2002) |
| VIP and PACAP receptors | VPAC1 receptor | 7 | (Yadav et al., 2011) |
| VIP and PACAP receptors | VPAC2 receptor | 7 | (Voice et al., 2003) |
| Adhesion Class GPCRs | ADGRA1 | 1 | (Nijmeijer et al., 2016) |
| Adhesion Class GPCRs | ADGRA2 | 2 | (Nijmeijer et al., 2016) |
| Adhesion Class GPCRs | ADGRA3 | 1 | (Nijmeijer et al., 2016) |
| Adhesion Class GPCRs | ADGRB1 | 5 | (Billings et al., 2016) |
| Adhesion Class GPCRs | ADGRB2 | 2 | (Nijmeijer et al., 2016) |
| Adhesion Class GPCRs | ADGRB3 | 2 | (Nijmeijer et al., 2016) |

-continued

| Type | Subtype | Level of Evidence | Reference |
|---|---|---|---|
| Adhesion Class GPCRs | CELSR1 | 2 | (Nijmeijer et al., 2016) |
| Adhesion Class GPCRs | CELSR2 | 2 | (Nijmeijer et al., 2016) |
| Adhesion Class GPCRs | CELSR3 | 2 | (Nijmeijer et al., 2016) |
| Adhesion Class GPCRs | ADGRD1 | 1 | (Nijmeijer et al., 2016) |
| Adhesion Class GPCRs | ADGRD2 | 1 | (Nijmeijer et al., 2016) |
| Adhesion Class GPCRs | ADGRE1 | 7 | (Lin et al., 2005) |
| Adhesion Class GPCRs | ADGRE2 | 7 | (Chen et al., 2011) |
| Adhesion Class GPCRs | ADGRE3 | 7 | (Stacey et al., 2001) |
| Adhesion Class GPCRs | ADGRE4P | 6 | (Caminschi et al., 2006) |
| Adhesion Class GPCRs | ADGRE5 | 7 | (Galle et al., 2006) |
| Adhesion Class GPCRs | ADGRF1 | 6 | (Harvey et al., 2010) |
| Adhesion Class GPCRs | ADGRF2 | 1 | (Nijmeijer et al., 2016) |
| Adhesion Class GPCRs | ADGRF3 | 2 | (Nijmeijer et al., 2016) |
| Adhesion Class GPCRs | ADGRF4 | 1 | (Nijmeijer et al., 2016) |
| Adhesion Class GPCRs | ADGRF5 | 1 | (Nijmeijer et al., 2016) |
| Adhesion Class GPCRs | ADGRG1 | 6 | (Peng et al., 2011) |
| Adhesion Class GPCRs | ADGRG2 | 1 | (Nijmeijer et al., 2016) |
| Adhesion Class GPCRs | ADGRG3 | 6 | (Peng et al., 2011) |
| Adhesion Class GPCRs | ADGRG4 | 2 | (Nijmeijer et al., 2016) |
| Adhesion Class GPCRs | ADGRG5 | 6 | (Peng et al., 2011) |
| Adhesion Class GPCRs | ADGRG6 | 1 | (Nijmeijer et al., 2016) |
| Adhesion Class GPCRs | ADGRG7 | 1 | (Nijmeijer et al., 2016) |
| Adhesion Class GPCRs | ADGRL1 | 1 | (Nijmeijer et al., 2016) |
| Adhesion Class GPCRs | ADGRL2 | 1 | (Nijmeijer et al., 2016) |
| Adhesion Class GPCRs | ADGRL3 | 1 | (Nijmeijer et al., 2016) |
| Adhesion Class GPCRs | ADGRL4 | 1 | (Nijmeijer et al., 2016) |
| Adhesion Class GPCRs | ADGRV1 | 2 | (Nijmeijer et al., 2016) |

Family C GPCRs and the current level of evidence for their involvement in inflammation (see key above):

| Type | Subtype | Level of Evidence | Reference |
|---|---|---|---|
| Calcium-sensing receptors | CaS receptor | 7 | (Bandyopadhyay et al., 2007) |
| Calcium-sensing receptors | GPRC6 receptor | 6 | (Wellendorph & Bräuner-Osborne, 2004) |
| GABAB receptors | GABAB1 | 5 | (Ito et al., 2013) |
| GABAB receptors | GABAB2 | 5 | (Ito et al., 2013) |
| GABAB receptors | GABAB receptor | 5 | (Ito et al., 2013) |
| Metabotropic glutamate receptors | mGlu1 receptor | 7 | (Bhave et al., 2001) |
| Metabotropic glutamate receptors | mGlu2 receptor | 5 | (Zammataro et al., 2011) |
| Metabotropic glutamate receptors | mGlu3 receptor | 5 | (Boxall et al., 1997) |
| Metabotropic glutamate receptors | mGlu4 receptor | 6 | (Fallarino et al., 2010) |
| Metabotropic glutamate receptors | mGlu5 receptor | 7 | (Bhave et al., 2001) |
| Metabotropic glutamate receptors | mGlu6 receptor | 1 | (Volpi et al., 2012) |
| Metabotropic glutamate receptors | mGlu7 receptor | 6 | (Fallarino et al., 2010) |

| Subtype | | Level of Evidence | Reference |
|---|---|---|---|
| Metabotropic glutamate receptors | mGlu8 receptor | 6 | (Fallarino et al., 2010) |
| Taste 1 receptors | TAS1R1 | 6 | (Malki et al., 2015) |
| Taste 1 receptors | TAS1R2 | 6 | (Malki et al., 2015) |
| Taste 1 receptors | TAS1R3 | 6 | (Malki et al., 2015) |

-continued

| | | | |
|---|---|---|---|
| Class C Orphans | GPR156 | 5 | (Calderón-Garcidueñas et al., 2012) |
| Class C Orphans | GPR158 | 5 | (Sima et al., 2015) |
| Class C Orphans | GPR179 | 5 | (Kononikhin et al., 2016) |
| Class C Orphans | GPRC5A | 5 | (Deng et al., 2010) |
| Class C Orphans | GPRC5B | 5 | (Kim et al., 2012) |
| Class C Orphans | GPRC5C | 5 | (Chhuon et al., 2016) |
| Class C Orphans | GPRC5D | 6 | (Bräuner-Osborne et al., 2001) |

Frizzled Family GPCRs and the current level of evidence for their involvement in

| | | |
|---|---|---|
| FZD1 | 6 | (Neumann et al., 2010) |
| FZD2 | 6 | (Zhao et al., 1995) |
| FZD3 | 6 | (Lu et al., 2004) |
| FZD4 | 5 | (You et al., 2008) |
| FZD5 | 5 | (You et al., 2008) |
| FZD6 | 7 | (Wu et al., 2009) |
| FZD7 | 5 | (Wada et al., 2013) |
| FZD8 | 5 | (Gregory et al., 2010) |
| FZD9 | 5 | (Wada et al., 2013) |
| FZD10 | 1 | (Dijksterhuis et al., 2014) |
| SMO | 1 | (Dijksterhuis et al., 2014) |

Other 7TM proteins that have been classified as members of the GPCR superfamily and the current level of evidence for their involvement in inflammation (see key above):

| Subtype | Level of Evidence | Reference |
|---|---|---|
| GPR107 | 5 | (Mo et al., 2013) |
| GPR137 | 4 | (Fischer et al., 2012) |
| OR51E1 | 6 | (Uhlén et al., 2015) |
| TPRA1 | 4 | (Guénard et al., 2015) |
| GPR143 | 6 | (Hohenhaus et al., 2013) |
| GPR157 | 4 | (Jia et al., 2012) |

In one embodiment, the certain activated co-located GPCRs of the invention are GPCRs selected from the following (Group A): ADGRA2, ADGRB2, ADGRB3, ADGRF3, ADGRG4, ADGRV1, CELSR1, CELSR2, CELSR3, OX1 receptor, OX2 receptor, PTH1 receptor, PTH2 receptor, AMY1 receptor, AMY2 receptor, AMY3 receptor, AM1 receptor, AM2 receptor, GPR63, GPR75, NMU2 receptor, OPN5, V1B receptor, y6 receptor, 5-HT4 receptor, GPR101, GPR119, GPR135, GPR137, GPR141, GPR149, GPR150, GPR151, GPR152, GPR157, GPR19, GPR25, GPR37, GPR37L1, GPR50, GPR62, LGR5, MRGPRE, MRGPRF, NTS2 receptor, OPN4, OPN4, OR10A7, OR10AG1, OR10Q1, OR10W1, OR12D3, OR13C2, OR13C3, OR13C4, OR13C5, OR13C8, OR13F1, OR13G1, OR1A2, OR1L1, OR1S1, OR1S2, OR2AK2, OR2D2, OR2D3, OR4A15, OR4C11, OR4C12, OR4C13, OR4C15, OR4C16, OR4K13, OR4K14, OR4K15, OR4K17, OR4N5, OR5AC2, OR5AK2, OR5AP2, OR5AR1, OR5AS1, OR5B12, OR5B17, OR5B2, OR5B21, OR5B3, OR5D13, OR5D14, OR5D16, OR5D18, OR5F1, OR5I1, OR5J2, OR5K3, OR5L1, OR5L2, OR5M1, OR5M10, OR5M11, OR5M3, OR5M8, OR5M9, OR5R1, OR5T1, OR5T2, OR5T3, OR5W2, OR6C74, OR6K6, OR6M1, OR6Q1, OR6X1, OR8H1, OR8H2, OR8H3, OR8J1, OR8J3, OR8K1, OR8K3, OR8K5, OR8U1, OR8U8, OR9A4, OR9G1, OR9G4, OR9G9, OR9Q2, TAAR3, TPRA1, Y4 receptor, 5-HT1D receptor, 5-HT1E receptor, ADGRB1, AT2 receptor, BB1 receptor, BB3 receptor, CGRP receptor, CRF1 receptor, CRF2 receptor, ETA receptor, ETB receptor, FZD4, FZD5, FZD7, FZD8, FZD9, GABAB receptor, GABAB1, GABAB2, GAL1 receptor, GIP receptor, GLP-1 receptor, GLP-2 receptor, glucagon receptor, GnRH2 receptor, GPER, GPR107, GPR139, GPR156, GPR158, GPR161, GPR171, GPR179, GPR39, GPR45, GPR88, GPRC5A, GPRC5B, GPRC5C, H3 receptor, HCA1 receptor, LPA1 receptor, LPA3 receptor, LPA4 receptor, MC2 receptor, MC4 receptor, mGlu2 receptor, mGlu3 receptor, motilin receptor, MRGPRD, MRGPRX1, MRGPRX3, NK2 receptor, NPFF1 receptor, NPFF2 receptor, NPS receptor, NTS1 receptor, OR1D2, OR2AG1, OT receptor, PAC1 receptor, RXFP1 receptor, secretin receptor, TSH receptor, UT receptor, V1A receptor, V2 receptor, α2A-adrenoceptor, α2B-adrenoceptor, α2C-adrenoceptor, β1-adrenoceptor, β3-adrenoceptor, 5-HT1B receptor, 5-HT1F receptor, 5-HT2B receptor, 5-HT2C receptor, 5-HT5A receptor, 5-HT6 receptor, 5-HT7 receptor, ADGRE4P, ADGRF1, ADGRG1, ADGRG3, ADGRG5, calcitonin receptor-like receptor, CB1 receptor, CB2 receptor, CCK1 receptor, CCK2 receptor, CT receptor, D1 receptor, D2 receptor, D3 receptor, D4 receptor, D5 receptor, FFA1 receptor, FFA3 receptor, FSH receptor, FZD1, FZD2, FZD3, GHRH receptor, GnRH1 receptor, GPBA receptor, GPR1, GPR119, GPR12, GPR142, GPR143, GPR146, GPR148, GPR153, GPR160, GPR162, GPR17, GPR173, GPR174, GPR176, GPR18, GPR182, GPR20, GPR22, GPR26, GPR27, GPR3, GPR33, GPR35, GPR6, GPR61, GPR78, GPR82, GPR83, GPR84, GPR85, GPR87, GPRC5D, GPRC6 receptor, HCA2 receptor, HCA3 receptor, kisspeptin receptor, LGR4, LGR6, LH receptor, LPA2 receptor, LPA6 receptor, M1 receptor, M2 receptor, M3 receptor, M4 receptor, M5 receptor, MAS1L, MC3 receptor, MC5 receptor, MCH2 receptor, mGlu4 receptor, mGlu7 receptor, mGlu8 receptor, MRGPRG, NOP receptor, NPBW1 receptor, NPBW2 receptor, OPN3, OR11H1, OR2A1, OR2A2, OR2A4, OR2A42, OR2A7, OR2B11, OR2B6, OR2C1, OR2C3, OR2J3, OR2L13, OR2T11, OR2T34, OR2W3, OR3A3, OR4D10, OR4M1, OR4Q3, OR51A2, OR51A4, OR51A7, OR51B2, OR51B4, OR51B5, OR51B6, OR51D1, OR51E1, OR51E1, OR51E2, OR51F1, OR51F2, OR51G1, OR51G2, OR51I1, OR51I2, OR51J1, OR51L1, OR51M1, OR51Q1, OR51S1, OR51T1, OR51V1, OR52A1, OR52A4, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR56A1, OR56A3, OR56A4, OR56A5, OR56B1, OR56B4, OR6V1, OR7D2, OR9A2, oxoglutarate receptor, P2RY10, P2RY8, P2Y12 receptor, P2Y4 receptor, PrRP receptor, QRFP receptor, RXFP2 receptor, RXFP4 receptor, sst1 receptor, sst2 receptor, sst3 receptor, sst4 receptor, sst5 receptor, TA1 receptor, TAAR2, TAAR5, TAAR6, TAAR8, TAAR9, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TRH1 receptor, Y1 receptor, Y2 receptor, Y5 receptor, α1A-adrenoceptor, α1B-adrenoceptor, α1D-adrenoceptor, δ receptor, 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group A immediately above with the exception of CCR4.

In one embodiment, the certain activated co-located GPCRs of the invention are GPCRs selected from the Group A above with the exception of CCR5.

In one embodiment, the certain activated co-located GPCRs of the invention are GPCRs selected from the Group A above with the exception of CCR4 and CCR5.

In one embodiment, the certain activated co-located GPCRs of the invention are GPCRs selected from the Group A above with the exception of CCR4, CCR5, CCR10 and CXCR3.

In one embodiment, the certain activated co-located GPCRs of the invention are GPCRs selected from the Group A above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group A above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR4, CCR5, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group A above with the exception of adrenergic α1A receptor, CCR3, M2 receptor and OX1 receptor.

In one embodiment, the certain activated co-located GPCRs of the invention are GPCRs selected from the Group A above with the exception of adrenergic α1A receptor, CCR3, CCR4, M2 receptor and OX1 receptor.

In one embodiment, the certain activated co-located GPCRs of the invention are GPCRs selected from the Group A above with the exception of adrenergic α1A receptor, CCR3, CCR5, M2 receptor and OX1 receptor.

In one embodiment, the certain activated co-located GPCRs of the invention are GPCRs selected from the Group A above with the exception of adrenergic α1A receptor, CCR3, CCR4, CCR5, M2 receptor and OX1 receptor.

In one embodiment, the certain activated co-located GPCRs of the invention are GPCRs selected from the Group A above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, M2 receptor, neurotensin NTS2 receptor, OX1 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group A above with the exception of adrenergic α1A receptor, CCR3, CCR4, CCR5, CCR10, CXCR3, M2 receptor and OX1 receptor.

In one embodiment, the certain activated co-located GPCRs of the invention are GPCRs selected from the Group A above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, M2 receptor, neurotensin NTS2 receptor, OX1 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the following (Group B): OX1 receptor, OX2 receptor, PTH1 receptor, PTH2 receptor, AMY1 receptor, AMY2 receptor, AMY3 receptor, AM1 receptor, AM2 receptor, GPR63, GPR75, NMU2 receptor, OPN5, V1B receptor, y6 receptor, 5-HT4 receptor, GPR101, GPR119, GPR135, GPR137, GPR141, GPR149, GPR150, GPR151, GPR152, GPR157, GPR19, GPR25, GPR37, GPR37L1, GPR50, GPR62, LGR5, MRGPRE, MRGPRF, NTS2 receptor, OPN4, OPN4, OR10A7, OR10AG1, OR10Q1, OR10W1, OR12D3, OR13C2, OR13C3, OR13C4, OR13C5, OR13C8, OR13F1, OR13G1, OR1A2, OR1L1, OR1S1, OR1S2, OR2AK2, OR2D2, OR2D3, OR4A15, OR4C11, OR4C12, OR4C13, OR4C15, OR4C16, OR4K13, OR4K14, OR4K15, OR4K17, OR4N5, OR5AC2, OR5AK2, OR5AP2, OR5AR1, OR5AS1, OR5B12, OR5B17, OR5B2, OR5B21, OR5B3, OR5D13, OR5D14, OR5D16, OR5D18, OR5F1, OR5I1, OR5J2, OR5K3, OR5L1, OR5L2, OR5M1, OR5M10, OR5M11, OR5M3, OR5M8, OR5M9, OR5R1, OR5T1, OR5T2, OR5T3, OR5W2, OR6C74, OR6K6, OR6M1, OR6Q1, OR6X1, OR8H1, OR8H2, OR8H3, OR8J1, OR8J3, OR8K1, OR8K3, OR8K5, OR8U1, OR8U8, OR9A4, OR9G1, OR9G4, OR9G9, OR9Q2, TAAR3, TPRA1, Y4 receptor, 5-HT1D receptor, 5-HT1E receptor, ADGRB1, AT2 receptor, BB1 receptor, BB3 receptor, CGRP receptor, CRF1 receptor, CRF2 receptor, ETA receptor, ETB receptor, FZD4, FZD5, FZD7, FZD8, FZD9, GABAB receptor, GABAB1, GABAB2, GAL1 receptor, GIP receptor, GLP-1 receptor, GLP-2 receptor, glucagon receptor, GnRH2 receptor, GPER, GPR107, GPR139, GPR156, GPR158, GPR161, GPR171, GPR179, GPR39, GPR45, GPR88, GPRC5A, GPRC5B, GPRC5C, H3 receptor, HCA1 receptor, LPA1 receptor, LPA3 receptor, LPA4 receptor, MC2 receptor, MC4 receptor, mGlu2 receptor, mGlu3 receptor, motilin receptor, MRGPRD, MRGPRX1, MRGPRX3, NK2 receptor, NPFF1 receptor, NPFF2 receptor, NPS receptor, NTS1 receptor, OR1D2, OR2AG1, OT receptor, PAC1 receptor, RXFP1 receptor, secretin receptor, TSH receptor, UT receptor, V1A receptor, V2 receptor, α2A-adrenoceptor, α2B-adrenoceptor, α2C-adrenoceptor, β1-adrenoceptor, β3-adrenoceptor, 5-HT1B receptor, 5-HT1F receptor, 5-HT2B receptor, 5-HT2C receptor, 5-HT5A receptor, 5-HT6 receptor, 5-HT7 receptor, ADGRE4P, ADGRF1, ADGRG1, ADGRG3, ADGRG5, calcitonin receptor-like receptor, CB1 receptor, CB2 receptor, CCK1 receptor, CCK2 receptor, CT receptor, D1 receptor, D2 receptor, D3 receptor, D4 receptor, D5 receptor, FFA1 receptor, FFA3 receptor, FSH receptor, FZD1, FZD2, FZD3, GHRH receptor, GnRH1 receptor, GPBA receptor, GPR1, GPR119, GPR12, GPR142, GPR143, GPR146, GPR148, GPR153, GPR160, GPR162, GPR17, GPR173, GPR174, GPR176, GPR18, GPR182, GPR20, GPR22, GPR26, GPR27, GPR3, GPR33, GPR35, GPR6, GPR61, GPR78, GPR82, GPR83, GPR84, GPR85, GPR87, GPRC5D, GPRC6 receptor, HCA2 receptor, HCA3 receptor, kisspeptin receptor, LGR4, LGR6, LH receptor, LPA2 receptor, LPA6 receptor, M1 receptor, M2 receptor, M3 receptor, M4 receptor, M5 receptor, MAS1L, MC3 receptor, MC5 receptor, MCH2 receptor, mGlu4 receptor, mGlu7 receptor, mGlu8 receptor, MRGPRG, NOP receptor, NPBW1 receptor, NPBW2 receptor, OPN3, OR11H1, OR2A1, OR2A2, OR2A4, OR2A42, OR2A7, OR2B11, OR2B6, OR2C1, OR2C3, OR2J3, OR2L13, OR2T11, OR2T34, OR2W3, OR3A3, OR4D10, OR4M1, OR4Q3, OR51A2, OR51A4, OR51A7, OR51B2, OR51B4, OR51B5, OR51B6, OR51D1, OR51E1, OR51E1, OR51E2, OR51F1, OR51F2, OR51G1, OR51G2, OR51I1, OR51I2, OR51J1, OR51L1, OR51M1, OR51Q1, OR51S1, OR51T1, OR51V1, OR52A1, OR52A4, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR56A1, OR56A3, OR56A4, OR56A5, OR56B1, OR56B4, OR6V1, OR7D2, OR9A2, oxoglutarate receptor, P2RY10, P2RY8, P2Y12 receptor, P2Y4 receptor, PrRP receptor, QRFP receptor, RXFP2 receptor, RXFP4 receptor, sst1 receptor, sst2 receptor, sst3 receptor, sst4 receptor, sst5 receptor, TA1 receptor, TAAR2, TAAR5, TAAR6, TAAR8, TAAR9, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TRH1 receptor, Y1 receptor, Y2 receptor, Y5 receptor, α1A-adrenoceptor, α1B-adrenoceptor, α1D-adrenoceptor, δ receptor, 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group B above with the exception of CCR4.

In one embodiment, the certain activated co-located GPCRs of the invention are GPCRs selected from the Group B above with the exception of CCR5.

In one embodiment, the certain activated co-located GPCRs of the invention are GPCRs selected from the Group B above with the exception of CCR4 and CCR5.

In one embodiment, the certain activated co-located GPCRs of the invention are GPCRs selected from the Group B above with the exception of CCR4, CCR5, CCR10 and CXCR3.

In one embodiment, the certain activated co-located GPCRs of the invention are GPCRs selected from the Group B above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group B above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR4, CCR5, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the group: OX1 receptor, OX2 receptor, PTH1 receptor, PTH2 receptor, AMY1 receptor, AMY2 receptor, AMY3 receptor, AM1 receptor, AM2 receptor.

In one embodiment, the certain activated co-located GPCRs of the invention are GPCRs selected from the Group B above with the exception of adrenergic α1A receptor, CCR3, M2 receptor and OX1 receptor.

In one embodiment, the certain activated co-located GPCRs of the invention are GPCRs selected from the Group B above with the exception of adrenergic α1A receptor, CCR3, CCR4, M2 receptor and OX1 receptor.

In one embodiment, the certain activated co-located GPCRs of the invention are GPCRs selected from the Group B above with the exception of adrenergic α1A receptor, CCR3, CCR5, M2 receptor and OX1 receptor.

In one embodiment, the certain activated co-located GPCRs of the invention are GPCRs selected from the Group B above with the exception of adrenergic α1A receptor, CCR3, CCR4, CCR5, M2 receptor and OX1 receptor.

In one embodiment, the certain activated co-located GPCRs of the invention are GPCRs selected from the Group B above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, M2 receptor, neurotensin NTS2 receptor, OX1 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group B above with the exception of adrenergic 1A receptor, CCR3, CCR4, CCR5, CCR10, CXCR3, M2 receptor and OX1 receptor.

In one embodiment, the certain activated co-located GPCRs of the invention are GPCRs selected from the Group B above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, M2 receptor, neurotensin NTS2 receptor, OX1 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the following (Group C): 5-HT4 receptor, GPR101, GPR119, GPR135, GPR137, GPR141, GPR149, GPR150, GPR151, GPR152, GPR157, GPR19, GPR25, GPR37, GPR37L1, GPR50, GPR62, LGR5, MRGPRE, MRGPRF, NTS2 receptor, OPN4, OPN4, OR10A7, OR10AG1, OR10Q1, OR10W1, OR12D3, OR13C2, OR13C3, OR13C4, OR13C5, OR13C8, OR13F1, OR13G1, OR1A2, OR1L1, OR1S1, OR1S2, OR2AK2, OR2D2, OR2D3, OR4A15, OR4C11, OR4C12, OR4C13, OR4C15, OR4C16, OR4K13, OR4K14, OR4K15, OR4K17, OR4N5, OR5AC2, OR5AK2, OR5AP2, OR5AR1, OR5AS1, OR5B12, OR5B17, OR5B2, OR5B21, OR5B3, OR5D13, OR5D14, OR5D16, OR5D18, OR5F1, OR5I1, OR5J2, OR5K3, OR5L1, OR5L2, OR5M1, OR5M10, OR5M11, OR5M3, OR5M8, OR5M9, OR5R1, OR5T1, OR5T2, OR5T3, OR5W2, OR6C74, OR6K6, OR6M1, OR6Q1, OR6X1, OR8H1, OR8H2, OR8H3, OR8J1, OR8J3, OR8K1, OR8K3, OR8K5, OR8U1, OR8U8, OR9A4, OR9G1, OR9G4, OR9G9, OR9Q2, TAAR3, TPRA1, Y4 receptor, 5-HT1D receptor, 5-HT1E receptor, ADGRB1, AT2 receptor, BB1 receptor, BB3 receptor, CGRP receptor, CRF1 receptor, CRF2 receptor, ETA receptor, ETB receptor, FZD4, FZD5, FZD7, FZD8, FZD9, GABAB receptor, GABAB1, GABAB2, GAL1 receptor, GIP receptor, GLP-1 receptor, GLP-2 receptor, glucagon receptor, GnRH2 receptor, GPER, GPR107, GPR139, GPR156, GPR158, GPR161, GPR171, GPR179, GPR39, GPR45, GPR88, GPRC5A, GPRC5B, GPRC5C, H3 receptor, HCA1 receptor, LPA1 receptor, LPA3 receptor, LPA4 receptor, MC2 receptor, MC4 receptor, mGlu2 receptor, mGlu3 receptor, motilin receptor, MRGPRD, MRGPRX1, MRGPRX3, NK2 receptor, NPFF1 receptor, NPFF2 receptor, NPS receptor, NTS1 receptor, OR1D2, OR2AG1, OT receptor, PAC1 receptor, RXFP1 receptor, secretin receptor, TSH receptor, UT receptor, V1A receptor, V2 receptor, α2A-adrenoceptor, α2B-adrenoceptor, α2C-adrenoceptor, β1-adrenoceptor, β3-adrenoceptor, 5-HT1B receptor, 5-HT1F receptor, 5-HT2B receptor, 5-HT2C receptor, 5-HT5A receptor, 5-HT6 receptor, 5-HT7 receptor, ADGRE4P, ADGRF1, ADGRG1, ADGRG3, ADGRG5, calcitonin receptor-like receptor, CB1 receptor, CB2 receptor, CCK1 receptor, CCK2 receptor, CT receptor, D1 receptor, D2 receptor, D3 receptor, D4 receptor, D5 receptor, FFA1 receptor, FFA3 receptor, FSH receptor, FZD1, FZD2, FZD3, GHRH receptor, GnRH1 receptor, GPBA receptor, GPR1, GPR119, GPR12, GPR142, GPR143, GPR146, GPR148, GPR153, GPR160, GPR162, GPR17, GPR173, GPR174, GPR176, GPR18, GPR182, GPR20, GPR22, GPR26, GPR27, GPR3, GPR33, GPR35, GPR6, GPR61, GPR78, GPR82, GPR83, GPR84, GPR85, GPR87, GPRC5D, GPRC6 receptor, HCA2 receptor, HCA3 receptor, kisspeptin receptor, LGR4, LGR6, LH receptor, LPA2 receptor, LPA6 receptor, M1 receptor, M2 receptor, M3 receptor, M4 receptor, M5 receptor, MAS1L, MC3 receptor, MC5 receptor, MCH2 receptor, mGlu4 receptor, mGlu7 receptor, mGlu8 receptor, MRGPRG, NOP receptor, NPBW1 receptor, NPBW2 receptor, OPN3, OR11H1, OR2A1, OR2A2, OR2A4, OR2A42, OR2A7, OR2B11, OR2B6, OR2C1, OR2C3, OR2J3, OR2L13, OR2T11, OR2T34, OR2W3, OR3A3, OR4D10, OR4M1, OR4Q3, OR51A2, OR51A4, OR51A7, OR51B2, OR51B4, OR51B5, OR51B6, OR51D1, OR51E1, OR51E1, OR51E2, OR51F1, OR51F2, OR51G1, OR51G2, OR51I1, OR51I2, OR51J1, OR51L1, OR51M1, OR51Q1, OR51S1, OR51T1, OR51V1, OR52A1, OR52A4, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR56A1, OR56A3, OR56A4, OR56A5, OR56B1, OR56B4, OR6V1, OR7D2, OR9A2, oxoglutarate receptor, P2RY10, P2RY8, P2Y12 receptor, P2Y4 receptor, PrRP receptor, QRFP receptor, RXFP2 receptor, RXFP4 receptor, sst1 receptor, sst2 receptor, sst3 receptor, sst4 receptor, sst5 receptor, TA1 receptor, TAAR2, TAAR5, TAAR6, TAAR8, TAAR9, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TRH1 receptor, Y1 receptor, Y2 receptor, Y5 receptor, α1A-adrenoceptor, α1B-adrenoceptor, α1D-adrenoceptor, δ receptor, 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group C above with the exception of CCR4.

In one embodiment, the certain activated co-located GPCRs of the invention are GPCRs selected from the Group C above with the exception of CCR5.

In one embodiment, the certain activated co-located GPCRs of the invention are GPCRs selected from the Group C above with the exception of CCR4 and CCR5.

In one embodiment, the certain activated co-located GPCRs of the invention are GPCRs selected from the Group C above with the exception of CCR4, CCR5, CCR10 and CXCR3.

In one embodiment, the certain activated co-located GPCRs of the invention are GPCRs selected from the Group C above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group C above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR4, CCR5, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group C above with the exception of adrenergic α1A receptor, CCR3 and M2 receptor.

In one embodiment, the certain activated co-located GPCRs of the invention are GPCRs selected from the Group C above with the exception of adrenergic α1A receptor, CCR3, CCR4 and M2 receptor.

In one embodiment, the certain activated co-located GPCRs of the invention are GPCRs selected from Group C above with the exception of adrenergic α1A receptor, CCR3, CCR5 and M2 receptor.

In one embodiment, the certain activated co-located GPCRs of the invention are GPCRs selected from the Group C above with the exception of adrenergic α1A receptor, CCR3, CCR4, CCR5 and M2 receptor.

In one embodiment, the certain activated co-located GPCRs of the invention are GPCRs selected from the Group C above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group C above with the exception of adrenergic α1A receptor, CCR3, CCR4, CCR5, CCR10, CXCR3 and M2 receptor.

In one embodiment, the certain activated co-located GPCRs of the invention are GPCRs selected from the Group C above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the following (Group D): 5-HT1D receptor, 5-HT1E receptor, ADGRB1, AT2 receptor, BB1 receptor, BB3 receptor, CGRP receptor, CRF1 receptor, CRF2 receptor, ETA receptor, ETB receptor, FZD4, FZD5, FZD7, FZD8, FZD9, GABAB receptor, GABAB1, GABAB2, GAL1 receptor, GIP receptor, GLP-1 receptor, GLP-2 receptor, glucagon receptor, GnRH2 receptor, GPER, GPR107, GPR139, GPR156, GPR158, GPR161, GPR171, GPR179, GPR39, GPR45, GPR88, GPRC5A, GPRC5B, GPRC5C, H3 receptor, HCA1 receptor, LPA1 receptor, LPA3 receptor, LPA4 receptor, MC2 receptor, MC4 receptor, mGlu2 receptor, mGlu3 receptor, motilin receptor, MRGPRD, MRGPRX1, MRGPRX3, NK2 receptor, NPFF1 receptor, NPFF2 receptor, NPS receptor, NTS1 receptor, OR1D2, OR2AG1, OT receptor, PAC1 receptor, RXFP1 receptor, secretin receptor, TSH receptor, UT receptor, V1A receptor, V2 receptor, α2A-adrenoceptor, α2B-adrenoceptor, α2C-adrenoceptor, β1-adrenoceptor, β3-adrenoceptor, 5-HT1B receptor, 5-HT1F receptor, 5-HT2B receptor, 5-HT2C receptor, 5-HT5A receptor, 5-HT6 receptor, 5-HT7 receptor, ADGRE4P, ADGRF1, ADGRG1, ADGRG3, ADGRG5, calcitonin receptor-like receptor, CB1 receptor, CB2 receptor, CCK1 receptor, CCK2 receptor, CT receptor, D1 receptor, D2 receptor, D3 receptor, D4 receptor, D5 receptor, FFA1 receptor, FFA3 receptor, FSH receptor, FZD1, FZD2, FZD3, GHRH receptor, GnRH1 receptor, GPBA receptor, GPR1, GPR119, GPR12, GPR142, GPR143, GPR146, GPR148, GPR153, GPR160, GPR162, GPR17, GPR173, GPR174, GPR176, GPR18, GPR182, GPR20, GPR22, GPR26, GPR27, GPR3, GPR33, GPR35, GPR6, GPR61, GPR78, GPR82, GPR83, GPR84, GPR85, GPR87, GPRC5D, GPRC6 receptor, HCA2 receptor, HCA3 receptor, kisspeptin receptor, LGR4, LGR6, LH receptor, LPA2 receptor, LPA6 receptor, M1 receptor, M2 receptor, M3 receptor, M4 receptor, M5 receptor, MAS1L, MC3 receptor, MC5 receptor, MCH2 receptor, mGlu4 receptor, mGlu7 receptor, mGlu8 receptor, MRGPRG, NOP receptor, NPBW1 receptor, NPBW2 receptor, OPN3, OR11H1, OR2A1, OR2A2, OR2A4, OR2A42, OR2A7, OR2B11, OR2B6, OR2C1, OR2C3, OR2J3, OR2L13, OR2T11, OR2T34, OR2W3, OR3A3, OR4D10, OR4M1, OR4Q3, OR51A2, OR51A4, OR51A7, OR51B2, OR51B4, OR51B5, OR51B6, OR51D1, OR51E1, OR51E1, OR51E2, OR51F1, OR51F2, OR51G1, OR51G2, OR51I1, OR51I2, OR51J1, OR51L1, OR51M1, OR51Q1, OR51S1, OR51T1, OR51V1, OR52A1, OR52A4, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR56A1, OR56A3, OR56A4, OR56A5, OR56B1, OR56B4, OR6V1, OR7D2, OR9A2, oxoglutarate receptor, P2RY10, P2RY8, P2Y12 receptor, P2Y4, receptor, PrRP receptor, QRFP receptor, RXFP2 receptor, RXFP4 receptor, sst1 receptor, sst2 receptor, sst3 receptor, sst4 receptor, sst5 receptor, TA1 receptor, TAAR2, TAAR5, TAAR6, TAAR8, TAAR9, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TRH1 receptor, Y1 receptor, Y2 receptor, Y5 receptor, α1A-adrenoceptor, α1B-adrenoceptor, α1D-adrenoceptor, δ receptor, 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group D above with the exception of CCR4.

In one embodiment, the certain activated co-located GPCRs of the invention are GPCRs selected from the Group D above with the exception of CCR5.

In one embodiment, the certain activated co-located GPCRs of the invention are GPCRs selected from the Group D above with the exception of CCR4 and CCR5.

In one embodiment, the certain activated co-located GPCRs of the invention are GPCRs selected from the Group D above with the exception of CCR4, CCR5, CCR10 and CXCR3.

In one embodiment, the certain activated co-located GPCRs of the invention are GPCRs selected from the Group D above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR8, CCR10, CXCR1, CXCR3, CXCR6, CXCR7, dopamine D2 receptor, glucagon-like peptide receptor 1, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group D above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR4, CCR5, CCR8, CCR10, CXCR1, CXCR3, CXCR6, CXCR7, dopamine D2 receptor, glucagon-like peptide receptor 1, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group D above with the exception of adrenergic α1A receptor, CCR3 and M2 receptor.

In one embodiment, the certain activated co-located GPCRs of the invention are GPCRs selected from the Group D above with the exception of adrenergic α1A receptor, CCR3, CCR4 and M2 receptor.

In one embodiment, the certain activated co-located GPCRs of the invention are GPCRs selected from the Group D above with the exception of adrenergic α1A receptor, CCR3, CCR5 and M2 receptor.

In one embodiment, the certain activated co-located GPCRs of the invention are GPCRs selected from the Group D above with the exception of adrenergic α1A receptor, CCR3, CCR4, CCR5 and M2 receptor.

In one embodiment, the certain activated co-located GPCRs of the invention are GPCRs selected from the Group D above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group D above with the exception of adrenergic α1A receptor, CCR3, CCR4, CCR5, CCR10, CXCR3 and M2 receptor.

In one embodiment, the certain activated co-located GPCRs of the invention are GPCRs selected from the Group D above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the following (Group E): 5-HT1B receptor, 5-HT1F receptor, 5-HT2B receptor, 5-HT2C receptor, 5-HT5A receptor, 5-HT6 receptor, 5-HT7 receptor, ADGRE4P, ADGRF1, ADGRG1, ADGRG3, ADGRG5, calcitonin receptor-like receptor, CB1 receptor, CB2 receptor, CCK1 receptor, CCK2 receptor, CT receptor, D1 receptor, D2 receptor, D3 receptor, D4 receptor, D5 receptor, FFA1 receptor, FFA3 receptor, FSH receptor, FZD1, FZD2, FZD3, GHRH receptor, GnRH1 receptor, GPBA receptor, GPR1, GPR119, GPR12, GPR142, GPR143, GPR146, GPR148, GPR153, GPR160, GPR162, GPR17, GPR173, GPR174, GPR176, GPR18, GPR182, GPR20, GPR22, GPR26, GPR27, GPR3, GPR33, GPR35, GPR6, GPR61, GPR78, GPR82, GPR83, GPR84, GPR85, GPR87, GPRC5D, GPRC6 receptor, HCA2 receptor, HCA3 receptor, kisspeptin receptor, LGR4, LGR6, LH receptor, LPA2 receptor, LPA6 receptor, M1 receptor, M2 receptor, M3 receptor, M4 receptor, M5 receptor, MAS1L, MC3 receptor, MC5 receptor, MCH2 receptor, mGlu4 receptor, mGlu7 receptor, mGlu8 receptor, MRGPRG, NOP receptor, NPBW1 receptor, NPBW2 receptor, OPN3, OR11H1, OR2A1, OR2A2, OR2A4, OR2A42, OR2A7, OR2B11, OR2B6, OR2C1, OR2C3, OR2J3, OR2L13, OR2T11, OR2T34, OR2W3, OR3A3, OR4D10, OR4M1, OR4Q3, OR51A2, OR51A4, OR51A7, OR51B2, OR51B4, OR51B5, OR51B6, OR51D1, OR51E1, OR51E1, OR51E2, OR51F1, OR51F2, OR51G1, OR51G2, OR51I1, OR51I2, OR51J1, OR51L1, OR51M1, OR51Q1, OR51S1, OR51T1, OR51V1, OR52A1, OR52A4, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR56A1, OR56A3, OR56A4, OR56A5, OR56B1, OR56B4, OR6V1, OR7D2, OR9A2, oxoglutarate receptor, P2RY10, P2RY8, P2Y12 receptor, P2Y4 receptor, PrRP receptor, QRFP receptor, RXFP2 receptor, RXFP4 receptor, sst1 receptor, sst2 receptor, sst3 receptor, sst4 receptor, sst5 receptor, TA1 receptor, TAAR2, TAAR5, TAAR6, TAAR8, TAAR9, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TRH1 receptor, Y1 receptor, Y2 receptor, Y5 receptor, α1A-adrenoceptor, α1B-adrenoceptor, α1D-adrenoceptor, δ receptor, 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group E above with the exception of CCR4.

In one embodiment, the certain activated co-located GPCRs of the invention are GPCRs selected from the Group E above with the exception of CCR5.

In one embodiment, the certain activated co-located GPCRs of the invention are GPCRs selected from the Group E above with the exception of CCR4 and CCR5.

In one embodiment, the certain activated co-located GPCRs of the invention are GPCRs selected from the Group E above with the exception of CCR4, CCR5, CCR10 and CXCR3.

In one embodiment, the certain activated co-located GPCRs of the invention are GPCRs selected from the Group E above with the exception of adenosine A2A receptor, adenosine A2B receptor, adenosine A3 receptor, adrenergic β2 receptor, apelin receptor, CCR8, CCR10, CXCR1, CXCR3, CXCR6, CXCR7, dopamine D2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group E above with the exception of adenosine A2A receptor, adenosine A2B receptor, adenosine A3 receptor, adrenergic β2 receptor, apelin receptor, CCR4, CCR5, CCR8, CCR10, CXCR1, CXCR3, CXCR6, CXCR7, dopamine D2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group E above with the exception of adrenergic α1A receptor, CCR3 and M2 receptor.

In one embodiment, the certain activated co-located GPCRs of the invention are GPCRs selected from the Group E above with the exception of adrenergic α1A receptor, CCR3, CCR4 and M2 receptor.

In one embodiment, the certain activated co-located GPCRs of the invention are GPCRs selected from the Group E above with the exception of adrenergic α1A receptor, CCR3, CCR5 and M2 receptor.

In one embodiment, the certain activated co-located GPCRs of the invention are GPCRs selected from the Group E above with the exception of adrenergic α1A receptor, CCR3, CCR4, CCR5 and M2 receptor.

In one embodiment, the certain activated co-located GPCRs of the invention are GPCRs selected from the Group E above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group E above with the exception of adrenergic α1A receptor, CCR3, CCR4, CCR5, CCR10, CXCR3 and M2 receptor.

In one embodiment, the certain activated co-located GPCRs of the invention are GPCRs selected from the Group E above with the exception of adenosine A2A receptor, adenosine A2B receptor, adenosine A3 receptor, adrenergic α1A receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, M2 receptor, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the following (Group F): 5-HT1A receptor, 5-HT2A receptor, A1 receptor, A2A receptor, A2B receptor, A3 receptor, ACKR1, ACKR2, ACKR3, ACKR4, ADGRE1, ADGRE2, ADGRE3, ADGRE5, apelin receptor, AT1 receptor, B1 receptor, B2 receptor, BB2 (GRP) receptor, BLT1 receptor, BLT2 receptor, C3a receptor, C5a1 receptor, C5a2 receptor, CaS receptor, CCR1, CCR10, CCR2, CCR3, CCR4, CCR5, CCR6, CCR7, CCR8, CCR9, CCRL2, chemerin receptor, CX3CR1, CXCR1, CXCR2, CXCR3, CXCR4, CXCR5, CXCR6, CysLT1 receptor, CysLT2 receptor, DP1 receptor, DP2 receptor, EP1 receptor, EP2 receptor, EP3 receptor, EP4 receptor, FFA2 receptor, FFA4 receptor, FP receptor, FPR1, FPR2/ALX, FPR2/ALX, FPR3, FZD6, GAL2 receptor, GAL3 receptor, ghrelin receptor, GPR132, GPR15, GPR18, GPR183, GPR21, GPR31, GPR32, GPR34, GPR4, GPR55, GPR55, GPR65, GPR68, H1 receptor, H2 receptor, H4 receptor, IP receptor, LPA5 receptor, MAS1, MC1 receptor, MCH1 receptor, mGlu1 receptor, mGlu5 receptor, MRGPRX2, MT1 receptor, MT2 receptor, NK1 receptor, NK3 receptor, NMU1 receptor, OXE receptor, P2Y1 receptor, P2Y11 receptor, P2Y13 receptor, P2Y14 receptor, P2Y2 receptor, P2Y6 receptor, PAF receptor, PAR1, PAR2, PAR3, PAR4, PKR1, PKR2, S1P1 receptor, S1P2 receptor, S1P3 receptor, S1P4 receptor, S1P5 receptor, succinate receptor, TP receptor, VPAC1 receptor, VPAC2 receptor, XCR1, β2-adrenoceptor, κ receptor, μ receptor.

In one embodiment, the certain activated co-located GPCRs of the invention are GPCRs selected from the Group F above with the exception of CCR4.

In one embodiment, the certain activated co-located GPCRs of the invention are GPCRs selected from the Group F above with the exception of CCR5.

In one embodiment, the certain activated co-located GPCRs of the invention are GPCRs selected from the Group F above with the exception of CCR4 and CCR5.

In one embodiment, the certain activated co-located GPCRs of the invention are GPCRs selected from the Group F above with the exception of CCR4, CCR5, CCR10 and CXCR3.

In one embodiment, the certain activated co-located GPCRs of the invention are GPCRs selected from Group F above with the exception of adenosine A2A receptor, adenosine A2B receptor, adenosine A3 receptor, adrenergic β2 receptor, apelin receptor, CCR8, CCR10, CXCR1, CXCR3, CXCR6, CXCR7, platelet activating factor receptor, prostaglandin E2 receptor, prostaglandin E3 receptor, and prostaglandin E4 receptor.

In one embodiment, the certain activated co-located GPCRs of the invention are GPCRs selected from the Group F above with the exception of adenosine A2A receptor, adenosine A2B receptor, adenosine A3 receptor, adrenergic β2 receptor, apelin receptor, CCR4, CCR5, CCR8, CCR10, CXCR1, CXCR3, CXCR6, CXCR7, platelet activating factor receptor, prostaglandin E2 receptor, prostaglandin E3 receptor, and prostaglandin E4 receptor.

In one embodiment, the certain activated co-located GPCRs of the invention are GPCRs selected from the Group F above with the exception of CCR3.

In one embodiment, the certain activated co-located GPCRs of the invention are GPCRs selected from the Group F above with the exception of CCR3 and CCR4.

In one embodiment, the certain activated co-located GPCRs of the invention are GPCRs selected from the Group F above with the exception of CCR3 and CCR5.

In one embodiment, the certain activated co-located GPCRs of the invention are GPCRs selected from the Group F above with the exception of CCR3, CCR4, and CCR5.

In one embodiment, the certain activated co-located GPCRs of the invention are GPCRs selected from the Group F above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR3, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the Group F above with the exception of CCR3, CCR4, CCR5, CCR10 and CXCR3.

In one embodiment, the certain activated co-located GPCRs of the invention are GPCRs selected from the Group F above with the exception of adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR3, CCR4, CCR5, CCR8, CCR10, CXCR1, CXCR3, CXCR6, CXCR7, dopamine D2 receptor, glucagon-like peptide receptor 1, neurotensin NTS2 receptor, platelet activating factor receptor, prostaglandin E2 receptor, prostaglandin E3 receptor, prostaglandin E4 receptor, somatostatin 1 receptor and somatostatin 3 receptor.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR2, CXCR4, CXCR6 and CXCR7.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR1, CXCR2, CXCR4, CXCR6 and CXCR7.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR1, CXCR2, CXCR4 and CXCR6.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR2, CXCR4 and CXCR6.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR1, CXCR2 and CXCR6.

In one embodiment, the certain activated co-located GPCRs of the invention are GPCRs selected from the group: angiotensin receptors, including $AT_1R$, and certain chemokine receptors, including CCR1, CCR2, CCR6, CCR7, CXCR2 and CXCR6.

In one embodiment, the activated co-located GPCR of the invention is vasopressin receptor 2.

In one embodiment, certain chemokine receptors are chemokine receptors that are co-expressed in the same cell as RAGE.

In one embodiment, certain chemokine receptors are chemokine receptors that are co-expressed in the same cell as RAGE, are implicated in inflammation, and are selected from the group: CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR4, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR5, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR6, CCR7, CCR8, CCR9, CXCR1, CXCR2, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR4, CCR5, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR4, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR5, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR6, CCR7, CCR8, CCR9, CCR10, CXCR1, CXCR2, CXCR3, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR6, CCR7, CCR8, CCR9, CXCR1, CXCR2, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR6, CCR7, CCR8, CCR9, CXCR1, CXCR2, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR6, CCR7, CCR8, CCR9, CXCR2, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR3, CCR6, CCR7, CCR8, CCR9, CXCR2, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR6, CCR7, CCR8, CCR9, CXCR1, CXCR2, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR6, CCR7, CCR8, CCR9, CXCR2, CXCR4, CXCR5, CXCR6, CXCR7, CX3CR1, XCR1.

In one embodiment, certain chemokine receptors are chemokine receptors that are co-expressed in the same cell as RAGE, are implicated in inflammation, and are selected from the group: CCR1, CCR2, CCR6, CCR7, CCR8, CCR9, CXCR2, CXCR5, CXCR6, CXCR7, CX3CR1, XCR1.

In one form of the invention, the certain activated co-located GPCRs of the invention are GPCRs selected from the group: adenosine 1A receptor, adrenergic α1A receptor, adrenergic α1B receptor, adrenergic α2B receptor, angiotensin receptor $AT_1R$, bradykinin receptor B2, CCR1, CCR2, CCR3, CCR4, CCR5, CCR6, CCR7, CCR9, CXCR2, CXCR4, CXCR5, dopamine D1 receptor, endothelin receptor type A, endothelin receptor type B, histamine H3 receptor, muscarinic M1 receptor, muscarinic M2 receptor, muscarinic M3 receptor, neuropeptide Y1 receptor, neurotensin 1 receptor, orexin receptor 1, orexin receptor 2, prostaglandin E1 receptor, serotonin 5-HT1a receptor, serotonin 5-HT2a receptor, serotonin 5-HT2b receptor, serotonin 5-HT2c receptor, serotonin 5-HT4b receptor, somatostatin 2 receptor, sphingosine 1-phosphate receptor S1P1, sphingosine 1-phosphate receptor S1P3, thyrotrophin-releasing hormone receptor 1, vasopressin receptor 1A, vasopressin receptor 1B or vasopressin receptor 2.

In one embodiment, the certain activated co-located GPCRs of the invention are GPCRs selected from the group in paragraph with the exception of CCR4.

In one embodiment, the certain activated co-located GPCRs of the invention are GPCRs selected from the group in paragraph with the exception of CCR5.

In one embodiment, the certain activated co-located GPCRs of the invention are GPCRs selected from the group in paragraph with the exception of CCR4 and CCR5.

In one embodiment, the certain activated co-located GPCRs of the invention are GPCRs selected from the group in paragraph with the exception of CCR4, CCR5 and CXCR4.

In one embodiment, the certain activated co-located GPCRs of the invention are GPCRs selected from the group in paragraph with the exception of adrenergic α1A receptor, CCR3, muscarinic M2 receptor and orexin receptor 1.

In one embodiment, the certain activated co-located GPCRs of the invention are GPCRs selected from the group in paragraph with the exception of adrenergic α1A receptor, CCR3, CCR4, muscarinic M2 receptor and orexin receptor 1.

In one embodiment, the certain activated co-located GPCRs of the invention are GPCRs selected from the group in paragraph with the exception of adrenergic α1A receptor, CCR3, CCR5, muscarinic M2 receptor and orexin receptor 1.

In one embodiment, the certain activated co-located GPCRs of the invention are GPCRs selected from the group in paragraph with the exception of adrenergic α1A receptor, CCR3, CCR4, CCR5, muscarinic M2 receptor and orexin receptor 1.

In one embodiment, the certain activated co-located GPCRs of the invention are GPCRs selected from the group in paragraph with the exception of adrenergic α1A receptor, CCR3, CXCR4, muscarinic M2 receptor and orexin receptor 1.

In a preferred form of the invention, the certain activated co-located GPCRs of the invention are GPCRs selected from the following (Group G): adrenergic α1A receptor, adrenergic α1B receptor, angiotensin receptor $AT_1R$, bradykinin receptor B2, CCR2, CCR3, CCR4, CCR6, CCR9, CXCR4, CXCR5, dopamine D1 receptor, endothelin receptor type B, histamine H3 receptor, muscarinic M2 receptor, neuropeptide Y1 receptor, neurotensin 1 receptor, orexin receptor 1, orexin receptor 2, prostaglandin E1 receptor, serotonin 5-HT2b receptor, serotonin 5-HT2c receptor, serotonin 5-HT4b receptor, somatostatin 2 receptor, sphingosine 1-phosphate receptor S1P3, vasopressin receptor 1A or vasopressin receptor 1B.

In one embodiment, the certain activated co-located GPCRs of the invention are GPCRs selected from the Group G above with the exception of CCR4.

In one embodiment, the certain activated co-located GPCRs of the invention are GPCRs selected from the Group G above with the exception of CCR4 and CXCR4.

In one embodiment, the certain activated co-located GPCRs of the invention are GPCRs selected from the Group G above with the exception of adrenergic α1A receptor, CCR3, muscarinic M2 receptor and orexin receptor 1.

In one embodiment, the certain activated co-located GPCRs of the invention are GPCRs selected from the Group G above with the exception of adrenergic α1A receptor, CCR3, CCR4, muscarinic M2 receptor and orexin receptor 1.

In one embodiment, the certain activated co-located GPCRs of the invention are GPCRs selected from the Group G above with the exception of adrenergic α1A receptor, CCR3, CCR4, CXCR4, muscarinic M2 receptor and orexin receptor 1.

In a particularly preferred form of the invention, the certain activated co-located GPCRs of the invention are GPCRs selected from the group: adrenergic α1A receptor, adrenergic α1B receptor, angiotensin receptor AT$_1$R, bradykinin receptor B2, CCR2, CCR6, CCR9, CXCR4, CXCR5, dopamine D1 receptor, endothelin receptor type B, histamine H3 receptor, muscarinic M2 receptor, neuropeptide Y1 receptor, orexin receptor 1, orexin receptor 2, prostaglandin E1 receptor, serotonin 5-HT2c receptor, serotonin 5-HT4b receptor, somatostatin 2 receptor, sphingosine 1-phosphate receptor S1P3, vasopressin receptor 1A or vasopressin receptor 1B.

In one embodiment, the certain activated co-located GPCRs of the invention are GPCRs selected from the group in paragraph with the exception of CXCR4.

In one embodiment, the certain activated co-located GPCRs of the invention are GPCRs selected from the group in paragraph with the exception of adrenergic α1A receptor, CCR3, muscarinic M2 receptor and orexin receptor 1.

In one embodiment, the certain activated co-located GPCRs of the invention are GPCRs selected from the group in paragraph with the exception of adrenergic α1A receptor, CCR3, CXCR4, muscarinic M2 receptor and orexin receptor 1.

In one form of the invention, the certain activated co-located GPCRs of the invention are GPCRs selected from the following (Group H): adenosine A1 receptor (ADORA1), adrenergic α2B receptor, angiotensin receptor AT$_1$ (AT1R), bradykinin receptor 2 (B2R), CCR1, CCR2, CCR4, CCR5, CCR6, CCR7, CCR9, CXCR2, CXCR4, CXCR5, neuropeptide Y1 receptor (NPY1R), orexin receptor 2, sphingosine 1-phosphate receptor 1 (S1PR1), thyrotropin-releasing hormone receptor 1 (TRHR1), vasopressin receptor 1A (V1aR), vasopressin receptor 1B (V1bR) and vasopressin receptor 2 (V2R).

In one embodiment, the certain activated co-located GPCRs of the invention are GPCRs selected from the Group H above with the exception of CCR4.

In one embodiment, the certain activated co-located GPCRs of the invention are GPCRs selected from the Group H above with the exception of CCR5.

In one embodiment, the certain activated co-located GPCRs of the invention are GPCRs selected from the Group H above with the exception of CCR4 and CCR5.

In one embodiment, the certain activated co-located GPCRs of the invention are GPCRs selected from the Group H above with the exception of CXCR4.

In one embodiment, the certain activated co-located GPCRs of the invention are GPCRs selected from the Group H above with the exception of CCR4, CCR5 and CXCR4.

In a preferred form of the invention, the certain activated co-located GPCRs of the invention are GPCRs selected from the following (Group I): adrenergic α2B receptor, angiotensin receptor AT$_1$ (AT1R), bradykinin receptor 2 (B2R), CCR1, CCR2, CCR4, CCR5, CCR6, CCR9, CXCR2, CXCR4, neuropeptide Y1 receptor (NPY1R), orexin receptor 2, sphingosine 1-phosphate receptor 1 (S1PR1), thyrotropin-releasing hormone receptor 1 (TRHR1), vasopressin receptor 1A (V1aR), vasopressin receptor 1B (V1bR) and vasopressin receptor 2 (V2R).

In one embodiment, the certain activated co-located GPCRs of the invention are GPCRs selected from the Group I above with the exception of CCR4.

In one embodiment, the certain activated co-located GPCRs of the invention are GPCRs selected from the Group I above with the exception of CCR5.

In one embodiment, the certain activated co-located GPCRs of the invention are GPCRs selected from the Group I above with the exception of CCR4 and CCR5.

In one embodiment, the certain activated co-located GPCRs of the invention are GPCRs selected from the Group I above with the exception of CXCR4.

In one embodiment, the certain activated co-located GPCRs of the invention are GPCRs selected from the Group I above with the exception of CCR4, CCR5 and CXCR4.

In a specific form of the invention, the activated co-located GPCR of the invention is an angiotensin receptor.

In a specific form of the invention, the activated co-located GPCR of the invention is AT$_1$R.

In a specific form of the invention, the activated co-located GPCR of the invention is a certain chemokine receptor, selected from the group: CCR1, CCR2, CCR6, CCR7, CXCR2, CXCR4, CXCR6 and CXCR7.

In a specific form of the invention, the activated co-located GPCR of the invention is a certain chemokine receptor, selected from the group: CCR1, CCR2, CCR6, CCR7, CXCR1, CXCR2 and CXCR6.

In a specific form of the invention, the activated co-located GPCR of the invention is a certain chemokine receptor, selected from the group: CCR1, CCR2, CCR6, CCR7, CXCR2 and CXCR6.

In a specific form of the invention, the activated co-located GPCR of the invention is a certain chemokine receptor selected from CCR2 and CCR6.

In a specific form of the invention, the activated co-located GPCR of the invention is CCR2.

In a specific form of the invention, the activated co-located GPCR of the invention is CXCR4.

In one form of the invention, a RAGE ligand is a ligand that interacts with the ectodomain of RAGE to modulate activation of RAGE. Thus, in this form of the invention, RAGE ligand-independent activation of RAGE means activation of RAGE that does not occur by way of a ligand interacting with the ectodomain of RAGE.

Preferably, a RAGE ligand is a ligand that interacts with the ectodomain of RAGE to modulate activation of RAGE and does not interact with the transmembrane domain or cytosolic tail of RAGE or motifs contained therein. Thus, in this preferred form of the invention, RAGE ligand-independent activation of RAGE means activation of RAGE that does not occur by way of a ligand interacting with the ectodomain of RAGE unless the ligand also interacts with the transmembrane domain or cytosolic tail of RAGE or motifs contained therein.

The ectodomain (also known as the extracellular domain) of RAGE includes three immunoglobulin-like regions: an N-terminal V-type domain followed by two C-type domains (termed C and C' or alternatively C1 and C2). The principal ligand-binding portion is the V-domain, however RAGE activation may also be mediated by ligand binding to the C-domains. Most ligands tend to bind to the V domain and/or the C1 domain since ligands tend to be negatively charged, however, there is at least one example of a ligand binding to the C2 domain (S100A6; Leclerc et al., 2007). Though the C1- and C2-domains may not generally directly bind ligands, they could have important roles in stabilizing the V-domain for mediating its interaction(s) with ligands. RAGE has a single transmembrane-spanning domain and a cytosolic tail. In humans, the cytosolic tail of RAGE is 43 amino acids long (residue 362 to residue 404). This cytosolic tail contains motifs which are critical for RAGE-dependent cellular activation.

In one form of the invention, a RAGE ligand is a ligand that interacts with the extracellular V, C1 and/or C2 domains of the RAGE ectodomain to activate RAGE. In this form of the invention, RAGE ligand-independent activation of RAGE means activation of RAGE that does not occur by way of a ligand interacting with the extracellular V, C1 or C2 domains of the RAGE ectodomain.

Preferably, the RAGE ligand does not interact with the transmembrane domain or cytosolic tail of RAGE or motifs contained therein. In this form of the invention, RAGE ligand-independent activation of RAGE means activation of RAGE that does not occur by way of a ligand interacting with the extracellular V, C1 or C2 domains of the RAGE ectodomain unless the ligand also interacts with the transmembrane domain or cytosolic tail of RAGE or motifs contained therein.

In one form of the invention, a modulator that modulates RAGE ligand-independent activation of RAGE by an activated co-located GPCR, such as activated angiotensin receptor, such as $AT_1R$, or CCR2, also modulates RAGE ligand-dependent activation of RAGE.

In preferred embodiments of the invention, modulators of the invention do not modulate, or modulate differently, or modulate to a different extent, RAGE-independent signalling pathways associated with the certain activated co-located GPCR.

In a preferred embodiment, modulators of the invention do not inhibit, or inhibit to a lesser extent, one or more RAGE independent certain co-located GPCR signalling pathways.

In one form of the invention, the RAGE-independent certain co-located GPCR signalling pathway is the Gq signalling pathway. In one form of the invention, the RAGE-independent certain co-located GPCR signalling pathway is the Gi/o signalling pathway. In one form of the invention, the RAGE-independent certain co-located GPCR signalling pathway is the Gs signalling pathway. In one form of the invention, the RAGE-independent certain co-located GPCR signalling pathway is the calcium signalling pathway. In one form of the invention, the RAGE-independent certain co-located GPCR signalling pathway is the phospholipase C signalling pathway. In another form of the invention, the RAGE-independent certain co-located GPCR signalling pathway is β-arrestin-mediated extracellular regulated kinase (ERK) signalling.

In a particularly preferred embodiment, where the activated co-located GPCR is activated $AT_1R$, modulators of the invention do not modulate, or modulate to a lesser extent, one or more RAGE independent $AT_1R$ signalling pathways.

In a particularly preferred embodiment, where the activated co-located GPCR is activated $AT_1R$, modulators of the invention do not inhibit, or inhibit to a lesser extent, one or more RAGE independent $AT_1R$ signalling pathways.

In one form of the invention, the RAGE-independent $AT_1R$ signalling pathway is the Gq signalling pathway. In another form of the invention, the RAGE-independent $AT_1R$ signalling pathway is β-arrestin-mediated extracellular regulated kinase (ERK) signalling.

In another particularly preferred embodiment, where the activated co-located GPCR is activated CCR2, modulators of the invention do not modulate, or modulate to a lesser extent, one or more RAGE independent CCR2 signalling pathways.

In another particularly preferred embodiment, where the activated co-located GPCR is activated CCR2, modulators of the invention do not inhibit, or inhibit to a lesser extent, one or more RAGE independent CCR2 signalling pathways.

In one form of the invention, the RAGE-independent $AT_1R$ signalling pathway is the Gi/o signalling pathway. In another form of the invention, the RAGE-independent CCR2 signalling pathway is β-arrestin-mediated extracellular regulated kinase (ERK) signalling. In another form of the invention, the RAGE-independent CCR2 signalling pathway is the phospholipase C signalling pathway.

Modulators

In one form of the invention, a modulator of the invention is an activator, an inhibitor, an allosteric modulator, or a functional or non-functional substitute for the cytosolic tail of RAGE. A functional substitute is a modulator that takes the place of the cytosolic tail of RAGE in the presence of certain co-located GPCRs and is able to be activated by them to induce downstream RAGE-dependent signalling in the presence or absence of expression of wild-type RAGE. A non-functional substitute is a modulator that takes the place of the cytosolic tail of RAGE in the presence of certain co-located GPCRs, is not able to be activated by them or induce downstream RAGE-dependent signalling, and inhibits signalling that normally occurs through activation of the cytosolic tail of RAGE and RAGE-dependent signalling resulting therefrom.

In one form of the invention, a modulator of the invention is an activator, an inhibitor, an allosteric modulator, or a non-functional substitute for the transmembrane domain of RAGE or part thereof.

A non-functional substitute is a modulator that takes the place of the transmembrane domain of RAGE in the presence of certain co-located GPCRs, is not able to be activated by them or induce downstream RAGE-dependent signalling, and inhibits signalling that normally occurs through activation of the cytosolic tail of RAGE and RAGE-dependent signalling resulting therefrom.

In one form of the invention, the modulator comprises a transmembrane domain of RAGE or a part thereof and a fragment of the RAGE ectodomain.

In one form of the invention, the modulator comprises a transmembrane domain of RAGE or a part thereof and a fragment of the cytosolic tail of RAGE.

In one form of the invention, the modulator comprises a transmembrane domain of RAGE or part thereof and a fragment of the RAGE ectodomain and a fragment of the cytosolic tail of RAGE.

In one form of the invention, modulators of the invention contain a fragment of the ectodomain of RAGE, which is not greater than 40, not greater than 20, not greater than 10 or not greater than 5 amino acids in length.

By way of example of a modulator, the inventors have demonstrated that RAGE$_{362-404}$ is a functional substitute for RAGE and is able to be activated by certain co-located GPCRs, such as AT$_1$R and CCR2, and induce downstream RAGE-dependent signalling resulting from RAGE ligand-independent activation of RAGE, in the presence or absence of expression of wild-type RAGE. Furthermore, when RAGE$_{362-404}$ is fused to a cell penetrating peptide (TAT) and a marker protein (mCherry), treatment with TAT-mCherry-RAGE$_{362-404}$ oligopeptide following activation of AT$_1$R by Ang II is able to restore Ang II-dependent inflammation and atherogenesis in Ager Apoe DKO mice in the absence of expression of wild-type RAGE.

The sequence of RAGE$_{362-404}$ is SEQ ID NO: 1:
[L$_{362}$WQRRQRRGEERKAPENQEEEEERAEL-NQSEEPEAGESSTGGP$_{404}$]

By way of an additional example of a modulator, the inventors have demonstrated that S391A-RAGE$_{362-404}$ is a non-functional substitute for RAGE that in the presence of certain co-located GPCRs is not activated by them and inhibits RAGE-dependent signalling. Expression of S391A-RAGE$_{362-404}$ inhibits RAGE ligand-independent activation of wild-type RAGE by activated AT$_1$R and RAGE ligand-dependent activation of wild-type RAGE by the RAGE ligand S100A8/A9. Furthermore, when S391A-RAGE$_{362-404}$ is fused to a cell penetrating peptide (TAT) and a marker protein (mCherry), treatment with TAT-mCherry-S391A-RAGE$_{362-404}$ oligopeptide inhibits RAGE ligand-independent activation of RAGE by activated AT$_1$R to attenuate Ang II-dependent inflammation and atherogenesis in apolipoprotein E knockout mice. Further examples are provided below.

```
The sequence of S391A-RAGE362-404 is SEQ ID NO: 2:
[L362WQRRQRRGEERKAPENQEEEEERAELNQAEEPEAGESSTGGP404]
```

By way of another example of a modulator, the inventors have demonstrated that RAGE$_{338-361}$ inhibits RAGE ligand-independent activation of wild-type RAGE by activated AT$_1$R. This inhibition is overcome by co-expression of mCherry-RAGE$_{362-404}$.

```
The sequence of RAGE338-361 is SEQ ID 3
[L338GTLALALGILGGLGTAALLIGVI361]
```

In one form, the present invention comprises modulators of RAGE ligand-independent activation of RAGE by certain activated co-located GPCRs that modulate transactivation of the cytosolic tail of RAGE triggered by activation of such certain activated co-located GPCRs, such as an angiotensin receptor, such as AT$_1$R, or a chemokine receptor, such as CCR2.

In one form, the present invention comprises modulators of RAGE ligand-independent activation of the cytosolic tail of RAGE by certain activated co-located GPCRs that bind to Ras GTPase-activating-like protein (IQGAP1) or other RAGE-associated proteins, including protein kinase C zeta (PKCζ), Dock7, MyD88, TIRAP, IRAK4, ERK1/2, olfactory receptor 2T2, ADP/ATP translocase 2, Protein phosphatase 1G, Intercellular adhesion molecule 1, Protein DJ-1 (PARK7), Calponin-3, Drebrin, Filamin B, Ras-related protein Rab-13, Radixin/Ezrin/Moesin, Proteolipid protein 2, Coronin, S100 A11, Succinyl-CoA ligase [GDP-forming] subunit alpha, Hsc70-interacting protein, Apoptosis Inhibitor 5, neuropilin, cleavage stimulation factor, growth factor receptor-bound protein 2, sec61 beta subunit, or Nck1, or disrupt the binding of these elements to RAGE, in order to modulate RAGE transactivation by certain activated co-located GPCRs, such as an angiotensin receptor, such as AT$_1$R, or a chemokine receptor, such as CCR2.

In one form of the invention, the modulators of the invention bind to the cytosolic elements of the certain activated co-located GPCR, RAGE and/or elements complexed with either, including IQGAP-1, PKCζ, Dock7, MyD88, TIRAP, IRAK4, ERK1/2, olfactory receptor 2T2, ADP/ATP translocase 2, Protein phosphatase 1G, Intercellular adhesion molecule 1, Protein DJ-1 (PARK7), Calponin-3, Drebrin, Filamin B, Ras-related protein Rab-13, Radixin/Ezrin/Moesin, Proteolipid protein 2, Coronin, S100 A11, Succinyl-CoA ligase [GDP-forming] subunit alpha, Hsc70-interacting protein, Apoptosis Inhibitor 5, neuropilin, cleavage stimulation factor, growth factor receptor-bound protein 2, sec61 beta subunit, or Nck1 to modulate RAGE ligand-independent signalling through the cytosolic tail of RAGE, by modulating these signalling elements required for RAGE transactivation by certain activated co-located GPCRs, such as an angiotensin receptor, such as AT$_1$R, or such as a chemokine receptor, such as CCR2.

In one form of the invention, modulators of RAGE ligand-independent activation of RAGE by certain activated co-located GPCRs also modulate RAGE ligand-dependent activation of the cytosolic tail of RAGE, by binding to cytosolic elements of RAGE and/or elements that complex with RAGE in the cytosol (such as IQGAP-1, PKCζ, Dock7, MyD88, IRAK4, TIRAP, ERK1/2, olfactory receptor 2T2, ADP/ATP translocase 2, Protein phosphatase 1G, Intercellular adhesion molecule 1, Protein DJ-1 (PARK7), Calponin-3, Drebrin, Filamin B, Ras-related protein Rab-13, Radixin/Ezrin/Moesin, Proteolipid protein 2, Coronin, S100 A11, Succinyl-CoA ligase [GDP-forming] subunit alpha, Hsc70-interacting protein, Apoptosis Inhibitor 5, neuropilin, cleavage stimulation factor, growth factor receptor-bound protein 2, sec61 beta subunit, or Nck1) to inhibit RAGE ligand-mediated signalling through these elements.

In specific embodiments, the modulator comprises, consists, or consists essentially of an amino acid sequence as set forth in SEQ ID NO: 1, or an analogue, fragment or derivative thereof.

In some embodiments, the modulator is introduced by gene delivery (such as by using a virus or artificial non-viral gene delivery such as electroporation, microinjection, gene gun, impalefection, hydrostatic pressure, continuous infusion, sonication, lipofection, liposomes, nanobubbles and polymeric gene carriers) and the peptide fragment, biologically-active analogue or derivative being generated by the cell as a consequence of transcriptional and translational processes.

In some embodiments of this aspect, the modulator has a modified capacity to form a complex with certain co-located GPCRs, such as AT$_1$R or CCR2, or elements that complex with them. For example, the RAGE analogue or derivative may be distinguished from a wild-type RAGE polypeptide or fragment sequence by the substitution, addition, or deletion of at least one amino acid residue or addition or substitution of unusual or non-conventional amino-acids or non-amino acid residues.

In some embodiments, the modulator lacks or has a modification of serine-391 that is normally present in a wild-type human RAGE polypeptide. In illustrative examples of this type, the fragment, analogue or derivative of the cytosolic tail of RAGE lacks a serine at position 391 of the wild-type RAGE sequence (for example, the $RAGE_{370-390}$ construct is truncated at Glu390). Suitably, the serine at position 391 is deleted or substituted with another amino acid residue, an analogue or derivative, in order to impair or abolish signalling conferred by a serine at this site following activation of a co-located GPCR. In one embodiment, the serine at position 391 is deleted or substituted with another amino acid residue selected from the group: alanine, aspartate, phenylalanine, histidine, lysine, arginine, tyrosine, asparagine, valine, glycine, cysteine or glutamate.

In some embodiments, the modulator retains the serine-391 that is normally present in a wild-type human RAGE polypeptide or be substituted by another amino acid that retains the same function of a serine at the 391 position, or an analogue or derivative thereof. In illustrative examples of this type, the fragment of the cytosolic tail of RAGE retains a serine at position 391 of the wild-type RAGE sequence (for example, the $RAGE_{370-404}$ construct). Suitably, the serine at position 391 is substituted with another amino acid residue or an analogue or derivative thereof, in order to replicate signalling conferred following activation of a co-located GPCR by RAGE constructs containing a serine at this site. In one embodiment the serine at position 391 is substituted with another amino acid residue selected from the group: proline, glutamine, threonine, leucine, isoleucine, methionine, or tryptophan.

In some embodiments, the modulator lacks or has an impaired ability to bind Diaphanous 1 (Diaph1) relative to human wild-type RAGE. In illustrative examples of this type, the peptide, or analogue, fragment or derivative thereof, either lacks the RAGE-Diaph1 binding site (such as $RAGE_{370-390}$, $RAGE_{374-390}$, or $RAGE_{379-390}$) or has an altered Diaph1 binding site (such as 366A/367A) in order to abolish or impair this site. Suitably, the residues at 366/367 are deleted or substituted with other residues (such as with alanine) in order to impair or abolish this site, and in doing so, improve affinity for binding to other targets, by reducing constraints induced by wild-type binding to Diaph1.

In one aspect of the invention, the modulator of the present invention includes isolated or purified peptides which comprise, consist, or consists essentially of an amino acid sequence represented by Formula I:

$$Z1 M Z2 \quad (I)$$

wherein:
  Z1 is absent or is selected from at least one of a proteinaceous moiety comprising from about 1 to about 50 amino acid residues; and
  M is the amino acid sequence as set forth in SEQ ID NO: 1, or an analogue, fragment or derivative thereof; and
  Z2 is absent or is a proteinaceous moiety comprising from about 1 to about 50 amino acid residues.

In some embodiments of the invention described above, the modulator (such as a fragment of the RAGE cytosolic tail, an analogue or derivative thereof as broadly described above and elsewhere herein) is able to penetrate a cell membrane. In non-limiting examples of this type, the RAGE modulator is conjugated, fused or otherwise linked to a cell membrane penetration molecule (e.g., the HIV TAT motif, as set forth in SEQ ID NO: 4 below).

SEQ ID NO: 4:
[YGRKKRRQRRR].

In some forms of the invention, the modulator is a non-peptide molecule that shares with the peptide modulator described above the capacity to bind to and/or interfere with elements associated with RAGE ligand-independent activation of RAGE by certain activated co-located GPCRs. These non-peptide modulators may or may not contain structural similarities to functionally important domains contained in peptide modulators.

In a preferred form, the non-peptide modulator contains structural similarities to functionally important domains contained in the peptide modulators, as represented by the pharmacophore described herein below in the paragraph beginning "[a] pharmacophore for $RAGE_{379-390}$ peptide derived from the structure model4_$RAGE_{370-390}$ is represented below:".

In preferred forms of the invention, the modulator is an inhibitor.

In certain forms of the invention, in addition to being an inhibitor of RAGE ligand-independent activation of RAGE by a certain activated co-located GPCR, the modulator is an inhibitor of the certain co-located GPCR and/or an inhibitor of the certain co-located GPCR signalling pathway.

In certain forms of the invention, in addition to being an inhibitor of RAGE ligand-independent activation of RAGE by a certain activated co-located GPCR, the modulator is an inhibitor of RAGE ligand-dependent activation of RAGE and/or an inhibitor of constitutively-active RAGE and/or an inhibitor of a RAGE signalling pathway.

In certain forms of the invention, where the certain co-located GPCR is $AT_1R$, in addition to being an inhibitor of RAGE ligand-independent activation of RAGE, the modulator is an $AT_1R$ inhibitor and/or an inhibitor of an $AT_1R$ signalling pathway.

In certain forms of the invention, in addition to being an inhibitor of RAGE ligand-independent activation of RAGE by activated angiotensin receptor, preferably activated $AT_1R$, the modulator is an inhibitor of RAGE ligand-dependent activation of RAGE and/or an inhibitor of constitutively-active RAGE and/or an inhibitor of a RAGE signalling pathway.

In certain forms of the invention, in addition to being an inhibitor of RAGE ligand-independent activation of RAGE by a certain activated co-located GPCR, the modulator is an inhibitor of the certain co-located GPCR and/or an inhibitor of the certain co-located GPCR signalling pathway and an inhibitor of RAGE ligand-dependent activation of RAGE and/or an inhibitor of constitutively-active RAGE and/or an inhibitor of a RAGE signalling pathway.

In certain forms of the invention, in addition to being an inhibitor of RAGE ligand-independent activation of RAGE by activated angiotensin receptor, preferably activated $AT_1R$, the modulator is an $AT_1R$ inhibitor and/or an inhibitor of an $AT_1R$ signalling pathway and an inhibitor of RAGE ligand-dependent activation of RAGE and/or an inhibitor of constitutively-active RAGE and/or an inhibitor of a RAGE signalling pathway.

In certain forms of the invention, where the certain co-located GPCR is a certain chemokine receptor, preferably CCR2, in addition to being an inhibitor of RAGE ligand-independent activation of RAGE, the modulator is a certain chemokine receptor inhibitor, preferably a CCR2 inhibitor, and/or an inhibitor of a certain chemokine signalling pathway, preferably a CCR2 signalling pathway.

In certain forms of the invention, in addition to being an inhibitor of RAGE ligand-independent activation of RAGE by activated certain chemokine receptor, preferably activated CCR2, the modulator is an inhibitor of RAGE ligand-dependent activation of RAGE and/or an inhibitor of constitutively-active RAGE and/or an inhibitor of a RAGE signalling pathway.

In certain forms of the invention, in addition to being an inhibitor of RAGE ligand-independent activation of RAGE by activated chemokine receptor, preferably activated CCR2, the modulator is a certain chemokine receptor inhibitor, preferably a CCR2 inhibitor, and/or an inhibitor of a certain chemokine signalling pathway, preferably a CCR2 signalling pathway and an inhibitor of RAGE ligand-dependent activation of RAGE and/or an inhibitor of constitutively-active RAGE and/or an inhibitor of a RAGE signalling pathway.

In certain forms of the invention, the modulator is a functional substitute for the cytosolic tail of RAGE or a part thereof and is able to be activated by certain co-located GPCRs, such as activated $AT_1R$ and activated CCR2, and induce downstream RAGE-dependent signalling in the presence or absence of expression of wild-type RAGE.

In certain forms of the invention, the modulator is a non-functional substitute for the cytosolic tail of RAGE or a part thereof, which is not able to be activated by a co-located GPCR or facilitate downstream RAGE-dependent signalling and inhibits signalling that occurs through the cytosolic tail of RAGE and RAGE-dependent signalling.

In certain forms of the invention, the modulator is a non-functional substitute for the transmembrane domain of RAGE or a part thereof, which is not able to be activated by a co-located GPCR or facilitate downstream RAGE-dependent signalling and inhibits signalling that occurs through the cytosolic tail of RAGE and RAGE-dependent signalling.

In certain forms of the invention, the modulator comprises a transmembrane domain of RAGE or a part thereof and a fragment of the RAGE ectodomain. In certain forms of the invention, the modulator comprises a transmembrane domain of RAGE or a part thereof and a fragment of the cytosolic tail of RAGE.

In certain forms of the invention, the modulator comprises a transmembrane domain of RAGE or part thereof and a fragment of the RAGE ectodomain and a fragment of the cytosolic tail of RAGE.

In certain forms of the invention, the modulators of RAGE ligand-independent activation of RAGE by certain activated co-located GPCRs contain a fragment of the ligand-binding ectodomain of human wild-type RAGE, which is not greater than 40, not greater than 20, not greater than 10 or not greater than 5 amino acids in length.

The inventors have further discovered that a peptide comprising residues 370-390 of the cytosolic tail of RAGE (see SEQ ID NO: 5) is an inhibitory peptide, inhibiting both RAGE ligand-independent and RAGE ligand-dependent activation of wild-type RAGE.

```
SEQ ID NO: 5:
[G370EERKAPENQEEEEERAELNQ390].
```

A solution NMR structure exists for $RAGE_{363-404}$ (Rai V et al., 2012) showing that the N-terminus (residues 363-376) of this peptide is ordered. A Rosetta-derived model exists for RAGE-362-404 (model4) which is consistent with the NMR structure (http://www.rcsb.org/pdb/explore/explore.do?structureId=2LMB, accessed 25 Aug. 2016)) and also suggests that the remainder of the peptide forms an alpha helix.

An initial model of $RAGE_{370-390}$ was constructed by truncating model4 (model4_370-390). Model4 is a theoretical model of the RAGE cytosolic tail, generated by inputting the sequence into the I-Tasser web server (http://zhanglab.ccmb.med.umich.edu/I-TASSER/). See also Yang et al (2015), Roy et al (2010) and Y Zhang (2008). All five models presented by the I-Tasser server predicted the region 370-390 to form a helix. The models and the NMR structure were aligned by the C-alpha carbons of the backbones of the peptide sequences. Model 4 was selected as the preferred model, as the predicted structure of the region corresponding to the Diaphanous 1 binding site in model4 was closest to the documented NMR structure for this region.

A 20 ns molecular dynamics simulation of model4 in water was run using GROMACS (Hess et al., 2008). The molecular dynamics simulation suggests that the alpha helix region of model4_370-390 is stable. Strong interactions are observed between a number of charged side chains, suggesting that these interactions stabilise the folded structure and that any conservation of these residues might result from their role in stabilising the peptide structure.

A Blast search was used to identify homologous sequences for $RAGE_{370-390}$. The sequences were aligned as follows:

```
CLUSTAL 2.0.10 multiple sequence alignment
model4_370-390.pdb            ----GEERKAPENQ--EEEEERAELNQ--- gi|505855911|ref|XP_004621364.  RRRRGEERKVPENQ--EEEEERAELKQSGE gi|836716008|ref|XP_012791097.  RRRRGEERKVPENQ--EEEEERAELKQSGE gi|830242517|ref|XP_012589882.  RRR-GEQRKAPENR--EEEEERAELNQSEE gi|830242520|ref|XP_012589883.  RRR-GEQRKAPENR--EEEEERAELNQSEE gi|830242532|ref|XP_012589884.  RRR-GEQRKAPENR--EEEEERAELNQSEE gi|859958468|ref|XP_012905636.  RPR-REERKAPENQ--EEEEERAELNQSEE gi|505855913|ref|XP_004621365.  RRRRGEERKVPENQ--EEEEERAELKQSGE gi|859958474|ref|XP_012905637.  RPR-REERKAPENQ--EEEEERAELNQSEE gi|674092933|ref|XP_008819684.  QHR-GEERKTPENQ--EDEEERAELNQSEE
```

```
gi|852803202|ref|XP_012890437.  QHR-GEERKAPENQ--EEEEERAELNQSEE
gi|586986169|ref|XP_006931651.  RRQ-GEERKAPENQEEEEEEREELNQSGE
gi|752437365|ref|XP_011235981.  RHR-REERKAPENQ--EEEEERAELNQSEE
gi|671038558|ref|XP_008710071.  RHR-REERKAPENQ--EEEEERAELNQSVE
gi|859958450|ref|XP_012905633.  RPR-REERKAPENQ--EEEEERAELNQSEE
gi|1040099494|gb|OBS60144.1|    QPR-GEERKTPENQ--EDEEERAELNQSED
gi|674092931|ref|XP_008819683.  QHR-GEERKTPENQ--EDEEERAELNQSEE
gi|641730582|ref|XP_008155542.  RHR-GEERKAPENQA-EEEEERAELNQSQE
gi|641730580|ref|XP_008155541.  RHR-GEERKAPENQA-EEEEERAELNQSQE
gi|946738855|ref|XP_014389946.  RRR-GEERKAPENQ--EEEEERAELHQSQE
gi|940771956|ref|XP_006104444.  RRR-GEERKAPENQ--EEEEERAELHQSQE
gi|355748446|gb|EHH52929.1|     RRQ-GEERKASENQ--EEEEERAELNQSEE
gi|355561569|gb|EHH18201.1|     RRQ-GEERKASENQ--EEEEERAELNQSEE
gi|544428837|ref|XP_005553456.  RRQ-GEERKASENQ--EEEEERAELNQSEE
gi|635095937|ref|XP_007971201.  RRQ-GEERKASENQ--EEEEERAELNQSEE
gi|402866556|ref|XP_003897445.  RRQ-REERKASENQ--EEEEERAELNQSEE
gi|795466133|ref|XP_011890032.  RRQ-GEERKASENQ--EEEEERAELNQSEE
gi|795466129|ref|XP_011890031.  RRQ-GEERKASENQ--EEEEERAELNQSEE
gi|795317622|ref|XP_011824818.  RRQ-GEERKASENQ--EEEEERAELNQSEE
gi|326693968|ref|NP_001192046.  RRQ-GEERKASENQ--EEEEERAELNQSEE
gi|724802002|ref|XP_010376439.  RRQ-GEERKAPENQ--EEEEERAELNQSEE
gi|724801999|ref|XP_010376432.  RRQ-GEERKAPENQ--EEEEERAELNQSEE
gi|795178216|ref|XP_011800170.  RRQ-GEERKAPENQ--EEEEERAELNQSEE
gi|312182478|gb|ADQ42279.1|     RRQ-GEERKASENQ--EEEEERAELNQSEE
gi|795178211|ref|XP_011800169.  RRQ-GEERKAPENQ--EEEEERAELNQSEE
gi|332800965|ref|NP_001193858.  QRR-GEERKAPENQ--EEEEERAELNQSEE
gi|10835203|ref|NP_001127.1|    QRR-GEERKAPENQ--EEEEERAELNQSEE
gi|332800967|ref|NP_001193861.  QRR-GEERKAPENQ--EEEEERAELNQSEE
gi|823672830|gb|AKI71626.1|     QRR-GEERKAPENQ--EEEEERAELNQSEE
gi|190846|gb|AAA03574.1|        QRR-GEERKAPENQ--EEEEERAELNQSEE
gi|194389738|dbj|BAG60385.1|    QRR-GEERKAPENQ--EEEEERAELNQSEE
gi|694915715|ref|XP_009449249.  QRQ-GEERKAPENQ--EEEEERAELNQSEE
gi|694915717|ref|XP_009449250.  QRQ-GEERKAPENQ--EEEEERAELNQSEE
gi|694915721|ref|XP_009449252.  QRQ-GEERKAPENQ--EEEEERAELNQSEE
gi|397519329|ref|XP_003829814.  QRQ-GEERKAPENQ--EEEEERAELNQSEE
gi|397519323|ref|XP_003829811.  QRQ-GEERKAPENQ--EEEEERAELNQSEE
gi|820970747|ref|XP_012358508.  RRQ-GEERKAPENQ--EEEEERAELNQSEE
gi|820970749|ref|XP_012358509.  RRQ-GEERKAPENQ--EEEEERAELNQSEE
gi|817330292|ref|XP_012292176.  RRR-GEERKAPENQ--EEEEEHAELNQSEE
gi|817330294|ref|XP_012292177.  RRR-GEERKAPENQ--EEEEEHAELNQSEE
gi|725608250|ref|XP_010330526.  RRR-GEERKAPENQ--EEEEEHAELNQSEE
```

-continued

```
gi|725608252|ref|XP_010330527.  RRR-GEERKAPENQ--EEEEEHAELNQSEE
gi|296197788|ref|XP_002746422.  RRRRGEERKAPENQ--EEEEEHAELNQSEE
gi|826320184|ref|XP_012509111.  RGQ-GEERKAPENQ--EEEEERAELNQSEE
gi|826320169|ref|XP_012509105.  RGQ-GEERKAPENQ--EEEEERAELNQSEE
gi|826320175|ref|XP_012509107.  RGQ-GEERKAPENQ--EEEEERAELNQSEE
gi|826320172|ref|XP_012509106.  RGQ-GEERKAPENQ--EEEEERAELNQSEE
gi|829933710|ref|XP_012596554.  RHQ-GEERKAPENQ--EEEEERAELNQSEE
gi|829933718|ref|XP_012596557.  RHQ-GEERKAPENQ--EEEEERAELNQSEE
gi|829933722|ref|XP_012596558.  RHQ-GEERKAPENQ--EEEEERAELNQSEE
gi|743731194|ref|XP_010959751.  QRR-GEERKAPENQ-EEEEEERAELNQQEE
gi|560905029|ref|XP_006178871.  QRR-GEERKAPENQ-EEEEEERAELNQQEE
gi|593759840|ref|XP_007118666.  QRR-GEERKAPENQ-EEEEEERTELNQPEE
gi|560986474|ref|XP_006215428.  QRR-GEERKAPENQ-EEEEEERAELNQQEE
gi|927155182|ref|XP_013833109.  QRR-GQERKAPENQ-EEDEEERAELNQPED
gi|147225137|emb|CAN13265.1|    QRR-GQERKAPENQ-EEDEEERAELNQPED
gi|178056480|ref|NP_001116690.  QRR-GQERKAPENQ-EEDEEERAELNQPED
gi|162138238|gb|ABX82823.1|     QRR-GQERKAPENQ-EEDEEERAELNQPED
gi|471418692|ref|XP_004390841.  KHR-GEERKAPENQ--EEEEEHAELNQSEE
gi|471418700|ref|XP_004390845.  KHR-GEERKAPENQ--EEEEEHAELNQSEE
gi|471418694|ref|XP_004390842.  KHR-GEERKAPENQ--EEEEEHAELNQSEE
gi|829933714|ref|XP_012596556.  RHQ-GEERKAPENQ--EEEEERAELNQSEE
gi|831224940|ref|XP_012660273.  QCQ-GEERKAPENQ--EEEEERTELNQSEE
gi|984103351|ref|XP_015342983.  RRQ-GEERKAPENQ--EEEEERAELNQSEE
gi|532108558|ref|XP_005339001.  RRQ-GEERKAPENQ--EEEEERAELNQSEE
gi|955504646|ref|XP_014638416.  QHR-REERKAPENQ--EEEEERAELNQSEE
gi|478500097|ref|XP_004424372.  QHR-REERKAPENQ--EEEEERAELNQSEE
gi|955504650|ref|XP_014638417.  QHR-REERKAPENQ--EEEEERAELNQSEE
gi|1048457071|ref|XP_017510394  QCR-GEERKAPENQ--EEEEERAELSQSEE
gi|589966171|ref|XP_006995615.  QPR-REERKAPENQ--EDEEERAELNQSED
gi|589966173|ref|XP_006995616.  QPR-REERKAPENQ--EDEEERAELNQSED
gi|532056239|ref|XP_005370828.  QPR--EERKAPENE--EDEEERAELNQSED
gi|532056241|ref|XP_005370829.  QPR--EERKAPENE--EDEEERAELNQSED
gi|532056245|ref|XP_005370831.  QPR--EERKAPENE--EDEEERAELNQSED
gi|641730578|ref|XP_008155540.  RHR-GEERKAPENQA-EEEEERAELNQSQE
```

This analysis identified a number of strongly conserved residues in RAGE$_{370-390}$ marked with as follows: * (asterisk) indicates positions which have a single, fully conserved residue. : (colon) indicates conservation between groups of strongly similar properties—scoring >0.5 in the Gonnet PAM 250 matrix. . (period) indicates conservation between groups of weakly similar properties—scoring=<0.5 in the Gonnet PAM 250 matrix:

```
         :  :  *  *  .  .  *  *  *  .  *  :  *  *  *  :  .  *  *  .  *
RAGE-    G  E  E  R  K  A  P  E  N  Q  E  E  E  E  E  R  A  E  L  N  Q
```

Highly conserved residues are likely to play a structural role. Residues underlined are located on one face of the helix and likely represent the binding pharmacophore.

Examination of the model4_RAGE$_{370-390}$ structure and the molecular dynamics simulation results shows that a number of salt bridges are present in the structure. The molecular dynamics simulations show that these interactions are important structural features. Structural function is a likely reason for the conserved nature of these amino acids.

A number of strongly conserved amino acids are not involved in salt-bridge formation. These are present on one face of the RAGE$_{370-390}$ helix and likely represent the binding interface. These are Glu380, Glu384, Glu387 and Leu388. Another highly conserved residue, Glu377 is also present on this face of the peptide and may also be involved in binding, in addition to forming an alpha-helix-stabilising salt bridge to Lys374.

As shown in FIG. 12D, replacement of the key hydrophobic residue L388 with alanine (e.g. L388A-RAGE$_{370-390}$) does not result in the loss of the inhibition achieved by RAGE$_{370-390}$ when acting on wild type RAGE. N-Truncation of RAGE eliminating both 380 and 384 (e.g. RAGE$_{385-390}$ and RAGE$_{385-404}$) results in the loss of the modulatory actions of these RAGE constructs. By contrast, N-truncation of RAGE eliminating both 374 & 377 does not result in a loss of function of RAGE peptides either as an inhibitor (RAGE$_{379-390}$) or as a functional substitute of wild type RAGE (e.g. RAGE$_{379-404}$), implying that these conserved residues (374 and 377) are not essential for modulatory activity, even though they may play a role stabilizing the alpha helical tertiary structure of the cytosolic tail of RAGE.

Consistent with the conserved nature of these four amino acids that represent the binding interface, the inventors have further discovered that a peptide comprising only residues 379-390 of the cytosolic tail of RAGE (i.e. RAGE$_{379-390}$) is an inhibitory peptide, inhibiting both ligand-independent and ligand-dependent activation of wild-type RAGE, and that RAGE$_{379-404}$ is able to be activated by certain co-located GPCRs in CHO cells.

In a preferred form of the invention, the modulator of RAGE ligand-independent activation of RAGE by a certain activated co-located GPCR, such as an angiotensin receptor, such as AT$_1$R, or a certain chemokine receptor, such as CCR2, is a peptide Q$_{379}$EEEEERAELNQ$_{390}$ as set forth in SEQ ID NO: 6, or a derivative thereof.

SEQ ID NO: 6:
[Q$_{379}$EEEEERAELNQ$_{390}$]

A pharmacophore for RAGE$_{379-390}$ peptide derived from the structure model4_RAGE$_{370-390}$ is represented below:

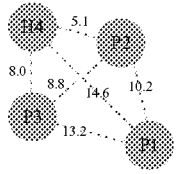

H4 is a hydrophobic residue, and P1-P3 are polar residues, and distances are shown in Angstroms. A matrix of distances between site points is as follows, where P represents a polar site point (hydrogen bonding or charged), and H represents a hydrophobic site point. Distances are in Angstroms. A tolerance should be applied to the position of each point.

| AA seq # | 380 (P1) | 384 (P2) | 387 (P3) | 388 (H4) |
|---|---|---|---|---|
| 380 | 0 | | | |
| 384 | 10.2 Å | 0 | | |
| 387 | 13.2 Å | 8.8 Å | 0 | |
| 388 | 14.6 Å | 5.1 Å | 8 Å | 0 |

The molecular dynamics simulations show that the interacting groups of RAGE$_{379-390}$ are mobile and a tolerance should be applied to the position of each group of up to ±10 Å provided the distances between the site points is positive in magnitude.

As would be understood by a person skilled in the art, additional, smaller pharmacophores can be generated by taking subsets of the above, and the present invention encompasses such pharmacophores, methods for using such to identify compounds, and compounds so identified.

In one form, the present invention further comprises a modulator of RAGE ligand-independent activation of RAGE by a certain activated co-located GPCR comprising two or more features selected from the group: a first charged or hydrogen bonding group (A), a second charged or hydrogen bonding group (B), a third charged or hydrogen bonding group (C), and a hydrophobic group (D) wherein the distances between the site points of the features are as follows, within a tolerance of up to ±10 Å, provided the distances between the site points is positive in magnitude:

| | A | B | C | D |
|---|---|---|---|---|
| A | | | | |
| B | 10.2 Å | | | |
| C | 13.2 Å | 8.8 Å | | |
| D | 14.6 Å | 5.1 Å | 8 Å | |

In a preferred form of the invention, the tolerance is up to ±5 Å, provided the distances between the site points is positive in magnitude. In a preferred form of the invention, the tolerance is up to ±2 Å, provided the distances between the site points is positive in magnitude. In a preferred form of the invention, the tolerance is up to ±1 Å, provided the distances between the site points is positive in magnitude.

In a preferred form of the invention, the modulator comprises three or more features selected from the above-specified group.

In a preferred form of the invention, the modulator comprises four features from the above-specified group.

In one form of the invention, there is provided a modulator characterised in that the modulator comprises at least two features chosen from one of the following combinations: AB, AC, AD, BC, BD, and CD.

In one form of the invention, there is provided a modulator, characterised in that the modulator comprises at least three features chosen from one of the following combinations: ABC, ABD, ACD, and BCD.

In one form of the invention, there is provided a modulator characterised in that the modulator comprises at least four features chosen from one of the following combinations: ABCD.

In one form of the invention, there is provided a modulator characterised in that the modulator comprises an additional charged or hydrogen bonding group (P1), consistent with the conserved stabilizing actions of E377 in RAGE$_{370-390}$, and therefore comprises two or more features selected from the group: a first charged or hydrogen bonding group (A), a second charged or hydrogen bonding group (B), a third charged or hydrogen bonding group (C), a fourth charged or hydrogen group (D), and a hydrophobic group (E) wherein the distances between the site points of the features are as follows, within a tolerance of ±10 Å:

| AA seq # | 377 (P1) A | 380 (P2) B | 384 (P3) C | 387 (P4) D | 388 (H5) E |
|---|---|---|---|---|---|
| A | | | | | |
| B | 7.4 Å | | | | |
| C | 13.9 Å | 10.2 Å | | | |
| D | 19.5 Å | 13.2 Å | 8.8 Å | | |
| E | 18.5 Å | 14.6 Å | 5.1 Å | 8 Å | |

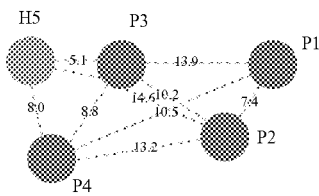

The modulator of RAGE ligand-independent activation of RAGE may be a peptide, or a non-peptidyl compound.

In one form of the invention, the hydrophobic group is an amino acid residue selected from the group: Ala, Val, Leu, Ile, Phe, Trp, Tyr.

In one form of the invention, the hydrophobic group is a chemical moiety selected from the group: $C_{1-8}$ alkyl, $C_{1-8}$ alkenyl, $C_{3-6}$ cycloalkyl, aryl, substituted aryl, alkyl aryl, heteroaryl, alkyl heteroaryl.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain.

"Lower alkyl" means a group having about 1 to about 6 carbon atoms in the chain which may be straight or branched. The alkyl group may be optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkenyl chain.

"Lower alkenyl" means about 2 to about 6 carbon atoms in the chain which may be straight or branched. Non-limiting examples of suitable alkenyl groups include ethenyl, propenyl, 2-butenyl and 3-methylbutenyl. The term "substituted alkenyl" means that the alkenyl group may be substituted by one or more substituents which may be the same or different, each substituent being independently selected from the group consisting of alkyl, aryl and cycloalkyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain.

"Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aliphatic" means and includes straight or branched chains of paraffinic, olefinic or acetylenic carbon atoms. The aliphatic group can be optionally substituted by one or more substituents which may be the same or different, each substituent being independently selected from the group consisting of H, halo, halogen, alkyl, aryl, cycloalkyl, cycloalkylamino, alkenyl, heterocyclic, alkynyl, cycloalkylaminocarbonyl, hydroxyl, thio, cyano, hydroxy, alkoxy, alkylthio, amino, —NH(alkyl), —NH(cycloalkyl), —N(alkyl)2) carboxyl, —C(O)O-alkyl, heteroaryl, aralkyl, alkylaryl, aralkenyl, heteroaralkyl, alkylheteroaryl, heteroaralkenyl, heteroalkyl, carbonyl, hydroxyalkyl, aryloxy, aralkoxy, acyl, aroyl, nitro, amino, amido, ester, carboxylic acid aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkenyl, heterocyclyl, heterocyclenyl, carbamate, urea, ketone, aldehyde, cyano, sulfonamide, sulfoxide, sulfone, sulfonyl urea, sulfonyl, hydrazide, hydroxamate, S(alkyl)Y1Y2N-alkyl-, Y1Y2N-alkyl-, Y1Y2NC(O)— and Y1Y2NSO$_2$—, wherein Y1 and Y2 can be the same or different and are independently selected from the group consisting of hydrogen, alkyl, aryl, and aralkyl.

"Heteroaliphatic" means an otherwise aliphatic group that contains at least one heteroatom (such as oxygen, nitrogen or sulfur). The term heteroaliphatic includes substituted heteroaliphatic.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroalkyl" means an alkyl as defined above, wherein one or more hydrogen atoms are substituted by a heteroatom selected from N, S, or O.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2, 4-thiadiazolyl, pyrazinyl, pyridazinyl, quinoxalinyl, phthalazinyl, oxindolyl, imidazo[1,2-a]pyridinyl, imidazo [2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. "Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y1Y2N-, Y1Y2N-alkyl-, Y1Y2NC(O)—, Y1Y2NSO$_2$— and —SO$_2$NY1Y2, wherein Y1 and Y2 can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, —C(CH$_3$)$_2$— and the like which form moieties such as, for example:

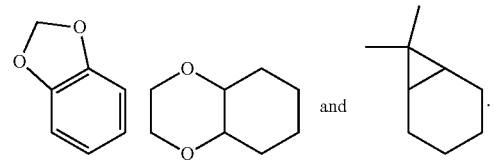

It should be noted that in hetero-atom containing ring systems of this invention, there are no hydroxyl groups on carbon atoms adjacent to a N, O or S1 as well as there are no N or S groups on carbon adjacent to another heteroatom. Thus, for example, in the ring:

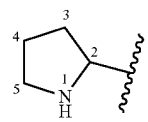

there is no —OH attached directly to carbons marked 2 and 5.

It should also be noted that tautomeric forms such as, for example, the moieties:

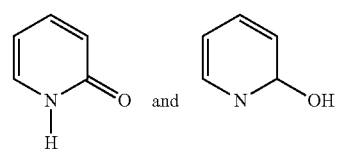 [SMILES: O=c1cccc[nH]1 ; OC1C=CC=CN1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, Greene et al (1991).

When any variable (e.g., aryl, heterocycle, R2) occurs more than one time in any constituent or in the present invention, its definition on each occurrence is independent of its definition at every other occurrence.

In one form of the invention, each of the charged or hydrogen bonding groups is an amino acid residue selected, independently, from the group: Asp, Glu.

In one form of the invention, each of the charged or hydrogen bonding groups is an amino acid residue having a carboxylic acid moiety.

In one form of the invention, each of the charged or hydrogen bonding groups is a chemical moiety selected, independently, from the group: carboxylic acid, Hydroxaymic acids, phosphonic and phosphinic acids, sulfonic and sulfinic acids, sulphonamides, acylsulfonamides and sulfonylureas, 2,2,2-Trifluoroethan-1-ol and Trifluoromethylketones, tetrazoles, 5-Oxo-1,2,4-oxadiazole and 5-Oxo-1,2,4-thiadiazoles, Thiazolidinedione, Oxazolidinedione, and Oxadiazolidine-diones, 3-Hydroxyisoxazole and 3-Hydroxyisothiazoles, substituted phenols, squaric acids, 3- and 4-Hydroxyquinolin-2-ones, Tetronic and Tetramic Acids, Cyclopentane-1,3-diones and other cyclic and acyclic structures, including boronic acids, mercaptoazoles, and sulfonimidamides (Ballatore et al., 2013).

In one form, the invention provides a method for identifying a modulator of RAGE ligand-independent activation of RAGE by a certain activated co-located GPCR, such as an angiotensin receptor, such as $AT_1R$, or a certain chemokine receptor, such as CCR2, said method comprising the steps of: (1) comparing the three dimensional structure of the compound with a pharmacophore comprising two or more features selected from the group: a first charged or hydrogen bonding group (A), a second charged or hydrogen bonding group (B), a third charged or hydrogen bonding group (C), and a hydrophobic group (D) wherein the distances in between the features are as follows, within a tolerance of ±10 Å:

|   | A | B | C | D |
|---|---|---|---|---|
| A |   |   |   |   |
| B | 10.2 Å |   |   |   |
| C | 13.2 Å | 8.8 Å |   |   |
| D | 14.6 Å | 5.1 Å | 8 Å |   | and (2) selecting a compound with hydrophobic and/or charged or hydrogen bonding chemical moieties so located.

The modulator of RAGE ligand-independent activation of RAGE identified by the abovementioned method comprising comparison to a pharmacophore may be a peptide, or a non-peptidyl compound.

In a preferred form of the invention, the tolerance is up to ±5 Å, provided the distances between the site points is positive in magnitude. In a preferred form of the invention, the tolerance is up to ±2 Å, provided the distances between the site points is positive in magnitude. In a preferred form of the invention, the tolerance is up to ±1 Å, provided the distances between the site points is positive in magnitude.

In a preferred form of the invention, the modulator comprises three or more features selected from the above-specified group.

In a preferred form of the invention, the modulator comprises four features from the above-specified group.

In one form of the invention, comparison of the three dimensional structure of the compound with the pharmacophore involves comparison of a minimum energy structure of the compound with the pharmacophore.

An efficient means to select a compound from a potentially large number of compounds involves comparing compounds against the pharmacophore of the invention using a computer program, for example Catalyst (MSI), to screen one or more computerised databases of three dimensional chemical structures of compounds.

In one form of the invention, the modulator of RAGE ligand-independent activation of RAGE by a certain activated co-located GPCR, such as an angiotensin receptor, such as $AT_1R$, or a certain chemokine receptor, such as CCR2, is a peptide that has an amino acid sequence as set forth in SEQ ID NO: 1, or an analogue, fragment or derivative thereof that contains at least residues 379-390.

In one form of the invention, the modulator of RAGE ligand-independent activation of RAGE by a certain activated co-located GPCR, such as an angiotensin receptor, such as $AT_1R$, or a certain chemokine receptor, such as CCR2, is a peptide of the formula SEQ ID NO: 1, or an analogue or derivative thereof.

In one form of the invention, the modulator of RAGE ligand-independent activation of RAGE by a certain activated co-located GPCR, such as an angiotensin receptor, such as $AT_1R$, or a certain chemokine receptor, such as CCR2, is a peptide of the formula SEQ ID NO: 2, or an analogue or derivative thereof.

In one form of the invention, the modulator of RAGE ligand-independent activation of RAGE by a certain activated co-located GPCR, such as an angiotensin receptor, such as $AT_1R$, or a certain chemokine receptor, such as CCR2, is a peptide of the formula SEQ ID NO: 5, or an analogue or derivative thereof.

In one form of the invention, the modulator of RAGE ligand-independent activation of RAGE by a certain activated co-located GPCR, such as an angiotensin receptor, such as $AT_1R$, or a certain chemokine receptor, such as CCR2, is a peptide of the formula SEQ ID NO: 6, or an analogue or derivative thereof.

In one form of the invention, the modulator of RAGE ligand-independent activation of RAGE by a certain activated co-located GPCR, such as an angiotensin receptor, such as $AT_1R$, or a certain chemokine receptor, such as CCR2, is a S391A-E392X-RAGE peptide as set forth in SEQ ID NO: 7, or an analogue or derivative thereof.

SEQ ID NO: 7:
[$L_{362}$WQRRQRRGEERKAPENQEEEERAELNQA$_{391}$]

In one form of the invention, the modulator of RAGE ligand-independent activation of RAGE by a certain activated co-located GPCR, such as an angiotensin receptor, such as $AT_1R$, or a certain chemokine receptor, such as CCR2, is a S391X-RAGE peptide as set forth in of SEQ ID NO: 8, or an analogue or derivative thereof.

SEQ ID NO: 8:
[$L_{362}$WQRRQRRGEERKAPENQEEEERAELNQ$_{390}$]

Preferred specific derivatives include $Q_{379}$EEEEERAELNR$_{390}$, as set forth in SEQ ID NO: 9, $Q_{379}$EEEEERAELNK$_{390}$ as set forth in SEQ ID NO: 10, $K_{379}$EEEEERAELNQ$_{390}$ as set forth in SEQ ID NO: 11, $K_{379}$EEEERAELNK$_{390}$ as set forth in SEQ ID NO: 12, and $K_{379}$EEEEERAELNR$_{390}$ as set forth in SEQ ID NO: 13 below.

SEQ ID NO: 9:
[$Q_{379}$EEEEERAELNR$_{390}$]

SEQ ID NO: 10:
[$Q_{379}$EEEEERAELNK$_{390}$]

SEQ ID NO: 11:
[$K_{379}$EEEEERAELNQ$_{390}$]

SEQ ID NO: 12:
[$K_{379}$EEEEERAELNK$_{390}$]

SEQ ID NO: 13:
[$K_{379}$EEEEERAELNR$_{390}$]

The term "derivative" as used herein in connection with modulators of the invention, such as SEQ ID NO: 1, 2, 5 to 13, refers to a modulator characterised in that its primary structure is taken from or owes its derivation to the C-terminal cytosolic tail of RAGE or fragment thereof, but which includes amino acid additions, substitutions, truncations, chemical and/or biochemical modifications (acetylation, carboxylation, phosphorylation, glycosylation, ubiquitination, side chain methylation), labelling with radionucleotides or halogens, unusual or artificial amino acids (such as D-amino acids, N-methylated amino acids, tetra-substitution, β-peptides, pyroglutamic acid; 2-Aminoadipic acid; 3-Aminoadipic acid; beta-Alanine; beta-Aminopropionic acid; 2-Aminobutyric acid; 4-Aminobutyric acid; Piperidinic acid; 6-Aminocaproic acid; 2-Aminoheptanoic acid; 2-Aminoisobutyric acid; 3-Aminoisobutyric acid; 2-Aminopimelic acid; 2,4-Diaminobutyric acid; Desmosine; 2,2"-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; Sarcosine; N-Methylisoleucine; N-Methylvaline; Norvaline; Norleucine; Ornithine; Statine), retroinverted sequences, cyclic peptides, peptoids, or linkage to a non-peptide drug, non-peptide label, non-peptide carrier, or non-peptide resin.

The inventors have further discovered that a peptide comprising residues 343-361 of wild-type RAGE (SEQ ID NO: 14) is an inhibitory peptide, that inhibits both RAGE ligand-independent and RAGE ligand-dependent activation of RAGE.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (e.g. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed. Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone sidechain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide. Sulphydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. In a preferred form of the invention, any modification of cysteine residues must not affect the ability of the peptide to form the necessary disulfide bonds. It is also possible to replace the sulphydryl groups of cysteine with selenium equivalents such that the peptide forms a di-selenium bond in place of one or more of the disulfide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate. Proline residues may be modified by, for example, hydroxylation in the 4-position.

A list of some amino acids having modified side chains and other unnatural amino acids is shown in the following table:

| Non-conventional amino acid | Code | Non-conventional amino acid | Code |
|---|---|---|---|
| L-α-aminobutyric acid | Abu | L-α-methylhistidine | Mhis |
| α-amino-α-methylbutyrate | Mgabu | L-α-methylisoleucine | Mile |
| aminocyclopropane-carboxylate | Cpro | L-α-methylleucine | Mleu |
| | | L-α-methylmethionine | Mmet |
| aminoisobutyric acid | Aib | L-α-methylnorvaline | Mnva |
| aminonorbornyl-carboxylate | Norb | L-α-methylphenylalanine | Mphe |
| | | L-α-methylserine | Mser |
| cyclohexylalanine | Chexa | L-α-methyltryptophan | Mtrp |
| cyclopentylalanine | Cpen | L-α-methylvaline | Mval |
| D-alanine | DAla | N-(N-(2,2-diphenylethyl) carbamylmethylglycine | Nnbhm |
| D-arginine | DArg | | |
| D-asparagine | DAsn | 1-carboxy-1-(2,2-diphenyl-ethylamino)cyclopropane | Nmbc |
| D-aspartic acid | DAsp | | |
| D-cysteine | DCys | L-N-methylalanine | Nmala |
| D-glutamine | DGln | L-N-methylarginine | Nmarg |
| D-glutamic acid | DGlu | L-N-methylaspartic acid | Nmasp |
| D-histidine | DHis | L-N-methylcysteine | Nmcys |
| D-isoleucine | DIle | L-N-methylglutamine | Nmgln |
| D-leucine | DLeu | L-N-methylglutamic acid | Nmglu |
| D-lysine | DLys | L-N-methylhistidine | Nmhis |
| D-methionine | DMet | L-N-methylisolleucine | Nmile |
| D-ornithine | DOrn | L-N-methylleucine | Nmleu |
| D-phenylalanine | DPhe | L-N-methyllysine | Nmlys |
| D-proline | DPro | L-N-methylmethionine | Nmmet |
| D-serine | DSer | L-N-methylnorleucine | Nmnle |
| D-threonine | DThr | L-N-methylnorvaline | Nmnva |
| D-tryptophan | DTrp | L-N-methylornithine | Nmorn |
| D-tyrosine | DTyr | L-N-methylphenylalanine | Nmphe |
| D-valine | DVal | L-N-methylproline | Nmpro |
| D-α-methylalanine | DMala | L-N-methylserine | Nmser |
| D-α-methylarginine | DMarg | L-N-methylthreonine | Nmthr |
| D-α-methylasparagine | DMasn | L-N-methyltryptophan | Nmtrp |
| D-α-methylaspartate | DMasp | L-N-methyltyrosine | Nmtyr |
| D-α-methylcysteine | DMcys | L-N-methylvaline | Nmval |
| D-α-methylglutamine | DMgln | L-N-methylethylglycine | Nmetg |
| D-α-methylhistidine | DMhis | L-N-methyl-t-butylglycine | Nmtbug |
| D-α-methylisoleucine | DMile | L-norleucine | Nle |
| D-α-methylleucine | DMleu | L-norvaline | Nva |
| D-α-methyllysine | DMlys | α-methyl-aminoisobutyrate | Maib |
| D-α-methylmethionine | DMmet | α-methyl-γ-aminobutyrate | Mgabu |
| D-α-methylornithine | DMorn | α-methylcyclohexylalanine | Mchexa |
| D-α-methylphenylalanine | DMphe | α-methylcyclopentylalanine | Mcpen |
| D-α-methylproline | DMpro | α-methyl-α-napthylalanine | Manap |
| D-α-methylserine | DMser | α-methylpenicillamine | Mpen |
| D-α-methylthreonine | DMthr | N-(4-aminobutyl)glycine | Nglu |
| D-α-methyltryptophan | DMtrp | N-(2-aminoethyl)glycine | Naeg |
| D-α-methyltyrosine | DMty | N-(3-aminopropyl)glycine | Norn |
| D-α-methylvaline | DMval | N-amino-α-methylbutyrate | Nmaabu |
| D-N-methylalanine | DNmala | α-napthylalanine | Anap |
| D-N-methylarginine | DNmarg | N-benzylglycine | Nphe |
| D-N-methylasparagine | DNmasn | N-(2-carbamylethyl)glycine | Ngln |
| D-N-methylaspartate | DNmasp | N-(carbamylmethyl)glycine | Nasn |
| D-N-methylcysteine | DNmcys | N-(2-carboxyethyl)glycine | Nglu |
| D-N-methylglutamine | DNmgln | N-(carboxymethyl)glycine | Nasp |
| γ-carboxyglutamate | Gla | N-cyclobutylglycine | Ncbut |
| 4-hydroxyproline | Hyp | N-cyclodecylglycine | Ncdec |
| 5-hydroxylysine | Hlys | N-cylcododecylglycine | Ncdod |
| 2-aminobenzoyl (anthraniloyl) | Abz | N-cyclooctylglycine | Ncoct |
| | | N-cyclopropylglycine | Ncpro |
| Cyclohexylalanine | Cha | N-cycloundecylglycine | Ncund |
| Phenylglycine | Phg | N-(2,2-diphenylethyl)glycine | Nbhm |
| 4-phenyl-phenylalanine | Bib | N-(3,3-diphenylpropyl)glycine | Nbhe |
| L-Citrulline | Cit | N-(hydroxyethyl)glycine | Nser |
| L-1,2,3,4-tetrahydroiso- | Tic | N-(imidazolylethyl)glycine | Nhis |

These types of modifications may be important to stabilise the peptide if administered to an individual or for use as a diagnostic reagent.

Conservative amino acid substitutions, as used herein, may include amino acid residues within a group which have sufficiently similar physicochemical properties, so that a substitution between members of the group will preserve the biological activity of the molecule (see for example Grantham, R., 1974). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Ile) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art. The isomer form should preferably be maintained, e.g. K is preferably substituted for R or H, while k is preferably substituted for r and h.

When considering replacement amino acids, preferred replacements of the present invention are those described as having a D of less than 100 in Grantham, R. (1974), the contents of which are incorporated by reference. Most preferred replacements are those described as having a D of less than 50.

Peptide modulators of the present invention include retro inverso isomers of, or modified or substituted variants of, SEQ ID NO: 1, 2, 5, 6, 7, 8, 9, 10, 11, 12 or 13, or peptides formed by additions or deletions (Li et al., 2010).

Methods for Treating, Preventing or Managing RAGE-Related Disorders

In another related aspect, the present invention provides methods for treating, preventing or managing a RAGE-related disorder in a patient in need of such treatment, the method comprising administration of an effective amount of a modulator of RAGE ligand-independent activation of RAGE by a certain activated co-located GPCR of the invention.

In another aspect, the present invention comprises use of a modulator of RAGE ligand-independent activation of RAGE by a certain activated co-located GPCR for the manufacture of a medicament for treating, preventing or managing a RAGE-related disorder in a patient in need of such treatment.

In another aspect, the present invention comprises use of a modulator of RAGE ligand-independent activation of RAGE by a certain activated co-located GPCR for treating, preventing or managing a RAGE-related disorder in a patient in need of such treatment.

In a preferred form of the invention, the certain co-located GPCR is an angiotensin receptor. In a preferred form of the invention, the certain co-located GPCR is $AT_1R$.

In a preferred form of the invention, the certain co-located GPCR is a certain chemokine receptor. In a preferred form of the invention, the certain co-located GPCR is CCR2.

Furthermore, the present invention provides methods for treating, preventing or managing a RAGE-related disorder in a patient in need of such treatment, the method comprising administration of an effective amount of a combination of a modulator of RAGE ligand-independent activation of RAGE by a certain activated co-located GPCR of the invention with a modulator of the certain co-located GPCR and/or a modulator of the certain co-located GPCR signalling pathway.

In a preferred form of the invention, the certain co-located GPCR is an angiotensin receptor. In a preferred form of the invention, the certain co-located GPCR is $AT_1R$.

In a preferred form of the invention, the certain co-located GPCR is a certain chemokine receptor. In a preferred form of the invention, the certain co-located GPCR is CCR2.

The method may comprise administration of an effective amount of a combination of a modulator of RAGE ligand-independent activation of RAGE by activated certain co-located GPCR of the invention with a modulator of the certain co-located GPCR and/or a modulator of the certain co-located GPCR signalling pathway, wherein the modulator of the certain co-located GPCR and/or the modulator of the certain co-located GPCR signalling pathway is administered at a lower dose than normally administered for the treatment of a disorder related to the certain co-located GPCR.

The method may comprise administration of an effective amount of a combination of a modulator of RAGE ligand-independent activation of RAGE by activated certain co-located GPCR of the invention with a modulator of the certain co-located GPCR and/or a modulator of the certain co-located GPCR signalling pathway, wherein the modulator of the certain co-located GPCR and/or the modulator of the certain co-located GPCR signalling pathway is administered at a lower dose than normally administered for the treatment of a disorder related to RAGE.

In a particularly preferred form of the invention, the method comprises administration of an effective amount of a combination of a modulator of RAGE ligand-independent activation of RAGE by activated angiotensin receptor of the invention with a modulator of $AT_1R$ and/or a modulator of an $AT_1R$ signalling pathway, wherein the modulator of the $AT_1R$ and/or the modulator of an $AT_1R$ signalling pathway is administered at a lower dose than normally administered for the treatment of an $AT_1R$-related disorder.

In another particularly preferred form of the invention, the method comprises administration of an effective amount of a combination of a modulator of RAGE ligand-independent activation of RAGE by activated certain chemokine receptor of the invention with a modulator of CCR2 and/or a modulator of a CCR2 signalling pathway, wherein the modulator of the CCR2 and/or the modulator of a CCR2 signalling pathway is administered at a lower dose than normally administered for the treatment of a CCR2-related disorder.

Furthermore, the present invention provides methods for treating, preventing or managing a RAGE-related disorder in a patient in need of such treatment, the method comprising administration of an effective amount of a combination of a modulator of RAGE ligand-independent activation of RAGE by activated certain co-located GPCR of the invention with a modulator of RAGE ligand-dependent activation of RAGE and/or a modulator of constitutively-active RAGE and/or a modulator of a RAGE signalling pathway.

In a particularly preferred form of the invention, the method comprises administration of an effective amount of a combination of a modulator of RAGE ligand-independent activation of RAGE by activated certain co-located GPCR of the invention with a modulator of RAGE ligand-dependent activation of RAGE and/or a modulator of constitutively-active RAGE and/or a modulator of a RAGE signalling pathway, wherein the modulator of RAGE ligand-dependent activation of RAGE and/or a modulator of constitutively-active RAGE and/or the modulator of a RAGE signalling pathway is administered at a lower dose than normally administered for the treatment of a RAGE-related disorder.

Furthermore, the present invention provides methods for treating, preventing or managing a RAGE-related disorder in a patient in need of such treatment, the method comprising administration of an effective amount of a combination of a modulator of RAGE ligand-independent activation of RAGE by activated certain co-located GPCR of the invention with a modulator of the certain co-located GPCR and/or a modulator of the certain co-located GPCR signalling pathway.

For example, the present invention provides methods for treating, preventing or managing a RAGE-related disorder in a patient in need of such treatment, the method comprising administration of an effective amount of a combination of a modulator of RAGE ligand-independent activation of RAGE by activated angiotensin receptor of the invention with a modulator of RAGE ligand-dependent activation of RAGE and/or a modulator of constitutively-active RAGE and/or a modulator of a RAGE signalling pathway, and a modulator of $AT_1R$ and/or a modulator of an $AT_1R$ signalling pathway.

For example, the present invention provides methods for treating, preventing or managing a RAGE-related disorder in a patient in need of such treatment, the method comprising administration of an effective amount of a combination of a modulator of RAGE ligand-independent activation of RAGE by activated certain chemokine receptor of the invention with a modulator of RAGE ligand-dependent activation of RAGE and/or a modulator of constitutively-active RAGE and/or a modulator of a RAGE signalling pathway, and a modulator of CCR2 and/or a modulator of a CCR2 signalling pathway.

In a particularly preferred form of the invention, the method comprises administration of an effective amount of a combination of a modulator of RAGE ligand-independent activation of RAGE by activated certain co-located GPCR of the invention with a modulator of the certain co-located GPCR and/or a modulator of a signalling pathway of the certain co-located GPCR and a modulator of RAGE ligand-dependent activation of RAGE and/or a modulator of constitutively-active RAGE and/or a modulator of a RAGE signalling pathway, wherein the modulator of RAGE ligand-dependent activation of RAGE and/or a modulator of constitutively-active RAGE and/or the modulator of a RAGE signalling pathway is administered at a lower dose than normally administered for the treatment of a RAGE-related disorder, and/or the modulator of the certain co-located GPCR and/or the modulator of a signalling pathway of the certain co-located GPCR is administered at a lower dose than normally administered for the treatment of a disorder related to the GPCR.

In a particularly preferred form of the invention, the method comprises administration of an effective amount of a combination of a modulator of RAGE ligand-independent activation of RAGE by activated angiotensin receptor of the invention with a modulator of $AT_1R$ and/or a modulator of an $AT_1R$ signalling pathway and a modulator of RAGE ligand-dependent activation of RAGE and/or a modulator of constitutively-active RAGE and/or a modulator of a RAGE signalling pathway, wherein the modulator of RAGE ligand-dependent activation of RAGE and/or a modulator of constitutively-active RAGE and/or the modulator of a RAGE signalling pathway is administered at a lower dose than normally administered for the treatment of a RAGE-related disorder, and/or the modulator of $AT_1R$ and/or the modulator of an $AT_1R$ signalling pathway is administered at a lower dose than normally administered for the treatment of an $AT_1R$-related disorder.

In a particularly preferred form of the invention, the method comprises administration of an effective amount of a combination of a modulator of RAGE ligand-independent activation of RAGE by activated certain chemokine receptor of the invention with a modulator of CCR2 and/or a modulator of a CCR2 signalling pathway and a modulator of RAGE ligand-dependent activation of RAGE and/or a modulator of constitutively-active RAGE and/or a modulator of a RAGE signalling pathway, wherein the modulator of RAGE ligand-dependent activation of RAGE and/or a modulator of constitutively-active RAGE and/or the modulator of a RAGE signalling pathway is administered at a lower dose than normally administered for the treatment of a RAGE-related disorder, and/or the modulator of CCR2 and/or the modulator of a CCR2 signalling pathway is administered at a lower dose than normally administered for the treatment of a CCR2-related disorder.

A RAGE-related disorder is defined as a disorder that is dependent upon the expression of RAGE. It does not exclude disorders related to the certain co-located GPCR, such as $AT_1R$-related disorders or CCR2-related disorders, that are also dependent upon the expression of RAGE. Indeed a disorder can be both RAGE-related and related to the certain co-located GPCR, including $AT_1R$-related or CCR2-related.

A disorder related to the certain co-located GPCR is defined as a disorder that is dependent upon the expression of the certain co-located GPCR. It does not exclude RAGE-related disorders that are also dependent upon the expression of the certain co-located GPCR. Indeed a disorder can be both RAGE-related and related to the certain co-located GPCR, including $AT_1R$-related or CCR2-related.

In one form of the invention, a RAGE-related disorder is a disorder selected from the group: cardiovascular disorders; digestive disorders; cancers; neurological disorders, respiratory disorders, connective tissue disorders, kidney disorders, genital disorders, skin disorders, eye disorders and endocrine disorders.

In one form of the invention, the RAGE-related disorder is a cardiovascular disorder selected from the group: atherosclerosis, ischaemic heart disease, myocarditis, endocarditis, cardiomyopathy, acute rheumatic fever, chronic rhematic heart disease, cerebrovascular disease/stroke, heart failure, vascular calcification, peripheral vascular disease, and lymphangitis.

In one form of the invention, the RAGE-related disorder is a digestive system disorder selected from the group: periodontitis, oesophagitis, gastritis, gastro-duodenal ulceration, Crohn disease, ulcerative colitis, ischaemic colitis, enteritis and enterocolitis, peritonitis, alcoholic liver disease, hepatitis, toxic liver disease, biliary cirrhosis, hepatic fibrosis/cirrhosis, non-alcoholic fatty liver disease/non-alcoholic steatohepatitis (NAFLD/NASH), liver trauma and recovery from liver injury, trauma or surgery.

In one form of the invention, the RAGE-related disorder is a cancer selected from the group: malignant neoplasms of lip, oral cavity and pharynx, malignant neoplasms of digestive organs, malignant neoplasms of respiratory and intrathoracic organs, malignant neoplasms of bone and articular cartilage, melanoma and other malignant neoplasms of skin, malignant neoplasms of mesothelial and soft tissue, malignant neoplasm of breast, malignant neoplasms of female genital organs, malignant neoplasms of male genital organs, malignant neoplasms of urinary tract, malignant neoplasms of eye, brain and other parts of central nervous system, malignant neoplasms of thyroid and other endocrine glands, malignant neoplasms of lymphoid, haematopoietic and related tissue, malignant neoplasms of ill-defined, secondary and/or unspecified sites.

In one form of the invention, the RAGE-related disorder is a neurological disorder and is selected from the group: inflammatory diseases of the central nervous system, systemic atrophies primarily affecting the central nervous system, extrapyramidal and movement disorders, Parkinson's disease, demyelinating diseases of the central nervous system, Alzheimer's disease, circumscribed brain atrophy, Lewy body disease, epilepsy, migraine, neuropathic pain, diabetic neuropathy, polyneuropathies, glioma development and progression, spinal cord trauma, and ischaemic brain injury/stroke, brain trauma and recovery from brain injury, trauma or surgery.

In one form of the invention, the RAGE-related disorder is a mental disorder and is selected from the group: dementia, Alzheimer's disease, vascular dementia, addiction, schizophrenia, major affective disorder, depression, mania, bipolar disorder, and anxiety disorder.

In one form of the invention, the RAGE-related disorder is a respiratory (pulmonary) disorder and is selected from the group: Acute upper respiratory infections, rhinitis, nasopharyngitis, sinusitis, laryngitis, influenza and pneumonia, acute bronchitis, acute bronchiolitis, asthma, chronic obstructive pulmonary disease (COPD), bronchiectasis, emphysema, chronic lung diseases due to external agents, Acute Respiratory Distress Syndrome (ARDS), pulmonary eosinophilia, and pleuritic, lung trauma and recovery from lung injury, trauma or surgery.

In one form of the invention, the RAGE-related disorder is a connective tissue disorder and is selected from the group: osteoarthritis, infectious arthritis, rheumatoid arthritis, psoriatic and enteropathic arthropathies, juvenile arthritis, gout and other crystal arthropathies, diabetic arthropathy, polyarteritis nodosa, Churg-Strauss, mucocutaneous lymph node syndrome [Kawasaki], hypersensitivity angiitis, Goodpasture syndrome, thrombotic microangiopathy, Wegener granulomatosis, Aortic arch syndrome [Takayasu], giant cell arteritis, polymyalgia rheumatica, microscopic polyangiitis, hypocomplementaemic vasculitis, systemic lupus erythematosus, dermatopolymyositis, polymyositis, systemic sclerosis, CR(E)ST syndrome, Sicca syndrome [Sjögren], mixed connective tissue disease, Behçet disease, traumatic muscle damage, sprain, strain, and fracture.

In one form of the invention, the RAGE-related disorder is a kidney disorder and is selected from the group: glomerulonephritis, nephritis, diabetic kidney disease, interstitial nephritis, obstructive and reflux nephropathy, acute renal failure, and chronic kidney disease.

In one form of the invention, the RAGE-related disorder is a genital disorder and is selected from the group: prostatitis, prostatic hypertrophy, prostatic dysplasia, salpingitis, oophoritis, pelvic inflammatory disease (PID), polycystic ovarian syndrome, cervicitis, cervical dysplasia, vaginitis, vulvitis.

In one form of the invention, the RAGE-related disorder is a skin disorder selected from the group: dermatitis, eczema, pemphigus/pemphygoid, psoriasis, *Pityriasis rosea*, lichen planus, urticarial, erythrema multiforme, erythema nordosum, sunburn, keratosis, photoageing skin ulceration, superficial skin injury, and open wound.

In one form of the invention, the RAGE-related disorder is an eye disorder selected from the group: keratitis, conjunctivitis, retinitis, glaucoma, scleritis, episcleritis, chorioretinal inflammation, diabetic retinopathy, macular oedema, retinopathy of prematurity, and optic neuritis, eye trauma and recovery from eye injury, trauma or surgery.

In one form of the invention, the RAGE-related disorder is an endocrine disorder selected from the group: diabetes mellitus, insulin resistance, impaired glucose tolerance and thyroiditis.

In one form of the invention, the inhibitor that inhibits $AT_1R$ or inhibits an $AT_1R$ signalling pathway is selected from the group: Eprosartan (market name Teveten®, Abbott Laboratories USA), Losartan (market name Cozaar®, Merck & Co), Valsartan (market name Diovan®, Novartis), Telmisartan (market name Micardis®, Boehringer Ingelheim), Irbesartan (market name Avapro®, SanofiAventis), Olmesartan (market name Benicar®, Daiichi Sankyo Inc), Azilsartan (market name Edarbi, Takeda), Candesartan (market name Atacand®, AstraZeneca), ZD-7115, Saralasin ((Sar1-Ala8)AngII), Sarthran ((Sar1-Thr8)AngII) and DuP753. This list also includes pro-drugs of these inhibitors, including Candesartan (Candesartan cilexetil), Azilsartan (Azilsartan medoxomil) and Olmesartan (Olmesartan medoxomil), that may be the form in which they are administered, as well as active metabolites (such as EXP-3174, the active metabolite of Losartan). Note a partial agonist can act to inhibit endogenous Ang II as a partial agonist does not result in maximal efficacy even though it exhibits agonism, and so therapeutically may act as an inhibitor.

In one form of the invention, the inhibitor that inhibits the certain chemokine receptor or inhibits the certain chemokine signalling pathway is selected from the group: Propagermanium (also known as 3-[(2-Carboxyethyl-oxogermyl)oxy-oxogermyl]propanoic acid, proxigermanium, Ge-132, bis (2-carboxyethylgermanium) sesquioxide (CEGS), 2-carboxyethylgermasesquioxane, SK-818, organic germanium, germanium sesquioxide, 3,3'-(1,3-dioxo-1,3-digermanoxanediyl) bispropionic acid, 3-oxygermylpropionic acid polymer, poly-trans-(2-carboxyethyl) germasesquioxane, proxigermanium, repagermanium and Serocion; CCR2), BMS CCR2 22 (CCR2), resveratrol (CCR2), RS504393 (CCR2), RS102895 (CCR2), MLN-1202 (Millennium Pharmaceuticals; CCR2), INCB8696 (Incyte Pharmaceuticals; CCR2), MK-0812 (Merck; CCR2), CCX140 (ChemoCentryx; CCR2), PF-4136309 (Pfizer; CCR2), BMS-741672 (Bristol-Myers Squibb; CCR2); Repertaxin (CXCR2), TAK-779 (CCR5), TAK-220 (CCR5), TAK-652 (CCR5), AK692 (CCR5), CMPD167 (CCR5), BX-471 (CCR1), AMD3100 (CXCR4), AMD11070 (CXCR4), FC131 (CXCR4), MLN3897 (CCR1), CP-481715 (CCR1), GW-873140 (CCR5), SB 225002 (CXCR2) and SB 265610 (CXCR2).

In one form of the invention, the inhibitor that inhibits CCR2 or inhibits a CCR2 signalling pathway is selected from the group: Propagermanium (also known as 3-[(2-Carboxyethyl-oxogermyl)oxy-oxogermyl]propanoic acid, proxigermanium, Ge-132, bis (2-carboxyethylgermanium) sesquioxide (CEGS), 2-carboxyethylgermasesquioxane, SK-818, organic germanium, germanium sesquioxide, 3,3'-(1,3-dioxo-1,3-digermanoxanediyl) bispropionic acid, 3-oxygermylpropionic acid polymer, poly-trans-(2-carboxyethyl) germasesquioxane, proxigermanium, repagermanium and Serocion), BMS CCR2 22 (CCR2), resveratrol (CCR2), RS504393, RS102895, MLN-1202 (Millennium Pharmaceuticals), INCB8696 (Incyte Pharmaceuticals), MK-0812 (Merck), CCX140 (ChemoCentryx), PF-4136309 (Pfizer), BMS-741672 (Bristol-Myers Squibb).

In one form of the invention, the inhibitor of RAGE ligand-dependent activation of RAGE and/or an inhibitor of constitutively-active RAGE and/or the inhibitor of a RAGE signalling pathway is selected from the group: Azeliragon (TTP488/PF-04494700) (an oral, small-molecule inhibitor of RAGE-ligand interactions targeting the V-domain); TTP4000 (a soluble fusion protein inhibitor of RAGE, using the ligand-binding ectodomains of RAGE linked to a human Ig Fc domain as described in U.S. Pat. No. 7,981,423); antibodies that bind specifically to RAGE and RAGE-binding fragments thereof as described in WO2007109747; FPS-ZM127 (a tertiary amide that blocks Aβ/RAGE interaction with high affinity); peptides that antagonise RAGE ligand-induced signalling as described in US 20100249038; lysophosphatidic acid (LPA) antagonists as described in WO2012109569; 2-aminopyrimidines as described in Han et al (2012); pyrazole-5-carboxamides as described in Han et al (2014); 4,6-bisphenyl-2-(3-alkoxyanilino)pyrimidine as described in Han et al (2015); small molecule inhibitors of Ligand-Stimulated RAGE-DIAPH1 Signal Transduction as described in Manigrasso et al (2016); polypeptides consisting essentially of all or a portion of the cytosolic tail of RAGE, or consisting essentially of a portion of Diaphanous-1 that binds to the cytosolic tail of RAGE as described in US20090220484.

In specific embodiments, the modulator is administered to the subject on the basis that it is identified as a modulator of RAGE ligand-independent activation of RAGE by activated certain co-located GPCR, such as angiotensin receptor, such as $AT_1R$, or a certain chemokine receptor, such as CCR2, using the screening methods or methods for identifying modulators broadly described herein.

An $AT_1R$-related disorder is defined as a disorder that is dependent upon the expression of $AT_1R$. It does not exclude RAGE-related disorders that are also dependent upon expression of $AT_1R$. Indeed a disorder can be both RAGE-related and $AT_1R$-related.

A certain chemokine receptor-related disorder is defined as a disorder that is dependent upon the expression of a certain chemokine receptor. It does not exclude RAGE-related disorders that are also dependent upon expression of a certain chemokine receptor. Indeed a disorder can be both RAGE-related and certain chemokine receptor-related.

A CCR2-related disorder is defined as a disorder that is dependent upon the expression of CCR2. It does not exclude RAGE-related disorders that are also dependent upon the expression of CCR2. Indeed a disorder can be both RAGE-related and CCR2-related.

The following doses are "normally" administered for the combination agents.

| RAS inhibitors | Dosing |
| --- | --- |
| Candesartan (market name Atacand ®) | Hypertension: Oral: Initial: 16 mg once daily. Range: 4 to 32 mg once daily. Dosage must be individualized. It can be administered once or twice daily with total daily doses ranging from 8-32 mg. Congestive Heart Failure: Oral: Initial: 4 mg once daily. Double the dose at 2-week intervals, as tolerated; target dose: 32 mg. |
| Eprosartan (market name Teveten ®) | Hypertension: Oral: Usual initial dose is 600 mg once daily. Dosage must be individualized. Can administer once or twice daily with total daily doses of 400 to 800 mg. Limited clinical experience with doses greater than 800 mg. |
| Irbesartan (market name Avapro ®) | Hypertension: Oral: 150 mg once daily. Patients may be titrated to 300 mg once daily. Note: Starting dose in volume-depleted patients should be 75 mg. |
| Losartan (market name Cozaar ®), | Usual starting dose: 50 mg once daily; can be administered once or twice daily with total daily doses ranging from 25-100 mg |
| Olmesartan (market name Benicar ®) | Hypertension: Oral: Initial: Usual starting dose is 20 mg once daily. If initial response is inadequate, may be increased to 40 mg once daily after 2 weeks. Consider lower starting dose in patients with possible volume deficits. |
| Telmisartan (market name Micardis ®) | Hypertension: Oral: Initial: 40 mg once daily. Usual maintenance dose range: 20 to 80 mg per day. Patients with volume depletion should be initiated on the lower dosage with close supervision. |
| Valsartan (market name Diovan ®) | Hypertension: Initial: 80 mg or 160 mg once daily (in patients who are not volume depleted). Dose may be increased to achieve desired effect. Maximum recommended dose: 320 mg per day. Congestive Heart Failure: Initial: 40 mg twice daily. Titrate dose to 80 to 160 mg twice daily, as tolerated. Maximum daily dose: 320 mg. |
| Azilsartan (market name Edarbi ®) | The recommended dose in adults is 80 mg taken once daily. Consider a starting dose of 40 mg for patients who are treated with high doses of diuretics. |

Methods of Screening Candidate Agents

In one form, the present invention comprises methods of screening candidate agents for their ability to modulate RAGE activity where such RAGE activity is induced by an active co-located GPCR, the method comprising the steps of: contacting a RAGE polypeptide with a GPCR polypeptide in the presence of a candidate agent where the GPCR polypeptide is constitutively active and/or is activated by addition of an agonist, partial agonist or allosteric modulator of that GPCR; and detecting whether the candidate agent is a modulator of RAGE ligand-independent activation of RAGE by activated co-located GPCR by detecting an effect indicative of modulation of RAGE activation by the presence of the candidate agent and/or by detecting RAGE-dependent signalling that is modulated by the presence of the candidate agent.

In one form, the present invention comprises methods of screening candidate agents for their ability to modulate (i.e. activate, inhibit or allosterically modulate), RAGE ligand-independent activation of RAGE by, activated certain co-located GPCR, such as angiotensin receptor, such as $AT_1R$, or certain chemokine receptor, such as CCR2 (also known as RAGE ligand-independent transactivation of RAGE). These methods generally comprise, consist or consist essentially of:

a. contacting a RAGE polypeptide with a GPCR polypeptide in the presence of a candidate agent where the GPCR polypeptide is constitutively active and/or is activated by addition of an agonist, partial agonist or allosteric modulator of that GPCR; and b. detecting whether the candidate agent is a modulator of RAGE ligand-independent activation of RAGE by activated co-located GPCR by detecting an effect indicative of modulation of RAGE activation by the presence of the candidate agent and/or by detecting RAGE-dependent signalling that is modulated by the presence of the candidate agent.

In some embodiments, the screening methods further comprise detecting whether the candidate agent is a modulator (such as activator, inhibitor or allosteric modulator) of the certain co-located GPCR, such as angiotensin receptor, such as an $AT_1R$ or certain chemokine receptor, such as CCR2, or a signalling pathway of the certain co-located GPCR, such as an angiotensin receptor signalling pathway, such as an $AT_1R$ signalling pathway or such as a certain chemokine receptor signalling pathway, such as a CCR2 signalling pathway, in the presence or absence of RAGE. In some embodiments, the candidate agent that results in greater modulation of the signal when the RAGE polypeptide is present compared to when it is absent is selective for modulating RAGE-ligand independent activation of RAGE by activated co-located GPCR over RAGE-independent signalling resulting from activation of the co-located GPCR.

In one form, the invention comprises peptides identified as modulators by said methods. In one form, the invention comprises compounds identified as modulators by said methods.

In some embodiments, the screening methods further comprise detecting whether the candidate agent is a modulator (such as activator, inhibitor, allosteric modulator or functional substitute) of RAGE or a RAGE signalling pathway in the presence or absence of the certain co-located GPCR, such as an angiotensin receptor, such as $AT_1R$ or such as a certain chemokine receptor, such as CCR2. In some embodiments, the candidate agent that results in greater modulation of the RAGE-dependent signal when the GPCR polypeptide is present compared to when it is absent is selective for modulating RAGE-ligand independent activation of RAGE by activated co-located GPCR.

In some embodiments, the screening methods further comprise detecting whether the candidate agent is a modulator (such as activator, inhibitor, allosteric modulator or functional substitute) of a RAGE polypeptide or a RAGE signalling pathway as well as the certain co-located GPCR, such as angiotensin receptor, such as an $AT_1R$ or certain chemokine receptor, such as CCR2, or a signalling pathway of the certain co-located GPCR, such as an angiotensin receptor signalling pathway, such as an $AT_1R$ signalling pathway or such as a certain chemokine receptor signalling pathway, such as a CCR2 signalling pathway.

In some embodiments, the screening method further comprises the step of using an inhibitor of RAGE ligand binding to the RAGE ectodomain that as such inhibits activation of RAGE in a RAGE ligand-dependent manner.

In some embodiments, the screening method further comprises use of a RAGE polypeptide that is mutated and/or truncated such that it is not able to bind RAGE ligands to its ectodomain and as such is not able to be activated in a RAGE ligand-dependent manner.

In some embodiments, binding of RAGE ligands to the ectodomain of RAGE is impaired by exposing the cell to a modulator that modulates the binding of RAGE ligands to RAGE.

In some embodiments the use of a RAGE polypeptide that is mutated and/or truncated such that it is not able to bind RAGE ligands and as such is not able to be activated in a RAGE ligand-dependent manner occurs before, after or in parallel with a screen involving a RAGE polypeptide that is able to bind RAGE ligands.

Suitably, a candidate agent or a derivative of a candidate agent, which modulates RAGE ligand-independent activation of RAGE by activated certain co-located GPCR, such as angiotensin receptor, such as $AT_1R$, or certain chemokine receptor, such as CCR2, and that suitably modulates a certain co-located GPCR, such as angiotensin receptor, such as $AT_1R$, or certain chemokine receptor, such as CCR2 and/or a signalling pathway of the certain co-located GPCR, such as an angiotensin receptor signalling pathway, such as an $AT_1R$ signalling pathway or such as a certain chemokine receptor signalling pathway, such as a CCR2 signalling pathway and/or that inhibits RAGE ligand-dependent activation of RAGE and/or inhibits constitutively-active RAGE and/or a RAGE signalling pathway, is particularly useful for treating, preventing or managing a RAGE-related disorder.

In certain embodiments of the screening method of the invention wherein if the candidate agent modulates the RAGE-dependent signal detected when a RAGE polypeptide is contacted with a GPCR polypeptide, the method further comprises determining whether, and/or the extent to which the candidate agent modulates the RAGE-dependent signal in the absence of the GPCR polypeptide such that the candidate agent that results in greater modulation of the RAGE-dependent signal when the GPCR polypeptide is present is selective for modulating RAGE-ligand independent activation of RAGE by activated co-located GPCR.

In certain embodiments of the screening method of the invention wherein if the candidate agent modulates the signal detected when a RAGE polypeptide is contacted with a GPCR polypeptide, the method further comprises determining whether, and/or the extent to which the signal is generated in the absence of the RAGE polypeptide and if the signal is generated in the absence of the RAGE polypeptide, determining whether, and/or the extent to which the candidate agent modulates the signal in the absence of the RAGE polypeptide such that the candidate agent that results in greater modulation of the signal when the RAGE polypeptide is present is selective for modulating RAGE-ligand independent activation of RAGE by activated co-located GPCR over RAGE-independent signalling resulting from activation of the co-located GPCR.

In certain embodiments, the screening method assesses proximity of the RAGE polypeptide to the certain co-located GPCR, such as angiotensin receptor, such as $AT_1R$, or certain chemokine receptor, such as CCR2 using a proximity screening assay. In illustrative examples of this type, the RAGE polypeptide is coupled (e.g., conjugated or otherwise linked) to a first reporter component and the certain co-located GPCR, such as angiotensin receptor, such as $AT_1R$, or certain chemokine receptor, such as CCR2 is coupled (e.g., conjugated or otherwise linked) to a second reporter component. Proximity of the first and second reporter components generates a signal capable of detection by the detector. The first and second reporter components constitute a complementary pair, in the sense that the first reporter component may be interchanged with the second reporter component without appreciably affecting the functioning of the invention. The first and second reporter components can be the same or different.

In one embodiment, the proximity screening assay is that described in patent WO2008055313 (Dimerix Bioscience Pty Ltd; also U.S. Pat. Nos. 8,283,127, 8,568,997, EP2080012, CA2669088, CN101657715), also known as Receptor Heteromer Investigation Technology or Receptor-HIT (Jaeger et al., 2014). With this method, RAGE is coupled to a first reporter component, the certain co-located GPCR, such as angiotensin receptor, such as $AT_1R$, or certain chemokine receptor, such as CCR2, is unlabeled with respect to the proximity screening assay, and a GPCR-interacting group is linked to the complementary second reporter component, whose interaction with the complex is modulated upon binding a ligand selective for the unlabeled GPCR or the heteromer complex specifically. Preferred examples of GPCR-interacting groups are arrestins, G proteins and ligands. Alternatively, the certain co-located GPCR, such as angiotensin receptor, such as $AT_1R$, or certain chemokine receptor, such as CCR2, is coupled to a first reporter component, RAGE is unlabeled with respect to the proximity screening assay, and a RAGE-interacting group is linked to the complementary second reporter component, whose interaction with the complex is modulated upon binding a ligand selective for the unlabeled RAGE or the heteromer complex specifically. Preferred examples of RAGE-interacting groups are proteins interacting with the cytosolic tail of RAGE, such as IQGAP-1, Diaphanous 1, Dock7, MyD88, TIRAP, IRAK4, ERK1/2, and PKCζ (Jules et al., 2013; Ramasamy et al., 2016).

Reporter components can include enzymes, luminescent or bioluminescent molecules, fluorescent molecules, and transcription factors or other molecules coupled to RAGE, the certain co-located GPCR or the interacting group by linkers incorporating enzyme cleavage sites. In short any known molecule, organic or inorganic, proteinaceous or non-proteinaceous or complexes thereof, capable of emitting a detectable signal as a result of their spatial proximity.

Preferably, signal generated by the proximity of the first and second reporter components in the presence of the reporter component initiator is selected from the group consisting of: luminescence, fluorescence and colorimetric change.

In some embodiments, the luminescence is produced by a bioluminescent protein selected from the group consisting of luciferase, galactosidase, lactamase, peroxidase, or any protein capable of luminescence in the presence of a suitable substrate.

Preferable combinations of first and second reporter components include those detailed in U.S. Pat. No. 8,283,127, however, useful combinations of first and second reporter components are by no means limited to such.

In some embodiments, the screening methods further comprise detecting proximity of the first and second reporter components to one another to thereby determine whether the candidate agent modulates the interaction between the RAGE polypeptide and the certain co-located GPCR, such as angiotensin receptor, such as $AT_1R$, or certain chemokine receptor, such as CCR2. Generally, this is achieved when proximity of the first and second reporter components generates a proximity signal that is altered by the modulation by the candidate agent of the proximity between the RAGE polypeptide and the certain co-located GPCR, such as angiotensin receptor, such as $AT_1R$, or certain chemokine receptor, such as CCR2.

One or both of the RAGE and certain co-located GPCR, such as angiotensin receptor, such as $AT_1R$, or certain chemokine receptor, such as CCR2 may be in soluble form or expressed on the cell surface.

In some embodiments, the RAGE and certain co-located GPCR, such as angiotensin receptor, such as $AT_1R$, or certain chemokine receptor, such as CCR2 are located in, partially in, or on a single membrane; for example, both are expressed at the surface of a host cell.

In another embodiment of the invention, the certain co-located GPCR, such as an angiotensin receptor, such as $AT_1R$, or certain chemokine receptor, such as CCR2 is pre-assembled with RAGE in a pre-formed complex at the cell membrane.

In another embodiment of the invention, following activation of the certain co-located GPCR, such as angiotensin receptor, such as $AT_1R$, or certain chemokine receptor, such as CCR2 by engagement of cognate ligand, such as Ang II for $AT_1R$ or MCP-1 for CCR2, signalling is triggered that involves the cytosolic tail of RAGE.

In one embodiment of the invention, activation of the cytosolic tail of RAGE is associated with changes in its structural conformation and/or affinity for binding partners.

In one embodiment of the invention, monitoring of the structural conformation of RAGE and/or affinity for binding partners occurs when the cytosolic tail of RAGE has been mutated and/or truncated such that it can no longer be activated by RAGE ligands or by RAGE ligand-independent activation of RAGE by certain activated co-located GPCRs.

In one embodiment of the invention, monitoring structural conformation and/or affinity for binding partners occurs in the presence of agents that inhibit binding and/or activation of RAGE by RAGE ligands or RAGE ligand-independent activation of RAGE by certain activated co-located GPCRs.

In one embodiment of the invention, monitoring recruitment of binding partners occurs prior to activation of RAGE by RAGE ligands or RAGE ligand-independent activation of RAGE by certain activated co-located GPCRs.

In one embodiment of the invention, monitoring recruitment and activation of signalling mediators and/or binding partners to the RAGE cytosolic tail occurs subsequent to activation of RAGE by RAGE ligands or RAGE ligand-independent activation of RAGE by certain activated co-located GPCRs.

In one embodiment of the invention, monitoring recruitment of binding partners following activation of RAGE by RAGE ligands or RAGE ligand-independent activation of RAGE by certain activated co-located GPCRs occurs in the presence of agents that inhibit binding and/or activation of RAGE by RAGE ligands.

Further embodiments of the invention comprise methods of screening candidate agents for their ability to modulate (such as activate, inhibit or otherwise modulate) RAGE ligand-independent activation of RAGE by a certain co-located GPCR, such as angiotensin receptor, such as $AT_1R$, or certain chemokine receptor, such as CCR2, by detecting modulation of the RAGE-mediated signalling. Such methods may include the step of measuring canonical activation of NFκB, by measuring one or more of the following:

Activity of IkB kinase (IKK) by monitoring in vitro phosphorylation of a substrate, such as GST-IκBα;

Detection of IkB Degradation Dynamics including phosphorylation/ubiquitination and/or degradation of IκB and/or IκB-α;

Detection of p65(Rel-A) phosphorylation/ubiquitination, such as by using antibodies, gel-shift, EMSA, or mass spectroscopy;

Detection of cytoplasmatic to nuclear shuttling/translocation of NFκB components/subunits, such as p65/phospho-p65;

Detection of NFκB subunit dimerization/complexation;

Detection of active NFκB components/subunits by binding to immobilized DNA sequence/oligonucleotide containing the NFκB response element/consensus NFκB binding, such as by using Electrophoretic mobility shift assay or gel shift assay, SELEX, protein-binding microarray, or sequencing-based approaches;

Chromatin-immunoprecipitation (ChIP) assays to detect NFκB in situ binding to DNA to the promoters and enhancers of specific genes;

In vitro kinase assay for NFκB kinase activity;

Measurement of NFκB transcriptional activity using NFκB reporter assays via transgene expression of reporter constructs, such as LacZ Fluc, eGFP SEAP, NF-gluc, using approaches such as plasmid transfection, reporter cell lines, mini-circles, retrovirus, or lentivirus;

Measuring changes in expression of downstream targets of NFκB (such as cytokines, growth factors, adhesion molecules and mitochondrial anti-apoptotic genes by real-time PCR, protein, or functional assays) (Note the pleiotropic nature of NFκB is reflected in its transcriptional targets that presently number over 500 (see http://www.bu.edu/nf-kb/gene-resources/target-genes/ accessed 2 Aug. 2017) and;

Measuring changes in function or structure induced by NFκB-dependent signalling, such as POLKADOTS in T-cells, adhesion in endothelial cells, activation in leucocytes, or oncogencity.

Additionally or alternately, such methods may include measuring signals arising from the non-canonical actions of NF-κB, by measuring one or more of the following:

Detection of NIK (NFκB-Inducing Kinase);
Detecting IKKα Activation/phosphorylation;
Detection of NIK kinase activity by ability to autophosphorylate or to phosphorylate a substrate by performing a kinase assay;
Generation of p52-containing NFκB dimers, such as p52/RelB;
Detection of Phospho-NFκB2 p100(Ser866/870);
Detection of partial degradation (called processing) of the precursor p100 into p52;
Detecting p52/RelB translocation into the nucleus;
Detecting p52/RelB binding to κB sites;
Measurement of NFκB transcriptional activity using NFκB reporter assays via transgene expression of reporter constructs, such as LacZ Fluc, eGFP SEAP, NF-gluc, using approaches such as plasmid transfection, reporter cell lines, mini-circles, retrovirus, or lentivirus;
Measuring changes in expression of downstream targets of non-canonical signalling of NFκB (such as CXCL12) by real-time PCR, protein expression or by functional assays.

In another aspect, the present invention provides methods of identifying a modulator (such as activator, inhibitor, allosteric modulator or functional substitute) that modulates (i.e., activates, inhibits or otherwise modulates) RAGE ligand-independent activation of RAGE following activation of a certain co-located GPCR by a cognate ligand, such as $AT_1R$ by AngII, or CCR2 by MCP-1, or if the certain co-located GPCR is constitutively active, and that suitably modulates a certain co-located GPCR, such as an angiotensin receptor, such as $AT_1R$, or certain chemokine receptor, such as CCR2 and/or that modulates a RAGE polypeptide or a RAGE signalling pathway. In a preferred form of the invention, such a modulator is an inhibitor of one or both of the RAGE or certain co-located GPCR, such as an angiotensin receptor, such as $AT_1R$, or certain chemokine receptor, such as CCR2 or of the RAGE signalling pathway. In a particularly preferred form of the invention, the modulation of the RAGE signalling pathway is distinct from and/or occurs to a significantly different extent to the modulation of classical certain co-located GPCR signalling pathways, such as $AT_1R$ signalling pathways, such as the Gq signalling pathway, or CCR2 signalling pathways, such as the Gi signalling pathway. In a particularly preferred form of the invention, the inhibition of the RAGE signalling pathway is distinct from and/or greater than the inhibition of classical certain co-located GPCR signalling pathways, such as $AT_1R$ signalling pathways, such as the Gq signalling pathway, or CCR2 signalling pathways, such as the Gi signalling pathway.

Constructs

In a related aspect, the present invention provides construct systems for identifying modulators of proximity between RAGE and certain co-located GPCR, such as angiotensin receptor, such as $AT_1R$, or certain chemokine receptor, such as CCR2.

In some embodiments, these construct systems comprise a first construct that comprises a regulatory sequence that is operably connected to a first coding sequence, wherein the first coding sequence comprises a nucleic acid sequence that encodes a polypeptide corresponding to a RAGE polypeptide and a nucleic acid sequence that encodes a proximity signal or energy donor molecule; and a second construct that comprises a regulatory sequence that is operably connected to a second coding sequence, wherein the second coding sequence comprises a nucleic acid sequence that encodes a polypeptide corresponding to a certain co-located GPCR, such as angiotensin receptor, such as $AT_1R$, or certain chemokine receptor, such as CCR2, and a nucleic acid sequence that encodes a proximity signal or energy acceptor molecule. In specific embodiments, the energy donor molecule is a bioluminescent or fluorescent molecule and the energy acceptor molecule is a fluorescent acceptor molecule.

In other embodiments, the construct systems of the present invention comprise a first construct that comprises a regulatory sequence that is operably connected to a first coding sequence, wherein the first coding sequence comprises a nucleic acid sequence that encodes polypeptide corresponding to a certain co-located GPCR, such as angiotensin receptor, such as $AT_1R$, or certain chemokine receptor, such as CCR2, and a nucleic acid sequence that encodes a proximity signal or energy donor molecule; and a second construct that comprises a regulatory sequence that is operably connected to a second coding sequence, wherein the second coding sequence comprises a nucleic acid sequence that encodes a polypeptide corresponding to a RAGE polypeptide and a nucleic acid sequence that encodes a proximity signal or energy acceptor molecule. In specific embodiments, the energy donor molecule is a bioluminescent or fluorescent molecule and the energy acceptor molecule is a fluorescent acceptor molecule.

In other embodiments, the construct systems of the present invention comprise a first construct that comprises a regulatory sequence that is operably connected to a first coding sequence, wherein the first coding sequence comprises a nucleic acid sequence that encodes polypeptide corresponding to a certain co-located GPCR, such as angiotensin receptor, such as $AT_1R$, or certain chemokine receptor, such as CCR2; and a second construct that comprises a regulatory sequence that is operably connected to a second coding sequence, wherein the second coding sequence comprises a nucleic acid sequence that encodes a polypeptide corresponding to a RAGE polypeptide whereby the RAGE polypeptide has deleted one or more of the ectodomains of the native sequence.

Methods for Modulating RAGE Ligand-Independent Activation of RAGE

In a related aspect, the present invention provides methods for modulating RAGE ligand-independent activation of RAGE by an activated certain co-located GPCR, such as angiotensin receptor, such as $AT_1R$, or certain chemokine receptor, such as CCR2, in a cell or tissue of an animal or of animal origin (which may or may not be of a human or of human origin).

Methods for Specifically Modulating RAGE Ligand-Independent Activation of RAGE

In another related aspect, the present invention provides methods for specifically modulating RAGE ligand-independent activation of RAGE by activated certain co-located GPCR, such as angiotensin receptor, such as $AT_1R$, or certain chemokine receptor, such as CCR2, and subsequent downstream signalling pathways in a cell. These methods comprise truncating or mutating RAGE such that it is unable to bind RAGE ligands to its ectodomain, or that binding RAGE ligands to its ectodomain is impaired by exposing the cell to a modulator that modulates the binding of RAGE ligands to RAGE.

In a preferred form of the invention, the modulation of the RAGE ligand-independent signalling pathway, is distinct from and/or significantly more than the modulation of the RAGE ligand-dependent signalling pathway.

In a particularly preferred form of the invention, the inhibition of the RAGE ligand-independent signalling pathway, is distinct from and/or significantly more than the inhibition of the RAGE ligand-dependent signalling pathway.

Methods for Modulating Both RAGE Ligand-Dependent and RAGE Ligand-Independent Activation of RAGE In another related aspect, the present invention provides methods for inhibiting RAGE ligand-dependent activation of RAGE by RAGE ligands, (including AGE-modified proteins, lipids or DNA, members of the S100 calgranulin family of proteins, HMGB1, amyloid and Mac-1) and subsequent downstream signalling pathways in a cell, tissue or animal in addition to modulating RAGE ligand-independent activation of RAGE by certain activated co-located GPCRs.

In one aspect of the invention, these methods comprise using a modulator as described herein, including fragments, analogues or derivatives of the cytosolic tail of RAGE, to take the place of the cytosolic tail of RAGE in binding interactions and therein prevent activation of both RAGE-ligand dependent activation of RAGE and RAGE ligand-independent activation of RAGE by certain activated co-located GPCRs. In one aspect of the invention, RAGE-dependent signalling is impaired by exposing the cell to an inhibitor that inhibits the binding of signalling elements to the cytosolic tail of RAGE resulting in inhibition of both RAGE ligand-mediated activation of RAGE and RAGE ligand-independent activation of RAGE by certain activated co-located GPCRs.

In one aspect of the invention, these methods comprise using a modulator as described herein, including fragments, analogues or derivatives of the transmembrane domain of RAGE, to take the place of the transmembrane domain of RAGE and therein prevent activation of both RAGE-ligand dependent activation of RAGE and RAGE ligand-independent activation of RAGE by certain activated co-located GPCRs. In one aspect of the invention, the modulator comprises a transmembrane domain of RAGE or a part thereof and a fragment of the RAGE ectodomain. In one aspect of the invention, the modulator comprises a transmembrane domain of RAGE or a part thereof and a fragment of the cytosolic tail of RAGE. In one aspect of the invention, the modulator comprises a transmembrane domain of RAGE or part thereof and a fragment of the RAGE ectodomain and a fragment of the cytosolic tail of RAGE.

In one aspect of the invention, the modulators of RAGE ligand-independent activation of RAGE by certain activated co-located GPCRs contain a fragment of the ligand-binding ectodomain of RAGE, which is not greater than 40, not greater than 20, not greater than 10 or not greater than 5 amino acids in length.

In one aspect, inhibition of the RAGE ligand-dependent activation of RAGE occurs at the same time as inhibition of the RAGE ligand-independent activation of RAGE by certain activated co-located GPCR.

In one aspect, these methods comprise silencing, truncating, modifying or mutating RAGE such that RAGE, or analogues, fragments or derivatives thereof, are a non-functional substitute for the cytosolic tail of wild type RAGE or a part thereof, which are unable to be activated by either RAGE ligand-dependent or RAGE ligand-independent pathways (such as S391A-RAGE mutation) or facilitate downstream RAGE-dependent signalling and so inhibit signalling that occurs through the cytosolic tail of RAGE and RAGE-dependent signalling.

In one aspect, these methods comprise silencing, truncating, modifying or mutating RAGE such that RAGE, or analogues, fragments or derivatives thereof, are a non-functional substitute for the transmembrane domain of wild type RAGE or a part thereof, which are unable to be activated by either RAGE ligand-dependent or RAGE ligand-independent pathways or facilitate downstream RAGE-dependent signalling and so inhibit signalling that occurs through the cytosolic tail of RAGE and RAGE-dependent signalling. In one aspect of the invention, the modulator comprises a transmembrane domain of RAGE or a part thereof and a fragment of the RAGE ectodomain. In one aspect of the invention, the modulator comprises a transmembrane domain of RAGE or a part thereof and a fragment of the cytosolic tail of RAGE. In one aspect of the invention, the modulator comprises a transmembrane domain of RAGE or part thereof and a fragment of the RAGE ectodomain and a fragment of the cytosolic tail of RAGE.

In one aspect, the modulators of RAGE ligand-independent activation of RAGE by certain activated co-located GPCRs contain a fragment of the ligand-binding ectodomain of RAGE, which is not greater than 40, not greater than 20, not greater than 10 or not greater than 5 amino acids in length.

In one aspect, these methods comprise silencing, truncating, modifying or mutating RAGE such that RAGE, or analogues, fragments or derivatives thereof, modulate common elements involved in signalling mediated by the cytosolic tail of RAGE (such as PKCζ, Diaph1, MyD88, TIRAP, NFκB). Association with activation of RAGE by either RAGE ligand-dependent or RAGE ligand-independent activation pathways.

In one aspect, these methods comprise the use of a modulator that modulates RAGE ligand-independent activation of RAGE by activated certain co-located GPCR, such as angiotensin receptor, such as $AT_1R$, or certain chemokine receptor, such as CCR2, in addition to a modulator that modulates RAGE ligand-dependent activation of RAGE (such as by a modulator that modulates the binding of RAGE ligands to the RAGE ectodomain).

Methods for Modulating RAGE Ligand-Independent Activation of RAGE by Certain Activated Co-Located GPCRs while Also Modulating RAGE-Independent Signalling Via Certain Co-Located GPCRs.

In one aspect, the invention provides a method for modulating a RAGE-independent, certain co-located GPCR signalling pathway induced following activation by a cognate ligand as well as modulating RAGE ligand-independent activation of RAGE by a certain activated co-located GPCR.

In one form, the invention provides a method for modulating a RAGE-independent, certain co-located GPCR signalling pathway induced following activation by a cognate ligand at the same time as modulating RAGE ligand-independent activation of RAGE by a certain activated co-located GPCR.

In one form, the RAGE-independent, certain co-located GPCR signalling pathway induced following activation by a cognate ligand is the Gq signalling pathway, such as for $AT_1R$ activated by Ang II. In another form, the RAGE-independent, certain co-located GPCR signalling pathway is the Gi signalling pathway, such as for CCR2 activated by MCP-1. In another form, the RAGE-independent, certain co-located GPCR signalling pathway is beta-arrestin-mediated extracellular regulated kinase (ERK) signalling. In another form, the RAGE-independent, certain co-located GPCR signalling pathway is changes in intracellular signalling intermediates (such as inositol phosphate or calcium).

BRIEF DESCRIPTION OF THE DRAWINGS

Example 1

Data are mean±SEM; n=8 per group, *vs control apoE KO mice, # vs apoE KO +Ang II, $p<0.05$.

Example 2

Figure 2A:
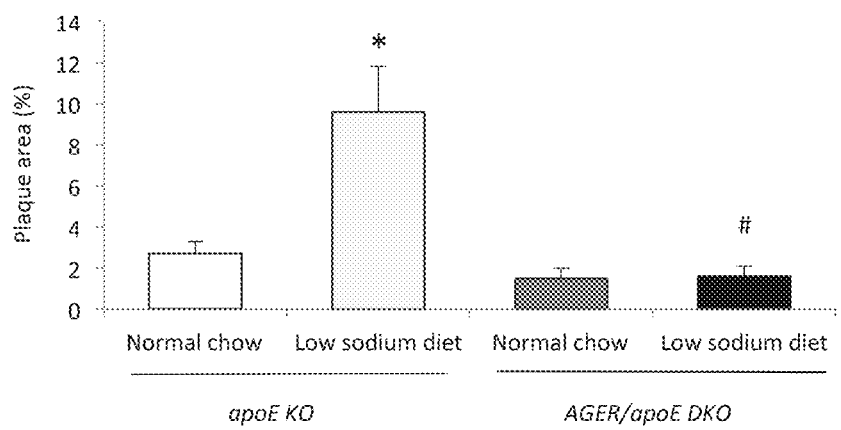

FIG. 2A. Quantitated plaque area expressed as the percentage of the aortic arch surface area staining positive to Sudan IV in apoE KO mice and AGER/apoE DKO mice following six-weeks of a 0.05% (low) sodium diet or normal chow.

Figure 2B:
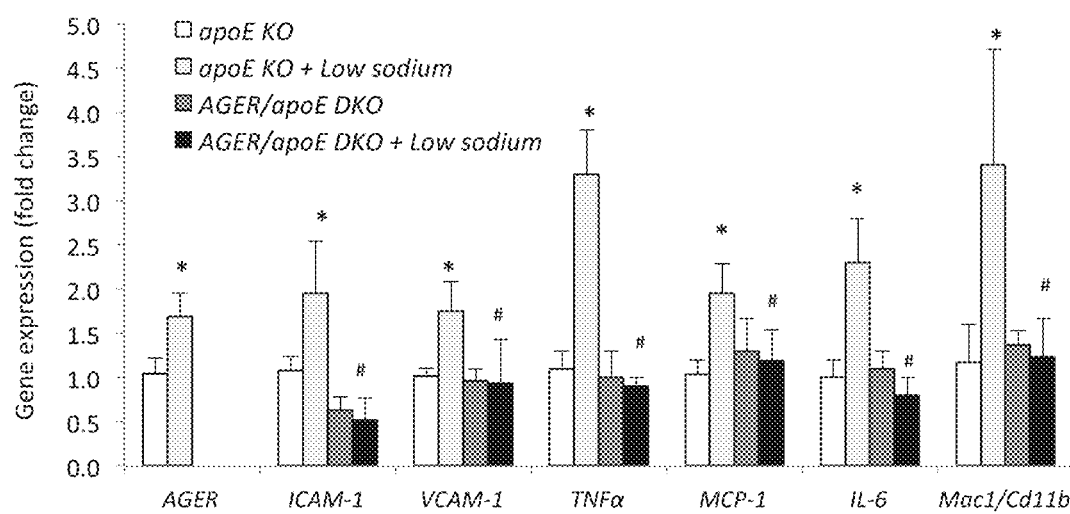

FIG. 2B. The expression of pro-atherosclerotic mediators including AGER itself, adhesion molecules (ICAM-1, VCAM-1), inflammatory cytokines and chemokines (TNFα, MCP-1 and IL-6) and the macrophage marker (Mac-1/Cd11b), as measured by real time RT-PCR in aortic homogenates of apoE KO mice and AGER/apoE DKO mice following six-weeks of a 0.05% (low) sodium diet or normal chow.

Figure 2C:
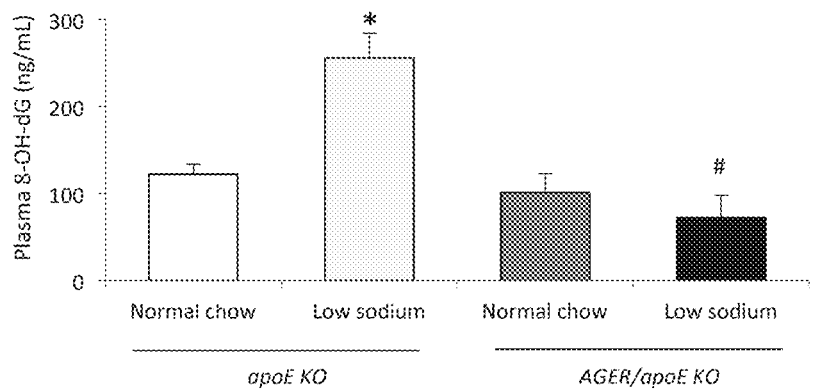

FIG. 2C. Markers of oxidative stress in apoE KO mice and AGER/apoE DKO mice following six-weeks of a 0.05% (low) sodium diet or normal chow, as estimated by (i) plasma 8-hydroxydeoxyguanosine (8-OH-dG), a marker of oxidative DNA damage and (ii) induction of the gene expression of the NADPH oxidase subunits, NOX-1 and NOX-4 in the aortae of apoE KO mice and AGER/apoE DKO mice, as estimated by real time RT-PCR in aortic homogenates.

Figure 2D:
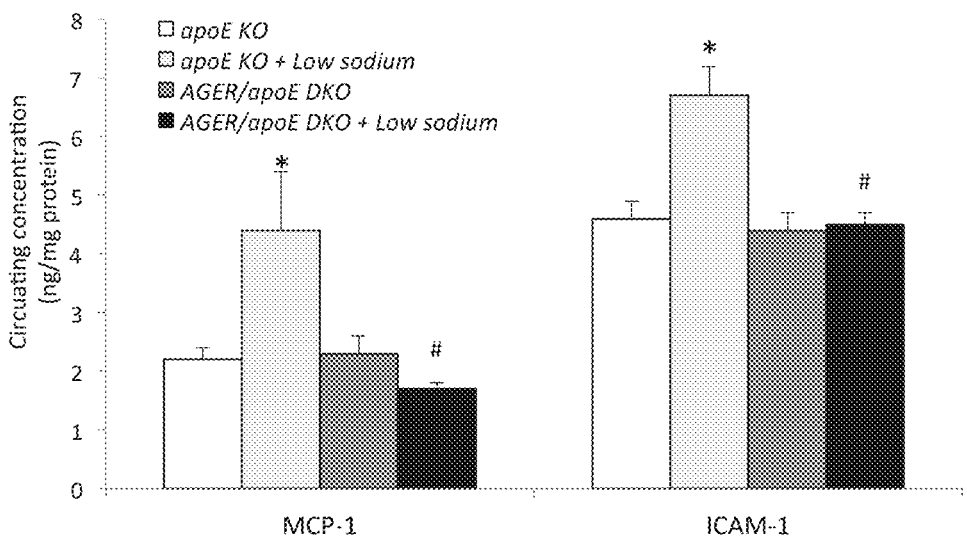

FIG. 2D. Circulating levels of soluble MCP-1 and ICAM-1, as measured by ELISA in apoE KO mice and AGER/apoE DKO mice exposed to a 0.05% (low) sodium diet or normal chow for six weeks.

Figure 2E:
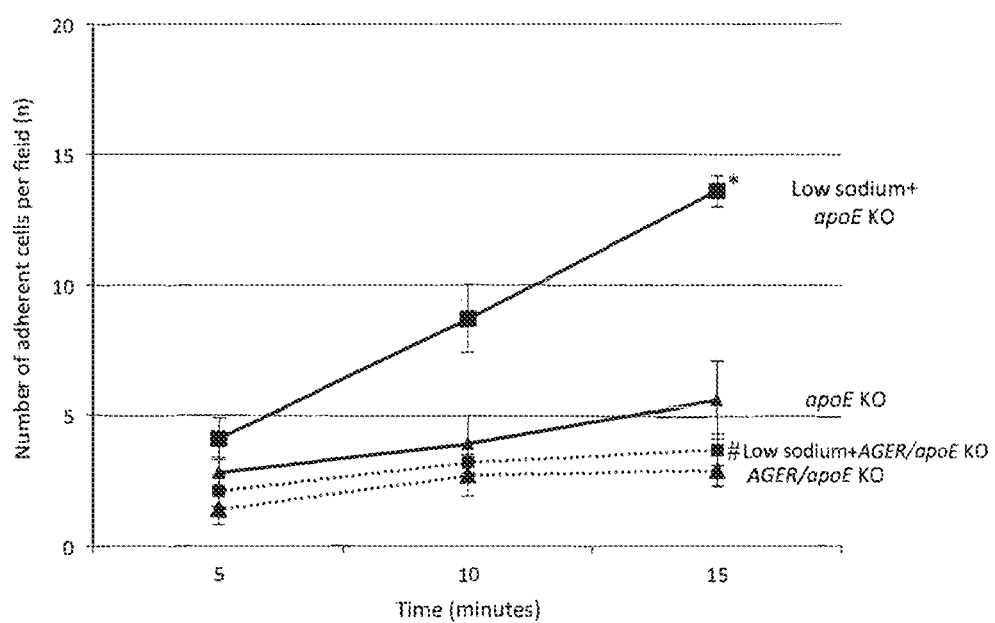

FIG. 2E. The number of labelled-leucocytes adhering ex vivo to the aortic surface of apoE KO mice and AGER/apoE DKO mice subsequent to 1-week prior exposure to a low sodium diet or normal chow, as measured by dynamic flow assay.

Figure 2F:
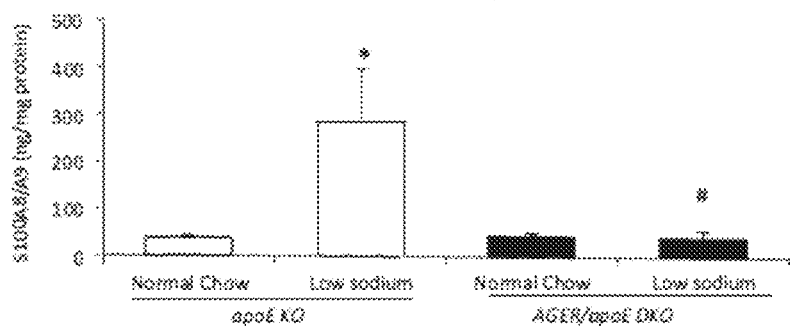
Figure 2F:
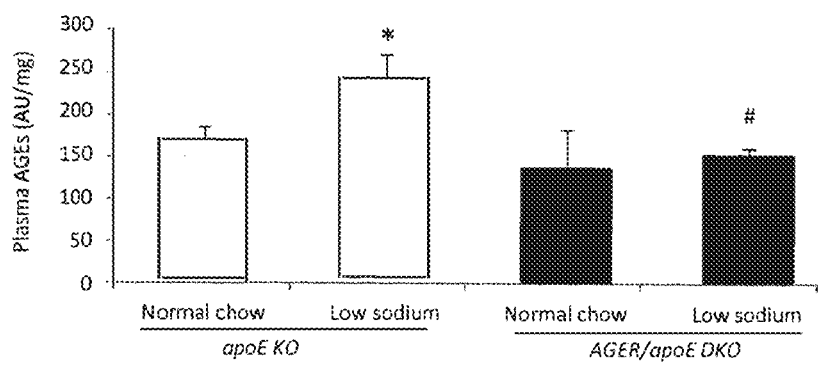
Figure 2F:
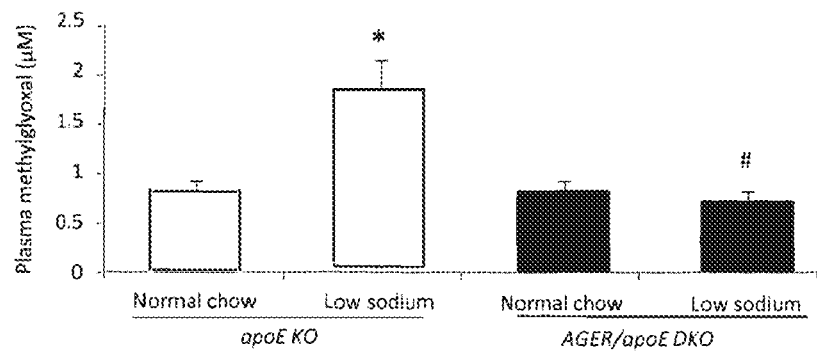

FIG. 2F. The expression of RAGE ligands, including (i) circulating plasma levels of S100A8/A9, as measured by commercial ELISA, (ii) plasma AGE levels, as measured by in-house ELISA, and (iii) the circulating AGE-precursor, methylglyoxal levels as measured by HPLC in apoE KO mice and AGER/apoE DKO mice following six-weeks of a 0.05% (low) sodium diet or normal chow.

Figure 2G:
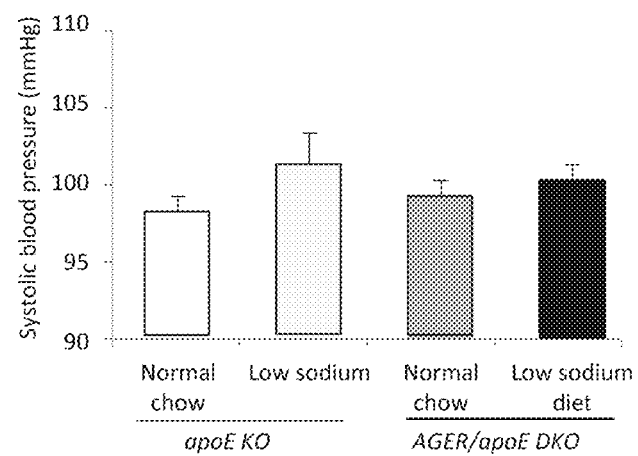

FIG. 2G. Systolic blood pressure as measured by tail-cuff plethysmography in apoE KO mice and AGER/apoE DKO mice following six-weeks of a 0.05% (low) sodium diet or normal chow.

Figure 2H:
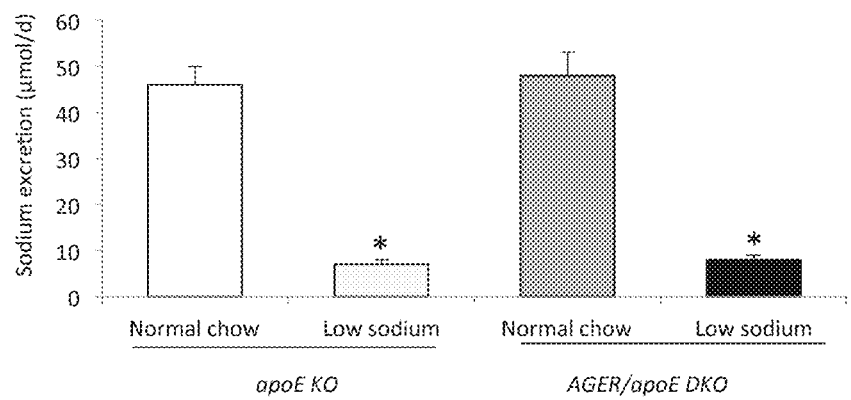
Figure 2H:
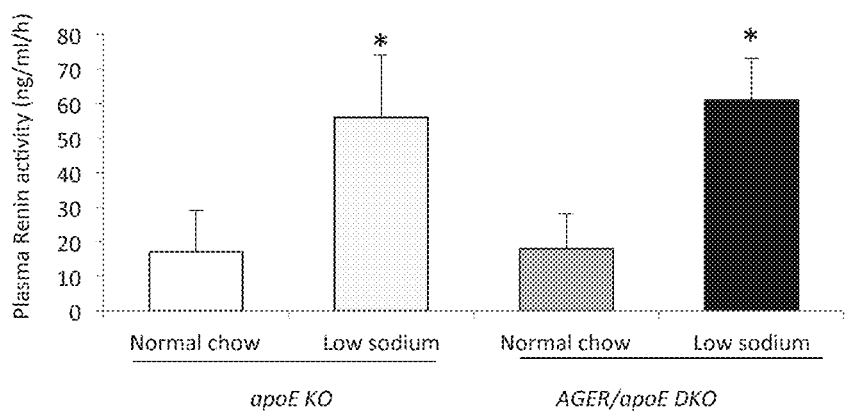
Figure 2H:
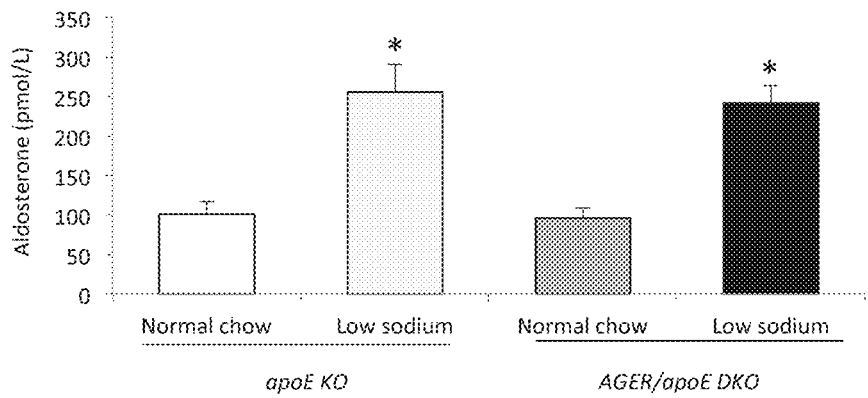

FIG. 2H. Markers of activation of the RAAS including (i) reduced sodium excretion, (ii) increased plasma renin activity and (iii) increased plasma aldosterone levels as measured by radioimmunoassay in apoE KO mice and AGER/apoE DKO mice following six-weeks of a 0.05% (low) sodium diet or normal chow.

Data are mean±SEM; n=8 per group, *vs apoE KO mice on normal chow, $p<0.05$. # vs apoE KO mice+low sodium.

Example 3

Figure 3A:
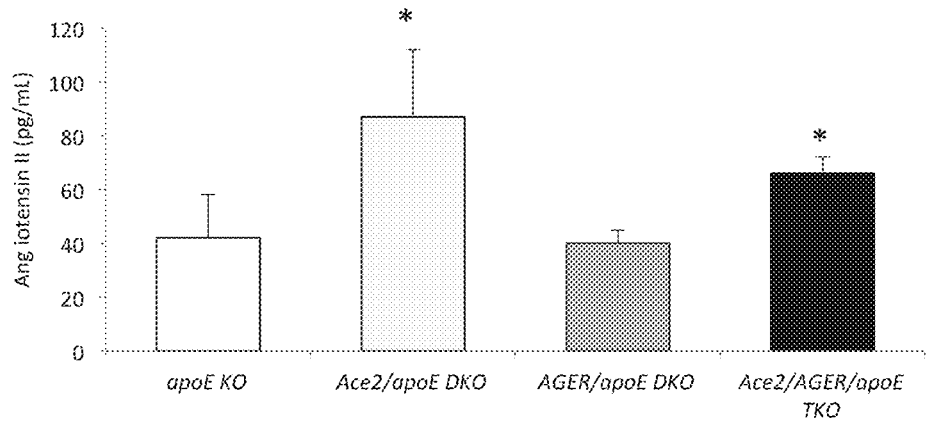

FIG. 3A. Circulating Ang II concentrations in apoE KO mice and AGER/apoE KO mice with or without genetic Ace2 deficiency, as measured by radioimmunoassay.

Figure 3B:
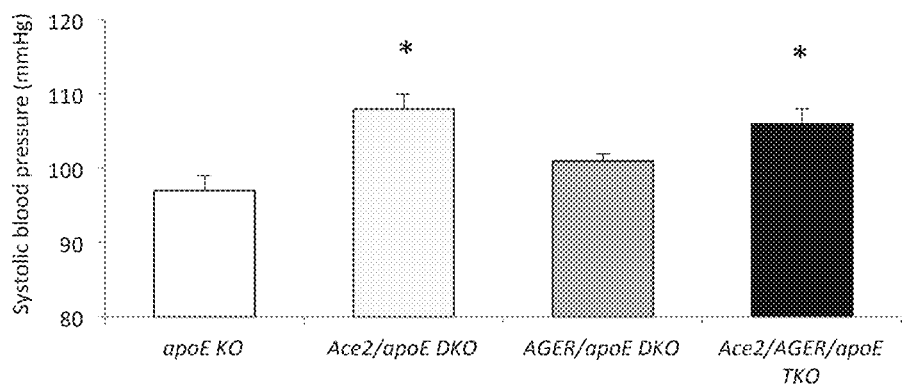

FIG. 3B. Systolic blood pressure as measured by tail-cuff plethysmography in 18-week old apoE KO mice and AGER/apoE KO mice with or without genetic Ace2 deficiency.

Figure 3C:
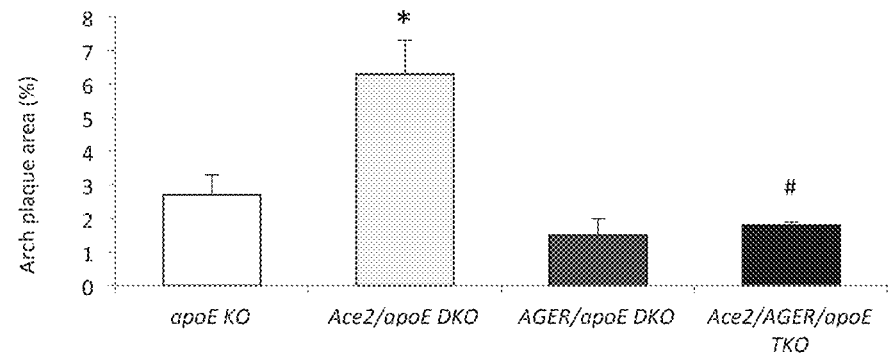

FIG. 3C. Quantitated plaque area expressed as the percentage of the aortic arch surface area staining positive to Sudan IV in 18-week old apoE KO mice and AGER/apoE KO mice with or without genetic Ace2 deficiency.

Figure 3D:
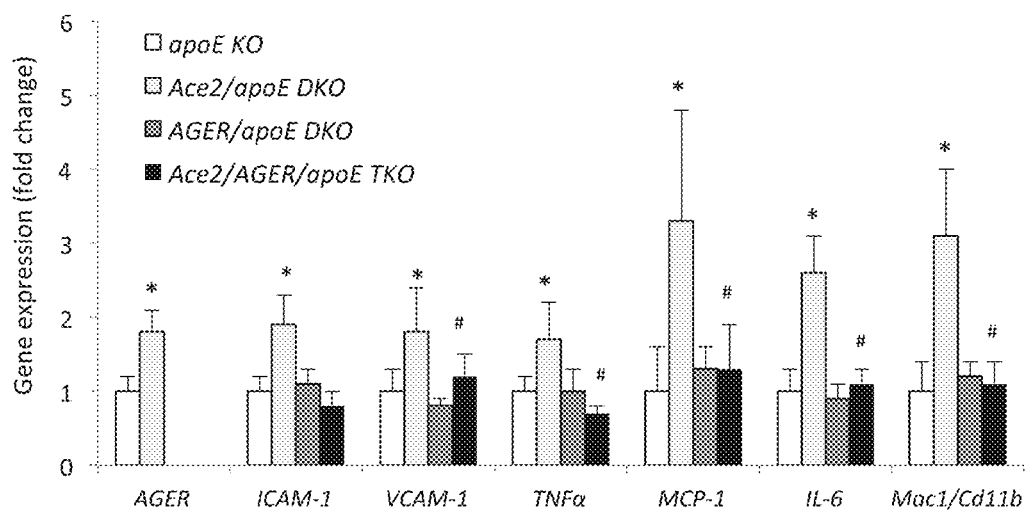

FIG. 3D. The aortic expression of pro-atherosclerotic mediators including AGER itself, adhesion molecules (ICAM-1, VCAM-1), inflammatory cytokines and chemokines (TNFα, MCP-1 and IL-6) and the macrophage marker (Mac-1/Cd11b), as measured by real time RT-PCR in aortic homogenates from apoE KO mice in the presence or absence of Ace2 and or RAGE.

Figure 3E:
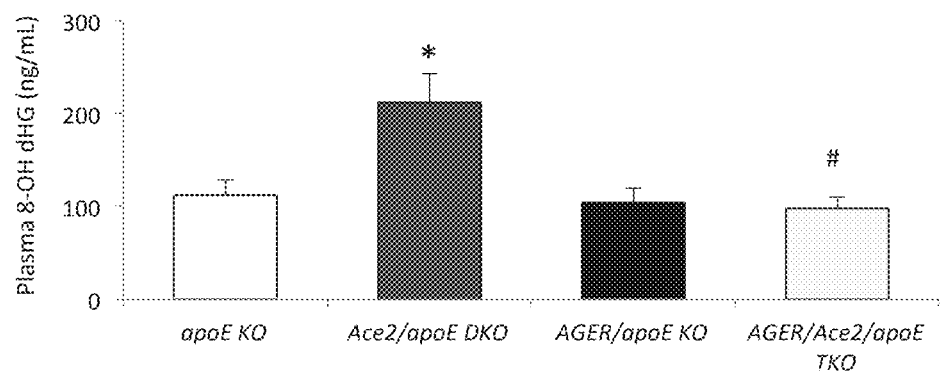

FIG. 3E. Oxidative stress in 18-week old apoE KO mice, Ace2/apoE DKO mice, AGER/apoE DKO and Ace2/AGER/apoE triple KO (TKO) mice, as estimated by plasma 8-hydroxydeoxyguanosine (8-OH-dG), a marker of oxidative DNA damage.

Figure 3F:
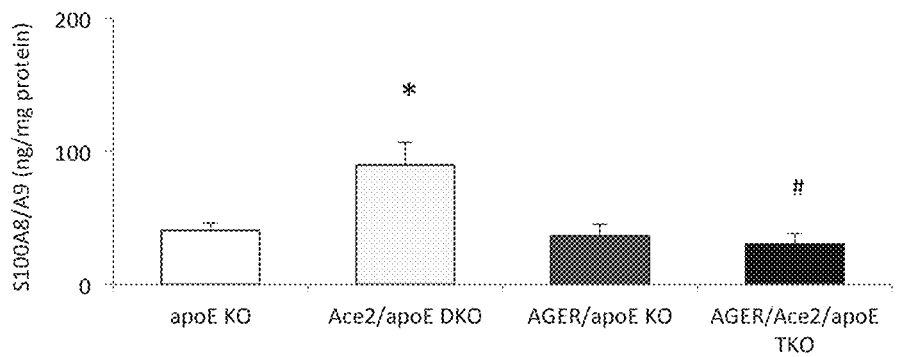
Figure 3F:
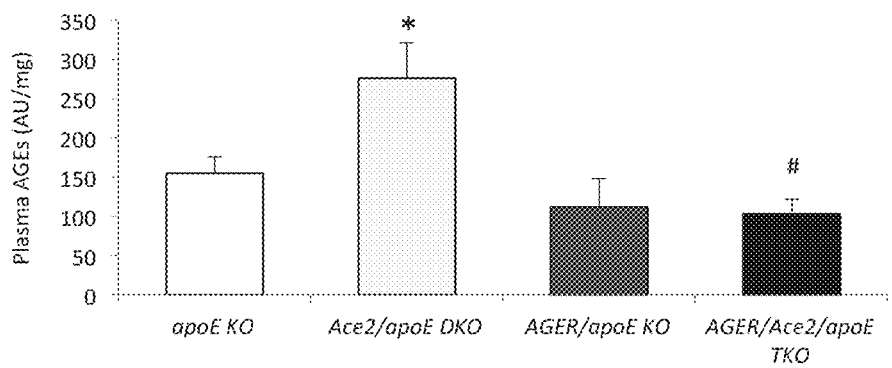

FIG. 3F. The expression of RAGE ligands, including (i) circulating plasma levels of S100A8/A9, as measured by commercial ELISA, (ii) plasma AGE levels, as measured by in-house ELISA, in 18-week old apoE KO mice, Ace2/apoE DKO mice, AGER/apoE DKO and Ace2/AGER/apoE TKO mice.

Data are mean±SEM; n=8 per group, *vs apoE KO control; # vs Ace2/apoE DKO mice.

Example 4

Figure 4A:
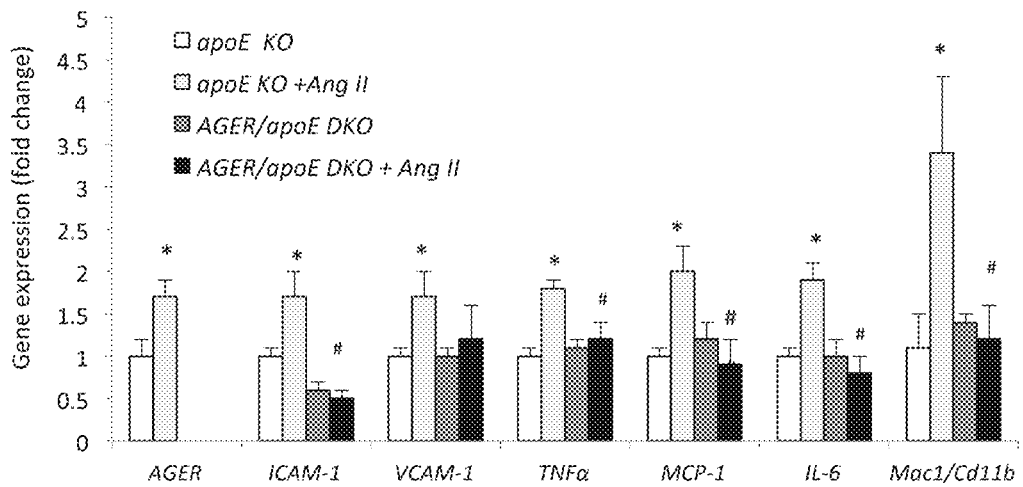

FIG. 4A. The aortic expression of pro-atherosclerotic mediators including AGER itself, adhesion molecules (ICAM-1, VCAM-1), inflammatory cytokines and chemokines (TNFα, MCP-1 and IL-6) and the macrophage marker (Mac-1/Cd11b) in apoE KO mice and AGER/apoE DKO, as measured by real time RT-PCR in aortic homogenates following their exposure ex vivo to Ang II or vehicle. Data are mean±SEM; n=6 per group, *vs untreated apoE KO control; # vs apoE KO+Ang II; p<0.05

Figure 4B:
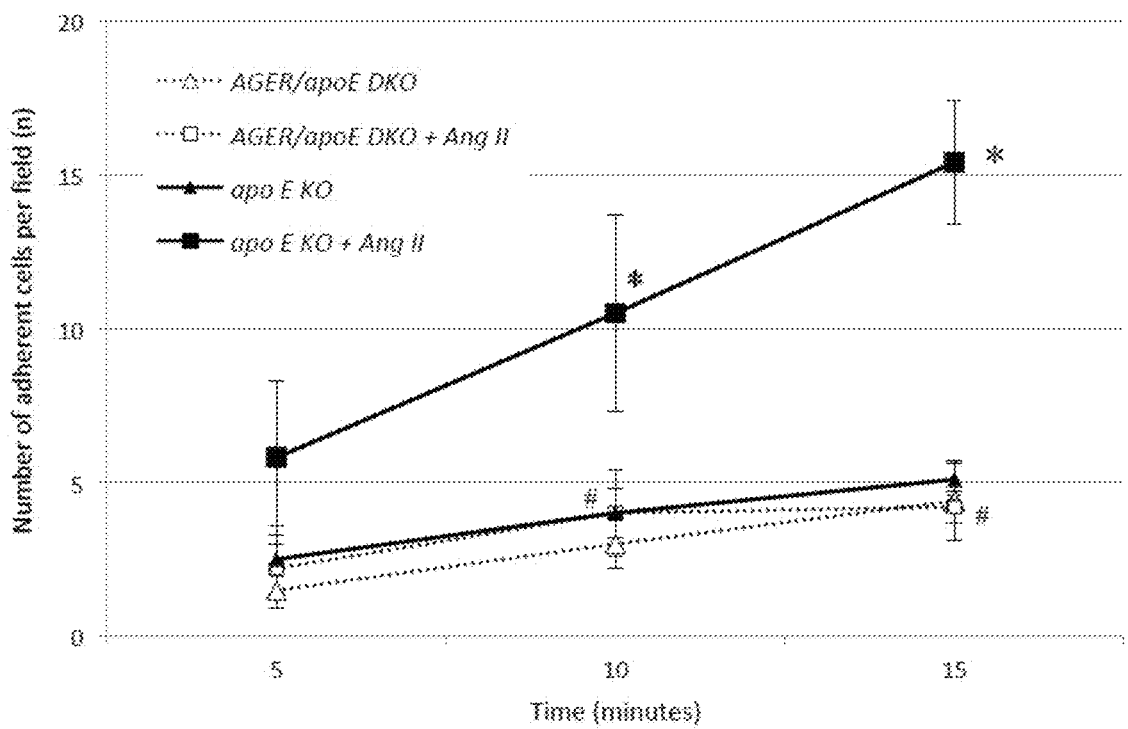

FIG. 4B. The number of labelled-leucocytes adhering to the aortic surface of apoE KO mice and AGER/apoE DKO as a marker of endothelial activation after four-hours ex vivo exposure to Ang II (1 µM) or vehicle control, as measured by dynamic flow assay. Data are mean±SEM; n=6 per group, *vs untreated apoE KO control; #AGER/apoE DKO+Ang II vs apoE KO+Ang II; p<0.05

Figure 4C:
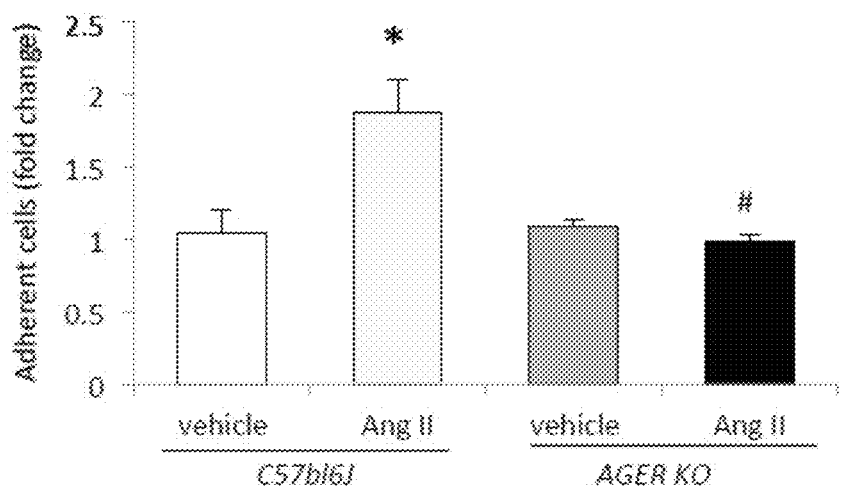

FIG. 4C. The number of labelled THP-1 monocytes adherent to a monolayer of primary murine aortic endothelial cells (PMAEC) from C57bl6 or AGER KO mice in the presence or absence of pre-treatment with Ang II (1 µM for 2 hours).

Figure 4D:
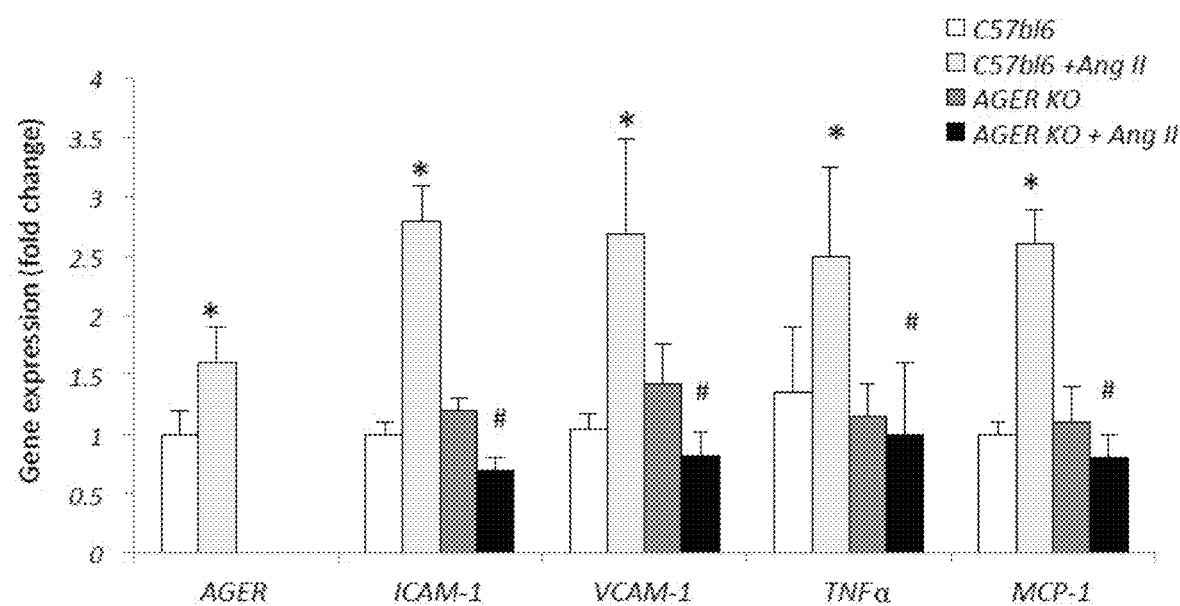

FIG. 4D. The expression of pro-atherosclerotic mediators including AGER itself, key adhesion molecules (ICAM-1, VCAM-1), inflammatory cytokines and chemokines (TNFα and MCP-1), as measured by real time RT-PCR in primary murine aortic endothelial cells (PMAEC) from C57bl6 and PMAEC from AGER KO mice following exposure to Ang II (1 µM) or vehicle control.

Figure 4E:
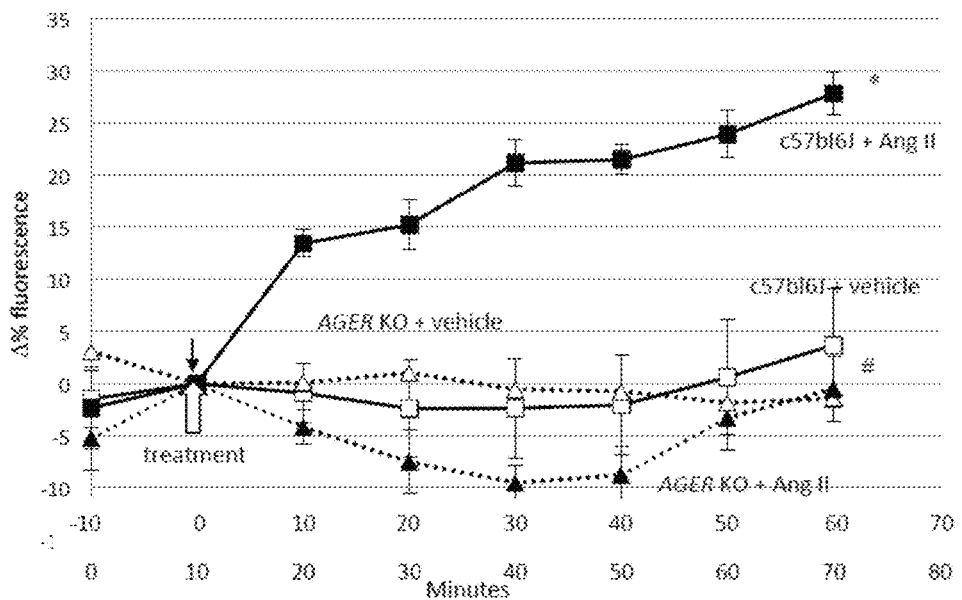
Figure 4E:
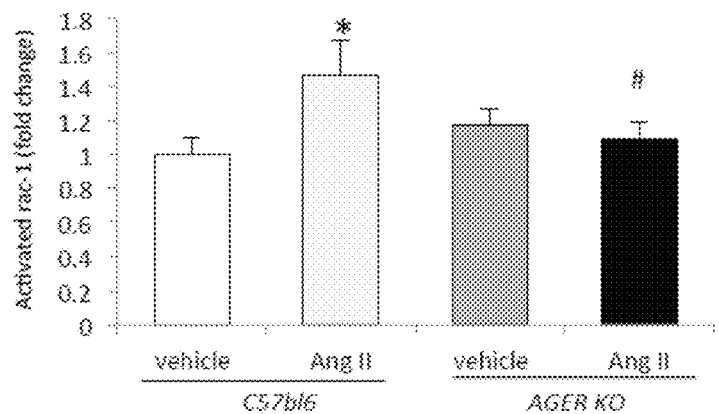
Figure 4E:
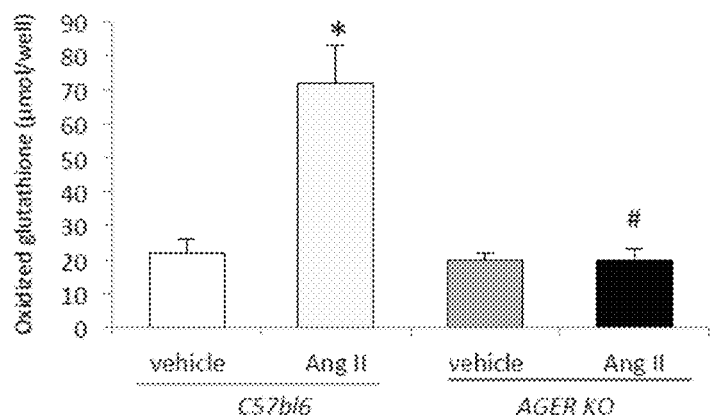

FIG. 4E. Markers of oxidative stress following exposure to Ang II or vehicle control in PMAEC from c57bl6 mice and AGER KO mice, as estimated by (i) the induction of DCFH fluorescence in a flow chamber assay, and (ii) levels of the GTP-activated NADPH oxidase subunit, Rac-1 and (iii) levels of oxidized glutathione.

Figure 4F:
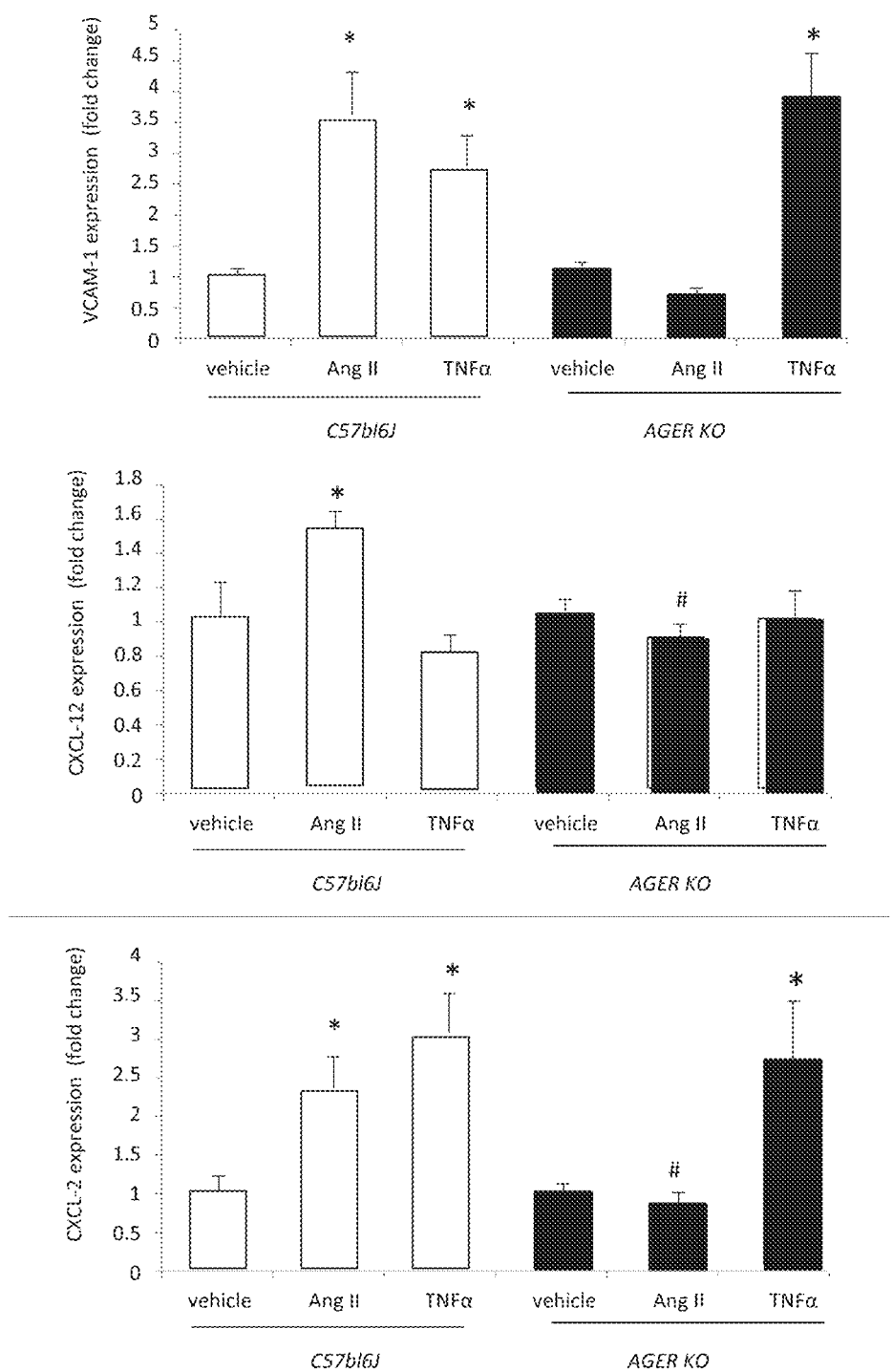

FIG. 4F. The gene expression of VCAM-1 and markers of non-canonical and canonical signalling via NFκB (CXCL12 and CXCL2, respectively) in a monolayer of primary murine aortic endothelial cells (PMAEC) from C57bl6 and AGER KO mice following exposure to Ang II. PMAEC, as measured by real time RT-PCR. TNFα is shown as a canonical specific control. VCAM-1 is shown as a target-specific control, replicating data in FIG. 4D.

Figure 4G:
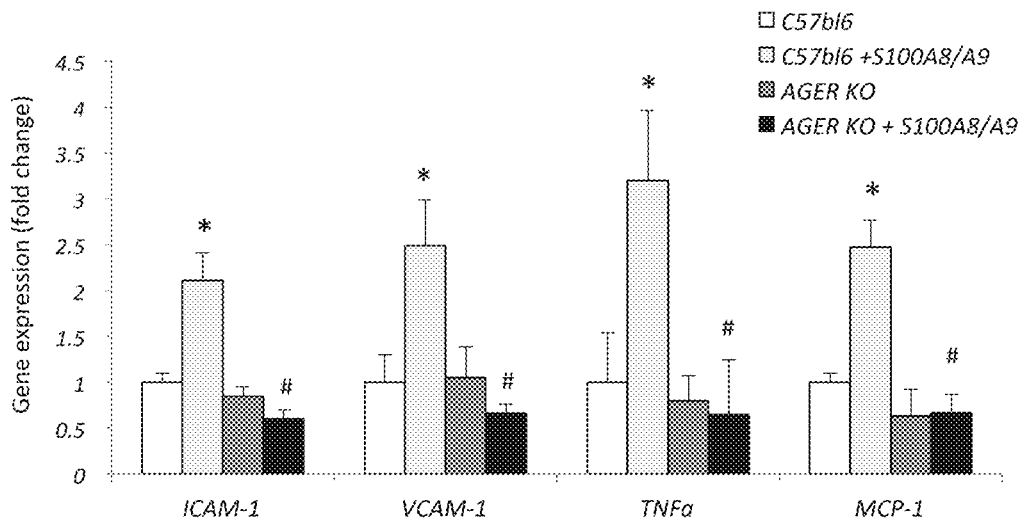

FIG. 4G. The expression of pro-atherosclerotic mediators including adhesion molecules (ICAM-1, VCAM-1), and inflammatory cytokines and chemokines (TNFα and MCP-1), in primary murine aortic endothelial cells (PMAEC) from C57bl6 and AGER KO mice treated with the RAGE ligand, S100A8/A9 (5 ng/ml), as measured by real time RT-PCR. Data are mean±SEM; n=6 per group, symbols denote *vs untreated wild type PMAEC; # vs S100A8/A9-treated wild type PMAEC, p<0.05.

Figure 4H:
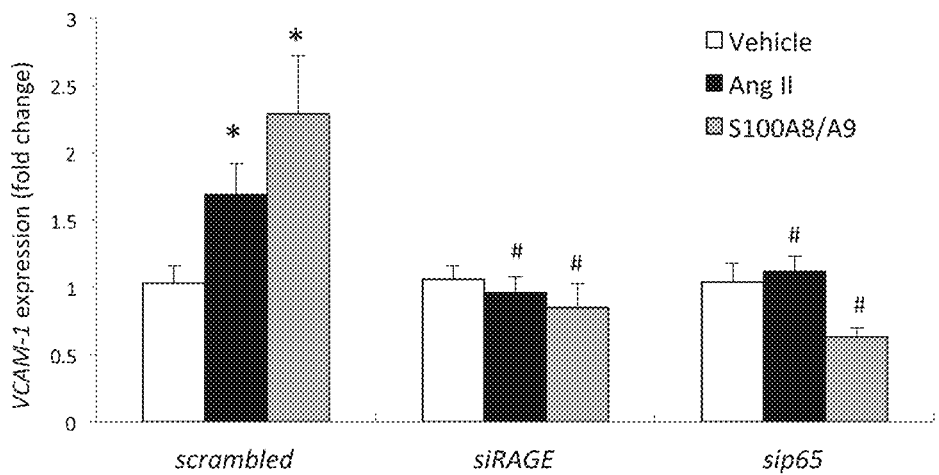

FIG. 4H. The gene expression of key adhesion protein, VCAM-1 in a monolayer of PMAEC, in which the expression of RAGE or the NFκB subunit p65 has been selectively silenced using siRNA or unaltered (scrambled RNA control) and subsequently exposed to Ang II (1 µM) or the RAGE ligand, S100A8/A9 (5 ng/mL), as estimated by real time RT-PCR.

Figure 4I:
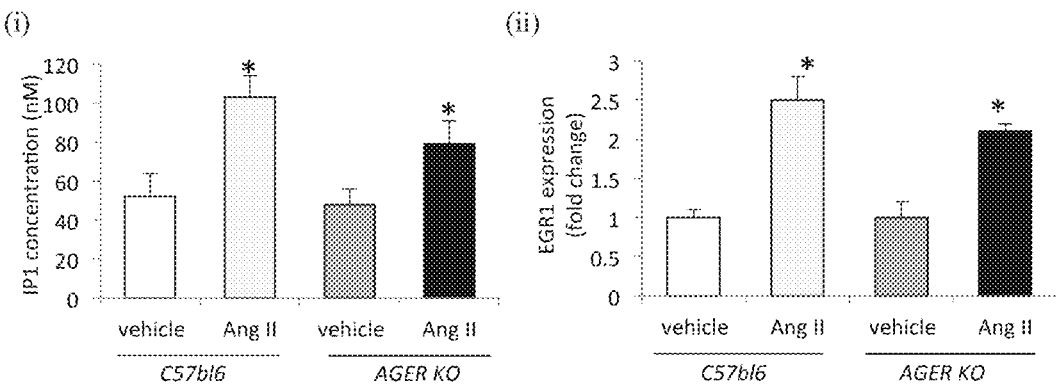

FIG. 4I. Markers of Gq-mediated signalling induced following activation of the $AT_1R$ by Ang II (1 µM) in a monolayer of PMAEC from c57bl6 mice and AGER KO mice, including (i) induction of inositol phosphate synthesis as estimated by IP-1 and (ii) downstream induction of the early growth response gene (EGR1).

Data are mean±SEM; n=6 per group, * vs untreated wild type control PMAEC and # vs Ang II treated wild type control unless otherwise stated, p<0.05.

Example 5

Figure 5A:
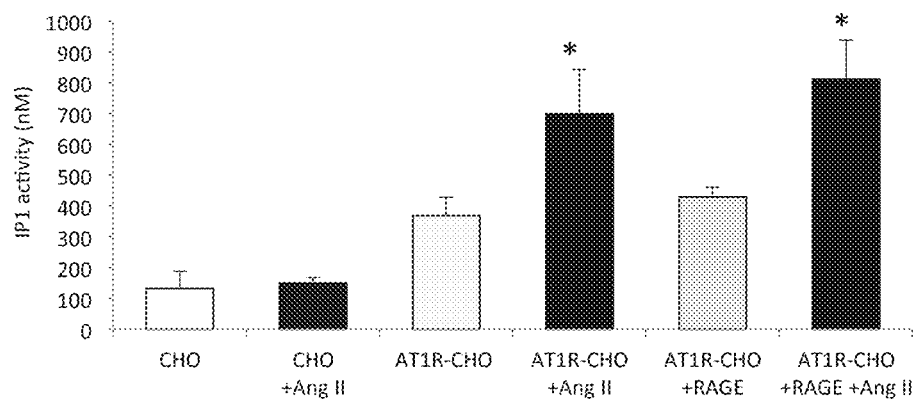

FIG. 5A. The induction of inositol phosphate synthesis in response to Ang II (1 µM), a marker of classical responsiveness to exogenous Ang II, as estimated by IP-1 levels in CHO cells in the presence or absence of expression of human $AT_1R$, with or without the additional expression of full length human RAGE.

Figure 5B:
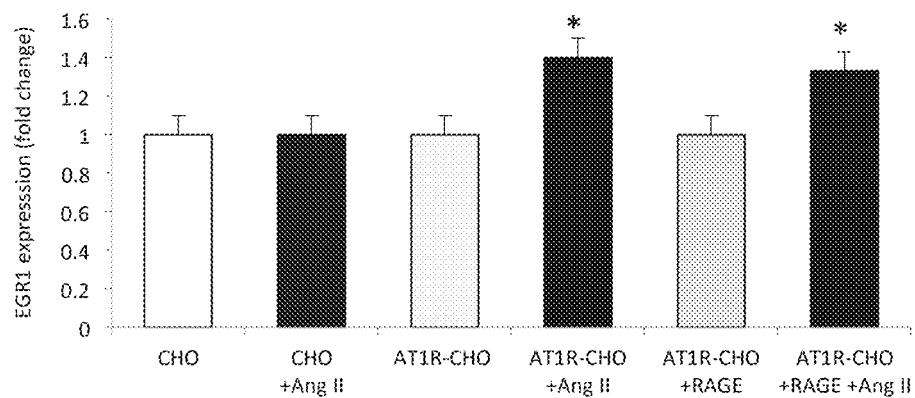

FIG. 5B. The induction of EGR1 expression in response to Ang II (1 µM), a marker of responsiveness to exogenous Ang II, as estimated by downstream induction of the EGR1 gene in CHO cells in the presence or absence of expression of human $AT_1R$, with or without the additional expression of full length human RAGE.

Figure 5C:
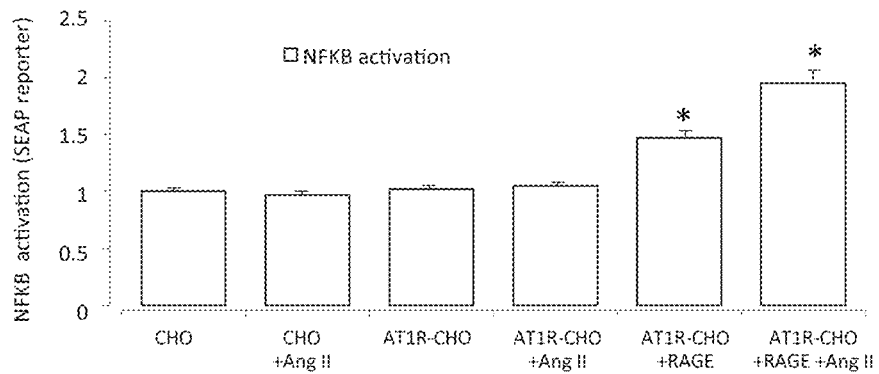
Figure 5C:
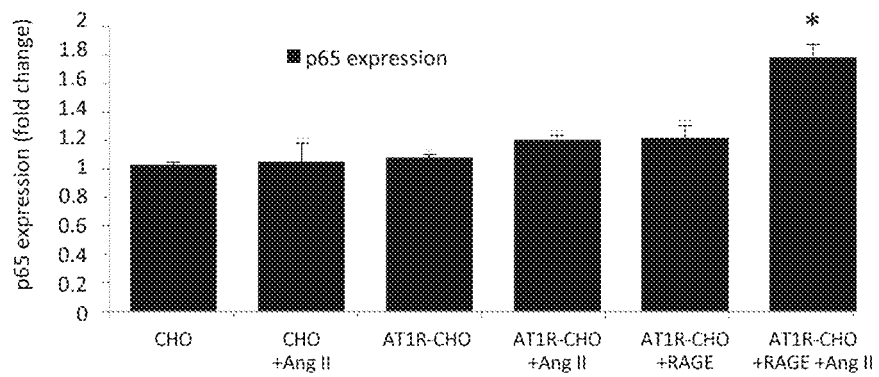
Figure 5C:
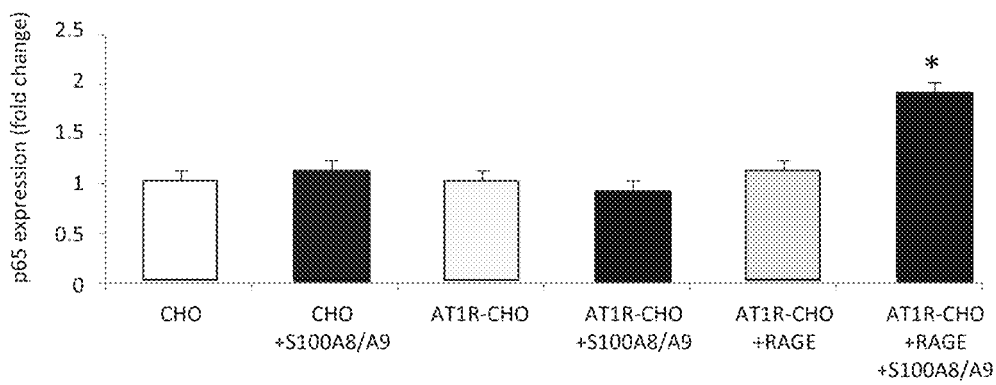

FIG. 5C. NFκB activation following exposure to Ang II (1 µM), as measured by (i) chemiluminescent SEAP reporter gene assay and (ii) the induction in the gene expression of the NFκB subunit, p65, in the presence or absence of expression in CHO cells of human $AT_1R$, with or without the additional expression of full length human RAGE and (iii) following exposure to the RAGE ligand, S100A8/A9 (5 ng/ml), as a control for the integrity of RAGE signalling in CHO cells.

Figure 5D:
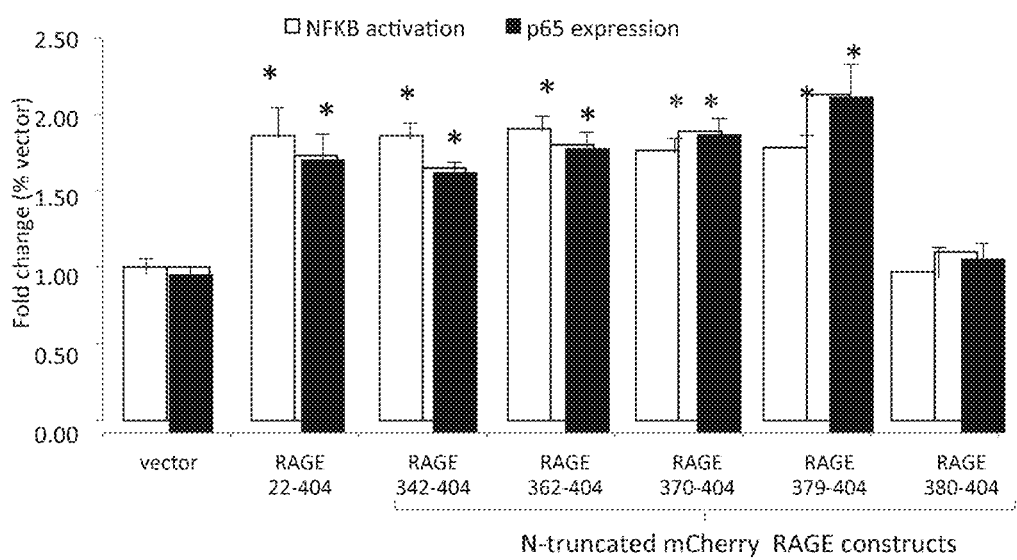

FIG. 5D. NFκB activation following exposure to Ang II (1 µM) in $AT_1R$—CHO cells, as measured by the induction in the gene expression of the NFκB subunit, p65, and chemiluminescent SEAP reporter gene assay for NFκB activity in the presence or absence of expression of the full-length human RAGE and N-truncated mCherry-RAGE constructs. Data are mean±SEM, n=6 per group, *vs vector (neo)-transfected $AT_1R$—CHO, p<0.05.

Figure 5E:
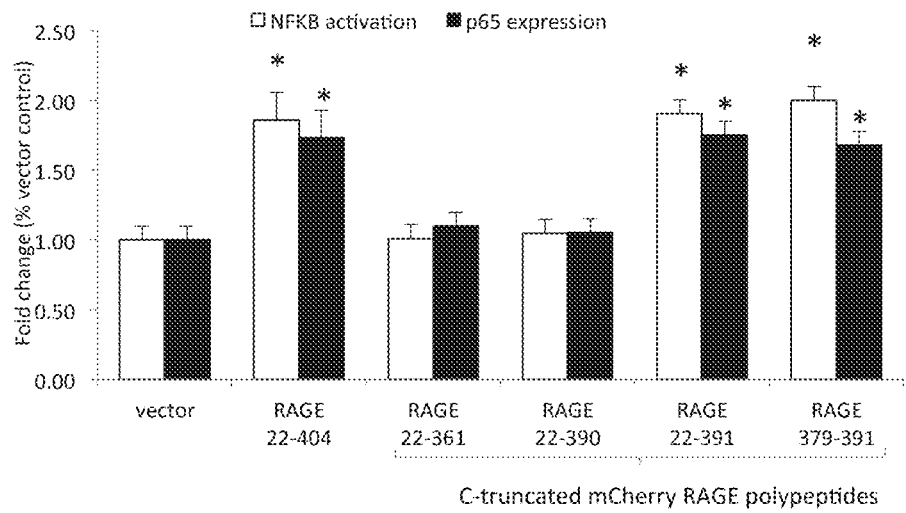

FIG. 5E. NFκB activation following exposure to Ang II (1 µM) in $AT_1R$—CHO as estimated by the induction in the gene expression of the NFκB subunit, p65, and chemiluminescent SEAP reporter gene assay for NFκB activity in the presence or absence of expression of the full-length human RAGE and C-truncated mCherry-RAGE constructs. Data are mean±SEM, n=6 per group, *vs vector (neo)-transfected $AT_1R$—CHO, p<0.05.

Figure 5F:
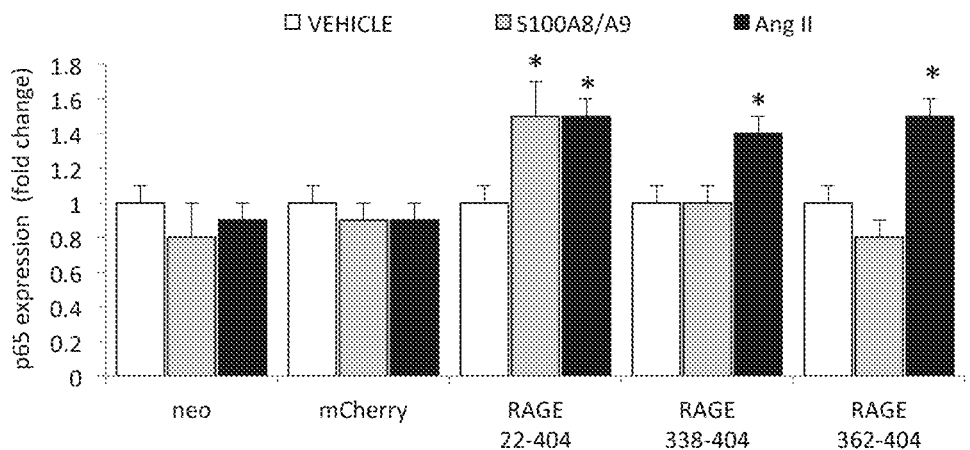

FIG. 5F. NFκB activation following exposure to S100A8/A9 (5 ng/ml) or Ang II (1 µM) in $AT_1R$—CHO as estimated by the induction in the gene expression of the NFκB subunit, p65, in the presence or absence of expression of the full-length human RAGE and N-truncated mCherry-RAGE constructs. Data are mean±SEM, n=6 per group, *vs vector (neo)-transfected $AT_1R$—CHO, p<0.05.

Figure 5G:
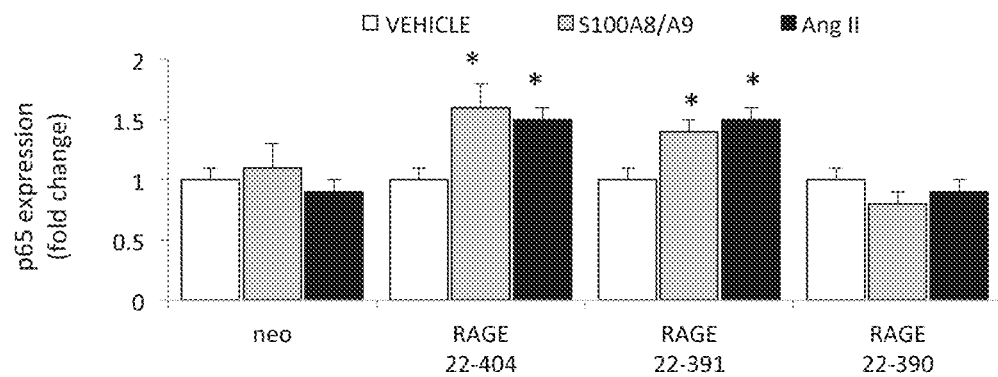

FIG. 5G. NFκB activation following exposure to S100A8/A9 (5 ng/ml) or Ang II (1 µM) in $AT_1R$—CHO as estimated by the induction in the gene expression of the NFκB subunit, p65, in the presence or absence of expression of the full-length human RAGE and C-truncated mCherry-RAGE constructs. Data are mean±SEM, n=6 per group, *vs vector (neo)-transfected $AT_1R$—CHO, p<0.05.

Figure 5H:
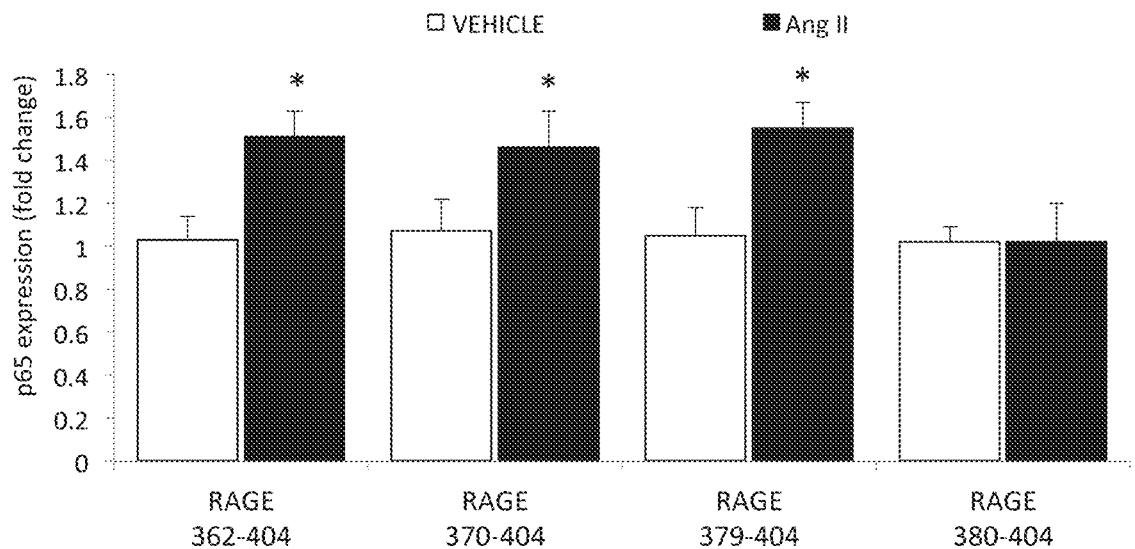

FIG. 5H. NFκB activation following exposure to Ang II (1 µM) in $AT_1R$—CHO as estimated by the induction in the gene expression of the NFκB subunit, p65, in the presence of expression of the N-truncated RAGE constructs without fusion to mCherry.

Data are mean±SEM, n=6 per group, *vs untreated $AT_1R$—CHO unless otherwise stated, p<0.05.

Example 6

Figure 6A:
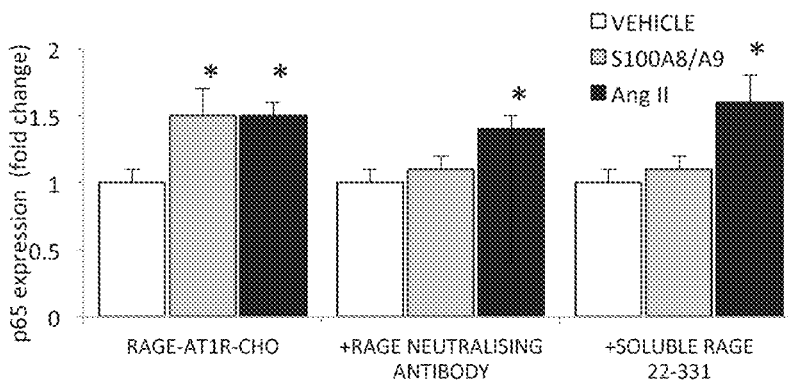

FIG. 6A. A RAGE neutralizing antibody targeting the ectodomain of RAGE (RAGEab) or a decoy receptor with ligand-binding affinity (soluble $RAGE_{22-331}$) inhibit the induction of pro-inflammatory signalling by the RAGE ligand S100A8/A9 but not by Ang II (1 µM) in RAGE-$AT_1R$—CHO cells, as estimated by the expression of the NFκB subunit, p65 as measured by RT-PCR. Data show mean±SEM; n=6 per group * vs vehicle alone, p<0.05.

Figure 6B:
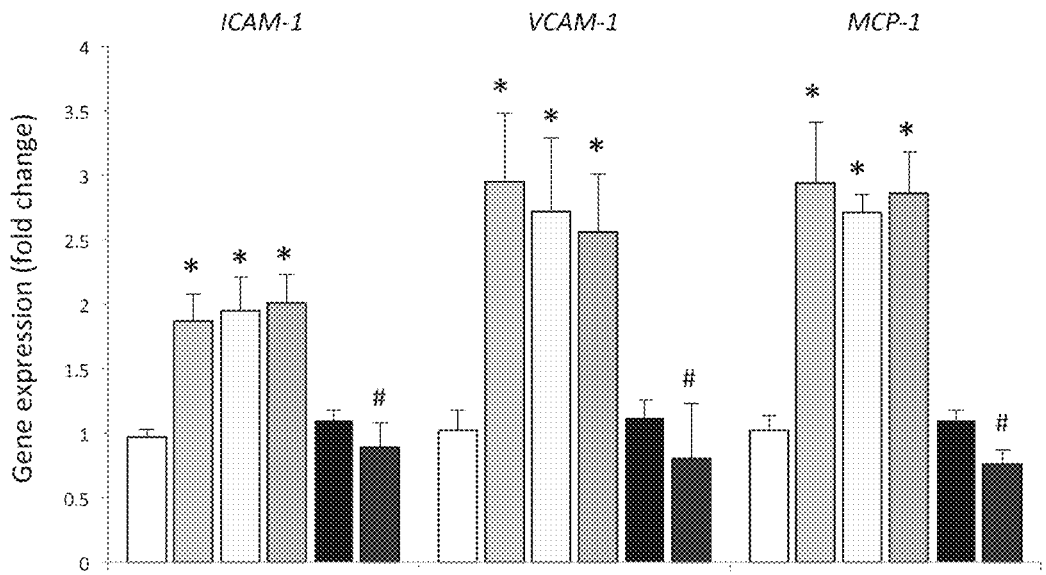

FIG. 6B. A RAGE neutralizing antibody targeting the ectodomain of RAGE (RAGEab) or a decoy receptor with ligand-binding affinity (soluble $RAGE_{22-331}$; SRAGE) do not inhibit the induction of pro-inflammatory signalling by Ang II (1 µM) in PMAEC from wild type mice, as estimated by the induction of key adhesion genes, ICAM-1 and VCAM-1, and an inflammatory chemokine gene (MCP-1). Data from AGER KO mice are shown as a negative control. Data show mean±SEM; n=6 per group * vs control cells treated with vehicle alone (white bar), # vs control cells treated with Ang II alone, p<0.05.

Figure 6C:
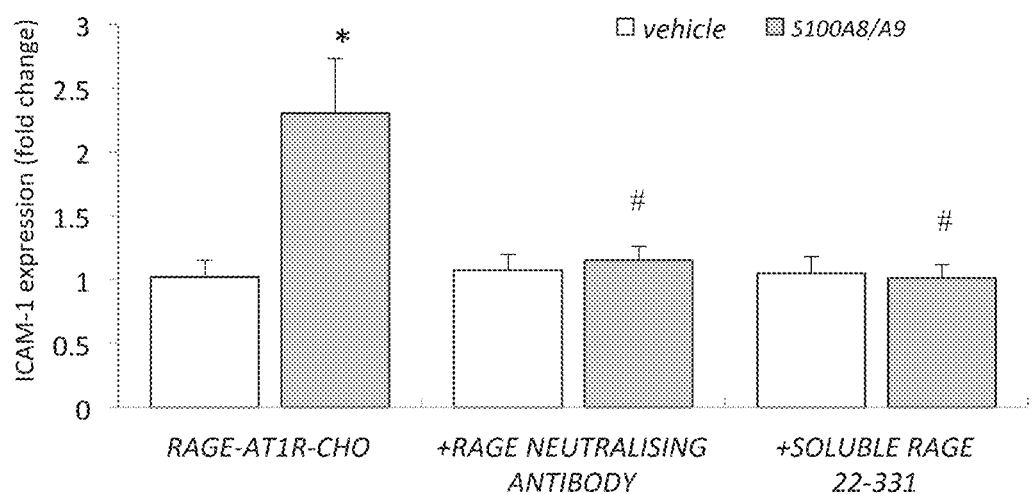

FIG. 6C. A RAGE neutralizing antibody targeting the ectodomain of RAGE (RAGEab) or a decoy receptor with ligand-binding affinity (soluble $RAGE_{22-331}$) inhibit the induction of pro-inflammatory signalling by the RAGE ligand S100A8/A9 in PMAEC from wild type mice, as estimated by the induction of key adhesion gene, ICAM-1. Data show mean±SEM; n=6 per group * vs control cells treated with vehicle alone (white bar), # vs control cells treated with S100A8/A9 alone, p<0.05.

Example 7

Figure 7A:
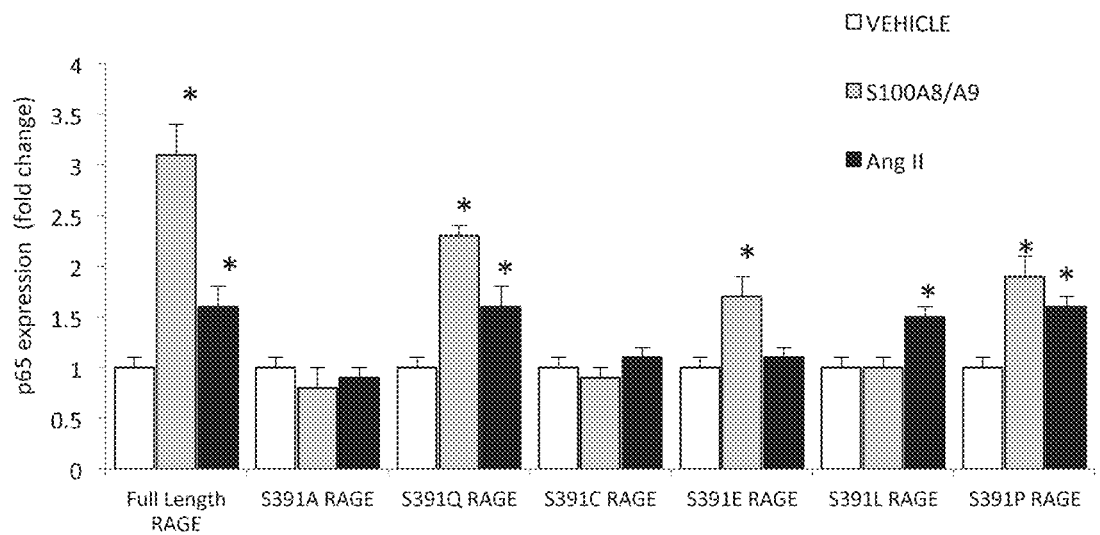

FIG. 7A. The induction of pro-inflammatory signalling by the RAGE ligand S100A8/A9 (5 ng/ml; grey bars) or Ang II (1 µM; black bars) in $AT_1R$—CHO cells also expressing full-length wild type $RAGE_{22-404}$ or selected S391-$RAGE_{22-404}$ mutants, as measured by the induction in the gene expression of the NFκB subunit, p65. Data show mean±SEM; n=6-8 per group * vs vehicle treated $AT_1R$—CHO cell expressing full length RAGE, p<0.05.

Figure 7B:
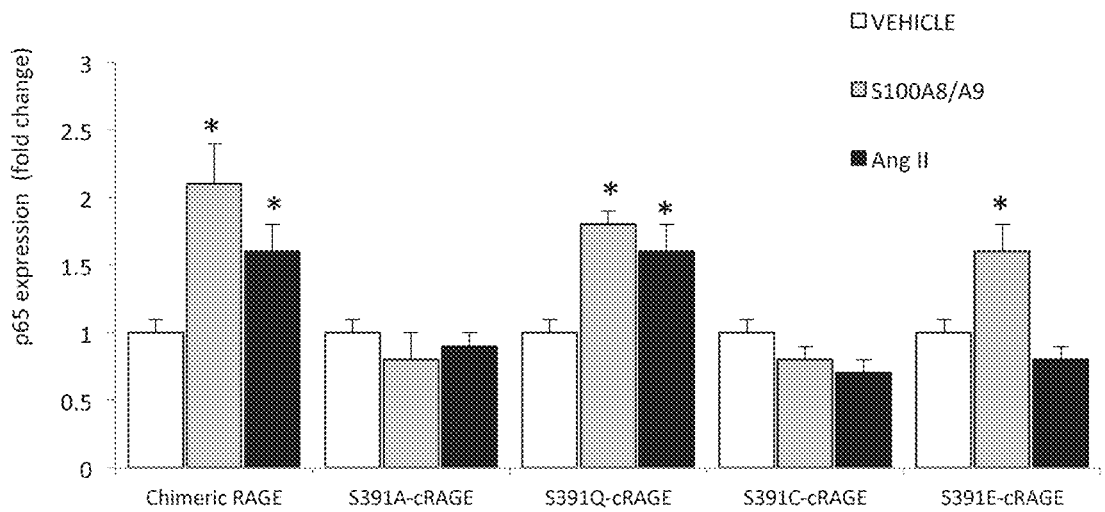

FIG. 7B. The induction of pro-inflammatory signalling by the RAGE ligand S100A8/A9 (5 ng/ml) or Ang II (1 µM) in $AT_1R$—CHO cells also expressing chimeric RAGE lacking phosphorylatable motifs in the cytosolic tail other than S391 (Chimeric RAGE; cRAGE), and S391 cRAGE mutants completely lacking any phosphorylatable motifs in the cytosolic tail, as measured by the induction in the gene expression of the NFκB subunit, p65, in $AT_1R$—CHO cells. Data show mean±SEM; n=6-8 per group * vs vehicle treated $AT_1R$—CHO cells expressing full length chimeric RAGE; p<0.05.

Figure 7C:
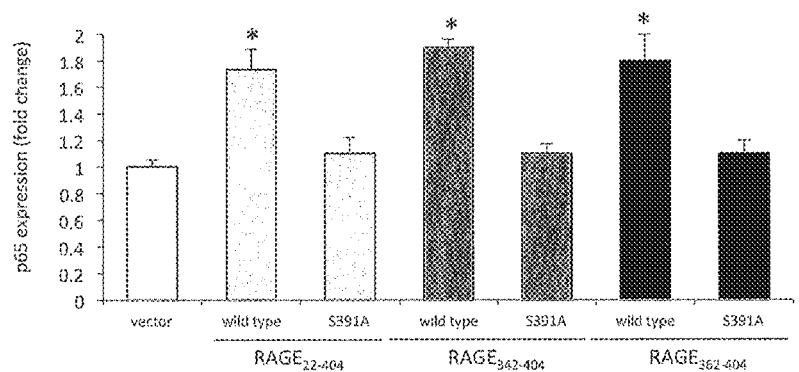

FIG. 7C. The induction of pro-inflammatory signalling by Ang II (1 µM) in $AT_1R$—CHO cells also expressing full length or N-truncated S391A-RAGE mutants, as measured by the induction in the gene expression of the NFκB subunit, p65. Data show mean±SEM; n=6-8 per group * vs vector transfected $AT_1R$—CHO cells, p<0.05.

Figure 7D:
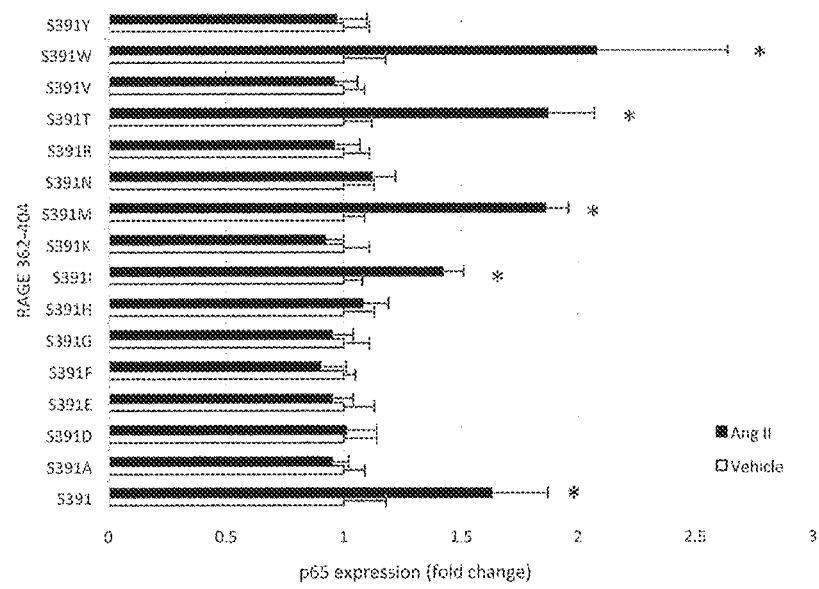

FIG. 7D. The induction of pro-inflammatory signalling by Ang II (1 µM) in the presence of wild type mCherry-$RAGE_{362-404}$ in $AT_1R$—CHO cells also expressing S391-$RAGE_{362-404}$ mutants, as measured by the induction in the gene expression of the NFκB subunit, p65. Data show mean±SEM; n=6-8 per group * vs vehicle control; p<0.05.

Example 8

Figure 8A:
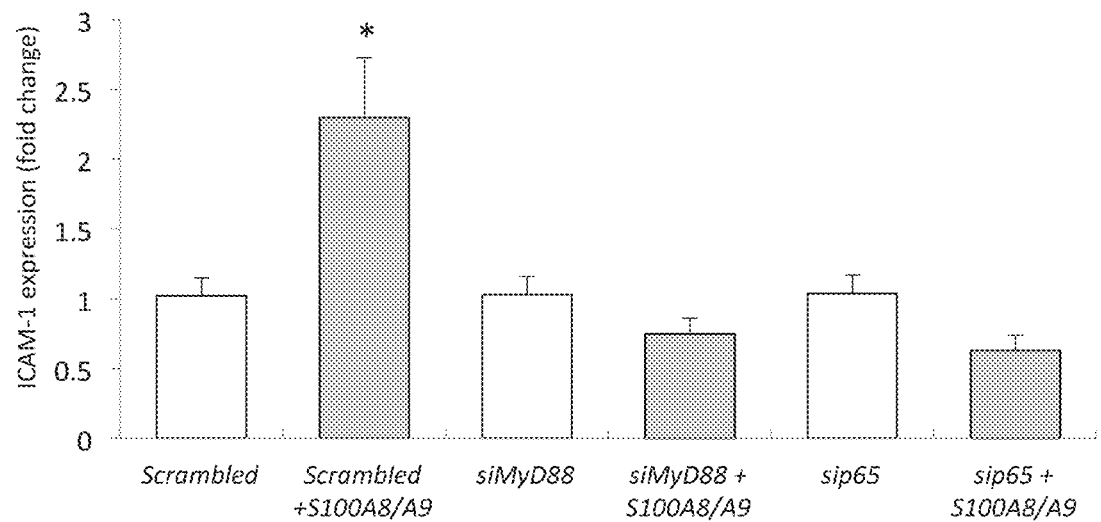

FIG. 8A. The effect of selective suppression of MyD88 expression using siRNA or scrambled control on the induction of RAGE ligand-dependent induction of pro-inflammatory signalling by the RAGE ligand S100A8/A9 (5 ng/ml) in a monolayer of PMAEC from C57bl6 mice, as estimated by the expression of ICAM-1 measured by real time RT-PCR. The selective suppression of p65 expression, another downstream mediator of RAGE signalling, using siRNA is shown as a positive control.

Figure 8B:
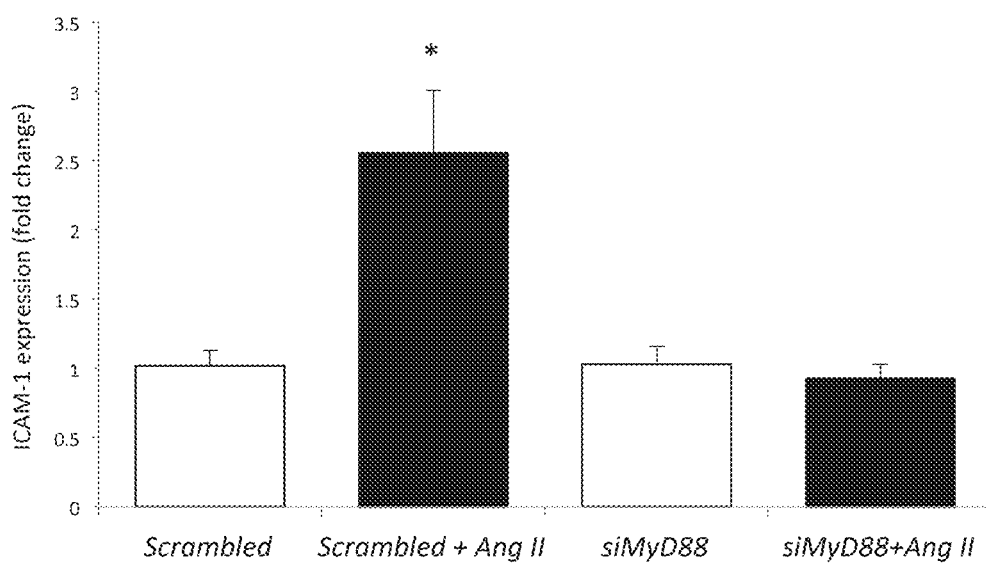

FIG. 8B. The effect of selective suppression of MyD88 expression using siRNA or scrambled control in a monolayer of PMAEC from C57bl6 mice on the induction of RAGE ligand-independent induction of pro-inflammatory signalling by Ang II (1 µM), as estimated by the expression of ICAM-1 measured by real time RT-PCR.

Figure 8C:
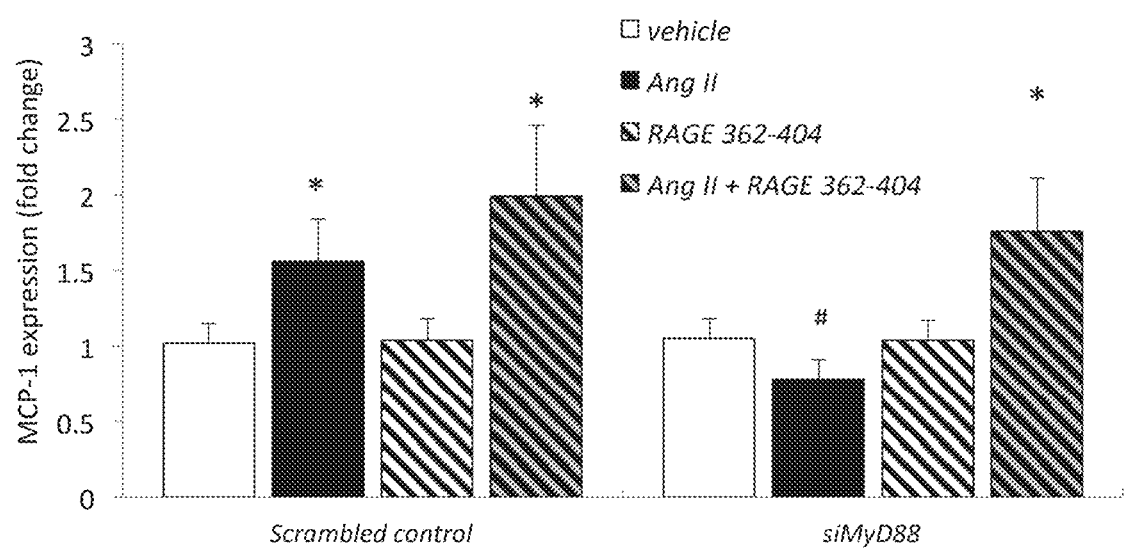

FIG. 8C. The effect of selective suppression of MyD88 expression using siRNA or scrambled control in a monolayer of HMEC on the induction of RAGE ligand-independent induction of pro-inflammatory signalling by Ang II (1 µM) in the presence and absence of $RAGE_{362-404}$, as estimated by the expression of MCP-1 measured by real time RT-PCR.

Data are mean±SEM; n=6-8 per group, * vs scrambled control, p<0.05.

Example 9

Figure 9A:
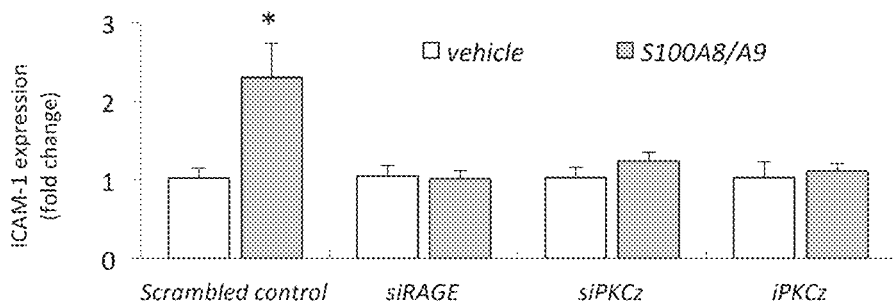

FIG. 9A. The effect of selective suppression of PKCζ using a pseudo-substrate for PKCζ (iPKCz), or siRNA targeted against the expression of PKCζ (siPKCz) or RAGE (siRAGE) or scrambled control, in a monolayer of PMAEC from C57bl6 mice on the induction of RAGE ligand-dependent signalling by the RAGE ligand S100A8/A9, as estimated by the expression of ICAM-1 measured by real time RT-PCR.

Figure 9B:
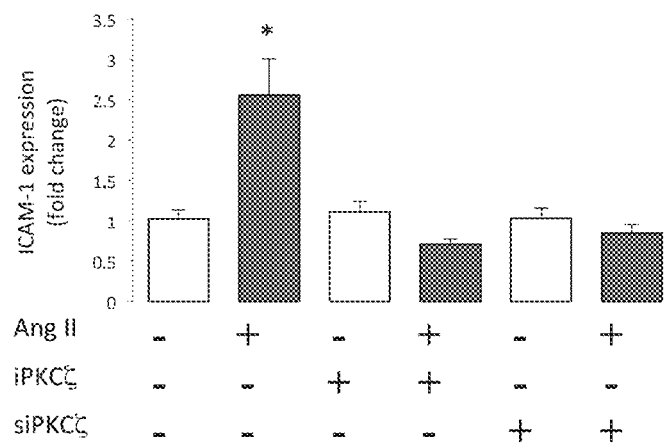

FIG. 9B. The effect of selective suppression of PKCζ expression using a pseudo-substrate for PKCζ (iPKCζ), or siRNA targeted against PKCζ (siPKCζ), in a monolayer of PMAEC from C57bl6 mice on RAGE ligand-independent induction of pro-inflammatory signalling by Ang II (1 µM), as estimated by the gene expression of ICAM-1 measured by real time RT-PCR. Columns 1 and 2 contain scrambled siRNA control.

Figure 9C:
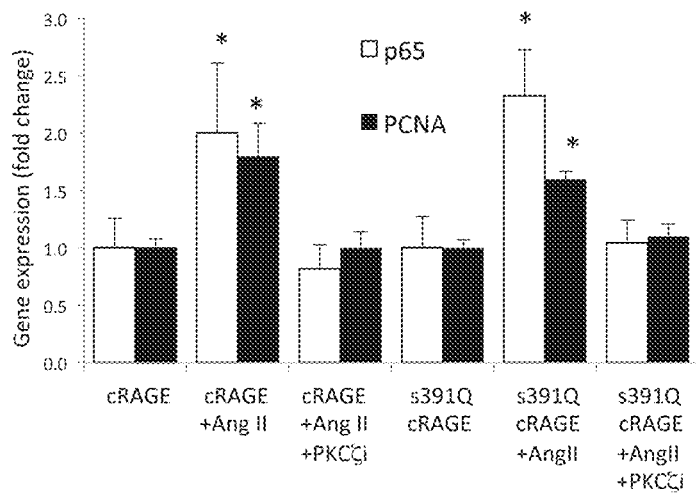

FIG. 9C. The effect of selective suppression of PKCζ expression using a pseudo-substrate for PKCζ (PKCζi) on RAGE ligand-independent induction of p65 and PCNA by Ang II (1 µM), in CHO cells expressing chimeric RAGE lacking phosphorylatable motifs in the cytosolic tail other than S391 (cRAGE) as well as cRAGE also containing the S391Q-RAGE mutation (S319Q-cRAGE) thereby removing all phosphorylation sites in the cytosolic tail, as estimated by the gene expression of RelA/p65 and PCNA measured by real time RT-PCR.

Figure 9D:
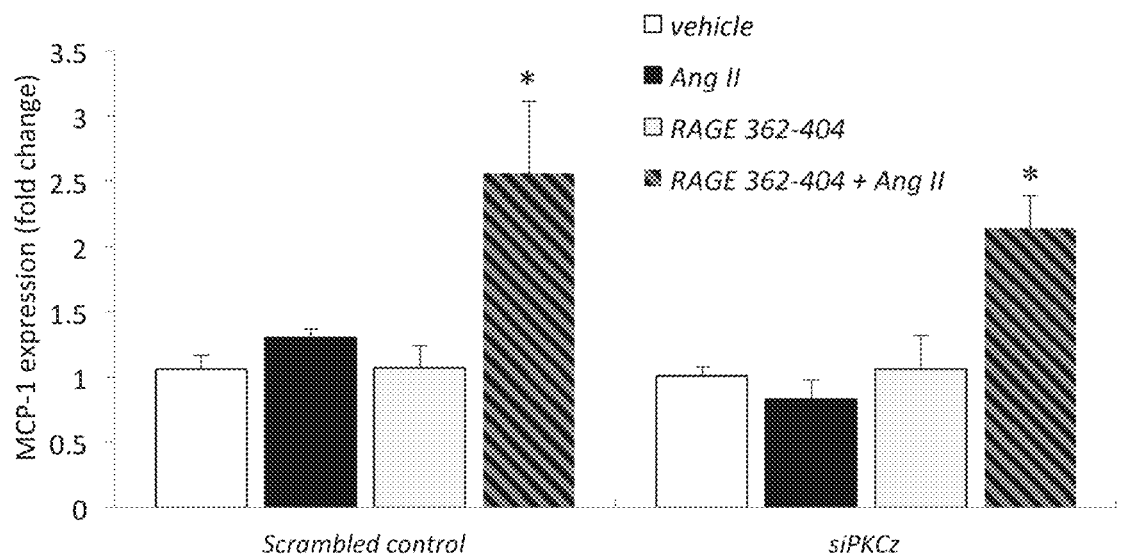

FIG. 9D. The effect of selective suppression of PKCζ expression using siRNA or scrambled control in a monolayer of HMEC on the induction of RAGE ligand-independent induction of pro-inflammatory signalling by Ang II (1 µM) in the presence and absence of $RAGE_{362-404}$, as estimated by the expression of MCP-1 measured by real time RT-PCR.

Data are mean±SEM; n=6-8 per group, * vs un-treated control, p<0.05.

Example 10

Figure 10A:
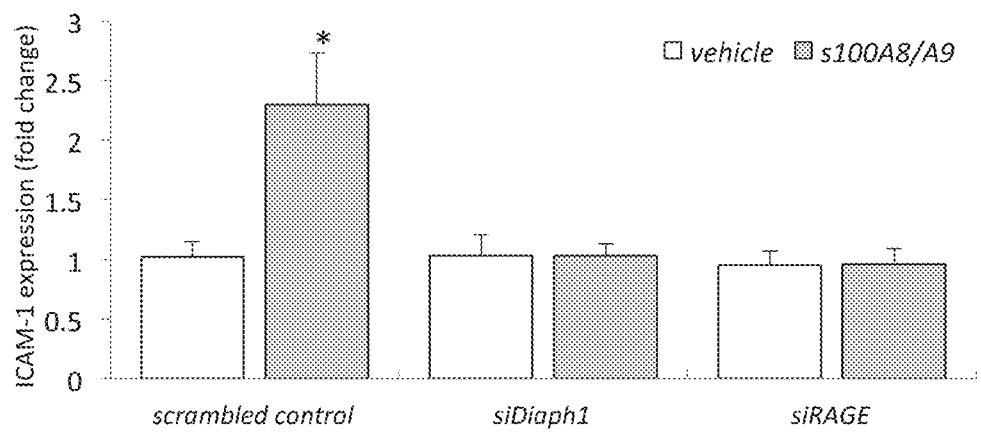

FIG. 10A. The effect of selective suppression of Diaph1 expression using siRNA in a monolayer of PMAEC from C57bl6 mice on the induction of RAGE ligand-dependent signalling by the RAGE ligand S100A8/A9, as estimated by the expression of ICAM-1 measured by real time RT-PCR. Data with siRAGE are included as a control.

Figure 10B:
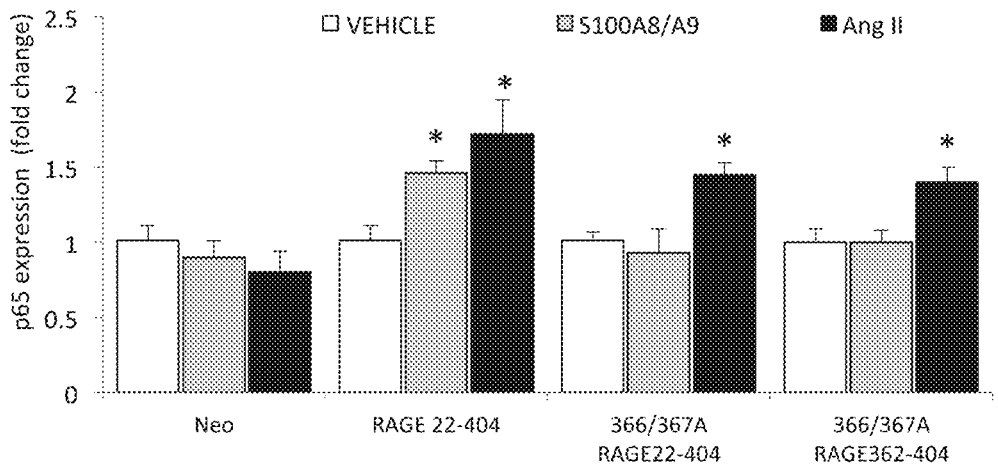

FIG. 10B. The differential effect of a R366A-Q367A-RAGE mutation that selectively disrupts a charged patch through which Diaph1 and RAGE putatively interact, on signalling induced by the RAGE ligand, S100A8/A9, and RAGE ligand-independent signalling induced by Ang II in $AT_1R$—CHO cells.

Figure 10C:
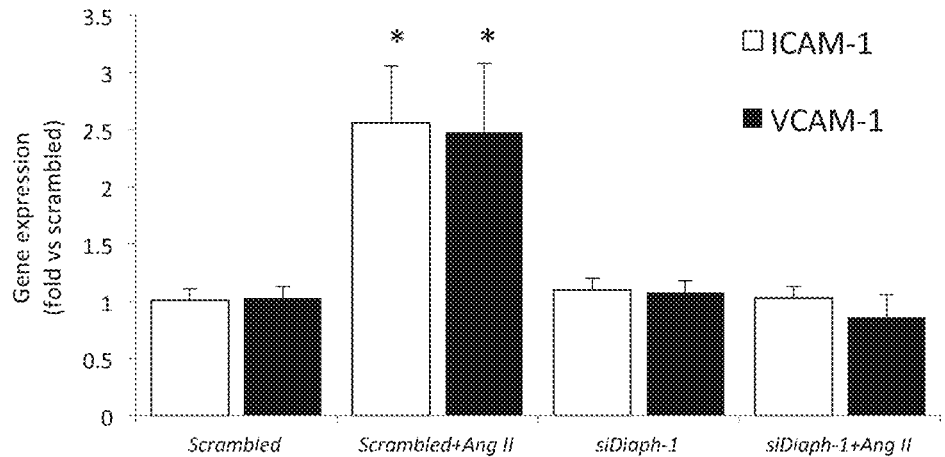

FIG. 10C. The effect of selective suppression of Diaph1 expression using siRNA in a monolayer of PMAEC from C57bl6 mice on the induction of RAGE ligand-independent signalling induced by Ang II (1 μM) as estimated by the expression of ICAM-1 and VCAM-1 as measured by real time RT-PCR. Data are mean±SEM; n=6 per group, * vs scrambled control, p<0.05.

Figure 10D:
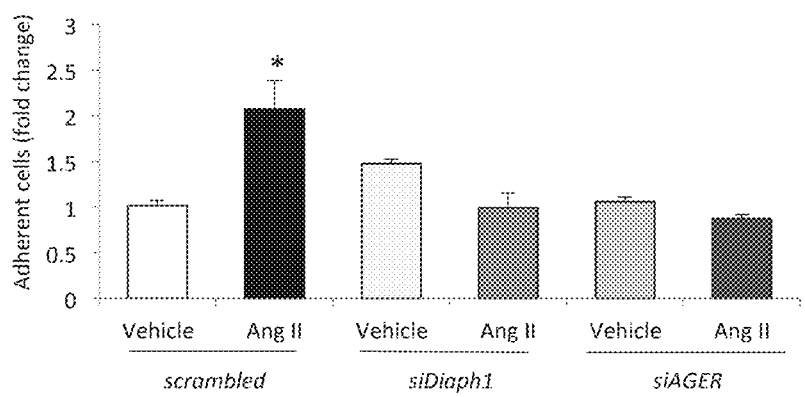

FIG. 10D. Selective suppression of Diaph1 or AGER expression using siRNA, in contrast to scrambled control, in a monolayer of SVEC on the induction of leukocyte adhesion to an endothelial monolayer following exposure to Ang II. Data are mean±SEM; n=6-8 per group, * vs scrambled control, p<0.05.

Figure 10E:
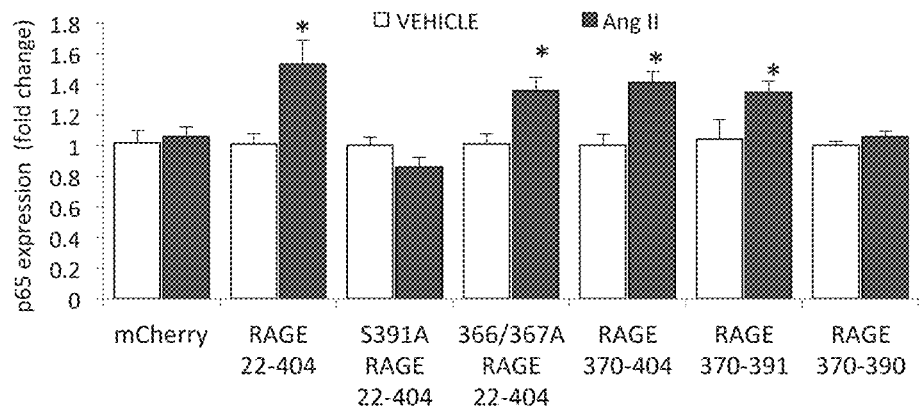

FIG. 10E. The effect of transfection with R366A-Q367A-RAGE mutants in which the charged patch through which Diaph1 and RAGE putatively interact is disrupted, or deleted, on signalling induced by Ang II as measured by the induction in the gene expression of the NFκB subunit, p65, in $AT_1R$—CHO cells. Data are mean±SEM; n=6 per group, * vs mCherry control, p<0.05.

Figure 10F:
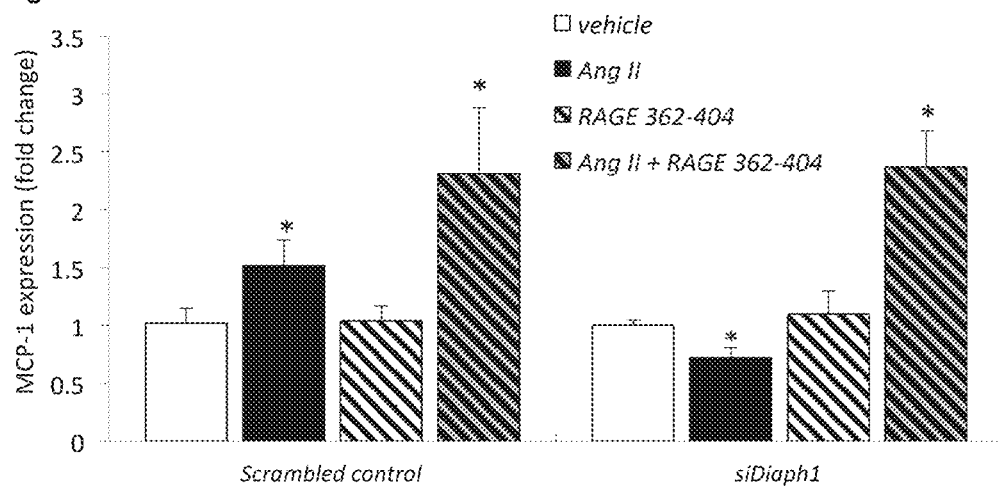

FIG. 10F. The effect of selective suppression of Diaph1 expression using siRNA or scrambled control in a monolayer of HMEC on the induction of RAGE ligand-independent induction of pro-inflammatory signalling by Ang II (1 μM) in the presence and absence of $RAGE_{362-404}$, as estimated by the expression of MCP-1 as measured by real time RT-PCR. Data are mean±SEM; n=6-8 per group, * vs vehicle control treated with scrambled siRNA, p<0.05.

Figure 10G:
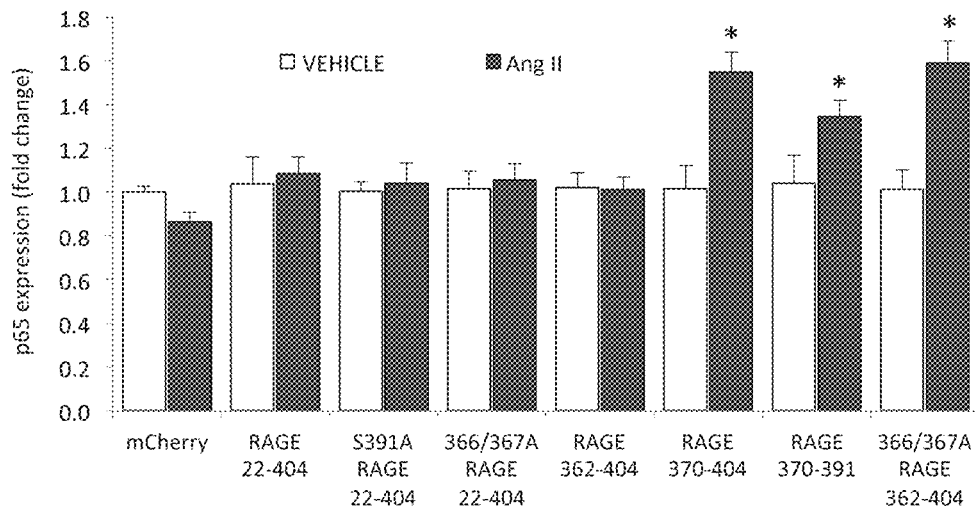

FIG. 10G. The effect of transfection with full length RAGE, truncated RAGE or RAGE mutants in $AT_1R$—CHO cells pre-treated with the inhibitory peptide, S391A-$RAGE_{362-404}$, on signalling induced by Ang II as measured by the induction in the gene expression of the NFκB subunit, p65. Data are mean±SEM; n=6-8 per group, * vs mCherry control, p<0.05

Data are mean±SEM; n=6-8 per group, * vs vehicle control, p<0.05, unless stated otherwise.

Example 11

FIG. 11A. The effect of selective suppression of IQGAP-1 expression using siRNA targeting IQGAP-1, in contrast to scrambled control, in a monolayer of PMAEC from C57bl6 mice on the induction of RAGE ligand-independent induction of pro-inflammatory signalling by Ang II (1 μM), as estimated by the expression of ICAM-1 measured by real time RT-PCR.

FIG. 11B. The effect of selective suppression of IQGAP-1 expression using SIRNA, in contrast to scrambled control, in a monolayer of PMAEC from C57bl6 mice on the induction of RAGE ligand-dependent induction of pro-inflammatory signalling by the RAGE ligand S100A8/A9, as estimated by the expression of ICAM-1 and VCAM-1 measured by real time RT-PCR.

FIG. 11C. Pull down of a protein identified as IQGAP-1 from other cytosolic components using a column coated with the mutant RAGE cytosolic tail (S391A-$RAGE_{362-404}$), as well as IQGAP-1 associated proteins, ezrin/radixin/moesin and the GPCR olfactory receptor 2T2.

Figure 11D:
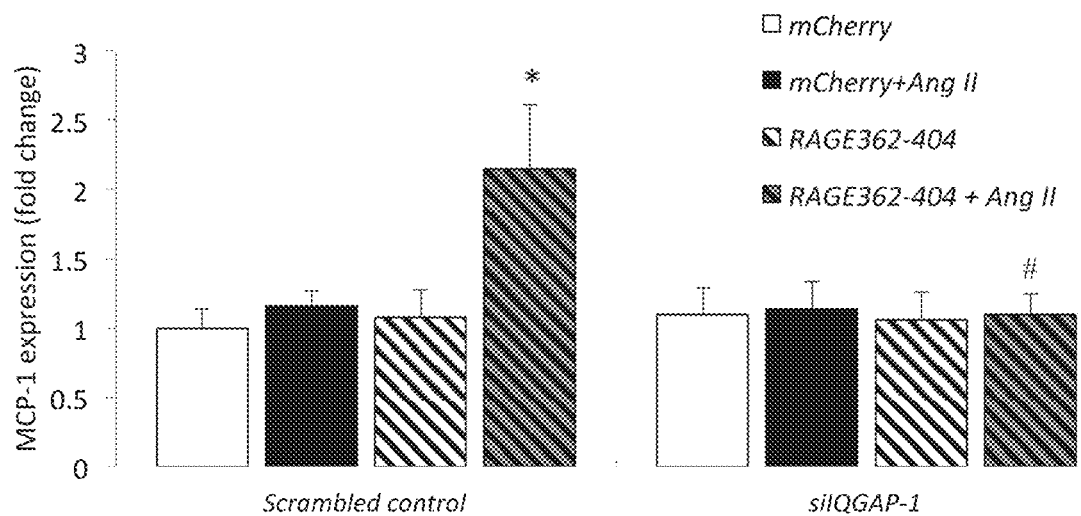

FIG. 11D. The effect of selective suppression of IQGAP-1 expression using siRNA or scrambled control in a monolayer of HMEC on the induction of RAGE ligand-independent induction of pro-inflammatory signalling by Ang II (1 μM) in the presence and absence of $RAGE_{362-404}$, as estimated by the expression of MCP-1, as measured by real time RT-PCR.

Data are mean±SEM; n=6-8 per group, *vs scrambled control, p<0.05, # vs scrambled+ligand (Ang II or s100A8/A9 as applicable), p<0.05.

Example 12

Figure 12A:
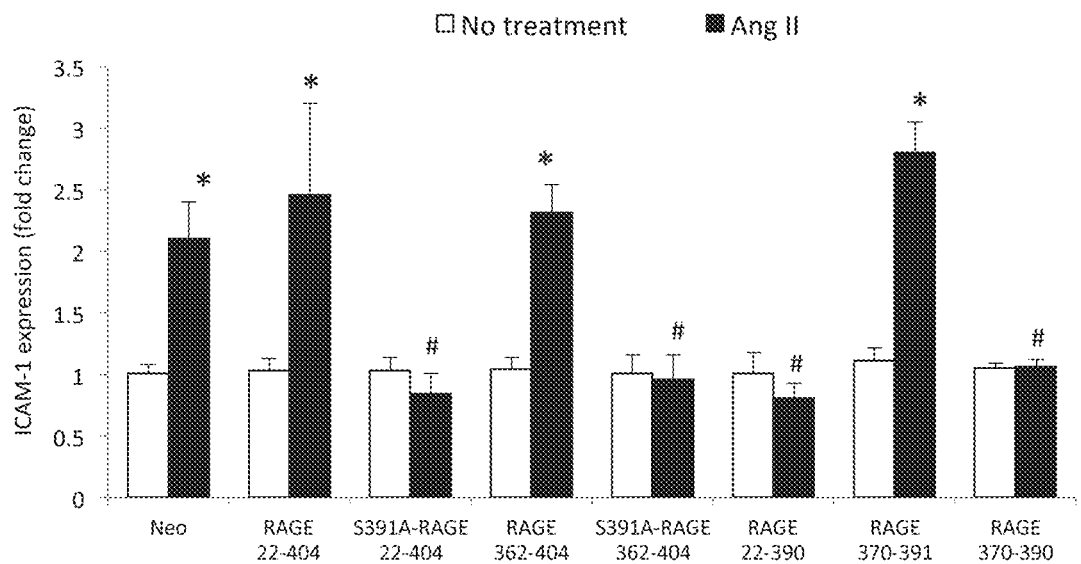

FIG. 12A. The effect of transfection of murine SVEC with RAGE or RAGE mutants on the induction of ICAM-1 by Ang II compared to vector alone (pc-Neo) as a control, as measured by RT-PCR. Data are mean±SEM; n=6-8 per group. * vs untreated control, # vs neo+Ang II, p<0.05.

Figure 12B:
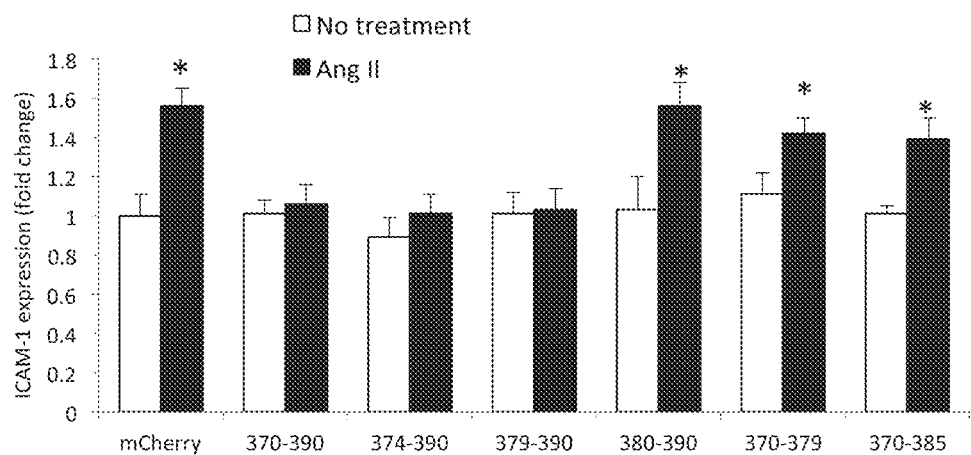

FIG. 12B. The effect of transfection with truncated RAGE mutants on the induction of ICAM-1 by Ang II in murine SVEC to identify the smallest fragments with inhibitory activity. Data are mean±SEM; n=6-8 per group, * vs no treatment control, p<0.05.

Figure 12C:
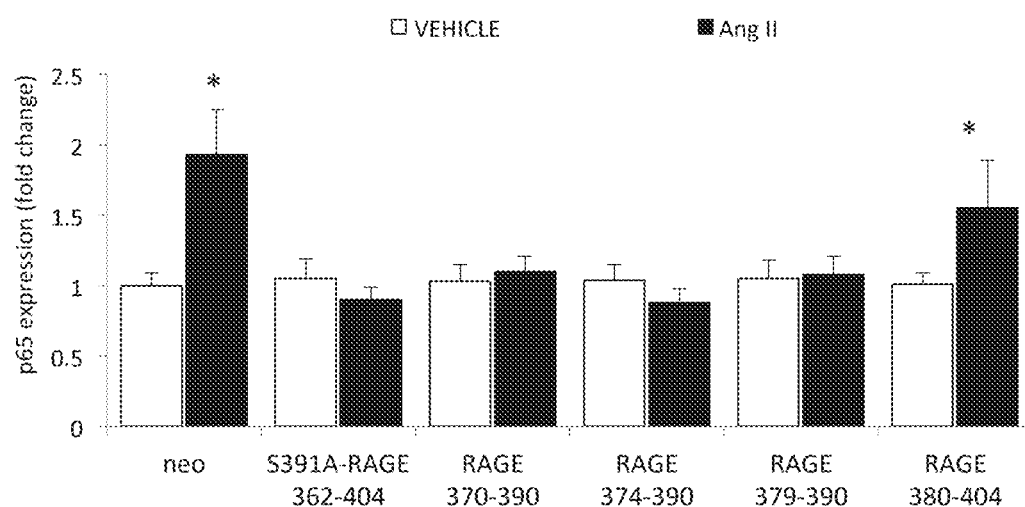

FIG. 12C. Inhibition of NFκB activation following exposure to Ang II (1 μM) in RAGE-$AT_1R$—CHO as estimated by the induction in the gene expression of the NFκB subunit, p65, in the presence of expression of mutant and N-truncated RAGE constructs without fusion to mCherry. Data are mean±SEM; n=6-8 per group, * vs no treatment control, p<0.05.

Figures 12D, 12E:
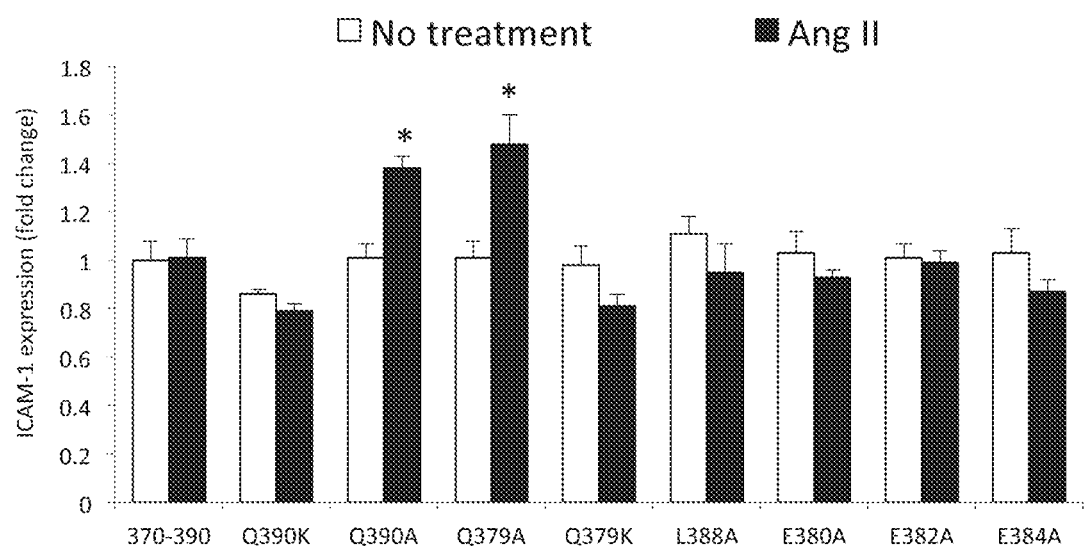

FIG. 12D. The effect of transfection with single site-specific alanine or lysine mutants of $RAGE_{370-390}$ on the induction of ICAM-1 by Ang II in murine SVEC. Data are mean±SEM; n=6-8 per group, * vs no treatment control, p<0.05.

FIG. 12E. Sequence homology between $RAGE_{379-390}$ and anti-inflammatory proteins in *Streptomyces* and proteins from other microorganisms.

Example 13

Figure 13A:
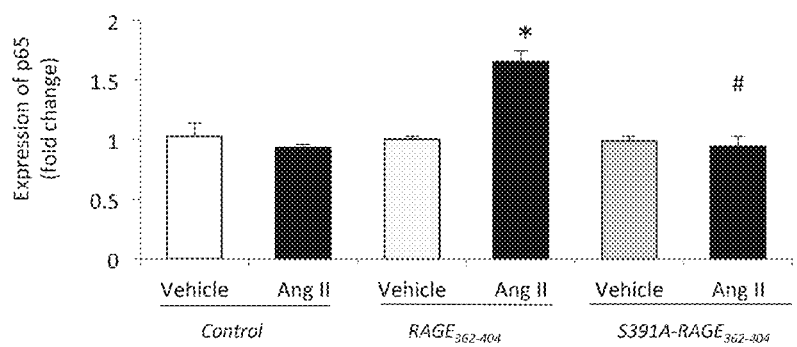

FIG. 13A. The effects of TAT-mCherry-$RAGE_{362-404}$ (0.4 ng/ml) without or with a S391A-RAGE mutation, on the induction of gene expression of the NFκB subunit, p65 by Ang II (1 μM; black bars) in $AT_1R$—CHO cells when compared to TAT-Cherry alone (8 μg). Data are mean±SEM; n=6-8 per group, * vs no treatment control, p<0.05.

Figure 13B:
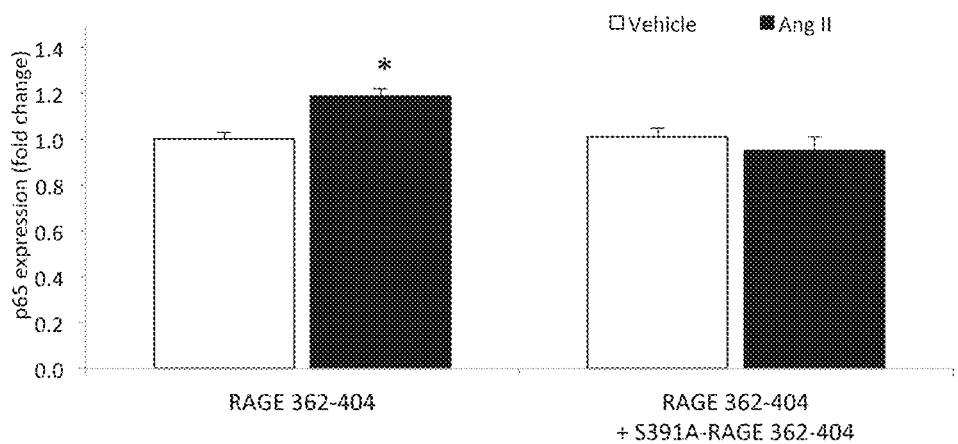

FIG. 13B. The inhibition of signalling achieved by the S391A-$RAGE_{362-404}$ peptide on Ang II-dependent induction of gene expression of the NFκB subunit, p65 in $AT_1R$—CHO cells is not reversed by pre-treatment with the wild-type $RAGE_{362-404}$ peptide. Data are mean±SEM; n=6-8 per group, * vs no treatment control; p<0.05.

Figure 13C:
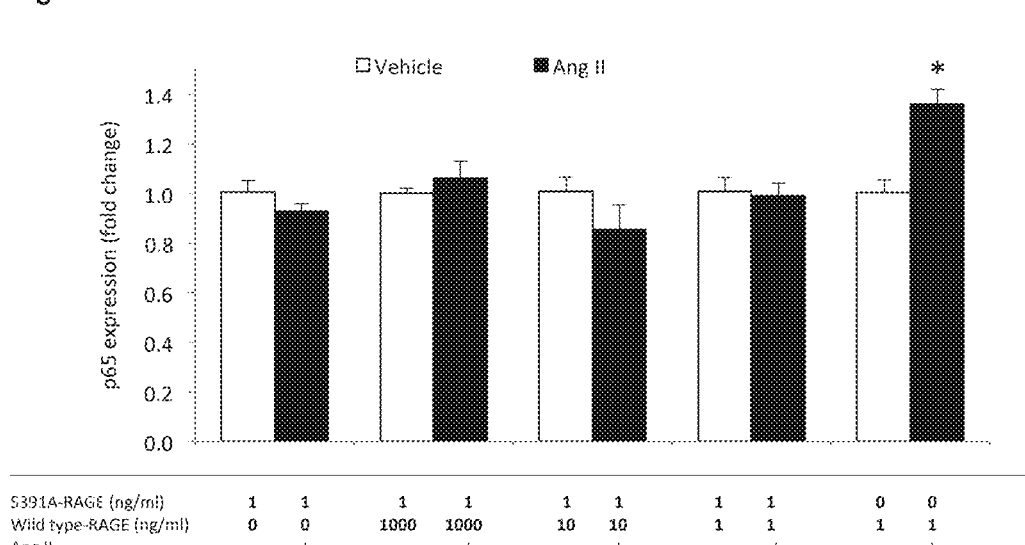

FIG. 13C. The inhibition of signalling achieved by the S391A-$RAGE_{362-404}$ peptide on Ang II-dependent induction of gene expression of the NFκB subunit, p65 in $AT_1R$—CHO cells is observed regardless of subsequent treatment with the wild-type RAGE$_{362-404}$ peptide in a thousand-fold excess. Data are mean±SEM; n=6-8 per group, * vs no treatment control, p<0.05.

Figure 13D:
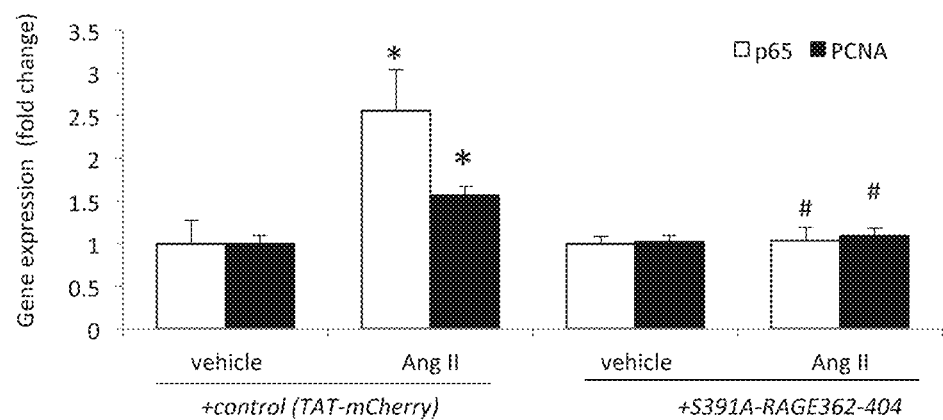

FIG. 13D. The inhibitory effects of S391A-RAGE$_{362-404}$ peptide on induction of p65 and PCNA gene expression in response to Ang II in AT$_1$R—CHO cells transfected with full length S391Q-cRAGE with no available targets for phosphorylation. Data are mean±SEM; n=6-8 per group, * vs Ang II # versus full length wild type RAGE; p<0.05.

Figure 13E:
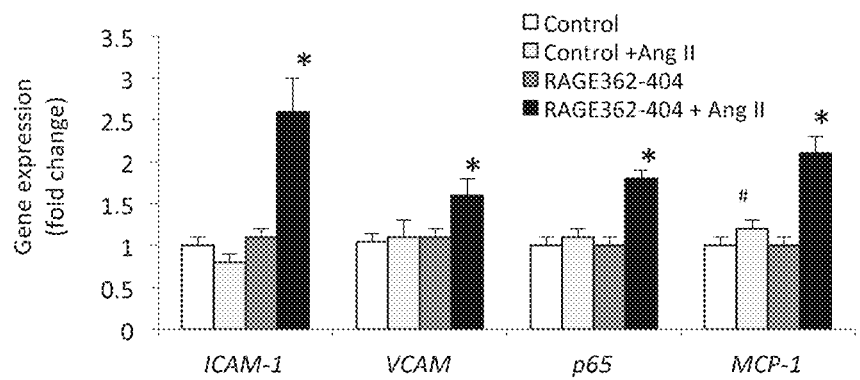

FIG. 13E. The effects of the wild-type RAGE$_{362-404}$ peptide (0.4 ng/ml) on induction of pro-inflammatory gene expression in RAGE-deficient PMAECs in response to Ang II. Data are mean±SEM; n=6-8 per group, * vs no treatment control, p<0.05.

Figure 13F:
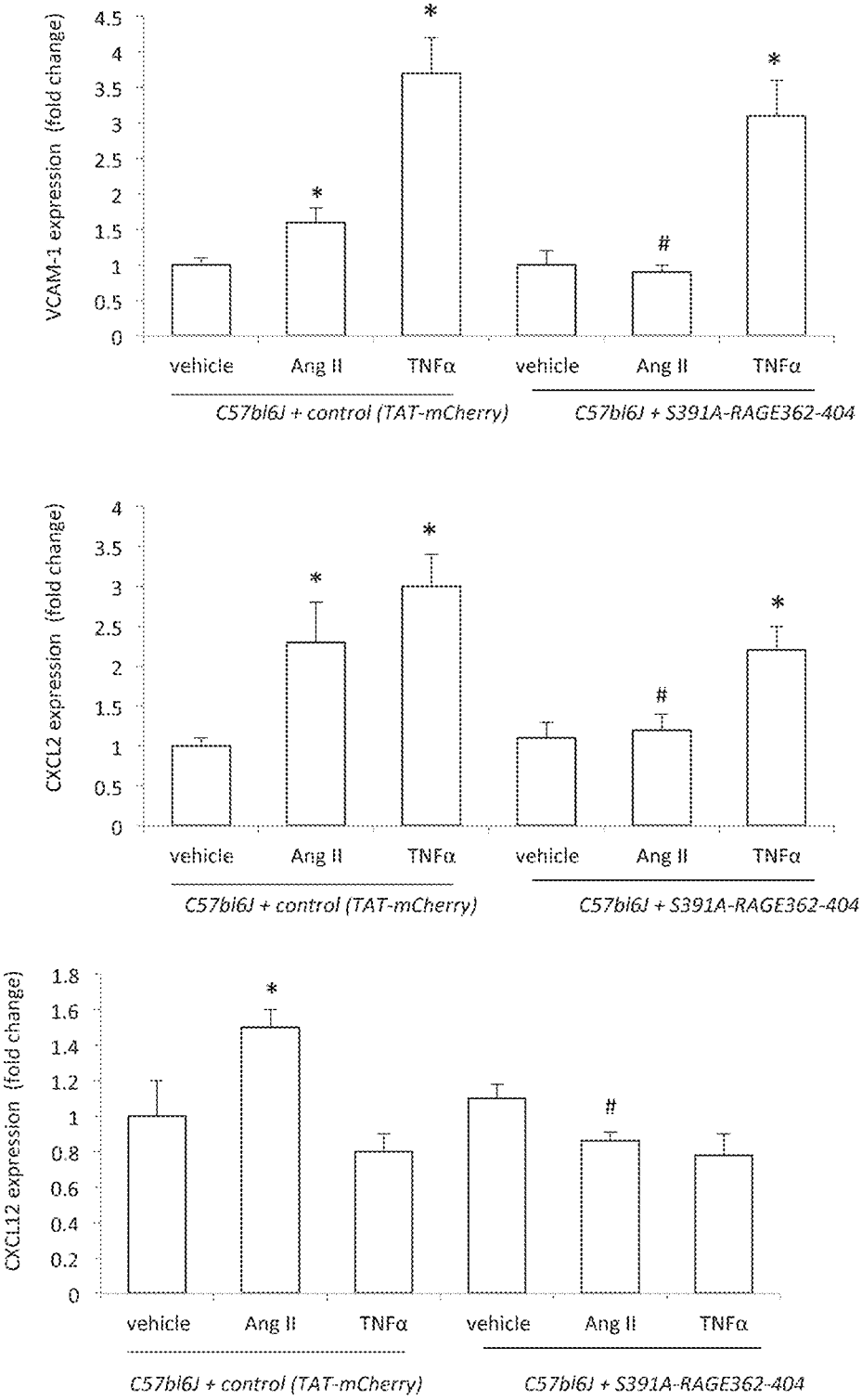

FIG. 13F. The effect of S391A-RAGE$_{362-404}$ peptide on induction of pro-inflammatory VCAM-1, CXCL2 and CXCL12 gene expression in PMAECs in response to Ang II, with response to TNFα as a control. Data are mean±SEM; n=6-8 per group, * vs vehicle and control (TAT) treated, # vs Ang II and control (TAT) treated; p<0.05.

Figure 13G:
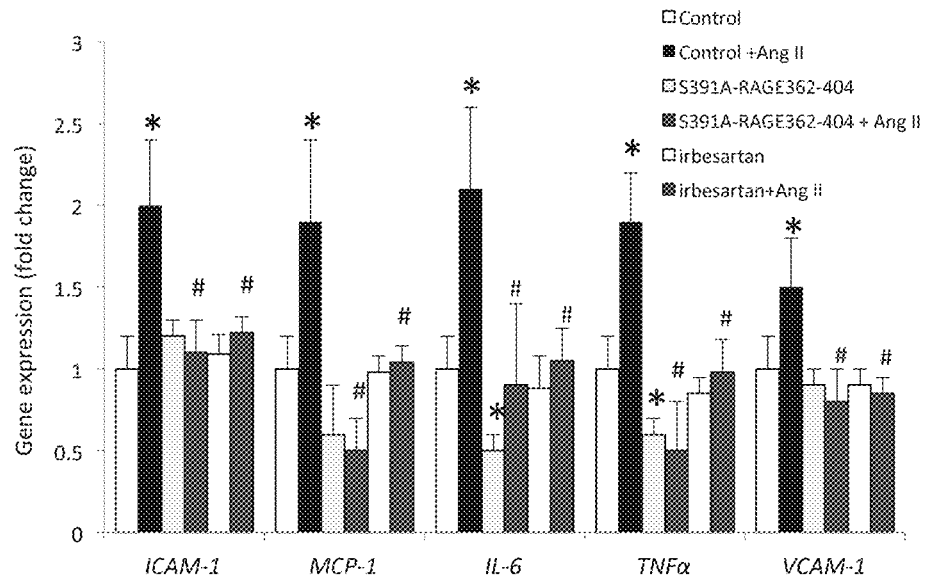

FIG. 13G. The effect of S391A-RAGE$_{362-404}$ peptide and the AT$_1$R blocker, irbesartan, on induction of pro-inflammatory gene expression in response to Ang II in HAECs.

Figure 13H:
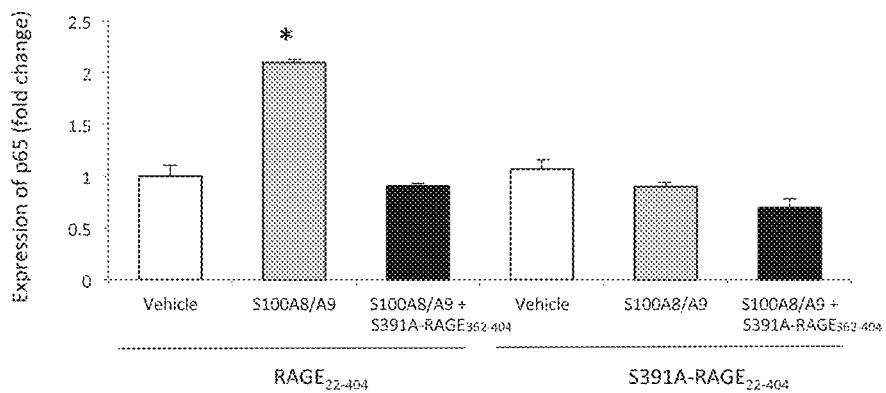
Figure 13H:
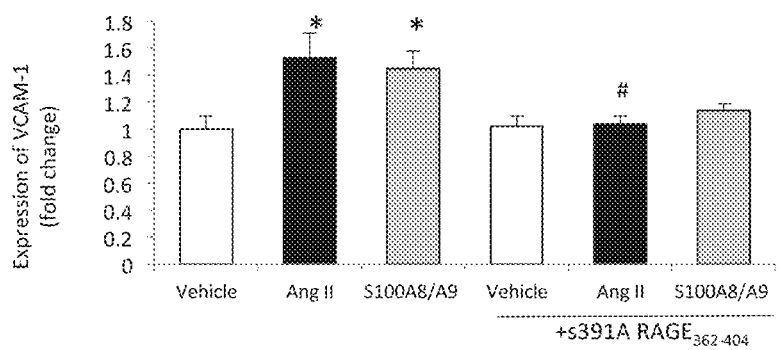

FIG. 13H. (i) The inhibitory effect of the S391A-RAGE$_{362-404}$ peptide on induction of pro-inflammatory gene expression (p65) in response to the RAGE ligand S100A8/A9 in AT$_1$R—CHO cells also expressing full length RAGE, with AT$_1$R—CHO cells expressing the inactive full length S391A-RAGE mutant shown as a control. (ii) The inhibitory effect of S391A-RAGE$_{362-404}$ peptide on induction of pro-inflammatory gene expression (VCAM-1) in response to Ang II or the RAGE ligand S100A8/A9 in PMAEC endogenously replete in RAGE.

Data are mean±SEM; n=6-8 per group, * vs vehicle control, p<0.05, # vs control +Ang II, p<0.05, unless stated otherwise.

Example 14

Figure 14A:
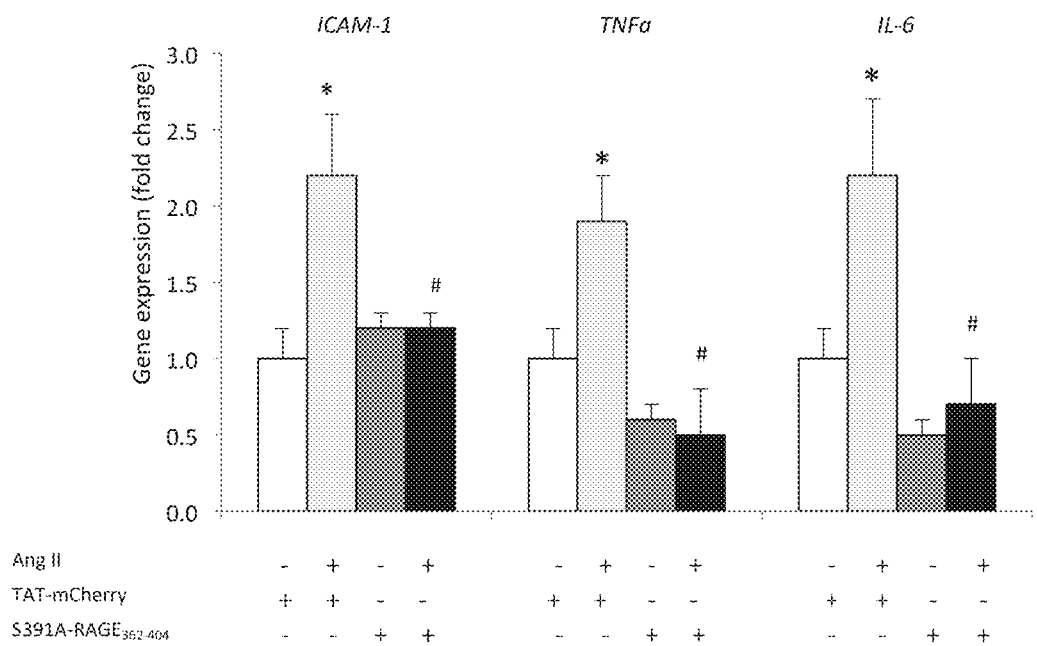

FIG. 14A. The effect of S391A-RAGE$_{362-404}$ on Ang II-dependent induction of pro-inflammatory markers following ex vivo exposure of whole aortae from apoE KO mice to Ang II (1 μM). Data are mean±SEM; n=6 per group, * vs apoE KO+vehicle+TAT-mCherry control, p<0.05, # vs apoE KO+TAT-mCherry control+Ang II, p<0.05.

Figure 14B:
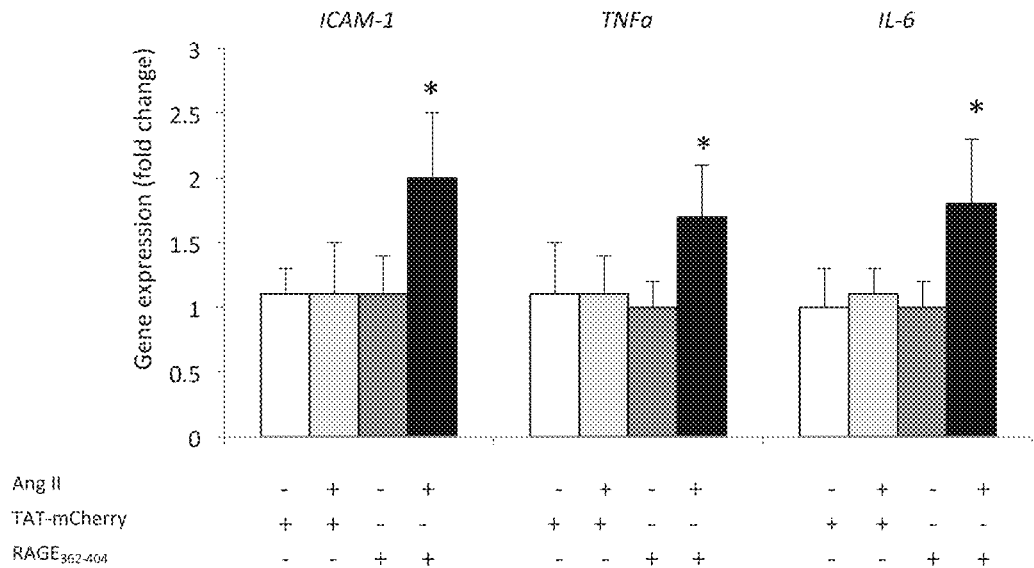

FIG. 14B. The effect of wild-type RAGE$_{362-404}$ on Ang II-dependent induction of pro-inflammatory markers following ex vivo exposure of whole aortae from AGER/apoE KO mice to Ang II (1 μM). Data are mean±SEM; n=8 per group, * vs apoE KO+vehicle+TAT-mCherry control, p<0.05.

Example 15

Figure 15A:
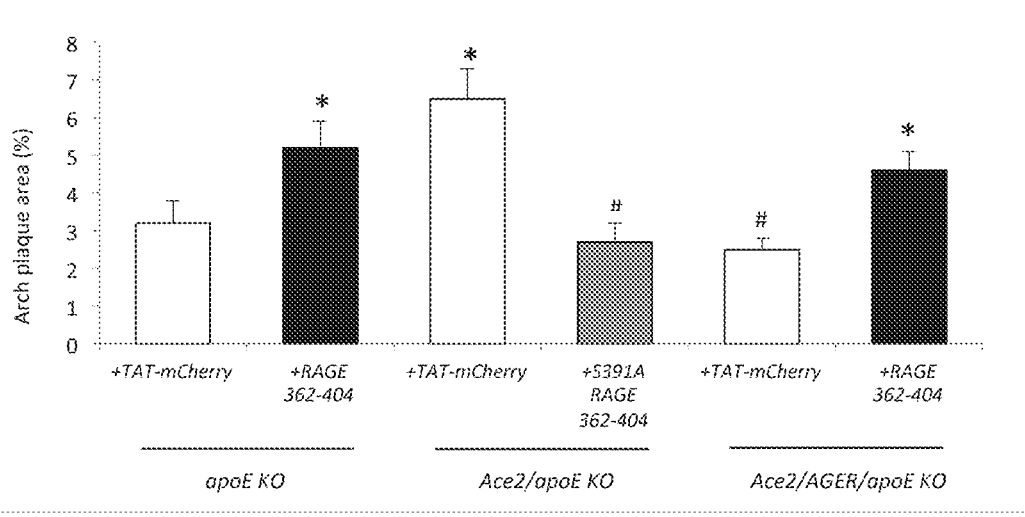

FIG. 15A. The pro-atherosclerotic effect of TAT-mCherry-RAGE$_{362-404}$ comprising the C-terminal 42 amino acids of RAGE tagged with mCherry fluorescent protein and an HIV-TAT motif to facilitate cellular penetration, on Ang II-dependent induction of aortic atherosclerosis in apoE KO and Ace2/AGER/apoE triple KO mice. This is compared to the anti-atherosclerotic effect of TAT-mCherry-S391A-RAGE$_{362-404}$ on Ang II-dependent induction of aortic atherosclerosis in Ace2/apoE DKO mice. Data are mean±SEM; n=8 per group; * vs apoE KO control; # vs Ace2/apoE DKO control; p<0.05.

Figure 15B:
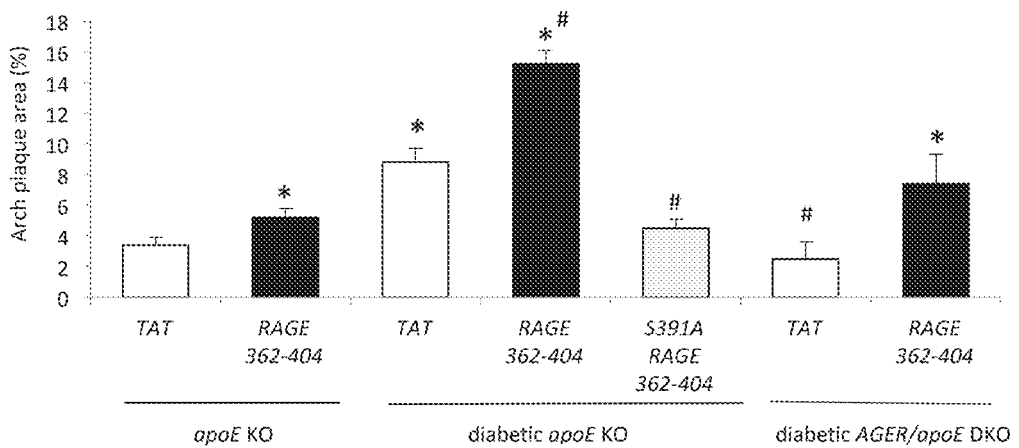

FIG. 15B. The pro-atherosclerotic effect of TAT-mCherry-RAGE$_{362-404}$ peptide, comprising the C-terminal 42 amino acids of RAGE tagged with mCherry fluorescent protein and an HIV-TAT motif to facilitate cellular penetration, on Ang II-dependent induction of aortic atherosclerosis in diabetic apoE KO and diabetic AGER/apoE DKO mice. This is compared to the anti-atherosclerotic effect of TAT-mCherry-S391A-RAGE$_{362-404}$ on Ang II-dependent induction of aortic atherosclerosis in diabetic apoE KO mice. Data are mean±SEM; n=8 per group; * vs apoE KO control # vs diabetic apoE DKO control; p<0.05.

Figure 15C:
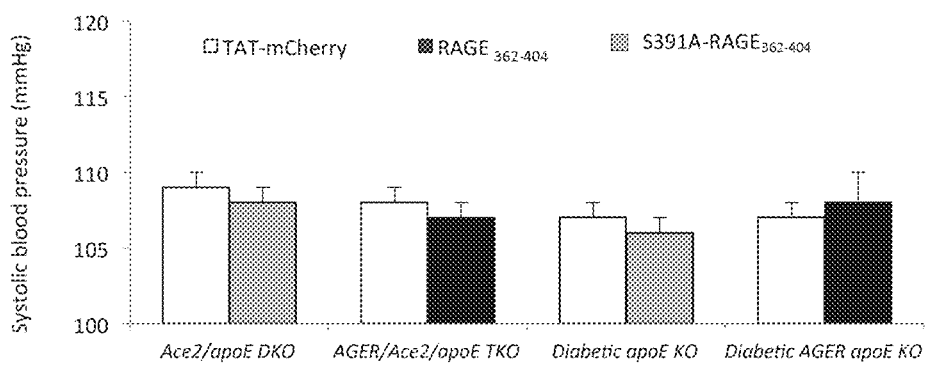

FIG. 15C. The lack of effect of TAT-mCherry-RAGE$_{362-404}$ and TAT-mCherry-S391A-RAGE$_{362-404}$ on systolic blood pressure in mice and diabetic apoE KO mice with or without AGER expression, as shown.

Example 16

Figure 16A:
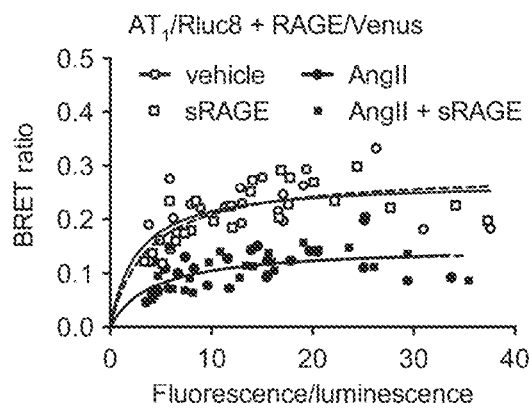

FIG. 16A. BRET saturation curves with AT$_1$/Rluc8 and RAGE/Venus generated 60 minutes following addition of Ang II or vehicle with or without soluble RAGE$_{22-331}$ (sRAGE). Data are combined from 3 independent experiments.

Figure 16B:
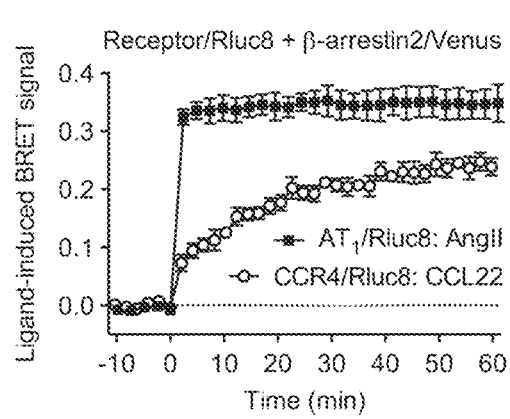

FIG. 16B. Ang II-induced recruitment of βarrestin2/Venus to AT$_1$/Rluc8 and CCL22-induced recruitment of βarrestin2/Venus to CCR4/Rluc8 as controls.

Figure 16C:
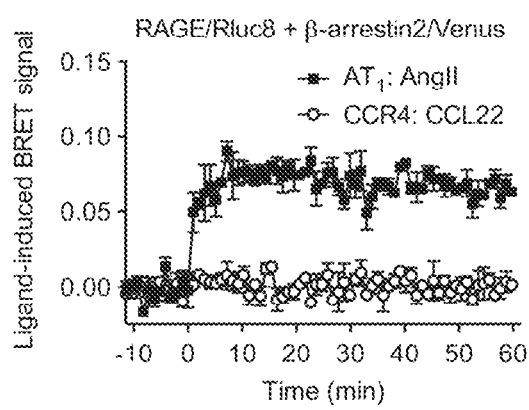

FIG. 16C. Ang II-induced recruitment of β-arrestin2/Venus proximal to RAGE/Rluc8 in the presence of AT1 receptor following exposure to Ang II, and not in the presence of CCR4 following exposure to CCL22.

Figure 16D:
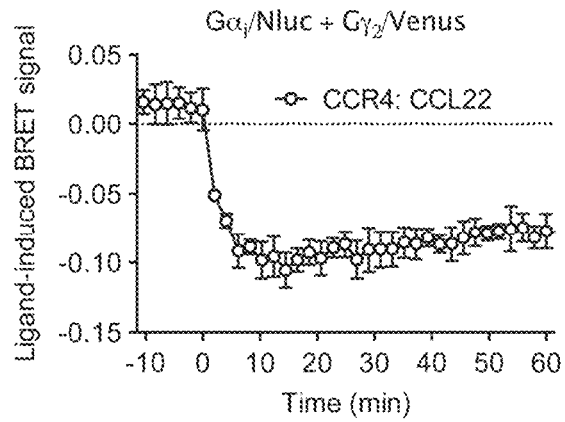

FIG. 16D. CCL22-induced BRET signal is observed when Gαi/Nluc and Gγ2/Venus are co-expressed in the presence of untagged CCR4.

Example 17

Figure 17A:
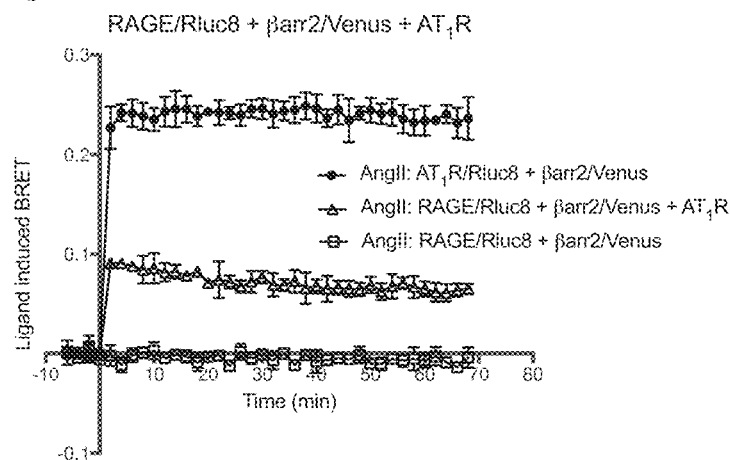

FIG. 17A. Ang II-induced recruitment of β-arrestin2/Venus (β-arr2/Venus) proximal to RAGE/Rluc8 in the presence, but not in the absence, of AT1 receptor. Ang II-induced recruitment of βarrestin2/Venus to AT$_1$/Rluc8 included as a control.

Figure 17B:
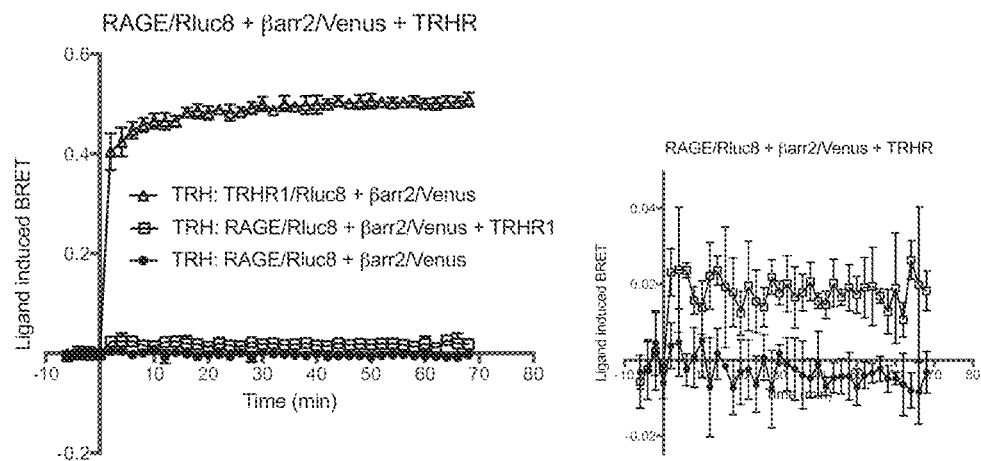

FIG. 17B. Thyrotrophin-releasing hormone (TRH)-induced weak recruitment of β-arrestin2/Venus (β-arr2/Venus) proximal to RAGE/Rluc8 in the presence, but not in the absence, of TRH receptor 1 (TRHR1). TRH-induced recruitment of βarrestin2/Venus to TRHR1/Rluc8 included as a control. Inset shows same data with expanded y-axis scale.

Figure 17C:
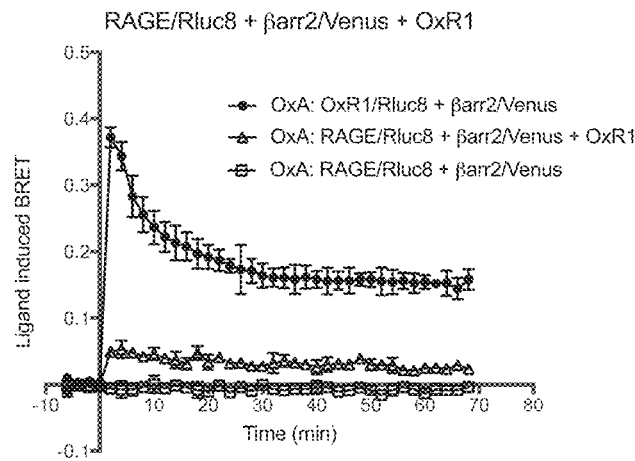

FIG. 17C. Orexin A (OxA)-induced recruitment of β-arrestin2/Venus (β-arr2/Venus) proximal to RAGE/Rluc8 in the presence, but not in the absence, of orexin receptor 1 (OxR1). OxA-induced recruitment of βarrestin2/Venus to OxR1/Rluc8 included as a control.

Figure 17D:
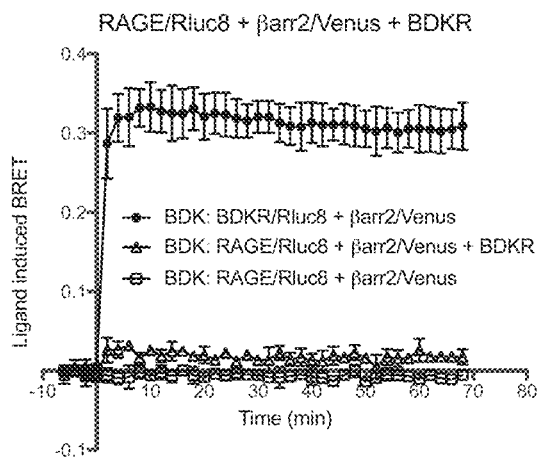
Figure 17D:
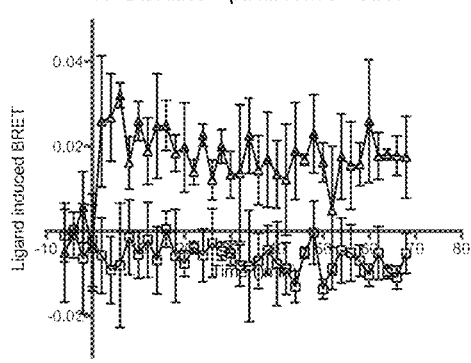

FIG. 17D. Bradykinin (BDK)-induced weak recruitment of β-arrestin2/Venus (β-arr2/Venus) proximal to RAGE/Rluc8 in the presence, but not in the absence, of BDK receptor 2 (BDKR). BDK-induced recruitment of βarrestin2/Venus to BDKR/Rluc8 included as a control. Inset shows same data with expanded y-axis scale.

Figure 17E:
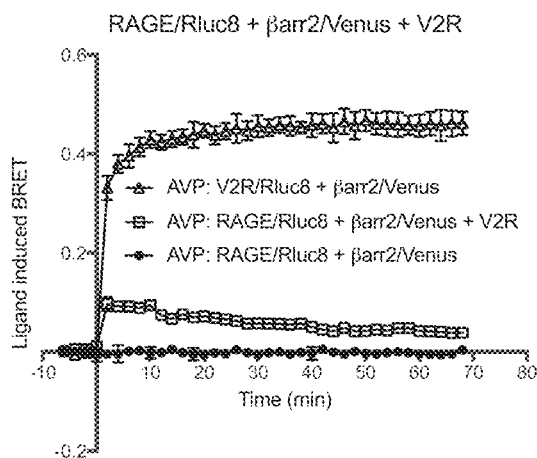

FIG. 17E. Arginine vasopressin (AVP)-induced recruitment of β-arrestin2/Venus (β-arr2/Venus) proximal to RAGE/Rluc8 in the presence, but not in the absence, of vasopressin receptor 2 (V2R). AVP-induced recruitment of βarrestin2/Venus to V2R/Rluc8 included as a control.

Figure 17F:
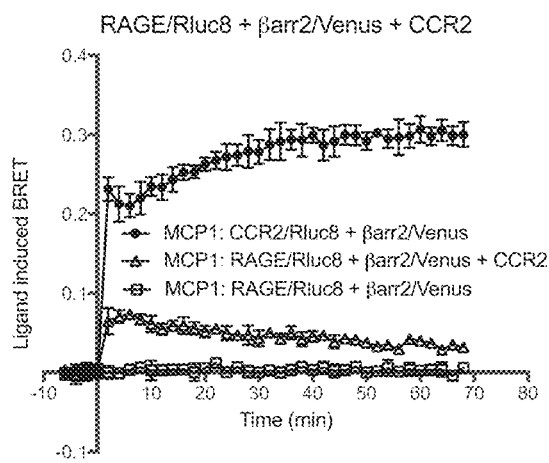

FIG. 17F. CCL2 (MCP1)-induced recruitment of β-arrestin2/Venus (β-arr2/Venus) proximal to RAGE/Rluc8 in the presence, but not in the absence, of CCR2. MCP1-induced recruitment of βarrestin2/Venus to CCR2/Rluc8 included as a control.

Figure 17G:
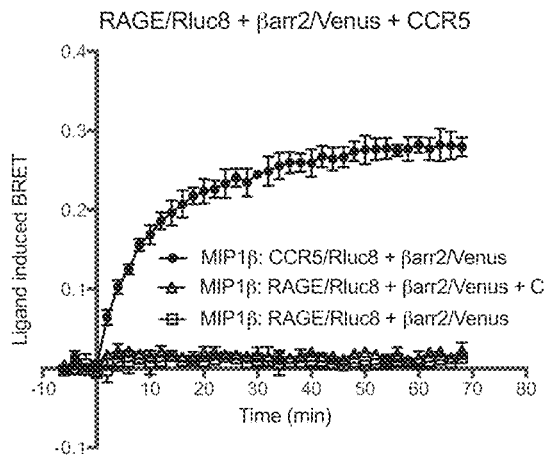
Figure 17G:
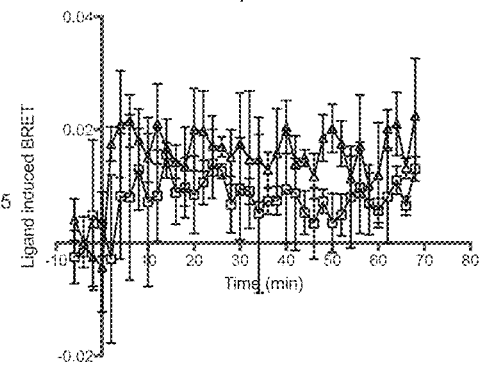

FIG. 17G. CCL4 (MIP1β)-induced particularly weak recruitment of β-arrestin2/Venus (β-arr2/Venus) proximal to RAGE/Rluc8 in the presence of CCR5 following exposure to MIP1β, especially compared to the control in the absence of CCR5. MIP1β-induced recruitment of βarrestin2/Venus to CCR5/Rluc8 included as a further control. Inset shows same data with expanded y-axis scale.

All data are mean±SEM of 3 independent experiments.

Example 18

Figure 18A:
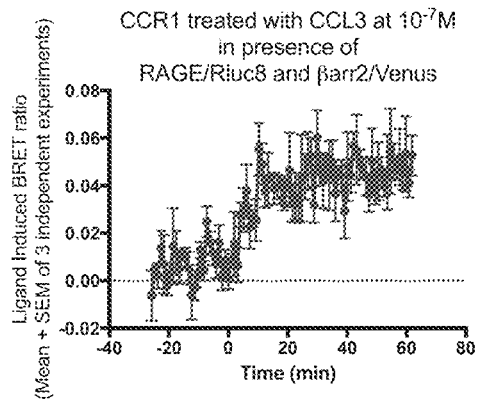

FIG. 18A. CCL3-induced recruitment of β-arr2/Venus proximal to RAGE/Rluc8 in the presence of CCR1.

Figure 18B:
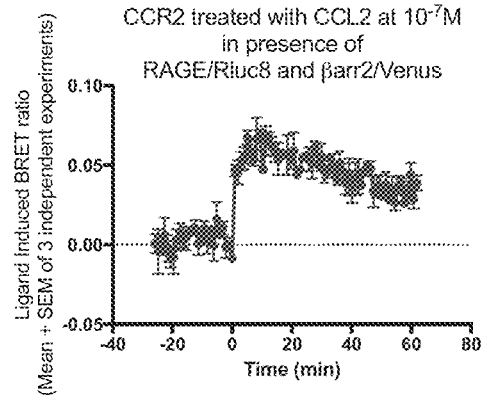

FIG. 18B. CCL2-induced recruitment of β-arr2/Venus proximal to RAGE/Rluc8 in the presence of CCR2.

Figure 18C:
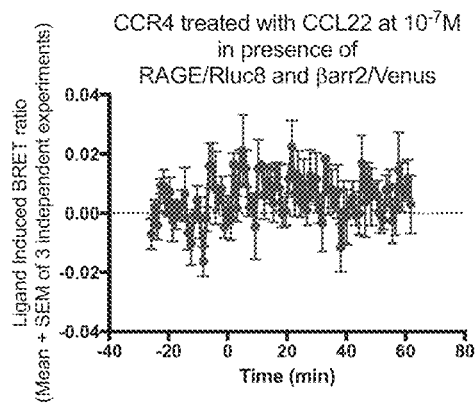

FIG. 18C. Lack of CCL22-induced recruitment of β-arr2/Venus proximal to RAGE/Rluc8 in the presence of CCR4.

Figure 18D:
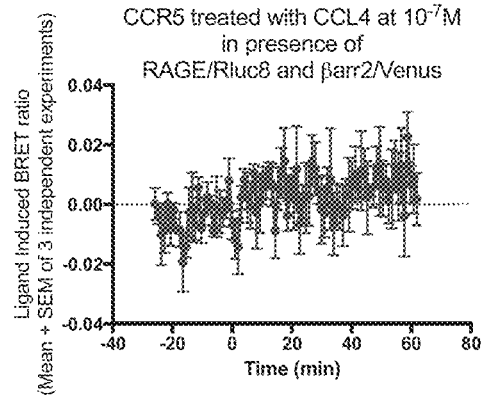

FIG. 18D. Lack of CCL4-induced recruitment of β-arr2/Venus proximal to RAGE/Rluc8 in the presence of CCR5.

Figure 18E:
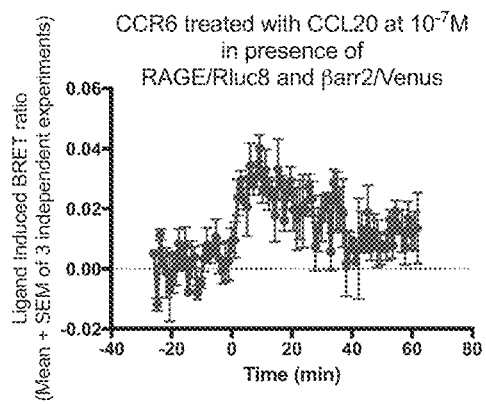

FIG. 18E. CCL20-induced recruitment of β-arr2/Venus proximal to RAGE/Rluc8 in the presence of CCR6.

Figure 18F:
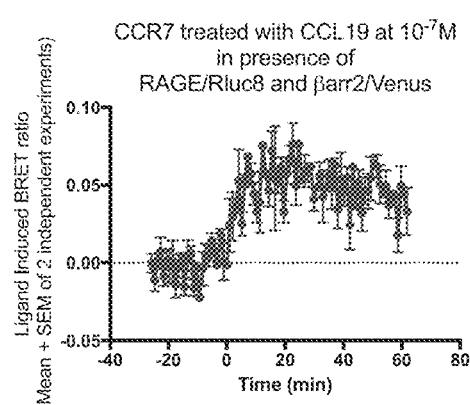

FIG. 18F. CCL19-induced recruitment of β-arr2/Venus proximal to RAGE/Rluc8 in the presence of CCR7.

Figure 18G:
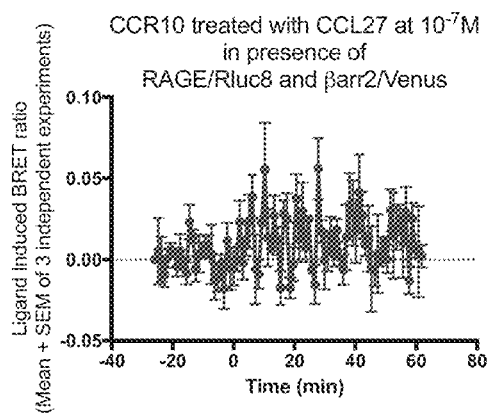

FIG. 18G. Lack of CCL27-induced recruitment of β-arr2/Venus proximal to RAGE/Rluc8 in the presence of CCR10.

Figure 18H:
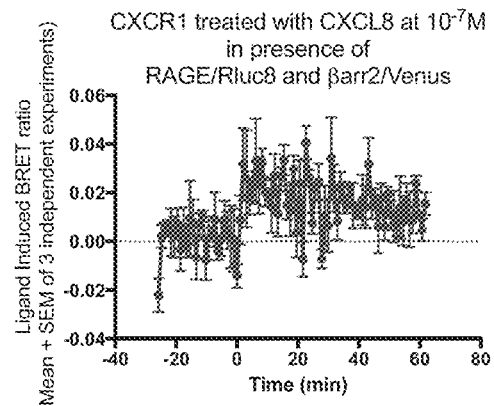

FIG. 18H. Weak CXCL8-induced recruitment of β-arr2/Venus proximal to RAGE/Rluc8 in the presence of CXCR1.

Figure 18I:
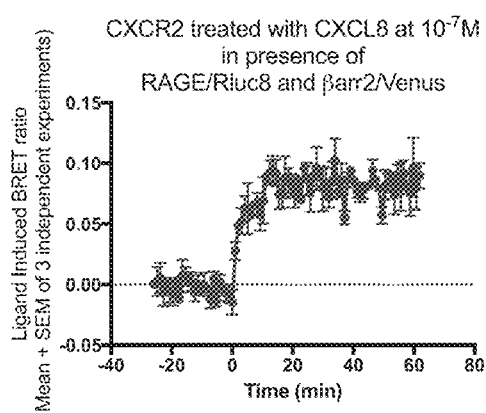

FIG. 18I. CXCL8-induced recruitment of β-arr2/Venus proximal to RAGE/Rluc8 in the presence of CXCR2.

Figure 18J:
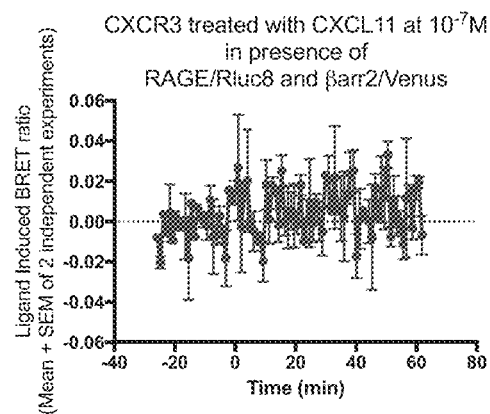

FIG. 18J. Lack of CXCL11-induced recruitment of β-arr2/Venus proximal to RAGE/Rluc8 in the presence of CXCR3.

Figure 18K:
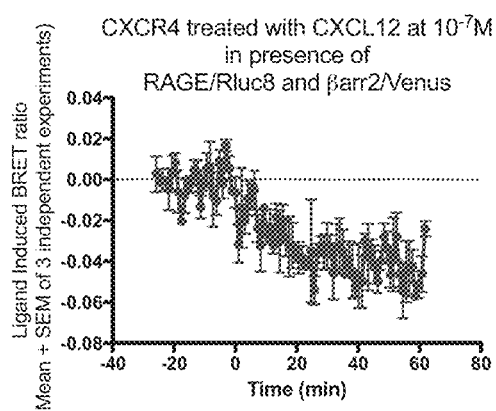

FIG. 18K. CXCL 12-induced reduction in β-arr2/Venus proximity to RAGE/Rluc8 in the presence of CXCR4.

Figure 18L:
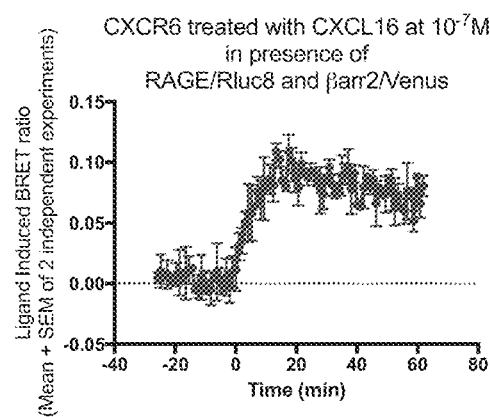

FIG. 18L. CXCL16-induced recruitment of β-arr2/Venus proximal to RAGE/Rluc8 in the presence of CXCR6.

All data are mean±SEM of 3 independent experiments.

Example 19

Figure 19L:
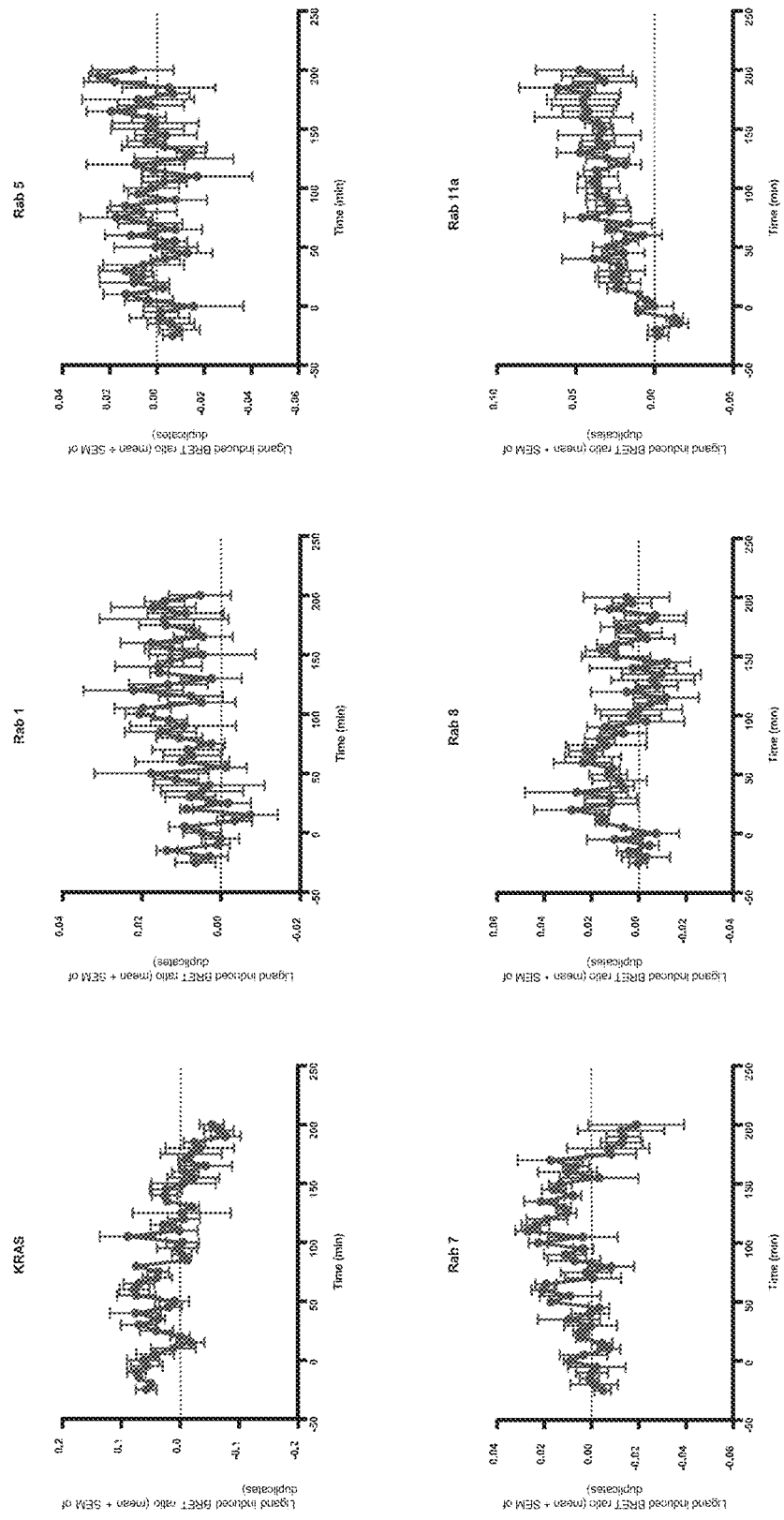

FIG. 19A-OO. Proximity of Rluc8-tagged RAGE to Venus-tagged indicated subcellular compartment markers, in the presence of the indicated non-BRET tagged GPCR activated by the indicated ligand at the indicated concentration at time zero.

Example 20

Figure 20A:
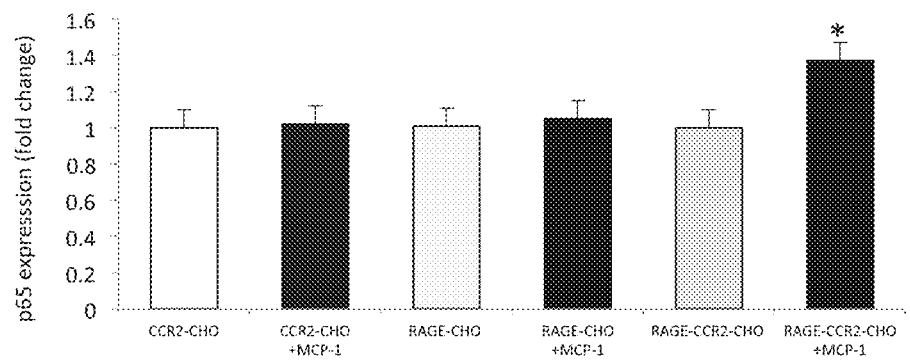

FIG. 20A. Activation of NFκB, as measured by the induction in gene expression of the NFκB subunit, p65, by CCL2 (MCP-1) in CHO cells expressing CCR2 in the presence or absence of RAGE co-expression.

Figure 20B:
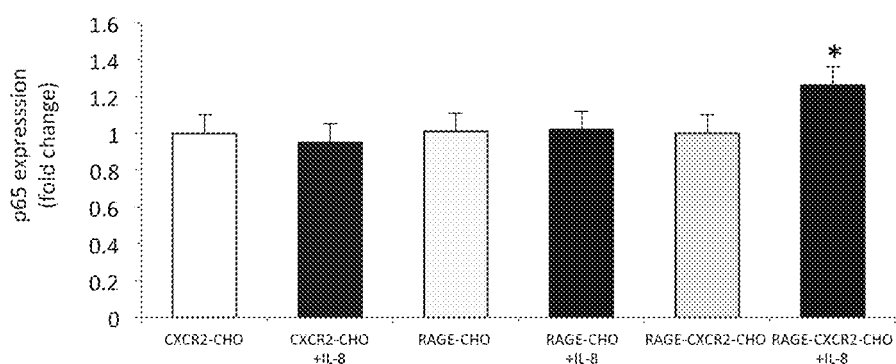

FIG. 20B. Activation of NFκB, as measured by the induction in gene expression of the NFκB subunit, p65, by CXCL2 (IL-8) in CHO cells expressing CXCR2 in the presence or absence of RAGE co-expression.

Figure 20C:
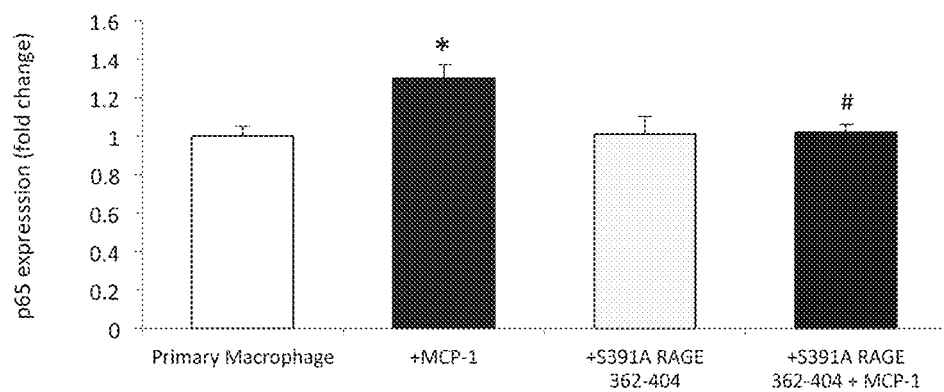

FIG. 20C. Activation of NFκB, as measured by the induction in gene expression of the NFκB subunit, p65, by CCL2 (MCP-1) in bone marrow-derived primary macrophages in the presence or absence of the peptide inhibitor of RAGE activation, S391A-RAGE$_{362-404}$.

Figure 20D:
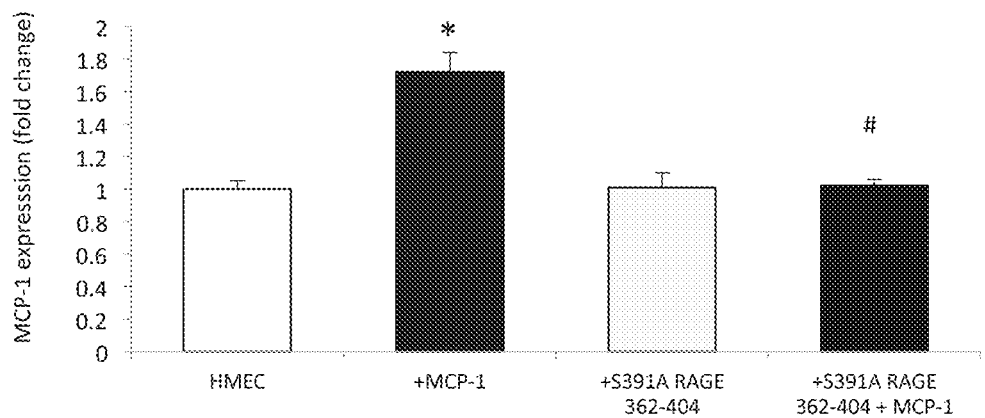

FIG. 20D. Activation of NFκB, as measured by the auto-induction in gene expression of MCP-1, by CCL2 (MCP-1) in HMEC in the presence or absence of the peptide inhibitor of RAGE activation, S391A-RAGE$_{362-404}$.

Figure 20E:
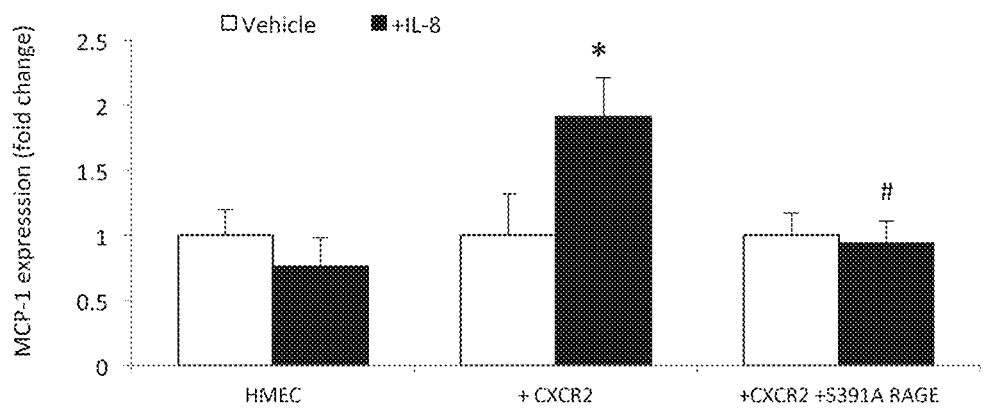

FIG. 20E. Activation of NFκB, as measured by the induction in gene expression of MCP-1, by IL-8 in HMEC expressing CXCR2, in the presence or absence of the peptide inhibitor of RAGE activation, S391A-RAGE$_{362-404}$.

Example 21

Figure 21A:
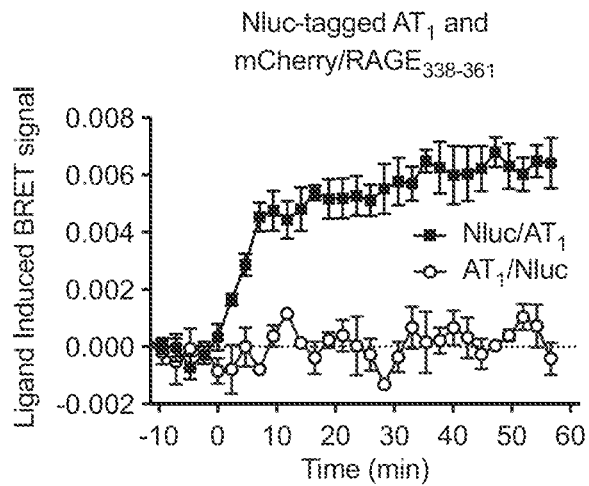

FIG. 21A. BRET between mCherry/RAGE$_{338-361}$ and Nluc/AT$_1$ is increased with Ang II. Data are presented as mean±SEM; n=3-5.

Figure 21B:
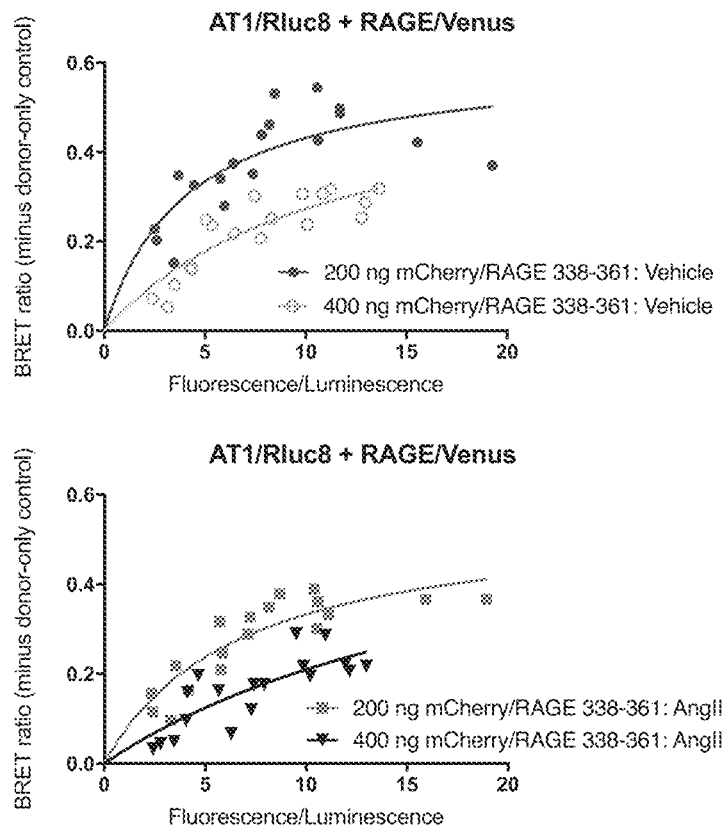

FIG. 21B. BRET saturation curves with AT 1/Rluc8 and RAGE/Venus, where cells were also transfected with either 200 ng or 400 ng of mCherry/RAGE$_{338-361}$ cDNA, generated 60 minutes following addition of vehicle or Ang II as indicated. Data are combined from 3 independent experiments.

Figure 21C:
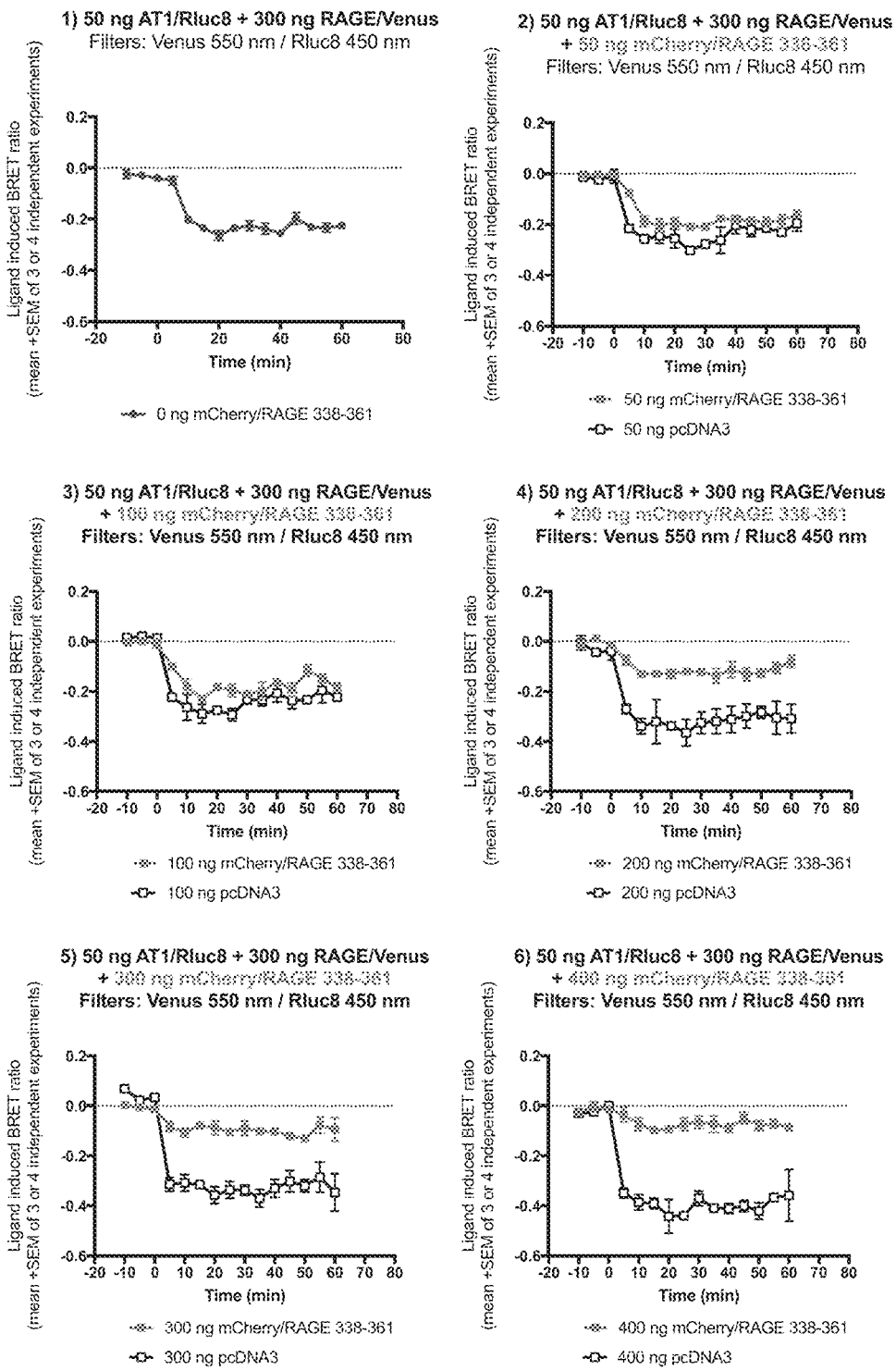

FIG. 21C. Ang II-induced modulation of BRET signal between AT$_1$/Rluc8 and RAGE/Venus where cells were also transfected with 0, 50, 100, 200, 300 or 400 ng of mCherry/RAGE$_{338-361}$ cDNA or pcDNA3 control plasmid as indicated. Data are presented as mean±SEM; n=3-4. Filters: Venus 550 nm/Rluc8 450 nm.

Figure 21D:
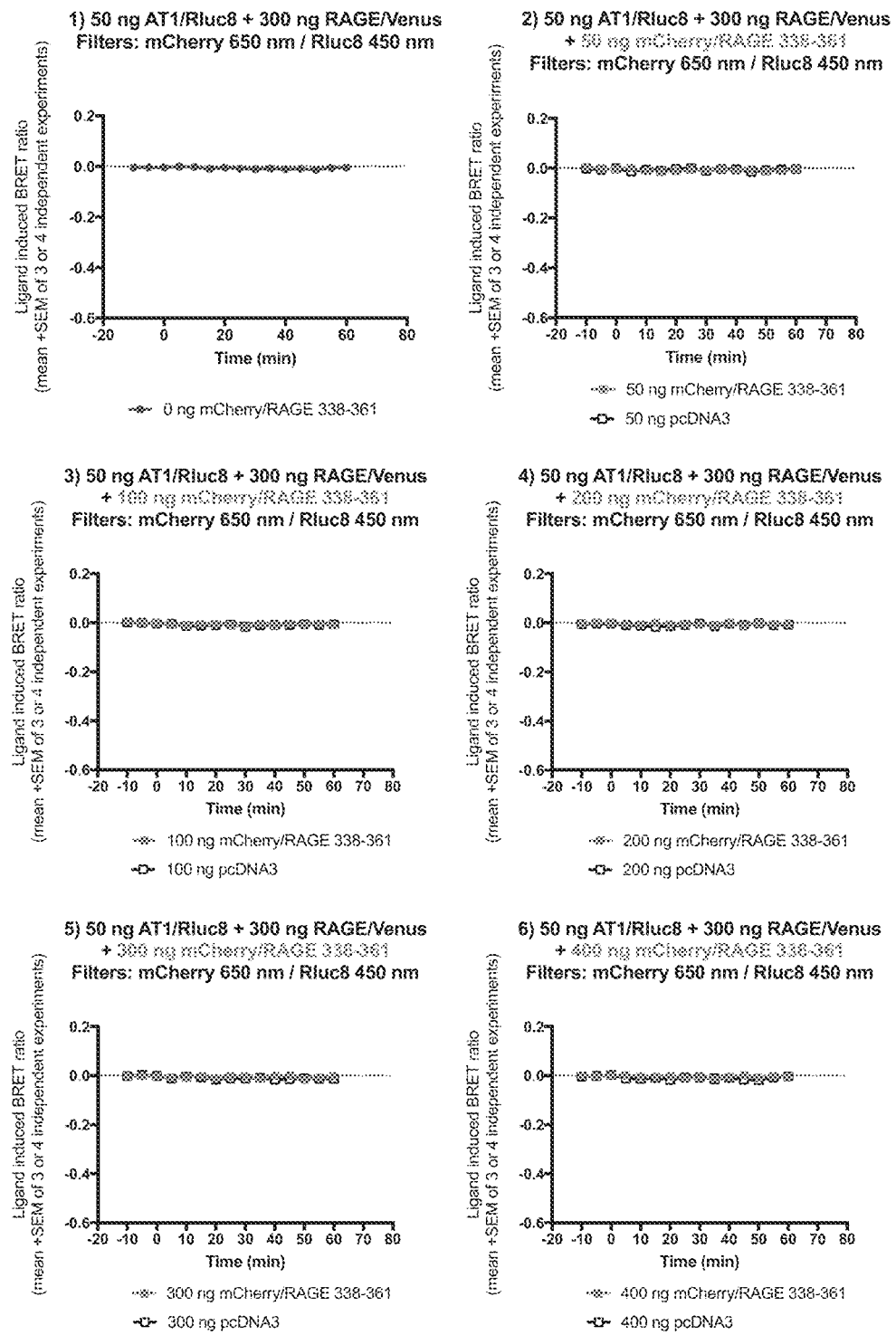

FIG. 21D. Lack of Ang II-induced BRET signal between AT$_1$/Rluc8 and mCherry/RAGE$_{338-361}$ where cells were transfected with 50 ng AT$_1$/Rluc8 cDNA, 300 ng RAGE/Venus cDNA and 0, 50, 100, 200, 300 or 400 ng of mCherry/RAGE$_{338-361}$ cDNA or pcDNA3 control plasmid as indicated. Data are presented as mean±SEM; n=3-4. Filters: mCherry 650 nm/Rluc8 450 nm.

Figure 21E:
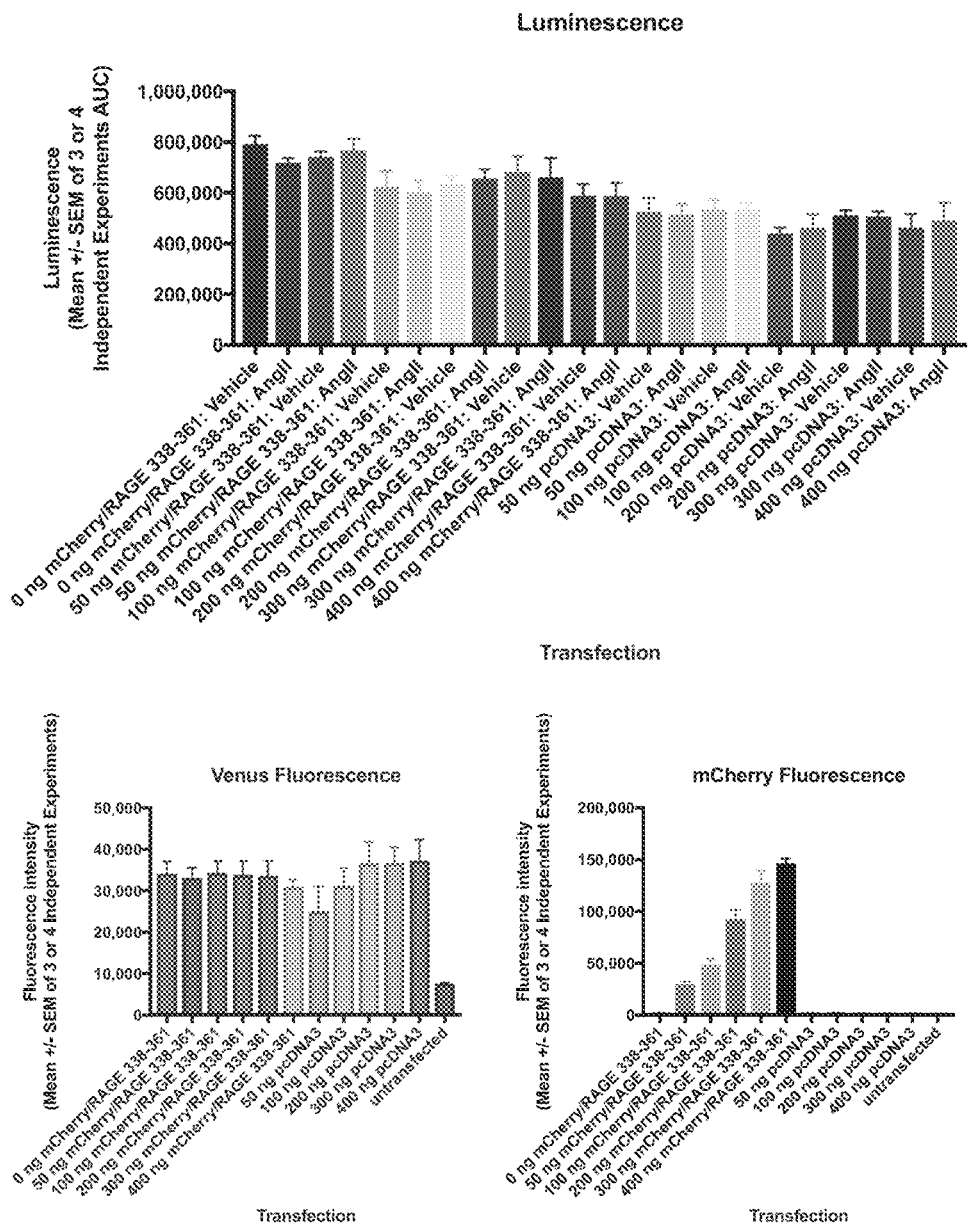

FIG. 21E. Luminescence from AT$_1$/Rluc8, fluorescence from RAGE/Venus and fluorescence from mCherry/RAGE$_{338-361}$ in experiments shown in FIGS. 21C and 21D. Data are presented as mean±SEM; n=3-4.

FIGS. 21F1-21F4. Ligand-induced modulation of BRET signal between GPCR/Rluc8 and RAGE/Venus where cells were also transfected with mCherry/RAGE$_{338-361}$ cDNA or pcDNA3 control plasmid as indicated. Data are presented as mean±SEM; n=2-4. Filters: Venus 550 nm/Rluc8 450 nm. Amounts of cDNA transfected: 50 ng GPCR/Rluc8+300 ng RAGE/Venus+400 ng of mCherry/RAGE$_{338-361}$ or pcDNA3. Indicated Rluc8-tagged GPCR activated by indicated ligand, at indicated concentration, at time zero.

Figure 21G:
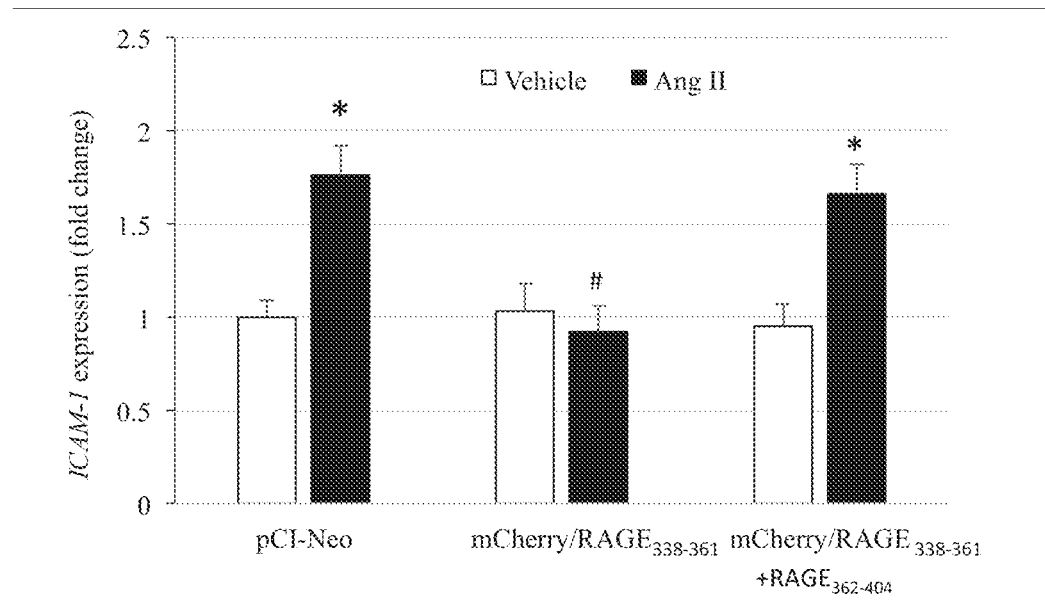

FIG. 21G. AngII-mediated pro-inflammatory signaling (ICAM-1 expression) in HMEC1 inhibited by mCherry/RAGE$_{338-361}$ is rescued by mCherry/RAGE$_{362-404}$. Data are presented as mean±SEM; n=6-8.

Figure 21H:
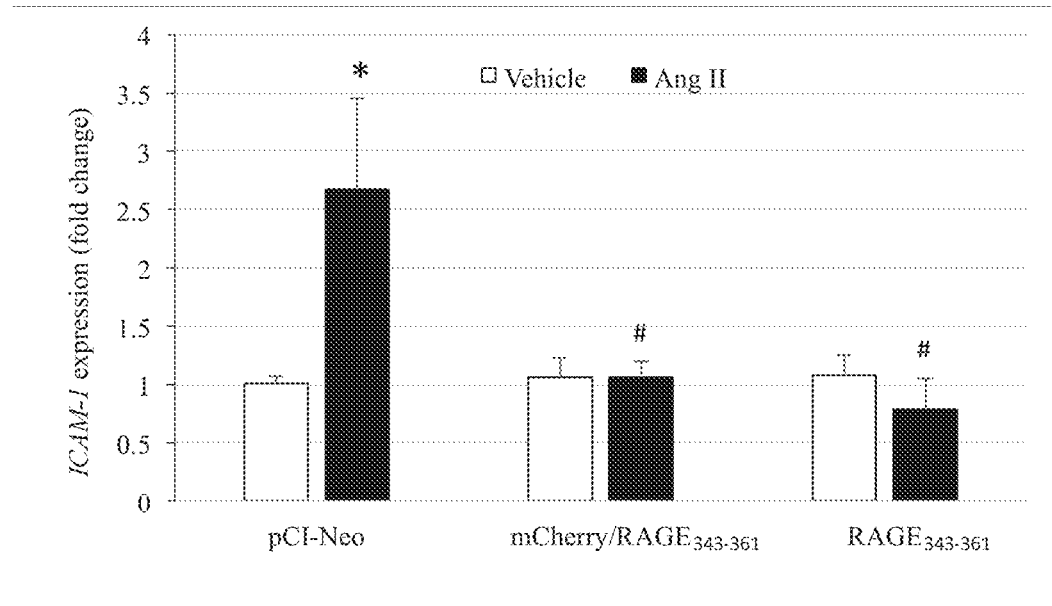

FIG. 21H. The induction of proinflammatory signalling by Ang II in HMEC cells is inhibited by overexpression of the RAGE transmembrane domain RAGE$_{343-361}$ with or without an N-terminal mCherry fusion to monitor expression, as denoted by the expression of ICAM1 as measured using real time RT-PCR. Data are presented as mean±SEM; n=6-8.

Figure 21I:
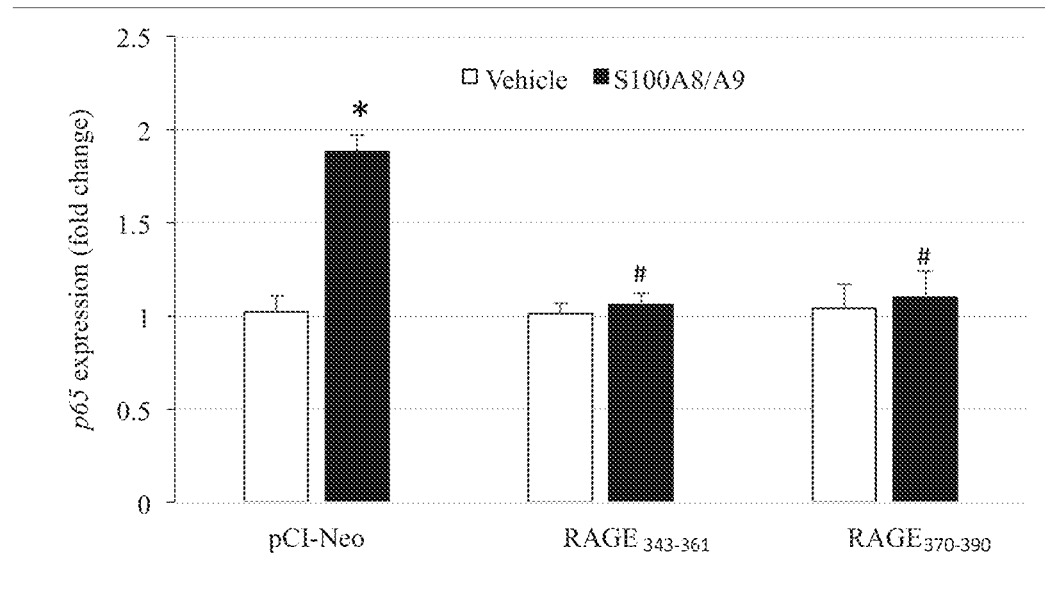

FIG. 21I. The induction of proinflammatory signalling by the RAGE ligand, S100A8/A9, in RAGE-CHO cells is inhibited by overexpression of the RAGE transmembrane domain RAGE$_{343-361}$ alone, or RAGE$_{370-390}$, as denoted by the expression of p65 as measured using real time RT-PCR. Data are presented as mean±SEM; n=6-8.

Figure 21J:
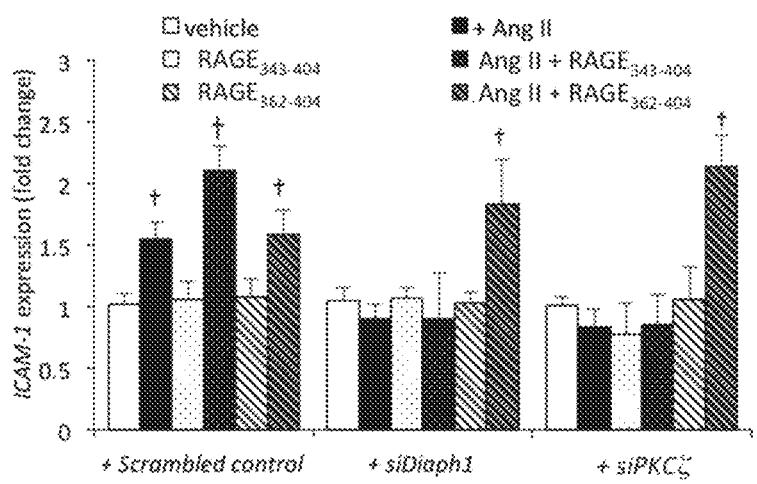

FIG. 21J. The induction of proinflammatory signalling by Ang II in HMEC cells is inhibited by siRNA targeting Diaph1 or PKCz, as denoted by the expression of ICAM-1 as measured by real time RT-PCR. This inhibition is rescued by RAGE$_{362-404}$, but not RAGE$_{343-404}$. Data are presented as mean±SEM; n=6-8.

BRIEF DESCRIPTION OF THE SEQUENCES

| SEQUENCE ID NUMBER | SEQUENCE | LENGTH |
|---|---|---|
| SEQ ID NO: 1 | Polypeptide sequence of $RAGE_{362-404}$ | 43 aa |
| SEQ ID NO: 2 | Polypeptide sequence of $S391A\text{-}RAGE_{362-404}$ | 43 aa |
| SEQ ID NO: 3 | Polypeptide sequence of $RAGE_{338-361}$ | 24 aa |
| SEQ ID NO: 4 | HIV TAT cell penetrating motif (YGRKKRRQRRR) | 11 aa |
| SEQ ID NO: 5 | Polypeptide sequence of $RAGE_{370-390}$ | 21 aa |
| SEQ ID NO: 6 | Polypeptide sequence of $RAGE_{379-390}$ | 12 aa |
| SEQ ID NO: 7 | Polypeptide sequence of $S391A\text{-}RAGE_{362-391}$ | 30 aa |
| SEQ ID NO: 8 | Polypeptide sequence of $RAGE_{362-390}$ | 29 aa |
| SEQ ID NO: 9 | Polypeptide sequence of Q390R $RAGE_{379-390}$ | 12 aa |
| SEQ ID NO: 10 | Polypeptide sequence of Q390K $RAGE_{379-390}$ | 12 aa |
| SEQ ID NO: 11 | Polypeptide sequence of Q379K $RAGE_{379-390}$ | 12 aa |
| SEQ ID NO: 12 | Polypeptide sequence of Q379K Q390K $RAGE_{379-390}$ | 12 aa |
| SEQ ID NO: 13 | Polypeptide sequence of Q379K Q390R $RAGE_{379-390}$ | 12 aa |
| SEQ ID NO: 14 | Full length polypeptide sequence of wild-type human RAGE. | 404 aa |
| SEQ ID NO: 15 | Full length polynucleotide sequence of human AGER gene. | 1704 nts |
| SEQ ID NO: 16 to 58 | Full length polypeptide sequences of wild-type human G protein-coupled receptors. | various |
| SEQ ID NO: 59 | Wild-type Renilla reniformis luciferase polypeptide sequence. | 311 aa |
| SEQ ID NO: 60 | Cys124Ala/Met185Val variant Renilla reniformis luciferase polypeptide sequence. | 311 aa |
| SEQ ID NO: 61 | Variant Renilla reniformis luciferase polypeptide sequence (RLuc8). | 311 aa |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

A "receptor heteromer" is defined as a "macromolecular complex composed of at least two (functional) receptor units with biochemical properties that are demonstrably different from those of its individual components." (Ferre et al., 2009).

The articles "a" and "an" are used herein to refer to one or to more than one (i.e. to at least one) of the grammatical object of the article. By way of example, "an element" means one element or more than one element.

By "about" is meant a measurement, quantity, level, value, number, frequency, percentage, dimension, size, amount, weight or length that varies by as much as 10, 9, 8, 7, 6, 5, 4, 3, 2 or 1% to a reference measurement, quantity, level, value, number, frequency, percentage, dimension, size, amount, weight or length.

As used herein, "and/or" refers to and encompasses any and all possible combinations of one or more of the associated listed items, as well as the lack of combinations when interpreted in the alternative (or).

The term "agent", "candidate agent", "modulatory agent", "modulator" "substitute", "functional substitute", "non-functional substitute" or "inhibitor" includes a chemical compound, a mixture of chemical compounds, a biological macromolecule, an extract made from biological materials, a biological organism or part thereof, or other material, which induces a desired pharmacological and/or physiological effect. These terms also encompass pharmaceutically acceptable and pharmacologically active ingredients of those compounds specifically mentioned herein including but not limited to salts, esters, amides, prodrugs, active metabolites, analogues and the like. When the above term is used, then it is to be understood that this includes the active agent per se as well as pharmaceutically acceptable, pharmacologically active salts, esters, amides, prodrugs, metabolites, and analogues. The term "agent", "modulator" "substitute" or "inhibitor" is not to be construed narrowly but extends to small molecules, proteinaceous molecules such as peptides, polypeptides and proteins as well as compositions comprising them and genetic molecules such as RNA, DNA and mimetics and chemical analogues thereof as well as cellular agents. The term "agent", "modulator" "substitute" or "inhibitor" includes a cell that is capable of producing and secreting a polypeptide referred to herein as well as a polynucleotide comprising a nucleotide sequence that encodes that polypeptide. Thus, the term "agent", "modulator" "substitute" or "inhibitor" extends to nucleic acid constructs including vectors such as viral or non-viral vectors, expression vectors and plasmids for expression in and secretion in a range of cells.

The term "inhibitor" is used in its broadest sense, and includes any compound including a protein, polypeptide, peptide, antibody, antibody fragment, large molecule, or small molecule (less than 10 kDa), which decreases at least one aspect of the activity, activation or function of another molecule. For example, an inhibitor may decrease the activity, activation or function of RAGE and/or a certain co-located GPCR, such as an angiotensin receptor such as $AT_1R$ or a certain chemokine receptor such as CCR2, and/or suitably RAGE ligand-independent activation of RAGE by activated certain co-located GPCR such as angiotensin receptor such as $AT_1R$ or a certain chemokine receptor such as CCR2. Thus, an "inhibitor of RAGE ligand-independent activation of RAGE by a certain activated co-located GPCR" refers to an agent that is capable of substantially reducing, inhibiting, antagonising, blocking, negatively modulating and/or mitigating RAGE ligand-independent activation of RAGE by a certain activated co-located GPCR. Inhibition of RAGE ligand-independent activation of RAGE by a certain activated co-located GPCR by an inhibitor suitably reduces or inhibits the biological effect thereof, including the production of pro-inflammatory mediators including pro-inflammatory cytokines by the cell or the modulation of other cellular elements that are associated with aberrant RAGE ligand-independent activation of RAGE disease symptoms. Note a partial agonist can act as an inhibitor as it does not result in maximal efficacy even though it exhibits agonism. Therefore, by competing for or modulating the agonistic activity of a more efficacious agonist, such as the endogenous agonist, it may effectively act as an inhibitor of a receptor polypeptide and/or its signalling pathway as it reduces the signalling output compared to if it was absent. Consequently a partial agonist may act in a therapeutic setting as an inhibitor. An inhibitor does not necessarily inhibit all aspects of the activity, activation or function of another molecule and indeed, may inhibit some aspects while activating other aspects and/or not modulating yet further aspects. Therefore an inhibitor may exhibit ligand bias.

The term "ligand bias" refers to the phenomenon whereby, for the same receptor, distinct ligand-stabilised receptor states can exist that selectively promote or inhibit activation of different signalling pathways (Mustafa et al., 2010). This phenomenon has been given multiple names, including but not limited to: ligand-biased signalling, ligand-induced biased signalling, agonist trafficking of receptor signals, cell-based functional selectivity, receptor active-state based selectivity, stimulus trafficking, biased agonism, collateral efficacy and ligand-induced selective signalling (Mustafa et al., 2010). By way of example, this includes the concept that not all agonists activate all signalling pathways normally activated by a reference agonist, which is often the/an endogenous agonist. An agonist may activate some pathways but not others, relative to the reference, thereby exhibiting bias. Furthermore, an antagonist or inverse agonist or inhibitor may only inhibit some pathways but not others and may act at the orthosteric ligand-binding site and/or an allosteric binding site. Orthosteric and allosteric binding sites are defined as commonly known in the art, and allosterism can occur across complexes from one receptor to another such that binding of a ligand to one receptor can result in allosteric modulation of another receptor in the same macromolecular complex. Allosteric modulators can also exhibit ligand bias and modulate some signalling pathways but not others. It is also known in the art that ligands can potentially, for example, act as an agonist for one signalling pathway while acting as an inhibitor for another signalling pathway and/or not affect a third signalling pathway. Indeed, multiple variations and combinations of signalling modulatory effects can occur. Ligand bias is also not absolute in that a ligand may, for example, reduce signalling via one pathway without completely inhibiting it, and/or incompletely activate another signalling pathway. Pathways can be modulated to different extents and this can be measured by multiple parameters, including but not limited to differences in potency and/or efficacy and/or temporal aspects of signalling and/or spatial aspects of signalling.

The term "functional substitute" is used in its broadest sense, and includes any compound including a protein, polypeptide, peptide, antibody, antibody fragment, large molecule, or small molecule (less than 10 kDa), which in taking the place of another molecule is able to mimic or increases at least one aspect of the activity, activation or function of that molecule. For example, a functional substitute of RAGE may replicate the activity, activation or function of RAGE and/or a certain co-located GPCR, such as an angiotensin receptor such as $AT_1R$ or a certain chemokine receptor such as CCR2, and/or suitably RAGE ligand-independent activation of RAGE by activated certain co-located GPCR such as angiotensin receptor such as $AT_1R$ or a certain chemokine receptor such as CCR2, in a system otherwise devoid of RAGE expression. Thus, "a functional substitute" of RAGE ligand-independent activation of RAGE by a certain activated co-located GPCR" refers to an agent that is capable of substantially increasing, augmenting, agonising, and/or positively modulating RAGE ligand-independent activation of RAGE by a certain activated co-located GPCR. Restoring signalling capability of RAGE ligand-independent activation of RAGE by a certain activated co-located GPCR by a functional substitute suitably restores or augments the biological effect thereof, including the production of pro-inflammatory mediators including pro-inflammatory cytokines by the cell or the modulation of other cellular elements that are associated with RAGE ligand-independent activation of RAGE disease symptoms. A functional substitute does not necessarily mimic all aspects of the activity, activation or function of another molecule and indeed, may inhibit some aspects while activating other aspects and/or not modulate yet further aspects. Therefore a functional substitute may also exhibit ligand bias.

The term "non functional substitute" is used in its broadest sense, and includes any compound including a protein, polypeptide, peptide, antibody, antibody fragment, large molecule, or small molecule (less than 10 kDa), which in taking the place of another molecule is able to inhibit, antagonise or reduce at least one aspect of the activity, activation or function of that molecule. For example, a non functional substitute of RAGE may inhibit the activity, activation or function of RAGE and/or a certain co-located GPCR, such as an angiotensin receptor such as $AT_1R$ or a certain chemokine receptor such as CCR2, and/or suitably RAGE ligand-independent activation of RAGE by activated certain co-located GPCR such as angiotensin receptor such as $AT_1R$ or a certain chemokine receptor such as CCR2. Thus, "a non functional substitute" of RAGE ligand-independent activation of RAGE by a certain activated co-located GPCR" refers to an agent that is capable of substantially reducing, inhibiting, antagonising, and/or negatively modulating RAGE ligand-independent activation of RAGE by a certain activated co-located GPCR. Reducing signalling capability of RAGE ligand-independent activation of RAGE by a certain activated co-located GPCR by a non functional substitute suitably reduces or inhibits the biological effect thereof, including the production of pro-inflammatory mediators including pro-inflammatory cytokines by the cell or the modulation of other cellular elements that are associated with RAGE ligand-independent activation of RAGE disease symptoms. Note a partial agonist can also act as an inhibitor as it does not result in maximal efficacy even though it exhibits agonism. Therefore, by competing for or modulating the agonistic activity of a more efficacious agonist, such as the endogenous agonist, it may effectively act as an inhibitor of a receptor polypeptide and/or its signalling pathway as it reduces the signalling output compared to if it was absent. Consequently a partial agonist may act in a therapeutic setting as an inhibitor. A non functional substitute does not necessarily reduce all aspects of the activity, activation or function of another molecule and indeed, may inhibit some aspects while facilitating other aspects and/or not modulating yet further aspects. Therefore a non functional substitute may also exhibit ligand bias.

The term "binding" and its grammatical equivalents refer to a physical association between molecules, due to, for example, covalent, electrostatic, hydrophobic, and ionic and/or hydrogen-bond interactions under physiological conditions, and includes interactions such as salt bridges and water bridges, as well as any other conventional means of binding. Binding may occur directly or via interactions with one or more other intermediary molecules.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be contained within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

By "effective amount", in the context of treating or preventing a condition is meant the administration of an amount of an agent or modulator, such as an inhibitor, or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "expression" with respect to a gene sequence refers to transcription of the gene to produce a RNA transcript (e.g. mRNA, antisense RNA, siRNA, shRNA, miRNA) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence. "Expression" may also refer to the location of a gene product in, on or outside a cell, including cell compartments or structures, illustrative examples of which include cytoplasm, nucleus, ribosome, lysosome and cell membrane or surface.

By "expression vector" is meant any genetic element capable of directing the transcription of a polynucleotide contained within the vector and suitably the synthesis of a peptide or polypeptide encoded by the polynucleotide. Such expression vectors are known to practitioners in the art.

As used herein, the term "function" refers to a biological, enzymatic, or therapeutic function.

As used herein, the term "gene" refers to a nucleic acid molecule capable of being used to produce mRNA, antisense RNA, siRNA, shRNA, miRNA and the like. Genes may or may not be capable of being used to produce a functional protein. Genes can include both coding and non-coding regions (e.g., introns, regulatory elements, promoters, enhancers, termination sequences and 5' and 3' untranslated regions).

The term "host cell" refers to a cell into which a polynucleotide or nucleic acid construct is introduced. Host cells of the invention include, but need not be limited to, bacterial, yeast and animal (including vertebrate animals falling within the scope of the term "subject" as defined herein). Host cells can be unicellular, or can be grown in tissue culture as liquid cultures, monolayers or the like. Host cells may also be derived directly or indirectly from tissues or may exist within an organism including animals (including vertebrate animals falling within the scope of the term "subject" as defined herein).

The term "interaction" refers to the effect based on intermolecular force between two molecules, and examples thereof include ion-to-ion interaction, interaction by a hydrogen bond, dipole-dipole interaction, hydrophobic interaction, and combinations thereof, and includes binding between molecules. Interaction can occur directly or via one or more other intermediary molecules.

The term "functional interaction" refers to one molecule affecting the function of another molecule and does not necessarily mean that the two molecules are physically interacting with each other.

The term "luciferase" means a polypeptide corresponding to a luciferase protein, that emits light upon oxidation of its substrate. An exemplary luciferase protein is *Renilla* luciferase or a derivative thereof, that oxidises coelenterazine. Another example luciferase protein is NanoLuc.

The term "analogue" refers to a small molecule that, because of its structural analogy to the endogenous peptide, is capable of mimicking at least one biological function of the peptide to which it is analogous. A "peptide analogue" is an analogue that is a peptide in nature as it contains peptide bonds and has a modular structure composed of amino acids or their derivatives. A "non-peptide analogue" is an analogue that is not a peptide in nature as it does not contain peptide bonds and does not have a modular structure composed of amino acids or their derivatives as building blocks.

By way of illustration, a RAGE analogue may mimic the ability of RAGE to form a heteromer complex with $AT_1R$ but suitably inhibits transactivation of RAGE by an $AT_1R$ ligand acting via $AT_1R$.

The term "derivative" refers to a molecule that its primary structure is taken from or owes its derivation to the cytosolic tail of RAGE or fragment thereof, but which includes amino acid additions, substitutions, truncations, chemical and/or biochemical modifications, retro-inverted sequences, cyclic peptides, peptoids, β-peptides, or linkage to a non-peptide drug, non-peptide label, non-peptide carrier, or non-peptide resin.

As used herein, the terms "modulating", "regulating" and their grammatical equivalents refer to an effect of altering a biological activity or effect (e.g., cytokine production, cellular adhesion, GPCR signalling, RAGE signalling). For example, an agonist, antagonist, inverse agonist or allosteric modulator of a particular biomolecule modulates the activity of that biomolecule, e.g., a receptor, by either increasing/stimulating (e.g., agonist, activator, positive allosteric modulator), or decreasing/inhibiting (e.g., antagonist, inhibitor, inverse agonist, negative allosteric modulator) the activity or effect (e.g., cytokine production, cellular adhesion, receptor signalling) of the biomolecule, such as a receptor.

The term "operably connected" or "operably linked" as used herein refers to a juxtaposition wherein the components so described are in a relationship permitting them to function in their intended manner. For example, a regulatory sequence "operably linked" to a coding sequence refers to positioning and/or orientation of the regulatory sequence relative to the coding sequence to permit expression of the coding sequence under conditions compatible with the regulatory sequence.

By "pharmaceutically acceptable carrier" is meant a pharmaceutical vehicle comprised of a material that is not biologically or otherwise undesirable, i.e., the material may be administered to a subject along with the selected active agent or modulator, such as an inhibitor, without causing any or a substantial adverse reaction. Carriers may include excipients and other additives such as diluents, detergents, colouring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that is not biologically or otherwise undesirable.

The terms "polynucleotide," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogues of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

By "proximity" refers to the distance between two integers (generally, polypeptides). For example, the proximity of a RAGE polypeptide and a GPCR polypeptide is meant the relative distance between the two polypeptides. If two polypeptides directly interact, they are considered to be spatially near one another, or described as being in close proximity. If two polypeptides are part of the same heteromer and/or macromolecular complex but are not directly interacting they are also considered to be in close proximity. More specifically, for the purposes of the present invention a distance of around 30 nm or less, 10 nm or less, or 5 nm or less would be considered to be within close proximity.

By "proximity screening assay" is meant an assay, system or experimental approach that comprises the bringing of a first and second reporter component into proximity to generate a detectable proximity signal. Proximity of the first and second reporter components generates a proximity signal capable of detection by the detector. The first and second reporter components constitute a complementary pair, in the sense that the first reporter component may be interchanged with the second reporter component (i.e. the first reporter component coupled to the RAGE polypeptide and the second reporter component coupled to the GPCR polypeptide or the first reporter component coupled to the GPCR polypeptide and the second reporter component coupled to the RAGE polypeptide) without appreciably affecting the functioning of the invention. Direct physical contact between the RAGE polypeptide and the GPCR polypeptide or between the reporter components is not required and may be mediated by one or more linkage molecule(s). Preferably, the proximity signal generated by the proximity of the first and second reporter components in the presence of the reporter component initiator is selected from the group consisting of: luminescence, fluorescence and colorimetric change. In some embodiments, the luminescence is produced by a bioluminescent protein selected from the group consisting of luciferase, galactosidase, lactamase, peroxidase, or any protein capable of luminescence in the presence of a suitable substrate.

The term "reporter component" can be any known compound, organic or inorganic, proteinaceous or non-proteinaceous or complex thereof, that when in proximity to another reporter component is capable of resulting in the emission of a detectable proximity signal. In some embodiments, the reporter component is selected from the group comprising, consisting or consisting essentially of an enzyme, a luminescent molecule or part thereof, a fluorescent molecule or part thereof and a transcription factor or other molecule coupled to the RAGE polypeptide and/or the certain co-located GPCR polypeptide, such as angiotensin receptor such as $AT_1R$ or certain chemokine receptors such as CCR2. In some embodiments, reporter components can include enzymes, luminescent or bioluminescent molecules, fluorescent molecules, and transcription factors or other molecules coupled to the RAGE polypeptide and/or the certain co-located GPCR polypeptide by linkers incorporating enzyme cleavage sites.

In some aspects of the present invention, the proximity reporter system involves combinations of pairs of reporter components, capable of being a donor and/or acceptor molecule. Accordingly, the reporter components that can be used according to the present invention can be selected based on the physical properties thereof, as is known in the art of resonance energy transfer (RET), the two being selected so that they together comprise the donor and acceptor molecules of a RET pair. If one of the reporter components within a RET pair is a bioluminescent protein, the RET is known as bioluminescence RET (BRET). If both reporter components forming a RET pair are fluorophores the resulting RET is known as fluorescence RET (FRET). Examples of known suitable donor and acceptor pairs include: *Renilla* luciferase (or variant thereof) and yellow fluorescent protein; *Renilla* luciferase (or variant thereof) and green fluorescent protein (or variant thereof); NanoLuc and yellow fluorescent protein; NanoLuc and mCherry fluorescent protein; NanoLuc and HaloTag (with suitable HaloTag ligand); Cyan fluorescent protein and yellow fluorescent protein; fluorescein and tetramethylrhodamine; 5-(2'-aminoethyl) aminonaphthalene-1-sulfonic acid (EDANS) and fluorescein (See generally R. Haugland, Handbook of Fluorescent Probes and Research Chemicals, Sixth Ed. 1995). One or both of the fluorophores can be a fluorescent protein such as green fluorescent protein, and it is particularly advantageous to employ a fluorescent protein as the fluorophore by preparing a fusion protein of the RAGE polypeptide or the certain co-located GPCR polypeptide and a fluorescent protein.

Preferable combinations of first and second reporter components include a luminescent reporter component with a fluorescent reporter component, a luminescent reporter component with a non-fluorescent quencher, a fluorescent reporter component with a non-fluorescent quencher, first and second fluorescent reporter components capable of resonance energy transfer. However, useful combinations of first and second reporter components are by no means limited to such. Alternate combinations of first and second reporter components that may be utilised by the present invention include those exemplified in U.S. Pat. No. 6,893,827 (Applera Corporation); U.S. Pat. No. 6,800,445 (Applera Corporation); U.S. Pat. No. 7,049,076 (Sentigen Biosciences, Inc., and The Trustees of Columbia University of the City of New York); U.S. Pat. No. 6,110,693 (Duke University); U.S. Pat. No. 5,891,646 (Duke University); WO/2005/031309 (ODYSSEY THERA INC.); and U.S. Pat. No. 8,101,373 (DiscoveRx Corporation).

The terms "coupled", "coupled directly" and "coupled indirectly" as used herein means that the reporter component is attached to or associated with the RAGE polypeptide and/or certain co-located GPCR polypeptide to form an entity that is capable of being analysed or detected. The direct or indirect coupling of the reporter components to the RAGE polypeptide and/or certain co-located GPCR polypeptide may be by any known covalent or non-covalent means of coupling two molecules, including chemical cross-linking, chemical modification of proteins, chemical modification of amino acids, chemical modification of nucleic acids, chemical modification of carbohydrates, chemical modification of lipids, chemical modification of any other organic or inorganic molecule, biotin-avidin interactions, antigen-antibody interaction and nucleic acid hybridisation. In one form of the invention, the reporter components are coupled indirectly to the RAGE polypeptide and/or certain co-located GPCR polypeptide by a linker. In some embodiments, the linker comprises an enzyme cleavage site. An example of a direct method of coupling a RAGE polypeptide and/or certain co-located GPCR polypeptide and a proteinaceous reporter component is genetic fusion, wherein the genes encoding the RAGE polypeptide and/or the certain co-located GPCR polypeptide and the bioluminescent or fluorescent protein are fused to produce a single polypeptide chain. Another example of a direct coupling method is conjugation, wherein the coupling of the RAGE polypeptide and/or the certain co-located GPCR polypeptide with the reporter component uses enzymes such as ligases, hydrolases, particularly phosphatases, esterases and glycosidases, or oxidoreductases, particularly peroxidases.

In a preferred embodiment of the invention, the RAGE polypeptide forms a single polypeptide chain with a reporter component and/or the certain co-located GPCR polypeptide forms a single polypeptide chain with a reporter component. In a particularly preferred form of the invention, the reporter components are different. Additional functionality may form part of the same polypeptide chain. For example, the single polypeptide chain additionally comprises: a sequence coding for a peptide sequence used for affinity purification of a fusion construct; and/or a sequence coding for a peptide sequence which directs the fusion construct to a subcellular compartment of a eukaryotic cell; and/or a sequence coding for a peptide sequence that facilitates the penetration of a eukaryotic cell membrane; and/or a sequence enabling expression levels to be assessed by the use of antibodies or otherwise.

By "regulatory sequence" is meant a nucleic acid sequence (e.g., DNA) that expresses an operably linked nucleotide sequence (e.g., a coding sequence) in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

The terms "salts," "derivatives" and "prodrugs" includes any pharmaceutically acceptable salt, ester, hydrate, or any other compound which, upon administration to the recipient, is capable of providing (directly or indirectly) a compound of the invention, or an active metabolite or residue thereof. Suitable pharmaceutically acceptable salts include salts, of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl, and butyl chlorides, bromides and iodides; dialkyl sulfates like dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs and derivatives can be carried out by methods known in the art. For example, metal salts can be prepared by reaction of a compound of the invention with a metal hydroxide. An acid salt can be prepared by reacting an appropriate acid with a compound of the invention.

The term "selective" refers to compounds that modulate an interaction, suitably a physical interaction (e.g., binding) between a RAGE polypeptide and certain co-located GPCR polypeptide without substantially modulating another biological interaction of the RAGE polypeptide or the certain co-located GPCR polypeptide. Accordingly, a compound that is selective for the direct RAGE—certain co-located GPCR interaction exhibits a selectivity of greater than about 2-fold, 5-fold, 10-fold, 20-fold, 50-fold or greater than about 100-fold with respect to modulation of another binding activity of RAGE or of the certain co-located GPCR to another substrate or binding partner.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, California, USA) using standard defaults as used in the reference manual accompanying the software.

"Similarity" refers to the percentage number of amino acids that are identical or constitute conservative substitutions as defined below.

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

As used herein a "small molecule" refers to a composition that has a molecular weight of less than 3 kilodaltons (kDa), and typically less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kDa, less than 1.5 kDa, or even less than about 1 kDa.

"Stringency" as used herein, refers to the temperature and ionic strength conditions, and presence or absence of certain organic solvents, during hybridization and washing procedures. The higher the stringency, the higher the degree of complementarity will be between immobilized target nucleotide sequences and probe nucleotide sequences that remain hybridized to the target after washing. Stringency conditions include low, medium, high and very high stringency conditions, which describe certain conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at room temperature. One embodiment of low stringency conditions includes hybridization in 6×sodium chloride/sodium citrate (SSC) at about 45 C, followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO4 (pH 7.2), 7% SDS for hybridization at 65° C., and (i) 2 xx SSC, 0.1% SDS; or (ii) 0.5% BSA, 1 mM EDTA, 40 mM NaHPO4 (pH 7.2), 5% SDS for washing at 60-65° C. One embodiment of medium stringency conditions includes hybridizing in 6 xx SSC at about 45° C., followed by one or more washes in 0.2 xx SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO4 (pH 7.2), 7% SDS for hybridization at 65° C., and (i) 0.2 xx SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6 xx SSC at about 45° C., followed by one or more washes in 0.2 xx SSC, 0.1% SDS at 65° C. In certain embodiments, a peptide or polypeptide is encoded by a polynucleotide that hybridizes to a reference nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C. Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the Tm for formation of a DNA-DNA hybrid. It is well known in the art that the Tm is the melting temperature, or temperature at which two complementary polynucleotide sequences dissociate. Methods for estimating Tm are well known in the art (see Ausubel et al., supra at page 2.10.8). In general, the Tm of a perfectly matched duplex of DNA may be predicted as an approximation by the formula:

$$Tm=81.5+16.6(\log 10 M)+0.41(\% G+C)-0.63(\% formamide)-(600/length)$$

wherein:

M is the concentration of Na+, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The Tm of a duplex DNA decreases by approximately 1° C. with every increase of 1% in the number of randomly mismatched base pairs. Washing is generally carried out at Tm—15° C. for high stringency, or Tm—30° C. for moderate stringency. In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA) containing labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

The terms "subject," "host", "individual" or "patient," used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars), marine mammals (e.g., dolphins, whales), reptiles (e.g., snakes, frogs, lizards), and fish. In specific embodiments, the subject is a primate such as a human. However, it will be understood that the terms "patient," "subject," "host" or "individual" do not imply that symptoms are present.

As used herein, the terms "treatment", "treating", and the like, refer to obtaining a desired pharmacologic and/or physiologic effect. The effect may be therapeutic in terms of a partial or complete cure for a disease or condition (e.g., a hematologic malignancy) and/or adverse effect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

The term "variant" is employed broadly to refer to a protein that differs in some way from a reference wild-type protein, where the protein may retain biological properties of the reference wild-type protein, or may have biological properties that differ from the reference wild-type protein. The term "biological property" of the subject proteins includes, but is not limited to, spectral properties, such as emission maximum, quantum yield, brightness, and the like; in vivo and/or in vitro stability (e.g. half-life); and the like. Variants can include single amino acid changes (substitutions), deletions of one or more amino acids (point deletions), N-terminal truncations, C-terminal truncations, insertions, and the like. Polypeptide variants can be generated using standard techniques well known in molecular biology.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integratable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, or two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

Unless the context requires otherwise, "RAGE" or "RAGE polypeptide" shall indicate the protein product or products generated from transcription and translation and/or alternative splicing of the AGER gene, also known as the AGER nucleotide or AGER polynucleotide, or the RAGE nucleotide or RAGE polynucleotide.

Unless the context requires otherwise, "$AT_1R$" or "$AT_1R$ polypeptide" or "$AT_1$ receptor", or "$AT_1R$" shall indicate the protein product or products generated from transcription and translation and/or alternative splicing of the AGTR1, Agtr1a or Agtr1b genes, also known as $AT_1R$ nucleotide or $AT_1R$ polynucleotide. For example, in humans, one gene codes for $AT_1R$ located on chromosome 3q21-q25 (IUPHAR database, www.guidetopharmacology.org). In mouse, two genes code for $AT_1R$, Agtr1a located on chromosome 13 16.0 cM and Agtr1b located on chromosome 3 7.6 cM (IUPHAR database, www.guidetopharmacology.org). In rat, two genes code for $AT_1R$, Agtr1a located on chromosome 17q12 and Agtr1b located on chromosome 2q24 (IUPHAR database, www.guidetopharmacology.org).

In some instances, the protein product or products of the Agtr1a gene may be referred to as $AT_{1a}R$ and the protein product or products of the Agtr1b gene may be referred to as $AT_{1b}R$, however, the protein product or products of the Agtr1a and Agtr1b genes may both be referred to as $AT_1R$.

Each embodiment described herein is to be applied mutatis mutandis to each and every embodiment unless specifically stated otherwise.

2. Abbreviations

The following abbreviations are used throughout the application:
aa=amino acid(s);
d=day;
h=hour;
kb=kilobase(s) or kilobase pair(s);
kDa=kilodalton(s);
nm=nanometre;
nt=nucleotide;
nts=nucleotides;
s=seconds

3. Receptor Polypeptides, as Well as Constructs and Nucleotide Sequences Encoding Polypeptides In some embodiments a polynucleotide encoding a receptor polypeptide is operably connected to a nucleic acid sequence encoding a bioluminescent or fluorescent donor molecule or fluorescent acceptor molecule or other suitable reporter component of a proximity screening assay. Once coding sequences for the desired polypeptides have been isolated or synthesised they can be cloned into any suitable construct for expression (e.g., transient or stable expression). Numerous constructs including cloning and expression vectors are known to those of skill in the art, and the selection of appropriate constructs is well within the skill of a practitioner in the field.

In some embodiments, the receptor polynucleotide coding sequences are inserted into locations within a suitable construct using routine technologies and molecular biological methods including DNA synthesis, PCR mutagenesis, and restriction endonuclease digestion followed by PCR ligation. Any coding sequence for a core protein is suitable for preparing nucleic acid sequences encoding the chimeric polypeptides of the present invention.

General texts which describe molecular biological techniques, which are applicable to the present invention such as cloning, mutation, and the like, include Berger and Kimmel, Guide to Molecular Cloning Techniques, Methods in Enzymology volume 152 Academic Press, Inc., San Diego, Calif. (Berger); Sambrook et al., Molecular Cloning-A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and expression of chimeric core proteins.

3.1 Receptor for Advanced Glycation End-Products (RAGE) Polypeptides

A significant role of RAGE is to bind to advanced glycation end-products (AGE), including glycated proteins on which amino groups have been modified non-enzymatically through the Maillard reaction. RAGE is often referred to as a pattern recognition receptor due to its ability to detect a class of ligands through a common motif.

In specific embodiments of the present invention, the RAGE polypeptide comprises a RAGE protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a RAGE protein sequence. In some embodiments, the RAGE protein sequence corresponds to a mammalian RAGE protein sequence. In some embodiments the RAGE protein sequence is derived from a mammal selected from the group comprising human (UniProtKB Accession No. Q15109), mouse (UniProtKB Accession No. Q62151), cow (UniProtKB Accession No. Q28173), rat (UniProtKB Accession No. Q63495), macaca (UniProtKB Accession No. G7P2Q8), and dog (UniProtKB Accession No. Q20JV7). In preferred embodiments, the RAGE protein sequence corresponds to a human wild-type RAGE protein sequence (for example, UniProtKB Accession No. Q15109) or a functional fragment of this sequence. The human full-length wild-type protein sequence, as defined by UniProtKB Accession No. Q15109, is set forth as follows:

[SEQ ID NO: 14]
MAAGTAVGAWVLVLSLWGAVVGAQNITARIGEPLVLKCKGAPKKPPQRLE

WKLNTGRTEAWKVLSPQGGGPWDSVARVLPNGSLFLPAVGIQDEGIFRCQ

AMNRNGKETKSNYRVRVYQIPGKPEIVDSASELTAGVPNKVGTCVSEGSY

PAGTLSWHLDGKPLVPNEKGVSVKEQTRRHPETGLFTLQSELMVTPARGG

DPRPTFSCSFSPGLPRHRALRTAPIQPRVWEPVPLEEVQLVVEPEGGAVA

PGGTVTLTCEVPAQPSPQIHWMKDGVPLPLPPSPVLILPEIGPQDQGTYS

CVATHSSHGPQESRAVSISIIEPGEEGPTAGSVGGSGLGTLALALGILGG

LGTAALLIGVILWQRRQRRGEERKAPENQEEEEERAELNQSEEPEAGESS

TGGP.

The wild-type RAGE comprises five distinct domains. The ectodomain of RAGE bears three immunoglobulin-like (Ig) domains, the V, C1 and C2 domains (residues 23-342 of SEQ ID NO: 14). These Ig domains belong to the V-, C- and S-type, respectively. The fourth domain comprises a single transmembrane (TM) spanning helix (residues 343-361 of SEQ ID NO: 14), and finally a cytosolic tail (residues 362-404 of SEQ ID NO: 14, as set forth in SEQ ID NO: 1) that is devoid of kinase activity and presumed to be unstructured (see, Neepers, 1992). In addition, the human wild-type RAGE protein sequence comprises a 22 amino acid N-terminal signal peptide, which has previously been shown to play a role in trafficking the RAGE protein to the plasma membrane.

Throughout this specification, unless the context requires otherwise, reference to the ectodomain of RAGE means a reference to amino acid residues 23-342 of wild-type RAGE (SEQ ID NO: 14).

Throughout this specification, unless the context requires otherwise, reference to the transmembrane domain (or TM) of RAGE means a reference to amino acid residues 343-361 of wild-type RAGE (SEQ ID NO: 14).

Throughout this specification, unless the context requires otherwise, reference to the cytosolic tail of RAGE means a reference to amino acid residues 362-404 of wild-type RAGE (SEQ ID NO: 14).

In one form of the invention, the RAGE polypeptide comprises a truncated form of a mammalian wild-type RAGE protein sequence. For example, the RAGE polypeptide sequence may comprise the human wild-type RAGE protein sequence in which one or more of the ligand-binding regions (V, C or S-type Ig domains) of the ectodomain of RAGE are mutated or deleted so as to impair RAGE ligand induced signalling. By way of a non-limiting illustrative example, a RAGE polypeptide suitable for using with the present invention comprised amino acid residues 362 to 404 of the human wild-type RAGE protein sequence as set forth in SEQ ID NO: 1.

The RAGE cytosolic tail (residues 362-404 of SEQ ID NO: 1) is responsible for signal transduction. In some embodiments the RAGE polypeptide of the present invention comprises, consists or consists essentially of the RAGE cytosolic tail, or a fragment thereof or mutated, truncated or fusion fragments. For example, the RAGE polypeptide may comprise, consist or consist essentially of residues 362 to 404 of the human wild-type RAGE as set forth in SEQ ID NO: 1.

3.2 Vectors and Nucleotide Sequences Encoding RAGE Polypeptides.

The present invention also encompasses isolated polynucleotide sequences and constructs encoding RAGE polypeptides as broadly described above and elsewhere herein. Also contemplated are host cells comprising those polynucleotide sequences or constructs.

In some embodiments, the polynucleotide sequences comprise a sequence that correspond to a mouse AGER nucleotide sequence, as set forth, for example, in Genbank Accession No. L33412.1, EU570247.1, EU570246.1, EU570245.1, EU570244.1, EU570242.1, EU570241.1, EU570240.1.

In some embodiments, the polynucleotide sequences comprise a sequence that corresponds to a bovine AGER nucleotide sequence as set forth for example in GenBank Accession Nos. M91212.1, or NM_173982.3.

In some embodiments, the polynucleotide sequences comprise a sequence that corresponds to a rat AGER nucleotide sequence as set forth for example in GenBank Accession Nos. L33413.1, NM_053336.2.

In some embodiments, the polynucleotide sequences comprise a sequence that corresponds to a macaca AGER nucleotide sequence as set forth for example in GenBank Accession Nos. CM001279.1, NM_001205117.1, GU139408.1, GU139409.1, GU139410.1, GU139411.1, GU139412.1, GU139413.1, GU139414.1, GU139415.1, GU139416.1, GU139417.1, GU139418.1, GU139419.1, GU139420.1, GU139421.1, GU139422.1.

In some embodiments, the polynucleotide sequences comprise a sequence that correspond to a canine AGER nucleotide sequence as set forth, for example, in Genbank Accession Nos. DQ125936.1, DQ125937.1, DQ125938.1, DQ125940.1, or DQ125939.

In some embodiments, the polynucleotide sequences comprise a sequence that corresponds to a human AGER nucleotide sequence as set forth for example in GenBank Accession Nos. AF001095.1, AB061668.1, AJ012753.1, Y18060.1, EU826620.1, EU826618.1, EU826617.1, EU826616.1, AF065213.1, AF065212.1, AF065210.1, CU690977.1, CU690976.1, AJ238896.1, Y18762.1. In some embodiments of this type, the polynucleotide comprises a AGER nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an AGER polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian RAGE protein, or a fragment thereof. In some embodiments, the AGER polynucleotide comprises a nucleotide sequence that hybridises to an open reading frame for a wild type mammalian RAGE protein, or a fragment thereof under low, medium or high stringency conditions.

3.3 Type-1 Angiotensin II Receptor (AT$_1$R) Polypeptides

The G protein-dependent signalling by AT$_1$R is vital for normal cardiovascular homeostasis, yet detrimental in chronic dysfunction, which associates with cell death and tissue fibrosis, and leads to cardiac hypertrophy and heart failure (Ma et al., 2010).

Despite its high medical relevance and decades of research, the structure of AT$_1$R and the binding mode of well established AT$_1$R blockers (ARBs) were only recently elucidated (Zhang et al., 2015). The structure indicated that the extracellular part of AT$_1$R consists of the N-terminal segment ECL1 (Glu91-Phe96 of the human AT$_1$R) linking helices II and III, ECL2 (His166 to Ile191 of the human AT$_1$R) linking helices IV and V, and ECL3 (Ile270 to Cys274 of the human AT$_1$R) linking helices VI to VII. Two disulphide bonds help to shape the extracellular side of AT$_1$R with Cys18-Cys 274 connecting the N terminus and ECL3, and Cys101-Cys180 connecting helix III and ECL2 (similar to the chemokine receptor CXCR4, which shares around 36% sequence identity with AT$_1$R).

In specific embodiments of the present invention, the AT$_1$R polypeptide comprises a AT$_1$R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an AT$_1$R protein sequence.

In some embodiments, the AT$_1$R protein sequence corresponds to a mammalian AT$_1$R protein sequence. Suitable AT$_1$R sequences may suitably be from mammal selected from the group comprising human (UniProtKB Accession No. P30556), sheep (UniProtKB Accession No. O77590), cow (UniProtKB Accession No. P25104), rabbit (UniProtKB Accession No. P34976), guinea pig (UniProtKB Accession No. Q9WV26), pig (UniProtKB Accession No. P30555), chimpanzee (UniProtKB Accession No. Q9GLN9), gerbil (UniProtKB Accession No. O35210, rat (UniProtKB Accession No. P29089), mouse (UniProtKB Accession No. P29754), cat (UniProtKB Accession No. M3VVA2), Tasmanian devil (UniProtKB Accession No. G3WOM6), horse (UniProtKB Accession No. F7D1NO), and panda (UniProtKB Accession No. D2HWD9).

In some preferred embodiments, the AT$_1$R protein sequence corresponds to a human AT$_1$R protein sequence. In some embodiments, the AT$_1$R polypeptide comprises a human full-length wild-type AT$_1$R protein sequence (UniProtKB Accession No. P30556), as set forth below, or a functional fragment of the wild-type AT$_1$R protein sequence.

[SEQ ID NO: 16]
MILNSSTEDGIKRIQDDCPKAGRHNYIFVMIPTLYSIIFWGIFGNSLVVI

VIYFYMKLKTVASVFLLNLALADLCFLLTLPLWAVYTAMEYRWPFGNYLC

KIASASVSFNLYASVFLLTCLSIDRYLAIVHPMKSRLRRTMLVAKVTCII

IWLLAGLASLPAIIHRNVFFIENTNITVCAFHYESQNSTLPIGLGLTKNI

LGFLFPFLIILTSYTLIWKALKKAYEIQKNKPRNDDIFKIIMAIVLFFFF

-continued
SWIPHQIFTFLDVLIQLGIIRDCRIADIVDTAMPITICIAYFNNCLNPLF

YGFLGKKFKRYFLQLLKYIPPKAKSHSNLSTKMSTLSYRPSDNVSSSTKK

PAPCFEVE.

In one form of the invention, the AT$_1$R polypeptide comprises a truncated form of a mammalian wild-type AT$_1$R protein sequence. For example, the AT$_1$R polypeptide sequence may comprise the human wild-type AT$_1$R protein sequence with a C-terminal truncation (e.g., amino acid residues 320-359 may be truncated). Alternatively or in addition, the AT$_1$R polypeptide sequence may comprise the wild-type AT$_1$R protein sequence with a N-terminal truncation. Alternatively or in addition to a C-terminal or N-terminal truncation, a truncation may be performed to remove an internal section of the wild-type AT$_1$R protein sequence (e.g., amino acid residues 7-16 may be truncated). By way of a non-limiting illustrative example, a AT$_1$R polypeptide suitable for using with the present invention comprised amino acid residues 2-6 and 17-319 of the human wild-type AT$_1$R protein sequence as set forth in SEQ ID NO: 16.

3.4 Constructs and Nucleotide Sequences Encoding AT$_1$R Polypeptides.

The present invention also encompasses isolated polynucleotide sequences and constructs encoding AT$_1$R polypeptides as broadly described above and elsewhere herein. Also contemplated are host cells comprising those polynucleotide sequences or constructs.

In some embodiments, the polynucleotide sequences comprise a sequence that corresponds to a human AT$_1$R nucleotide (i.e., corresponding to the AGTR1 gene) sequence as set forth for example in GenBank Accession Nos. KR711424.1, KR711423.1, KR711422.1, KR711421.1, KJ896399.1, KJ896398.1, NM_032049.3, NM_031850.3, NM_004835.4, NM_000685.4, NM_009585.3, DQ895601.2, BC068494.1, BC022447.1, DQ892388.2, and AK291541.1. In representative examples of this type, the polynucleotide comprises an AT$_1$R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an AT$_1$R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian AT$_1$R polynucleotide, or a fragment thereof. In some embodiments, the AT$_1$R polynucleotide comprises a nucleotide sequence that hybridises to an open reading frame for a wild type mammalian AT$_1$R protein, or a fragment thereof under low, medium or high stringency conditions.

3.5 Adenosine 1 Receptor (A1R) Polypeptides

The A1R is an important regulator of the cardiovascular system, and also has various other roles such as those in neurological, metabolic and skeletal processes (Fredholm et al., 2011).

To date, a crystal structure of the A1R has not yet been published, so the structural and ligand-binding features of the receptor has to be inferred through indirect approaches such as mutagenesis and homology modelling. The extracellular part of A1R consists of the N-terminal segment (Met1-Ser4 of the human A1R), ECL1 (Pro73-Thr75 of the human A1R) linking helices II and III, ECL2 (Trp146-Ile175 of the human A1R) linking helices IV and V, and ECL3 (Pro261-Lys265 of the human A1R) linking helices VI to VII. It is believed that four disulphide bonds may form on the extracellular side of A1R (as seen in the crystal structure of A2A) which help to stabilise the ligand-binding cleft (Piirainen et al., 2011).

In specific embodiments of the present invention, the A1R polypeptide comprises a A1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an A1R protein sequence.

In some embodiments, the A1R protein sequence corresponds to a mammalian A1R protein sequence. Suitable A1R sequences may suitably be from mammal selected from the group comprising chimpanzee (UniProtKB Accession No. H2Q0X8), cow (UniProtKB Accession No. P28190), dog (UniProtKB Accession No. P11616), guinea pig (UniProtKB Accession No. P47745), horse (UniProtKB Accession No. F6RAN5), human (UniProtKB Accession No. P30542), mouse (UniProtKB Accession No. Q60612), panda (UniProtKB Accession No. G1MOW2), pig (UniProtKB Accession No. I3LEN5), rabbit (UniProtKB Accession No. P34970), rat (UniProtKB Accession No. O08766), rat (UniProtKB Accession No. P25099), sheep (UniProtKB Accession No. W5NSY0), Tasmanian devil (UniProtKB Accession No. G3WVA4).

In some preferred embodiments, the A1R protein sequence corresponds to a human A1R protein sequence. In some embodiments, the A1R polypeptide comprises a human full-length wild-type A1R protein sequence (UniProtKB Accession No. P30542), as set forth below, or a functional fragment of the wild-type A1R protein sequence.

[SEQ ID NO: 17]
MPPSISAFQAAYIGIEVLIALVSVPGNVLVIWAVKVNQALRDATFCFIVS

LAVADVAVGALVIPLAILINIGPQTYFHTCLMVACPVLILTQSSILALLA

IAVDRYLRVKIPLRYKMVVTPRRAAVAIAGCWILSFWGLTPMFGWNNLSA

VERAWAANGSMGEPVIKCEFEKVISMEYMVYFNFFVWVLPPLLLMVLIYL

EVFYLIRKQLNKKVSASSGDPQKYYGKELKIAKSLALILFLFALSWLPLH

LINCITLFCPSCHKPSILTYIAIFLTHGNSAMNPIVYAFRIQKFRVTFLK

IWNDHFRCQPAPPIDEDLPEERPDD.

In one form of the invention, the A1R polypeptide comprises a truncated form of a mammalian wild-type A1R protein sequence. For example, the A1R polypeptide sequence may comprise the human wild-type A1R protein sequence with a C-terminal truncation (e.g., amino acid residues 315-326 may be truncated). Alternatively or in addition, the A1R polypeptide sequence may comprise the wild-type A1R protein sequence with a N-terminal truncation. Alternatively or in addition to a C-terminal or N-terminal truncation, a truncation may be performed to remove an internal section of the wild-type A1R protein sequence (e.g., amino acid residues 154-161 may be truncated). By way of a non-limiting illustrative example, an A1R polypeptide suitable for using with the present invention comprised amino acid residues 2-153 and 162-314 of the human wild-type A1R protein sequence as set forth in SEQ ID NO: 17.

3.6 Constructs and Nucleotide Sequences Encoding A1R Polypeptides

The present invention also encompasses isolated polynucleotide sequences and constructs encoding A1R polypeptides as broadly described above and elsewhere herein. Also contemplated are host cells comprising those polynucleotide sequences or constructs.

In some embodiments, the polynucleotide sequences comprise a sequence that corresponds to a human A1R nucleotide (i.e., corresponding to the ADORA1 gene) sequence as set forth for example in GenBank Accession Nos. CR541749.1, NM_000674.2, NM_001048230.1, NG_052917.1, KC884744.1, KC881108.1, L22214.1, AY136746.1 and BC026340.1. In representative examples of this type, the polynucleotide comprises an A1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an A1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian A1R polynucleotide, or a fragment thereof. In some embodiments, the A1R polynucleotide comprises a nucleotide sequence that hybridises to an open reading frame for a wild type mammalian A1R protein, or a fragment thereof under low, medium or high stringency conditions.

3.7 Adrenergic α1A Receptor (α1A-AR) Polypeptides

The α1A-AR is involved in cardiovascular system regulation, and in particular appears to mediate increases in blood pressure and cardiac contractility (Chen & Minneman, 2005).

To date, a crystal structure of the α1A-AR has not yet been published, so the structural and ligand-binding features of the receptor have to be inferred through indirect approaches such as mutagenesis and homology modelling. The extracellular part of α1A-AR consists of the N-terminal segment (Met1-Asn22 of the human α1A-AR), ECL1 (Gly90-Phe94 of the human α1A-AR) linking helices II and III, ECL2 (Trp165-Glu180 of the human α1A-AR) linking helices IV and V, and ECL3 (Pro299-Pro303 of the human α1A-AR) linking helices VI to VII. Like most GPCR's, the α1A-AR likely contains a disulphide bond connecting ECL1 and ECL2 (Finch et al., 2006).

In specific embodiments of the present invention, the α1A-AR polypeptide comprises a α1A-AR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an α1A-AR protein sequence.

In some embodiments, the α1A-AR protein sequence corresponds to a mammalian α1A-AR protein sequence. Suitable α1A-AR sequences may suitably be from mammal selected from the group comprising cat (UniProtKB Accession No. M3WRU5), chimpanzee (UniProtKB Accession No. H2ROT2), cow (UniProtKB Accession No. F1MY16), dog (UniProtKB Accession No. AOAOAOMPB9), gerbil (UniProtKB Accession No. E0AE55), gorilla (UniProtKB Accession No. G3QE17), guinea pig (UniProtKB Accession No. Q9WU25), horse (UniProtKB Accession No. F6UTQ3), human (UniProtKB Accession No. E7EW16), mouse (UniProtKB Accession No. Q8BUE5), rabbit (UniProtKB Accession No. G1TM07), rat (UniProtKB Accession No. P70648), rhesus (UniProtKB Accession No. F7DLK7), sheep (UniProtKB Accession No. W5PJ34).

In some preferred embodiments, the α1A-AR protein sequence corresponds to a human α1A-AR protein sequence. In some embodiments, the α1A-AR polypeptide comprises a human full-length wild-type α1A-AR protein sequence (UniProtKB Accession No. E7EW16), as set forth below, or a functional fragment of the wild-type α1A-AR protein sequence.

[SEQ ID NO: 18]
MVFLSGNASDSSNCTQPPAPVNISKAILLGVILGGLILFGVLGNILVILS

VACHRHLHSVTHYYIVNLAVADLLLTSTVLPFSAIFEVLGYWAFGRVFCN

IWAAVDVLCCTASIMGLCIISIDRYIGVSYPLRYPTIVTQRRGLMALLCV

WALSLVISIGPLFGWRQPAPEDETICQINEEPGYVLFSALGSFYLPLAII

LVMYCRVYVVAKRESRGLKSGLKTDKSDSEQVTLRIHRKNAPAGGSGMAS

AKTKTHFSVRLLKFSREKKAAKTLGIVVGCFVLCWLPFFLVMPIGSFFPD

FKPSETVFKIVFWLGYLNSCINPIIYPCSSQEFKKAFQNVLRIQCLCRKQ

SSKHALGYTLHPPSQAVEGQHKDMVRIPVGSRETFYRISKTDGVCEWKFF

SSMPRGSARITVSKDQSSCTTARSSGF.

In one form of the invention, the α1A-AR polypeptide comprises a truncated form of a mammalian wild-type α1A-AR protein sequence. For example, the α1A-AR polypeptide sequence may comprise the human wild-type α1A-AR protein sequence with a C-terminal truncation (e.g., amino acid residues 342-413 may be truncated). Alternatively or in addition, the α1A-AR polypeptide sequence may comprise the wild-type α1A-AR protein sequence with a N-terminal truncation. Alternatively or in addition to a C-terminal or N-terminal truncation, a truncation may be performed to remove an internal section of the wild-type α1A-AR protein sequence (e.g., amino acid residues 174-185 may be truncated). By way of a non-limiting illustrative example, a α1A-AR polypeptide suitable for using with the present invention comprised amino acid residues 2-173 and 186-341 of the human wild-type α1A-AR protein sequence as set forth in SEQ ID NO: 18.

3.8 Constructs and Nucleotide Sequences Encoding α1A-AR Polypeptides.

The present invention also encompasses isolated polynucleotide sequences and constructs encoding α1A-AR polypeptides as broadly described above and elsewhere herein. Also contemplated are host cells comprising those polynucleotide sequences or constructs.

In some embodiments, the polynucleotide sequences comprise a sequence that corresponds to a human α1A-AR nucleotide (i.e., corresponding to the ADRA1A gene) sequence as set forth for example in GenBank Accession Nos. AY389505.1, NG_029395.1, NM_001322504.1, NM_001322502.1, NM_033304.3, NM_033303.4, NM_033302.3, NR_136343.1, NM_000680.3, NM_001322503.1, AY491781.1, AY491780.1, AY491779.1, AY491778.1, AY491777.1 and AY491776.1. In representative examples of this type, the polynucleotide comprises an α1A-AR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an α1A-AR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian α1A-AR polynucleotide, or a fragment thereof. In some embodiments, the α1A-AR polynucleotide comprises a nucleotide sequence that hybridises to an open reading frame for a wild type mammalian α1A-AR protein, or a fragment thereof under low, medium or high stringency conditions.

3.9 Adrenergic α1B Receptor (α1B-AR) Polypeptides

The α1B-AR is involved in cardiovascular system regulation, locomotor activity and glucose metabolism (Chen & Minneman, 2005).

To date, a crystal structure of the α1B-AR has not yet been published, so the structural and ligand-binding features of the receptor have to be inferred through indirect approaches such as mutagenesis and homology modelling. The extracellular part of α1B-AR consists of the N-terminal segment (Met1-Thr36 of the human α1B-AR), ECL1 (Gly109-Leu113 of the human α1B-AR) linking helices II and III, ECL2 (Lys185-Glu199 of the human α1B-AR) linking helices IV and V, and ECL3 (Ser321-Pro325 of the human α1B-AR) linking helices VI to VII. Like most GPCR's, the α1B-AR likely contains a disulphide bond connecting ECL1 and ECL2 (Finch et al., 2006).

In specific embodiments of the present invention, the α1B-AR polypeptide comprises a α1B-AR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an α1B-AR protein sequence.

In some embodiments, the α1B-AR protein sequence corresponds to a mammalian α1B-AR protein sequence. Suitable α1B-AR sequences may suitably be from mammal selected from the group comprising chimpanzee (UniProtKB Accession No. H2QRX4), cow (UniProtKB Accession No. F1MGA6), dog (UniProtKB Accession No. F1PK71), gorilla (UniProtKB Accession No. G3S977), guinea pig (UniProtKB Accession No. H0WBQ9), hamster (UniProtKB Accession No. P18841), horse (UniProtKB Accession No. F7ATM9), human (UniProtKB Accession No. P35368), marmoset (UniProtKB Accession No. U3DR86), mouse (UniProtKB Accession No. P97717), pig (UniProtKB Accession No. F1RR36), rabbit (UniProtKB Accession No. U3KM59), rat (UniProtKB Accession No. P15823), Tasmanian devil (UniProtKB Accession No. G3VWX9).

In some preferred embodiments, the α1B-AR protein sequence corresponds to a human α1B-AR protein sequence. In some embodiments, the α1B-AR polypeptide comprises a human full-length wild-type α1B-AR protein sequence (UniProtKB Accession No. P35368), as set forth below, or a functional fragment of the wild-type α1B-AR protein sequence.

[SEQ ID NO: 19]
MNPDLDTGHNTSAPAHWGELKNANFTGPNQTSSNSTLPQLDITRAISVGL

VLGAFILFAIVGNILVILSVACNRHLRTPTNYFIVNLAMADLLLSFTVLP

FSAALEVLGYWVLGRIFCDIWAAVDVLCCTASILSLCAISIDRYIGVRYS

LQYPTLVTRRKAILALLSVWVLSTVISIGPLLGWKEPAPNDDKECGVTEE

PFYALFSSLGSFYIPLAVILVMYCRVYIVAKRTTKNLEAGVMKEMSNSKE

LTLRIHSKNFHEDTLSSTKAKGHNPRSSIAVKLFKFSREKKAAKTLGIWG

MFILCWLPFFIALPLGSLFSTLKPPDAVFKVVFWLGYFNSCLNPIIYPCS

SKEFKRAFVRILGCQCRGRGRRRRRRRRLGGCAYTYRPWTRGGSLERSQ

SRKDSLDDSGSCLSGSQRTLPSASPSPGYLGRGAPPPVELCAFPEWKAPG

ALLSLPAPEPPGRRGRHDSGPLFTFKLLTEPESPGTDGGASNGGCEAAAD

VANGQPGFKSNMPLAPGQF.

In one form of the invention, the α1B-AR polypeptide comprises a truncated form of a mammalian wild-type α1B-AR protein sequence. For example, the α1B-AR polypeptide sequence may comprise the human wild-type α1B-AR protein sequence with a C-terminal truncation (e.g., amino acid residues 365-520 may be truncated). Alternatively or in addition, the α1B-AR polypeptide sequence may comprise the wild-type α1B-AR protein sequence with a N-terminal truncation. Alternatively or in addition to a C-terminal or N-terminal truncation, a truncation may be performed to remove an internal section of the wild-type α1B-AR protein sequence (e.g., amino acid residues 186-196 may be truncated). By way of a non-limiting illustrative example, a α1B-AR polypeptide suitable for using with the present invention comprised amino acid residues 2-185 and 197-364 of the human wild-type α1B-AR protein sequence as set forth in SEQ ID NO: 19.

3.10 Constructs and Nucleotide Sequences Encoding α1B-AR Polypeptides.

The present invention also encompasses isolated polynucleotide sequences and constructs encoding α1B-AR polypeptides as broadly described above and elsewhere herein. Also contemplated are host cells comprising those polynucleotide sequences or constructs.

In some embodiments, the polynucleotide sequences comprise a sequence that corresponds to a human α1B-AR nucleotide (i.e., corresponding to the ADRA1B gene) sequence as set forth for example in GenBank Accession Nos. NM_000679.3, AY530191.1, EU332831.1, BC136569.1 and BC136568.1. In representative examples of this type, the polynucleotide comprises an α1B-AR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an α1B-AR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian α1B-AR polypeptide, or a fragment thereof. In some embodiments, the α1B-AR polynucleotide comprises a nucleotide sequence that hybridises to an open reading frame for a wild type mammalian α1B-AR protein, or a fragment thereof under low, medium or high stringency conditions.

3.11 Adrenergic α2B Receptor (α2B-AR) Polypeptides

The α2B-AR is a poorly characterised GPCR, however it appears to be involved in blood pressure regulation as well as having a role in developmental processes (Kable et al., 2000).

To date, a crystal structure of the α2B-AR has not yet been published, so the structural and ligand-binding features of the receptor have to be inferred through indirect approaches such as mutagenesis and homology modelling. The extracellular part of α2B-AR consists of the N-terminal segment (Met1-Ser8 of the human α2B-AR), ECL1 (Gly76-Phe80 of the human α2B-AR) linking helices II and III, ECL2 (Lys151-Gln168 of the human α2B-AR) linking helices IV and V, and ECL3 (Pro395-Val400 of the human α2B-AR) linking helices VI to VII.

In specific embodiments of the present invention, the α2B-AR polypeptide comprises a α2B-AR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an α2B-AR protein sequence.

In some embodiments, the α2B-AR protein sequence corresponds to a mammalian α2B-AR protein sequence. Suitable α2B-AR sequences may suitably be from mammal selected from the group comprising cat (UniProtKB Accession No. M3X1F7), chimpanzee (UniProtKB Accession No. H2RHZ6), cow (UniProtKB Accession No. G3X6S2), dog (UniProtKB Accession No. F1Q1Q4), gorilla (UniProtKB Accession No. G3RMW6), guinea pig (UniProtKB Accession No. Q60475), horse (UniProtKB Accession No. F7BW54), human (UniProtKB Accession No. P18089), marmoset (UniProtKB Accession No. F7IPR3), mouse (UniProtKB Accession No. P30545), pig (UniProtKB Accession No. Q38PTO), rabbit (UniProtKB Accession No. G1TQL5), rat (UniProtKB Accession No. P19328), Tasmanian devil (UniProtKB Accession No. G3VWZ4).

In some preferred embodiments, the α2B-AR protein sequence corresponds to a human α2B-AR protein sequence. In some embodiments, the α2B-AR polypeptide comprises a human full-length wild-type α2B-AR protein sequence (UniProtKB Accession No. P18089), as set forth below, or a functional fragment of the wild-type α2B-AR protein sequence.

[SEQ ID NO: 20]
MDHQDPYSVQATAAIAAAITFLILFTIFGNALVILAVLTSRSLRAPQNLF

LVSLAAADILVATLIIPFSLANELLGYWYFRRTWCEVYLALDVLFCTSSI

VHLCAISLDRYWAVSRALEYNSKRTPRRIKCIILTVWLIAAVISLPPLIY

KGDQGPQPRGRPQCKLNQEAWYILASSIGSFFAPCLIMILVYLRIYLIAK

RSNRRGPRAKGGPGQGESKQPRPDHGGALASAKLPALASVASAREVNGHS

KSTGEKEEGETPEDTGTRALPPSWAALPNSGQGQKEGVCGASPEDEAEEE

EEEEEEEECEPQAVPVSPASACSPPLQQPQGSRVLATLRGQVLLGRGVG

AIGGQWWRRRAQLTREKRFTFVLAWIGVFVLCWFPFFFSYSLGAICPKHC

KVPHGLFQFFFWIGYCNSSLNPVIYTIFNQDFRRAFRRILCRPWTQTAW.

In one form of the invention, the α2B-AR polypeptide comprises a truncated form of a mammalian wild-type α2B-AR protein sequence. For example, the α2B-AR polypeptide sequence may comprise the human wild-type α2B-AR protein sequence with a C-terminal truncation (e.g., amino acid residues 440-447 may be truncated). Alternatively or in addition, the α2B-AR polypeptide sequence may comprise the wild-type α2B-AR protein sequence with a N-terminal truncation. Alternatively or in addition to a C-terminal or N-terminal truncation, a truncation may be performed to remove an internal section of the wild-type α2B-AR protein sequence (e.g., amino acid residues 153-161 may be truncated). By way of a non-limiting illustrative example, a α2B-AR polypeptide suitable for using with the present invention comprised amino acid residues 2-152 and 162-439 of the human wild-type α2B-AR protein sequence as set forth in SEQ ID NO: 20.

3.12 Constructs and Nucleotide Sequences Encoding α2B-AR Polypeptides.

The present invention also encompasses isolated polynucleotide sequences and constructs encoding α2B-AR polypeptides as broadly described above and elsewhere herein. Also contemplated are host cells comprising those polynucleotide sequences or constructs.

In some embodiments, the polynucleotide sequences comprise a sequence that corresponds to a human α2B-AR nucleotide (i.e., corresponding to the ADRA2B gene) sequence as set forth for example in GenBank Accession Nos. NM_000682.6, HF583494.1, EU332847.1, NG_032950.1, AF316895.1, DQ057076.1, BC136537.1, BC133021.1 and AY548167.1. In representative examples of this type, the polynucleotide comprises an α2B-AR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an α2B-AR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian α2B-AR polynucleotide, or a fragment thereof. In some embodiments, the α2B-AR polynucleotide comprises a nucleotide sequence that hybridises to an open reading frame for a wild type mammalian α2B-AR protein, or a fragment thereof under low, medium or high stringency conditions.

3.13 Bradykinin Receptor B2 (B2R) Polypeptides

The B2R is most commonly associated with having hypotensive actions through its mediation of vasodilation and water and salt loss, however it also involved in inflammation, proliferation, apoptosis and angiogensis (Blaes & Girolami, 2013).

To date, a crystal structure of the B2R has not yet been published, so the structural and ligand-binding features of the receptor have to be inferred through indirect approaches such as mutagenesis and homology modelling. The extracellular part of B2R consists of the N-terminal segment (Met1-Gly54 of the human B2R), ECL1 (Asn120-Phe125 of the human B2R) linking helices II and III, ECL2 (Thr197-Ile219 of the human B2R) linking helices IV and V, and ECL3 (Ile300-Ser302 of the human B2R) linking helices VI to VII. Like most GPCRs, the B2R likely contains a disulphide bond connecting ECL1 and ECL2 (Leeb-Lundberg et al., 2005).

In specific embodiments of the present invention, the B2R polypeptide comprises a B2R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a B2R protein sequence.

In some embodiments, the B2R protein sequence corresponds to a mammalian B2R protein sequence. Suitable B2R sequences may suitably be from mammal selected from the group comprising bat (UniProtKB Accession No. G1Q158), cat (UniProtKB Accession No. M3WR05), chimpanzee (UniProtKB Accession No. H2Q8W1), cow (UniProtKB Accession No. F1MWKO), dog (UniProtKB Accession No. Q9BDQ4), guinea pig (UniProtKB Accession No. O70526), human (UniProtKB Accession No. P30411), marmoset (UniProtKB Accession No. U3CVS9), mouse (UniProtKB Accession No. P32299), panda (UniProtKB Accession No. G1LAZ3), pig (UniProtKB Accession No. Q9GLX8), rabbit (UniProtKB Accession No. Q28642), rat (UniProtKB Accession No. P25023), sheep (UniProtKB Accession No. W5Q382).

In some preferred embodiments, the B2R protein sequence corresponds to a human B2R protein sequence. In some embodiments, the B2R polypeptide comprises a human full-length wild-type B2R protein sequence (UniProtKB Accession No. P30411), as set forth below, or a functional fragment of the wild-type B2R protein sequence.

[SEQ ID NO: 21]
MFSPWKISMFLSVREDSVPTTASFSADMLNVTLQGPTLNGTFAQSKCPQV

EWLGWLNTIQPPFLWVLFVLATLENIFVLSVFCLHKSSCTVAEIYLGNLA

-continued

AADLILACGLPFWAITISNNFDWLFGETLCRVVNAIISMNLYSSICFLML

VSIDRYLALVKTMSMGRMRGVRWAKLYSLVIWGCTLLLSSPMLVFRTMKE

YSDEGHNVTACVISYPSLIWEVFTNMLLNVVGFLLPLSVITFCTMQIMQV

LRNNEMQKFKEIQTERRATVLVLVVLLLFIICWLPFQISTFLDTLHRLGI

LSSCQDERIIDVITQIASFMAYSNSCLNPLVYVIVGKRFRKKSWEVYQGV

CQKGGCRSEPIQMENSMGTLRTSISVERQIHKLQDWAGSRQ.

In one form of the invention, the B2R polypeptide comprises a truncated form of a mammalian wild-type B2R protein sequence. For example, the B2R polypeptide sequence may comprise the human wild-type B2R protein sequence with a C-terminal truncation (e.g., amino acid residues 351-391 may be truncated). Alternatively or in addition, the B2R polypeptide sequence may comprise the wild-type B2R protein sequence with a N-terminal truncation. Alternatively or in addition to a C-terminal or N-terminal truncation, a truncation may be performed to remove an internal section of the wild-type B2R protein sequence (e.g., amino acid residues 199-208 may be truncated). By way of a non-limiting illustrative example, a B2R polypeptide suitable for using with the present invention comprised amino acid residues 2-198 and 209-350 of the human wild-type B2R protein sequence as set forth in SEQ ID NO: 21.

3.14 Constructs and Nucleotide Sequences Encoding B2R Polypeptides.

The present invention also encompasses isolated polynucleotide sequences and constructs encoding B2R polypeptides as broadly described above and elsewhere herein. Also contemplated are host cells comprising those polynucleotide sequences or constructs.

In some embodiments, the polynucleotide sequences comprise a sequence that corresponds to a human B2R nucleotide (i.e., corresponding to the BDKRB2 gene) sequence as set forth for example in GenBank Accession Nos. HF583430.1, AY275465.1, NM_000623.3, KJ950628.1, AF378542.2, BC074894.2 and BC074895.2. In representative examples of this type, the polynucleotide comprises a B2R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a B2R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian B2R polynucleotide, or a fragment thereof. In some embodiments, the B2R polynucleotide comprises a nucleotide sequence that hybridises to an open reading frame for a wild type mammalian B2R protein, or a fragment thereof under low, medium or high stringency conditions.

3.15 CC Chemokine Receptor CCR1 (CCR1) Polypeptides

Like all chemokine receptors, the CCR1 is involved in the mediation of inflammatory processes. It is found in T cells, monocytes, eosinophils and basophils and is associated with Rheumatoid arthritis and multiple sclerosis (Charo & Ransohoff, 2006).

To date, a crystal structure of the CCR1 has not yet been published, so the structural and ligand-binding features of the receptor have to be inferred through indirect approaches such as mutagenesis and homology modelling. The extracellular part of CCR1 consists of the N-terminal segment (Met1-Asn28 of the human CCR1), ECL1 (Asp 97-Phe101 of the human CCR1) linking helices II and III, ECL2 (Lys173-Ser191 of the human CCR1) linking helices IV and V, and ECL3 (Thr270-His271 of the human CCR1) linking helices VI to VII. Like all chemokine receptors the N-terminus appears to be crucial for ligand binding and receptor activation (Kufareva et al., 2015).

In specific embodiments of the present invention, the CCR1 polypeptide comprises a CCR1 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR1 protein sequence.

In some embodiments, the CCR1 protein sequence corresponds to a mammalian CCR1 protein sequence. Suitable CCR1 sequences may suitably be from mammal selected from the group comprising cat (UniProtKB Accession No. B6DXF4), chimpanzee (UniProtKB Accession No. H2QMG4), cow (UniProtKB Accession No. AOJN72), dog (UniProtKB Accession No. Q2VOQ7), gorilla (UniProtKB Accession No. G3RL29), horse (UniProtKB Accession No. F6UOD1), human (UniProtKB Accession No. P32246), marmoset (UniProtKB Accession No. Q9MYJ8), mouse (UniProtKB Accession No. P51675), pig (UniProtKB Accession No. Q6YSTO), rabbit (UniProtKB Accession No. Q9MYJ9), rat (UniProtKB Accession No. Q9JLY8), rhesus (UniProtKB Accession No. F6QJR2), sheep (UniProtKB Accession No. W5PXX5).

In some preferred embodiments, the CCR1 protein sequence corresponds to a human CCR1 protein sequence. In some embodiments, the CCR1 polypeptide comprises a human full-length wild-type CCR1 protein sequence (UniProtKB Accession No. P32246), as set forth below, or a functional fragment of the wild-type CCR1 protein sequence.

[SEQ ID NO: 22]
METPNTTEDYDTTTEFDYGDATPCQKVNERAFGAQLLPPLYSLVFVIGLV

GNILVVLVLVQYKRLKNMTSIYLLNLAISDLLFLFTLPFWIDYKLKDDWV

FGDAMCKILSGFYYTGLYSEIFFIILLTIDRYLAIVHAVFALRARTVTFG

VITSIIIWALAILASMPGLYFSKTQWEFTHHTCSLHFPHESLREWKLFQA

LKLNLFGLVLPLLVMIICYTGIIKILLRRPNEKKSKAVRLIFVIMIIFFL

FWTPYNLTILISVFQDFLFTHECEQSRHLDLAVQVTEVIAYTHCCVNPVI

YAFVGERFRKYLRQLFHRRVAVHLVKWLPFLSVDRLERVSSTSPSTGEHE

LSAGF.

In one form of the invention, the CCR1 polypeptide comprises a truncated form of a mammalian wild-type CCR1 protein sequence. For example, the CCR1 polypeptide sequence may comprise the human wild-type CCR1 protein sequence with a C-terminal truncation (e.g., amino acid residues 318-355 may be truncated). Alternatively or in addition, the CCR1 polypeptide sequence may comprise the wild-type CCR1 protein sequence with a N-terminal truncation. Alternatively or in addition to a C-terminal or N-terminal truncation, a truncation may be performed to remove an internal section of the wild-type CCR1 protein sequence (e.g., amino acid residues 174-182 may be truncated). By way of a non-limiting illustrative example, a CCR1 polypeptide suitable for using with the present invention comprised amino acid residues 2-173 and 183-317 of the human wild-type CCR1 protein sequence as set forth in SEQ ID NO: 22.

3.16 Constructs and Nucleotide Sequences Encoding CCR1 Polypeptides.

The present invention also encompasses isolated polynucleotide sequences and constructs encoding CCR1 polypeptides as broadly described above and elsewhere herein. Also contemplated are host cells comprising those polynucleotide sequences or constructs.

In some embodiments, the polynucleotide sequences comprise a sequence that corresponds to a human CCR1 nucleotide (i.e., corresponding to the CCR1 gene) sequence as set forth for example in GenBank Accession Nos. NM_001295.2, AF051305.1, BC064991.1 and BC051306.1. In representative examples of this type, the polynucleotide comprises a CCR1 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR1 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR1 polynucleotide, or a fragment thereof. In some embodiments, the CCR1 polynucleotide comprises a nucleotide sequence that hybridises to an open reading frame for a wild type mammalian CCR1 protein, or a fragment thereof under low, medium or high stringency conditions.

3.17 CC Chemokine Receptor CCR2 (CCR2) Polypeptides

Like all chemokine receptors, the CCR2 is involved in the mediation of inflammatory processes. It is found in monocytes, dendritic cells and memory T cells and is associated with atherosclerosis, rheumatoid arthritis, multiple sclerosis, resistance to intracellular pathogens and type 2 diabetes mellitus (Charo & Ransohoff, 2006).

The crystal structure of the CCR2 has recently been published (Zheng et al., 2016), giving insight to its ligand-binding mode and activation process. The extracellular part of CCR2 consists of the N-terminal segment (Met1-D36 of the human CCR2), ECL1 (Glu105-Phe108 of the human CCR2) linking helices II and III, ECL2 (Lys180-Phe194 of the human CCR2) linking helices IV and V, and ECL3 (Leu274-Ser275 of the human CCR2) linking helices VI to VII. Like all chemokine receptors, the CCR2 is expected to have two conserved disulfide bonds in its ectodomains (Zheng et al., 2016).

In specific embodiments of the present invention, the CCR2 polypeptide comprises a CCR2 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR2 protein sequence.

In some embodiments, the CCR2 protein sequence corresponds to a mammalian CCR2 protein sequence. Suitable CCR2 sequences may suitably be from mammal selected from the group comprising chimpanzee (UniProtKB Accession No. H2QMG5), cow (UniProtKB Accession No. D9ZDD9), gorilla (UniProtKB Accession No. G3S6T3), guinea pig (UniProtKB Accession No. HOVII5), horse (UniProtKB Accession No. B3SPX1), human (UniProtKB Accession No. P41597), marmoset (UniProtKB Accession No. F7DT70), mouse (UniProtKB Accession No. P51683), panda (UniProtKB Accession No. G1MMF1), pig (UniProtKB Accession No. Q6YT42), rabbit (UniProtKB Accession No. G1SK57), rat (UniProtKB Accession No. O55193), rhesus (UniProtKB Accession No. O18793), sheep (UniProtKB Accession No. W5PXU4).

In some preferred embodiments, the CCR2 protein sequence corresponds to a human CCR2 protein sequence. In some embodiments, the CCR2 polypeptide comprises a human full-length wild-type CCR2 protein sequence (UniProtKB Accession No. P41597), as set forth below, or a functional fragment of the wild-type CCR2 protein sequence.

[SEQ ID NO: 23]
MLSTSRSRFIRNTNESGEEVTTFFDYDYGAPCHKFDVKQIGAQLLPPLYS

LVFIFGFVGNMLVVLILINCKKLKCLTDIYLLNLAISDLLFLITLPLWAH

SAANEVWFGNAMCKLFTGLYHIGYFGGIFFIILLTIDRYLAIVHAVFALK

ARTVTFGVVTSVITWLVAVFASVPGIIFTKCQKEDSVYVCGPYFPRGWNN

FHTIMRNILGLVLPLLIMVICYSGILKTLLRCRNEKKRHRAVRVIFTIMI

VYFLFWTPYNIVILLNTFQEFFGLSNCESTSQLDQATQVTETLGMTHCCI

NPIIYAFVGEKFRSLFHIALGCRIAPLQKPVCGGPGVRPGKNVKVTTQGL

LDGRGKGKSIGRAPEASLQDKEGA.

In one form of the invention, the CCR2 polypeptide comprises a truncated form of a mammalian wild-type CCR2 protein sequence. For example, the CCR2 polypeptide sequence may comprise the human wild-type CCR2 protein sequence with a C-terminal truncation (e.g., amino acid residues 322-374 may be truncated). Alternatively or in addition, the CCR2 polypeptide sequence may comprise the wild-type CCR2 protein sequence with a N-terminal truncation. Alternatively or in addition to a C-terminal or N-terminal truncation, a truncation may be performed to remove an internal section of the wild-type CCR2 protein sequence (e.g., amino acid residues 182-199 may be truncated). By way of a non-limiting illustrative example, a CCR2 polypeptide suitable for using with the present invention comprised amino acid residues 2-181 and 200-321 of the human wild-type CCR2 protein sequence as set forth in SEQ ID NO: 23.

3.18 Constructs and Nucleotide Sequences Encoding CCR2 Polypeptides.

The present invention also encompasses isolated polynucleotide sequences and constructs encoding CCR2 polypeptides as broadly described above and elsewhere herein. Also contemplated are host cells comprising those polynucleotide sequences or constructs.

In some embodiments, the polynucleotide sequences comprise a sequence that corresponds to a human CCR2 nucleotide (i.e., corresponding to the CCR2 gene) sequence as set forth for example in GenBank Accession Nos. NM_001123396.1, NM_001123041.2, NG_021428.1, KC248079.1, KC248078.1, KC248077.1, KC248076.1, KC248075.1, KC248074.1, KC248073.1, KC248072.1, KC248071.1, KC248070.1, AF545480.1, BC126452.1 and BC095540.1. In representative examples of this type, the polynucleotide comprises a CCR2 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR2 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR2 polynucleotide, or a fragment thereof. In some embodiments, the CCR2 polynucleotide comprises a nucleotide sequence that hybridises to an open reading frame for a wild type mammalian CCR2 protein, or a fragment thereof under low, medium or high stringency conditions.

3.19 CC Chemokine Receptor CCR3 (CCR3) Polypeptides

Like all chemokine receptors, the CCR3 is involved in the mediation of inflammatory processes. It is found in eosinophils, basophils, mast cells, Th2 cells and platelets and is associated with allergic asthma and rhinitis (Charo & Ransohoff, 2006).

To date, a crystal structure of the CCR3 has not yet been published, so the structural and ligand-binding features of the receptor have to be inferred through indirect approaches such as mutagenesis and homology modelling. The extracellular part of CCR3 consists of the N-terminal segment (Met1-Asp28 of the human CCR3), ECL1 (His97-Phe101 of the human CCR3) linking helices II and III, ECL2 (Glu173-Thr191 of the human CCR3) linking helices IV and V, and ECL3 (Gly270-Asn271 of the human CCR3) linking helices VI to VII. Like all chemokine receptors, the CCR3 is expected to have two conserved disulfide bonds in its ectodomains (Zheng et al., 2016).

In specific embodiments of the present invention, the CCR3 polypeptide comprises a CCR3 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR3 protein sequence.

In some embodiments, the CCR3 protein sequence corresponds to a mammalian CCR3 protein sequence. Suitable CCR3 sequences may suitably be from mammal selected from the group comprising cat (UniProtKB Accession No. M3WZ27), chimpanzee (UniProtKB Accession No. H2ROZ4), cow (UniProtKB Accession No. F1MP16), dog (UniProtKB Accession No. Q64H34), guinea pig (UniProtKB Accession No. Q9Z213), horse (UniProtKB Accession No. F6UH12), human (UniProtKB Accession No. P51677), marmoset (UniProtKB Accession No. F7DTA4), mouse (UniProtKB Accession No. Q8BHB8), panda (UniProtKB Accession No. G1MMC8), pig (UniProtKB Accession No. Q75ZH4), rabbit (UniProtKB Accession No. B5SU39), rat (UniProtKB Accession No. O54814), sheep (UniProtKB Accession No. W5PXW1).

In some preferred embodiments, the CCR3 protein sequence corresponds to a human CCR3 protein sequence. In some embodiments, the CCR3 polypeptide comprises a human full-length wild-type CCR3 protein sequence (UniProtKB Accession No. P51677), as set forth below, or a functional fragment of the wild-type CCR3 protein sequence.

[SEQ ID NO: 24]
MTTSLDTVETFGTTSYYDDVGLLCEKADTRALMAQFVPPLYSLVFTVGLL

GNVVVVMILIKYRRLRIMTNIYLLNLAISDLLFLVTLPFWIHYVRGHNWV

FGHGMCKLLSGFYHTGLYSEIFFIILLTIDRYLAIVHAVFALRARTVTFG

VITSIVTWGLAVLAALPEFIFYETEELFEETLCSALYPEDTVYSWRHFHT

LRMTIFCLVLPLLVMAICYTGIIKTLLRCPSKKKYKAIRLIFVIMAVFFI

FWTPYNVAILLSSYQSILFGNDCERSKHLDLVMLVTEVIAYSHCCMNPVI

YAFVGERFRKYLRHFFHRHLLMHLGRYIPFLPSEKLERTSSVSPSTAEPE

LSIVF.

In one form of the invention, the CCR3 polypeptide comprises a truncated form of a mammalian wild-type CCR3 protein sequence. For example, the CCR3 polypeptide sequence may comprise the human wild-type CCR3 protein sequence with a C-terminal truncation (e.g., amino acid residues 318-355 may be truncated). Alternatively or in addition, the CCR3 polypeptide sequence may comprise the wild-type CCR3 protein sequence with a N-terminal truncation. Alternatively or in addition to a C-terminal or N-terminal truncation, a truncation may be performed to remove an internal section of the wild-type CCR3 protein sequence (e.g., amino acid residues 175-187 may be truncated). By way of a non-limiting illustrative example, a CCR3 polypeptide suitable for using with the present invention comprised amino acid residues 2-174 and 188-317 of the human wild-type CCR3 protein sequence as set forth in SEQ ID NO: 24.

3.20 Constructs and Nucleotide Sequences Encoding CCR3 Polypeptides.

The present invention also encompasses isolated polynucleotide sequences and constructs encoding CCR3 polypeptides as broadly described above and elsewhere herein. Also contemplated are host cells comprising those polynucleotide sequences or constructs.

In some embodiments, the polynucleotide sequences comprise a sequence that corresponds to a human CCR3 nucleotide (i.e., corresponding to the CCR3 gene) sequence as set forth for example in GenBank Accession Nos. NM_178329.2, NM_001837.3, NM_001164680.1, NM_178328.1, AH009867.2, AF247361.1, AF262303.1, AF262302.1, AF262301.1, AF262300.1, AF262299.1, AH010691.2, AF224495.1, AF247360.1, AF247359.1 and AF026535.1In representative examples of this type, the polynucleotide comprises a CCR3 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR3 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR3 polynucleotide, or a fragment thereof. In some embodiments, the CCR3 polynucleotide comprises a nucleotide sequence that hybridises to an open reading frame for a wild type mammalian CCR3 protein, or a fragment thereof under low, medium or high stringency conditions.

3.21 CC Chemokine Receptor CCR4 (CCR4) Polypeptides

Like all chemokine receptors, the CCR4 is involved in the mediation of inflammatory processes. It is found in T cells (Th2), dendritic cells (mature), basophils, macrophages and platelets and is associated with parasitic infection, graft rejection and T-cell homing to skin (Charo & Ransohoff, 2006).

To date, a crystal structure of the CCR4 has not yet been published, so the structural and ligand-binding features of the receptor have to be inferred through indirect approaches such as mutagenesis and homology modelling. The extracellular part of CCR4 consists of the N-terminal segment (Met1-Gly33 of the human CCR4), ECL1 (Gln102-Phe105 of the human CCR4) linking helices II and III, ECL2 (Thr177-Asn194 of the human CCR4) linking helices IV and V, and ECL3 (Leu273-Gln274 of the human CCR4) linking helices VI to VII. Like all chemokine receptors, the CCR4 is expected to have two conserved disulfide bonds in its ectodomains (Zheng et al., 2016).

In specific embodiments of the present invention, the CCR4 polypeptide comprises a CCR4 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR4 protein sequence.

In some embodiments, the CCR4 protein sequence corresponds to a mammalian CCR4 protein sequence. Suitable CCR4 sequences may suitably be from mammal selected from the group comprising cat (UniProtKB Accession No. M3VZE0), chimpanzee (UniProtKB Accession No. H2QM91), cow (UniProtKB Accession No. A6QLA5), dog (UniProtKB Accession No. Q8MJW8), gorilla (UniProtKB Accession No. G3RC17), guinea pig (UniProtKB Accession No. H0V3A3), horse (UniProtKB Accession No. F6RJT2), human (UniProtKB Accession No. P51679), marmoset (UniProtKB Accession No. F7F2B0), mouse (UniProtKB Accession No. P51680), pig (UniProtKB Accession No. 13L552), rabbit (UniProtKB Accession No. G1TXVO), rat (UniProtKB Accession No. Q91ZH4), sheep (UniProtKB Accession No. W5Q1A7).

In some preferred embodiments, the CCR4 protein sequence corresponds to a human CCR4 protein sequence. In some embodiments, the CCR4 polypeptide comprises a human full-length wild-type CCR4 protein sequence (UniProtKB Accession No. P51679), as set forth below, or a functional fragment of the wild-type CCR4 protein sequence.

[SEQ ID NO: 25]
MNPTDIADTTLDESIYSNYYLYESIPKPCTKEGIKAFGELFLPPLYSLVF

VFGLLGNSVVVLVLFKYKRLRSMTDVYLLNLAISDLLFVFSLPFWGYYAA

DQWVFGLGLCKMISWMYLVGFYSGIFFVMLMSIDRYLAIVHAVFSLRART

LTYGVITSLATWSVAVFASLPGFLFSTCYTERNHTYCKTKYSLNSTTWKV

LSSLEINILGLVIPLGIMLFCYSMIIRTLQHCKNEKKNKAVKMIFAVWLF

LGFVVTPYNIVLFLETLVELEVLQDCTFERYLDYAIQATETLAFVHCCLN

PIIYFFLGEKFRKYILQLFKTCRGLFVLCQYCGLLQIYSADTPSSSYTQS

TMDHDLHDAL.

In one form of the invention, the CCR4 polypeptide comprises a truncated form of a mammalian wild-type CCR4 protein sequence. For example, the CCR4 polypeptide sequence may comprise the human wild-type CCR4 protein sequence with a C-terminal truncation (e.g., amino acid residues 321-360 may be truncated). Alternatively or in addition, the CCR4 polypeptide sequence may comprise the wild-type CCR4 protein sequence with a N-terminal truncation. Alternatively or in addition to a C-terminal or N-terminal truncation, a truncation may be performed to remove an internal section of the wild-type CCR4 protein sequence (e.g., amino acid residues 179-189 may be truncated). By way of a non-limiting illustrative example, a CCR4 polypeptide suitable for using with the present invention comprised amino acid residues 2-178 and 190-320 of the human wild-type CCR4 protein sequence as set forth in SEQ ID NO: 25.

3.22 Constructs and Nucleotide Sequences Encoding CCR4 Polypeptides.

The present invention also encompasses isolated polynucleotide sequences and constructs encoding CCR4 polypeptides as broadly described above and elsewhere herein.

Also contemplated are host cells comprising those polynucleotide sequences or constructs.

In some embodiments, the polynucleotide sequences comprise a sequence that corresponds to a human CCR4 nucleotide (i.e., corresponding to the CCR4 gene) sequence as set forth for example in GenBank Accession Nos. AY322539.1, NC_000005.10, NM_005508.4, EF064759.1, BC074935.2, BC071751.1 and BC069139.1. In representative examples of this type, the polynucleotide comprises a CCR4 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR4 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR4 polynucleotide, or a fragment thereof. In some embodiments, the CCR4 polynucleotide comprises a nucleotide sequence that hybridises to an open reading frame for a wild type mammalian CCR4 protein, or a fragment thereof under low, medium or high stringency conditions.

3.23 CC Chemokine Receptor CCR5 (CCR5) Polypeptides

Like all chemokine receptors, the CCR5 is involved in the mediation of inflammatory processes. It is found in T cells and monocytes and is associated with HIV-1 infection and transplant rejection (Charo & Ransohoff, 2006).

The crystal structure of the CCR5 has been solved (Tan et al., 2013), giving insight to its ligand-binding mode and activation process. The extracellular part of CCR5 consists of the N-terminal segment (Met1-Asn24 of the human CCR5), ECL1 (Gln93-Phe96 of the human CCR5) linking helices II and III, ECL2 (Arg168-Gln186 of the human CCR5) linking helices IV and V, and ECL3 (Leu266-Asn267 of the human CCR5) linking helices VI to VII. As expected for all chemokine receptors, the CCR5 has two conserved disulfide bonds in its ectodomains (Tan et al., 2013).

In specific embodiments of the present invention, the CCR5 polypeptide comprises a CCR5 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR5 protein sequence.

In some embodiments, the CCR5 protein sequence corresponds to a mammalian CCR5 protein sequence. Suitable CCR5 sequences may suitably be from mammal selected from the group comprising cat (UniProtKB Accession No. A4ZY83), chimpanzee (UniProtKB Accession No. P56440), cow (UniProtKB Accession No. Q2HJ17), dog (UniProtKB Accession No. Q5ECR9), goat (UniProtKB Accession No. F5B6L8), gorilla (UniProtKB Accession No. P56439), horse (UniProtKB Accession No. A4ZZ54), human (UniProtKB Accession No. P51681), marmoset (UniProtKB Accession No. Q6WN98), mouse (UniProtKB Accession No. P51682), pig (UniProtKB Accession No. Q6YT41), rabbit (UniProtKB Accession No. Q1ZY22), rat (UniProtKB Accession No. O08556), sheep (UniProtKB Accession No. B7T903).

In some preferred embodiments, the CCR5 protein sequence corresponds to a human CCR5 protein sequence. In some embodiments, the CCR5 polypeptide comprises a human full-length wild-type CCR5 protein sequence (UniProtKB Accession No. P51681), as set forth below, or a functional fragment of the wild-type CCR5 protein sequence.

[SEQ ID NO: 26]
MDYQVSSPIYDINYYTSEPCQKINVKQIAARLLPPLYSLVFIFGFVGNML

VILILINCKRLKSMTDIYLLNLAISDLFFLLTVPFWAHYAAAQWDFGNTM

CQLLTGLYFIGFFSGIFFIILLTIDRYLAVVHAVFALKARTVTFGVVTSV

ITWVVAVFASLPGIIFTRSQKEGLHYTCSSHFPYSQYQFWKNFQTLKIVI

LGLVLPLLVMVICYSGILKTLLRCRNEKKRHRAVRLIFTIMIVYFLFWAP

YNIVLLLNTFQEFFGLNNCSSSNRLDQAMQVTETLGMTHCCINPIIYAFV

GEKFRNYLLVFFQKHIAKRFCKCCSIFQQEAPERASSVYTRSTGEQEISV

GL.

In one form of the invention, the CCR5 polypeptide comprises a truncated form of a mammalian wild-type CCR5 protein sequence. For example, the CCR5 polypeptide sequence may comprise the human wild-type CCR5 protein sequence with a C-terminal truncation (e.g., amino acid residues 314-352 may be truncated). Alternatively or in addition, the CCR5 polypeptide sequence may comprise the wild-type CCR5 protein sequence with a N-terminal truncation. Alternatively or in addition to a C-terminal or N-terminal truncation, a truncation may be performed to remove an internal section of the wild-type CCR5 protein sequence (e.g., amino acid residues 171-181 may be truncated). By way of a non-limiting illustrative example, a CCR5 polypeptide suitable for using with the present invention comprised amino acid residues 2-170 and 182-313 of the human wild-type CCR5 protein sequence as set forth in SEQ ID NO: 26.

3.24 Constructs and Nucleotide Sequences Encoding CCR5 Polypeptides.

The present invention also encompasses isolated polynucleotide sequences and constructs encoding CCR5 polypeptides as broadly described above and elsewhere herein. Also contemplated are host cells comprising those polynucleotide sequences or constructs.

In some embodiments, the polynucleotide sequences comprise a sequence that corresponds to a human CCR5 nucleotide (i.e., corresponding to the CCR5 gene) sequence as set forth for example in GenBank Accession Nos. AY463215.1, GQ121035.1, AH005786.2, NM_000579.3, NM_001100168.1, AF056019.1, AB182990.1, AB182984.1, AB182986.1, AF011537.1, AF011532.1, AF011525.1, AF011521.1, JQ291232.1, EF202089.1, AF052539.1. In representative examples of this type, the polynucleotide comprises a CCR5 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR5 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR5 polynucleotide, or a fragment thereof. In some embodiments, the CCR5 polynucleotide comprises a nucleotide sequence that hybridises to an open reading frame for a wild type mammalian CCR5 protein, or a fragment thereof under low, medium or high stringency conditions.

3.25 CC Chemokine Receptor CCR6 (CCR6) Polypeptides

Like all chemokine receptors, the CCR6 is involved in the mediation of inflammatory processes. It is found in T cells (T regulatory and memory), B cells and dendritic cells and is associated with mucosal humoral immunity, allergic asthma, and intestinal T-cell homing (Charo & Ransohoff, 2006).

To date, a crystal structure of the CCR4 has not yet been published, so the structural and ligand-binding features of the receptor have to be inferred through indirect approaches such as mutagenesis and homology modelling. The extracellular part of CCR6 consists of the N-terminal segment (Met1-Glu40 of the human CCR6), ECL1 (Gly109-Phe113 of the human CCR6) linking helices II and III, ECL2 (Gln187-Glu206 of the human CCR6) linking helices IV and V, and ECL3 (Asn285-Arg286 of the human CCR6) linking helices VI to VII. Like all chemokine receptors, the CCR6 is expected to have two conserved disulfide bonds in its ectodomains (Zheng et al., 2016).

In specific embodiments of the present invention, the CCR6 polypeptide comprises a CCR6 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR6 protein sequence.

In some embodiments, the CCR6 protein sequence corresponds to a mammalian CCR6 protein sequence. Suitable CCR6 sequences may suitably be from mammal selected from the group comprising cat (UniProtKB Accession No. M3WPJ2), chimpanzee (UniProtKB Accession No. H2QU13), cow (UniProtKB Accession No. F1MT56), dog (UniProtKB Accession No. J9P4Z8), gorilla (UniProtKB Accession No. G3R6S8), guinea pig (UniProtKB Accession No. H0WBT8), horse (UniProtKB Accession No. F6PP77), human (UniProtKB Accession No. P51684), marmoset (UniProtKB Accession No. F6PMZ8), mouse (UniProtKB Accession No. O54689), pig (UniProtKB Accession No. I3LB15), rabbit (UniProtKB Accession No. G1U041), rat (UniProtKB Accession No. Q5BK58), sheep (UniProtKB Accession No. W5P4D1).

In some preferred embodiments, the CCR6 protein sequence corresponds to a human CCR6 protein sequence. In some embodiments, the CCR6 polypeptide comprises a human full-length wild-type CCR6 protein sequence (UniProtKB Accession No. P51684), as set forth below, or a functional fragment of the wild-type CCR6 protein sequence.

[SEQ ID NO: 27]
MSGESMNFSDVFDSSEDYFVSVNTSYYSVDSEMLLCSLQEVRQFSRLFVP

IAYSLICVFGLLGNILVVITFAFYKKARSMTDVYLLNMAIADILFVLTLP

FWAVSHATGAWVFSNATCKLLKGIYAINFNCGMLLLTCISMDRYIAIVQA

TKSFRLRSRTLPRSKIICLVVWGLSVIISSSTFVFNQKYNTQGSDVCEPK

YQTVSEPIRWKLLMLGLELLFGFFIPLMFMIFCYTFIVKTLVQAQNSKRH

KAIRVIIAVVLVFLACQIPHNMVLLVTAANLGKMNRSCQSEKLIGYTKTV

TEVLAFLHCCLNPVLYAFIGQKFRNYFLKILKDLWCVRRKYKSSGFSCAG

RYSENISRQTSETADNDNASSFTM.

In one form of the invention, the CCR6 polypeptide comprises a truncated form of a mammalian wild-type CCR6 protein sequence. For example, the CCR6 polypeptide sequence may comprise the human wild-type CCR6 protein sequence with a C-terminal truncation (e.g., amino acid residues 333-374 may be truncated). Alternatively or in addition, the CCR6 polypeptide sequence may comprise the wild-type CCR6 protein sequence with a N-terminal truncation. Alternatively or in addition to a C-terminal or N-terminal truncation, a truncation may be performed to remove an internal section of the wild-type CCR6 protein sequence (e.g., amino acid residues 191-202 may be truncated). By way of a non-limiting illustrative example, a CCR6 polypeptide suitable for using with the present invention comprised amino acid residues 2-190 and 203-332 of the human wild-type CCR6 protein sequence as set forth in SEQ ID NO: 27.

3.26 Constructs and Nucleotide Sequences Encoding CCR6 Polypeptides.

The present invention also encompasses isolated polynucleotide sequences and constructs encoding CCR6 polypeptides as broadly described above and elsewhere herein. Also contemplated are host cells comprising those polynucleotide sequences or constructs.

In some embodiments, the polynucleotide sequences comprise a sequence that corresponds to a human CCR6 nucleotide (i.e., corresponding to the CCR6 gene) sequence as set forth for example in GenBank Accession Nos. NM_004367.5, NM_031409.3, AY242126.1, BC037960.1 and U45984.1. In representative examples of this type, the polynucleotide comprises a CCR6 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR6 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR6 polynucleotide, or a fragment thereof. In some embodiments, the CCR6 polynucleotide comprises a nucleotide sequence that hybridises to an open reading frame for a wild type mammalian CCR6 protein, or a fragment thereof under low, medium or high stringency conditions.

3.27 CC Chemokine Receptor CCR7 (CCR7) Polypeptides

Like all chemokine receptors, the CCR7 is involved in the mediation of inflammatory processes. It is found in T cells and mature dendritic cells and is associated with transport of T cells and dendritic cells to lymph node, antigen presentation, and cellular immunity (Charo & Ransohoff, 2006).

To date, a crystal structure of the CCR7 has not yet been published, so the structural and ligand-binding features of the receptor have to be inferred through indirect approaches such as mutagenesis and homology modelling. The extracellular part of CCR7 consists of the N-terminal segment (Met1-Asp52 of the human CCR7), ECL1 (Ser121-Phe124 of the human CCR7) linking helices II and III, ECL2 (Asp198-Val217 of the human CCR7) linking helices IV and V, and ECL3 (Thr294-Ser296 of the human CCR7) linking helices VI to VII. Like all chemokine receptors, the CCR7 is expected to have two conserved disulfide bonds in its ectodomains (Zheng et al., 2016).

In specific embodiments of the present invention, the CCR7 polypeptide comprises a CCR7 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR7 protein sequence.

In some embodiments, the CCR7 protein sequence corresponds to a mammalian CCR7 protein sequence. Suitable CCR7 sequences may suitably be from mammal selected from the group comprising mouse (UniProtKB Accession No. P47774), human (UniProtKB Accession No. P32248), rat (UniProtKB Accession No. Q6U2D6), pig (UniProtKB Accession No. Q861S1), cow (UniProtKB Accession No. AOJNA6), dog (UniProtKB Accession No. J9P893), rabbit (UniProtKB Accession No. G1TKJ1), marmoset (UniProtKB Accession No. F6R3A6), chimpanzee (UniProtKB Accession No. H2R9P0), tasmanian devil (UniProtKB Accession No. G3WAF3), sheep (UniProtKB Accession No. W5PZG4), guinea pig (UniProtKB Accession No. H0VL65), cat (UniProtKB Accession No. M3WBU1), horse (UniProtKB Accession No. F6SPH5).

In some preferred embodiments, the CCR7 protein sequence corresponds to a human CCR7 protein sequence. In some embodiments, the CCR7 polypeptide comprises a human full-length wild-type CCR7 protein sequence (UniProtKB Accession No. P32248), as set forth below, or a functional fragment of the wild-type CCR7 protein sequence.

[SEQ ID NO: 28]
MDLGKPMKSVLVVALLVIFQVCLCQDEVTDDYIGDNTTVDYTLFESLCSK

KDVRNFKAWFLPIMYSIICFVGLLGNGLVVLTYIYFKRLKTMTDTYLLNL

AVADILFLLTLPFWAYSAAKSWVFGVHFCKLIFAIYKMSFFSGMLLLLCI

SIDRYVAIVQAVSAHRHRARVLLISKLSCVGIWILATVLSIPELLYSDLQ

RSSSEQAMRCSLITEHVEAFITIQVAQMVIGFLVPLLAMSFCYLVIIRTL

LQARNFERNKAIKVIIAVVVVFIVFQLPYNGVVLAQTVANFNITSSTCEL

SKQLNIAYDVTYSLACVRCCVNPFLYAFIGVKFRNDLFKLFKDLGCLSQE

QLRQWSSCRHIRRSSMSVEAETTTTFSP.

In one form of the invention, the CCR7 polypeptide comprises a truncated form of a mammalian wild-type CCR7 protein sequence. For example, the CCR7 polypeptide sequence may comprise the human wild-type CCR7 protein sequence with a C-terminal truncation (e.g., amino acid residues 358-378 may be truncated). Alternatively or in addition, the CCR7 polypeptide sequence may comprise the wild-type CCR7 protein sequence with a N-terminal truncation. Alternatively or in addition to a C-terminal or N-terminal truncation, a truncation may be performed to remove an internal section of the wild-type CCR7 protein sequence (e.g., amino acid residues 201-209 may be truncated). By way of a non-limiting illustrative example, a CCR7 polypeptide suitable for using with the present invention comprised amino acid residues 2-200 and 210-357 of the human wild-type CCR7 protein sequence as set forth in SEQ ID NO: 28.

3.28 Constructs and Nucleotide Sequences Encoding CCR7 Polypeptides

The present invention also encompasses isolated polynucleotide sequences and constructs encoding CCR7 polypeptides as broadly described above and elsewhere herein. Also contemplated are host cells comprising those polynucleotide sequences or constructs.

In some embodiments, the polynucleotide sequences comprise a sequence that corresponds to a human CCR7 nucleotide (i.e., corresponding to the CCR7 gene) sequence as set forth for example in GenBank Accession Nos. NM_001301718.1, NM_001301717.1, NM_001301716.1, NM_001301714.1, NM_001838.3, EF064758.1, NC_000017.11, NC_018928.2, CM000268.1, BC035343.1. In representative examples of this type, the polynucleotide comprises a CCR7 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR7 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR7 polynucleotide, or a fragment thereof. In some embodiments, the CCR7 polynucleotide comprises a nucleotide sequence that hybridises to an open reading frame for a wild type mammalian CCR7 protein, or a fragment thereof under low, medium or high stringency conditions.

3.29 CC Chemokine Receptor CCR9 (CCR9) Polypeptides

Like all chemokine receptors, the CCR9 is involved in the mediation of inflammatory processes. It is found in T cells and IgA+ plasma cells and is associated with homing of T cells and IgA+ plasma cells to the intestine and inflammatory bowel disease (Charo & Ransohoff, 2006).

To date, a crystal structure of the CCR9 has not yet been published, so the structural and ligand-binding features of the receptor have to be inferred through indirect approaches such as mutagenesis and homology modelling. The extracellular part of CCR9 consists of the N-terminal segment (Met1-Asn42 of the human CCR9), ECL1 (Gln111-Phe114 of the human CCR9) linking helices II and III, ECL2 (Gln188-Glu206 of the human CCR9) linking helices IV and V, and ECL3 (Phe285-Ser287 of the human CCR9) linking helices VI to VII. Like all chemokine receptors, the CCR9 is expected to have two conserved disulphide bonds in its ectodomains (Zheng et al., 2016).

In specific embodiments of the present invention, the CCR9 polypeptide comprises a CCR9 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CCR9 protein sequence.

In some embodiments, the CCR9 protein sequence corresponds to a mammalian CCR9 protein sequence. Suitable CCR9 sequences may suitably be from mammal selected from the group comprising cat (UniProtKB Accession No. M3W6KO), chimpanzee (UniProtKB Accession No. H2QMG2), cow (UniProtKB Accession No. F6RMK7), dog (UniProtKB Accession No. E2RQ21), gorilla (UniProtKB Accession No. G3QQ18), guinea pig (UniProtKB Accession No. H0VWP5), horse (UniProtKB Accession No. F6X7N4), human (UniProtKB Accession No. P51686), marmoset (UniProtKB Accession No. F7F023), mouse (UniProtKB Accession No. Q9WUT7), panta (UniProtKB Accession No. G1MOT5), pig (UniProtKB Accession No. Q6YT47), rabbit (UniProtKB Accession No. G1SUQ1), sheep (UniProtKB Accession No. Q1WLP9).

In some preferred embodiments, the CCR9 protein sequence corresponds to a human CCR9 protein sequence. In some embodiments, the CCR9 polypeptide comprises a human full-length wild-type CCR9 protein sequence (UniProtKB Accession No. P51686), as set forth below, or a functional fragment of the wild-type CCR9 protein sequence.

[SEQ ID NO: 29]
MTPTDFTSPIPNMADDYGSESTSSMEDYVNFNFTDFYCEKNNVRQFASHF

LPPLYWLVFIVGALGNSLVILVYWYCTRVKTMTDMFLLNLAIADLLFLVT

LPFWAIAAADQWKFQTFMCKVVNSMYKMNFYSCVLLIMCISVDRYIAIAQ

```
-continued
AMRAHTWREKRLLYSKMVCFTIWVLAAALCIPEILYSQIKEESGIAICTM

VYPSDESTKLKSAVLTLKVILGFFLPFVVMACCYTIIIHTLIQAKKSSKH

KALKVTITVLTVFVLSQFPYNCILLVQTIDAYAMFISNCAVSTNIDICFQ

VTQTIAFFHSCLNPVLYVFVGERFRRDLVKTLKNLGCISQAQWVSFTRRE

GSLKLSSMLLETTSGALSL.
```

In one form of the invention, the CCR9 polypeptide comprises a truncated form of a mammalian wild-type CCR9 protein sequence. For example, the CCR9 polypeptide sequence may comprise the human wild-type CCR9 protein sequence with a C-terminal truncation (e.g., amino acid residues 334-369 may be truncated). Alternatively or in addition, the CCR9 polypeptide sequence may comprise the wild-type CCR9 protein sequence with a N-terminal truncation. Alternatively or in addition to a C-terminal or N-terminal truncation, a truncation may be performed to remove an internal section of the wild-type CCR9 protein sequence (e.g., amino acid residues 190-204 may be truncated). By way of a non-limiting illustrative example, a CCR9 polypeptide suitable for using with the present invention comprised amino acid residues 2-189 and 205-333 of the human wild-type CCR9 protein sequence as set forth in SEQ ID NO: 29.

3.30 Constructs and Nucleotide Sequences Encoding CCR9 Polypeptides.

The present invention also encompasses isolated polynucleotide sequences and constructs encoding CCR9 polypeptides as broadly described above and elsewhere herein. Also contemplated are host cells comprising those polynucleotide sequences or constructs.

In some embodiments, the polynucleotide sequences comprise a sequence that corresponds to a human CCR9 nucleotide (i.e., corresponding to the CCR9 gene) sequence as set forth for example in GenBank Accession Nos. AY242127.1, NM_001256369.1, NM_031200.2, NM_006641.3, AF145207.1, NG_029472.1, AF145440.1, AF145439.1, BC095516.1, BC069678.1 and AJ132337.1. In representative examples of this type, the polynucleotide comprises a CCR9 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CCR9 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CCR9 polynucleotide, or a fragment thereof. In some embodiments, the CCR9 polynucleotide comprises a nucleotide sequence that hybridises to an open reading frame for a wild type mammalian CCR9 protein, or a fragment thereof under low, medium or high stringency conditions.

3.31 CXC Chemokine Receptor CXCR2 (CXCR2) Polypeptides

Like all chemokine receptors, the CXCR2 is involved in the mediation of inflammatory processes. It is found in neutrophils, monocytes and micro-vascular endothelial cells and is associated with inflammatory lung disease, COPD and is angiogenic for tumor growth (Charo & Ransohoff, 2006).

To date, a crystal structure of the CXCR2 has not yet been published, so the structural and ligand-binding features of the receptor have to be inferred through indirect approaches such as mutagenesis and homology modelling. The extracellular part of CXCR2 consists of the N-terminal segment (Met1-Glu42 of the human CXCR2), ECL1 (Gly111-Phe114 of the human CXCR2) linking helices II and III, ECL2 (Arg185-Ala205 of the human CXCR2) linking helices IV and V, and ECL3 (Val281-Glu284 of the human CXCR2) linking helices VI to VII. Like all chemokine receptors, the CXCR2 is expected to have two conserved disulfide bonds in its ectodomains (Zheng et al., 2016).

In specific embodiments of the present invention, the CXCR2 polypeptide comprises a CXCR2 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CXCR2 protein sequence.

In some embodiments, the CXCR2 protein sequence corresponds to a mammalian CXCR2 protein sequence. Suitable CXCR2 sequences may suitably be from mammal selected from the group comprising human (UniProtKB Accession No. P25025), mouse (UniProtKB Accession No. P35343), rat (UniProtKB Accession No. P35407), rabbit (UniProtKB Accession No. P35344), dog (UniProtKB Accession No. O97571), cow (UniProtKB Accession No. Q28003), chimpanzee (UniProtKB Accession No. Q28807), gorilla (UniProtKB Accession No. Q28422), marmoset (UniProtKB Accession No. F6Y118), bat (UniProtKB Accession No. G1P3F4), cat (UniProtKB Accession No. M3XFH4), guinea pig (UniProtKB Accession No. Q810T4), pig (UniProtKB Accession No. F1SS05), sheep (UniProtKB Accession No. W5QDX4).

In some preferred embodiments, the CXCR2 protein sequence corresponds to a human CXCR2 protein sequence. In some embodiments, the CXCR2 polypeptide comprises a human full-length wild-type CXCR2 protein sequence (UniProtKB Accession No. P25025), as set forth below, or a functional fragment of the wild-type CXCR2 protein sequence.

```
                                          [SEQ ID NO: 30]
MEDFNMESDSFEDFWKGEDLSNYSYSSTLPPFLLDAAPCEPESLEINKYF

VVIIYALVFLLSLLGNSLVMLVILYSRVGRSVTDVYLLNLALADLLFALT

LPIWAASKVNGWIFGTFLCKVVSLLKEVNFYSGILLLACISVDRYLAIVH

ATRTLTQKRYLVKFICLSIWGLSLLLALPVLLFRRTVYSSNVSPACYEDM

GNNTANWRMLLRILPQSFGFIVPLLIMLFCYGFTLRTLFKAHMGQKHRAM

RVIFAVVLIFLLCWLPYNLVLLADTLMRTQVIQETCERRNHIDRALDATE

ILGILHSCLNPLIYAFIGQKFRHGLLKILAIHGLISKDSLPKDSRPSFVG

SSSGHTSTTL.
```

In one form of the invention, the CXCR2 polypeptide comprises a truncated form of a mammalian wild-type CXCR2 protein sequence. For example, the CXCR2 polypeptide sequence may comprise the human wild-type CXCR2 protein sequence with a C-terminal truncation (e.g., amino acid residues 346-360 may be truncated). Alternatively or in addition, the CXCR2 polypeptide sequence may comprise the wild-type CXCR2 protein sequence with a N-terminal truncation. Alternatively or in addition to a C-terminal or N-terminal truncation, a truncation may be performed to remove an internal section of the wild-type CXCR2 protein sequence (e.g., amino acid residues 187-202 may be truncated). By way of a non-limiting illustrative example, a CXCR2 polypeptide suitable for using with the present invention comprised amino acid residues 2-186 and 203-345 of the human wild-type CXCR2 protein sequence as set forth in SEQ ID NO: 30.

3.32 Constructs and Nucleotide Sequences Encoding CXCR2 Polypeptides

The present invention also encompasses isolated polynucleotide sequences and constructs encoding CXCR2 polypeptides as broadly described above and elsewhere herein. Also contemplated are host cells comprising those polynucleotide sequences or constructs.

In some embodiments, the polynucleotide sequences comprise a sequence that corresponds to a human CXCR2 nucleotide (i.e., corresponding to the CXCR2 gene) sequence as set forth for example in GenBank Accession Nos. NM_001168298.1, NM_001557.3, AB032734.1, AB032733.1, NG_052975.1, XM_017003992.1, XM_017003991.1, XM_017003990.1, XM_005246530.3. In representative examples of this type, the polynucleotide comprises a CXCR2 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CXCR2 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CXCR2 polynucleotide, or a fragment thereof. In some embodiments, the CXCR2 polynucleotide comprises a nucleotide sequence that hybridises to an open reading frame for a wild type mammalian CXCR2 protein, or a fragment thereof under low, medium or high stringency conditions.

3.33 CXC Chemokine Receptor CXCR4 (CXCR4) Polypeptides

Like all chemokine receptors, the CXCR4 is involved in the mediation of inflammatory processes. It is widely expressed throughout the immune system and is associated with HIV-infection, tumour metastases and hematopoiesis (Charo & Ransohoff, 2006).

To date, two studies have reported solving the crystal structure of the CXCR4, providing insight into how it binds its ligands (Wu et al., 2010; Qin et al., 2015). The extracellular part of CXCR4 consists of the N-terminal segment (Met1-Phe29 of the human CXCR4), ECL1 (Asn101-Phe104 of the human CXCR4) linking helices II and III, ECL2 (Asn176-Asn192 of the human CXCR4) linking helices IV and V, and ECL3 (Ile269-Gln272 of the human CXCR4) linking helices VI to VII. As expected for most chemokine receptors, the CXCR4 has two conserved disulfide bonds in its ectodomain (Wu et al., 2010).

In specific embodiments of the present invention, the CXCR4 polypeptide comprises a CXCR4 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CXCR4 protein sequence.

In some embodiments, the CXCR4 protein sequence corresponds to a mammalian CXCR4 protein sequence. Suitable CXCR4 sequences may suitably be from mammal selected from the group comprising cat (UniProtKB Accession No. P56498), chimpanzee (UniProtKB Accession No. P61072), cow (UniProtKB Accession No. P25930), dog (UniProtKB Accession No. Q3LSL6), hedgehog (UniProtKB Accession No. A0A1S2ZV52), horse (UniProtKB Accession No. F6Y9M7), human (UniProtKB Accession No. P61073), lion (UniProtKB Accession No. B5LVX6), marmoset (UniProtKB Accession No. Q8HZU1), mouse (UniProtKB Accession No. A0A0R4J0N8), pig (UniProtKB Accession No. Q764M9), rabbit (UniProtKB Accession No. G1SGF1), rat (UniProtKB Accession No. A0A0G2K9U1), sheep (UniProtKB Accession No. W5PLA4).

In some preferred embodiments, the CXCR4 protein sequence corresponds to a human CXCR4 protein sequence. In some embodiments, the CXCR4 polypeptide comprises a human full-length wild-type CXCR4 protein sequence (UniProtKB Accession No. P61073), as set forth below, or a functional fragment of the wild-type CXCR4 protein sequence.

[SEQ ID NO: 31]
MEGISIYTSDNYTEEMGSGDYDSMKEPCFREENANFNKIFLPTIYSIIFL

TGIVGNGLVILVMGYQKKLRSMTDKYRLHLSVADLLFVITLPFWAVDAVA

NWYFGNFLCKAVHVIYTVNLYSSVLILAFISLDRYLAIVHATNSQRPRKL

LAEKVVYVGVWIPALLLTIPDFIFANVSEADDRYICDRFYPNDLWVVVFQ

FQHIMVGLILPGIVILSCYCIIISKLSHSKGHQKRKALKTTVILILAFFA

CWLPYYIGISIDSFILLEIIKQGCEFENTVHKWISITEALAFFHCCLNPI

LYAFLGAKFKTSAQHALTSVSRGSSLKILSKGKRGGHSSVSTESESSSFH

SS.

In one form of the invention, the CXCR4 polypeptide comprises a truncated form of a mammalian wild-type CXCR4 protein sequence. For example, the CXCR4 polypeptide sequence may comprise the human wild-type CXCR4 protein sequence with a C-terminal truncation (e.g., amino acid residues 319-352 may be truncated). Alternatively or in addition, the CXCR4 polypeptide sequence may comprise the wild-type CXCR4 protein sequence with a N-terminal truncation. Alternatively or in addition to a C-terminal or N-terminal truncation, a truncation may be performed to remove an internal section of the wild-type CXCR4 protein sequence (e.g., amino acid residues 179-188 may be truncated). By way of a non-limiting illustrative example, a CXCR4 polypeptide suitable for using with the present invention comprised amino acid residues 2-178 and 189-318 of the human wild-type CXCR4 protein sequence as set forth in SEQ ID NO: 31.

3.34 Constructs and Nucleotide Sequences Encoding CXCR4 Polypeptides.

The present invention also encompasses isolated polynucleotide sequences and constructs encoding CXCR4 polypeptides as broadly described above and elsewhere herein. Also contemplated are host cells comprising those polynucleotide sequences or constructs.

In some embodiments, the polynucleotide sequences comprise a sequence that corresponds to a human CXCR4 nucleotide (i.e., corresponding to the CXCR4 gene) sequence as set forth for example in GenBank Accession Nos. AY242129.1, AJ224869.1, NM_003467.2, NM_001008540.2, NM_001348056.1, NM_001348060.1, NM_001348059.1, AF147204.2, AY826773.1, KU245647.1, KU245646.1, Y14739.1, AF025375.1, AF052572.1, AF348491.1 and U81003.1. In representative examples of this type, the polynucleotide comprises a CXCR4 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CXCR4 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CXCR4 polynucleotide, or a fragment thereof. In some embodiments, the CXCR4 polynucleotide comprises a nucleotide sequence that hybridises to an open reading frame for a wild type mammalian CXCR4 protein, or a fragment thereof under low, medium or high stringency conditions.

3.35 CXC Chemokine Receptor CXCR5 (CXCR5) Polypeptides

Like all chemokine receptors, the CXCR5 is involved in the mediation of inflammatory processes. It is expressed in B cells and follicular helper T cells and is involved in the formation of B-cell follicles (Charo & Ransohoff, 2006).

To date, a crystal structure of the CCR9 has not yet been published, so the structural and ligand-binding features of the receptor have to be inferred through indirect approaches such as mutagenesis and homology modelling. The extracellular part of CXCR5 consists of the N-terminal segment (Met1-Glu42 of the human CXCR5), ECL1 (Gly114-Leu117 of the human CXCR5) linking helices II and III, ECL2 (Lys189-Glu211 of the human CXCR5) linking helices IV and V, and ECL3 (Ala289-Asn292 of the human CXCR5) linking helices VI to VII. Like all chemokine receptors, the CCR9 is expected to have two conserved disulfide bonds in its ectodomains (Zheng et al., 2016).

In specific embodiments of the present invention, the CXCR5 polypeptide comprises a CXCR5 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CXCR5 protein sequence.

In some embodiments, the CXCR5 protein sequence corresponds to a mammalian CXCR5 protein sequence. Suitable CXCR5 sequences may suitably be from mammal selected from the group comprising cat (UniProtKB Accession No. M3XAS4), chimpanzee (UniProtKB Accession No. H2Q4W8), cow (UniProtKB Accession No. G3N3U0), dog (UniProtKB Accession No. E2RR03), gorilla (UniProtKB Accession No. G3RDW5), guinea pig (UniProtKB Accession No. H0W611), human (UniProtKB Accession No. P32302), marmoset (UniProtKB Accession No. F7A1S1), mouse (UniProtKB Accession No. Q04683), panda (UniProtKB Accession No. G1KZK8), pig (UniProtKB Accession No. F1SAJ4), rabbit (UniProtKB Accession No. G1TNG1), rat (UniProtKB Accession No. P34997), sheep (UniProtKB Accession No. W5PPW1).

In some preferred embodiments, the CXCR5 protein sequence corresponds to a human CXCR5 protein sequence. In some embodiments, the CXCR5 polypeptide comprises a human full-length wild-type CXCR5 protein sequence (UniProtKB Accession No. P32302), as set forth below, or a functional fragment of the wild-type CXCR5 protein sequence.

[SEQ ID NO: 32]
MNYPLTLEMDLENLEDLFWELDRLDNYNDTSLVENHLCPATEGPLMASFK

AVFVPVAYSLIFLLGVIGNVLVLVILERHRQTRSSTETFLFHLAVADLLL

VFILPFAVAEGSVGWVLGTFLCKTVIALHKVNFYCSSLLLACIAVDRYLA

IVHAVHAYRHRRLLSIHITCGTIWLVGFLLALPEILFAKVSQGHHNNSLP

RCTFSQENQAETHAWFTSRFLYHVAGFLLPMLVMGWCYVGVVHRLRQAQR

RPQRQKAVRVAILVTSIFFLCWSPYHIVIFLDTLARLKAVDNTCKLNGSL

-continued
PVAITMCEFLGLAHCCLNPMLYTFAGVKFRSDLSRLLTKLGCTGPASLCQ

LFPSWRRSSLSESENATSLTTF.

In one form of the invention, the CXCR5 polypeptide comprises a truncated form of a mammalian wild-type CXCR5 protein sequence. For example, the CXCR5 polypeptide sequence may comprise the human wild-type CXCR5 protein sequence with a C-terminal truncation (e.g., amino acid residues 339-372 may be truncated). Alternatively or in addition, the CXCR5 polypeptide sequence may comprise the wild-type CXCR5 protein sequence with a N-terminal truncation. Alternatively or in addition to a C-terminal or N-terminal truncation, a truncation may be performed to remove an internal section of the wild-type CXCR5 protein sequence (e.g., amino acid residues 193-208 may be truncated). By way of a non-limiting illustrative example, a CXCR5 polypeptide suitable for using with the present invention comprised amino acid residues 2-192 and 209-338 of the human wild-type CXCR5 protein sequence as set forth in SEQ ID NO: 32.

3.36 Constructs and Nucleotide Sequences Encoding CXCR5 Polypeptides.

The present invention also encompasses isolated polynucleotide sequences and constructs encoding CXCR5 polypeptides as broadly described above and elsewhere herein. Also contemplated are host cells comprising those polynucleotide sequences or constructs.

In some embodiments, the polynucleotide sequences comprise a sequence that corresponds to a human CXCR5 nucleotide (i.e., corresponding to the CXCR5 gene) sequence as set forth for example in GenBank Accession Nos. NM_001716.4, NM_032966.2 and BC110352.1. In representative examples of this type, the polynucleotide comprises a CXCR5 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CXCR5 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CXCR5 polynucleotide, or a fragment thereof. In some embodiments, the CXCR5 polynucleotide comprises a nucleotide sequence that hybridises to an open reading frame for a wild type mammalian CXCR5 protein, or a fragment thereof under low, medium or high stringency conditions.

3.37 CXC Chemokine Receptor CXCR6 (CXCR6) Polypeptides

Like all chemokine receptors, the CXCR6 is involved in the mediation of inflammatory processes. It is found in CD8+ T cells, natural killer cells, and memory CD4+ T cells and is associated with inflammatory liver disease and atherosclerosis (Charo & Ransohoff, 2006).

To date, a crystal structure of the CXCR6 has not yet been published, so the structural and ligand-binding features of the receptor have to be inferred through indirect approaches such as mutagenesis and homology modelling. The extracellular part of CXCR6 consists of the N-terminal segment (Met1-Asp25 of the human CXCR6), ECL1 (Glu94-Phe97 of the human CXCR6) linking helices II and III, ECL2 (Asn171-Glu185 of the human CXCR6) linking helices IV and V, and ECL3 (Trp258-Ala262 of the human CXCR6) linking helices VI to VII. Like all chemokine receptors, the CXCR6 is expected to have two conserved disulfide bonds in its ectodomains (Zheng et al., 2016).

In specific embodiments of the present invention, the CXCR6 polypeptide comprises a CXCR6 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CXCR6 protein sequence.

In some embodiments, the CXCR6 protein sequence corresponds to a mammalian CXCR6 protein sequence. Suitable CXCR6 sequences may suitably be from mammal selected from the group comprising human (UniProtKB Accession No. O00574), chimpanzee (UniProtKB Accession No. Q9TV16), mouse (UniProtKB Accession No. Q9EQ16), rat (UniProtKB Accession No. A7ISD5), pig (UniProtKB Accession No. Q6YT44), cow (UniProtKB Accession No. Q5EA94), dog (UniProtKB Accession No. F1PMU3), tasmanian devil (UniProtKB Accession No. G3W5Z9), marmoset (UniProtKB Accession No. F7DTR0), cat (UniProtKB Accession No. M3W6K1), bat (UniProtKB Accession No. G1P8C6), rabbit (UniProtKB Accession No. G1SLJ0), guinea pig (UniProtKB Accession No. H0W823), horse (UniProtKB Accession No. F6XQ88).

In some preferred embodiments, the CXCR6 protein sequence corresponds to a human CXCR6 protein sequence. In some embodiments, the CXCR6 polypeptide comprises a human full-length wild-type CXCR6 protein sequence (UniProtKB Accession No. O00574), as set forth below, or a functional fragment of the wild-type CXCR6 protein sequence.

[SEQ ID NO: 33]
MAEHDYHEDYGFSSFNDSSQEEHQDFLQFSKVFLPCMYLVVFVCGLVGNS

LVLVISIFYHKLQSLTDVFLVNLPLADLVFVCTLPFWAYAGIHEWVFGQV

MCKSLLGIYTINFYTSMLILTCITVDRFIVVVKATKAYNQQAKRMTWGKV

TSLLIWVISLLVSLPQIIYGNVFNLDKLICGYHDEAISTVVLATQMTLGF

FLPLLTMIVCYSVIIKTLLHAGGFQKHRSLKIIFLVMAVFLLTQMPFNLM

KFIRSTHWEYYAMTSFHYTIMVTEAIAYLRACLNPVLYAFVSLKFRKNFW

KLVKDIGCLPYLGVSHQWKSSEDNSKTFSASHNVEATSMFQL.

In one form of the invention, the CXCR6 polypeptide comprises a truncated form of a mammalian wild-type CXCR6 protein sequence. For example, the CXCR6 polypeptide sequence may comprise the human wild-type CXCR6 protein sequence with a C-terminal truncation (e.g., amino acid residues 318-342 may be truncated). Alternatively or in addition, the CXCR6 polypeptide sequence may comprise the wild-type CXCR6 protein sequence with a N-terminal truncation. Alternatively or in addition to a C-terminal or N-terminal truncation, a truncation may be performed to remove an internal section of the wild-type CXCR6 protein sequence (e.g., amino acid residues 172-180 may be truncated). By way of a non-limiting illustrative example, a CXCR6 polypeptide suitable for using with the present invention comprised amino acid residues 2-171 and 181-317 of the human wild-type CXCR6 protein sequence as set forth in SEQ ID NO: 33.

3.38 Constructs and Nucleotide Sequences Encoding CXCR6 Polypeptides

The present invention also encompasses isolated polynucleotide sequences and constructs encoding CXCR6 polypeptides as broadly described above and elsewhere herein. Also contemplated are host cells comprising those polynucleotide sequences or constructs.

In some embodiments, the polynucleotide sequences comprise a sequence that corresponds to a human CXCR6 nucleotide (i.e., corresponding to the CXCR6 gene) sequence as set forth for example in GenBank Accession Nos. NM_006564.1, XM_005264809.2, XM_011533291.2, XM_011533290.2, EU076974.1, EF064741.1, AK313754.1. In representative examples of this type, the polynucleotide comprises a CXCR6 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CXCR6 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CXCR6 polynucleotide, or a fragment thereof. In some embodiments, the CXCR6 polynucleotide comprises a nucleotide sequence that hybridises to an open reading frame for a wild type mammalian CXCR6 protein, or a fragment thereof under low, medium or high stringency conditions.

3.39 CXC Chemokine Receptor CXCR7 (Also Known as Atypical Chemokine Receptor 3; ACKR3) Polypeptides Like all chemokine receptors, the CXCR7 is involved in the mediation of inflammatory processes. It is found in reticulocytes, post capillary venules, epithelial cells of the kidneys and lungs, and cerebellar neurons. The CXCR7 has been associated with various autoimmune diseases, transplant complications, HIV infection, pre-eclampsia and malignancy (Horne & Woolley, 2009).

To date, a crystal structure of the CXCR7 has not yet been published, so the structural and ligand-binding features of the receptor have to be inferred through indirect approaches such as mutagenesis and homology modelling. The extracellular part of CXCR7 consists of the N-terminal segment (Met1-Ser41 of the human CXCR7), ECL1 (His107-Met112 of the human CXCR7) linking helices II and III, ECL2 (Lys184-Glu207 of the human CXCR7) linking helices IV and V, and ECL3 (Tyr282-Phe285 of the human CXCR7) linking helices VI to VII. The extracellular amino-terminal domain harbors three potential N-glycosylation sites at residues 16, 27, and 33 (Czerwinski et al., 2007).

In specific embodiments of the present invention, the CXCR7 polypeptide comprises a CXCR7 protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a CXCR7 protein sequence.

In some embodiments, the CXCR7 protein sequence corresponds to a mammalian CXCR7 protein sequence. Suitable CXCR7 sequences may suitably be from mammal selected from the group comprising human (UniProtKB Accession No. P25106), rat (UniProtKB Accession No. O89039), mouse (UniProtKB Accession No. P56485), dog (UniProtKB Accession No. P11613), cow (UniProtKB Accession No. A4IF77), macaque (UniProtKB Accession No. F7GTL4), marmoset (UniProtKB Accession No. F7HZX1), chimpanzee (UniProtKB Accession No. H2QJP1), mink (UniProtKB Accession No. U6DE19).

In some preferred embodiments, the CXCR7 protein sequence corresponds to a human CXCR7 protein sequence. In some embodiments, the CXCR7 polypeptide comprises a human full-length wild-type CXCR7 protein sequence (Uni- ProtKB Accession No. P25106), as set forth below, or a functional fragment of the wild-type CXCR7 protein sequence.

[SEQ ID NO: 34]
MDLHLFDYSEPGNFSDISWPCNSSDCIVVDTVMCPNMPNKSVLLYTLSFI

YIFIFVIGMIANSVVVWVNIQAKTTGYDTHCYILNLAIADLWVVLTIPVW

VVSLVQHNQWPMGELTCKVTHLIFSINLFGSIFFLTCMSVDRYLSITYFT

NTPSSRKKMVRRVVCILVWLLAFCVSLPDTYYLKTVTSASNNETYCRSFY

PEHSIKEWLIGMELVSVVLGFAVPFSIIAVFYFLLARAISASSDQEKHSS

RKIIFSYVVVFLVCWLPYHVAVLLDIFSILHYIPFTCRLEHALFTALHVT

QCLSLVHCCVNPVLYSFINRNYRYELMKAFIFKYSAKTGLTKLIDASRVS

ETEYSALEQSTK.

In one form of the invention, the CXCR7 polypeptide comprises a truncated form of a mammalian wild-type CXCR7 protein sequence. For example, the CXCR7 polypeptide sequence may comprise the human wild-type CXCR7 protein sequence with a C-terminal truncation (e.g., amino acid residues 339-362 may be truncated). Alternatively or in addition, the CXCR7 polypeptide sequence may comprise the wild-type CXCR7 protein sequence with a N-terminal truncation. Alternatively or in addition to a C-terminal or N-terminal truncation, a truncation may be performed to remove an internal section of the wild-type CXCR7 protein sequence (e.g., amino acid residues 187-204 may be truncated). By way of a non-limiting illustrative example, a CXCR7 polypeptide suitable for using with the present invention comprised amino acid residues 2-186 and 205-338 of the human wild-type CXCR7 protein sequence as set forth in SEQ ID NO: 34.

3.40 Constructs and Nucleotide Sequences Encoding CXCR7 Polypeptides

The present invention also encompasses isolated polynucleotide sequences and constructs encoding CXCR7 polypeptides as broadly described above and elsewhere herein. Also contemplated are host cells comprising those polynucleotide sequences or constructs.

In some embodiments, the polynucleotide sequences comprise a sequence that corresponds to a human CXCR7 nucleotide (i.e., corresponding to the ACKR3 gene) sequence as set forth for example in GenBank Accession Nos. NM_020311.2, XM_017004516.1, XM_005246098.3, XM_005246097.2, BC036661.2. In representative examples of this type, the polynucleotide comprises a CXCR7 nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a CXCR7 polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian CXCR7 polynucleotide, or a fragment thereof. In some embodiments, the CXCR7 polynucleotide comprises a nucleotide sequence that hybridises to an open reading frame for a wild type mammalian CXCR7 protein, or a fragment thereof under low, medium or high stringency conditions.

3.41 Dopamine D1 Receptor (D1R) Polypeptides

In the central nervous system (CNS) the D1R has numerous functions, including stimulation of locomotor activity, involvement in reward and reinforcement mechanisms, and roles in learning, memory and other cognitive functions. Outside of the CNS, the D1R regulates renin secretion and maintenance of renal function (Beaulieu & Gainetdinov, 2011).

To date, a crystal structure of the D1R has not yet been published, so the structural and ligand-binding features of the receptor have to be inferred through indirect approaches such as mutagenesis and homology modelling. The extracellular part of D1R consists of the N-terminal segment (Met1-Leu14 of the human D1R), ECL1 (Ala87-Phe92 of the human D1R) linking helices II and III, ECL2 (Trp163-Leu190 of the human D1R) linking helices IV and V, and ECL3 (Gly299-Pro305 of the human D1R) linking helices VI to VII.

In specific embodiments of the present invention, the D1R polypeptide comprises a D1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a D1R protein sequence.

In some embodiments, the D1R protein sequence corresponds to a mammalian D1R protein sequence. Suitable D1R sequences may suitably be from mammal selected from the group comprising cat (UniProtKB Accession No. M3VVD1), chimpanzee (UniProtKB Accession No. H2QS18), cow (UniProtKB Accession No. Q95136), dog (UniProtKB Accession No. F1PI21), gorilla (UniProtKB Accession No. G3RXE8), guinea pig (UniProtKB Accession No. H0VES0), human (UniProtKB Accession No. P21728), mouse (UniProtKB Accession No. Q61616), panda (UniProtKB Accession No. G1LK07), pig (UniProtKB Accession No. P50130), rabbit (UniProtKB Accession No. G1SML2), rat (UniProtKB Accession No. P18901), sheep (UniProtKB Accession No. W5PPK6), Tasmanian devil (UniProtKB Accession No. G3VDD8).

In some preferred embodiments, the D1R protein sequence corresponds to a human D1R protein sequence. In some embodiments, the D1R polypeptide comprises a human full-length wild-type D1R protein sequence (UniProtKB Accession No. P21728), as set forth below, or a functional fragment of the wild-type D1R protein sequence.

[SEQ ID NO: 35]
MRTLNTSAMDGTGLVVERDFSVRILTACFLSLLILSTLLGNTLVCAAVIR

FRHLRSKVTNFFVISLAVSDLLVAVLVMPWKAVAEIAGFWPFGSFCNIWV

AFDIMCSTASILNLCVISVDRYWAISSPFRYERKMTPKAAFILISVAWTL

SVLISFIPVQLSWHKAKPTSPSDGNATSLAETIDNCDSSLSRTYAISSSV

ISFYIPVAIMIVTYTRIYRIAQKQIRRIAALERAAVHAKNCQTTTGNGKP

VECSQPESSFKMSFKRETKVLKTLSVIMGVFVCCWLPFFILNCILPFCGS

GETQPFCIDSNTFDVFVWFGWANSSLNPIIYAFNADFRKAFSTLLGCYRL

CPATNNAIETVSINNNGAAMFSSHHEPRGSISKECNLVYLIPHAVGSSED

LKKEEAAGIARPLEKLSPALSVILDYDTDVSLEKIQPITQNGQHPT.

In one form of the invention, the D1R polypeptide comprises a truncated form of a mammalian wild-type D1R protein sequence. For example, the D1R polypeptide sequence may comprise the human wild-type D1R protein sequence with a C-terminal truncation (e.g., amino acid residues 348-446 may be truncated). Alternatively or in addition, the D1R polypeptide sequence may comprise the wild-type D1R protein sequence with a N-terminal truncation. Alternatively or in addition to a C-terminal or N-terminal truncation, a truncation may be performed to remove an internal section of the wild-type D1R protein sequence (e.g., amino acid residues 166-186 may be truncated). By way of a non-limiting illustrative example, a D1R polypeptide suitable for using with the present invention comprised amino acid residues 2-165 and 187-347 of the human wild-type D1R protein sequence as set forth in SEQ ID NO: 35.

3.42 Constructs and Nucleotide Sequences Encoding D1R Polypeptides.

The present invention also encompasses isolated polynucleotide sequences and constructs encoding D1R polypeptides as broadly described above and elsewhere herein. Also contemplated are host cells comprising those polynucleotide sequences or constructs.

In some embodiments, the polynucleotide sequences comprise a sequence that corresponds to a human D1R nucleotide (i.e., corresponding to the DRD1 gene) sequence as set forth for example in GenBank Accession Nos. CR541922.1, EU249297.1, KR712133.1, KR712132.1, KR712131.1, KR712130.1, KJ896726.1, NM_000794.3, and NG_011802.1. In representative examples of this type, the polynucleotide comprises a D1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a D1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian D1R polynucleotide, or a fragment thereof. In some embodiments, the D1R polynucleotide comprises a nucleotide sequence that hybridises to an open reading frame for a wild type mammalian D1R protein, or a fragment thereof under low, medium or high stringency conditions.

3.43 Endothelin Receptor Type A (ETAR) Polypeptides

The ETAR mediates many functions including vasoconstriction, cardiovascular remodelling, cell proliferation, cell differentiation, extracellular matrix production, and control of water and sodium secretion. It is also implicated in the development of various diseases such as pulmonary hypertension, atherosclerosis, diabetes, and cardiac remodelling after myocardial ischemia (Horinouchi et al., 2013).

To date, a crystal structure of the ETAR has not yet been published, so the structural and ligand-binding features of the receptor have to be inferred through indirect approaches such as mutagenesis and homology modelling. The extracellular part of ETAR consists of the N-terminal segment (Met1-Cys69 of the human ETAR), ECL1 (Gly144-Phe148 of the human ETAR) linking helices II and III, ECL2 (Val225-Ser245 of the human ETAR) linking helices IV and V, and ECL3 (Asn334-Asn339 of the human ETAR) linking helices VI to VII.

In specific embodiments of the present invention, the ETAR polypeptide comprises a ETAR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an ETAR protein sequence.

In some embodiments, the ETAR protein sequence corresponds to a mammalian ETAR protein sequence. Suitable ETAR sequences may suitably be from mammal selected from the group comprising cat (UniProtKB Accession No. M3WMJ5), chimpanzee (UniProtKB Accession No. H2QQ94), cow (UniProtKB Accession No. P21450), dog (UniProtKB Accession No. Q5KSU9), horse (UniProtKB Accession No. F7CHF1), human (UniProtKB Accession No. P25101), marmoset (UniProtKB Accession No. F6YN68), mouse (UniProtKB Accession No. Q61614), panda (UniProtKB Accession No. G1L5F1), pig (UniProtKB Accession No. Q29010), rabbit (UniProtKB Accession No. A5A8K3), rat (UniProtKB Accession No. P26684), sheep (UniProtKB Accession No. Q95L55), Tasmanian devil (UniProtKB Accession No. G3VXK8).

In some preferred embodiments, the ETAR protein sequence corresponds to a human ETAR protein sequence. In some embodiments, the ETAR polypeptide comprises a human full-length wild-type ETAR protein sequence (UniProtKB Accession No. P25101), as set forth below, or a functional fragment of the wild-type ETAR protein sequence.

[SEQ ID NO: 36]
METLCLRASFWLALVGCVISDNPERYSTNLSNHVDDFTTFRGTELSFLVT

THQPTNLVLPSNGSMHNYCPQQTKITSAFKYINTVISCTIFIVGMVGNAT

LLRIIYQNKCMRNGPNALIASLALGDLIYVVIDLPINVFKLLAGRWPFDH

NDFGVFLCKLFPFLQKSSVGITVLNLCALSVDRYRAVASWSRVQGIGIPL

VTAIEIVSIWILSFILAIPEAIGFVMVPFEYRGEQHKTCMLNATSKFMEF

YQDVKDWWLFGFYFCMPLVCTAIFYTLMTCEMLNRRNGSLRIALSEHLKQ

RREVAKTVFCLWIFALCWFPLHLSRILKKTVYNEMDKNRCELLSFLLLMD

YIGINLATMNSCINPIALYFVSKKFKNCFQSCLCCCCYQSKSLMTSVPMN

GTSIQWKNHDQNNHNTDRSSHKDSMN.

In one form of the invention, the ETAR polypeptide comprises a truncated form of a mammalian wild-type ETAR protein sequence. For example, the ETAR polypeptide sequence may comprise the human wild-type ETAR protein sequence with a C-terminal truncation (e.g., amino acid residues 387-427 may be truncated). Alternatively or in addition, the ETAR polypeptide sequence may comprise the wild-type ETAR protein sequence with a N-terminal truncation. Alternatively or in addition to a C-terminal or N-terminal truncation, a truncation may be performed to remove an internal section of the wild-type ETAR protein sequence (e.g., amino acid residues 228-242 may be truncated). By way of a non-limiting illustrative example, a ETAR polypeptide suitable for using with the present invention comprised amino acid residues 2-227 and 243-386 of the human wild-type ETAR protein sequence as set forth in SEQ ID NO: 36.

3.44 Constructs and Nucleotide Sequences Encoding ETAR Polypeptides.

The present invention also encompasses isolated polynucleotide sequences and constructs encoding ETAR polypeptides as broadly described above and elsewhere herein. Also contemplated are host cells comprising those polynucleotide sequences or constructs.

In some embodiments, the polynucleotide sequences comprise a sequence that corresponds to a human ETAR nucleotide (i.e., corresponding to the EDNRA gene) sequence as set forth for example in GenBank Accession Nos. NM_001957.3, NG_013343.1, NR_045958.1, NM_001256283.1, NM_001166055.1, AY275462.1, L06622.1 and AY422989.1. In representative examples of this type, the polynucleotide comprises an ETAR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an ETAR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian ETAR polynucleotide, or a fragment thereof. In some embodiments, the ETAR polynucleotide comprises a nucleotide sequence that hybridises to an open reading frame for a wild type mammalian ETAR protein, or a fragment thereof under low, medium or high stringency conditions.

3.45 Endothelin Receptor Type B (ETBR) Polypeptides

The ETBR is believed to mediate vasodilation through endothelial production of nitric oxide and prostacyclin. In addition, it is thought to attenuate many of the pathological actions of the ETAR by depleting levels of endogenous ligands (Horinouchi et al., 2013).

The crystal structure of the ETBR has recently been solved, giving insight to its ligand-binding mode and activation process (Shihoya et al., 2016). The extracellular part of ETBR consists of the N-terminal segment (Met1-Cys90 of the human ETBR), ECL1 (Glu165-Phe169 of the human ETBR) linking helices II and III, ECL2 (Asp241-Thr263 of the human ETBR) linking helices IV and V, and ECL3 (Asn351-Asn356 of the human ETBR) linking helices VI to VII. The ETBR contains two disulphide bonds in its ectodomains (Shihoya et al., 2016).

In specific embodiments of the present invention, the ETBR polypeptide comprises a ETBR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an ETBR protein sequence.

In some embodiments, the ETBR protein sequence corresponds to a mammalian ETBR protein sequence. Suitable ETBR sequences may suitably be from mammal selected from the group comprising cat (UniProtKB Accession No. M3WRP2), chimpanzee (UniProtKB Accession No. K7DEA2), cow (UniProtKB Accession No. P28088), dog (UniProtKB Accession No. P56497), fox (UniProtKB Accession No. 16UG97), gorilla (UniProtKB Accession No. G3RES6), horse (UniProtKB Accession No. O62709), human (UniProtKB Accession No. P24530), mouse (UniProtKB Accession No. P48302), panda (UniProtKB Accession No. G1LGC8), pig (UniProtKB Accession No. P35463), rabbit (UniProtKB Accession No. Q9N0W7), rat (UniProtKB Accession No. P21451), sheep (UniProtKB Accession No. W5NPP6).

In some preferred embodiments, the ETBR protein sequence corresponds to a human ETBR protein sequence. In some embodiments, the ETBR polypeptide comprises a human full-length wild-type ETBR protein sequence (UniProtKB Accession No. P24530), as set forth below, or a functional fragment of the wild-type ETBR protein sequence.

[SEQ ID NO: 37]
MQPPPSLCGRALVALVLACGLSRIWGEERGFPPDRATPLLQTAEIMTPPT

KTLWPKGSNASLARSLAPAEVPKGDRTAGSPPRTISPPPCQGPIEIKETF

KYINTVVSCLVFVLGIIGNSTLLRIIYKNKCMRNGPNILIASLALGDLLH

IVIDIPINVYKLLAEDWPFGAEMCKLVPFIQKASVGITVLSLCALSIDRY

-continued

RAVASWSRIKGIGVPKWTAVEIVLIWVVSVVLAVPEAIGFDIITMDYKGS

YLRICLLHPVQKTAFMQFYKTAKDWWLFSFYFCLPLAITAFFYTLMTCEM

LRKKSGMQIALNDHLKQRREVAKTVFCLVLVFALCWLPLHLSRILKLTLY

NQNDPNRCELLSFLLVLDYIGINMASLNSCINPIALYLVSKRFKNCFKSC

LCCWCQSFEEKQSLEEKQSCLKFKANDHGYDNFRSSNKYSSS.

In one form of the invention, the ETBR polypeptide comprises a truncated form of a mammalian wild-type ETBR protein sequence. For example, the ETBR polypeptide sequence may comprise the human wild-type ETBR protein sequence with a C-terminal truncation (e.g., amino acid residues 404-442 may be truncated). Alternatively or in addition, the ETBR polypeptide sequence may comprise the wild-type ETBR protein sequence with a N-terminal truncation. Alternatively or in addition to a C-terminal or N-terminal truncation, a truncation may be performed to remove an internal section of the wild-type ETBR protein sequence (e.g., amino acid residues 245-260 may be truncated). By way of a non-limiting illustrative example, a ETBR polypeptide suitable for using with the present invention comprised amino acid residues 2-244 and 261-403 of the human wild-type ETBR protein sequence as set forth in SEQ ID NO: 37.

3.46 Constructs and Nucleotide Sequences Encoding ETBR Polypeptides.

The present invention also encompasses isolated polynucleotide sequences and constructs encoding ETBR polypeptides as broadly described above and elsewhere herein. Also contemplated are host cells comprising those polynucleotide sequences or constructs.

In some embodiments, the polynucleotide sequences comprise a sequence that corresponds to a human ETBR nucleotide (i.e., corresponding to the EDNRB gene) sequence as set forth for example in GenBank Accession Nos. AY275463.1, NM_000115.4, NM_001122659.2, NM_003991.3, NM_001201397.1, L06623.1, NG_011630.2, AY547312.1, AY275463.1, AB209198.1 and BC014472.1. In representative examples of this type, the polynucleotide comprises an ETBR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an ETBR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian ETBR polynucleotide, or a fragment thereof. In some embodiments, the ETBR polynucleotide comprises a nucleotide sequence that hybridises to an open reading frame for a wild type mammalian ETBR protein, or a fragment thereof under low, medium or high stringency conditions.

3.47 Histamine H3 Receptor (H3R) Polypeptides

The H3R regulates serotonergic, noradrenergic, cholinergic, and dopaminergic neurotransmitter release and is involved in locomotion, mammalian hibernation and gastric acid secretion. It may also have roles in immune responses and multiple sclerosis (Panula et al., 2015).

To date, a crystal structure of the H3R has not yet been published, so the structural and ligand-binding features of the receptor have to be inferred through indirect approaches such as mutagenesis and homology modelling. The extracellular part of H3R consists of the N-terminal segment (Met1-Ser30 of the human H3R), ECL1 (Gly98-Phe102 of the human H3R) linking helices II and III, ECL2 (Trp174-Tyr194 of the human H3R) linking helices IV and V, and ECL3 (His385-Val389 of the human H3R) linking helices VI to VII.

In specific embodiments of the present invention, the H3R polypeptide comprises a H3R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an H3R protein sequence.

In some embodiments, the H3R protein sequence corresponds to a mammalian H3R protein sequence. Suitable H3R sequences may suitably be from mammal selected from the group comprising chimpanzee (UniProtKB Accession No. H2R2N9), cow (UniProtKB Accession No. F1MML8), dog (UniProtKB Accession No. F1PSJ0), gorilla (UniProtKB Accession No. G3SJN4), guinea pig (UniProtKB Accession No. Q9JI35), horse (UniProtKB Accession No. F6UMY9), human (UniProtKB Accession No. Q9Y5N1), marmoset (UniProtKB Accession No. U3EPT7), mouse (UniProtKB Accession No. P58406), orangutan (UniProtKB Accession No. H2P210), platypus (UniProtKB Accession No. F6VA72), rat (UniProtKB Accession No. Q9QYN8), sheep (UniProtKB Accession No. W5PY09), Tasmanian devil (UniProtKB Accession No. G3WQV4).

In some preferred embodiments, the H3R protein sequence corresponds to a human H3R protein sequence. In some embodiments, the H3R polypeptide comprises a human full-length wild-type H3R protein sequence (UniProtKB Accession No. Q9Y5N1), as set forth below, or a functional fragment of the wild-type H3R protein sequence.

[SEQ ID NO: 38]
MERAPPDGPLNASGALAGEAAAAGGARGFSAAWTAVLAALMALLIVATVL

GNALVMLAFVADSSLRTQNNFFLLNLAISDFLVGAFCIPLYVPYVLTGRW

TFGRGLCKLWLVVDYLLCTSSAFNIVLISYDRFLSVTRAVSYRAQQGDTR

RAVRKMLLVWVLAFLLYGPAILSWEYLSGGSSIPEGHCYAEFFYNWYFLI

TASTLEFFTPFLSVTFFNLSIYLNIQRRTRLRLDGAREAAGPEPPPEAQP

SPPPPPGCWGCWQKGHGEAMPLHRYGVGEAAVGAEAGEATLGGGGGGSV

ASPTSSSGSSSRGTERPRSLKRGSKPSASSASLEKRMKMVSQSFTQRFRL

SRDRKVAKSLAVIVSIFGLCWAPYTLLMIIRAACHGHCVPDYWYETSFWL

LWANSAVNPVLYPLCHHSFRRAFTKLLCPQKLKIQPHSSLEHCWK.

In one form of the invention, the H3R polypeptide comprises a truncated form of a mammalian wild-type H3R protein sequence. For example, the H3R polypeptide sequence may comprise the human wild-type H3R protein sequence with a C-terminal truncation (e.g., amino acid residues 429-445 may be truncated). Alternatively or in addition, the H3R polypeptide sequence may comprise the wild-type H3R protein sequence with a N-terminal truncation. Alternatively or in addition to a C-terminal or N-terminal truncation, a truncation may be performed to remove an internal section of the wild-type H3R protein sequence (e.g., amino acid residues 177-192 may be truncated). By way of a non-limiting illustrative example, a H3R polypeptide suitable for using with the present invention comprised amino acid residues 2-176 and 193-428 of the human wild-type H3R protein sequence as set forth in SEQ ID NO: 38.

3.48 Constructs and Nucleotide Sequences Encoding H3R Polypeptides.

The present invention also encompasses isolated polynucleotide sequences and constructs encoding H3R polypeptides as broadly described above and elsewhere herein. Also contemplated are host cells comprising those polynucleotide sequences or constructs.

In some embodiments, the polynucleotide sequences comprise a sequence that corresponds to a human H3R nucleotide (i.e., corresponding to the HRH3 gene) sequence as set forth for example in GenBank Accession Nos. NM_007232.2, AF346904.1, AF346903.1, AF321913.1, AF321912.1, AF321911.1, AF321910.1, AF363791.1, BC096840.1, AJ296652.1 and AJ278250.1. In representative examples of this type, the polynucleotide comprises an H3R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an H3R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian H3R polynucleotide, or a fragment thereof. In some embodiments, the H3R polynucleotide comprises a nucleotide sequence that hybridises to an open reading frame for a wild type mammalian H3R protein, or a fragment thereof under low, medium or high stringency conditions.

3.49 Muscarinic M1 Receptor (M1R) Polypeptides

The M1R plays important roles in learning, memory and cognition. It is viewed as a promising target for a variety of CNS disorders, such as Alzheimer's disease, schizophrenia, and drug addiction (Thal et al., 2016).

The crystal structure of the M1R has recently been solved, giving insight to its ligand-binding mode and activation process (Thal et al., 2016). The extracellular part of M1R consists of the N-terminal segment (Met1-Gly21 of the human M1R), ECL1 (Gly89-Leu93 of the human M1R) linking helices II and III, ECL2 (Glu170-Ser184 of the human M1R) linking helices IV and V, and ECL3 (Lys392-Val395 of the human M1R) linking helices VI to VII. It contains a disulphide bridge in its ectodomains (Thal et al., 2016).

In specific embodiments of the present invention, the M1R polypeptide comprises a M1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a M1R protein sequence.

In some embodiments, the M1R protein sequence corresponds to a mammalian M1R protein sequence. Suitable M1R sequences may suitably be from mammal selected from the group comprising cat (UniProtKB Accession No. M3VUK2), chimpanzee (UniProtKB Accession No. H2Q3X5), cow (UniProtKB Accession No. F1N5C5), dog (UniProtKB Accession No. F1PT23), gorilla (UniProtKB Accession No. G3RJP5), guinea pig (UniProtKB Accession No. H0W4R2), hedgehog (UniProtKB Accession No. A0A1S3WFM0), horse (UniProtKB Accession No. F6SLG5), human (UniProtKB Accession No. P11229), marmoset (UniProtKB Accession No. F7IPY9), mouse (UniProtKB Accession No. P12657), pig (UniProtKB Accession No. P04761), rabbit (UniProtKB Accession No. G1SR55), rat (UniProtKB Accession No. P08482).

In some preferred embodiments, the M1R protein sequence corresponds to a human M1R protein sequence. In some embodiments, the M1R polypeptide comprises a human full-length wild-type M1R protein sequence (UniProtKB Accession No. P11229), as set forth below, or a functional fragment of the wild-type M1R protein sequence.

[SEQ ID NO: 39]
MNTSAPPAVSPNITVLAPGKGPWQVAFIGITTGLLSLATVTGNLLVLISF

KVNTELKTVNNYFLLSLACADLIIGTFSMNLYTTYLLMGHWALGTLACDL

WLALDYVASNASVMNLLLISFDRYFSVTRPLSYRAKRTPRRAALMIGLAW

LVSFVLWAPAILFWQYLVGERTVLAGQCYIQFLSQPIITFGTAMAAFYLP

VTVMCTLYWRIYRETENRARELAALQGSETPGKGGGSSSSSERSQPGAEG

SPETPPGRCCRCCRAPRLLQAYSWKEEEEEDEGSMESLTSSEGEEPGSEV

VIKMPMVDPEAQAPTKQPPRSSPNTVKRPTKKGRDRAGKGQKPRGKEQLA

KRKTFSLVKEKKAARTLSAILLAFILTVVTPYNIMVLVSTFCKDCVPETL

WELGYWLCYVNSTINPMCYALCNKAFRDTFRLLLLCRWDKRRWRKIPKRP

GSVHRTPSRQC.

In one form of the invention, the M1R polypeptide comprises a truncated form of a mammalian wild-type M1R protein sequence. For example, the M1R polypeptide sequence may comprise the human wild-type M1R protein sequence with a C-terminal truncation (e.g., amino acid residues 435-460 may be truncated). Alternatively or in addition, the M1R polypeptide sequence may comprise the wild-type M1R protein sequence with a N-terminal truncation. Alternatively or in addition to a C-terminal or N-terminal truncation, a truncation may be performed to remove an internal section of the wild-type M1R protein sequence (e.g., amino acid residues 171-182 may be truncated). By way of a non-limiting illustrative example, a M1R polypeptide suitable for using with the present invention comprised amino acid residues 2-170 and 183-434 of the human wild-type M1R protein sequence as set forth in SEQ ID NO: 39.

3.50 Constructs and Nucleotide Sequences Encoding M1R Polypeptides.

The present invention also encompasses isolated polynucleotide sequences and constructs encoding M1R polypeptides as broadly described above and elsewhere herein. Also contemplated are host cells comprising those polynucleotide sequences or constructs.

In some embodiments, the polynucleotide sequences comprise a sequence that corresponds to a human M1R nucleotide (i.e., corresponding to the CHRM1 gene) sequence as set forth for example in GenBank Accession Nos. NM_000738.2, BC007740.2, BC022984.1, BT007166.1 and AF385587.1. In representative examples of this type, the polynucleotide comprises a M1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a M1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian M1R polynucleotide, or a fragment thereof. In some embodiments, the M1R polynucleotide comprises a nucleotide sequence that hybridises to an open reading frame for a wild type mammalian M1R protein, or a fragment thereof under low, medium or high stringency conditions.

3.51 Muscarinic M2 Receptor (M2R) Polypeptides

The M2R plays an important role in the regulation of cardiac function, and is also involved in many CNS processes, including cognition and pain perception (Kruse et al., 2013).

To date, two crystal structures of the M2R have been published (Haga et al., 2012; Kruse et al., 2013), providing insight into the ligand-binding and activation mechanisms of the receptor. The extracellular part of M2R consists of the N-terminal segment (Met1-Tyr18 of the human M2R), ECL1 (Gly87-Leu91 of the human M2R) linking helices II and III, ECL2 (Val168-Ser182 of the human M2R) linking helices IV and V, and ECL3 (Ala414-Ile417 of the human M2R) linking helices VI to VII. It contains two disulphide bridges in its ectodomains (Haga et al., 2012).

In specific embodiments of the present invention, the M2R polypeptide comprises a M2R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a M2R protein sequence.

In some embodiments, the M2R protein sequence corresponds to a mammalian M2R protein sequence. Suitable M2R sequences may suitably be from mammal selected from the group comprising bat (UniProtKB Accession No. G1PWZ4), cat (UniProtKB Accession No. M3WSG4), chimpanzee (UniProtKB Accession No. H2RAP9), cow (UniProtKB Accession No. P41985), dog (UniProtKB Accession No. F1PWR7), gorilla (UniProtKB Accession No. G3QKB8), human (UniProtKB Accession No. P08172), marmoset (UniProtKB Accession No. F7APE0), mouse (UniProtKB Accession No. Q9ERZ4), pig (UniProtKB Accession No. P06199), rabbit (UniProtKB Accession No. G1TBX1), rat (UniProtKB Accession No. P10980), sheep (UniProtKB Accession No. W5NSW2), Tasmanian devil (UniProtKB Accession No. G3VX75).

In some preferred embodiments, the M2R protein sequence corresponds to a human M2R protein sequence. In some embodiments, the M2R polypeptide comprises a human full-length wild-type M2R protein sequence (UniProtKB Accession No. P08172), as set forth below, or a functional fragment of the wild-type M2R protein sequence.

[SEQ ID NO: 40]
MNNSTNSSNNSLALTSPYKTFEVVFIVLVAGSLSLVTIIGNILVMVSIKV

NRHLQTVNNYFLFSLACADLIIGVFSMNLYTLYTVIGYWPLGPVVCDLWL

ALDYVVSNASVMNLLIISFDRYFCVTKPLTYPVKRTTKMAGMMIAAAVWL

SFILWAPAILFWQFIVGVRTVEDGECYIQFFSNAAVTFGTAIAAFYLPVI

IMTVLYWHISRASKSRIKKDKKEPVANQDPVSPSLVQGRIVKPNNNNMPS

SDDGLEHNKIQNGKAPRDPVTENCVQGEEKESSNDSTSVSAVASNMRDDE

ITQDENTVSTSLGHSKDENSKQTCIRIGTKTPKSDSCTPTNTTVEVVGSS

GQNGDEKQNIVARKIVKMTKQPAKKKPPPSREKKVTRTILAILLAFIITW

APYNVMVLINTFCAPCIPNTVWTIGYWLCYINSTINPACYALCNATFKKT

FKHLLMCHYKNIGATR.

In one form of the invention, the M2R polypeptide comprises a truncated form of a mammalian wild-type M2R protein sequence. For example, the M2R polypeptide sequence may comprise the human wild-type M2R protein sequence with a C-terminal truncation (e.g., amino acid residues 457-466 may be truncated). Alternatively or in addition, the M2R polypeptide sequence may comprise the wild-type M2R protein sequence with a N-terminal truncation. Alternatively or in addition to a C-terminal or N-terminal truncation, a truncation may be performed to remove an internal section of the wild-type M2R protein sequence (e.g., amino acid residues 172-177 may be truncated). By way of a non-limiting illustrative example, a M2R polypeptide suitable for using with the present invention comprised amino acid residues 2-171 and 178-456 of the human wild-type M2R protein sequence as set forth in SEQ ID NO: 40.

3.52 Constructs and Nucleotide Sequences Encoding M2R Polypeptides.

The present invention also encompasses isolated polynucleotide sequences and constructs encoding M2R polypeptides as broadly described above and elsewhere herein. Also contemplated are host cells comprising those polynucleotide sequences or constructs.

In some embodiments, the polynucleotide sequences comprise a sequence that corresponds to a human M2R nucleotide (i.e., corresponding to the CHRM2 gene) sequence as set forth for example in GenBank Accession Nos. AF498916.1, NM_001006632.1, NM_001006631.1, NM_001006630.1, NM_001006629.1, NM_001006628.1, NM_001006627.1, NM_001006626.1, NM_000739.2, NG_011846.2 and M16404.1. In representative examples of this type, the polynucleotide comprises a M2R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a M2R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian M2R polynucleotide, or a fragment thereof. In some embodiments, the M2R polynucleotide comprises a nucleotide sequence that hybridises to an open reading frame for a wild type mammalian M2R protein, or a fragment thereof under low, medium or high stringency conditions.

3.53 Muscarinic M3 Receptor (M3R) Polypeptides

The M3R is widely distributed both in the CNS and in peripheral tissues. It is a potential therapeutic target for several diseases, including Sjögren's syndrome, type 2 diabetes, obesity, peptic ulcer disease, overactive bladder, chronic obstructive pulmonary disease, irritable bowel syndrome and gastrointestinal spasms (Wess et al., 2007).

To date, a crystal structure of the M3R has not yet been published, so the structural and ligand-binding features of the receptor have to be inferred through indirect approaches such as mutagenesis and homology modelling. The extracellular part of M3R consists of the N-terminal segment (Met1-Thr64 of the human M3R), ECL1 (Asn132-Leu136 of the human M3R) linking helices II and III, ECL2 (Lys213-Ser227 of the human M3R) linking helices IV and V, and ECL3 (Asp518-Ile521 of the human M3R) linking helices VI to VII.

In specific embodiments of the present invention, the M3R polypeptide comprises a M3R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a M3R protein sequence.

In some embodiments, the M3R protein sequence corresponds to a mammalian M3R protein sequence. Suitable M3R sequences may suitably be from mammal selected from the group comprising bat (UniProtKB Accession No. G1Q9Z8), cat (UniProtKB Accession No. M3X7A6), chimpanzee (UniProtKB Accession No. Q9N2A4), cow (UniProtKB Accession No. P41984), dog (UniProtKB Accession No. F1PGZ2), gorilla (UniProtKB Accession No. Q9N2A3), human (UniProtKB Accession No. P20309), marmoset (UniProtKB Accession No. U3D417), mouse (UniProtKB Accession No. Q9ERZ3), panda (UniProtKB Accession No. G1MP56), pig (UniProtKB Accession No. P11483), rabbit (UniProtKB Accession No. G1U308), rat (UniProtKB Accession No. P08483), sheep (UniProtKB Accession No. W5Q8R1).

In some preferred embodiments, the M3R protein sequence corresponds to a human M3R protein sequence. In some embodiments, the M3R polypeptide comprises a human full-length wild-type M3R protein sequence (UniProtKB Accession No. P20309), as set forth below, or a functional fragment of the wild-type M3R protein sequence.

[SEQ ID NO: 41]
MTLHNNSTTSPLFPNISSSWIHSPSDAGLPPGTVTHFGSYNVSRAAGNFS

SPDGTTDDPLGGHTVWQVVFIAFLTGILALVTIIGNILVIVSFKVNKQLK

TVNNYFLLSLACADLIIGVISMNLFTTYIIMNRWALGNLACDLWLAIDYV

ASNASVMNLLVISFDRYFSITRPLTYRAKRTTKRAGVMIGLAWVISFVLW

APAILFWQYFVGKRTVPPGECFIQFLSEPTITFGTAIAAFYMPVTIMTIL

YWRIYKETEKRTKELAGLQASGTEAETENFVHPTGSSRSCSSYELQQQSM

KRSNRRKYGRCHFWFTTKSWKPSSEQMDQDHSSSDSWNNNDAAASLENSA

SSDEEDIGSETRAIYSIVLKLPGHSTILNSTKLPSSDNLQVPEEELGMVD

LERKADKLQAQKSVDDGGSFPKSFSKLPIQLESAVDTAKTSDVNSSVGKS

TATLPLSFKEATLAKRFALKTRSQITKRKRMSLVKEKKAAQTLSAILLAF

IITWTPYNIMVLVNTFCDSCIPKTFWNLGYWLCYINSTVNPVCYALCNKT

FRTTFKMLLLCQCDKKKRRKQQYQQRQSVIFHKRAPEQAL.

In one form of the invention, the M3R polypeptide comprises a truncated form of a mammalian wild-type M3R protein sequence. For example, the M3R polypeptide sequence may comprise the human wild-type M3R protein sequence with a C-terminal truncation (e.g., amino acid residues 560-590 may be truncated). Alternatively or in addition, the M3R polypeptide sequence may comprise the wild-type M3R protein sequence with a N-terminal truncation. Alternatively or in addition to a C-terminal or N-terminal truncation, a truncation may be performed to remove an internal section of the wild-type M3R protein sequence (e.g., amino acid residues 216-221 may be truncated). By way of a non-limiting illustrative example, a M3R polypeptide suitable for using with the present invention comprised amino acid residues 2-215 and 222-559 of the human wild-type M3R protein sequence as set forth in SEQ ID NO: 41.

3.54 Constructs and Nucleotide Sequences Encoding M3R Polypeptides.

The present invention also encompasses isolated polynucleotide sequences and constructs encoding M3R polypeptides as broadly described above and elsewhere herein. Also contemplated are host cells comprising those polynucleotide sequences or constructs.

In some embodiments, the polynucleotide sequences comprise a sequence that corresponds to a human M3R nucleotide (i.e., corresponding to the CHRM3 gene)

sequence as set forth for example in GenBank Accession Nos. AF498917.1, NG_032046.2, NM_001347716.1, NM_000740.3, AH011672.2, AF385589.1, U29589.1, AB041395.1, BC096844.1 and BC121026.2. In representative examples of this type, the polynucleotide comprises a M3R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a M3R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian M3R polynucleotide, or a fragment thereof. In some embodiments, the M3R polynucleotide comprises a nucleotide sequence that hybridises to an open reading frame for a wild type mammalian M3R protein, or a fragment thereof under low, medium or high stringency conditions.

3.55 Neuropeptide Y1 Receptor (Y1R) Polypeptides

The Y1R is expressed in a variety of tissues including the brain, heart, kidney, and gastrointestinal tract, and early studies showed that it mediated vasoconstriction and anxiolytic effects (Michel et al., 1998). It has been implicated in a variety of diseases, such as obesity, anxiety and depression, alcohol dependence, bone metabolism, pain, cancer, cardiovascular disease, intestinal disease, circadian disorders and Alzheimer's disease (Brothers & Wahlestedt, 2010).

To date, a crystal structure of the Y1R has not yet been published, so the structural and ligand-binding features of the receptor have to be inferred through indirect approaches such as mutagenesis and homology modelling. The extracellular part of Y1R consists of the N-terminal segment (Met1-A38 of the human Y1R), ECL1 (Glu104-Phe108 of the human Y1R) linking helices II and III, ECL2 (Val178-Ser204 of the human Y1R) linking helices IV and V, and ECL3 (His290-Ala294 of the human Y1R) linking helices VI to VII.

In specific embodiments of the present invention, the Y1R polypeptide comprises a Y1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a Y1R protein sequence.

In some embodiments, the Y1R protein sequence corresponds to a mammalian Y1R protein sequence. Suitable Y1R sequences may suitably be from mammal selected from the group comprising bat (UniProtKB Accession No. G1P047), cat (UniProtKB Accession No. M3W4X9), chimpanzee (UniProtKB Accession No. H2QQD5), cow (UniProtKB Accession No. Q1RMU8), dog (UniProtKB Accession No. O02813), gorilla (UniProtKB Accession No. G3QP89), guinea pig (UniProtKB Accession No. Q9WVD0), human (UniProtKB Accession No. P25929), marmoset (UniProtKB Accession No. F718A1), mouse (UniProtKB Accession No. Q04573), pig (UniProtKB Accession No. O02835), rabbit (UniProtKB Accession No. B6VRS4), rat (UniProtKB Accession No. P21555), sheep (UniProtKB Accession No. W5PW25).

In some preferred embodiments, the Y1R protein sequence corresponds to a human Y1R protein sequence. In some embodiments, the Y1R polypeptide comprises a human full-length wild-type Y1R protein sequence (UniProtKB Accession No. P25929), as set forth below, or a functional fragment of the wild-type Y1R protein sequence.

[SEQ ID NO: 42]
MNSTLFSQVENHSVHSNFSEKNAQLLAFENDDCHLPLAMIFTLALAYGAV

IILGVSGNLALIIIILKQKEMRNVTNILIVNLSFSDLLVAIMCLPFTFVY

TLMDHWVFGEAMCKLNPFVQCVSITVSIFSLVLIAVERHQLIINPRGWRP

NNRHAYVGIAVIWVLAVASSLPFLIYQVMTDEPFQNVTLDAYKDKYVCFD

QFPSDSHRLSYTTLLLVLQYFGPLCFIFICYFKIYIRLKRRNNMMDKMRD

NKYRSSETKRINIMLLSIVVAFAVCWLPLTIFNTVFDWNHQIIATCNHNL

LFLLCHLTAMISTCVNPIFYGFLNKNFQRDLQFFFNFCDFRSRDDDYETI

AMSTMHTDVSKTSLKQASPVAFKKINNNDDNEKI.

In one form of the invention, the Y1R polypeptide comprises a truncated form of a mammalian wild-type Y1R protein sequence. For example, the Y1R polypeptide sequence may comprise the human wild-type Y1R protein sequence with a C-terminal truncation (e.g., amino acid residues 336-384 may be truncated). Alternatively or in addition, the Y1R polypeptide sequence may comprise the wild-type Y1R protein sequence with a N-terminal truncation. Alternatively or in addition to a C-terminal or N-terminal truncation, a truncation may be performed to remove an internal section of the wild-type Y1R protein sequence (e.g., amino acid residues 183-195 may be truncated). By way of a non-limiting illustrative example, a Y1R polypeptide suitable for using with the present invention comprised amino acid residues 2-182 and 196-335 of the human wild-type Y1R protein sequence as set forth in SEQ ID NO: 42.

3.56 Constructs and Nucleotide Sequences Encoding Y1R Polypeptides.

The present invention also encompasses isolated polynucleotide sequences and constructs encoding Y1R polypeptides as broadly described above and elsewhere herein. Also contemplated are host cells comprising those polynucleotide sequences or constructs.

In some embodiments, the polynucleotide sequences comprise a sequence that corresponds to a human Y1R nucleotide (i.e., corresponding to the NPY1R gene) sequence as set forth for example in GenBank Accession Nos. AY548168.1, NM_000909.5, BC071720.1, BC036657.2 and AK312578.1. In representative examples of this type, the polynucleotide comprises a Y1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a Y1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian Y1R polynucleotide, or a fragment thereof. In some embodiments, the Y1R polynucleotide comprises a nucleotide sequence that hybridises to an open reading frame for a wild type mammalian Y1R protein, or a fragment thereof under low, medium or high stringency conditions.

3.57 Neurotensin 1 Receptor (NTS1R) Polypeptides

The NTS1R mediates most of the known effects of neurotensin, such as the modulation of dopamine neurotransmission, hypothermia, anti-nociception, and promotion of the growth of cancer cells. It has also been implicated in Parkinson's disease and the pathogenesis of schizophrenia (White et al., 2012).

A crystal structure of the NTS1R has been published (White et al., 2012), providing insight into the ligand-binding and activation mechanisms of the receptor. The extracellular part of NTS1R consists of the N-terminal segment (Met1-Asp59 of the human NTS1R), ECL1 (His131-Phe136 of the human NTS1R) linking helices II and III, ECL2 (Gly208-His229 of the human NTS1R) linking helices IV and V, and ECL3 (Ser330-Trp334 of the human NTS1R) linking helices VI to VII. It has a disufide bond linking helices ECL2 and III (White et al., 2012).

In specific embodiments of the present invention, the NTS1R polypeptide comprises a NTS1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a NTS1R protein sequence.

In some embodiments, the NTS1R protein sequence corresponds to a mammalian NTS1R protein sequence. Suitable NTS1R sequences may suitably be from mammal selected from the group comprising cat (UniProtKB Accession No. M3X9J3), chimpanzee (UniProtKB Accession No. H2QKR3), cow (UniProtKB Accession No. F1MWG2), dog (UniProtKB Accession No. E2RN63), gorilla (UniProtKB Accession No. G3RLF9), guinea pig (UniProtKB Accession No. H0W4P3), hedgehog (UniProtKB Accession No. A0A1S2ZJT3), horse (UniProtKB Accession No. F7BSR0), human (UniProtKB Accession No. P30989), marmoset (UniProtKB Accession No. U3D2G1), mouse (UniProtKB Accession No. O88319), rat (UniProtKB Accession No. P20789), sheep (UniProtKB Accession No. W5PSM7), Tasmanian devil (UniProtKB Accession No. G3VE69).

In some preferred embodiments, the NTS1R protein sequence corresponds to a human NTS1R protein sequence. In some embodiments, the NTS1R polypeptide comprises a human full-length wild-type NTS1R protein sequence (UniProtKB Accession No. P30989), as set forth below, or a functional fragment of the wild-type NTS1R protein sequence.

[SEQ ID NO: 43]
MRLNSSAPGTPGTPAADPFQRAQAGLEEALLAPGFGNASGNASERVLAAP

SSELDVNTDIYSKVLVTAVYLALFVVGTVGNTVTAFTLARKKSLQSLQST

VHYHLGSLALSDLLTLLLAMPVELYNFIWVHHPWAFGDAGCRGYYFLRDA

CTYATALNVASLSVERYLAICHPFKAKTLMSRSRTKKFISAIWLASALLA

VPMLFTMGEQNRSADGQHAGGLVCTPTIHTATVKVVIQVNTFMSFIFPMV

VISVLNTIIANKLTVMVRQAAEQGQVCTVGGEHSTFSMAIEPGRVQALRH

GVRVLRAVVIAFVVCWLPYHVRRLMFCYISDEQWTPFLYDFYHYFYMVTN

ALFYVSSTINPILYNLVSANFRHIFLATLACLCPVWRRRRKRPAFSRKAD

SVSSNHTLSSNATRETLY.

In one form of the invention, the NTS1R polypeptide comprises a truncated form of a mammalian wild-type NTS1R protein sequence. For example, the NTS1R polypeptide sequence may comprise the human wild-type NTS1R protein sequence with a C-terminal truncation (e.g., amino acid residues 380-418 may be truncated). Alternatively or in addition, the NTS1R polypeptide sequence may comprise the wild-type NTS1R protein sequence with a N-terminal truncation. Alternatively or in addition to a C-terminal or N-terminal truncation, a truncation may be performed to remove an internal section of the wild-type NTS1R protein sequence (e.g., amino acid residues 213-223 may be truncated). By way of a non-limiting illustrative example, a NTS1R polypeptide suitable for using with the present invention comprised amino acid residues 2-212 and 224-379 of the human wild-type NTS1R protein sequence as set forth in SEQ ID NO: 43.

3.58 Constructs and Nucleotide Sequences Encoding NTS1R Polypeptides.

The present invention also encompasses isolated polynucleotide sequences and constructs encoding NTS1R polypeptides as broadly described above and elsewhere herein. Also contemplated are host cells comprising those polynucleotide sequences or constructs.

In some embodiments, the polynucleotide sequences comprise a sequence that corresponds to a human NTS1R nucleotide (i.e., corresponding to the NTS1R gene) sequence as set forth for example in GenBank Accession Nos. AY429106.1 and NM_002531.2. In representative examples of this type, the polynucleotide comprises a NTS1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a NTS1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian NTS1R polynucleotide, or a fragment thereof. In some embodiments, the NTS1R polynucleotide comprises a nucleotide sequence that hybridises to an open reading frame for a wild type mammalian NTS1R protein, or a fragment thereof under low, medium or high stringency conditions.

3.59 Orexin Receptor 1 (OX1R) Polypeptides

The OX1R has important roles in the regulation of feeding, reward, nociception and stress. It is believed that antagonism of the OX1R could be beneficial in treating sleep disorders, obesity, pain and addiction (Yin et al., 2016).

A crystal structure of the OX1R has been published (Yin et al., 2016), providing insight into the ligand-binding and activation mechanisms of the receptor. The extracellular part of OX1R consists of the N-terminal segment (Met1-Tyr45 of the human OX1R), ECL1 (Glu110-Phe114 of the human OX1R) linking helices II and III, ECL2 (Glu184-Asp208 of the human OX1R) linking helices IV and V, and ECL3 (Gly325-Asp332 of the human OX1R) linking helices VI to VII.

In specific embodiments of the present invention, the OX1R polypeptide comprises a OX1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an OX1R protein sequence.

In some embodiments, the OX1R protein sequence corresponds to a mammalian OX1R protein sequence. Suitable OX1R sequences may suitably be from mammal selected from the group comprising cat (UniProtKB Accession No. M3WN13), chimpanzee (UniProtKB Accession No. H2PYJ1), cow (UniProtKB Accession No. Q0GBZ5), dog (UniProtKB Accession No. E2R2A3), guinea pig (UniProtKB Accession No. H0V9F2), horse (UniProtKB Accession No. F6Y1U3), human (UniProtKB Accession No. O43613), marmoset (UniProtKB Accession No. F7H2M7), mouse (UniProtKB Accession No. P58307), pig (UniProtKB Accession No. F1SVA1), pig (UniProtKB Accession No.

O97661), rabbit (UniProtKB Accession No. G1SPJ3), rat (UniProtKB Accession No. P56718), sheep (UniProtKB Accession No. W5NTE0).

In some preferred embodiments, the OX1R protein sequence corresponds to a human OX1R protein sequence. In some embodiments, the OX1R polypeptide comprises a human full-length wild-type OX1R protein sequence (UniProtKB Accession No. O43613), as set forth below, or a functional fragment of the wild-type OX1R protein sequence.

[SEQ ID NO: 44]
MEPSATPGAQMGVPPGSREPSPVPPDYEDEFLRYLWRDYLYPKQYEWVLI

AAYVAVFWALVGNTLVCLAVWRNHHMRTVTNYFIVNLSLADVLVTAICLP

ASLLVDITESWLFGHALCKVIPYLQAVSVSVAVLTLSFIALDRWYAICHP

LLFKSTARRARGSILGIWAVSLAIMVPQAAVMECSSVLPELANRTRLFSV

CDERWADDLYPKIYHSCFFIVTYLAPLGLMAMAYFQIFRKLWGRQIPGTT

SALVRNWKRPSDQLGDLEQGLSGEPQPRARAFLAEVKQMRARRKTAKMLM

VVLLVFALCYLPISVLNVLKRVFGMFRQASDREAVYACFTFSHWLVYANS

AANPIIYNFLSGKFREQFKAAFSCCLPGLGPCGSLKAPSPRSSASHKSLS

LQSRCSISKISEHVVLTSVTTVLP.

In one form of the invention, the OX1R polypeptide comprises a truncated form of a mammalian wild-type OX1R protein sequence. For example, the OX1R polypeptide sequence may comprise the human wild-type OX1R protein sequence with a C-terminal truncation (e.g., amino acid residues 374-425 may be truncated). Alternatively or in addition, the OX1R polypeptide sequence may comprise the wild-type OX1R protein sequence with a N-terminal truncation. Alternatively or in addition to a C-terminal or N-terminal truncation, a truncation may be performed to remove an internal section of the wild-type OX1R protein sequence (e.g., amino acid residues 189-196 may be truncated). By way of a non-limiting illustrative example, a OX1R polypeptide suitable for using with the present invention comprised amino acid residues 2-188 and 197-373 of the human wild-type OX1R protein sequence as set forth in SEQ ID NO: 44.

3.60 Constructs and Nucleotide Sequences Encoding OX1R Polypeptides.

The present invention also encompasses isolated polynucleotide sequences and constructs encoding OX1R polypeptides as broadly described above and elsewhere herein. Also contemplated are host cells comprising those polynucleotide sequences or constructs.

In some embodiments, the polynucleotide sequences comprise a sequence that corresponds to a human OX1R nucleotide (i.e., corresponding to the HCRTR1 gene) sequence as set forth for example in GenBank Accession Nos. AF041243.1, NM_001525.2 and BC074796.2. In representative examples of this type, the polynucleotide comprises an OX1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an OX1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian OX1R polynucleotide, or a fragment thereof. In some embodiments, the OX1R polynucleotide comprises a nucleotide sequence that hybridises to an open reading frame for a wild type mammalian OX1R protein, or a fragment thereof under low, medium or high stringency conditions.

3.61 Orexin Receptor 2 (OX2R) Polypeptides

Like the OX1R, it is believed that the OX2R could be beneficial in treating sleep disorders, obesity, pain and addiction. However the OX2R has distinct physiological functions from the OX1R, as it predominantly mediates the pro-arousal effects of the orexin peptides (Yin et al., 2016).

A crystal structure of the OX2R has been published (Yin et al., 2015), providing insight into the ligand-binding and activation mechanisms of the receptor. The extracellular part of OX2R consists of the N-terminal segment (Met1-Gu52 of the human OX2R), ECL1 (Glu118-Phe122 of the human OX2R) linking helices II and III, ECL2 (Glu192-Gly216 of the human OX2R) linking helices IV and V, and ECL3 (Gly331-Asp338 of the human OX2R) linking helices VI to VII.

In specific embodiments of the present invention, the OX2R polypeptide comprises a OX2R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an OX2R protein sequence.

In some embodiments, the OX2R protein sequence corresponds to a mammalian OX2R protein sequence. Suitable OX2R sequences may suitably be from mammal selected from the group comprising cat (UniProtKB Accession No. M3X961), chimpanzee (UniProtKB Accession No. H2QT82), cow (UniProtKB Accession No. F1MG23), dog (UniProtKB Accession No. Q9TUP7), gorilla (UniProtKB Accession No. G3SII0), horse (UniProtKB Accession No. F6XS13), human (UniProtKB Accession No. O43614), marmoset (UniProtKB Accession No. F7D3X8), mouse (UniProtKB Accession No. P58308), panda (UniProtKB Accession No. G1MGF7), pig (UniProtKB Accession No. O62809), rabbit (UniProtKB Accession No. G1STQ8), rat (UniProtKB Accession No. P56719), sheep (UniProtKB Accession No. W5P9D8).

In some preferred embodiments, the OX2R protein sequence corresponds to a human OX2R protein sequence. In some embodiments, the OX2R polypeptide comprises a human full-length wild-type OX2R protein sequence (UniProtKB Accession No. O43614), as set forth below, or a functional fragment of the wild-type OX2R protein sequence.

[SEQ ID NO: 45]
MSGTKLEDSPPCRNWSSASELNETQEPFLNPTDYDDEEFLRYLWREY

LHPKEYEWVLIAGYIIVFVVALIGNVLVCVAVWKNHHMRTVTNYFIV

NLSLADVLVTITCLPATLVVDITETWFFGQSLCKVIPYLQTVSVSVS

VLTLSCIALDRWYAICHPLMFKSTAKRARNSIVIIWIVSCIIMIPQA

IVMECSTVFPGLANKTTLFTVCDERWGGEIYPKMYHICFFLVTYMAP

LCLMVLAYLQIFRKLWCRQIPGTSSVVQRKWKPLQPVSQPRGPGQPT

KSRMSAVAAEIKQIRARRKTARMLMIVLLVFAICYLPISILNVLKRV

FGMFAHTEDRATVYAWFTFSHWLVYANSAANPIIYNFLSGKFREEFK

AAFSCCCLGVHHRQEDRLTRGRTSTESRKSLTTQISNFDNISKLSEQ

VVLTSISTLPAANGAGPLQNW.

In one form of the invention, the OX2R polypeptide comprises a truncated form of a mammalian wild-type OX2R protein sequence. For example, the OX2R polypeptide sequence may comprise the human wild-type OX2R protein sequence with a C-terminal truncation (e.g., amino acid residues 380-444 may be truncated). Alternatively or in addition, the OX2R polypeptide sequence may comprise the wild-type OX2R protein sequence with a N-terminal truncation. Alternatively or in addition to a C-terminal or N-terminal truncation, a truncation may be performed to remove an internal section of the wild-type OX2R protein sequence (e.g., amino acid residues 195-204 may be truncated). By way of a non-limiting illustrative example, a OX2R polypeptide suitable for using with the present invention comprised amino acid residues 2-194 and 205-379 of the human wild-type OX2R protein sequence as set forth in SEQ ID NO: 45.

3.62 Constructs and Nucleotide Sequences Encoding OX2R Polypeptides.

The present invention also encompasses isolated polynucleotide sequences and constructs encoding OX2R polypeptides as broadly described above and elsewhere herein. Also contemplated are host cells comprising those polynucleotide sequences or constructs.

In some embodiments, the polynucleotide sequences comprise a sequence that corresponds to a human OX2R nucleotide (i.e., corresponding to the HCRTR2 gene) sequence as set forth for example in GenBank Accession Nos. AF041245.2, NM_001526.4, KC812500.1, KC812499.1, NG_012447.2 and AF283760.1. In representative examples of this type, the polynucleotide comprises an OX2R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an OX2R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian OX2R polynucleotide, or a fragment thereof. In some embodiments, the OX2R polynucleotide comprises a nucleotide sequence that hybridises to an open reading frame for a wild type mammalian OX2R protein, or a fragment thereof under low, medium or high stringency conditions.

3.63 Prostaglandin E1 Receptor (EP1R) Polypeptides

The EP1R mediates stress responses (ACTH secretion and stress behaviour), promotes chemical carcinogenesis and mediates inflammatory thermal hyperalgesia (Sugimoto & Narumiya, 2007).

To date, a crystal structure of the EP1R has not yet been published, so the structural and ligand-binding features of the receptor have to be inferred through indirect approaches such as mutagenesis and homology modelling. The extracellular part of EP1R consists of the N-terminal segment (Met1-Ser27 of the human EP1R), ECL1 (Ala101-Ala106 of the human EP1R) linking helices II and III, ECL2 (Val176-Arg199 of the human EP1R) linking helices IV and V, and ECL3 (Trp324-Ser328 of the human EP1R) linking helices VI to VII.

In specific embodiments of the present invention, the EP1R polypeptide comprises a EP1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an EP1R protein sequence.

In some embodiments, the EP1R protein sequence corresponds to a mammalian EP1R protein sequence. Suitable EP1R sequences may suitably be from mammal selected from the group comprising human (UniProtKB Accession No. P34995), bat (UniProtKB Accession No. G1PBB3), cow (UniProtKB Accession No. F1MUY4), dog (UniProtKB Accession No. Q9BGL8), frog (UniProtKB Accession No. F7C7N3), gorilla (UniProtKB Accession No. G3S6M0), macaque (UniProtKB Accession No. Q564H5), marmoset (UniProtKB Accession No. F7HTH9), monkey (UniProtKB Accession No. A0A0D9R1Y9), mouse (UniProtKB Accession No. P35375), panda (UniProtKB Accession No. G1M4C2), rat (UniProtKB Accession No. P70597), Tasmanian devil (UniProtKB Accession No. G3VPS1).

In some preferred embodiments, the EP1R protein sequence corresponds to a human EP1R protein sequence. In some embodiments, the EP1R polypeptide comprises a human full-length wild-type EP1R protein sequence (UniProtKB Accession No. P34995), as set forth below, or a functional fragment of the wild-type EP1R protein sequence.

[SEQ ID NO: 46]
MSPCGPLNLSLAGEATTCAAPWVPNTSAVPPSGASPALPIFSMTLGA

VSNLLALALLAQAAGRLRRRRSAATFLLFVASLLATDLAGHVIPGAL

VLRLYTAGRAPAGGACHFLGGCMVFFGLCPLLLGCGMAVERCVGVTR

PLLHAARVSVARARLALAAVAAVALAVALLPLARVGRYELQYPGTWC

FIGLGPPGGWRQALLAGLFASLGLVALLAALVCNTLSGLALLRARWR

RRSRRPPPASGPDSRRRWGAHGPRSASASSASSIASASTFFGGSRSS

GSARRARAHDVEMVGQLVGIMVVSCICWSPMLVLVALAVGGWSSTSL

QRPLFLAVRLASWNQILDPWVYILLRQAVLRQLLRLLPPRAGAKGGP

AGLGLTPSAWEASSLRSSRHSGLSHF.

In one form of the invention, the EP1R polypeptide comprises a truncated form of a mammalian wild-type EP1R protein sequence. For example, the EP1R polypeptide sequence may comprise the human wild-type EP1R protein sequence with a C-terminal truncation (e.g., amino acid residues 378-402 may be truncated). Alternatively or in addition, the EP1R polypeptide sequence may comprise the wild-type EP1R protein sequence with a N-terminal truncation. Alternatively or in addition to a C-terminal or N-terminal truncation, a truncation may be performed to remove an internal section of the wild-type EP1R protein sequence (e.g., amino acid residues 185-189 may be truncated). By way of a non-limiting illustrative example, a EP1R polypeptide suitable for using with the present invention comprised amino acid residues 2-184 and 190-377 of the human wild-type EP1R protein sequence as set forth in SEQ ID NO: 46.

3.64 Constructs and Nucleotide Sequences Encoding EP1R Polypeptides.

The present invention also encompasses isolated polynucleotide sequences and constructs encoding EP1R polypeptides as broadly described above and elsewhere herein. Also contemplated are host cells comprising those polynucleotide sequences or constructs.

In some embodiments, the polynucleotide sequences comprise a sequence that corresponds to a human EP1R nucleotide (i.e., corresponding to the PTGER1 gene) sequence as set forth for example in GenBank Accession Nos. AY275470.1, NM_000955.2 and BC029768.1. In representative examples of this type, the polynucleotide comprises an EP1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an EP1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian EP1R polynucleotide, or a fragment thereof. In some embodiments, the EP1R polynucleotide comprises a nucleotide sequence that hybridises to an open reading frame for a wild type mammalian EP1R protein, or a fragment thereof under low, medium or high stringency conditions.

3.65 Serotonin 5-HT1a Receptor (5-HT1aR) Polypeptides

The 5-HT1aR is involved in mediating anxiety, stress responses, depression, schizophrenia and addiction. It is also believed to have neuroprotective actions against ischemic brain damage (Nichols & Nichols, 2008).

To date, a crystal structure of the 5-HT1aR has not yet been published, so the structural and ligand-binding features of the receptor have to be inferred through indirect approaches such as mutagenesis and homology modelling. The extracellular part of 5-HT1aR consists of the N-terminal segment (Met1-Thr32 of the human 5-HT1aR), ECL1 (Asn100-Leu104 of the human 5-HT1aR) linking helices II and III, ECL2 (Trp175-Lys191 of the human 5-HT1aR) linking helices IV and V, and ECL3 (Cys371-Met377 of the human 5-HT1aR) linking helices VI to VII. It is believed to form a disulphide bridge between helices III and ECL2 (Nichols & Nichols, 2008).

In specific embodiments of the present invention, the 5-HT1aR polypeptide comprises a 5-HT1aR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a 5-HT1aR protein sequence.

In some embodiments, the 5-HT1aR protein sequence corresponds to a mammalian 5-HT1aR protein sequence. Suitable 5-HT1aR sequences may suitably be from mammal selected from the group comprising human (UniProtKB Accession No. P08908), alligator (UniProtKB Accession No. A0A151MXE8), chicken (UniProtKB Accession No. D2K8P9), chimpanzee (UniProtKB Accession No. Q9N298), dog (UniProtKB Accession No. Q6XXX9), fox (UniProtKB Accession No. Q6XXY0), frog (UniProtKB Accession No. Q98998), gorilla (UniProtKB Accession No. Q9N297), horse (UniProtKB Accession No. Q0EAB6), mouse (UniProtKB Accession No. Q64264), orangutan (UniProtKB Accession No. Q9N296), rat (UniProtKB Accession No. P19327).

In some preferred embodiments, the 5-HT1aR protein sequence corresponds to a human 5-HT1aR protein sequence. In some embodiments, the 5-HT1aR polypeptide comprises a human full-length wild-type 5-HT1aR protein sequence (UniProtKB Accession No. P08908), as set forth below, or a functional fragment of the wild-type 5-HT1aR protein sequence.

[SEQ ID NO: 47]
MDVLSPGQGNNTTSPPAPFETGGNTTGISDVTVSYQVITSLLLGTLI

FCAVLGNACVVAAIALERSLQNVANYLIGSLAVTDLMVSVLVLPMAA

LYQVLNKWTLGQVTCDLFIALDVLCCTSSILHLCAIALDRYWAITDP

-continued

IDYVNKRTPRRAAALISLTWLIGFLISIPPMLGWRTPEDRSDPDACT

ISKDHGYTIYSTFGAFYIPLLLMLVLYGRIFRAARFRIRKTVKKVEK

TGADTRHGASPAPQPKKSVNGESGSRNWRLGVESKAGGALCANGAVR

QGDDGAALEVIEVHRVGNSKEHLPLPSEAGPTPCAPASFERKNERNA

EAKRKMALARERKTVKTLGIIMGTFILCWLPFFIVALVLPFCESSCH

MPTLLGAIINWLGYSNSLLNPVIYAYFNKDFQNAFKKIIKCKFCRQ.

In one form of the invention, the 5-HT1aR polypeptide comprises a truncated form of a mammalian wild-type 5-HT1aR protein sequence. For example, the 5-HT1aR polypeptide sequence may comprise the human wild-type 5-HT1aR protein sequence with a C-terminal truncation (e.g., amino acid residues 416-2 may be truncated). Alternatively or in addition, the 5-HT1aR polypeptide sequence may comprise the wild-type 5-HT1aR protein sequence with a N-terminal truncation. Alternatively or in addition to a C-terminal or N-terminal truncation, a truncation may be performed to remove an internal section of the wild-type 5-HT1aR protein sequence (e.g., amino acid residues 181-187 may be truncated). By way of a non-limiting illustrative example, a 5-HT1aR polypeptide suitable for using with the present invention comprised amino acid residues 2-180 and 188-415 of the human wild-type 5-HT1aR protein sequence as set forth in SEQ ID NO: 47.

3.66 Constructs and Nucleotide Sequences Encoding 5-HT1aR Polypeptides.

The present invention also encompasses isolated polynucleotide sequences and constructs encoding 5-HT1aR polypeptides as broadly described above and elsewhere herein. Also contemplated are host cells comprising those polynucleotide sequences or constructs.

In some embodiments, the polynucleotide sequences comprise a sequence that corresponds to a human 5-HT1aR nucleotide (i.e., corresponding to the HTR1A gene) sequence as set forth for example in GenBank Accession Nos. NM_000524.3, AF498978.1, NG_032816.1, AB041403.1, BC136263.1 and BC069159.1. In representative examples of this type, the polynucleotide comprises a 5-HT1aR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a 5-HT1aR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian 5-HT1aR polynucleotide, or a fragment thereof. In some embodiments, the 5-HT1aR polynucleotide comprises a nucleotide sequence that hybridises to an open reading frame for a wild type mammalian 5-HT1aR protein, or a fragment thereof under low, medium or high stringency conditions.

3.67 Serotonin 5-HT2a Receptor (5-HT2aR) Polypeptides

In the CNS, the 5-HT2aR is one of the key sites for hallucinogenic action. In the periphery, the 5-HT2aR has various other functions, including proliferation of arterial fibroblasts, migration of aortic smooth muscle cells, arterial vasoconstriction and analgesia (Nichols & Nichols, 2008).

To date, a crystal structure of the 5-HT2aR has not yet been published, so the structural and ligand-binding features of the receptor have to be inferred through indirect approaches such as mutagenesis and homology modelling.

The extracellular part of 5-HT2aR consists of the N-terminal segment (Met1-Glu73 of the human 5-HT2aR), ECL1 (Gly138-Leu143 of the human 5-HT2aR) linking helices II and III, ECL2 (Leu215-Ala-230 of the human 5-HT2aR) linking helices IV and V, and ECL3 (Lys350-Asn354 of the human 5-HT2aR) linking helices VI to VII. It is believed to form a disulphide bridge between helices III and ECL2 (Nichols & Nichols, 2008).

In specific embodiments of the present invention, the 5-HT2aR polypeptide comprises a 5-HT2aR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with a 5-HT2aR protein sequence.

In some embodiments, the 5-HT2aR protein sequence corresponds to a mammalian 5-HT2aR protein sequence. Suitable 5-HT2aR sequences may suitably be from mammal selected from the group comprising human (UniProtKB Accession No. P28223), chicken (UniProtKB Accession No. E1BVI5), cow (UniProtKB Accession No. Q75Z89), dog (UniProtKB Accession No. O46635), hamster (UniProtKB Accession No. P18599), hedgehog (UniProtKB Accession No. A0A1S2ZLM4), macaque (UniProtKB Accession No. P50128), mouse (UniProtKB Accession No. P35363), orangutan (UniProtKB Accession No. Q5R4Q6), pig (UniProtKB Accession No. P50129), rat (UniProtKB Accession No. P14842).

In some preferred embodiments, the 5-HT2aR protein sequence corresponds to a human 5-HT2aR protein sequence. In some embodiments, the 5-HT2aR polypeptide comprises a human full-length wild-type 5-HT2aR protein sequence (UniProtKB Accession No. P28223), as set forth below, or a functional fragment of the wild-type 5-HT2aR protein sequence.

[SEQ ID NO: 48]
MDILCEENTSLSSTTNSLMQLNDDTRLYSNDFNSGEANTSDAFNWTV

DSENRTNLSCEGCLSPSCLSLLHLQEKNWSALLTAVVIILTIAGNIL

VIMAVSLEKKLQNATNYFLMSLAIADMLLGFLVMPVSMLTILYGYRW

PLPSKLCAVWIYLDVLFSTASIMHLCAISLDRYVAIQNPIHHSRFNS

RTKAFLKIIAVWTISVGISMPIPVFGLQDDSKVFKEGSCLLADDNFV

LIGSFVSFFIPLTIMVITYFLTIKSLQKEATLCVSDLGTRAKLASFS

FLPQSSLSSEKLFQRSIHREPGSYTGRRTMQSISNEQKACKVLGIVF

FLFVVMWCPFFITNIMAVICKESCNEDVIGALLNVFVWIGYLSSAVN

PLVYTLFNKTYRSAFSRYIQCQYKENKKPLQLILVNTIPALAYKSSQ

LQMGQKKNSKQDAKTTDNDCSMVALGKQHSEEASKDNSDGVNEKVSC

V.

In one form of the invention, the 5-HT2aR polypeptide comprises a truncated form of a mammalian wild-type 5-HT2aR protein sequence. For example, the 5-HT2aR polypeptide sequence may comprise the human wild-type 5-HT2aR protein sequence with a C-terminal truncation (e.g., amino acid residues 396-471 may be truncated). Alternatively or in addition, the 5-HT2aR polypeptide sequence may comprise the wild-type 5-HT2aR protein sequence with a N-terminal truncation. Alternatively or in addition to a C-terminal or N-terminal truncation, a truncation may be performed to remove an internal section of the wild-type 5-HT2aR protein sequence (e.g., amino acid residues 219-224 may be truncated). By way of a non-limiting illustrative example, a 5-HT2aR polypeptide suitable for using with the present invention comprised amino acid residues 2-218 and 225-397 of the human wild-type 5-HT2aR protein sequence as set forth in SEQ ID NO: 48.

3.68 Constructs and Nucleotide Sequences Encoding 5-HT2aR Polypeptides.

The present invention also encompasses isolated polynucleotide sequences and constructs encoding 5-HT2aR polypeptides as broadly described above and elsewhere herein. Also contemplated are host cells comprising those polynucleotide sequences or constructs.

In some embodiments, the polynucleotide sequences comprise a sequence that corresponds to a human 5-HT2aR nucleotide (i.e., corresponding to the HTR2A gene) sequence as set forth for example in GenBank Accession Nos. NM_000621.4, NM_001165947.2, NG_013011.1, AF498982.1, EU796424.1, EU796429.1, EU796434.1, KC603613.1, BC074849.2, BC074848.2, BC069576.1 and BC069356.1. In representative examples of this type, the polynucleotide comprises a 5-HT2aR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a 5-HT2aR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian 5-HT2aR polynucleotide, or a fragment thereof. In some embodiments, the 5-HT2aR polynucleotide comprises a nucleotide sequence that hybridises to an open reading frame for a wild type mammalian 5-HT2aR protein, or a fragment thereof under low, medium or high stringency conditions.

3.69 Serotonin 5-HT2b Receptor (5-HT2bR) Polypeptides

In the CNS, the 5-HT2bR appears to have a role in the auditory system, and is associated with vulnerability to drug abuse. However it is more highly expressed in the periphery where it is important during development, coordinating the proper formation of the heart and brain (Nichols & Nichols, 2008).

To date, two studies have reported solving the crystal structure of the CXCR4, providing insight into how it binds its ligands (Liu et al., 2013; Wacker et al., 2013). The extracellular part of 5-HT2bR consists of the N-terminal segment (Met1-Lys53 of the human 5-HT2bR), ECL1 (Glu118-Leu123 of the human 5-HT2bR) linking helices II and III, ECL2 (Ile195-Arg213 of the human 5-HT2bR) linking helices IV and V, and ECL3 (Asp351-Asn354 of the human 5-HT2bR) linking helices VI to VII. It is believed to form a disulphide bridge between helix III and ECL2 (Nichols & Nichols, 2008).

In specific embodiments of the present invention, the 5-HT2bR polypeptide comprises a 5-HT2bR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an 5-HT2bR protein sequence.

In some embodiments, the 5-HT2bR protein sequence corresponds to a mammalian 5-HT2bR protein sequence. Suitable 5-HT2bR sequences may suitably be from mammal selected from the group comprising human (UniProtKB Accession No. P41595), cat (UniProtKB Accession No. M3WRH8), catfish (UniProtKB Accession No. W5UAH8), chimpanzee (UniProtKB Accession No. H2QJL0), cow (UniProtKB Accession No. F6QI78), frog (UniProtKB Accession No. F6WGJ8), guinea pig (UniProtKB Accession No. A3RL34), hedgehig (UniProtKB Accession No. A0A1S2ZHK9), horse (UniProtKB Accession No. F6V714), macaque (UniProtKB Accession No. F7HQF4), mouse (UniProtKB Accession No. Q02152), rat (UniProtKB Accession No. P30994), sheep (UniProtKB Accession No. W5QHN7), zebrafish (UniProtKB Accession No. Q0GH74).

In some preferred embodiments, the 5-HT2bR protein sequence corresponds to a human 5-HT2bR protein sequence. In some embodiments, the 5-HT2bR polypeptide comprises a human full-length wild-type 5-HT2bR protein sequence (UniProtKB Accession No. P41595), as set forth below, or a functional fragment of the wild-type 5-HT2bR protein sequence.

[SEQ ID NO: 49]
MALSYRVSELQSTIPEHILQSTFVHVISSNWSGLQTESIPEEMKQIV

EEQGNKLHWAALLILMVIIPTIGGNTLVILAVSLEKKLQYATNYFLM

SLAVADLLVGLFVMPIALLTIMFEAMWPLPLVLCPAWLFLDVLFSTA

SIMHLCAISVDRYIAIKKPIQANQYNSRATAFIKITVVWLISIGIAI

PVPIKGIETDVDNPNNITCVLTKERFGDFMLFGSLAAFFTPLAIMIV

TYFLTIHALQKKAYLVKNKPPQRLTWLTVSTVFQRDETPCSSPEKVA

MLDGSRKDKALPNSGDETLMRRTSTIGKKSVQTISNEQRASKVLGIV

FFLFLLMWCPFFITNITLVLCDSCNQTTLQMLLEIFVWIGYVSSGVN

PLVYTLFNKTFRDAFGRYITCNYRATKSVKTLRKRSSKIYFRNPMAE

NSKFFKKHGIRNGINPAMYQSPMRLRSSTIQSSSIILLDTLLLTENE

GDKTEEQVSYV.

In one form of the invention, the 5-HT2bR polypeptide comprises a truncated form of a mammalian wild-type 5-HT2bR protein sequence. For example, the 5-HT2bR polypeptide sequence may comprise the human wild-type 5-HT2bR protein sequence with a C-terminal truncation (e.g., amino acid residues 396-481 may be truncated). Alternatively or in addition, the 5-HT2bR polypeptide sequence may comprise the wild-type 5-HT2bR protein sequence with a N-terminal truncation. Alternatively or in addition to a C-terminal or N-terminal truncation, a truncation may be performed to remove an internal section of the wild-type 5-HT2bR protein sequence (e.g., amino acid residues 200-208 may be truncated). By way of a non-limiting illustrative example, a 5-HT2bR polypeptide suitable for using with the present invention comprised amino acid residues 2-199 and 209-395 of the human wild-type 5-HT2bR protein sequence as set forth in SEQ ID NO: 49.

3.70 Constructs and Nucleotide Sequences Encoding 5-HT2bR Polypeptides.

The present invention also encompasses isolated polynucleotide sequences and constructs encoding 5-HT2bR polypeptides as broadly described above and elsewhere herein. Also contemplated are host cells comprising those polynucleotide sequences or constructs.

In some embodiments, the polynucleotide sequences comprise a sequence that corresponds to a human 5-HT2bR nucleotide (i.e., corresponding to the HTR2B gene) sequence as set forth for example in GenBank Accession Nos. NM_001320758.1, NM_000867.4, EU796439.1, EU796444.1, AY114103.1, AH007819.3, AY136751.1 and BC063123.1. In representative examples of this type, the polynucleotide comprises an 5-HT2BR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an 5-HT2bR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian 5-HT2bR polynucleotide, or a fragment thereof. In some embodiments, the 5-HT2bR polynucleotide comprises a nucleotide sequence that hybridises to an open reading frame for a wild type mammalian 5-HT2bR protein, or a fragment thereof under low, medium or high stringency conditions.

3.71 Serotonin 5-HT2c Receptor (5-HT2cR) Polypeptides

The 5-HT2cR has been shown to modulate mesolimbic dopaminergic function. Additionally they are thought to play roles in mediation of anxiety, body weight regulation and psychostimulant abuse (Nichols & Nichols, 2008).

To date, a crystal structure of the 5-HT2cR has not yet been published, so the structural and ligand-binding features of the receptor have to be inferred through indirect approaches such as mutagenesis and homology modelling. The extracellular part of 5-HT2cR consists of the N-terminal segment (Met1-Val52 of the human 5-HT2cR), ECL1 (Asp117-Leu122 of the human 5-HT2cR) linking helices II and III, ECL2 (Leu194-Asn210 of the human 5-HT2cR) linking helices IV and V, and ECL3 (Glu338-Asn342 of the human 5-HT2cR) linking helices VI to VII. It is believed to form a disulphide bridge between helix III and ECL2 (Nichols & Nichols, 2008).

In specific embodiments of the present invention, the 5-HT2cR polypeptide comprises a 5-HT2cR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an 5-HT2cR protein sequence.

In some embodiments, the 5-HT2cR protein sequence corresponds to a mammalian 5-HT2cR protein sequence. Suitable 5-HT2cR sequences may suitably be from mammal selected from the group comprising human (UniProtKB Accession No. P28335), alligator (UniProtKB Accession No. A0A151N7D9), baboon (UniProtKB Accession No. A0A096MPH1, cat (UniProtKB Accession No. M3X5M0), chicken (UniProtKB Accession No. F1N989), chimpanzee (UniProtKB Accession No. Q5IS66), dog (UniProtKB Accession No. Q60F97), frog (UniProtKB Accession No. F7AZS9), hedgehog (UniProtKB Accession No. A0A1S3ADC2), horse (UniProtKB Accession No. F6PSU6), human (UniProtKB Accession No. P28335), macaque (UniProtKB Accession No. F7A578), mouse (UniProtKB Accession No. P34968), pig (UniProtKB Accession No. G8YY03), rat (UniProtKB Accession No. P08909).

In some preferred embodiments, the 5-HT2cR protein sequence corresponds to a human 5-HT2cR protein sequence. In some embodiments, the 5-HT2cR polypeptide comprises a human full-length wild-type 5-HT2cR protein sequence (UniProtKB Accession No. P28335), as set forth below, or a functional fragment of the wild-type 5-HT2cR protein sequence.

[SEQ ID NO: 50]
MVNLRNAVHSFLVHLIGLLVWQCDISVSPVAAIVTDIFNTSDGGRFK

FPDGVQNWPALSIVIIIMTIGGNILVIMAVSMEKKLHNATNYFLMS

```
-continued
LAIADMLVGLLVMPLSLLAILYDYVWLPRYLCPVWISLDVLFSTASI

MHLCAISLDRYVAIRNPIEHSRFNSRTKAIMKIAIVWAISIGVSVPI

PVIGLRDEEKVFVNNTTCVLNDPNFVLIGSFVAFFIPLTIMVITYCL

TIYVLRRQALMLLHGHTEEPPGLSLDFLKCCKRNTAEEENSANPNQD

QNARRRKKKERRPRGTMQAINNERKASKVLGIVFFVFLIMWCPFFIT

NILSVLCEKSCNQKLMEKLLNVFVWIGYVCSGINPLVYTLFNKIYRR

AFSNYLRCNYKVEKKPPVRQIPRVAATALSGRELNVNIYRHTNEPVI

EKASDNEPGIEMQVENLELPVNPSSVVSERISSV.
```

In one form of the invention, the 5-HT2cR polypeptide comprises a truncated form of a mammalian wild-type 5-HT2cR protein sequence. For example, the 5-HT2cR polypeptide sequence may comprise the human wild-type 5-HT2cR protein sequence with a C-terminal truncation (e.g., amino acid residues 384-458 may be truncated). Alternatively or in addition, the 5-HT2cR polypeptide sequence may comprise the wild-type 5-HT2cR protein sequence with a N-terminal truncation. Alternatively or in addition to a C-terminal or N-terminal truncation, a truncation may be performed to remove an internal section of the wild-type 5-HT2cR protein sequence (e.g., amino acid residues 198-205 may be truncated). By way of a non-limiting illustrative example, a 5-HT2cR polypeptide suitable for using with the present invention comprised amino acid residues 2-197 and 206-383 of the human wild-type 5-HT2cR protein sequence as set forth in SEQ ID NO: 50.

3.72 Constructs and Nucleotide Sequences Encoding 5-HT2cR Polypeptides

The present invention also encompasses isolated polynucleotide sequences and constructs encoding 5-HT2cR polypeptides as broadly described above and elsewhere herein. Also contemplated are host cells comprising those polynucleotide sequences or constructs.

In some embodiments, the polynucleotide sequences comprise a sequence that corresponds to a human 5-HT2cR nucleotide (i.e., corresponding to the HTR2C gene) sequence as set forth for example in GenBank Accession Nos. NM_001256760.2, NM_000868.3, NM_001256761.2, NG_012082.2, EU796454.1, AF498983.1 and BC095543.1. In representative examples of this type, the polynucleotide comprises an 5-HT2CR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an 5-HT2cR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian 5-HT2cR polypeptide, or a fragment thereof. In some embodiments, the 5-HT2cR polynucleotide comprises a nucleotide sequence that hybridises to an open reading frame for a wild type mammalian 5-HT2cR protein, or a fragment thereof under low, medium or high stringency conditions.

3.73 Serotonin 5-HT4 Receptor (5-HT4R) Polypeptides

In the CNS the 5-HT4R is believed to be involved in learning and memory, and mediation of locomotor activity. In the periphery they play a role in gastrointestinal and cardiovascular functions (Nichols & Nichols, 2008).

To date, a crystal structure of the 5-HT4R has not yet been published, so the structural and ligand-binding features of the receptor have to be inferred through indirect approaches such as mutagenesis and homology modelling. The extracellular part of 5-HT4R consists of the N-terminal segment (Met1-Ser10 of the human 5-HT4R), ECL1 (Glu84-Tyr88 of the human 5-HT4R) linking helices II and III, ECL2 (Trp161-Val188 of the human 5-HT4R) linking helices IV and V, and ECL3 (Glu286-Val289 of the human 5-HT4R) linking helices VI to VII. It is believed to form a disulphide bridge between helix III and ECL2 (Nichols & Nichols, 2008).

In specific embodiments of the present invention, the 5-HT4R polypeptide comprises a 5-HT4R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an 5-HT4R protein sequence.

In some embodiments, the 5-HT4R protein sequence corresponds to a mammalian 5-HT4R protein sequence. Suitable 5-HT4R sequences may suitably be from mammal selected from the group comprising human (UniProtKB Accession No. Q13639), alligator (UniProtKB Accession No. A0A151M6L1), cow (UniProtKB Accession No. Q5E9Q5), frog (UniProtKB Accession No. F7BIA5), guinea pig (UniProtKB Accession No. O70528), hedgehog (UniProtKB Accession No. A0A1S2ZAK9), horse (UniProtKB Accession No. D2Y0Z2), marmoset (UniProtKB Accession No. F7FE43), mouse (UniProtKB Accession No. P97288), pig (UniProtKB Accession No. F1RLB0), rat (UniProtKB Accession No. Q62758).

In some preferred embodiments, the 5-HT4R protein sequence corresponds to a human 5-HT4R protein sequence. In some embodiments, the 5-HT4R polypeptide comprises a human full-length wild-type 5-HT4R protein sequence (UniProtKB Accession No. Q13639), as set forth below, or a functional fragment of the wild-type 5-HT4R protein sequence.

```
                                            [SEQ ID NO: 51]
MDKLDANVSSEEGFGSVEKVVLLTFLSTVILMAILGNLLVMVAVCWD

RQLRKIKTNYFIVSLAFADLLVSVLVMPFGAIELVQDIWIYGEVFCL

VRTSLDVLLTTASIFHLCCISLDRYYAICCQPLVYRNKMTPLRIALM

LGGCWVIPTFISFLPIMQGWNNIGIIDLIEKRKFNQNSNSTYCVFMV

NKPYAITCSVVAFYIPFLLMVLAYYRIYVTAKEHAHQIQMLQRAGAS

SESRPQSADQHSTHRMRTETKAAKTLCIIMGCFCLCWAPFFVTNIVD

PFIDYTVPGQVWTAFLWLGYINSGLNPFLYAFLNKSFRRAFLIILCC

DDERYRRPSILGQTVPCSTTTINGSTHVLRDAVECGGQWESQCHPPA

TSPLVAAQPSDT.
```

In one form of the invention, the 5-HT4R polypeptide comprises a truncated form of a mammalian wild-type 5-HT4R protein sequence. For example, the 5-HT4R polypeptide sequence may comprise the human wild-type 5-HT4R protein sequence with a C-terminal truncation (e.g., amino acid residues 329-388 may be truncated). Alternatively or in addition, the 5-HT4R polypeptide sequence may comprise the wild-type 5-HT4R protein sequence with a N-terminal truncation. Alternatively or in addition to a C-terminal or N-terminal truncation, a truncation may be performed to remove an internal section of the wild-type 5-HT4R protein sequence (e.g., amino acid residues 166-183 may be truncated). By way of a non-limiting illustrative example, a 5-HT4R polypeptide suitable for using with the present invention comprised amino acid residues 2-165 and 184-328 of the human wild-type 5-HT4R protein sequence as set forth in SEQ ID NO: 51.

3.74 Constructs and Nucleotide Sequences Encoding 5-HT4R Polypeptides.

The present invention also encompasses isolated polynucleotide sequences and constructs encoding 5-HT4R polypeptides as broadly described above and elsewhere herein. Also contemplated are host cells comprising those polynucleotide sequences or constructs.

In some embodiments, the polynucleotide sequences comprise a sequence that corresponds to a human 5-HT4R nucleotide (i.e., corresponding to the HTR4 gene) sequence as set forth for example in GenBank Accession Nos. NM_000870.6, NM_001286410.1, NM_001040173.2, NM_001040172.2, NM_001040169.2, NM_199453.3, NR_104445.1, NG_029052.1, AM712912.1, AJ633645.1, AJ278982.1, AJ278981.1, AJ278980.1, AJ278979.1, AB070620.2 and AB070621.1. In representative examples of this type, the polynucleotide comprises an 5-HT4R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an 5-HT4R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian 5-HT4R polynucleotide, or a fragment thereof. In some embodiments, the 5-HT4R polynucleotide comprises a nucleotide sequence that hybridises to an open reading frame for a wild type mammalian 5-HT4R protein, or a fragment thereof under low, medium or high stringency conditions.

3.75 Somatostatin 2 Receptor (SST2R) Polypeptides

The SST2R is widely expressed throughout the body, including the brain, lung, heart, stomach, kidney, liver and numerous type of immune cells (De Martino et al., 2010). It is also believed to mediate cell cycle regulation, apoptosis and transcriptional regulation (Theodoropoulou & Stalla, 2013).

To date, a crystal structure of the SST2R has not yet been published, so the structural and ligand-binding features of the receptor have to be inferred through indirect approaches such as mutagenesis and homology modelling. The extracellular part of SST2R consists of the N-terminal segment (Met1-Glu39 of the human SST2R), ECL1 (Val106-Phe110 of the human SST2R) linking helices II and III, ECL2 (Gly182-Glu200 of the human SST2R) linking helices IV and V, and ECL3 (Ala283-Pro286 of the human SST2R) linking helices VI to VII. It is believed to form a disulphode bridge between helix III and ECL2 (Patel, 1999).

In specific embodiments of the present invention, the SST2R polypeptide comprises a SST2R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an SST2R protein sequence.

In some embodiments, the SST2R protein sequence corresponds to a mammalian SST2R protein sequence. Suitable SST2R sequences may suitably be from mammal selected from the group comprising human (UniProtKB Accession No. P30874), alligator (UniProtKB Accession No. A0A151N260), carp (UniProtKB Accession No. B2D1T6), cat (UniProtKB Accession No. M3W2Q8), chicken (UniProtKB Accession No. Q58G84), chimpanzee (UniProtKB Accession No. G2HFH4), cow (UniProtKB Accession No. P34993), dog (UniProtKB Accession No. Q49LX6), frog (UniProtKB Accession No. F6T888), macaque (UniProtKB Accession No. G7NJD6), mouse (UniProtKB Accession No. P30875), pig (UniProtKB Accession No. P34994), rabbit (UniProtKB Accession No. G1SX13), rat (UniProtKB Accession No. P30680), sheep (UniProtKB Accession No. W5NPT8).

In some preferred embodiments, the SST2R protein sequence corresponds to a human SST2R protein sequence. In some embodiments, the SST2R polypeptide comprises a human full-length wild-type SST2R protein sequence (UniProtKB Accession No. P30874), as set forth below, or a functional fragment of the wild-type SST2R protein sequence.

```
                                                [SEQ ID NO: 52]
MDMADEPLNGSHTWLSIPFDLNGSVVSTNTSNQTEPYYDLTSNAVLT

FIYFVVCIIGLCGNTLVIYVILRYAKMKTITNIYILNLAIADELFML

GLPFLAMQVALVHWPFGKAICRVVMTVDGINQFTSIFCLTVMSIDRY

LAVVHPIKSAKWRRPRTAKMITMAVWGVSLLVILPIMIYAGLRSNQW

GRSSCTINWPGESGAWYTGFIIYTFILGFLVPLTIICLCYLFIIIKV

KSSGIRVGSSKRKKSEKKVTRMVSIVVAVFIFCWLPFYIFNVSSVSM

AISPTPALKGMFDFVVVLTYANSCANPILYAFLSDNFKKSFQNVLCL

VKVSGTDDGERSDSKQDKSRLNETTETQRTLLNGDLQTSI.
```

In one form of the invention, the SST2R polypeptide comprises a truncated form of a mammalian wild-type SST2R protein sequence. For example, the SST2R polypeptide sequence may comprise the human wild-type SST2R protein sequence with a C-terminal truncation (e.g., amino acid residues 329-369 may be truncated). Alternatively or in addition, the SST2R polypeptide sequence may comprise the wild-type SST2R protein sequence with a N-terminal truncation. Alternatively or in addition to a C-terminal or N-terminal truncation, a truncation may be performed to remove an internal section of the wild-type SST2R protein sequence (e.g., amino acid residues 183-193 may be truncated). By way of a non-limiting illustrative example, a SST2R polypeptide suitable for using with the present invention comprised amino acid residues 2-182 and 194-328 of the human wild-type SST2R protein sequence as set forth in SEQ ID NO: 52.

3.76 Constructs and Nucleotide Sequences Encoding SST2R Polypeptides.

The present invention also encompasses isolated polynucleotide sequences and constructs encoding SST2R polypeptides as broadly described above and elsewhere herein. Also contemplated are host cells comprising those polynucleotide sequences or constructs.

In some embodiments, the polynucleotide sequences comprise a sequence that corresponds to a human SST2R nucleotide (i.e., corresponding to the SSTR2 gene) sequence as set forth for example in GenBank Accession Nos. NM_001050.2, NG_029371.1, L34689.1, AY236542.1, M81830.1, AF184174.1, L13033.1, BC095495.1 and BC019610.1. In representative examples of this type, the polynucleotide comprises an SST2R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an SST2R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian SST2R polynucleotide, or a fragment thereof. In some embodiments, the SST2R polynucleotide comprises a nucleotide sequence that hybridises to an open reading frame for a wild type mammalian SST2R protein, or a fragment thereof under low, medium or high stringency conditions.

3.77 Sphingosine 1-Phosphate Receptor 1 (S1P1R) Polypeptides

The S1P1R mediates a variety of physiological functions, including astrocyte migration, B cell chemotaxis and inhibition of egress, T cell chemotaxis and inhibition of egress, increased cardiomyocyte positive inotropy, early vascular system development and migration of neural stem cells (Rosen et al., 2009).

A crystal structure of the S1P1R has been published (Hanson et al., 2012), providing insight into the ligand-binding and activation mechanisms of the receptor. The extracellular part of S1P1R consists of the N-terminal segment (Met1-Lys41 of the human S1P1R), ECL1 (Ser105-Leu112 of the human S1P1R) linking helices II and III, ECL2 (Trp182-Tyr198 of the human S1P1R) linking helices IV and V, and ECL3 (Lys283-Cys287 of the human S1P1R) linking helices VI to VII. Two disulphide bonds help to shape the extracellular side of S1P1R (Hanson et al., 2012).

In specific embodiments of the present invention, the S1P1R polypeptide comprises a S1P1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an S1P1R protein sequence.

In some embodiments, the S1P1R protein sequence corresponds to a mammalian S1P1R protein sequence. Suitable S1P1R sequences may suitably be from mammal selected from the group comprising human (UniProtKB Accession No. P21453), aligator (UniProtKB Accession No. A0A151M4S4), cat (UniProtKB Accession No. M3W6R4), chimpanzee (UniProtKB Accession No. H2PZI1), cow (UniProtKB Accession No. Q5E9P3), dog (UniProtKB Accession No. W5VNF7), guinea pig (UniProtKB Accession No. H0V7G9), hedgehog (UniProtKB Accession No. A0A1S3A399), macaque (UniProtKB Accession No. H9EUW9), marmoset (UniProtKB Accession No. F7HBl1), mouse (UniProtKB Accession No. O08530), rabbit (UniProtKB Accession No. G1T9R2), rat (UniProtKB Accession No. P48303), Tasmanian devil (UniProtKB Accession No. G3WFF9), turtle (UniProtKB Accession No. K7F150).

In some preferred embodiments, the S1P1R protein sequence corresponds to a human S1P1R protein sequence. In some embodiments, the S1P1R polypeptide comprises a human full-length wild-type S1P1R protein sequence (UniProtKB Accession No. P21453), as set forth below, or a functional fragment of the wild-type S1P1R protein sequence.

[SEQ ID NO: 53]
MGPTSVPLVKAHRSSVSDYVNYDIIVRHYNYTGKLNISADKENSIKL

TSVVFILICCFIILENIFVLLTIWKTKKFHRPMYYFIGNLALSDLLA

GVAYTANLLLSGATTYKLTPAQWFLREGSMFVALSASVFSLLAIAIE

RYITMLKMKLHNGSNNFRLFLLISACWVISLILGGLPIMGWNCISAL

SSCSTVLPLYHKHYILFCTTVFTLLLLSIVILYCRIYSLVRTRSRRL

TFRKNISKASRSSEKSLALLKTVIIVLSVFIACWAPLFILLLLDVGC

KVKTCDILFRAEYFLVLAVLNSGTNPIIYTLTNKEMRRAFIRIMSCC

KCPSGDSAGKFKRPIIAGMEFSRSKSDNSSHPQKDEGDNPETIMSSG

NVNSSS.

In one form of the invention, the S1P1R polypeptide comprises a truncated form of a mammalian wild-type S1P1R protein sequence. For example, the S1P1R polypeptide sequence may comprise the human wild-type S1P1R protein sequence with a C-terminal truncation (e.g., amino acid residues 328-382 may be truncated). Alternatively or in addition, the S1P1R polypeptide sequence may comprise the wild-type S1P1R protein sequence with a N-terminal truncation. Alternatively or in addition to a C-terminal or N-terminal truncation, a truncation may be performed to remove an internal section of the wild-type S1P1R protein sequence (e.g., amino acid residues 187-193 may be truncated). By way of a non-limiting illustrative example, a S1P1R polypeptide suitable for using with the present invention comprised amino acid residues 2-186 and 194-327 of the human wild-type S1P1R protein sequence as set forth in SEQ ID NO: 53.

3.78 Constructs and Nucleotide Sequences Encoding S1P1R Polypeptides.

The present invention also encompasses isolated polynucleotide sequences and constructs encoding S1P1R polypeptides as broadly described above and elsewhere herein. Also contemplated are host cells comprising those polynucleotide sequences or constructs.

In some embodiments, the polynucleotide sequences comprise a sequence that corresponds to a human S1P1R nucleotide (i.e., corresponding to the S1PR1 gene) sequence as set forth for example in GenBank Accession Nos. NM_001320730.1, NM_001400.4, NG_016181.1 and BC018650.1. In representative examples of this type, the polynucleotide comprises an S1P1R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an S1P1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian S1P1R polynucleotide, or a fragment thereof. In some embodiments, the S1P1R polynucleotide comprises a nucleotide sequence that hybridises to an open reading frame for a wild type mammalian S1P1R protein, or a fragment thereof under low, medium or high stringency conditions.

3.79 Sphingosine 1-Phosphate Receptor 3 (S1P3R) Polypeptides

The S1P3R is found in the brain, heart, spleen, liver, lung, thymus, kidney, testis and skeletal muscle. It mediates a variety of physiological functions, including cardiomyocyte survival following ischemia-reperfusion and dendritic cell lethality/inflammation/coagulation (Rosen et al., 2009).

To date, a crystal structure of the S1P3R has not yet been published, so the structural and ligand-binding features of the receptor have to be inferred through indirect approaches such as mutagenesis and homology modelling. The extracellular part of S1P3R consists of the N-terminal segment (Met1-Ala35 of the human S1P3R), ECL1 (Ser99-Leu106 of the human S1P3R) linking helices II and III, ECL2

(Trp176-Tyr192 of the human S1P3R) linking helices IV and V, and ECL3 (Arg270-Cys274 of the human S1P3R) linking helices VI to VII.

In specific embodiments of the present invention, the S1P3R polypeptide comprises a S1P3R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an S1P3R protein sequence.

In some embodiments, the S1P3R protein sequence corresponds to a mammalian S1P3R protein sequence. Suitable S1P3R sequences may suitably be from mammal selected from the group comprising human (UniProtKB Accession No. Q99500), chimpanzee (UniProtKB Accession No. H2RBL8), cow (UniProtKB Accession No. A6QR17), dog (UniProtKB Accession No. E2RF74), guinea pig (UniProtKB Accession No. H0WDH2), hedgehog (UniProtKB Accession No. A0A1S3ASI7), macaque (UniProtKB Accession No. G7NEM6), marmoset (UniProtKB Accession No. F7F4H4), mouse (UniProtKB Accession No. Q9Z0U9), orangutan (UniProtKB Accession No. K7EVQ8), rabbit (UniProtKB Accession No. G1T9A8), rat (UniProtKB Accession No. F1M9D3), salmon (UniProtKB Accession No. A0A1S3LU52), Tasmanian devil (UniProtKB Accession No. G3VPD8).

In some preferred embodiments, the S1P3R protein sequence corresponds to a human S1P3R protein sequence. In some embodiments, the S1P3R polypeptide comprises a human full-length wild-type S1P3R protein sequence (UniProtKB Accession No. Q99500), as set forth below, or a functional fragment of the wild-type S1P3R protein sequence.

[SEQ ID NO: 54]
MATALPPRLQPVRGNETLREHYQYVGKLAGRLKEASEGSTLTTVLFL

VICSFIVLENLMVLIAIWKNNKFHNRMYFFIGNLALCDLLAGIAYKV

NILMSGKKTFSLSPTVWFLREGSMFVALGASTCSLLAIAIERHLTMI

KMRPYDANKRHRVFLLIGMCWLIAFTLGALPILGWNCLHNLPDCSTI

LPLYSKKYIAFCISIFTAILVTIVILYARIYFLVKSSSRKVANHNNS

ERSMALLRTVVIVVSVFIACWSPLFILFLIDVACRVQACPILFKAQW

FIVLAVLNSAMNPVIYTLASKEMRRAFFRLVCNCLVRGRGARASPIQ

PALDPSRSKSSSSNNSSHSPKVKEDLPHTAPSSCIMDKNAALQNGIF

CN.

In one form of the invention, the S1P3R polypeptide comprises a truncated form of a mammalian wild-type S1P3R protein sequence. For example, the S1P3R polypeptide sequence may comprise the human wild-type S1P3R protein sequence with a C-terminal truncation (e.g., amino acid residues 315-378 may be truncated). Alternatively or in addition, the S1P3R polypeptide sequence may comprise the wild-type S1P3R protein sequence with a N-terminal truncation. Alternatively or in addition to a C-terminal or N-terminal truncation, a truncation may be performed to remove an internal section of the wild-type S1P3R protein sequence (e.g., amino acid residues 181-188 may be truncated). By way of a non-limiting illustrative example, a S1P3R polypeptide suitable for using with the present invention comprised amino acid residues 2-180 and 189-314 of the human wild-type S1P3R protein sequence as set forth in SEQ ID NO: 54.

3.80 Constructs and Nucleotide Sequences Encoding S1P3R Polypeptides.

The present invention also encompasses isolated polynucleotide sequences and constructs encoding S1P3R polypeptides as broadly described above and elsewhere herein. Also contemplated are host cells comprising those polynucleotide sequences or constructs.

In some embodiments, the polynucleotide sequences comprise a sequence that corresponds to a human S1P3R nucleotide (i.e., corresponding to the S1PR3 gene) sequence as set forth for example in GenBank Accession Nos. NM_005226.3, BC060827.1 and BC069579.1. In representative examples of this type, the polynucleotide comprises an S1P3R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an S1P3R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian S1P3R polynucleotide, or a fragment thereof. In some embodiments, the S1P3R polynucleotide comprises a nucleotide sequence that hybridises to an open reading frame for a wild type mammalian S1P3R protein, or a fragment thereof under low, medium or high stringency conditions.

3.81 Thyrotrophin-Releasing Hormone Receptor 1 (TRH1R) Polypeptides

The TRH1R stimulates the release of prolactin and thyrotropin (Perret et al., 1988) and the action of TRH on TRH1R is essential for normal function of the thyroid axis (Hollenberg, 2008).

To date, a crystal structure of the TRH1R has not yet been published, so the structural and ligand-binding features of the receptor have to be inferred through indirect approaches such as mutagenesis and homology modelling. The extracellular part of TRH1R consists of the N-terminal segment (Met1-Ala21 of the human TRH1R), ECL1 (Tyr88-Tyr93 of the human TRH1R) linking helices II and III, ECL2 (Asp165-Ile183 of the human TRH1R) linking helices IV and V, and ECL3 (Ser293-Gln297 of the human TRH1R) linking helices VI to VII.

In specific embodiments of the present invention, the TRH1R polypeptide comprises a TRH1R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an TRH1R protein sequence.

In some embodiments, the TRH1R protein sequence corresponds to a mammalian TRH1R protein sequence. Suitable TRH1R sequences may suitably be from mammal selected from the group comprising human (UniProtKB Accession No. P34981), alligator (UniProtKB Accession No. A0A151P2B9), chicken (UniProtKB Accession No. O93603), cow (UniProtKB Accession No. O46639), frog (UniProtKB Accession No. F6X115), hedgehog (UniProtKB Accession No. A0A1S2ZTF7), macaque (UniProtKB Accession No. F7DWM0), mouse (UniProtKB Accession No. P21761), pig (UniProtKB Accession No. D5FUH1), rat (UniProtKB Accession No. Q01717), sheep (UniProtKB Accession No. Q28596).

In some preferred embodiments, the TRH1R protein sequence corresponds to a human TRH1R protein sequence. In some embodiments, the TRH1R polypeptide comprises a human full-length wild-type TRH1R protein sequence (Uni- ProtKB Accession No. P34981), as set forth below, or a functional fragment of the wild-type TRH1R protein sequence.

[SEQ ID NO: 55]
MENETVSELNQTQLQPRAVVALEYQVVTILLVLIICGLGIVGNIMVV

LVVMRTKHMRTPTNCYLVSLAVADLMVLVAAGLPNITDSIYGSWVYG

YVGCLCITYLQYLGINASSCSITAFTIERYIAICHPIKAQFLCTFSR

AKKIIIFVWAFTSLYCMLWFFLLDLNISTYKDAIVISCGYKISRNYY

SPIYLMDFGVFYVVPMILATVLYGFIARILFLNPIPSDPKENSKTWK

NDSTHQNTNLNVNTSNRCFNSTVSSRKQVTKMLAVVVILFALLWMPY

RTLVVVNSFLSSPFQENWFLLFCRICIYLNSAINPVIYNLMSQKFRA

AFRKLCNCKQKPTEKPANYSVALNYSVIKESDHFSTELDDITVTDTY

LSATKVSFDDTCLASEVSFSQS.

In one form of the invention, the TRH1R polypeptide comprises a truncated form of a mammalian wild-type TRH1R protein sequence. For example, the TRH1R polypeptide sequence may comprise the human wild-type TRH1R protein sequence with a C-terminal truncation (e.g., amino acid residues 337-398 may be truncated). Alternatively or in addition, the TRH1R polypeptide sequence may comprise the wild-type TRH1R protein sequence with a N-terminal truncation. Alternatively or in addition to a C-terminal or N-terminal truncation, a truncation may be performed to remove an internal section of the wild-type TRH1R protein sequence (e.g., amino acid residues 167-175 may be truncated). By way of a non-limiting illustrative example, a TRH1R polypeptide suitable for using with the present invention comprised amino acid residues 2-166 and 176-336 of the human wild-type TRH1R protein sequence as set forth in SEQ ID NO: 55.

3.82 Constructs and Nucleotide Sequences Encoding TRH1R Polypeptides.

The present invention also encompasses isolated polynucleotide sequences and constructs encoding TRHR polypeptides as broadly described above and elsewhere herein. Also contemplated are host cells comprising those polynucleotide sequences or constructs.

In some embodiments, the polynucleotide sequences comprise a sequence that corresponds to a human TRHR nucleotide (i.e., corresponding to the TRHR gene) sequence as set forth for example in GenBank Accession Nos. NM_003301.5, NG_017161.1, AJ011701.1, BC113360.1, BC105045.1 and AY493373.1. In representative examples of this type, the polynucleotide comprises an TRHR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a TRH1R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian TRH1R polynucleotide, or a fragment thereof. In some embodiments, the TRH1R polynucleotide comprises a nucleotide sequence that hybridises to an open reading frame for a wild type mammalian TRH1R protein, or a fragment thereof under low, medium or high stringency conditions.

3.83 Vasopressin Receptor 1A (V1AR) Polypeptides

The V1AR is expressed in many tissues including the liver, vascular smooth muscle cells and the brain. In the vasculature the receptor mediates vasoconstriction, while in the brain it mediates anxiety- and aggression-producing responses (Manning et al., 2008).

To date, a crystal structure of the V1AR has not yet been published, so the structural and ligand-binding features of the receptor have to be inferred through indirect approaches such as mutagenesis and homology modelling. The extracellular part of V1AR consists of the N-terminal segment (Met1-Asn47 of the human V1AR), ECL1 (Thr114-Phe117 of the human V1AR) linking helices II and III, ECL2 (Ser190-Ile208 of the human V1AR) linking helices IV and V, and ECL3 (Pro318-Trp322 of the human V1AR) linking helices VI to VII.

In specific embodiments of the present invention, the V1AR polypeptide comprises a V1AR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an V1AR protein sequence.

In some embodiments, the V1AR protein sequence corresponds to a mammalian V1AR protein sequence. Suitable V1AR sequences may suitably be from mammal selected from the group comprising human (UniProtKB Accession No. P37288), cat (UniProtKB Accession No. M3WKK5), chimpanzee (UniProtKB Accession No. H2Q6D6), cow (UniProtKB Accession No. A2VDS9), dog (UniProtKB Accession No. E2R8D3), frog (UniProtKB Accession No. F7B836), horse (UniProtKB Accession No. F6QLP1), macaque (UniProtKB Accession No. F6ZXQ6), mouse (UniProtKB Accession No. Q62463), pig (UniProtKB Accession No. A0A1D5NXS1), rabbit (UniProtKB Accession No. G1TLM4), rat (UniProtKB Accession No. P30560), sheep (UniProtKB Accession No. P48043), turtle (UniProtKB Accession No. K7FSS7), vole (UniProtKB Accession No. Q9WTV8).

In some preferred embodiments, the V1AR protein sequence corresponds to a human V1AR protein sequence. In some embodiments, the V1AR polypeptide comprises a human full-length wild-type V1AR protein sequence (UniProtKB Accession No. P37288), as set forth below, or a functional fragment of the wild-type V1AR protein sequence.

[SEQ ID NO: 56]
MRLSAGPDAGPSGNSSPWWPLATGAGNTSREAEALGEGNGPPRDVRN

EELAKLEIAVLAVTFAVAVLGNSSVLLALHRTPRKTSRMHLFIRHLS

LADLAVAFFQVLPQMCWDITYRFRGPDWLCRVVKHLQVFGMFASAYM

LVVMTADRYIAVCHPLKTLQQPARRSRLMIAAAWVLSFVLSTPQYFV

FSMIEVNNVTKARDCWATFIQPWGSRAYVTWMTGGIFVAPVVILGTC

YGFICYNIWCNVRGKTASRQSKGAEQAGVAFQKGFLLAPCVSSVKSI

SRAKIRTVKMTFVIVTAYIVCWAPFFIIQMWSVWDPMSVWTESENPT

ITITALLGSLNSCCNPWIYMFFSGHLLQDCVQSFPCCQNMKEKFNKE

DTDSMSRRQTFYSNNRSPTNSTGMWKDSPKSSKSIKFIPVST.

In one form of the invention, the V1AR polypeptide comprises a truncated form of a mammalian wild-type T V1AR protein sequence. For example, the V1AR polypeptide sequence may comprise the human wild-type V1AR protein sequence with a C-terminal truncation (e.g., amino acid residues 365-418 may be truncated). Alternatively or in addition, the V1AR polypeptide sequence may comprise the wild-type V1AR protein sequence with a N-terminal truncation. Alternatively or in addition to a C-terminal or N-terminal truncation, a truncation may be performed to remove an internal section of the wild-type V1AR protein sequence (e.g., amino acid residues 192-205 may be truncated). By way of a non-limiting illustrative example, a V1AR polypeptide suitable for using with the present invention comprised amino acid residues 2-191 and 206-364 of the human wild-type V1AR protein sequence as set forth in SEQ ID NO: 56.

3.84 Constructs and Nucleotide Sequences Encoding V1AR Polypeptides.

The present invention also encompasses isolated polynucleotide sequences and constructs encoding V1AR polypeptides as broadly described above and elsewhere herein. Also contemplated are host cells comprising those polynucleotide sequences or constructs.

In some embodiments, the polynucleotide sequences comprise a sequence that corresponds to a human V1AR nucleotide (i.e., corresponding to the AVPR1A gene) sequence as set forth for example in GenBank Accession Nos. NM_000706.4, KJ534780.1, KJ534779.1, BC074803.2, BC074804.2, AF208541.1 and AY322550.1. In representative examples of this type, the polynucleotide comprises an V1AR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a V1AR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian V1AR polypeptide, or a fragment thereof. In some embodiments, the V1AR polynucleotide comprises a nucleotide sequence that hybridises to an open reading frame for a wild type mammalian V1AR protein, or a fragment thereof under low, medium or high stringency conditions.

3.85 Vasopressin Receptor 1B (V1BR) Polypeptides

The V1BR is expressed in many tissues including the brain, kidney and the adrenal medulla. In the anterior pituitary it stimulates the release of adrenocorticotropic hormone and it is also believed to mediate anxiety and stress responses (Manning et al., 2008).

To date, a crystal structure of the V1BR has not yet been published, so the structural and ligand-binding features of the receptor have to be inferred through indirect approaches such as mutagenesis and homology modelling. The extracellular part of V1BR consists of the N-terminal segment (Met1-Glu30 of the human V1BR), ECL1 (Thr97-Phe100 of the human V1BR) linking helices II and III, ECL2 (Ser173-Gly191 of the human V1BR) linking helices IV and V, and ECL3 (Lys308-Glu312 of the human V1BR) linking helices VI to VII.

In specific embodiments of the present invention, the V1BR polypeptide comprises a V1BR protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an V1BR protein sequence.

In some embodiments, the V1BR protein sequence corresponds to a mammalian V1BR protein sequence. Suitable V1BR sequences may suitably be from mammal selected from the group comprising human (UniProtKB Accession No. P47901), cat (UniProtKB Accession No. M3W6E7), chicken (UniProtKB Accession No. F1NVW1), chimpanzee (UniProtKB Accession No. H2R1Q0), cow (UniProtKB Accession No. F1ME85), dog (UniProtKB Accession No. F1P9D6), frog (UniProtKB Accession No. F7EHY9), guinea pig (UniProtKB Accession No. H0V8M7), horse (UniProtKB Accession No. F7BNU0), macaque (UniProtKB Accession No. F7BAU2), mouse (UniProtKB Accession No. Q9WU02), pig (UniProtKB Accession No. F1SF06), rabbit (UniProtKB Accession No. G1SSV5), rat (UniProtKB Accession No. P48974), Tasmanian devil (UniProtKB Accession No. G3WX95).

In some preferred embodiments, the V1BR protein sequence corresponds to a human V1BR protein sequence. In some embodiments, the V1BR polypeptide comprises a human full-length wild-type V1BR protein sequence (UniProtKB Accession No. P47901), as set forth below, or a functional fragment of the wild-type V1BR protein sequence.

[SEQ ID NO: 57]
MDSGPLWDANPTPRGTLSAPNATTPWLGRDEELAKVEIGVLATVLVL

ATGGNLAVLLTLGQLGRKRSRMHLFVLHLALTDLAVALFQVLPQLLW

DITYRFQGPDLLCRAVKYLQVLSMFASTYMLLAMTLDRYLAVCHPLR

SLQQPGQSTYLLIAAPWLLAAIFSLPQVFIFSLREVIQGSGVLDCWA

DFGFPWGPRAYLTWTTLAIFVLPVTMLTACYSLICHEICKNLKVKTQ

AWRVGGGWRTWDRPSPSTLAATTRGLPSRVSSINTISRAKIRTVKM

TFVIVLAYIACWAPFFSVQMWSVWDKNAPDEDSTNVAFTISMLLGNL

NSCCNPWIYMGFNSHLLPRPLRHLACCGGPQPRMRRRLSDGSLSSRH

TTLLTRSSCPATLSLSLSLTLSGRPRPEESPRDLELADGEGTAETII

F.

In one form of the invention, the V1BR polypeptide comprises a truncated form of a mammalian wild-type T V1BR protein sequence. For example, the V1BR polypeptide sequence may comprise the human wild-type V1BR protein sequence with a C-terminal truncation (e.g., amino acid residues 355-424 may be truncated). Alternatively or in addition, the V1BR polypeptide sequence may comprise the wild-type V1BR protein sequence with a N-terminal truncation. Alternatively or in addition to a C-terminal or N-terminal truncation, a truncation may be performed to remove an internal section of the wild-type V1BR protein sequence (e.g., amino acid residues 175-183 may be truncated). By way of a non-limiting illustrative example, a V1BR polypeptide suitable for using with the present invention comprised amino acid residues 2-174 and 184-354 of the human wild-type V1BR protein sequence as set forth in SEQ ID NO: 57.

3.86 Constructs and Nucleotide Sequences Encoding V1BR Polypeptides.

The present invention also encompasses isolated polynucleotide sequences and constructs encoding V1BR polypeptides as broadly described above and elsewhere herein. Also contemplated are host cells comprising those polynucleotide sequences or constructs.

In some embodiments, the polynucleotide sequences comprise a sequence that corresponds to a human V1BR nucleotide (i.e., corresponding to the AVPR1B gene) sequence as set forth for example in GenBank Accession Nos. NM_000707.3, DQ194816.1 and EU432111.1. In representative examples of this type, the polynucleotide comprises a V1BR nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, a V1BR polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian V1BR polynucleotide, or a fragment thereof. In some embodiments, the V1BR polynucleotide comprises a nucleotide sequence that hybridises to an open reading frame for a wild type mammalian V1BR protein, or a fragment thereof under low, medium or high stringency conditions.

3.87 Vasopressin Receptor 2 (V2R) Polypeptides

The V2R mediates anti-diuresis through receptors present in the collecting duct of the kidney. Additionally it appears to mediate the pain response induced by vasopressin (Manning et al., 2008).

To date, a crystal structure of the V2R has not yet been published, so the structural and ligand-binding features of the receptor have to be inferred through indirect approaches such as mutagenesis and homology modelling. The extracellular part of V2R consists of the N-terminal segment (Met1-Glu33 of the human V2R), ECL1 (Thr102-Phe105 of the human V2R) linking helices II and III, ECL2 (Ala179-Ala197 of the human V2R) linking helices IV and V, and ECL3 (Pro298-Leu302 of the human V2R) linking helices VI to VII.

In specific embodiments of the present invention, the V2R polypeptide comprises a V2R protein sequence or shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with an V2R protein sequence.

In some embodiments, the V2R protein sequence corresponds to a mammalian V2R protein sequence. Suitable V2R sequences may suitably be from mammal selected from the group comprising human (UniProtKB Accession No. P30518), cat (UniProtKB Accession No. M3WF07), chicken (UniProtKB Accession No. F1NV74), chimpanzee (UniProtKB Accession No. H2RCC1), cow (UniProtKB Accession No. P48044), dog (UniProtKB Accession No. O77808), horse (UniProtKB Accession No. F6UX08), mouse (UniProtKB Accession No. O88721), pig (UniProtKB Accession No. P32307), rat (UniProtKB Accession No. Q00788), sheep (UniProtKB Accession No. W5NTL0), turkey (UniProtKB Accession No. G1NA17), turtle (UniProtKB Accession No. K7FJ45).

In some preferred embodiments, the V2R protein sequence corresponds to a human V2R protein sequence. In some embodiments, the V2R polypeptide comprises a human full-length wild-type V2R protein sequence (UniProtKB Accession No. P30518), as set forth below, or a functional fragment of the wild-type V2R protein sequence.

[SEQ ID NO: 58]
MLMASTTSAVPGHPSLPSLPSNSSQERPLDTRDPLLARAELALLSIV

FVAVALSNGLVLAALARRGRRGHWAPIHVFIGHLCLADLAVALFQVL

PQLAWKATDRFRGPDALCRAVKYLQMVGMYASSYMILAMTLDRHRAI

CRPMLAYRHGSGAHWNRPVLVAWAFSLLLSLPQLFIFAQRNVEGGSG

VTDCWACFAEPWGRRTYVTWIALMVFVAPTLGIAACQVLIFREIHAS

LVPGPSERPGGRRRGRRTGSPGEGAHVSAAVAKTVRMTLVIVVVYVL

-continued

CWAPFFLVQLWAAWDPEAPLEGAPFVLLMLLASLNSCTNPWIYASFS

SSVSSELRSLLCCARGRTPPSLGPQDESCTTASSSLAKDTSS.

In one form of the invention, the V2R polypeptide comprises a truncated form of a mammalian wild-type V2R protein sequence. For example, the V2R polypeptide sequence may comprise the human wild-type V2R protein sequence with a C-terminal truncation (e.g., amino acid residues 342-371 may be truncated). Alternatively or in addition, the V2R polypeptide sequence may comprise the wild-type V2R protein sequence with a N-terminal truncation. Alternatively or in addition to a C-terminal or N-terminal truncation, a truncation may be performed to remove an internal section of the wild-type V2R protein sequence (e.g., amino acid residues 187-191 may be truncated). By way of a non-limiting illustrative example, a V2R polypeptide suitable for using with the present invention comprised amino acid residues 2-186 and 192-341 of the human wild-type V2R protein sequence as set forth in SEQ ID NO: 58.

3.88 Constructs and Nucleotide Sequences Encoding V2R Polypeptides.

The present invention also encompasses isolated polynucleotide sequences and constructs encoding V2R polypeptides as broadly described above and elsewhere herein. Also contemplated are host cells comprising those polynucleotide sequences or constructs.

In some embodiments, the polynucleotide sequences comprise a sequence that corresponds to a human V2R nucleotide (i.e., corresponding to the AVPR2 gene) sequence as set forth for example in GenBank Accession Nos. NM_000054.4, NM_001146151.1, NR_027419.1, U04357.1, NG_008687.1, BC112181.1 and BC101484.1. In representative examples of this type, the polynucleotide comprises an V2R nucleotide sequence that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity with any one of these sequences.

In some embodiments, an V2R polynucleotide coding sequence comprises a nucleotide sequence that encodes a polypeptide having at least 50%, 55%, 60%, 65%, 70%, 75%, 80%, 85%, 90%, 92%, 95%, 99% or 100% sequence identity to a wild type mammalian V2R polynucleotide, or a fragment thereof. In some embodiments, the V2R polynucleotide comprises a nucleotide sequence that hybridises to an open reading frame for a wild type mammalian V2R protein, or a fragment thereof under low, medium or high stringency conditions.

4. Cells Expressing a Certain Co-Located GPCR and/or RAGE

Nucleic acid molecules (preferably in the form of constructs including vectors) encoding a certain co-located GPCR, such as an angiotensin receptor, such as $AT_1R$ or a certain chemokine receptor, such as CCR2, and/or RAGE can be transiently or stably transfected or co-transfected into a host cell, suitably any cell line, including stable cell lines. In preferred embodiments, the cell line is a mammalian-derived cell line. Preferred cell lines are those derived from the same organism as from which RAGE and the certain co-located GPCR are derived. Thus, the cell line used can be optimised for each specific purpose, for example, if the polynucleotides to be expressed in said cells encode human protein (or a polypeptide that is derived from a human protein), then a cell line that is derived from human cells will likely be the most suitable. However, this does not exclude using polypeptides and cells that are derived from different organisms. An example is expressing rat or mouse-derived polypeptides on the surface of a human-derived cell. Another example is expressing rat or human-derived polypeptides on the surface of a hamster-derived cell, such as a Chinese hamster ovary (CHO) cell.

One example of a human-derived cell line that is suitable for performing the present invention is a HEK293 cell line (e.g., a HEK293 cell line, or a HEK293FT cell line). Other examples of suitable cell lines include but are not limited to a COS-1 cell line, or a COS-7 cell line, or a CHO cell line, or a HeLa cell line.

Accordingly, the cells of the present invention express RAGE and a certain co-located GPCR, such as an angiotensin receptor, such as $AT_1R$ or a certain chemokine receptor, such as CCR2.

5. Candidate Agents

In certain aspects, the present invention provides methods of screening for agents that modulate signalling in a cell resulting from RAGE ligand-independent activation of RAGE by certain co-located activated GPCRs, including $AT_1R$ and CCR2. The agents can bind to one or both of the certain co-located activated GPCR and RAGE and/or proteins complexed with either, provided that they modulate (e.g., inhibit or signal) RAGE ligand-independent activation of RAGE by the certain co-located activated GPCR. Representative agents can bind to any domain of the certain co-located activated GPCR and RAGE or other proteins complexed with RAGE and/or the certain co-located activated GPCR other than the ectodomain of RAGE. Without wishing to be bound by any one theory or mode of operation, the inventors hypothesise that the site mediating RAGE ligand-independent activation of RAGE by the certain co-located activated GPCR is present on the cytoplasmic (cytosolic) side of the membrane. As such, in some embodiments the candidate agents screened are determined as being cell penetrable (i.e., able to transport through the plasma membrane) or are modified to be cell penetrable. In one embodiment, the cells of the present invention express a RAGE polypeptide lacking the ectodomain and a certain co-located activated GPCR. In another embodiment, the cells of the present invention express the cytosolic tail of RAGE, or a fragment thereof, and a certain co-located activated GPCR. In another embodiment, the cells of the present invention express a certain co-located activated GPCR but do not express endogenous RAGE.

Any known type of screening assay is contemplated as being suitable to identify candidate agents as being modulators of RAGE ligand-independent activation of RAGE by the certain co-located activated GPCR. In one embodiment, a proximity screening assay is used. One example of a proximity screening assay to run is a bioluminescence resonance energy transfer (BRET) assay to investigate a change in proximity between the certain co-located activated GPCR and RAGE. In some embodiments, a screening assay using soluble recombinant polypeptides and performed in vitro is envisaged. Examples of such screening assays are conventional two-hybrid, surface plasmon resonance (SPR) or complementation systems. In another embodiment, a binding assay is utilised, for example using a fluorescently-labelled peptide or other agent that binds to the certain co-located activated GPCR and/or RAGE. This may or may not be used with NanoLuc conjugated to the certain co-located activated GPCR or RAGE in order to utilise BRET (Stoddart et al., 2015). The fusion of NanoLuc to the certain co-located activated GPCR or RAGE may occur at the N-terminus, at the C-terminus, or at another suitable site within the certain co-located activated GPCR or RAGE polypeptide.

Immunoassays can also be used to analyse specific binding and include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al., eds., 1994, Current Protocols in Molecular Biology, Vol. 1, John Wiley & Sons, Inc., New York, which is incorporated by reference herein in its entirety). In some embodiments, a RAGE polypeptide is assayed for binding to a certain co-located GPCR, such as an angiotensin receptor such as $AT_1R$ or a certain chemokine receptor such as CCR2, using ELISA. In illustrative examples of this type, either a recombinant RAGE polypeptide or a recombinant certain co-located GPCR polypeptide together with a candidate agent is contacted to a microtitre plate whose bottom surface has been coated with the other binding partner, e.g., a limiting amount of the target. The plate is washed with buffer to remove non-specifically bound polypeptide and excess candidate agent. Then the amount of the RAGE polypeptide or the certain co-located GPCR polypeptide that is bound to the target on the plate is determined by probing the plate with an antibody that can recognize the RAGE polypeptide or the certain co-located GPCR polypeptide, e.g., a tag or constant portion of the polypeptide. The antibody is linked to a detection system (e.g., an enzyme such as alkaline phosphatase or horse radish peroxidase (HRP) which produces a colorimetric product when appropriate substrates are provided).

In other embodiments, the ability of a candidate agent to modulate the binding of a RAGE polypeptide to a certain co-located GPCR polypeptide is analysed using a homogenous assay, i.e., after all components of the assay are added, additional fluid manipulations are not required. For example, fluorescence resonance energy transfer (FRET) can be used as a homogenous assay (see, e.g., U.S. Pat. Nos. 5,631,169; and 4,868,103). A fluorophore label on the first molecule (e.g., the RAGE polypeptide) is selected such that resonance energy can be absorbed by a fluorescent acceptor on a second molecule (e.g., the certain co-located GPCR polypeptide) if the RAGE polypeptide is in proximity to the certain co-located GPCR polypeptide. The fluorescent acceptor on the certain co-located GPCR polypeptide fluoresces when it absorbs the transferred energy. Since the efficiency of energy transfer between the labels is related to the distance separating the molecules, the spatial relationship between the molecules can be assessed. In a situation in which the polypeptides are proximal, the fluorescence emission of the fluorescent acceptor in the assay should be detectable. The FRET can be conveniently measured through standard fluorometric detection means, e.g., using a fluorimeter.

In other embodiments, interaction between a RAGE polypeptide and a certain co-located GPCR polypeptide is analysed using Surface Plasmon Resonance (SPR). SPR or Biomolecular Interaction Analysis (BIA) detects biospecific interactions in real time, without labelling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which is measured as an indication of real-time reactions between biological molecules. Methods for using SPR are described, for example, in U.S. Pat. No. 5,641,640; Raether, 1988; Sjolander and Urbaniczky (1991), Szabo et al. (1995) and on-line resources provide by BIAcore International AB (Uppsala, Sweden).

Upon identification of a candidate agent's ability to modulate an interaction between a RAGE polypeptide and a certain co-located activated GPCR, such as angiotensin receptor such as $AT_1R$ or certain chemokine receptor such as CCR2, toxicity and/or efficacy of the candidate agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in mammals, including humans. The dosage of such agents lies suitably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, desirably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g. by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification or amidification, to produce structural analogues.

Screening may also be directed to known pharmacologically active compounds and chemical analogues thereof.

Compounds may be further tested in the animal models to identify those compounds having the most potent in vivo effects. These molecules may serve as "lead compounds" for the further development of pharmaceuticals by, for example, subjecting the compounds to sequential modifications, molecular modelling, and other routine procedures employed in rational drug design.

5.1 Fragments, Analogues and Derivatives of RAGE Polypeptide

In some embodiments the candidate agent is a fragment of the cytosolic tail of RAGE, wherein the candidate agent comprises a fragment of a RAGE polypeptide or DNA coding for a RAGE polypeptide from which the fragment is subsequently generated following gene delivery. Suitably, the candidate agent is a peptide that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with, or differs at no more than 1, 2, 3, 5 or even 10, 15 or 20 amino acid residues from, a fragment of the cytosolic tail of RAGE polypeptide sequence. As described above, in some embodiments of the invention the RAGE fragment amino acid sequence corresponds to the cytosolic tail of of the wild-type RAGE polypeptide (for example, amino acid residues 362 to 404 of the wild-type RAGE protein (SEQ ID NO: 1 or a fragment thereof).

In some preferred examples, the fragment corresponds to the C terminal cytosolic tail of a wild-type RAGE protein (i.e., amino acid residues 362 to 404 of the amino acid sequence set forth in SEQ ID NO: 1). The peptide analogue may also comprise additional amino acid residues at its N-terminal or C-terminal end, or derivative thereof. Similarly, the analogue may comprise any 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid fragment of the C-terminal cytosolic tail of a wild-type RAGE protein, or derivative thereof.

As such, the peptide may comprise the following amino acid sequence: [SEQ ID NO: 1].

Alternatively, the analogue can share at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with, or differs at no more than 1, 2, 3, 5 or even 10 amino acid residues from, the sequence set forth in SEQ ID NO: 1.

In some embodiments the candidate agent is an activator, an inhibitor, an allosteric modulator, or a non-functional substitute for the transmembrane domain of RAGE or part thereof, wherein the candidate agent comprises a fragment of a RAGE polypeptide or DNA coding for a RAGE polypeptide from which the fragment is subsequently generated following gene delivery. Suitably, the candidate agent is a peptide that shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with, or differs at no more than 1, 2, 3, 5 or even 10, 15 or 20 amino acid residues from, a fragment of the RAGE polypeptide sequence that comprises the transmembrane domain of RAGE or a fragment thereof. A non-functional substitute is a candidate agent that takes the place of the transmembrane domain of RAGE in the presence of certain co-located GPCRs, is not able to be activated by them or induce downstream RAGE-dependent signalling, and inhibits signalling that normally occurs through activation of the cytosolic tail of RAGE and RAGE-dependent signalling resulting therefrom. In some embodiments, the candidate agent comprises a transmembrane domain of RAGE or a part thereof and a fragment of the RAGE ectodomain. In some embodiments, the candidate agent comprises a transmembrane domain of RAGE or a part thereof and a fragment of the cytosolic tail of RAGE. In some embodiments, the candidate agent comprises a transmembrane domain of RAGE or part thereof and a fragment of the RAGE ectodomain and/or a fragment of the cytosolic tail of RAGE.

In some embodiments, the analogue amino acid sequence is distinguished from a wild-type RAGE polypeptide sequence by the substitution, addition or deletion of at least one (e.g., at least 1, 2, 3, 4, 5, 6, 7, 8, 9, 10) amino acid residues, which results in modulation of activation of the cytosolic tail of RAGE by a certain activated co-located GPCR such as an angiotensin receptor such as $AT_1R$ or a certain chemokine receptor such as CCR2.

In some embodiments, the peptide, analogue, fragment or derivative thereof suitably inhibits signalling resulting from a cognate ligand activating the certain co-located GPCR.

Thus, in some embodiments the peptide, analogue, fragment, or derivative thereof corresponds to a RAGE polypeptide sequence with an impaired certain activated co-located GPCR-binding site. The at least one amino acid substitution, addition or deletion is suitably located at any position corresponding to a key residue in the interaction between RAGE and the certain activated co-located GPCR such as an angiotensin receptor such as $AT_1R$ or a certain chemokine receptor such as CCR2. In illustrative examples of this type, the peptide analogue amino acid sequence is distinguished from the wild-type RAGE polypeptide sequence by a substitution, addition or deletion at amino acid residue position S391 of the cytosolic tail of wild-type RAGE protein (as set forth in SEQ ID NO: 1) with another amino acid residue.

In some embodiments, the peptide, analogue, fragment or derivative thereof corresponds to a RAGE polypeptide sequence with an impaired site at which the certain activated co-located GPCR exerts its functional interaction. The at least one amino acid substitution, addition or deletion is suitably located at any position corresponding to a key residue in the functional interaction between RAGE and the certain activated co-located GPCR such as an angiotensin receptor such as $AT_1R$ or a certain chemokine receptor such as CCR2.

The residue at amino acid position 391 is a site that the present inventors determined to be important in the RAGE ligand-independent activation of RAGE by a certain activated co-located GPCR, such as $AT_1R$ and CCR2. Suitably, in these embodiments, the serine 391 is removed or substituted with another amino acid (such as alanine, aspartate, phenylalanine, histidine, lysine, arginine, tyrosine, asparagine, valine, glycine, cysteine or glutamate) in order to inhibit activation of the cytosolic tail of RAGE. In other embodiments, the serine 391 is retained or substituted with another amino acid (such as proline, glutamine, leucine, isoleucine methionine, threonine or tryptophan), in order for it to be activated following activation of a certain co-located GPCR, and thereby induce RAGE-dependent signalling, with or without requiring the expression of wild type RAGE. Without wishing to be bound by theory, the inventors believe the substitution or removal of S391 influences the conformation of the alpha-helical coil (e.g. $RAGE_{379-390}$) proximal to this residue (i.e. $RAGE_{379-390}$) and/or its affinity for binding partners.

In other examples of this type, the peptide, analogue, fragment or derivative thereof is distinguished from the wild-type RAGE polypeptide sequence by a substitution, addition or deletion of any amino acid that is critical to the conformation of the alpha helix proximal to the S391 site (e.g., an amino acid directly adjacent to amino acid position S391). For example, the glutamine residue at amino acid position 390 of the wild-type RAGE protein sequence may, when substituted with a polar amino acid (e.g., arginine or lysine), enhance the capping of the alpha helix at its C-terminus [e.g. SEQ ID NO: 9 & 10]. Such substitutions result in a peptide that is an inhibitor of RAGE ligand-independent activation of RAGE by certain activated co-located GPCR such as an angiotensin receptor such as $AT_1R$ or a certain chemokine receptor such as CCR2.

Alternatively, the peptide, analogue, fragment or derivative thereof shares at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity or similarity with, or differs at no more than 1, 2, 3, 5 or even 10 amino acid residues from, the sequence set forth in SEQ ID NO: 5. Any truncations of the above peptide, analogue, fragment or derivative thereof, at either or both of the C-terminal or N terminal end, are also contemplated. Thus fragments comprising 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acids, from the sequence set forth in SEQ ID NO: 5 are suitable as peptides, analogues, fragments or derivatives thereof, providing they comprise a substitution or deletion corresponding to position Ser391 of the wild-type RAGE amino acid sequence of the cytosolic tail (as set forth in SEQ ID NO: 1).

In some embodiments, the RAGE peptide mimetics of the present invention are conjugated, fused or otherwise linked to a natural or synthetic protein transduction domain or mimetic or placed in a non-covalent carrier system (e.g. liposomes, PEP-1), which suitably targets the RAGE peptides into the intracellular component of a cell, and are well known in the art. Non-limiting examples of such molecules include fusions with the natural cell membrane penetrating peptides, including the HIV-TAT motif (SEQ ID NO:4: YGRKKRRQRRR, as reviewed in Schwarze et al., 2000), as well natural and/or synthetic cell membrane penetrating peptides such as those described for example in U.S. Pat. Appl. Nos. 2014/0213775, 2014/0141452, and 2013/0136742, which are incorporated herein by reference in their entirety.

6. Proximity Screening Assays

In certain embodiments, the screening method assesses whether a candidate agent can modulate the interaction between a RAGE polypeptide and a certain activated co-located GPCR such as an angiotensin receptor such as $AT_1R$ or a certain chemokine receptor such as CCR2 by assessing a change in proximity of the RAGE polypeptide to the AT$_1$R certain activated co-located GPCR. In illustrative examples of this type, the RAGE polypeptide is coupled (e.g., conjugated, fused or otherwise linked) to a first reporter component and the certain activated co-located GPCR is coupled (e.g., conjugated or otherwise linked) to a second reporter component. The first and second reporter components can be the same or different. For example, one reporter component may be a proximity signal or energy donor, and the other may be a proximity signal or energy acceptor. The first and second reporter components can be any known molecules (e.g., an organic molecule, an inorganic molecule, a proteinaceous molecule, a non-proteinaceous molecule, or a combination thereof) that are capable of emitting a detectable signal when in close proximity.

Screening assays suitable for assessing the proximity of interacting polypeptides are well established in the art, and any format of such assays is suitable for the methods of the present invention as described above and elsewhere herein. For example, U.S. Pat. No. 8,283,127 describes one such suitable system for the detection of molecular associations, the contents of which is incorporated herein by reference in its entirety.

By way of a generic example, to determine whether a candidate agent is capable of modulating the interaction between a RAGE polypeptide and a certain activated co-located GPCR such as an angiotensin receptor such as AT$_1$R or a certain chemokine receptor such as CCR2, each of the three components (i.e., (i) the RAGE polypeptide coupled to the first reporter component, (ii) the certain activated co-located GPCR coupled to a second reporter component, and (iii) the candidate agent) are provided to the assay system. The proximity signal from the first and second reporter components is observed and compared to a reference proximity signal that is emitted from the interacting RAGE and certain activated co-located GPCR in the absence of a candidate agent (i.e. the proximity signal emitted by the first and second reporter components when the RAGE polypeptide and the certain activated co-located GPCR such as an angiotensin receptor such as AT$_1$R or a certain chemokine receptor such as CCR2 are free to interact). When the candidate agent does not modulate the interaction between a RAGE polypeptide and a certain activated co-located GPCR, no change to the reference proximity signal is observed. However, when the candidate agent is capable of modulating the interaction between a RAGE polypeptide and a certain activated co-located GPCR, a change to the proximity signal emitted from the first and second reporter components is observed upon the presence of the candidate agent to the assay system. Typically, a decrease in the proximity signal when compared to the reference proximity signal is indicative of the candidate agent antagonising or otherwise inhibiting the interaction between a RAGE polypeptide and a certain activated co-located GPCR such as an angiotensin receptor such as AT$_1$R or a certain chemokine receptor such as CCR2. Conversely, an increase in proximity signal when compared to the reference proximity signal is generally indicative of the candidate agent agonising or otherwise stimulating the interaction between a RAGE polypeptide and a certain activated co-located GPCR. Representative reporter components are suitably selected from bioluminescent donor molecules, and fluorescent acceptor molecules. In some illustrative embodiments, the bioluminescent donor molecules and the fluorescent acceptor molecules are proteins.

The coupling of the certain activated co-located GPCR such as an angiotensin receptor such as AT$_1$R or certain chemokine receptor such as CCR2 and/or the RAGE polypeptide to a reporter component can be by direct or indirect coupling and may be by any known covalent or non-covalent means of coupling two molecules. Illustrative examples of coupling methods include chemical cross-linking, chemical modification of proteins, chemical modification of amino acids, chemical modification of nucleic acids, chemical modification of carbohydrates, chemical modification of lipids, chemical modification of any other organic or inorganic molecule, biotin-avidin interactions, antigen-antibody interaction and nucleic acid hybridisation. In some forms of the invention, the first and/or second reporter component is coupled indirectly to the RAGE and/or certain activated co-located GPCR such as an angiotensin receptor such as AT$_1$R or a certain chemokine receptor such as CCR2 by a linker. In some embodiments, the linker comprises an enzyme cleavage site.

Alternatively, the RAGE polypeptide and/or certain activated co-located GPCR such as an angiotensin receptor such as AT$_1$R or certain chemokine receptor such as CCR2 may be directly coupled to a proteinaceous reporter component. Approaches for directly conjugating proteinaceous molecules are well established in the art, for example, by genetic fusion, wherein nucleic acids encoding the RAGE polypeptide and/or certain activated co-located GPCR and the first and/or second reporter components are fused to produce a nucleic acid that encodes a single polypeptide.

In a particularly preferred embodiment of the invention, the RAGE polypeptide and/or certain activated co-located GPCR such as an angiotensin receptor such as AT$_1$R or certain chemokine receptor such as CCR2 and the first and/or second reporter components each respectively form part of single polypeptides. Additional functionality may form part of the same polypeptide. For example, the RAGE and/or certain activated co-located GPCR and the first and/or second reporter components respectively form part of a single polypeptide that additionally comprises any one or more of: an amino acid sequence for affinity purification; a amino acid sequence that directs the polypeptide to a subcellular compartment of a eukaryotic cell; an amino acid sequence that facilitates the penetration of a eukaryotic cell membrane; and an amino acid sequence enabling expression levels to be assessed by the use of antibodies or otherwise.

In some embodiments, the screening assay employs energy donor and energy acceptor molecules for assessing interaction between the certain activated co-located GPCR such as an angiotensin receptor such as AT$_1$R or a certain chemokine receptor such as CCR2 and RAGE polypeptides. The principle of energy transfer between two molecules can be exploited as a means to provide information about relative changes in their proximity and orientation to one another. Resonance Energy Transfer (RET) is the transfer of excited state energy from a donor to an acceptor molecule. Förster or fluorescence resonance energy transfer (FRET) is a distance-dependent interaction between the electronic excited states of two dye molecules in which excitation is transferred from a donor molecule to an acceptor molecule without emission of a photon. This can only occur if the absorption spectrum of the acceptor molecule overlaps with the emission spectrum of the donor. Förster determined that the degree of resonance energy transfer between the energy donor and energy acceptor is inversely proportional to the distance between the two molecules to the sixth power. In the case of FRET, an external light source of specific wavelength is used to excite the donor molecule.

Bioluminescence Resonance Energy Transfer (BRET) is described in Pfleger and Eidne (2006), U.S. Pat. No. 8,283, 127, Jaeger et al., 2014 and Stoddart et al. 2015. Luciferases that have been used in BRET include those from the firefly, *Renilla reniformis* and *Gaussia princeps*, as well as NanoLuc luciferase (Promega).

In specific embodiments, the screening assay uses a BRET technique or assay. In order to perform the BRET screening, three components are required: a bioluminescent donor, a modulator and a fluorescent acceptor. The fluorescent acceptor can accept energy from the bioluminescent donor and will generate luminescence when these components are in an appropriate special relationship and in the presence of the appropriate substrate (bioluminescence initiating compound). The modulator can either influence the proximity and/or orientation of the bioluminescent donor and the fluorescent acceptor and thereby modulate the energy transfer between the components, or it can play a different role in affecting the energy transfer between the bioluminescent donor-generated luminescence and the fluorescent acceptor.

One advantage of the BRET technique is that protein-protein interactions in living cells can be monitored and/or determined in real time following activation with ligands.

In some embodiments a certain activated co-located GPCR (such as an angiotensin receptor such as $AT_1R$ or a certain chemokine receptor such as CCR2) or a RAGE polypeptide is fused or otherwise linked to a bioluminescent donor. In some embodiments a certain activated co-located GPCR or a RAGE polypeptide is fused or otherwise linked to a fluorescent acceptor. For example, in one embodiment a certain activated co-located GPCR is fused or otherwise linked to a bioluminescent donor and a RAGE polypeptide is fused or otherwise linked to a fluorescent acceptor.

6.1 Bioluminescent Donors

As mentioned above, the bioluminescent donor includes, but is not limited to, a first target protein (a RAGE polypeptide or a certain activated co-located GPCR, such as an angiotensin receptor such as $AT_1R$ or a certain chemokine receptor such as CCR2) and a bioluminescent donor molecule. The bioluminescent donor molecule can include, but is not limited to, *Renilla* luciferases and fragments thereof; polypeptide variants of *Renilla* luciferase; and the like. In particular, the bioluminescent donor molecule can include, but is not limited to, any of the following *Renilla* luciferase protein sequences:

```
Wild-type Renilla luciferase:
                                    [SEQ ID NO: 59]
MTSKVYDPEQRKRMITGPQWWARCKQMNVLDSFINYYDSEKHAENAV

IFLHGNAASSYLWRHVVPHIEPVARCIIPDLIGMGKSGKSGNGSYRL

LDHYKYLTAWFELLNLPKKIIFVGHDWGACLAFHYSYEHQDKIKAIV

HAESVVDVIESWDEWPDIEEDIALIKSEEGEKMVLENNFFVETMLPS

KIMRKLEPEEFAAYLEPFKEKGEVRRPTLSWPREIPLVKGGKPDVVQ

IVRNYNAYLRASDDLPKMFIESDPGFFSNAIVEGAKKFPNTEFVKVK

GLHFSQEDAPDEMGKYIKSFVERVLKNEQ.

Cys124Ala/Met185Val variant Renilla luciferase:
                                    [SEQ ID NO: 60]
MTSKVYDPEQRKRMITGPQWWARCKQMNVLDSFINYYDSEKHAENAV

IFLHGNAASSYLWRHVVPHIEPVARCIIPDLIGMGKSGKSGNGSYRL

LDHYKYLTAWFELLNLPKKIIFVGHDWGAALAFHYSYEHQDKIKAIV

HAESVVDVIESWDEWPDIEEDIALIKSEEGEKMVLENNFFVETVLPS
```

```
-continued
KIMRKLEPEEFAAYLEPFKEKGEVRRPTLSWPREIPLVKGGKPDVVQ

IVRNYNAYLRASDDLPKMFIESDPGFFSNAIVEGAKKFPNTEFVKVK

GLHFSQEDAPDEMGKYIKSFVERVLKNEQ.

RLuc8 variant Renilla luciferase:
                                    [SEQ ID NO: 61]
MASKVYDPEQRKRMITGPQWWARCKQMNVLDSFINYYDSEKHAENAV

IFLHGNATSSYLWRHVVPHIEPVARCIIPDLIGMGKSGKSGNGSYRL

LDHYKYLTAWFELLNLPKKIIFVGHDWGAALAFHYAYEHQDRIKAIV

HMESVVDVIESWDEWPDIEEDIALIKSEEGEKMVLENNFFVETVLPS

KIMRKLEPEEFAAYLEPFKEKGEVRRPTLSWPREIPLVKGGKPDVVQ

IVRNYNAYLRASDDLPKLFIESDPGFFSNAIVEGAKKFPNTEFVKVK

GLHFLQEDAPDEMGKYIKSFVERVLKNEQ.
```

Other suitable bioluminescent donor molecules include, but are not limited to, other luciferases or photo-proteins such as NanoLuc luciferase (Promega), Coleoptera luciferase, firefly (*Photinus pyralis*) luciferase (fLuc), *Gaussia* luciferase, *Anachnocampa* sp luciferase, click beetle red luciferase and aequorin photoprotein. Alternative, non-luciferase, bioluminescent donor molecules that can be employed in this invention are any enzymes which can act on suitable substrates to generate a luminescent signal. Specific examples of such enzymes are β-galactosidase, lactamase, horseradish peroxidase, alkaline phophatase, β-glucuronidase and β-glucosidase. Synthetic luminescent substrates for these enzymes are well known in the art and are commercially available from companies, such as Tropix Inc. (Bedford, Mass., USA).

In a preferred embodiment, a bioluminescent donor molecule with a small molecular weight is used to prevent or minimise an inhibition of the interaction due to steric hindrance. The bioluminescent donor preferably consists of a single polypeptide chain. Also the bioluminescent proteins preferably do not form oligomers or aggregates. The bioluminescent donor molecules *Renilla* luciferase, *Gaussia* luciferase, Firefly luciferase and NanoLuc meet all or most of these criteria. In some preferred embodiments, the bioluminescent donor comprises a certain activated co-located GPCR (such as an angiotensin receptor such as $AT_1R$ or a certain chemokine receptor such as CCR2), as broadly defined above.

In some embodiments, the bioluminescent donor comprises a luciferase variant. The luciferase variants retain luciferase activity (i.e., catalyse the conversion of a coelenterazine substrate into a luminescent product in the presence of molecular oxygen). The luciferase variants may have at least one of the following properties relative to their corresponding reference wild-type protein: modulated stability; enhanced light output; modulated emission wavelength maximum; and modulated substrate utilization. In certain embodiments, the luciferase variants suitable for the present invention include two or more of the above properties (e.g., modulated stability and enhanced brightness, enhanced light output and modulated emission maximum, modulated stability and modulated emission maximum, and the like), or include three or more of the above properties (e.g., modulated stability, enhanced light output and modulated emission maximum).

As mentioned above, one such variant *Renilla* luciferase protein that is specifically contemplated includes, but is not limited to, eight amino acid substitutions in comparison to the wild-type amino acid sequence (SEQ ID NO: 61). These amino acid substitutions include Ala55Thr, Cys124Ala, Ser130Ala, Lys136Arg, Ala143Met, Met185Val, Met253Leu, and Ser287Leu. In addition, variant *Renilla* luciferase proteins can include one or more additional conservative substitution as long as the conservatively modified variant retains the characteristics of the mutated *Renilla* luciferase protein.

6.2 the Bioluminescent Donor Encoding Vector

In some embodiments, a vector encoding the bioluminescent donor can include, but is not limited to, polynucleotides that encode the bioluminescent donor (e.g., encoding a certain activated co-located GPCR such as an angiotensin receptor such as $AT_1R$ or a certain chemokine receptor such as CCR2 fused or otherwise linked to RLuc8). Methods of producing vectors (e.g., viral and non-viral) and polynucleotides are well known in the art. It should be noted that the bioluminescent donors can be expressed using other expression systems and the bioluminescent donor vector is merely an illustrative embodiment.

6.3 Fluorescent Acceptors

As mentioned above, the fluorescent acceptor includes, but is not limited to, a second target protein, wherein the second target protein consists of either a RAGE polypeptide or a certain activated co-located GPCR such as an angiotensin receptor such as $AT_1R$ or a certain chemokine receptor such as CCR2, and a fluorescent acceptor molecule. In general, fluorophores absorb electromagnetic and/or resonance energy at one wavelength and emit electromagnetic energy at a second wavelength. In some preferred embodiments, the fluorescent acceptor comprises a RAGE polypeptide, as broadly defined above and elsewhere herein.

Representative fluorescent acceptor molecules (i.e., fluorophores) can include, but are not limited to, sgGFP, sgBFP, blue-shifted GFP (Y66H), Blue Fluorescent Protein (BFP), Cyan Fluorescent Protein (CFP), Cyan GFP, DsRed, DsRed2, monomeric RFP, enhanced BFP (EBFP), enhanced CFP (ECFP), enhanced GFP (EGFP), destabilised EGFP, destabilised ECFP, destabilised EYFP, GFP (S65T), red-shifted GFP (rsGFP), wild-type GFP (GFP), GFPuv, HcRed, t-HcRed, rsGFP, Sapphire GFP, sgBFP™, sgBFP™ (super glow BFP), sgGFP™, sgGFP™ (super glow GFP), wild-type GFP, yellow variant GFP, YFP, Venus, Emerald, Topaz, Citrine, YPet, t-dimer2, t dimer2(12), mRFP1, pocilloporin, *Renilla* GFP, Monster GFP, paGFP, and Kaede protein. Favourably, Venus contains an amino acid substitution compared to the YFP sequence, which accelerates the oxidation of the chromophore at 37° C., the rate limiting step of maturation. Venus also has other substitutions (e.g., F63L, M153T, V163A, and S175G) that permit the fluorophore to fold well and improves the protein's tolerance to acidosis and Cl⁻.

Other representative fluorescent acceptor molecules (i.e., fluorophores) can include, but are not limited to: Alexa Fluor derivatives, BODIPY derivatives, and those referenced in U.S. Pat. No. 8,283,127, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxy-acridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs-AutoFluorescent Protein-(Quantum Biotechnologies); ALEXA FLUOR 350™; ALEXA FLUOR 430™; ALEXA FLUOR 488™; ALEXA FLUOR 532™; ALEXA FLUOR 546™; ALEXA FLUOR 568™; ALEXA FLUOR 594™; ALEXA FLUOR 633™; ALEXA FLUOR 647™; ALEXA FLUOR 660™; ALEXA FLUOR 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; BlancophorSV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; CALCIUM CRIMSON™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5TH; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DID-Lipophilic Tracer; DID (DiIC18(5)); DIDS; Dihydrorhodamine 123 (DHR); DiI (DiIC18(3)); Dinitrophenol; DiO (DiOC18(3)); DIR; DİR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DIR); Intrawhite Cf; JC-1; JO-JO-1; JO-PRO-1; LaserPro; Laurodan; LDS 751 (DNA); LDS 751

(RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium lodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); TEXAS RED™; TEXAS RED-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl-RodaminelsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

The fluorescent acceptor molecule may be a fluorophore conjugated to a molecule that enables attachment another molecule. An example of a molecule that enables attachment to another molecule is HaloTag. Examples of fluorophores that may or may not be used attached to HaloTag and may or may not be described as HaloTag ligands as a result are Oregon Green, tetramethylrhodamine (TMR) and nonchloro TOM (NCT).

6.4 Fluorescent Acceptor Vectors

The fluorescent acceptor vector can include, but is not limited to, a polynucleotide that encodes the fluorescent acceptor fusion protein (for example, a RAGE polypeptide and the green fluorescent protein variant, Venus) and degenerate nucleotide sequences thereof. Methods of producing polynucleotides and vectors (e.g., viral and non-viral) are well known in the art. It should be noted that the fluorescent fusion protein can be expressed using other expression systems and the fluorescent vector is merely an illustrative embodiment.

6.5 Bioluminescence Initiating Compound

The choice of the bioluminescence initiating compound can impact on the wavelength and the intensity of the light generated by the bioluminescent donor.

An exemplary bioluminescence initiating compound that is known to be suitable for BRET techniques is coelenterazine. Coelenterazine occurs in cnidarians, copepods, chaetgnaths, ctenophores, decapod shrimps, mysid shrimps, radiolarians and some fish taxa (Greer and Szalay, 2002). For *Renilla* luciferase and variants of *Renilla* luciferase, coelenterazine analogues and functional derivatives thereof are available that result in light emission between 418 and 512 nm (Inouye et al., 1997). Some coelenterazine analogues and functional derivatives thereof may result in light emission at wavelengths below 418 nm. Bisdeoxycoelenterazine (also known as DeepBlueC, also known as colelenterazine 400a) and derivatives thereof are examples of substrates with emission spectra that include light emission below 418 nm as well as light emission above 418 nm.

The bioluminescence initiating compound can include, but is not limited to, coelenterazine and analogues, and functional derivatives thereof. Exemplary derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine O, coelenterazine c, coelenterazine c, coelenterazine i, coelenterazine icp, coelenterazine 2-methyl, benzyl-coelenterazine bisdeoxycoelenterazine, EnduRen, ViviRen, deep blue coelenterazine (DBC; DeepBlueC) (described in more detail in U.S. Pat. Nos. 6,020,192; 5,968,750 and 5,874,304), furimazine and variants thereof.

In general, coelenterazines are known to luminesce when acted upon by a wide variety of bioluminescent proteins, specifically Luciferases. Useful, but non-limiting, coelenterazines are disclosed in U.S. patent application Ser. No. 10/053,482, the disclosure which is hereby incorporated by reference in its entirety. Coelenterazines are available from Promega Corporation (U.S.A.). and from Molecular Probes, Inc. (U.S.A.). Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

6.6 Methods of Performing the BRET Assay

As mentioned above, the present invention includes methods for determining (i.e., detecting, localizing, or quantifying) the proximity between a RAGE polypeptide and an $AT_1R$ polypeptide inside a living cell, tissue, or organ, or a living organism using the BRET system. For example, a living animal can be imaged using the BRET system to measure the proximity of a RAGE polypeptide and an $AT_1R$ polypeptide and the degree of that proximity. This approach facilitates the study of protein-protein interactions to understand fundamental cell biology and will enable the in vivo testing of candidate agents that have been identified as being a modulator of the RAGE-AT$_1$R complex.

For example, the BRET system can be used to measure and quantify the proximity between RAGE and AT$_1$R in living cells to determine the ability of candidate agents administered to modulate (i.e., increase or reduce) the proximity. Further, the BRET system can be used to measure the effects of candidate agents targeting the RAGE-AT$_1$R complex.

In some embodiments, a cell line transfected with vector constructs as described above and elsewhere herein that is developed utilizing coding regions for the RAGE polypeptides and the AT$_1$R polypeptides, followed by measurement in a suitable microplate reader or optical imaging to quantitate the proximity between RAGE and AT$_1$R in the presence and absence of candidate agents to identify whether said candidate agent modulates (i.e., stimulate or inhibit) proximity between RAGE and AT$_1$R. As will be appreciated by the skilled practitioner, this technique will significantly accelerate candidate agent validation by allowing testing in vivo.

As will be appreciated by one of skill in the art, such screening may also be done in cell culture. Preferably, the compounds screened are suitable for administering to mammals. Even more preferably, the compounds screened are suitable for administering to humans.

6.7 BRET Kits

The present invention encompasses kits which may include two or more, three or more, four or more, or all of the following: a bioluminescent donor (that comprises, for example, an AT$_1$R polypeptide fused or otherwise linked to the bioluminescent donor molecule RLuc8); a vector comprising a bioluminescent donor; a fluorescent acceptor (that comprises, for example, a RAGE polypeptide fused or otherwise linked to the fluorescent acceptor molecule Venus); a vector comprising a fluorescent acceptor; a bioluminescence initiating compound; a candidate agent; and directions (written instructions for their use). Accordingly, in some embodiments, the bioluminescent donor will comprises an AT$_1$R polypeptide and the fluorescent acceptor comprises a RAGE polypeptide. The kit can also include appropriate buffers and reagents known in the art for administering various combinations of the components listed above to a host cell or a host organism.

By way of a specific illustrative example, the kit may comprise a bioluminescent donor comprising an AT$_1$R polypeptide fused or otherwise linked to the bioluminescent donor molecule Rluc8; and a fluorescent acceptor comprising a RAGE polypeptide fused or otherwise linked to the fluorescent acceptor molecule Venus.

By way of a specific illustrative example, to perform the BRET assay the bioluminescent donor and the fluorescent acceptor are co-expressed in cells as broadly described above. The generation of a strong and saturable BRET signal indicates close proximity (for example, less than 10 nm) between the AT$_1$R polypeptide and the RAGE polypeptide, allowing energy resulting from the oxidation of a cell-permeable coelenterazine substrate by the donor to transfer to the acceptor, which in turn fluoresces at a longer characteristic wavelength. Accordingly, identification of a candidate agent as a modulator of the AT$_1$R polypeptide and the RAGE polypeptide proximity is made on the basis of a change (e.g., increase or reduction) of the BRET signal generated by a cell co-expressing labelled AT$_1$R polypeptide and labelled RAGE polypeptide, as a result of the cell being exposed to the candidate agent. Specifically, a reduction in the BRET signal generated by the cell in response to exposure to a candidate agent identifies the agent as an inhibitor of the proximity between RAGE and AT$_1$R. Conversely, an increase in the BRET signal generated by the cell in response to exposure to a candidate agent identifies the agent as an inducer of the proximity between RAGE and AT$_1$R.

7. Construct Systems

In accordance with the present invention, a construct system is provided for identifying modulators of proximity between a RAGE polypeptide and an AT$_1$R polypeptide. In one broad form, the system comprises a first synthetic construct encoding a RAGE polypeptide and an energy donor molecule (e.g., a bioluminescent donor molecule); and a second synthetic construct encoding an AT$_1$R polypeptide and an energy acceptor molecule (e.g., a fluorescent acceptor molecule). In another broad form, the system comprises a first synthetic construct encoding an AT$_1$R polypeptide and an energy donor molecule (e.g., a bioluminescent donor molecule); and a second synthetic construct encoding a RAGE polypeptide and an energy acceptor molecule (e.g., a fluorescent acceptor molecule).

The synthetic constructs of the invention each comprise a regulatory sequence that is operably connected to the bioluminescent donor coding sequence or the fluorescent acceptor coding sequence. The regulatory sequence suitably comprises transcriptional and/or translational control sequences, which will be compatible for expression in the cell or organism of interest. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the organism of interest or may be derived from an alternative source, where the region is functional in the chosen organism. The choice of promoter will differ depending on the intended host. For example, promoters which could be used for expression in plants include plant promoters such as: constitutive plant promoters examples of which include CaMV35S plant promoter, CaMV19S plant promoter, FMV34S plant promoter, sugarcane bacilliform badnavirus plant promoter, CsVMV plant promoter, *Arabidopsis* ACT2/ACT8 actin plant promoter, *Arabidopsis* ubiquitin UBQ1 plant promoter, barley leaf thionin BTH6 plant promoter, and rice actin plant promoter; tissue specific plant promoters examples of which include bean phaseolin storage protein plant promoter, DLEC plant promoter, PHS plant promoter, zein storage protein plant promoter, conglutin gamma plant promoter from soybean, AT2S1 gene plant promoter, ACT11 actin plant promoter from *Arabidopsis*, napA plant promoter from *Brassica napus* and potato patatin gene plant promoter; and inducible plant promoters examples of which include a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress. Alternatively, promoters which could be used for expression in mammals include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, adenovirus promoter, or a HPV promoter, particularly the HPV upstream regulatory region (URR) may also be used. All these promoters are well described and readily available in the art.

The synthetic constructs of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In specific embodiments, the synthetic constructs further contain a selectable marker gene to permit selection of an organism or a precursor thereof that contains a synthetic construct. Selection genes are well known in the art and will be compatible for expression in cell or organism of interest, or a progenitor or precursor thereof.

In some embodiments, the synthetic constructs of the invention are in the form of viral vectors, such as simian virus 40 (SV40) or bovine papilloma virus (BPV), which has the ability to replicate as extra-chromosomal elements (Eukaryotic Viral Vectors, Cold Spring Harbor Laboratory, Gluzman ed., 1982; Sarver et al., 1981, Mol. Cell. Biol. 1:486). Viral vectors include retroviral (lentivirus), adeno-associated virus (see, e.g., Okada, 1996, Gene Ther. 3:957-964; Muzyczka, 1994, J. Clin. Invst. 94:1351; U.S. Pat. Nos. 6,156,303; 6,143,548 5,952,221, describing AAV vectors; see also U.S. Pat. Nos. 6,004,799; 5,833,993), adenovirus (see, e.g., U.S. Pat. Nos. 6,140,087; 6,136,594; 6,133,028; 6,120,764), reovirus, herpesvirus or rotavirus genomes, modified for introducing and directing expression of a polynucleotide or transgene in cells. Retroviral vectors can include those based upon murine leukemia virus (see, e.g., U.S. Pat. No. 6,132,731), gibbon ape leukemia virus (see, e.g., U.S. Pat. No. 6,033,905), simian immuno-deficiency virus, human immuno-deficiency virus (see, e.g., U.S. Pat. No. 5,985,641), and combinations thereof.

Vectors also include those that efficiently deliver genes to animal cells in vivo (e.g., stem cells) (see, e.g., U.S. Pat. Nos. 5,821,235 and 5,786,340; Croyle et al., 1998, Gene Ther. 5:645; Croyle et al., 1998, Pharm. Res. 15:1348; Croyle et al., 1998, Hum. Gene Ther. 9:561; Foreman et al., 1998, Hum. Gene Ther. 9:1313; Wirtz et al., 1999, Gut 44:800). Adenoviral and adeno-associated viral vectors suitable for in vivo delivery are described, for example, in U.S. Pat. Nos. 5,700,470, 5,731,172 and 5,604,090. Additional vectors suitable for in vivo delivery include herpes simplex virus vectors (see, e.g., U.S. Pat. No. 5,501,979), retroviral vectors (see, e.g., U.S. Pat. Nos. 5,624,820, 5,693,508 and 5,674,703; and WO92/05266 and WO92/14829), bovine papilloma virus (BPV) vectors (see, e.g., U.S. Pat. No. 5,719,054), CMV-based vectors (see, e.g., U.S. Pat. No. 5,561,063) and parvovirus, rotavirus and Norwalk virus vectors. Lentiviral vectors are useful for infecting dividing as well as non-dividing cells (see, e.g., U.S. Pat. No. 6,013,516).

Vectors for insect cell expression commonly use recombinant variations of baculoviruses and other nucleopolyhedrovirus, e.g., *Bombyx mori* nucleopolyhedrovirus vectors (see, e.g., Choi, 2000, Arch. Virol. 145:171-177). For example, Lepidopteran and Coleopteran cells are used to replicate baculoviruses to promote expression of foreign genes carried by baculoviruses, e.g., *Spodoptera frugiperda* cells are infected with recombinant *Autographa californica* nuclear polyhedrosis viruses (AcNPV) carrying a heterologous, e.g., a human, coding sequence (see, e.g., Lee, 2000, J. Virol. 74:11873-11880; Wu, 2000, J. Biotechnol. 80:75-83). See, e.g., U.S. Pat. No. 6,143,565, describing use of the polydnavirus of the parasitic wasp Glyptapanteles indiensis to stably integrate nucleic acid into the genome of Lepidopteran and Coleopteran insect cell lines. See also, U.S. Pat. Nos. 6,130,074; 5,858,353; 5,004,687.

The invention further contemplates cells containing therein the synthetic constructs of the invention. In this regard, it will be appreciated that the construct system of the present invention is applicable to prokaryotic as well as eukaryotic host cells and includes for example unicellular organisms and cells derived from multicellular organisms, such as but not limited to yeast, plants and animals including vertebrate animals such as mammals, reptiles, fish and birds, as well as invertebrate animals such as metazoa, sponges, worms, molluscs, nematodes, crustaceans and echinoderms. In certain embodiments, the construct system is used to determine the translational efficiency of different synonymous codons in plant cells or animal cells or to determine the ability of a candidate agent to modulate proximity between a RAGE polypeptide and a $AT_1R$ polypeptide.

Illustrative examples of eukaryotic organisms include, but are not limited to, fungi such as yeast and filamentous fungi, including species of *Aspergillus, Trichoderma,* and *Neurospora*; animal hosts including vertebrate animals illustrative examples of which include fish (e.g., salmon, trout, tilapia, tuna, carp, flounder, halibut, swordfish, cod and zebrafish), birds (e.g., chickens, ducks, quail, pheasants and turkeys, and other jungle foul or game birds) and mammals (e.g., dogs, cats, horses, cows, buffalo, deer, sheep, rabbits, rodents such as mice, rats, hamsters and guinea pigs, goats, pigs, primates, marine mammals including dolphins and whales, as well as cell lines, such as human or other mammalian cell lines of any tissue or stem cell type (e.g., COS, NIH 3T3 CHO, BHK, HEK293, or Hela cells), and stem cells, including pluripotent and non-pluripotent and embryonic stem cells, and non-human zygotes), as well as invertebrate animals illustrative examples of which include nematodes (representative generae of which include those that infect animals such as but not limited to *Ancylostoma, Ascaridia, Ascaris, Bunostomum, Caenorhabditis, Capillaria, Chabertia, Cooperia, Dictyocaulus, Haemonchus, Heterakis, Nematodirus, Oesophagostomum, Ostertagia, Oxyuris, Parascaris, Strongylus, Toxascaris, Trichuris, Trichostrongylus, Tflichonema, Toxocara, Uncinaria,* and those that infect plants such as but not limited to *Bursaphalenchus, Criconerriella, Diiylenchus, Ditylenchus, Globodera, Helicotylenchus, Heterodera, Longidorus, Melodoigyne, Nacobbus, Paratylenchus, Pratylenchus,*

*Radopholus, Rotelynchus, Tylenchus,* and *Xiphinerna*) and other worms, *drosophila*, and other insects (such as from the families Apidae, Curculionidae, Scarabaeidae, Tephritidae, Tortricidae, representative orders of which include Coleoptera, Diptera, Lepidoptera, and Homoptera).

The synthetic constructs of the present invention may be introduced directly ex vivo or in cell culture into a cell of interest The synthetic constructs of the present invention may be introduced into a cell of interest using any suitable method, and the kind of method employed will differ depending on the intended cell type of interest. For example, four general classes of methods for delivering nucleic acid molecules into cells have been described: (1) chemical methods such as calcium phosphate precipitation, polyethylene glycol (PEG)-mediate precipitation and lipofection; (2) physical methods such as microinjection, electroporation, acceleration methods and vacuum infiltration; (3) vector based methods such as bacterial and viral vector-mediated transformation; and (4) receptor-mediated. Transformation techniques that fall within these and other classes are well known to workers in the art, and new techniques are continually becoming known. The particular choice of a transformation technology will be determined by its efficiency to transform certain host species as well as the experience and preference of the person practicing the invention with a particular methodology of choice. It will be apparent to the skilled person that the particular choice of a transformation system to introduce a synthetic construct of the invention into cells is not essential to or a limitation of the invention, provided it achieves an acceptable level of nucleic acid transfer. Thus, the synthetic constructs are introduced into tissues or host cells by any number of routes, including viral infection, phage infection, microinjection, electroporation, or fusion of vesicles, lipofection, infection by *Agrobacterium tumefaciens* or *A. rhizogenes*, or protoplast fusion. Jet injection may also be used for intramuscular administration (as described for example by Furth et al., 1992, Anal Biochem 205:365-368). The synthetic constructs may be coated onto microprojectiles, and delivered into a host cell or into tissue by a particle bombardment device, or "gene gun" (see, for example, Tang et al., 1992, Nature 356:152-154). Alternatively, the synthetic constructs can be fed directly to, or injected into, a host organism or it may be introduced into a cell (i.e., intracellularly) or introduced extracellularly into a cavity, interstitial space, into the circulation of an organism, or introduced orally. Methods for oral introduction include direct mixing of the synthetic constructs with food of the organism. In certain embodiments, a hydrodynamic nucleic acid administration protocol is employed (e.g., see Chang et al., 2001, J. Virol. 75:3469-3473; Liu et al., 1999, Gene Ther. 6:1258-1266; Wolff et al., 1990, Science 247: 1465-1468; Zhang et al., 1999, Hum. Gene Ther. 10:1735-1737; and Zhang et al., 1999, Gene Ther. 7:1344-1349). Other methods of nucleic acid delivery include, but are not limited to, liposome-mediated transfer, naked DNA delivery (direct injection) and receptor-mediated transfer (ligand-DNA complex).

8. Assays that Detect Downstream Signalling Mediated by Activation of RAGE

Activation of RAGE is known to trigger many intracellular signalling pathways involved in specific aspects of cellular function, depending on the specific cell type, its state and the duration of stimulation. These signalling pathways are activated through production of ROS via NADPH oxidase and activation of various kinases, including mitogen-activated protein kinases (MAPKs), such as extracellular signal-regulated kinases 1/2 (ERK1/2), stress-activated protein kinase (SAPK)/c-Jun N-terminal kinase (JNK), protein kinase C (PKC), p38-MAP kinase; Rho kinase (Rho), AMP kinase (AMPK), phosphoinositide 3 kinases/Akt (PI3K/Akt); Janus-activated kinase (JAK)/signal transducers and activators of transcription (STAT); glycogen synthase kinase 3 beta (GSK3B) (Batkulwar K B et al 2015). These kinases phosphorylate downstream signalling molecules and cause specific cellular responses often via activation of transcription factors nuclear factor kappa B (NF-κB), egr1 and specificity protein 1 (SP1), thereby modulating specific cellular processes, including inflammation, cell motility, adhesion, and structure.

The generation of ROS following the activation of RAGE can be measured by assays detecting ROS themselves (through modification of probes by ROS and detection of their adducts), measurement of modifications induced by ROS on endogenous or synthetic substrates, or the induction of signalling pathways resulting from them.

These specific downstream signals following the activation of RAGE can be measured by assays detecting the activation of these kinases (i.e. kinase activity assays), phosphorylation of synthetic or endogenous targets of kinase activity, or downstream induction of transcription factors (e.g. NFκB, AP-1, EGR-1), changes in gene expression, protein expression or changes in cellular function/phenotype resulting from them.

9. Pharmaceutical Compositions

Generally, upon identifying a candidate agent as a modulator of RAGE ligand-independent activation of RAGE by certain activated co-located GPCR such as an angiotensin receptor such as $AT_1R$ or a certain chemokine receptor such as CCR2, and thus selected as having therapeutic potential, the agents are manufactured in the form of pharmaceutical compositions that optionally comprise a pharmaceutically acceptable carrier, excipient and/or stabilizer (Remington's Pharmaceutical Sciences 16th edition, Osol, A. Ed. (1980)). These compositions are generally in the form of lyophilized formulations or aqueous solutions. Antibody crystals are also contemplated (see, U.S. Pat. Appl. 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801.

The pharmaceutical compositions contain the active compounds as necessary for the particular indication being treated, desirably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In some embodiments, and dependent on the intended mode of administration, the compositions will generally contain about 0.000001% to 90%, about 0.0001% to 50%, or about 0.01% to about 25%, by weight of the modulator, the remainder being suitable pharmaceutical carriers, diluents, or excipients. The dosage of the modulator can depend on a variety of factors, such as mode of administration, the species of the affected subject, age, sex, weight and general health condition, and can be easily determined by a person of skill in the art using standard protocols. The dosages will also take into consideration the binding affinity of the modulator to its binding partner (i.e., co-located GPCR such as $AT_1R$ and/or RAGE), its bioavailability and its in vivo and pharmacokinetic properties. In this regard, precise amounts of the agents for administration can also depend on the judgment of the practitioner. In determining the effective amount of the agents to be administered in the treatment or prevention of a cardiometabolic disease and/or condition, the physician or veterinarian may evaluate the progression of the disease or condition over time. In any event, those of skill in the art may readily determine suitable dosages of the agents of the invention without undue experimentation. The dosage of the actives administered to a patient should be sufficient to effect a beneficial response in the patient over time, and/or in the treatment and/or prevention of a cardiometabolic disease and/or condition). The dosages may be administered at suitable intervals to ameliorate the symptoms of the cardiometabolic disease and/or condition. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

For any modulator identified using the methods of the invention, the therapeutically effective dose can be estimated initially from cell culture assays. For example, a dose can be formulated in animal models to achieve a circulating concentration range that includes the IC50 as determined in cell culture (e.g., the concentration of a modulator which achieves a half-maximal inhibition of RAGE ligand-independent activation of RAGE by activated co-located GPCR such as an angiotensin receptor such as $AT_1R$ or a certain chemokine receptor such as CCR2). Such information can be used to more accurately determine useful doses in mammals, including humans.

Dosage amount and interval may be adjusted individually to provide plasma levels of the active agent, which are sufficient to maintain therapeutic effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m2/day, typically from 5-100 mg/m$^2$/day.

The modulator may be administered concurrently with at least one ancillary therapy that treats or ameliorates the symptoms or reverses or inhibits the development or progression of a cardio-metabolic disease and/or condition in a subject. The modulator may be used therapeutically after the ancillary therapy or may be used, before the therapy is administered, or together with the therapy. Accordingly, the present invention contemplates combination therapies, which employ a modulator and concurrent administration of an ancillary therapy (e.g., medical treatment), non-limiting examples of which include diuretics, beta blockers, alpha inhibitors, ACE inhibitors and angiotensin receptor blockers.

In order that the invention may be readily understood and put into practical effect, particular preferred embodiments will now be described by way of the following non-limiting examples.

EXAMPLES

In each of the following examples 1-21 independently, the following general materials and Methods apply, unless the context requires otherwise.

Animal Models

C57bl6 mice, AGER knockout (KO) mice, apoE KO mice, AGER/apoE double knockout (DKO), Ace2/apoE DKO and AGER/Ace2/apoE triple knockout (TKO) mice were sourced and generated in-house at the AMPREP animal house. All mice were bred on a C57bl6 background. For experimental studies, male mice aged 6-8 weeks and weighing between 20-25 g were used, with at least 8 animals per group for in vivo studies and n=6/group for ex vivo studies. Throughout the study animals were given access to mouse chow and water ad libitum. All experiments were approved by the animal ethics committee of the Alfred Medical Research Precinct and conducted in accordance with the Guide for the Care and Use of Laboratory Animals published by the US National Institutes of Health (NIH Publication No. 85-23, revised 1996).

Aortic Plaque Area Quantitation Method

Aortic arches were removed from mice, cleaned of excess fat, placed in 10% neutral buffered formalin and subsequently stained with Sudan IV-Herxheimer's solution (0.5% w/vol; Gurr, BDH Limited, Poole, UK). Aortae were then dissected longitudinally, and pinned flat onto a wax pad. Plaque accumulation across the aortic arch was quantitated as the percentage area stained red.

Aortic Expression of Pro-Inflammatory Mediators by Quantitative Real-Time PCR

At the end of each study period, thoracic and abdominal aortae were placed in TRIZOL, snap frozen and stored at −80° C. RNA extraction and cDNA synthesis was performed in aortic homogenates using the Trizol method. Gene expression of pro-atherogenic mediators including adhesion molecules, cytokines, inflammatory, oxidative stress and macrophage markers, were estimated in aortic homogenates by quantitative real-time RT-PCR, performed using the TaqMan system based on real-time detection of accumulated fluorescence (ABI Prism 7700, Perkin-Elmer Inc, PE Biosystems, Foster City, CA, USA). Gene expression was normalized to 18S mRNA and reported as fold change compared to the level of expression in untreated control mice/cells, which were given an arbitrary value of 1.

Induction of Oxidative Stress

The induction of oxidative stress in each animal model was estimated by the measurement of plasma levels of 8-hydroxydeoxyguanosine using the OxiSelect Oxidative DNA Damage ELISA Kit (8-OHdG Quantitation; Cell Biolabs, Inc), and performed as per manufacturer's instructions. In addition, gene expression of the superoxide-producing NADPH oxidase subunits, NOX-1 and NOX-4 were quantitated in the aortae of mice using real time RT-PCR, as detailed above.

Circulating Concentration of RAGE Ligands

Changes in circulating levels of RAGE ligands were assessed in animal models. S100A8/A9 levels were estimated by ELISA (Immundiagnostik, Germany) performed according to the manufacturer's instructions. Plasma AGEs were measured by in-house ELISA. Plasma methylglyoxal, a reactive precursor of AGEs, was measured by HPLC.

Systolic BP Measurement

Systolic blood pressure was measured by tail-cuff plethysmography in conscious, pre-warmed mice using a computerized, non-invasive, tail-cuff system (Kent Scientific, USA). Animals were habituated to the device before measuring the pressures to ensure accurate measurements.

In Vitro Studies

Cell Culture

Primary aortic endothelial cells (PMAEC) were isolated from the aortae of (wild-type) C57bl6 mice and AGER KO mice and cultured in Dulbecco's modified Eagle's medium (DMEM)/F12 endothelial cell growth supplement (ECGS) supplemented media. Chinese Hamster Ovary (CHO) cells were cultured using F12 media (10% FCS with 2 mM glutamine). Human microvascular endothelial cells (HMEC) were cultured in MCDB 131 medium (10% FCS with 10 mM glutamine, EGF and hydrocortisone).

Generation of Transgenic Chinese Hamster Ovary Cells 100 ng of $AT_1R$-Rluc8 construct was transfected into CHO cells using Lipofectamine 2000 (Thermo). Stable transfectants were selected using G418. $AT_1R$—CHO were then transiently transfected with RAGE constructs using Lipofectamine 2000 (Invitrogen) and incubated for 16 h. The *Homo sapiens* AGER transcript variant 1 coding sequence (NM_001136) was synthesised and cloned between the NheI and XbaI sites of pCIneo (Promega) to generate the vector pCIneo-RAGE. This plasmid was then used to generate a library of mutant AGER clones (NP_001127). Primers 1-RAGE-SP-5' and mCherry-XhoI-NotI-3' were used to amplify the coding sequence of mCherry from the vector pmCherry-C1. The resultant PCR product was then used as template for a second PCR using primers 2-RAGE-SP-5' and mCherry-XhoI-NotI-3'. The PCR product generated was digested with NheI and NotI and inserted between the NheI and NotI sites of pCIneo to generate pCIneo-SP-mCherry. The sequence of the insert was confirmed by DNA sequencing (Micromon, Monash University). For truncated RAGE constructs, primers 1-RAGE-SP-5' and mCherry-XhoI-NotI-3' were used to amplify the coding sequence of mCherry from the vector pmCherry-C1. The resultant PCR product was then used as template for a second PCR using primers 2-RAGE-SP-5' and mCherry-XhoI-NotI-3'. The PCR product generated was digested with NheI and NotI and inserted between the NheI and NotI sites of pCIneo to generate pCIneo-SP-mCherry. The sequence of the insert was confirmed by DNA sequencing (Micromon, Monash University).

Cellular Expression of Pro-Inflammatory Markers and Mediators by Quantitative Real-Time PCR After 2 hours of exposure to Ang II (1 μM) or the RAGE ligand, S100A8/A9 (5 ng/ml) cells were placed in Trizol, mRNA extracted and cDNA synthesized. Changes in the gene expression of the NFκB subunit, p65 (RelA) or NFκB-activated target genes (e.g ICAM-1, VCAM-1) were estimated by quantitative real-time RT-PCR, performed using the TaqMan system based on real-time detection of accumulated fluorescence (ABI Prism 7700, Perkin-Elmer Inc, PE Biosystems, Foster City, CA, USA). Gene expression was normalized to 18S mRNA and reported as fold change compared to the level of expression in untreated control mice/cells, which were given an arbitrary value of 1.

Selective Silencing of Gene Expression Using siRNA

PMAEC from C57b/6 mice were also transfected with siRNA to RAGE (2 nM) Ambion, ID:s62119), p65 (RelA) (10 nM; Ambion, ID:s72857), MyD88 (10 nM; Ambion. ID:s201719), PKCζ (10 nM; Ambion, ID:s71716), IQGAP-1, Ambion, ID:s78119), Diaph1 (10 nM; sense5'-UA-CAGAGGAAGCUGAUAUUGAAGCC, antisense 3'-GGCUUCAAUAUCAGCUUCCUCUGUA; Invitrogen) or scrambled control #1 (2 nM or 10 nM; Ambion) using Lipofectamine RNAiMAX (Invitrogen) as per manufacturer's instructions. Cells were allowed to recover in media containing 10% FBS for 16 hours prior to treatment with 1 μM Ang II or 5 ng/ml of the RAGE ligand, S100A8/A9, as a signalling control.

Generation of Peptides

Oligopeptides (Cherry-TAT (control), mCherry-TAT-$RAGE_{362-404}$ and mCherry-S391A-TAT-$RAGE_{362-404}$ were generated by transformation of the *Escherichia coli* strain ClearColi BL21 (DE3; Lucigen). A single transformed colony was inoculated into 50 ml 2YT medium containing 100 μg/ml ampicillin and the culture was grown overnight at 37° C. with shaking at 250 rev/min. 10 ml overnight culture was used to inoculate 1 litre 2YT medium containing 100 μg/ml ampicillin and the culture was grown at 37° C. with shaking at 250 rev/min. When the cultures reached an OD600 of 0.8, the temperature was shifted to 15° C. for 30 min after which protein expression was induced by the addition of 1 mM isopropyl β-D-1-thiogalacto-pyranoside (IPTG). Following the addition of IPTG the cultures were grown for ~16 h at 15° C. with shaking at 250 rev/min. Cells were harvested by centrifugation (3500 g, 4° C., 20 min) and resuspended in ice-cold lysis buffer (50 mM Tris pH 7.4, 300 mM NaCl, 10 mM imidazole and 5 mM beta-mercaptoethanol). The resuspended cells were sonicated and insoluble material was pelleted by centrifugation (13 000 g, 4° C., 30 min). The supernatant was filtered (0.2 μm) and applied onto a gravity-flow column with a 1 ml Ni-NTA Agarose resin bed volume (Qiagen) pre-equilibrated with lysis buffer. After the supernatant was passed over the resin, the column was washed with 100 ml of wash buffer (20 mM imidazole, 50 mM Tris pH 7.4, 150 mM NaCl, 5 mM beta-mercaptoethanol). His-tagged TAT-mCherry and TAT-mCherry-RAGE peptides were eluted from the resin using elution buffer (250 mM imidazole, 50 mM Tris pH 7.4, 150 mM NaCl, 5 mM beta-mercaptoethanol). The purity of the purified proteins was assessed by SDS-PAGE. Typically, 10 mg protein was produced per litre of culture. The eluted fractions containing protein were pooled and quantified by Nanodrop Spectrophotometry (Thermo Scientific) and BCA Protein Assay (Pierce).

Bioluminescence Resonance Energy Transfer (BRET)

BRET is an established technology for studying protein-protein proximity in live cells, particularly involving GPCRs (Pfleger and Eidne, 2006). One protein of interest was linked to a bioluminescent donor enzyme, Rluc8, a variant of Renilla luciferase, and a second linked to an acceptor fluorophore, Venus, a variant of green fluorescent protein. If in close proximity (<10 nm), energy resulting from the rapid oxidation of a cell-permeable coelenterazine substrate by the donor can transfer to the acceptor, which in turn fluoresces at a longer characteristic wavelength.

Plasmids were transiently co-expressed in human embryonic kidney (HEK) 293FT cells and BRET measurements taken at 37° C. using a POLARstar Omega or LUMIstar plate reader (BMG Labtech, Mornington, Victoria, Australia) with 460-490 nm ('donor emission') and 520-550 nm ('acceptor emission') filters, or a VICTOR Light plate reader (Perkin Elmer, Glen Waverley, Victoria, Australia) with 400-475 nm ('donor emission') and 520-540 nm ('acceptor emission') filters, or a CLARIOstar plate reader (BMG Labtech, Mornington, Victoria, Australia) with 420-480 nm ('donor emission') and 520-620 nm ('acceptor emission') filters.

The BRET ratio was calculated by subtracting the ratio of 'acceptor emission' over 'donor emission' for a cell sample expressing Rluc8-tagged protein alone from the same ratio for a cell sample expressing both Rluc8 and Venus-tagged proteins. Alternatively, the ligand-induced BRET signal was calculated by subtracting the ratio of 'acceptor emission' over 'donor emission' for a vehicle-treated cell sample from the same ratio for a second aliquot of the same cells treated with agonist.

For BRET kinetic assays, the final pre-treatment reading is presented at the zero time point (time of ligand/vehicle addition). For the saturation assay, fluorescence after light excitation was measured on an EnVision 2102 multi-label plate reader (PerkinElmer, Glen Waverley, Victoria, Australia) using a 485/14 excitation filter, 535/25 emission filter and D505 mirror. The fluorescence/luminescence ratio was generated by dividing the fluorescence values in arbitrary units (obtained with the EnVision) by the luminescence values also in arbitrary units (obtained as part of the BRET assay).

For Receptor-HIT assays with RAGE/Rluc8 and β-arrestin2/Venus, GPCRs untagged with respect to the BRET system were co-expressed in the HEK293FT cells. These cells were then treated with an appropriate cognate agonist selective for the co-expressed GPCR, in order to promote recruitment of β-arrestin2/Venus to that GPCR. A ligand-induced BRET signal was indicative of recruitment of the β-arrestin2/Venus proximal to RAGE/Rluc8, thereby indicating close proximity between RAGE and the activated GPCR.

The BRET measurements in FIG. 21B,C,D were taken at 37° C. using a CLARIOstar plate reader (BMG Labtech, Mornington, Victoria, Australia) with 420-480 nm ('donor emission') and 520-580 nm ('acceptor emission') filters.

The luminescence measurements in FIG. 21E were taken as part of the BRET measurements ('donor emission'). The fluoresence measurements in FIG. 21E were taken using a CLARIOstar plate reader with a 497/15 nm excitation filter, 540/20 nm emission filter and 517.2 nm dichroic mirror for Venus, and a 580/8 nm excitation filter, 615/10 nm emission filter and 597 nm dichroic mirror for mCherry.

Statistics

Continuous data are expressed as mean±SEM. Differences in the mean among groups were compared using 2-way ANOVA. Pair-wise multiple comparisons were made with Student-Newman-Keuls post-hoc analysis to detect significant differences between groups. $P<0.05$ was considered statistically significant.

Example 1. Atherogenesis Associated with an Infusion of Ang II is Reduced in Ager/apoE DKO Mice This example demonstrates that the expression of RAGE is required for an infusion of angiotensin II (Ang II) to increase atherogenesis in atherosclerosis-susceptible apoE KO mice.

Figure 1A:
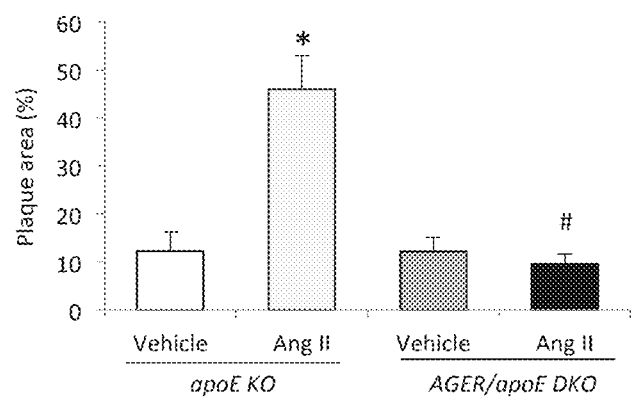
FIG. 1A. Quantitated plaque area expressed as the percentage of the aortic arch surface area staining positive to Sudan IV following a four-week infusion of Ang II (1 μg/kg/min) or vehicle control in male apoE KO mice and AGER/apoE double knockout (DKO) mice.

A four-week infusion of Ang II (1 μg/kg/min) increases atherogenesis in atherosclerosis-susceptible apoE KO mice when compared to untreated apoE KO mice, as demonstrated by an increased percentage of the aortic arch surface area staining positive to Sudan IV denoting the presence of atherosclerotic plaque (FIG. 1A).

Figure 1B:
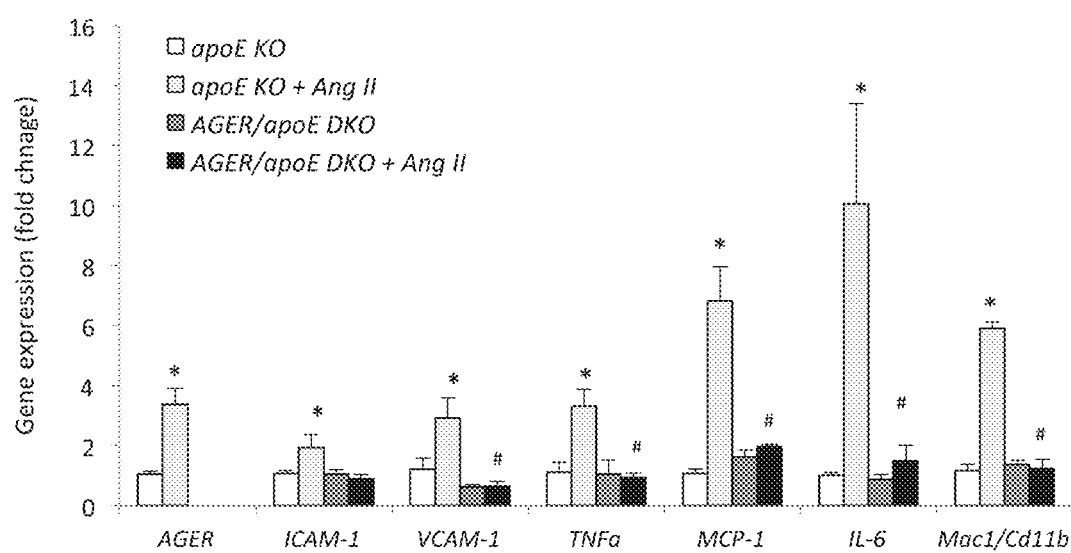
FIG. 1B. The expression of pro-atherosclerotic mediators including AGER itself, adhesion molecules (ICAM-1, VCAM-1), inflammatory cytokines and chemokines (TNFα, MCP-1 and IL-6) and the macrophage marker (Mac-1/Cd11b), as measured by real time RT-PCR in aortic homogenates from apoE KO mice and AGER/apoE DKO mice following a four-week infusion of Ang II (1 μg/kg/min) or vehicle control.
Figure 1C:
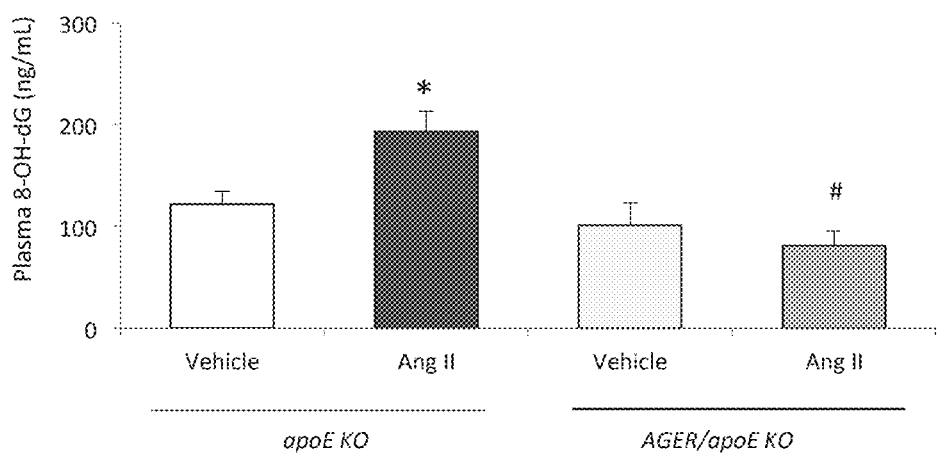
FIG. 1C. Markers of oxidative stress following a 4-week infusion of Ang II (1 μg/kg/min) or vehicle control in apoE KO mice and AGER/apoE DKO mice, as estimated by (i) plasma 8-hydroxydeoxyguanosine (8-OH-dG), a marker of oxidative DNA damage and (ii) induction of the gene expression of the NADPH oxidase subunits, NOX-1 and NOX-4 in the aortae of apoE KO mice and AGER/apoE DKO mice, as estimated by real time RT-PCR in aortic homogenates.
Figure 1C:
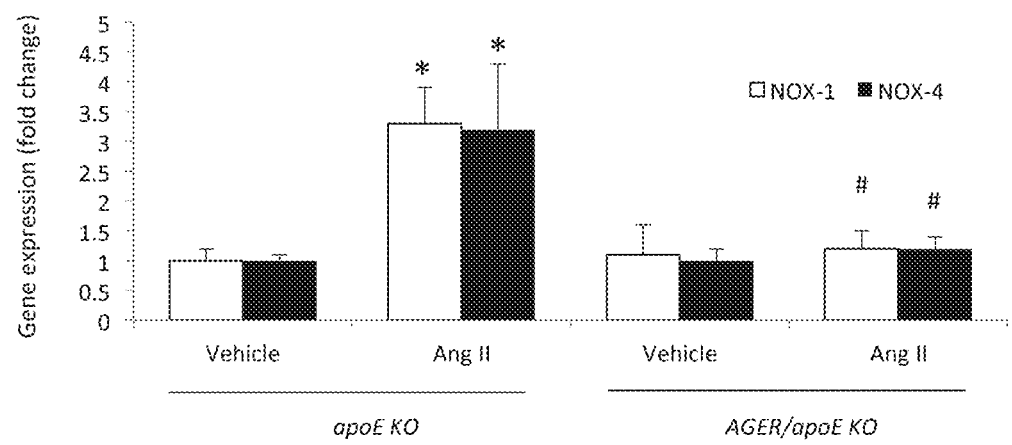

A four-week infusion of Ang II (1 μg/kg/min) also increases the aortic expression of genes coding for pro-atherogenic mediators (FIG. 1B) and markers of oxidative stress (FIG. 1C).

In apoE KO mice, a four-week infusion of Ang II (1 μg/kg/min) also increases circulating levels of RAGE ligands, including S100A8/A9, AGEs and their reactive dicarbonyl precursors (FIG. 1D), as well as increasing the gene expression of RAGE ligand Mac1/CD11b in the aorta of Ang II-treated mice (FIG. 1B).

Figure 1D:
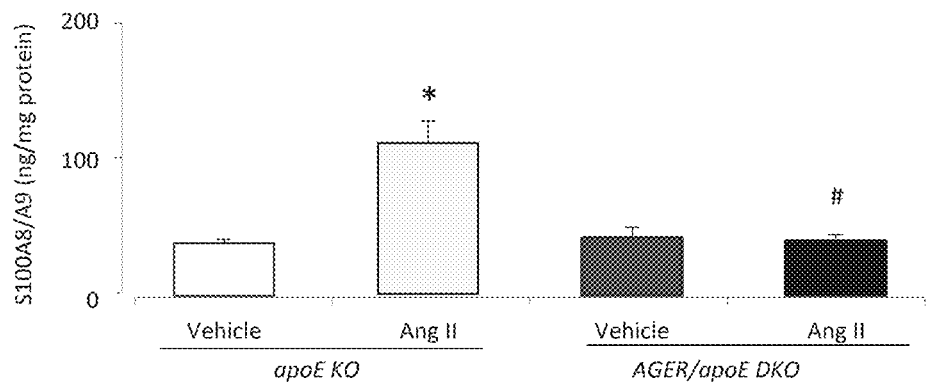
FIG. 1D. The expression of RAGE ligands, including (i) circulating plasma levels of S100A8/A9, as measured by commercial ELISA, (ii) plasma AGE levels, as measured by in-house ELISA, (iii) the circulating AGE-precursor, methylglyoxal levels as measured by HPLC in apoE KO mice and AGER/apoE DKO mice following a 4-week infusion of Ang II (1 μg/kg/min) or vehicle.
Figure 1D:
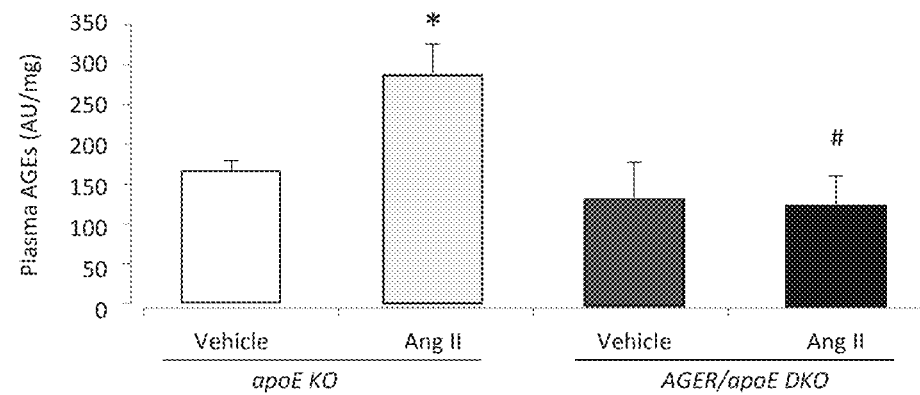
Figure 1D:
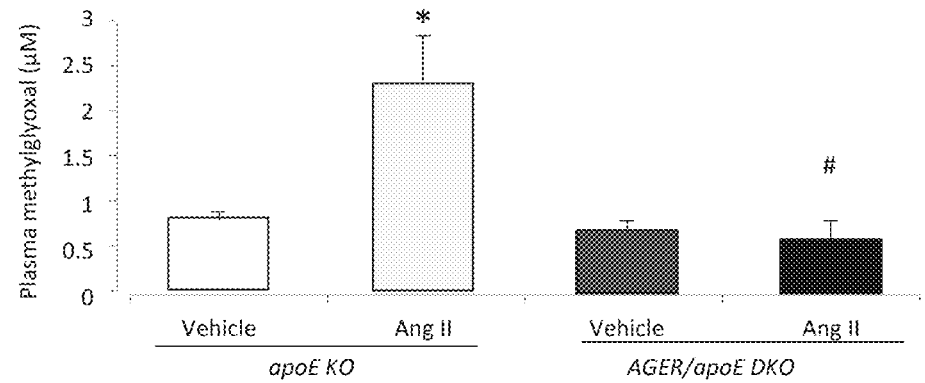
Figure 1E:
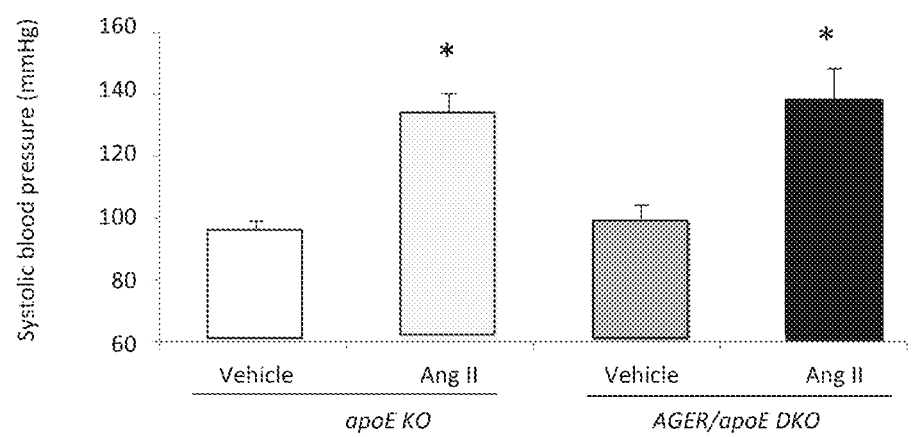
FIG. 1E. Systolic blood pressure as measured by tail-cuff plethysmography following a 4-week infusion of Ang II (1 μg/kg/min) or vehicle control in apoE KO mice and AGER/apoE DKO mice.

Genetic deletion of RAGE prevents the increase in atherogenesis observed following a four-week infusion of Ang II (1 μg/kg/min) in AGER/apoE DKO mice (FIG. 1A), as well as preventing Ang II-induced aortic expression of pro-atherogenic mediators (FIG. 1B), Ang II-induced oxidative stress (FIG. 1C) and Ang II-induced circulating levels of RAGE ligands that are observed in apoE KO mice following an infusion of Ang II (FIG. 1D).

Systolic blood pressure levels are increased to a similar extent following a four-week infusion of Ang II (1 μg/kg/min) in both apoE KO and AGER/apoE DKO mice (FIG. 1E) showing that RAGE deficiency has no impact on hemodynamic signalling induced by Ang II via the $AT_1R$.

Additional Materials and Methods

Angiotensin Infusion Model

Male apoE KO and AGER/apoE DKO mice (n=8/group), aged 6-8 weeks were randomized to receive Ang II (1 μg/kg/min; Sigma-Aldrich, Castle Hill, Australia) or vehicle via subcutaneous infusion for 4-weeks using an osmotic mini-pump (Model 2004, ALZET, BioScientific, Gymea, Australia) placed into the subcutaneous space along the dorsal midline of each mouse under general anaesthetic via intraperitoneal injection of ketamine (150 mg/kg) and xylazine (10 mg/kg). At the end of each study period in each Example 2. Atherogenesis Associated with a Low Sodium Diet that Activates the RAAS is Reduced in Ager/apoE DKO Mice This example shows that the expression of RAGE is required for RAAS activation associated with a low sodium diet to induce atherogenesis in atherosclerosis-susceptible apoE KO mice.

A low sodium diet is an accepted experimental model of physiological renin-angiotensin-aldosterone system (RAAS) activation and is a test of the capacity of the RAAS to appropriately retain salt as part of its homeostatic functions.

Six-weeks of exposure to a 0.05% (low) sodium diet results in RAAS-dependent increase in plaque accumulation in apoE KO mice (FIG. 2A), as demonstrated by an increased percentage of the aortic arch surface area staining positive to Sudan IV denoting the presence of atherosclerotic plaque.

Six-weeks of exposure to a 0.05% (low) sodium diet also results in increased aortic expression of pro-atherogenic mediators (FIG. 2B), increased markers of oxidative stress (FIG. 2C) and increased circulating concentrations of soluble MCP-1 and ICAM-1 (FIG. 2D).

More leukocytes adhere to aortae taken from apoE KO mice after 1-week of exposure to a low sodium diet when compared to aortae from apoE KO mice fed with normal chow (FIG. 2E).

In apoE KO mice, a low salt diet also increases circulating levels of RAGE ligands, including S100A8/A9, AGEs and their reactive dicarbonyl precursors (FIG. 2F), as well as the gene expression of RAGE ligand Mac1/CD11b in the aorta (FIG. 2B).

Genetic deletion of RAGE prevents the induction of atherogenesis in AGER/apoE DKO mice following four weeks of a low sodium diet when compared to apoE KO mice fed the same diet (FIG. 2A), and also prevents the increase in the aortic expression of markers of vascular inflammation, increases in markers of oxidative stress or increases in circulating inflammatory markers (FIGS. 2B, 2C & 2D).

Aortae taken from AGER/apoE DKO fed a low sodium diet for one week do not manifest the increased adhesiveness of labelled leucocytes to the aortic endothelium ex vivo when compared to apoE KO mice fed the same diet (FIG. 2E).

Increased circulating levels of the RAGE ligands, S100A8/A9 and AGEs in response to feeding with a low sodium diet seen in apoE KO mice are not observed in AGER/apoE KO mice treated with the same low sodium diet for four weeks (FIG. 2F).

Blood pressure levels are not modified by a low sodium diet in either apoE KO or AGER/apoE DKO mice (FIG. 2G).

The physiological induction of markers of RAAS activation (e.g. plasma aldosterone, plasma renin) and sodium retention associated with a low sodium diet are not significantly different between apoE KO and AGER/apoE DKO mice (FIG. 2H).

Additional Materials and Methods

Exposure of Mice to a 0.05% (Low) Sodium Diet

Exposure to a low sodium diet (0.05% sodium) is an accepted experimental model of physiological RAAS activation (Tikellis et al. 2012). In this study, apoE KO and AGER/apoE DKO mice (n=8/group) were randomized to receive an isocaloric diet with low-salt content (0.05% sodium) or normal salt-content (0.3% sodium) both containing 6% fat (Specialty Feeds, Perth, Australia) for 1-week or 6-weeks.

Plasma Renin and Aldosterone

Activation of the RAAS is associated with increased circulating levels of aldosterone and (pro)-renin. These RAAS components were estimated in each group by commercial radioimmunoassay (ProSearch International, Malvern, Australia).

Circulating Soluble MCP-1 and ICAM-1

Circulating soluble MCP-1 and ICAM-1 were estimated by ELISA (R&D Biosystems) each performed according to the manufacturer's instructions.

Urinary Sodium Excretion

After 6-weeks of a normal or low sodium diet, mice were placed into individual metabolic cages (Iffa Credo, L'Arbresele, France) for 24 hours and their weight, water and food (sodium) intake and urine output documented. The sodium concentration was measured in diluted urine with a (COBAS INTEGRA 400 auto-analyser; (Roche Diagnostics, Indianapolis, USA) using an ion-sensitive electrode and the total sodium excretion (umol/day) was estimated by multiplying with total daily urinary output.

Adherence of Labelled Leukocytes to Aortae

After 1 week of a low sodium or normal sodium diet, apoE KO and AGER/apoE DKO animals were humanely killed and aortae were isolated, cleaned of fat and mounted in a vessel chamber primed with Krebs buffer and maintained at physiological pH by infusing carbogen gas (95% $O_2$; 5% $CO_2$) through the buffer at 37° C., as previously described. Whole blood labelled with DilC18 (1:1000) was then perfused through the aorta at 0.12 ml/min. As a positive control, vessels (n=6/group) were pre-treated with TNFα (4 ng/ml) for 4 hrs at 37° C. or Ang II (1 μM). Images and videos of vessel wall-cell interactions were acquired using a fluorescence microscope (Zeiss Discovery.V20), coupled to a digital camera (HAMAMATSU ORCA-ER) and analysed with AxioVison software. Two to three frames were taken at each time point and the number of adherent cells per frame recorded.

Example 3. Atherogenesis in Ace2/apoE Double KO Mice is Reduced in Ace2/AGER/apoE Triple KO Mice This example shows that the expression of RAGE is required for genetic Ace2 deficiency to induce increased atherogenesis in atherosclerosis-susceptible Ace2/apoE DKO mice.

ACE2 is an enzyme that metabolises Ang II, the major effector of the RAAS. Genetic deficiency of Ace2 in Ace2/apoE DKO mice results in constitutive activation of the RAAS associated with increased circulating levels of Ang II (FIG. 3A), increased systolic blood pressure (FIG. 3B) and augmented plaque accumulation in the aortic arch when compared to apoE KO mice constitutively replete in Ace2 (FIG. 3C).

The aortae of Ace2/apoE DKO mice also show increased expression of pro-atherogenic mediators, when compared to apoE KO mice (FIG. 3D).

Ace2/apoE KO mice have increased circulating markers of oxidative stress (FIG. 3E) and elevated circulating levels of RAGE ligands, including S100A8/A9 and AGEs, when compared to apoE KO mice (FIG. 3F).

Genetic deletion of the AGER gene coding for RAGE in Ace2/AGER/apoE TKO mice prevents the increase in atherogenesis (FIG. 3C) and the induction of pro-inflammatory markers (FIG. 3D), markers of oxidative stress (FIG. 3E) and RAGE ligands (FIG. 3F) observed in Ace2/apoE DKO mice, restoring these markers to levels similar to those observed in apoE KO mice.

Blood pressure levels and circulating concentrations of Ang II are not significantly different between Ace2/apoE DKO or Ace2/AGER/apoE TKO (FIGS. 3A & 3B).

Additional Materials and Methods

Genetic Deficiency of Ace2 in apoE KO Mice

Ace2 is the major enzyme that metabolizes Ang II in the vasculature. Genetic deficiency of Ace2 in atherosclerosis-susceptible apoE KO mice results in increased circulating levels of Ang II and increased plaque accumulation when compared to wild-type apoE KO mice (Thomas et al. 2012). In these studies, male Ace2/apoE DKO and AGER/Ace2/apoE TKO mice were followed to 16-18 weeks of age, a time point associated with increased plaque accumulation in Ace2/apoE DKO mice.

Plasma Angiotensin II

Plasma angiotensin II levels were estimated by commercial radioimmunoassay (ProSearch International, Malvern, Australia).

Example 4. The Induction of Pro-Inflammatory Signalling in the Aorta and Endothelium by Exposure to Angiotensin II is Dependent on RAGE Expression This example shows that the expression of RAGE is required for exposure to Ang II to induce pro-inflammatory signalling in aortae and aortic endothelial cells taken from them.

Ex vivo exposure of isolated aortae from apoE KO mice to Ang II (1 µM) increases the expression of pro-atherogenic mediators (FIG. 4A) and results in an increased number of adherent leukocytes when compared to untreated aortae (FIG. 4B).

Genetic deletion of RAGE in AGER/apoE DKO mice prevents the induction of these atherogenic mediators (FIG. 4A) or increased endothelial adhesiveness of primed leucocytes (FIG. 4B) to the aorta following exposure to Ang II (1 µM) when compared to aortae from apoE KO mice.

In primary murine aortic endothelial cells (PMAEC) isolated from the aortae of C57bl6 mice, exposure to Ang II (1 µM) also results in the induction of pro-inflammatory signalling. This is associated with increased adhesion of labelled THP-1 (monocyte-type) cells to a monolayer of Ang II-treated PMAEC (FIG. 4C) and increased expression of key pro-inflammatory genes (FIG. 4D), as well as a rapid increase in the production of ROS and other markers of oxidative stress, activated rac-1 and oxidised glutathione (FIG. 4E).

In PMAEC isolated from the aortae of C57bl6 mice, exposure to Ang II also results in the induction of both canonical and non-canonical signalling downstream of NFκB, as demonstrated by the induction of classical markers CXCL2 and CXCL12 (FIG. 4F). TNFα is shown as a positive control for its ability to selectively induce canonical signalling downstream of NFκB activation. The expression of VCAM-1 is shown as an additional target response gene, replicating the data in FIG. 4D.

In PMAEC isolated from the aortae of C57bl6 mice, exposure to the RAGE ligand, S100A8/A9, also results in the induction of target NFκB-dependent pro-inflammatory genes, including ICAM-1, VCAM-1, TNFα and MCP-1 (FIG. 4G).

In PMAEC isolated from AGER KO mice, treatment with Ang II does not lead to the induction of key pro-inflammatory genes (FIG. 4D), markers of canonical or non-canonical activation of NFκB (FIG. 4F), an increase in ROS production and oxidative stress (FIG. 4E) or a functional increase in endothelial adhesiveness (FIG. 4C).

In PMAEC isolated from AGER KO mice, treatment with the RAGE ligand, S100A8/A9, does not lead to the induction of pro-inflammatory genes, including ICAM-1, VCAM-1 and MCP-1 (FIG. 4G).

Silencing of AGER expression in PMAEC using siRNA achieves a similar phenotype to genetic RAGE deletion, preventing the NFκB-dependent induction of VCAM-1 gene expression by Ang II or the RAGE ligand, S100A8/A9 (FIG. 4H). Silencing of p65 expression is shown as a positive control for NFκB-dependence of this signalling pathway.

Taken together, the findings in endothelial cells from AGER KO mice and PMAEC in which RAGE expression has been suppressed with siRNA, both demonstrate that the actions of S100A8/A9 in these cells are specifically mediated via RAGE, and that other receptors through which S100A8/A9 also has the potential to activate NFκB and downstream signalling pathways (e.g. Toll-Like Receptors) which are present in other cell systems (e.g. in leucocytes and glial cells) do not play a significant role in this phenomenon in PMAECs.

The observed attenuation in the effects of Ang II in PMAECs from AGER KO mice is not due to a loss of RAAS-signalling in the absence of RAGE, as exposure of RAGE-deficient PMAECs to Ang II leads to a similar increase in inositol phosphate synthesis as estimated by an increase in IP-1 and downstream induction of the early growth response gene (EGR1), both considered to be markers of competent Ang II-mediated signalling (FIG. 4I).

Additional Materials and Methods

Ex Vivo Studies in Isolated Aortae

Aortae were isolated from apoE KO and AGER/apoE DKO mice, divided and placed in Krebs buffer and maintained at physiological pH by infusing carbogen gas (95% $O_2$; 5% $CO_2$) through the buffer at 37° C. Vessels (n=6/group) were then treated with Ang II (1 µM) for 4 hours. After which time, whole blood labelled with DilC18 (1:1000) was then perfused through the aorta at 0.12 ml/min. Images and videos of vessel wall-cell interactions were observed using a fluorescence microscope (Zeiss Discovery.V20), coupled to a digital camera (HAMAMATSU ORCA-ER) and analysed with AxioVison software.

Static Adhesion Assay

Functional responsiveness to Ang II was determined in PMAEC using a static adhesion assay, in which PMAEC were seeded at 50,000 cells per well into six-well plates and allowed to grow to 70% confluency before treatment with 1 µM Ang II for 24 hours. Human THP-1 cells, which mimic monocytes and macrophages in the vasculature, were stained using CellVue Burgundy Fluorescent Cell labelling Kit (LICOR) as per manufacturer's instructions before seeding them onto the endothelial cell monolayers at $3 \times 10^5$ viable cells per well and incubated for 20 minutes at 37° C. The cells that had not adhered to the endothelial cell monolayer were removed and the wells washed with PBS before fixing with 4% formalin in PBS for 30 min. The adhesion of cells was then quantitated using the ODYSSEY infra-red imager (Licor). Additionally adhered cells were photographed at ×20 using light microscopy (Olympus CKX41).

Generation of Superoxide and Additional Markers of Oxidative Stress

To quantitate superoxide production induced by Ang II, a vessel chamber assay was used to measure total cytoplasmic and mitochondrial superoxide production in real time in PMAEC from AGER KO and C57Bl6 aortae. PMAEC were grown on collagen coated cover slips and mounted into a sealed glass chamber when they were 80% confluent. The chambers were perfused with Krebs buffer for an hour with fluorescent readings taken every 10 minutes to establish baseline readings. The cells were then perfused with 1 µM Ang II for 60 minutes and fluorescent readings were taken every 1 minute for a further 10 minutes. Fluorescence readings were expressed as change ($\Delta$) in fluorescence arbitrary units from baseline. Levels of the activated NADPH oxidase subunit, Rac-1 activation was also measured in cell lysates after exposure to Ang II using a Rac-1 G-LISA activation assay (Cytoskeleton), as per manufacturers' instructions. Additional markers of oxidative stress were also assayed including levels of oxidized glutathione, (Cayman Chemical Company, US), performed as per manufacturer's instructions.

Integrity of Signalling Via the $AT_1R$

To confirm that the $AT_1R$ signalling cascade was functional in PMAEC from AGER KO, we measured myo-Inositol phosphate (IP1), a stable downstream metabolite of inositol phosphate ($IP_3$), which accumulates in cells following Gq receptor activation using an IP-one HTRF assay (CisBio bioassays, Bagnols-sur-Cèze Cedex, France) using the manufacturer's instructions and changes in the gene expression of EGR1, and $AT_1R$ were then determined 2 hours after exposure to 1 µM Ang II, as assessed by real-time RT-PCR.

Example 5. The Modulatory Effects of Full Length and Truncated Human RAGE Constructs on Pro-Inflammatory Signalling in $AT_1R$—CHO Cells This example shows that for the exposure to Ang II to induce expression of the key pro-inflammatory transcription factor, p65-NFκB and increase NFκB activity in Chinese Hamster Ovary (CHO) cells, the expression of both $AT_1R$ and RAGE are also required.

CHO cells express few cell surface receptors, and specifically do not express endogenous $AT_1R$ or RAGE on their surface making them an ideal system to explore the role of the $AT_1R$-RAGE interaction. In addition, CHO cells do not express TLRs that potentially have the capacity to bind RAGE ligands and be activated by them, resulting in activation of NFκB.

Stable transfection of CHO cells with the human $AT_1R$ gene generates $AT_1R$—CHO cells, and confers classical responsiveness to exogenous Ang II (1 µM), as demonstrated by the induction of inositol phosphate synthesis (FIG. 5A) and the induction of early growth response gene, EGR1 (FIG. 5B).

By contrast, exogenous Ang II (1 µM) is unable to induce expression of the key pro-inflammatory transcription factor, p65-NFκB or increase NFκB activation in $AT_1R$—CHO cells (FIG. 5C).

Exogenous Ang II (1 µM) is able to induce activation of the key pro-inflammatory transcription factor, p65-NFκB only when $AT_1R$—CHO cells are also transfected with and expressing full-length human RAGE polypeptide (FIG. 5C). The RAGE ligand, S100A8/A9 (5 ng/ml) is also able to induce activation of the key pro-inflammatory transcription factor, p65-NFκB, only when cells are also expressing the RAGE polypeptide (FIG. 5C), which serves as a positive control for the transgenic expression of RAGE and the integrity of its signalling pathways in transfected CHO cells.

Transfection of $AT_1R$—CHO cells with N-truncated mCherry-RAGE constructs that are (i) lacking the ectodomain of RAGE (i.e. mCherry-$RAGE_{342-404}$), (ii) lacking the ectodomain and the transmembrane domain of RAGE (i.e. mCherry-$RAGE_{362-404}$) or (iii) lacking the ectodomain, the transmembrane domain and the Diaphanous-1 binding domain (366-367) of RAGE (i.e. mCherry-$RAGE_{370-404}$) retain the ability of full length $RAGE_{22-404}$ to mediate pro-inflammatory signalling in response to Ang II when compared to empty plasmid alone (vector), provided that Q379 is retained (FIG. 5D). N-Truncation beyond Q379 (e.g. mCherry-$RAGE_{380-404}$) results in an inactive mutant RAGE peptide that is unable to mediate pro-inflammatory signalling in response to Ang II.

Transfection of $AT_1R$—CHO cells with C-truncated RAGE constructs retain the ability to mediate pro-inflammatory signalling in response to Ang II, provided that at least Ser391 of the C-terminal of wild-type RAGE remains intact (i.e. $RAGE_{22-391}$; FIG. 5E).

The smallest construct retaining the ability to mediate pro-inflammatory signalling in response to Ang II in $AT_1R$—CHO cells is the 13-mer construct mCherry-$RAGE_{379-391}$ (FIG. 5E).

N-truncated mCherry-RAGE constructs lacking the RAGE ligand-binding ectodomain are not able to facilitate signalling when transfected into $AT_1R$—CHO cells in response to the RAGE ligand S100A8/A9 (FIG. 5F) as RAGE ligand-dependent activation of RAGE requires this ligand-binding ectodomain to bind the ligand, in addition to other parts of RAGE to subsequently transfer its signal, recruiting and activating its intracellular signalling cascade.

C-truncated RAGE constructs are able retain the ability to mediate pro-inflammatory signalling when transfected into $AT_1R$—CHO cells in response to S100A8/A9, provided that at least Ser391 of the C-terminal of wild-type RAGE remains intact (i.e. $RAGE_{22-391}$; FIG. 5G).

The additional mCherry protein provides a practical means to ensure expression of transgene constructs in cell models. However, it plays no role in the pro-inflammatory signalling actions of N-truncated RAGE as (i) the expression of mCherry on its own has no effect on signalling pathways (i.e. mCherry control in FIG. 5F) and (ii)N-truncated RAGE constructs in which the mCherry protein has been omitted (FIG. 5H) achieve the same levels of signalling function in response to Ang II as those expressing the mCherry-RAGE fusion protein (FIG. 5D, 5F). Similarly N-truncation beyond Q379 destabilises the alpha helix and results in a loss of signalling function in contructs with and without mCherry-RAGE fusion (FIGS. 5F and 5H respectively).

Additional Materials and Methods

Classical GPCR Signalling

Classical GPCR signalling was confirmed in cells treated with 1 µM Ang II, by the induction of myo-Inositol phosphate (IP1), a stable downstream metabolite of $IP_3$, which accumulates in cells following Gq receptor activation using an IP-one HTRF assay (CisBio bioassays, Bagnols-sur-Cèze Cedex, France) using the manufacturer's instructions.

NFκB Activity Assay

To measure the induction of NFκB activity by 1 µM Ang II, or 5 ng/ml of the RAGE-ligand S100A8/A9 as a signalling control, $AT_1R$—CHO cells were transfected with 0.4 µg of plasmids encoding NFκB-SEAP or β-galactosidase (β-Gal) using Lipofectamine 2000 (Invitrogen) as per manufacturer's instructions. After 24 hours, cells transfected with each plasmid combination were then treated with Ang II (1 µM) or left untreated and incubated for 4 hours before cell supernatants and cell lysates were collected. Cell supernatants were analysed using a chemiluminescent SEAP reporter gene assay (Roche Applied Science) to detect SEAP production after treatment. To control for transfection efficiency, cell lysates were assayed for β-Gal using a commercially available kit (Promega).

Example 6. RAGE Ligand-Independent Activation of RAGE Following Activation of the $AT_1R$ with Ang II This example shows that activation of RAGE following binding of Ang II to $AT_1R$ occurs via a RAGE ligand-independent pathway and not via liberation of a RAGE ligand.

Activation of the $AT_1R$ is known to trigger activation of tyrosine-kinase receptors due to activation of pathways leading to protease-mediated extracellular "shedding" of membrane-tethered ligands, which are then freed to bind to and activate these tyrosine kinase receptors.

Pre-treatment with a neutralizing antibody targeting the ligand-binding ectodomain of RAGE (RAGEab) or a soluble RAGE decoy with ligand-binding affinity ($sRAGE_{22-331}$) both block RAGE ligand-dependent induction of pro-inflammatory signalling by the RAGE ligand S100A8/A9 in RAGE-$AT_1R$—CHO cells expressing both full length RAGE and $AT_1R$ (FIG. 6A).

Pre-treatment with a neutralizing antibody targeting the ligand-binding ectodomain of RAGE (RAGEab) or a soluble RAGE decoy with ligand-binding affinity ($sRAGE_{22-331}$) do not affect RAGE ligand-independent induction of pro-inflammatory signalling by Ang II in RAGE-$AT_1R$—CHO (FIG. 6A).

Pre-treatment with a neutralizing antibody targeting the ligand-binding ectodomain of RAGE (RAGEab) or a soluble RAGE decoy with ligand-binding affinity ($sRAGE_{22-331}$) also does not attenuate Ang II-$AT_1R$-dependent induction of pro-inflammatory signalling in PMAEC, endogenously replete in both $AT_1R$ and RAGE (FIG. 6B). PMAEC from AGER KO mice are shown as a negative control.

By contrast, pre-treatment with a neutralizing antibody targeting the ligand-binding ectodomain of RAGE (RAGEab) or a soluble RAGE decoy with ligand-binding affinity (sRAGE22-331) is able to attenuate pro-inflammatory signalling induced following exposure to the RAGE ligand S100A8/A9 in PMAEC, endogenously replete in both $AT_1R$ and RAGE (FIG. 6C).

Taken together with the findings using N-truncated RAGE constructs detailed in Example 5, these data confirm that activation of the RAGE receptor following exposure to Ang II is independent of the liberation of RAGE ligands or the activation of the ectodomain of RAGE by such liberated ligands.

Additional Materials and Methods

Additional experiments were conducted in the presence and absence of a 1 hour pre-treatment with a neutralizing antibody to RAGE (RAGEab; R&D systems; 1 µg/mL) or soluble $RAGE_{22-331}$ (sRAGE; 1 µg/mL) prior to exposure to 1 µM Ang II or 5 ng/ml of the RAGE ligand, S100A8/A9.

Example 7. RAGE Ligand-Independent Activation of RAGE by Co-Located GPCR does not Require Phosphorylation of the Cytosolic Tail to Induce Pro-Inflammatory Signalling This example shows that RAGE ligand-independent activation of RAGE by a certain co-located GPCR does not require phosphorylation of RAGE to induce pro-inflammatory signalling.

Phosphorylation of Ser391 has been previously thought to be important for ligand-dependent signalling via RAGE, possibly by facilitating the recruitment of adaptor proteins to the RAGE cytosolic tail, which then transduce pro-inflammatory signalling.

However, many other mammals have another amino acid other than serine at the 391 position of RAGE that cannot be phosphorylated. For example, camels have a glutamine at 391, while a proline is naturally found in the same position in cattle, sheep, goats, pigs, deer as well as some other mammals. These residues are unable to sustain phosphorylation, and yet these animals have intact RAGE signalling pathways.

Transfection of $AT_1R$—CHO cells with full length RAGE constructs in which S391 is mutated to glutamine (S391Q-RAGE) or proline (S391P-RAGE), thereby blocking potential phosphorylation at this site, continue to mediate Ang II-dependent induction of p65-NFκB gene expression. Transfection with full length RAGE constructs in which the putative phosphorylation site at S391 is mutated to glutamine (S391Q-RAGE) or proline (S391P-RAGE) also continue to mediate S100A8/A9-dependent induction of NFκB expression in $AT_1R$—CHO cells (FIG. 7A).

Blockade of all other potential phosphorylation sites on the human RAGE cytosolic tail (i.e. S399, S400 and T401) was achieved by replacing the last eleven C-terminal residues of RAGE 394-404 with those residues found in the murine RAGE cytosolic tail that naturally do not contain potential phosphorylation sites (i.e. $hRAGE_{394-404}$; $P_{394}EAGESSTGGP$ is replaced with $mRAGE_{392-404}$; $A_{394}EMPENGAGGP$, generating a chimeric RAGE (cRAGE) with no potential sites for phosphorylation (S391Q-cRAGE); Notably this construct was able to signal the same as wild-type RAGE in $AT_1R$—CHO cells in response to Ang II (FIG. 7B), confirming that signalling-induced phosphorylation of RAGE is not necessary for ligand-independent pro-inflammatory signalling via RAGE, and that other sites do not convey redundancy for RAGE phosphorylation when S391 is mutated.

S391Q-cRAGE was also shown to mediate S100A8/A9-induced signalling in $AT_1R$—CHO cells (FIG. 7B). These data confirm that signalling-induced phosphorylation of RAGE is also not necessary for ligand-dependent pro-inflammatory signalling via RAGE or that other phosphorylation sites in the cytosolic tail can convey redundancy for RAGE phosphorylation when S391 is mutated.

RAGE constructs in which S391 has been deleted (e.g. $RAGE_{22-390}$) have no ability to mediate Ang II-dependent induction of NFκB activation or p65 expression in $AT_1R$—CHO cells (see Example 5, FIG. 5G).

Full length RAGE constructs in which only S391 is mutated to alanine (S391A-RAGE) have no ability to mediate Ang II-dependent or S100A8/A9-dependent induction of NFκB expression or activity (as determined by p65 expression) in AT₁R—CHO cells (FIG. 7A), despite the presence of other potential phosphorylation sites at S399, S400 and T401 in human RAGE.

Full length and N-truncated RAGE constructs in which only the S391 is selectively mutated to alanine (S391A-RAGE) also have no ability to mediate Ang II-dependent induction of NFκB expression or activity (as determined by p65 expression) in AT₁R—CHO cells (FIG. 7C).

RAGE constructs in which only the S391 is mutated to cysteine (S391C-RAGE) also have no ability to mediate Ang II-dependent or S100A8/A9 dependent induction of NFκB expression or activity (as determined by p65 expression) in AT₁R—CHO cells (FIG. 7A).

Full length RAGE constructs in which S391 is mutated to leucine (S391L-RAGE) retain the ability to mediate Ang II-dependent induction of NFκB expression in AT₁R—CHO cells, but lose signalling induced by the RAGE ligand S100A8/A9 (FIG. 7A).

By contrast, full length RAGE constructs in which S391 is mutated to glutamic acid (S391E-RAGE) lose the ability to mediate Ang II-dependent induction of NFκB expression in AT₁R—CHO cells (FIG. 7A), but retain the ability to signal following exposure to the RAGE ligand, S100A8/A9 (FIG. 7A).

Transfection of AT₁R—CHO cells with N-truncated mCherry-RAGE$_{362-404}$ constructs in which the S391 is mutated to isoleucine, methionine, threonine, or tryptophan retain the ability of transfection with wild type RAGE$_{362-404}$ to mediate Ang II-dependent induction of NFκB expression (as determined by p65 expression) (FIG. 7D). By contrast, transfection with N-truncated RAGE$_{362-404}$ constructs in which the S391 is mutated to alanine, aspartate, glutamate, phenylalanine, glycine, histidine, lysine, asparagine, arginine, valine or tyrosine fail to restore Ang II-dependent induction of NFκB expression or activity (as determined by p65 expression) in AT₁R—CHO cells when compared to wild type RAGE (FIG. 7D).

Example 8. The Common Role of MyD88 in RAGE Ligand-Independent Activation of RAGE by Co-Located GPCR and RAGE Ligand-Dependent Activation of RAGE This example describes the common role of myeloid differentiation factor 88 (myD88) in RAGE ligand-independent activation of RAGE by a certain co-located GPCR as well as RAGE ligand-dependent activation of RAGE.

The common adaptor protein, myD88, has been previously shown to be important for downstream pro-inflammatory signalling following activation of RAGE as well as many other receptors including all Toll-like receptors (TLRs) except TLR-3. Ligand-dependent activation of RAGE is thought to facilitate the recruitment of MyD88 and other common adaptor proteins including, Toll Interleukin-1 receptor domain containing adaptor protein (TIRAP) to the cytosolic tail of RAGE, which then recruit and transduce signalling through IRAK4, ultimately leading to NFκB activation.

Silencing of myD88 expression using siRNA inhibits the NFκB-dependent induction of the key adhesion molecule, ICAM-1, induced by the RAGE ligand S100A8/A9 in PMAECs (FIG. 8A). This effect is comparable to silencing of p65, its downstream target.

Silencing of MyD88 expression using siRNA also inhibits signalling induced by RAGE ligand-independent activation of RAGE by Ang II in PMAECs, including the NFκB-dependent activation of gene expression of the key adhesion molecule, ICAM-1 (FIG. 8B).

Silencing of MyD88 expression using siRNA also inhibits NFκB-dependent activation of gene expression of the key adhesion molecule, MCP-1 induced by RAGE ligand-independent activation of RAGE by Ang II in HMECs (FIG. 8C). This inhibition is rescued by RAGE$_{362-404}$ (FIG. 8C), confirming the functional substitute of RAGE identified by the inventors, is functioning independent of MyD88.

Example 9. The Common Role of PKC-Zeta in RAGE Ligand-Independent Activation of RAGE by Co-Located GPCR and RAGE Ligand-Dependent Activation of RAGE This example describes the common role of PKCζ in RAGE ligand-independent activation of RAGE by a certain co-located GPCR and ligand-dependent activation of RAGE.

The atypical PKC, PKCζ has been previously shown to be important for RAGE ligand-dependent activation of RAGE and subsequent activation of downstream pathways. PKCζ has been shown to bind to the cytosolic tail of RAGE as well as Diaph1, another RAGE binding partner.

PKCζ is a pleiotropic kinase involved in many signalling pathways including MAP kinase signalling, NFκB-activation, cell polarity, insulin-mediated glucose uptake and long-term memory potentiation. PKCζ is also involved in many other signalling pathways including TLR2/4-dependent induction of pro-inflammatory signalling. PKCζ also modulates the phosphorylation status of activated GPCRs, a key event in receptor downstream signalling and functioning.

Silencing of PKCζ expression using siRNA or inhibition of PKCζ with a pseudo-substrate (iPKCζ) inhibits signalling induced by the RAGE ligand S100A8/A9 in PMAEC (FIG. 9A), with an equivalent effect to silencing of RAGE expression. This further confirms that silencing or inhibition of PKCζ is not acting by silencing signalling of S100A8/A9 through TLR2/4, but rather specifically through altering signalling specifically through full length RAGE.

Silencing of PKCζ expression using siRNA or inhibition of PKCζ with a pseudo-substrate (iPKCζ) also inhibits signalling induced by RAGE ligand-independent activation of full length RAGE by Ang II, including the NFκB-dependent activation of the key adhesion molecule, ICAM-1 (FIG. 9B).

The inhibition of PKCζ with a pseudo-substrate (PKCζi) also inhibits signalling induced by RAGE ligand-independent activation of full-length S391Q-cRAGE22-404 (which contains no serines or threonines in the cytosolic tail capable of being phosphorylated), as assessed by the NFκB-dependent activation of p65 and PCNA following exposure to Ang II in AT₁R—CHO cells (FIG. 9C), confirming that PKCζ is not acting in the RAGE signalling pathway by inducing phosphorylation of RAGE.

By contrast, silencing of PKCζ expression using siRNA does not inhibit NFκB-dependent activation of gene expression of the key adhesion molecule, MCP-1 induced by RAGE ligand-independent activation of RAGE$_{362-404}$ by Ang II in HMECs (FIG. 9D), confirming that the functional substitute of RAGE identified by the inventors, is functioning independent of PKCζ.

Additional Materials and Methods

Additional experiments were conducted in the presence and absence of a 1 hour pre-treatment with a pseudo-substrate for PKCζ (iPKCζ, 5 μM, Tocris).

Example 10. The Differential Role of Diaphanous-1 in RAGE Ligand-Independent Activation of RAGE by Co-Located GPCR Compared to RAGE Ligand-Dependent Activation of RAGE This example describes the differential role of Diaphanous-1 (Diaph1) in RAGE ligand-independent activation of RAGE by a certain co-located GPCR compared to RAGE ligand-dependent activation of RAGE, specifically its dependence on the charged patch (R366-Q367) of RAGE and the alpha-turn it stabilises that are known to complex with Diaph1, indicating a key point of difference between RAGE ligand-dependent and RAGE ligand-independent (transactivation) induced signalling via RAGE.

The formin-type protein, Diaphanous-1 (Diaph1) is regarded as a key element for pro-inflammatory signalling induced by RAGE ligands.

Silencing of Diaph1 expression attenuates ligand-dependent signalling via full length RAGE induced by the RAGE ligand, S100A8/A9 (5 ng/ml) in PMAEC (FIG. 10A), with an effect equivalent to silencing of RAGE, which serves as a negative control.

The charged patch (R366-Q367) of RAGE is thought to form an alpha-turn that stabilises its complex with Diaph1 (Rai, et al. 2016). Mutation of R366-Q367 that selectively disrupts the charged patch through which Diaph1 and RAGE are thought to interact, is able to prevent S100A8/A9-induced signalling in $AT_1R$ CHO cells expressing full length R366A-Q367A-RAGE (FIG. 10B).

Silencing of Diaph1 expression also attenuates RAGE ligand-independent signalling via full-length RAGE induced by Ang II including the induction of ICAM-1 and VCAM-1 expression in PMAEC (FIG. 10C) and inhibits the functional induction of leukocyte adhesion to an endothelial monolayer following exposure to Ang II (FIG. 10D).

By contrast, mutated full-length R366A-Q367A-$RAGE_{22-404}$ and N-truncated mCherry-R366A-Q367A-$RAGE_{362-404}$ in which the charged patch through which Diaph1 and RAGE are thought to interact is disrupted, still mediate RAGE ligand-independent signalling induced by Ang II in $AT_1R$—CHO cells (FIG. 10B).

Furthermore, deletion of the charged patch through which Diaph1 and RAGE are thought to interact (e.g. in $RAGE_{370-404}$) does not prevent RAGE ligand-independent activation of RAGE and pro-inflammatory signalling induced by Ang II in $AT_1R$—CHO cells (FIG. 10E).

In addition, silencing of Diaph1 expression using siRNA does not inhibit NFκB-dependent activation of MCP-1 gene expression induced by RAGE ligand-independent activation of $RAGE_{362-404}$ by Ang II in HMECs (FIG. 10F), confirming that the functional substitute of RAGE identified by the inventors, is functioning independent of Diaph1.

Taken together, these data imply that methods to disrupt the interaction between the charged patch of RAGE and Diaph1 will have no direct effect on RAGE ligand-independent signalling via RAGE by a certain co-located GPCR.

Without wishing to be bound by theory, the inventors believe that mutation or deletion of the charged patch through which Diaph1 and full length RAGE are thought to interact alleviates binding constraints that occur through this interaction, meaning that N-truncated RAGE peptides without this binding domain (e.g. $RAGE_{370-404}$) or mutated peptides in which this domain is altered (e.g. R366A-Q367A-$RAGE_{362-404}$) are able to overcome the inhibition of transactivation conferred by pre-treatment with mCherry-S391A-$RAGE_{362-404}$ (0.4 ng/ml), a construct in which the charged patch remains present (FIG. 10G).

Example 11. The Common Role of IQGAP-1 in RAGE Ligand-Independent Activation of RAGE by Co-Located GPCR and RAGE Ligand-Dependent Activation of RAGE This example describes the role of IQGAP-1 in the activation of RAGE.

IQGAP-1 is a scaffold protein involved in regulating various cellular processes ranging from organization of the actin cytoskeleton, transcription, and cellular adhesion to regulating the cell cycle. IQGAP-1 is known to bind to RAGE effector molecules including active forms of Cdc42, Rac-1, calmodulin-1, and ERK 1/2.

Silencing of IQGAP-1 expression attenuates RAGE ligand-independent signalling via RAGE induced by Ang II in PMAEC (FIG. 11A) and RAGE ligand-dependent signalling induced by S100A8/A9 in PMAECs (FIG. 11B).

The mutant form of the RAGE cytosolic tail, S391A-$RAGE_{362-404}$, preferentially associates with IQGAP-1 as indicated by its ability to be differentially purified from other cytosolic components using a column coated with S391A-$RAGE_{362-404}$ (FIG. 11C). This strategy also pulled down the IQGAP-1 associated proteins, ezrin/radixin/moesin.

Silencing of IQGAP-1 expression using siRNA also inhibits NFκB-dependent activation of MCP-1 gene expression induced by RAGE ligand-independent activation of $RAGE_{362-404}$ by Ang II in HMECs (FIG. 11D), confirming that the functional substitute of RAGE identified by the inventors, is functionally dependent on IQGAP-1.

Additional Materials and Methods

Methods for Pull-Down Experiments

The TAT-Cherry-S391A-$RAGE_{362-404}$ peptide and TAT-mCherry control peptide were bound to a gravity flow NiNTA column, and equilibrated using lysis buffer (50 mM Tris pH 7.5, 300 mM NaCl, 5 mM βB-mercaptoethanol, 10 mM imidazole. $5 \times 10^7$ CHO cells stably transfected with Hs-$AT_1R$ were lysed using RIPA buffer (1×PBS supplemented with 1% NP-40, 0.5% Na-deoxycholate with protease and phosphatase inhibitors), diluted to 50 ml in lysis buffer and passed over the Ni-NTA column twice by gravity flow. The 1 ml column was washed extensively (200 ml wash buffer-50 mM Tris pH 7.4, 300 mM NaCl, 5 mM β-mercaptoethanol, 20 mM imidazole). After washing, 2 ml of elution buffer (50 mM Tris pH 7.4, 300 mM NaCl, 5 mM β-mercaptoethanol, 250 mM imidazole) was applied to the column, and used to elute proteins that had bound to either the A peptide or TAT-mCherry control peptide. 1 ml of sample was delivered for proteomic analysis by Mass Spectroscopy. Venny 2.1.0 was used to generate lists of the proteins differentially bound to the two proteins.

Example 12. Inhibition of RAGE-Ligand Independent Activation of RAGE by Co-Located GPCR in Murine SVEC This example describes using specific components of the RAGE cytosolic tail to inhibit RAGE ligand-independent signalling induced via RAGE in murine SVEC following exposure to Ang II.

Transfection of murine SVEC with full length S391A-RAGE$_{22-404}$ and N-truncated mCherry-S391A-RAGE$_{362-404}$ is able to prevent the induction of ICAM-1 gene expression by Ang II in murine SVEC that are endogenously replete in RAGE expression (FIG. 12A).

Transfection of murine SVEC with full length (RAGE$_{22-404}$) and N-truncated mCherry-RAGE constructs in which the wild-type conformation (S391) is retained does not affect the induction of ICAM-1 gene expression following exposure to Ang II (FIG. 12A).

Transfection of murine SVEC with C-truncated S391X-RAGE mutants (i.e. RAGE$_{22-390}$ and m-Cherry-RAGE$_{370-395}$) also prevents the induction of ICAM-1 by Ang II in murine SVEC that are endogenously replete in RAGE expression (FIG. 12A).

The smallest sequence demonstrated to be inhibitory for RAGE signalling in SVEC is mCherry-RAGE$_{379-390}$ (FIG. 12B). Further N- or C-terminal truncations (e.g. mCherry-RAGE$_{380-390}$) or peptides comprising other components of the cytosolic tail but not containing the RAGE$_{379-390}$ dodecapeptide show no inhibitory effect on the pro-inflammatory actions of Ang II via RAGE activation.

The additional mCherry protein provides a practical means to ensure expression of transgene constructs in cell models. However, it plays no role in the functional inhibitory actions of N-truncated RAGE as (i) the expression of mCherry (control) on its own has no inhibitory effect on signalling pathways (FIG. 12B) and (ii) N-truncated RAGE constructs in which the mCherry protein has been omitted achieve the same inhibition of Ang II-dependent signalling in RAGE-AT$_1$R—CHO cells (FIG. 12C), as constructs expressing the mCherry-RAGE fusion proteins, detailed above (FIG. 12B).

The peptide resulting from this RAGE sequence is predicted to be an alpha helix. As alpha helices can be stabilised or disrupted by changes to capping amino acids, additional selective mutation was performed. Notably, loss of either glutamine 379 or glutamine 390 by alanine substitution destabilised the helix and resulted in a loss of inhibition, while glutamine-to-lysine mutants Q390K-RAGE$_{370-390}$ and Q379K-RAGE$_{370-390}$ appeared to retain the greatest inhibitory effect, consistent with the known art that terminal lysine or arginine possess a greater effect in stabilising dodecapeptides in an alpha helix conformation (FIG. 12D).

This sequence of the dodecapeptide RAGE$_{379-390}$ has homology to sequences in immunomodulatory bacterial proteins from commensal organisms including *Streptomyces* (FIG. 12E). Although only mammals possess the gene for RAGE, the presence of RAGE inhibitory sequences in pathogens is consistent with a survival mechanism to avoid/attenuate mammalian host defences including inflammation.

Although the capacity for RAGE$_{370-390}$ to inhibit the induction of ICAM-1 expression following activation of the AT$_1$R with Ang II in SVEC cells is lost with the following glutamine-to-alanine mutations: Q390A-RAGE$_{370-390}$ or Q379A-RAGE$_{370-390}$ (FIG. 12D), L388A-RAGE$_{370-390}$, E384A-RAGE$_{370-390}$, E382A-RAGE$_{370-390}$ and E380A-RAGE$_{370-390}$, continue to inhibit signalling in SVEC cells as wild type RAGE$_{370-390}$.

Additional Materials and Methods

To explore the potential for RAGE constructs to inhibit transactivation of endogenous RAGE, additional experiments were conducted in immortalized mouse endothelial cells (Svec4-10, ATCC) cultured in 10% FBS/DMEM with 25 mM glucose were used. SVEC were transfected with truncated RAGE constructs using Lipofectamine 2000 (Invitrogen) as per manufacturer's instructions, or treated with RAGE oligopeptides (280 µM). Cells were allowed to recover in media containing 10% FBS for 16 hours prior to treatment with 1 µM Ang II.

Example 13. Targeting RAGE Ligand-Independent Activation of RAGE by Co-Located GPCR In Vitro In this example, we demonstrate that treatment of cells with a cell-penetrating peptide modulator of RAGE ligand-independent activation of RAGE by a certain co-located GPCR is able to modulate the induction of pro-inflammatory signalling via RAGE ligand-independent RAGE activation in cell culture.

To validate the therapeutic potential of targeting AT$_1$R-dependent signalling via activation of the cytosolic tail of RAGE, oligopeptides comprising the C-terminal 43 amino acids of RAGE tagged with mCherry-fluorescent protein (to quantify expression and delivery) and an HIV-TAT motif (to facilitate cellular penetration) were generated to act as substitutes. In one version, the serine residue at 391 was changed to alanine (S391A-RAGE$_{362-404}$; SEQ ID NO: 1) to neutralise its ability to signal and enhance its ability to inhibit activation of endogenous RAGE.

Treatment of AT$_1$R—CHO cells (not expressing RAGE) with the TAT-mCherry-S391A-RAGE$_{362-404}$ fusion protein; 0.4 ng/ml), different at only one amino acid residue from the activating wild type-construct, does not facilitate the induction of expression of p65-NFκB by Ang II (FIG. 13A).

In AT$_1$R—CHO cells pre-treated with the wild-type TAT-mCherry-RAGE$_{362-404}$ fusion peptide (1 ng/ml) subsequent treatment with TAT-mCherry-S391A-RAGE$_{362-404}$ fusion protein (1 ng/ml), is able to prevent the restoration of Ang II-induced pro-inflammatory signalling by the wild-type peptide (FIG. 13B).

In AT$_1$R—CHO cells treated with TAT-mCherry-S391A-RAGE$_{362-404}$ fusion protein (1 ng/ml), subsequent treatment with wild-type TAT-mCherry-RAGE$_{362-404}$ fusion peptide, even in 1000-fold excess, is not able to restore responsiveness to Ang II-induced expression of p65 when compared to untreated cells (FIG. 13C).

In AT$_1$R—CHO cells expressing S391Q-cRAGE$_{22-404}$ (i.e. a construct with no phosphorylatable elements) subsequent treatment with TAT-mCherry-S391A-RAGE$_{362-404}$ fusion protein (0.4 ng/ml), is able to prevent Ang II-induced induction of p65-NFκB and the proliferation marker PCNA, confirming that modulation is achieved independent of the phosphorylation of RAGE (FIG. 13D).

Treatment of PMAEC from AGER KO mice (deficient in RAGE) with the wild-type TAT-mCherry-RAGE$_{362-404}$ fusion peptide (0.4 ng/ml) is able to restore the Ang II-mediated induction of expression of p65-NFκB and NFκB-dependent pro-inflammatory genes, ICAM-1, VCAM-1 and MCP-1 (FIG. 13E).

Treatment of RAGE-replete PMAEC obtained from c57bl6 mice with TAT-mCherry-S391A-RAGE$_{362-404}$ fusion protein (0.4 ng/ml), blocks Ang II-induced induction of downstream signalling leading to activation of canonical and non-canonical pathways of NFκB activation (as detected by induction of the expression of CXCL12 and CXCL2 respectively) and the downstream NFκB-dependent induction of VCAM-1 gene expression (FIG. 13F). TNFα is shown as a positive control for canonical NFκB-signalling and is unaffected by TAT-mCherry-S391A-RAGE$_{362-404}$ fusion protein.

Treatment of RAGE-replete human AEC with TAT-mCherry-S391A-RAGE$_{362-404}$ fusion protein (0.4 ng/ml) also blocks Ang II-induced downstream signalling leading to the NFκB-dependent induction of pro-inflammatory genes, ICAM-1, VCAM-1, MCP-1, TNFα and IL-6 (FIG. 13G). The inhibitory effect is comparable to that achieved with the AT$_1$R blocker, irbesartan in HAECs.

Treatment with TAT-mCherry-S391A-RAGE$_{362-404}$ fusion protein (0.4 ng/ml) also inhibits subsequent induction of pro-inflammatory gene expression by the RAGE ligand, S100A8/A9 in (i) RAGE-AT$_1$R—CHO cells and (ii) PMAECs replete in RAGE (FIG. 13H).

Additional Material and Methods

To confirm the applicability of inhibition strategies to human tissues, additional experiments were undertaken in primary aortic endothelial cells from humans (Lonza). HAECs were grown in EGM-2 media. In each case cells were treated with mCherry-TAT (control), TAT-mCherry-RAGE$_{362-404}$ (wild type), or TAT-mCherry-S391A-RAGE$_{362-404}$ at a dose of 0.4 ng/ml for 30 min prior to treatment with either Ang II (1 μM), or S100A8/A9 (2 μg/ml; R&D systems) for 2h. As a further control, the inhibitory effect of the AT$_1$R blocker irbesartan (1 μM; 30 minutes before dosing with Ang II) was also explored in HAECs.

Example 14. Targeting RAGE Ligand-Independent Activation of RAGE by Co-Located GPCR in the Aorta Ex Vivo In this example, we demonstrate that treatment of aortae with a cell-penetrating peptide inhibitor of RAGE ligand-independent activation of RAGE (TAT-mCherry-S391A-RAGE$_{362-404}$ fusion protein, 8 ng/ml) is able to prevent the induction of RAAS-mediated inflammation ex vivo.

As also detailed in Example 4, ex vivo exposure to Ang II increases the expression of pro-atherogenic mediators (FIG. 14A) in isolated aortae from apoE KO mice. By contrast, ex vivo treatment of aortae taken from AGER/apoE DKO mice with Ang II does not lead to the induction of these atherogenic mediators (FIG. 14B).

Pre-treatment of aortae from apoE KO mice with a cell-penetrating peptide inhibitor of RAGE ligand-independent activation of RAGE (TAT-mCherry-S391A-RAGE$_{362-404}$ fusion protein, 8 ng/ml) prevents Ang II-dependent induction of adhesion molecules, as detected by gene expression measured by real time RT-PCR (FIG. 14A).

Pre-treatment of aortae from AGER/apoE DKO mice with a cell-penetrating wild-type RAGE peptide (TAT-mCherry-RAGE$_{362-404}$ fusion protein, 8 μg/ml) restores Ang II-dependent induction of adhesion molecules and inflammatory markers, as detected by gene expression measured by real time RT-PCR (FIG. 14B).

Additional Materials and Methods

Aortae were isolated from apoE KO and AGER/apoE DKO mice, divided and placed in Krebs buffer and maintained at physiological pH by infusing carbogen gas (95% O$_2$; 5% CO$_2$) through the buffer at 37° C. Aortae were randomised to receive pre-treatment with mCherry-TAT (control), mCherry-TAT-RAGE$_{362-404}$ (wild type), or mCherry-TAT-S391A-RAGE$_{362-404}$ oligopeptide (all 8 ng/ml). Thirty minutes later, aortae were exposed to Ang II (1 μM) for 4 hours. At the end of the incubation, aortae were placed in Trizol, mRNA extracted and cDNA synthesized. Gene expression of pro-atherogenic mediators was then estimated by quantitative real-time RT-PCR, as detailed above.

Example 15. Targeting RAGE Ligand-Independent Activation of RAGE by Co-Located GPCR (Transactivation) in Live Mice In this example, we demonstrate that treatment with a cell-penetrating peptide inhibitor of RAGE ligand-independent activation of RAGE is able to prevent the induction of RAAS-mediated atherosclerosis in apoE KO mice.

As detailed in Example 3, genetic deficiency of Ace2 in Ace2/apoE DKO mice results in augmented plaque accumulation at 16 weeks of age when compared to apoE KO mice replete in Ace2. Ace2/AGER/apoE triple KO mice are protected against this increase in atherosclerosis associated with genetic Ace2 deficiency (FIG. 15A).

Treatment of Ace2/apoE DKO mice with a cell-penetrating peptide inhibitor of RAGE ligand-independent activation of RAGE (TAT-mCherry-S391A-RAGE$_{362-404}$ fusion protein (S391A); 10 μg/kg/IP every second day for ten weeks) attenuates Ang II-dependent atherosclerosis in this model (FIG. 15A).

Treatment of Ace2/AGER/apoE triple KO mice with a cell-penetrating peptide transducer of RAGE ligand-independent activation of RAGE (TAT-mCherry-RAGE$_{362-404}$ fusion protein (WT); 10 μg/kg/IP every second day for ten weeks) restores atherosclerosis to that observed in Ace2/apoE DKO mice replete in RAGE (FIG. 15A) despite only restoring the signalling capable RAGE cytosolic tail and the ongoing absence of full-length RAGE and its associated ligand-binding domain.

Treatment of Ace2/apoE DKO mice with a cell-penetrating peptide inhibitor of RAGE ligand-independent activation of RAGE (TAT-mCherry-S391A-RAGE$_{362-404}$ fusion protein; 10 μg/kg/IP every second day for ten weeks) does not affect blood pressure levels (FIG. 15C).

Streptozotocin-induced diabetes is also a model associated with RAAS activation and increased atherosclerosis, which is prevented by RAAS inhibition, without lowering blood pressure or altering glucose control (Candido et al., 2002).

AGER/apoE DKO mice are protected against an increase in atherosclerosis following the induction of diabetes (Soro-Paavonen et al., 2008).

Treatment of diabetic apoE KO mice with a cell-penetrating peptide inhibitor of RAGE ligand-independent activation of RAGE (TAT-mCherry-S391A-RAGE$_{362-404}$ fusion protein (S391A); 10 μg/kg/IP every second day for ten weeks) attenuates atherosclerosis in this model (FIG. 15B) without affecting blood pressure levels (FIG. 15C).

Treatment of diabetic apoE KO mice with a cell-penetrating peptide transducer of RAGE ligand-independent activation of RAGE (TAT-mCherry-RAGE$_{362-404}$ fusion protein; 10 μg/kg/IP every second day for ten weeks) increases atherosclerosis beyond that seen with diabetes alone (FIG. 15B) despite only restoring the signalling capable RAGE cytosolic tail and the ongoing absence of full-length RAGE and its associated ligand-binding domain.

Treatment of diabetic AGER/apoE DKO mice with a cell-penetrating peptide transducer of RAGE ligand-independent activation of RAGE (TAT-mCherry-RAGE$_{362-404}$ fusion protein, 10 μg/kg/IP every second day for ten weeks) reverses the protection afforded by genetic RAGE deletion and increases atherosclerosis (FIG. 15B) to a level observed in RAGE replete mice, despite only restoring the signalling capable RAGE cytosolic tail and the ongoing absence of full-length RAGE and its associated ligand-binding domain.

Additional Materials and Methods

Male apoE KO mice, Ace2/apoE DKO mice and Ace2/AGER/apoETKO mice were randomized to receive the TAT-Cherry-S391A-RAGE$_{362-404}$ (inhibitor) peptide (10 µg/kg/IP every second day), TAT-Cherry-RAGE$_{362-404}$ (wild-type; 10 µg/kg/IP every second day) oligopeptide or mCherry-TAT (control; 10 µg/kg/IP every second day) for 10 weeks, at which time they were humanely killed.

In a second model of Ang II-dependent atherosclerosis, apoE KO mice and AGER/apoE DKO were randomly allocated to receive streptozotocin (55 mg/kg, Sigma Chemical Co, St. Louis, MO, USA) or buffer (sodium citrate buffer pH 4.5) delivered intraperitoneally in five consecutive daily doses (Soro-Pavinonen et al. 2008). This regimen induces an insulinopenic form of diabetes associated with hyperglycemia (blood glucose ~30 mM) but with sufficient beta-cell function to prevent ketosis or require insulin supplementation. The presence of diabetes was confirmed by a fasting blood glucose level >15 mM, one week after the first dose of streptozotocin. All diabetic mice also achieved an HbA1c>8% (median 11.2%) after ten weeks. After one week of diabetes, mice were further randomized to receive the mCherry-TAT-S391A-RAGE$_{362-404}$ (inhibitor) peptide (100 µg/kg/IP every second day), mCherry-TAT-RAGE$_{362-404}$ (wild-type; 100 µg/kg/IP every second day) oligopeptide or mCherry-TAT (control; 100 µg/kg/IP every second day) for 10 weeks, at which time they were humanely killed.

Example 16. BRET Indicates Close Proximity of AT$_1$R and RAGE when Co-Expressed in Live Cells In this example we demonstrate co-expression of Rluc8-labeled AT$_1$R (AT$_1$R/Rluc8) and Venus labelled-RAGE (RAGE/Venus) in HEK293FT cells results in the generation of a strong and saturable BRET signal consistent with their close proximity, which is reduced upon treatment with Ang II (FIG. 16A). The presence of soluble RAGE$_{22-331}$ (sRAGE) does not alter these results (FIG. 16A).

Treatment of cells co-expressing AT$_1$R/Rluc8 and β-arrestin2/Venus with Ang II results in the induction of a robust and stable ligand-induced BRET signal consistent with recruitment of β-arrestin2 to the AT$_1$R (FIG. 16B). Treatment of cells co-expressing Chemokine (C-C Motif) Receptor 4 (CCR4)/Rluc8 and β-arrestin2/Venus with its cognate ligand CCL22 also results in the induction of a robust ligand-induced BRET signal consistent with recruitment of β-arrestin2 to the CCR4 (FIG. 16B).

Treatment of cells co-expressing RAGE/Rluc8 and β-arrestin2/Venus with Ang II induces a BRET signal in the presence of untagged AT$_1$R (FIG. 16C), indicative of close proximity between RAGE and AT$_1$R.

By way of a control, this is not observed in the presence of untagged CCR4 when treated with its cognate ligand CCL22 (FIG. 16C).

As an additional control to demonstrate the expression/functioning of untagged CCR4, a CCL22-induced BRET signal is observed when Gαi/Nluc and Gγ2/Venus are co-expressed (FIG. 16D).

Additional Materials and Methods

An alternative BRET donor to Rluc8 is Nanoluc (Nluc) and this can be used in combination with Venus with a furimazine substrate, as described in Tiulpakov et al., 2016. This approach was used when monitoring the proximity of Gαi/Nluc and Gγ2/Venus to assess the functionality of CCR4.

Example 17. BRET Indicates Close Proximity of RAGE to Certain Activated GPCRS in Addition to AT$_1$R when Co-Expressed in Live Cells In this example, we demonstrate that close proximity between RAGE and AT$_1$R in live cells, described in Example 16 above, is also observed between RAGE and certain other activated co-located GPCRs.

Treatment of cells co-expressing an Rluc8-labelled GPCR and β-arrestin2/Venus with an appropriate cognate agonist for that GPCR resulted in the induction of a robust ligand-induced BRET signal consistent with recruitment of β-arrestin2 to the activated Rluc8-labelled GPCR. This was observed for AT$_1$R with Ang II (FIG. 17A), TRHR1 with TRH (FIG. 17B), OxR1 with OxA (FIG. 17C), bradykinin receptor 2 (BDKR) with bradykinin (FIG. 17D), V2R with AVP (FIG. 17E), CCR2 with MCP1 (FIG. 17F) and CCR5 with MIP1β (FIG. 17G).

Receptor-HIT: Treatment of cells co-expressing Rluc8-labelled RAGE (RAGE/Rluc8) and β-arrestin2/Venus in the presence of AT$_1$R (FIG. 17A), OxR1 (FIG. 17C), V2R (FIG. 17E) or CCR2 (FIG. 17F) with the appropriate cognate agonist for that GPCR resulted in the induction of a clear ligand-induced BRET signal consistent with recruitment of β-arrestin2 to the GPCR. This in turn is indicative of RAGE proximity to the activated GPCR. No ligand-induced BRET signal was observed in the absence of the co-expressed GPCR.

Treatment of cells co-expressing Rluc8-labelled RAGE (RAGE/Rluc8) and β-arrestin2/Venus in the presence of TRHR1 (FIG. 17B) or bradykinin receptor 2 (BDKR; FIG. 17D) with the appropriate cognate agonist for that GPCR resulted in the induction of a weak ligand-induced BRET signal discernible from the lack of ligand-induced BRET signal observed in the absence of the co-expressed GPCR and consistent with recruitment of β-arrestin2 to the GPCR. This in turn may be indicative of RAGE proximity to the activated GPCR, but this is not as clear as observed for AT$_1$R, OxR1, V2R or CCR2.

Treatment of cells co-expressing Rluc8-labelled RAGE (RAGE/Rluc8) and β-arrestin2/Venus in the presence of CCR5 (FIG. 17G) with MIP1β resulted in the induction of a weak ligand-induced BRET signal that was difficult to discern from that observed in the absence of the co-expressed GPCR.

Example 18. BRET Indicates Close Proximity of RAGE to Certain Activated Chemokine Receptors when Co-Expressed in Live Cells In this example, we demonstrate that close proximity between RAGE and certain chemokine receptors is observed in live cells using the Receptor-HIT assay configuration.

Treatment of cells co-expressing Rluc8-labelled RAGE (RAGE/Rluc8) and β-arrestin2/Venus in the presence of CCR1 (FIG. 18A), CCR2 (FIG. 18B), CCR6 (FIG. 18E), CCR7 (FIG. 18F), CXCR2 (FIG. 18I) or CXCR6 (FIG. 17F) with the appropriate cognate agonist for that GPCR (as labelled) resulted in the induction of a clear ligand-induced increase in BRET signal consistent with recruitment of β-arrestin2 to the GPCR. This in turn is indicative of RAGE proximity to the activated GPCR.

Treatment of cells co-expressing Rluc8-labelled RAGE (RAGE/Rluc8) and β-arrestin2/Venus in the presence of CXCR1 (FIG. 18H) with CXCL8 resulted in the induction of a discernible ligand-induced increase in BRET signal consistent with recruitment of β-arrestin2 to the GPCR. This in turn is indicative of RAGE proximity to the activated GPCR, but this is not as clear as for the aforementioned receptors.

Treatment of cells co-expressing Rluc8-labelled RAGE (RAGE/Rluc8) and β-arrestin2/Venus in the presence of CXCR4 (FIG. 18K) with CXCL12 resulted in the induction of a clear ligand-induced decrease in BRET signal consistent with a reduction in proximity between β-arrestin2 and RAGE, or a conformational change resulting in less resonance energy transfer between Rluc8 and Venus. This in turn is indicative of a change in proximity of RAGE to the activated GPCR to which the β-arrestin2/Venus is recruited.

Treatment of cells co-expressing Rluc8-labelled RAGE (RAGE/Rluc8) and β-arrestin2/Venus in the presence of CCR4 (FIG. 18C), CCR5 (FIG. 18D), CCR10 (FIG. 18G) or CXCR3 (FIG. 17J) with the appropriate cognate agonist for that GPCR (as labelled) did not result in the induction of a discernible ligand-induced change in BRET signal. This is despite very strong ligand-induced BRET signals being observed for CCL22-induced recruitment of β-arrestin2/Venus to CCR4/Rluc8 (FIG. 16B) and CCL4-induced recruitment of β-arrestin2/Venus to CCR5/Rluc8 (n=3; data not shown). Weaker, but still clear ligand-induced BRET signals were also observed for CCL27-induced recruitment of β-arrestin2/Venus to CCR10/Rluc8 and CXCL11-induced recruitment of β-arrestin2/Venus to CXCR3/Rluc8 (n=3; data not shown).

Example 19. BRET Indicates that Co-Located GPCR Activation Results in a Change in RAGE Subcellular Localisation in Live Cells In this example, we demonstrate that proximity between RAGE and subcellular compartment markers changes upon activation of certain co-located GPCRs, indicating an effect of GPCR activation on RAGE function for a number of GPCRs.

Venus-tagged subcellular compartment markers used were the plasma membrane marker KRAS, as well as RabGTPases Rab1 (endoplasmic reticulum trafficking to the cis-Golgi), Rab4 (early endosome recycling), Rab5 (early endosomes), Rab7 (late endosomes/lysosomes), Rab8 (trans-Golgi network to the plasma membrane), Rab9 (late endosome trafficking to the trans-Golgi network) and Rab11 (recycling endosomes). Proximity of Rluc8-tagged RAGE to Venus-tagged subcellular compartment markers was assessed in real-time before and after addition of an appropriate cognate agonist for the GPCR at time zero and at the concentration indicated.

For adrenergic α1A receptor, adrenergic α1B receptor, angiotensin receptor AT₁R, bradykinin receptor B2, CCR2, CCR6, CCR9, CXCR4, CXCR5, dopamine D1 receptor, endothelin receptor type B, histamine H3 receptor, muscarinic M2 receptor, neuropeptide Y1 receptor, orexin receptor 1, orexin receptor 2, prostaglandin E1 receptor, serotonin 5-HT2c receptor, serotonin 5-HT4b receptor, somatostatin 2 receptor, sphingosine 1-phosphate receptor S1P3, vasopressin receptor 1A and vasopressin receptor 1B, a particularly clear change in the ligand-induced BRET signal indicative of a change in proximity to at least one of the subcellular compartment markers was observed as a consequence of ligand addition.

For CCR3, CCR4, neurotensin 1 receptor and serotonin 5-HT2b receptor, a clear change in the ligand-induced BRET signal indicative of a change in proximity to at least one of the subcellular compartment markers was observed as a consequence of ligand addition.

For adenosine A1 receptor, adrenergic α2B receptor, CCR1, CCR5, CCR7, CXCR2, endothelin receptor type A, muscarinic M1 receptor, muscarinic M3 receptor, serotonin 5-HT1a receptor, serotonin 5-HT2a receptor, sphingosine 1-phosphate receptor S1P1, thyrotropin-releasing hormone receptor 1 and vasopressin receptor 2, a small yet discernible change in the ligand-induced BRET signal indicative of a change in proximity to at least one of the subcellular compartment markers was observed as a consequence of ligand addition.

For adenosine A2A receptor, adenosine A2B receptor, adenosine A3 receptor, adrenergic α2A receptor, adrenergic α2C receptor, adrenergic β1 receptor, adrenergic β2 receptor, adrenergic β3 receptor, apelin receptor, CCR8, CCR10, CXCR1, CXCR3, CXCR6, CXCR7, dopamine D2 receptor, glucagon-like peptide receptor 1, neurotensin 2 receptor, platelet activating factor receptor, prostaglandin E2 receptor, prostaglandin E3 receptor, prostaglandin E4 receptor, somatostatin 1 receptor and somatostatin 3 receptor, little discernible change in the ligand-induced BRET signal for any of the subcellular compartment markers was observed as a consequence of ligand addition (data not shown).

Example 20. RAGE Ligand-Independent Activation of RAGE by Certain Activated Co-Located GPCRS Other than AT₁ Receptor In this example, we demonstrate that the activation of certain chemokine receptors (CCR2 and CXCR2) by their cognate ligands (MCP-1 and CXCL8, respectively) to induce the expression of the key pro-inflammatory transcription factor, p65-NFκB, also requires the co-expression of RAGE.

In CHO cells stably transfected with a plasmid coding for CCR2 and expressing CCR2 on their surface (CCR2-CHO cells), transfection with RAGE and exposure to MCP-1 ($10^{-7}$) the cognate ligand for CCR2, results in the activation of NFκB and induction of the expression of p65 (FIG. 20A). In the absence of RAGE co-expression, MCP-1 does not induce the activation of NFκB to induce the expression of p65 in CCR2-CHO cells.

In CHO cells stably transfected with a plasmid coding for CXCR2 and expressing CXCR2 on their surface (CXCR2-CHO cells), transfection with RAGE and exposure to the cognate ligand, IL-8 (CXCL8), results in the increased expression of p65 in the presence of co-expressed RAGE (FIG. 20B). In the absence of RAGE, IL-8 does not induce the activation of NFκB to induce the expression of p65 in CXCR2-CHO cells.

In bone marrow-derived primary murine macrophages, exposure to MCP-1 ($10^{-7}$ M) the cognate ligand for CCR2, results in the activation of NFκB and induction of the expression of p65 (FIG. 20C). The induction of expression of p65-NFκB by MCP-1 in primary macrophages is blocked by pre-treatment with the TAT-mCherry-S391A-RAGE$_{362-404}$ fusion protein (0.4 ng/ml).

In HMEC exposure to MCP-1 ($10^{-7}$ M) the cognate ligand for CCR2, results in the activation of NFκB and auto-induction of the expression of MCP-1 (FIG. 20D). The auto-induction of MCP-1 expression of HMEC is blocked by pre-treatment with the TAT-mCherry-S391A-RAGE$_{362-404}$ fusion protein (0.4 ng/ml). Taken together these data confirm the role of co-located endogenous RAGE in the MCP-1/CCR2 signalling process.

In HMEC expressing CXCR2 exposure to IL-8 ($10^{-7}$ M), the cognate ligand for CXCR2, results in the activation of NFκB and induction of the expression of MCP-1 (FIG. 20E). The induction of MCP-1 expression of HMEC is blocked by pre-treatment with the TAT-mCherry-S391A-RAGE$_{362-404}$ fusion protein (0.4 ng/ml). Taken together these data confirm the role of co-located endogenous RAGE in the IL-8/CXCR2 signalling process.

Additional Materials and Methods

Generation of Transgenic Chinese Hamster Ovary Cells 100 ng of CCR2-Rluc8 construct or CXCR2-Rluc8 was transfected into CHO cells using Lipofectamine 2000 (Thermo). Stable transfectants were selected using G418. CCR2-CHO and CXCR2-CHO cells were then transiently transfected with full length RAGE constructs using Lipofectamine 2000 (Invitrogen) and incubated for 16h. CCR2-CHO cells were then exposed to MCP-1 ($10^{-7}$) the cognate ligand for CCR2 for two hours. CXCR2-CHO cells were exposed to the cognate ligand, IL-8 (CXCL8) for two hours. Cells were then placed in Trizol, mRNA extracted and cDNA synthesized. Changes in the gene expression of the NFκB subunit, p65 (RelA) were determined by quantitative real-time RT-PCR, performed using the TaqMan system based on real-time detection of accumulated fluorescence (ABI Prism 7700, Perkin-Elmer Inc, PE Biosystems, Foster City, CA, USA), as detailed in the general methods.

Primary Bone-Marrow Derived Macrophages

Primary bone marrow-derived macrophages were pre-treated with RAGE$_{362-404}$, the mutant RAGE peptide, S391A-RAGE$_{362-404}$ or TAT-cherry control for 1 hour. Cells were then exposed to MCP-1 ($10^{-7}$ M) the cognate ligand for CCR2 for two hours. Cells were then placed in Trizol, mRNA extracted and cDNA synthesized. Changes in the gene expression of the NFκB subunit, p65 (RelA) were determined by quantitative real-time RT-PCR, performed using the TaqMan system based on real-time detection of accumulated fluorescence (ABI Prism 7700, Perkin-Elmer Inc, PE Biosystems, Foster City, CA, USA), as detailed in the general methods.

Example 21. RAGE Ligand-Independent Activation of RAGE by Certain Co-Located GPCRS is Inhibited by Targeting the Transmembrane Domain of RAGE This example shows that RAGE ligand-independent activation of RAGE by a certain co-located GPCR and activation of RAGE by a RAGE ligand are inhibited following modulation of the transmembrane domain (TMD) of RAGE.

RAGE is a type 1 transmembrane protein that comprises a single transmembrane spanning helix (residues 343-361 of SEQ ID NO: 14). The RAGE TMD is highly conserved across all mammalian species.

The RAGE TMD is important for membrane targeting and anchoring, as RAGE isoforms lacking this hydrophobic domain (e.g. soluble RAGE; sRAGE) are secreted and not retained in the plasma membrane.

Homodimerization of RAGE on the cell surface is essential for RAGE-mediated signal transduction. The V, C1 and C2 domains of the extracellular portion of RAGE contain elements that promote RAGE dimerization (e.g. RAGE$_{22-331}$ is able to homodimerize) and dimerization of the RAGE can be inhibited by overexpression of sRAGE. The TMD of RAGE also potentially plays an active role in oligomerization, and the TMD has been previously shown to homodimerize, independent of the RAGE ectodomain (Su et al. 2013).

The RAGE TMD is also required for transmission of the RAGE ligand-induced signal from the ectodomain to signalling elements in the cytosolic domain. Without wishing to be bound by theory, the inventors believe that this occurs by the transduction of conformational changes (such as scissor-like motion to increase the distance between the C-termini to 100 Å) following ligand binding (Xue et al. 2017).

RAGE ligand binding is known to induce ectodomain shedding of RAGE$_{22-331}$ by the secretases ADAM10/17 and MMP9 following which the remaining membrane-bound C-terminal fragment of RAGE is processed by γ-secretase, an intramembrane cleaving protease. Inhibition of γ-secretase results in increased retention of the C-terminal fragment of RAGE in the membrane after RAGE ligand-binding as well as inhibiting RAGE ligand-induced signalling, suggesting that intramembrane proteolysis of RAGE transmembrane domain is a critical step for RAGE ligand-dependent signaling (Braley et al. 2016).

Taken together, these data provide a rationale for targeting the RAGE TMD as a means to modulate RAGE ligand-independent activation of RAGE following activation of certain co-located GPCRs.

We demonstrate that a BRET signal is observed between N-terminally tagged mCherry-RAGE$_{338-361}$ (the RAGE TMD with an extracellular juxta-membrane fragment linked to mCherry) and an extracellularly luciferase-tagged AT1 receptor (Nluc-AT$_1$; FIG. 21A), confirming that the TMD is also involved in the interaction between RAGE and certain GPCRs.

Overexpression of mCherry-RAGE$_{338-361}$ modulates BRET between full length RAGE and AT$_1$ in a dose dependent fashion, demonstrated with BRET saturation assays (FIG. 21B) and kinetic assays (FIG. 21C), confirming that BRET between full length RAGE and AT$_1$ is inhibited by a non-functional substitute of the RAGE TMD with a juxta-membrane portion of the ectodomain. Notably, sRAGE (i.e. the extracellular ligand-binding V-C1-C2 domains of RAGE; RAGE$_{22-331}$) does not inhibit BRET between AT$_1$R and RAGE (FIG. 16A).

Control experiments are shown in FIG. 21D showing that there is no ligand-induced BRET signal between AT$_1$/Rluc8 and mCherry/RAGE$_{338-361}$, even with the appropriate filter set. The mCherry tag is used to separately assess the relative expression level of the mCherry/RAGE$_{338-361}$ fusion protein, as shown in FIG. 21E, following excitation by an external light source. Also shown in FIG. 21E, similar expression levels of AT$_1$/Rluc8 across the various transfections are demonstrated by the similar relative luminescence emissions from the luciferase. Furthermore, similar expression levels of RAGE/Venus across the various transfections are demonstrated by the similar relative fluorescence emissions at the emission wavelength of Venus following excitation by an external light source.

For adrenergic α2B receptor, angiotensin receptor AT$_1$ (AT$_1$R), bradykinin receptor 2 (B2R), CCR1, CCR2, CCR4, CCR5, CCR6, CCR9, CXCR2, CXCR4, neuropeptide Y1 receptor (NPY1R), orexin receptor 2, sphingosine 1-phosphate receptor 1 (S1PR1), thyrotropin-releasing hormone receptor 1 (TRHR1), vasopressin receptor 1A (V1aR), vasopressin receptor 1B (V1bR) and vasopressin receptor 2 (V2R), a particularly clear inhibition of the change in the ligand-induced BRET signal between the Rluc8-tagged GPCR and RAGE/Venus was observed when mCherry- RAGE$_{338-361}$ was co-expressed (FIG. 21F), confirming that BRET between full length RAGE and these GPCRs is inhibited by a non-functional substitute of the RAGE TMD with a juxta-membrane portion of the ectodomain.

For adenosine A1 receptor (ADORA1), CCR7 and CXCR5, a small yet discernible inhibition of the change in the ligand-induced BRET signal between the Rluc8-tagged GPCR and RAGE/Venus was observed when mCherry-RAGE$_{338-361}$ was co-expressed (FIG. 21F), confirming that BRET between full length RAGE and these GPCRs is inhibited by a non-functional substitute of the RAGE TMD with a juxta-membrane portion of the ectodomain.

For adrenergic α1A receptor, CCR3, muscarinic acetylcholine receptor 2 (CHRM2) and orexin receptor 1, little discernible change in ligand-induced BRET signal was observed between the Rluc8-tagged GPCR and RAGE/Venus meaning that the effect of mCherry-RAGE$_{338-361}$ co-expression could not be determined (FIG. 21F).

As detailed above, transactivation of RAGE requires expression of the cytosolic domain (RAGE$_{379-391}$), consequently RAGE$_{338-361}$ cannot be activated. However, Ang II-mediated pro-inflammatory signaling, as indicated by ICAM-1 gene expression, induced following transactivation of full-length RAGE in human microvascular endothelial cells (HMEC) is inhibited by transfection with RAGE$_{338-361}$. This inhibition is rescued by additional expression of mCherry-RAGE$_{362-404}$ (i.e. the cytosolic domain of RAGE; FIG. 21G). This suggests that the TMD and the cytosolic domain are able to function independently, but are co-dependent in full length RAGE constructs. Notably, sRAGE (i.e. the RAGE ectodomain) does not inhibit RAGE ligand-independent activation of RAGE following activation of certain co-located GPCRs.

To validate the hypothesis that the TMD of RAGE alone can act as an inhibitor of RAGE ligand-independent activation of RAGE by certain co-located GPCRs, HMEC were transfected with only the TMD of RAGE (RAGE$_{343-361}$) or mCherry-TMD fusion. Expression of either construct was able to prevent the induction of both MCP1 and ICAM1 gene expression by Ang II in HMEC that are endogenously replete in RAGE expression (FIG. 21H).

To validate the hypothesis that the TMD of RAGE alone can also act as an inhibitor of RAGE ligand-dependent activation of RAGE, CHO cells expressing full length human RAGE were treated with the RAGE ligand S100A8/A9 in the presence and absence of transfection of a construct expressing only the TMD of RAGE (RAGE$_{343-361}$). Expression of this construct was able to prevent the induction of p65 gene expression by S100A8/A9, similar to RAGE$_{370-390}$ (FIG. 21I).

The actions of mDiaph1 and PKCζ in RAGE transactivation are mediated by their actions at the RAGE TMD, as silencing of mDiaph1 and PKCζ using siRNA inhibits signalling induced by RAGE$_{343-404}$ but not RAGE$_{362-404}$. (FIG. 21J).

Taken together these data confirm that specific modulation of the RAGE TMD is able to inhibit the transactivation of RAGE by certain co-located GPCRs as well as RAGE ligand-dependent signalling following activation of the RAGE ectodomain.

Example 22. Prophetic Examples of Screening for Potential Inhibitors of RAGE Ligand-Independent Activation of RAGE The following assays are prophetic examples of how the invention described herein would be logically applied to identify a potential inhibitor of RAGE ligand-independent RAGE signalling via activation of a certain co-located GPCR (e.g. AT$_1$R-induced or CCR2-mediated transactivation of RAGE).

Assay 1: Competition assays to measure inhibition of binding between the cytosolic tail of RAGE (full length or truncated, wild type or inhibitory mutants) and IQGAP-1 or fragments thereof.

Methods: Sandwich assay has either IQGAP or cytosolic tail of RAGE bound to plate or column (full length or truncated). Add binding partner (i.e. either IQGAP or cytosolic tail of RAGE) in presence of serial dilution of test compound/modulator. Presence of binding partner measured by intrinsic label (fluorescent label, enzyme fusion) or by way of detection probe (e.g. antibody to binding partner brings label). Absence of binding partner indicates added test compound is a competitive inhibitor of binding between cytosolic RAGE and IQGAP-1 or fragments thereof.

Assay 2. Yeast-two hybrid used to measure binding between the cytosolic tail of RAGE and IQGAP-1.

Methods: Yeast two hybrid assay expresses IQGAP-1 and cytosolic RAGE (full length or truncated, wild type or inhibitory mutants). Presence of binding partner measured by intrinsic label (e.g. fluorescent label, enzyme fusion, reporter system (e.g. KISS). Absence of binding partner indicates added test compound is a competitive inhibitor of binding between cytosolic tail of RAGE and IQGAP-1 or fragments thereof.

Assay 3: BRET used to measure binding between the cytosolic tail of RAGE (full length or truncated, wild type or inhibitory mutants) and IQGAP-1.

Methods: BRET assay expresses labelled IQGAP and cytosolic RAGE and measures the transfer of resonance energy between them, indicating their proximity. Inhibition of the BRET signal upon addition of the test compound/modulator indicates that the test compound/modulator is a competitive inhibitor of interaction between cytosolic RAGE and IQGAP or fragments thereof.

Assay 4: Inhibition of RAGE ligand-independent activation of RAGE by certain activated co-located GPCR (e.g. AT$_1$R-induced) by detecting the induction of downstream signalling via RAGE.

An inhibitor of RAGE ligand-independent (e.g. AT$_1$R-induced transactivation) RAGE signalling is indicated by a test compound that reduces RAGE-dependent downstream NFκB activation in CHO cells expressing both AT$_1$R and RAGE exposed to Ang II (or another GPCR exposed to its cognate ligand), but not RAGE signalling induced by S100A8/A9 or downstream NFκB activation induced by S100A8/A9 or other RAGE ligands, or RAGE-independent Gq signalling induced following activation of the AT$_1$R by Ang II (e.g. calcium influx, inositol phosphate levels, expression markers such as EGR).

Assay 5. Binding partners of RAGE$_{379-390}$.

Methods: Having demonstrated that RAGE$_{379-390}$ is an important signalling element for modulation of RAGE ligand independent activation of RAGE, identification of high-affinity specific binding partners to RAGE$_{379-390}$ is undertaken in silico or in vitro of screening peptide and non-peptide libraries (i.e. chemicals) or structure based drug design.

CONCLUSIONS

Activation of certain co-located GPCRs by their cognate ligands, such as activation of AT$_1$R by Ang II and CCR2 by MCP-1, triggers inflammation through pathways distinct from classical canonical signalling via GPCRs that induce, for example, calcium influx, inositol phosphate synthesis and activation of PKA. Here, the inventors show that RAGE ligand-independent activation of the cytosolic tail of RAGE by certain co-located GPCRs is a key determinant of this division. The inventors demonstrate that activation of NFκB, which is critical for the pro-inflammatory signalling downstream of many GPCRs, is mediated by RAGE ligand-independent activation of co-located RAGE. Consequently, many of the adverse vascular changes induced, for example, by Ang II-$AT_1R$ activation are attenuated when RAGE is deleted or when RAGE activation is inhibited. By contrast, $AT_1R$-dependent signalling via classic Gq pathways is unaffected by RAGE expression and RAGE deletion has no deleterious effect on vascular homeostasis in salt deficiency or blood pressure responsiveness to Ang II.

The inventors provide herein specific evidence that RAGE and GPCRs, including the $AT_1R$ or CCR2, form a heteromeric complex, with the generation of a clear Receptor-HIT BRET signal. This is further supported by the specific evidence provided by the inventors herein that the heteromeric complex formation and transactivation is inhibited by expression of a non-functional substitute of the transmembrane domain of RAGE with or without an additional juxta-membrane fragment of the ectodomain. Inactive state preassembly of GPCRs into transient complexes with signalling components is thought to enable rapid and augmented responsiveness. Without wishing to be bound by theory, the inventors believe that preassembly of RAGE with certain co-located GPCRs serves a similar role, enabling rapid RAGE ligand-independent activation of the cytosolic tail of RAGE and downstream pro-inflammatory signalling following activation of GPCRs.

The inventors also show that the conformation of residue 391 of RAGE is important for GPCR-dependent pro-inflammatory signalling, as S391A-RAGE and 390X-RAGE mutants do not induce pro-inflammatory signalling following activation of certain co-located GPCRs, such as the $AT_1R$ by Ang II, unlike wild-type RAGE which is different only at one amino acid (serine391). This is not because Ser391 is phosphorylated following RAGE activation, as previously suggested, because RAGE containing different amino acids at this position, namely Q391 and P391 (naturally found in camels and cattle, respectively) can also be activated by RAGE ligands as well as by RAGE ligand-independent activation by certain activated co-located GPCRs (see Example 7). Although PKCζ inhibition is able to prevent activation of full-length RAGE, it is not acting by preventing phosphorylation of RAGE, as it also inhibits signalling via a full-length S391Q chimeric RAGE mutant that contains no amino acids capable of sustaining phosphorylation (i.e. no serines, threonines or tyrosines).

The interaction of the cytosolic tail of RAGE with Diaph1 is known to be important for pro-inflammatory signalling, possibly as it facilitates recruitment and activation of PKCζ, with which Diaph1 also binds, and subsequent "scissor-like" changes in structure of RAGE mediated via interaction with the transmembrane domain. In the inventors' experiments, silencing of Diaph1 or PKCζ inhibits both Ang II and s100-induced pro-inflammatory signalling via full-length RAGE and signalling with Ang II mediated by N-truncated RAGE constructs retaining the RAGE TMD. However, N-truncated RAGE constructs missing the RAGE TMD are still able to be activated by Ang II following silencing of Diaph1 or PKCζ. Diaph1 is thought to interact with RAGE in the cytosol via a small charged patch. Alanine-substitution of this charged patch (R366A-Q367A) prevents signalling mediated by the RAGE ligand, s100A8/A9. However, mutation of this charged patch or deletion of the alpha-loop it stabilises (e.g. $RAGE_{370-404}$) has no effect on RAGE ligand-independent activation of the cytosolic tail of RAGE following activation of certain co-located GPCRs, such as the $AT_1R$ by Ang II. Consequently, proposed methods to disrupt the binding of Diaph-1 to RAGE using small molecules or other inhibitors (Ramasamy et al. 2016) will have no effect on RAGE ligand-independent activation of RAGE by certain activated co-located GPCRs. Moreover, the ability of N-trucated $RAGE_{362-404}$ to be activated by certain co-located GPCRs, such as the $AT_1R$ is not inhibited by inhibition of PKCζ or Diaph-1 using siRNA, confirming the mechanism of action of this domain is independent of both these RAGE binding partners.

Even though the RAGE ectodomain has historically been considered to be essential for its functions, without wishing to be bound by theory, the inventors believe the RAGE ligand-independent activation of the cytosolic tail of RAGE by certain activated co-located GPCRs appears to be the dominant mechanism inducing downstream effector activation and signalling. Consistent with this hypothesis, treatment with the wild-type $RAGE_{362-404}$ oligopeptide restores atherogenesis in diabetic AGER/apoE DKO mice, suggesting that the relative vasculo-protection observed in AGER KO mice is mediated through inhibition of this RAGE ligand-independent transactivation pathway, further highlighting its pathophysiological importance and rationale for inhibition of RAGE ligand-independent activation of the cytosolic tail of RAGE by certain activated co-located GPCRs.

Only some cells (e.g. endothelial cells, leucocytes) express RAGE under basal conditions, meaning that the RAGE ligand-independent activation of RAGE by certain activated co-located GPCRs described by the inventors is limited to these cell types under basal conditions. Most other cell types do not express RAGE under basal conditions. Over and above findings that RAGE expression has no effect on classic Gq signalling induced following $AT_1R$ activation, this limited distribution of expression may partly explain why RAGE deletion/inhibition does not impact on blood pressure, natriuresis or other homeostatic functions of the systemic RAAS. However, following injury, inflammation, stress or hypoxia, the de novo or enhanced expression of RAGE may provide a conduit for the pro-inflammatory effects of local GPCR activation.

Although systemic antagonists of GPCR-mediated signalling currently exist (e.g. $AT_1R$ antagonists, CCR2 antagonists), the inhibition achieved by this strategy removes all signalling arising from respective blocked GPCRs. This is likely to be suboptimal in some circumstances as it may induce feedback escape from inhibition or result in unwanted effects arising from inhibition of physiological signalling. For example, inhibition of the $AT_1R$ results in blood pressure lowering which may be undesirable in some settings (e.g. following a myocardial infarction, stroke or in severe heart failure), as well as inducing feedback 'escape' activation of the RAAS. The potential advantage of targeting only key cells in which this RAGE ligand-independent activation of RAGE is in operation, and then only the pro-inflammatory signals arising from GPCR activation, is that the limitations of systemic inhibition do not apply.

As a proof of principle, the inventors show that in endothelial cells replete in both RAGE and $AT_1R$, over-expression of S391A-RAGE or treatment with a TAT-S391A-$RAGE_{362-404}$ oligopeptide is able to inhibit Ang II-$AT_1R$ dependent pro-inflammatory signalling, as effectively as an $AT_1R$ blocker, but without modifying canonical IP-1-dependent signalling. The same oligopeptide applied to the aorta ex vivo is also able to block the induction of pro-inflammatory molecules following exposure to Ang II. In addition, when delivered to Ace2/apoE DKO mice or diabetic apoE KO mice for ten weeks, the S391A-$RAGE_{362-404}$ peptide was able to attenuate RAAS-dependent atherosclerosis, without affecting blood pressure levels. Furthermore, the inventors have shown that $RAGE_{338-361}$ or $RAGE_{343-361}$ can also inhibit Ang II-$AT_1R$ dependent pro-inflammatory signalling in endothelial cells replete in both RAGE and $AT_1R$. These data underline the therapeutic potential of specifically targeting this novel pro-inflammatory signalling pathway.

The inhibition achieved with the S391A-$RAGE_{362-404}$ oligopeptide is not overcome by excess wild-type $RAGE_{362-404}$, while low concentrations of S391A-$RAGE_{362-404}$ oligopeptide overcomes existing wild-type RAGE, suggesting its actions are not simply competitive. Moreover, that equivalent inhibition can be achieved using the dodecapeptide $RAGE_{379-390}$ shows that changes over a small region of an alpha helix, and specifically key residues over this region, alters the affinity of such RAGE mutants for signalling mediators, including IQGAP-1, which are then rendered blocked to endogenous signalling by wild type RAGE.

Notably, the efficacy of S391A-$RAGE_{362-404}$ in inhibiting pro-inflammatory signalling induced following activation of co-located GPCRs (e.g. CCR2 by MCP-1), and the actions of RAGE in mediating activation of NFκB following activation of GPCRs by their cognate ligands (e.g. activation of CCR2-CHO cells by MCP or CXCR2-CHO cells by IL-8), confirms that the effect of an activated co-located GPCR resulting in RAGE ligand-independent activation of RAGE is not exclusive to $AT_1R$, and generalizable to pro-inflammatory signalling induced following activation of certain other co-located GPCRs. Without wishing to be bound by theory, the inventors believe that the key RAGE pharmacophore identified herein interacts with signalling elements common to many GPCRs with pro-inflammatory effects, or by interaction with wild-type RAGE.

The inventors anticipate that mechanistic understanding of RAGE-GPCR heteromers will lead directly to the development of novel therapeutics that are able to specifically target the adverse effects of RAGE ligand-independent activation of RAGE by certain activated co-located GPCRs without compromising physiological signalling or induce feedback 'escape' from their inhibition. These data may be applicable across a broad range of conditions in which RAGE-mediated signalling has been implicated including atherosclerosis, neurodegenerative diseases, malignancy, diabetic complications and other important inflammatory and pro-proliferative conditions.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

As used herein, "isolated" when describing a peptide modulator of the invention means a peptide described herein that is not in a natural state (e.g. it is disassociated from a larger protein molecule or cellular debris in which it naturally occurs or is normally associated with), or is a non-naturally occurring fragment of a naturally occurring protein (e.g. the peptide comprises less than 25%, preferably less than 10% and most preferably less than 5% of the naturally occurring protein). Isolated also may mean that the amino acid sequence of the peptide does not occur in nature, for example, because the sequence is modified from a naturally occurring sequence (e.g. by alteration of certain amino acids, including basic (i.e. cationic) amino acids such as arginine, tryptophan, or lysine), or because the sequence does not contain flanking amino acids which are present in nature. The term "isolated" may mean that the peptide or amino acid sequence is a man-made sequence or polypeptide and may be non-naturally occurring.

Likewise, "isolated" as used in connection with nucleic acids which encode peptides embraces all of the foregoing, e.g. the isolated nucleic acids are disassociated from adjacent nucleotides with which they are associated in nature, and can be produced recombinantly, synthetically, by purification from biological extracts, and the like. Isolated nucleic acids can contain a portion that encodes one of the foregoing peptides and another portion that codes for another peptide or protein. The isolated nucleic acids also can be labeled. The nucleic acids include codons that are preferred for animal, bacterial, plant, or fungal usage. In certain embodiments, the isolated nucleic acid is a vector, such as an expression vector, which includes a nucleic acid that encodes one of the foregoing isolated peptides. A general method for the construction of any desired DNA sequence is provided, e.g., in Brown J. et al. (1979), Methods in Enzymology, 68:109; Sambrook J, Maniatis T (1989), supra.

The term "amino acid" or "residue" as used herein includes any one of the twenty naturally-occurring amino acids, the D-form of any one of the naturally-occurring amino acids, non-naturally occurring amino acids, and derivatives, analogues and mimetics thereof. Any amino acid, including naturally occurring amino acids, may be purchased commercially or synthesized by methods known in the art. Examples of non-naturally-occurring amino acids include norleucine ("Nle"), norvaline ("Nva"), β-Alanine, L- or D-naphthalanine, ornithine ("Orn"), homoarginine (homoArg) and others well known in the peptide art, including those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference.

Common amino acids may be referred to by their full name, standard single-letter notation (IUPAC), or standard three-letter notation for example: A, Ala, alanine; C, Cys, cysteine; D, Asp, aspartic acid (aspartate); E, Glu, glutamic acid (glutamate); F, Phe, phenylalanine; G, Gly, glycine; H, His, histidine; I, Ile isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine. Any and all of the amino acids in the compositions herein can be naturally occurring, synthetic, and derivatives or mimetics thereof.

Non-peptide analogues of peptides, e.g., those that provide a stabilized structure or lessened biodegradation, are also contemplated. Peptide mimetic analogues can be prepared based on a selected peptide by replacement of one or more residues by non-peptide moieties. Preferably, the non-peptide moieties permit the peptide to retain its natural conformation, or stabilize a preferred, e.g., bioactive, conformation. One example of methods for preparation of non-peptide mimetic analogues from peptides is described in Nachman et al., *Regul. Pept.* 57:359-370 (1995). The term "peptide" as used herein embraces all of the foregoing.

As mentioned above, the peptide of the present invention may be composed either of naturally occurring amino acids, i.e. L-amino acids, or of D-amino acids, i.e. of an amino acid sequence comprising D-amino acids in retro-inverso order as compared to the native sequence. The term "retro-inverso" refers to an isomer of a linear peptide in which the direction of the sequence is reversed and the chirality of each amino acid residue is inverted. Thus, any sequence herein, being present in L-form is also inherently disclosed herein as a D-enantiomeric (retro-inverso) peptide sequence. D-enantiomeric (retro-inverso) peptide sequences according to the invention can be constructed, e.g. by synthesizing a reverse of the amino acid sequence for the corresponding native L-amino acid sequence. In D-retro-inverso enantiomeric peptides, e.g. a component of the isolated peptide, the positions of carbonyl and amino groups in each single amide bond are exchanged, while the position of the side-chain groups at each alpha carbon is preserved.

Preparation of a component of the isolated peptide modulators of embodiments of the invention as defined above having D-enantiomeric amino acids can be achieved by chemically synthesizing a reverse amino acid sequence of the corresponding naturally occurring L-form amino acid sequence or by any other suitable method known to a skilled person. Alternatively, the D-retro-inverso-enantiomeric form of a peptide or a component thereof may be prepared using chemical synthesis as disclosed above utilizing an L-form of an peptide or a component thereof as a matrix for chemical synthesis of the D-retro-inverso-enantiomeric form.

Various changes may be made including the addition of various side groups that do not affect the manner in which a peptide modulator of embodiments of the invention functions, or which favourably affect the manner in which a peptide modulator of embodiments of the invention functions. Such changes may involve adding or subtracting charge groups, substituting amino acids, adding lipophilic moieties that do not affect binding but that affect the overall charge characteristics of the peptide modulator of embodiments of the invention facilitating delivery across the blood-brain barrier, etc. For each such change, no more than routine experimentation is required to test whether the molecule functions according to the invention. One simply makes the desired change or selects the desired peptide and applies it in a fashion as described in detail in the examples.

In one form of the invention, the term "sequence identity" as defined herein means that the sequences are compared as follows. To determine the percent identity of two amino acid sequences, the sequences can be aligned for optimal comparison purposes (e.g., gaps can be introduced in the sequence of a first amino acid sequence). The amino acids at corresponding amino acid positions can then be compared. When a position in the first sequence is occupied by the same amino acid as the corresponding position in the second sequence, then the molecules are identical at that position. The percent identity between the two sequences is a function of the number of identical positions shared by the sequences. For example, where a particular peptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Such a determination of percent identity of two sequences can be accomplished using a mathematical algorithm.

A preferred, non-limiting example of a mathematical algorithm utilized for the comparison of two sequences is the algorithm of Karlin et al. (1993), PNAS USA, 90:5873-5877. Such an algorithm is incorporated into the NBLAST program, which can be used to identify sequences having the desired identity to the amino acid sequence of the invention. To obtain gapped alignments for comparison purposes, Gapped BLAST can be utilized as described in Altschul et al., (1997), Nucleic Acids Res, 25:3389-3402. When utilizing BLAST and Gapped BLAST programs, the default parameters of the respective programs (e.g., NBLAST) can be used. The sequences further may be aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence. The described methods of determination of the percent identity of two amino acid sequences can be applied correspondingly to nucleic acid sequences.

In one embodiment a peptide modulator of embodiments of the invention may be linked directly or via a linker. A "linker" in the present context is usually a peptide, oligopeptide or polypeptide and may be used to link multiples of the peptides to one another. The peptides of the invention selected to be linked to one another can be identical sequences, or are selected from any of the peptides of the invention. A linker can have a length of 1-10 amino acids, more preferably a length of 1 to 5 amino acids and most preferably a length of 1 to 3 amino acids. In certain embodiments, the linker is not required to have any secondary structure forming properties, i.e. does not require a α-helix or β-sheet structure forming tendency, e.g. if the linker is composed of at least 35% of glycine residues. As mentioned hereinbefore, a linker can be a cleavable peptide such as an MMP peptide which can be cleaved intracellularly by normal cellular processes, effectively raising the intracellular dose of the previously linked peptides, while keeping the extracellular dose low enough to not be considered toxic. The use of a(n) intracellularly/endogenously cleavable peptide, oligopeptide, or polypeptide sequence as a linker permits the peptides to separate from one another after delivery into the target cell. Cleavable oligo- or polypeptide sequences in this context also include protease cleavable oligo- or polypeptide sequences, wherein the protease cleavage site is typically selected dependent on the protease endogenously expressed by the treated cell. The linker as defined above, if present as an oligo- or polypeptide sequence, can be composed either of D-amino acids or of naturally occurring amino acids, i.e. L-amino acids. As an alternative to the above, coupling or fusion of the peptides can be accomplished via a coupling or conjugating agent, e.g. a cross-linking reagent.

There are several intermolecular cross-linking reagents which can be utilized, see for example, Means and Feeney, Chemical Modification of Proteins, Holden-Day, 1974, pp. 39-43. Among these reagents are, for example, N-succinimidyl 3-(2-pyridyldithio)propionate (SPDP) or N,N'-(1,3-phenylene)bismaleimide; N,N'-ethylene-bis-(iodoacetamide) or other such reagent having 6 to 11 carbon methylene bridges; and 1,5-difluoro-2,4-dinitrobenzene. Other cross-linking reagents useful for this purpose include: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking reagents may be homobifunctional, i.e., having two functional groups that undergo the same reaction. A preferred homobifunctional cross-linking reagent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking reagents may also be heterobifunctional. Heterobifunctional cross-linking reagents have two different functional groups, for example an amine-reactive group and a thiol-reactive group, that will cross-link two proteins having free amines and thiols, respectively. Examples of heterobifunctional cross-linking reagents are succinimidyl 4-(N-maleimidomethyl) cyclohexane-1-carboxylate (SMCC), m-maleimidobenzoyl-N-hydroxysuccinimide ester (MBS), and succinimide 4-(p-maleimidophenyl)butyrate (SMPB), an extended chain analogue of MBS. The succinimidyl group of these cross-linking reagents with a primary amine, and the thiol-reactive maleimide forms a covalent bond with the thiol of a cysteine residue. Because cross-linking reagents often have low solubility in water, a hydrophilic moiety, such as a sulfonate group, may be added to the cross-linking reagent to improve its water solubility. Sulfo-MBS and sulfo-SMCC are examples of cross-linking reagents modified for water solubility. Many cross-linking reagents yield a conjugate that is essentially non-cleavable under cellular conditions. Therefore, some cross-linking reagents contain a covalent bond, such as a disulfide, that is cleavable under cellular conditions. For example, Traut's reagent, dithiobis (succinimidylpropionate) (DSP), and N-succinimidyl 3-(2-pyridyldithio) propionate (SPDP) are well-known cleavable cross-linkers. The use of a cleavable cross-linking reagent permits the peptides to be separated after delivery into the target cell, if desired, provided the cell is capable of cleaving a particular sequence of the crosslinker reagent. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g. proline. Alternatively, a spacer arm may be part of the cross-linking reagent, such as in "long-chain SPDP" (Pierce Chem. Co., Rockford, Ill., cat. No. 21651H). Numerous cross-linking reagents, including the ones discussed above, are commercially available. Detailed instructions for their use are readily available from the commercial suppliers. A general reference on protein cross-linking and conjugate preparation is: Wong, Chemistry of Protein Conjugation and Cross-Linking, CRC Press (1991).

In one embodiment, peptide modulators may also contain a "derivative", "variant", or "functional fragment", i.e. a sequence of a peptide that is derived from the naturally occurring (L-amino-acid) sequence of a peptide of the invention as defined above by way of substitution(s) of one or more amino acids at one or more sites of the amino acid sequence, by way of deletion(s) of one or more amino acids at any site of the naturally occurring sequence, and/or by way of insertion(s) of one or more amino acids at one or more sites of the naturally occurring peptide sequence. "Derivatives" shall retain their biological activity if used as peptides of the invention. Derivatives in the context of the present invention may also occur in the form of their L- or D-amino-acid sequences as defined above, or both.

If substitution(s) of amino acid(s) are carried out for the preparation of a derivative of the peptides of the invention, conservative (amino acid) substitutions are preferred. Conservative (amino acid) substitutions typically include substitutions within the following groups: glycine and alanine; valine, isoleucine and leucine; aspartic acid (aspartate) and glutamic acid (glutamate); asparagine and glutamine; serine and threonine; lysine and arginine; and phenylalanine and tyrosine. Thus, preferred conservative substitution groups are aspartate-glutamate; asparagine-glutamine; valine-leucine-isoleucine; alanine-valine; and phenylalanine-tyrosine. By such mutations e.g. stability and/or effectiveness of a peptide may be enhanced. If mutations are introduced into the peptide, the peptide remains (functionally) homologous, e.g. in sequence, in function, and in antigenic character or other function. Such mutated components of the peptide can possess altered properties that may be advantageous over the non-altered sequences of the peptides of the invention for certain applications (e.g. increased pH optimum, increased temperature stability etc.).

In one embodiment, a derivative of the peptide of the invention is defined as having substantial identity with the non-modified sequences of the peptide of the invention. Particularly preferred are amino acid sequences which have at least 30% sequence identity, preferably at least 50% sequence identity, even preferably at least 60% sequence identity, even preferably at least 75% sequence identity, even more preferably at least 80%, yet more preferably 90% sequence identity and most preferably at least 95% or even 99% sequence identity to the naturally occurring analogue. Appropriate methods for synthesis or isolation of a functional derivative of the peptides of the invention as well as for determination of percent identity of two amino acid sequences are described above. Additionally, methods for production of derivatives of the peptides as disclosed above are well known and can be carried out following standard methods which are well known by a person skilled in the art (see e.g., Sambrook J, Maniatis T (1989)).

As a further embodiment, the invention provides pharmaceutical compositions or medicaments comprising the modulators as defined herein. In certain embodiments, such pharmaceutical compositions or medicaments comprise the modulators as well as an optional linker, as defined herein.

Additionally, such a pharmaceutical composition or medicament can comprise a pharmaceutically acceptable carrier, adjuvant, or vehicle. A "pharmaceutically acceptable carrier, adjuvant, or vehicle" according to the invention refers to a non-toxic carrier, adjuvant or vehicle that does not destroy the pharmacological activity or physiological targeting of the modulator with which it is formulated. Pharmaceutically acceptable carriers, adjuvants or vehicles that can be used in the pharmaceutical compositions of this invention include, but are not limited to those that can be applied cranially or intracranially, or that can cross the blood-brain barrier (BBB). Notwithstanding this, the pharmaceutical compositions of the invention can include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally, cerebrally, or via an implanted reservoir.

The term "fragment" as used herein with reference to any domain of RAGE, or with reference to any other polypeptide sequence, is to be understood as meaning one or more amino acid residues less than the domain of RAGE or any other polypeptide sequence to which it refers.

The term parenteral as used herein includes subcutaneous, intravenous, intramuscular, intra-articular, intra-synovial, intrasternal, intrathecal, intrahepatic, intralesional and intracranial injection or infusion techniques. The pharmaceutical compositions are administered orally, intraperitoneally or intravenously. Sterile injectable forms of the pharmaceutical compositions of this invention may be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

As such, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavouring or colouring agents may also be added.

Alternatively, the pharmaceutical composition as defined herein may be administered in the form of suppository for rectal administration. Such a suppository can be prepared by mixing the agent with a suitable non-irritating excipient that is solid at room temperature but liquid at rectal temperature and, therefore, will melt in the rectum to release the drug. Such materials include cocoa butter, beeswax and polyethylene glycols.

The pharmaceutical composition as defined herein may also be administered topically, especially when the target of treatment includes areas or organs readily accessible by topical application, including diseases of the brain, other intra-cranial tissues, the eye, or the skin. Suitable formulations are readily prepared for each of these areas or organs.

For topical applications, the pharmaceutical composition as defined herein may be formulated in a suitable ointment containing modulators as identified herein, suspended or dissolved in one or more carriers. Carriers for topical administration of the peptide include, but are not limited to, mineral oil, liquid petrolatum, white petrolatum, propylene glycol, polyoxyethylene, polyoxypropylene compound, emulsifying wax and water. Alternatively, the pharmaceutical composition as defined herein can be formulated in a suitable lotion or cream containing the peptide suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutical composition as defined herein may also be administered by nasal aerosol or inhalation. Such a composition may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The pharmaceutically acceptable composition or medicament herein is formulated for oral or parenteral administration, e.g. by injection.

For treatment purposes, a non-toxic, effective amount of the modulator may be used for preparation of a pharmaceutical composition as defined above. Therefore, an amount of the modulator may be combined with the carrier material(s) to produce a composition as defined above.

The pharmaceutical composition is typically prepared in a single (or multiple) dosage form, which will vary depending upon the host treated and the particular mode of administration. Usually, the pharmaceutical composition is formulated so that a dosage range per dose of 0.0001 to 100 mg/kg body weight/day of the peptide can be administered to a patient receiving the pharmaceutical composition. Preferred dosage ranges per dose vary from 0.01 mg/kg body weight/day to 50 mg/kg body weight/day, even further preferred dosage ranges per dose range from 0.1 mg/kg body weight/day to 10 mg/kg body weight/day.

However, dosage ranges and treatment regimens as mentioned above may be adapted suitably for any particular patient dependent upon a variety of factors, including the activity of the specific modulator employed, the age, body weight, general health, sex, diet, time of administration, rate of excretion, drug combination, the judgment of the treating physician and the severity of the particular disease being treated. In this context, administration may be carried with in an initial dosage range, which may be varied over the time of treatment, e.g. by increasing or decreasing the initial dosage range within the range as set forth above. Alternatively, administration may be carried out in a continuous manner by administering a specific dosage range, thereby maintaining the initial dosage range over the entire time of treatment. Both administration forms may furthermore be combined, e.g. if the dosage range is to be adapted (increased or decreased) between various sessions of the treatment but kept constant within the single session so that dosage ranges of the various sessions differ from each other.

When used therapeutically, the modulators of the invention are administered in therapeutically effective amounts. In general, a therapeutically effective amount means an amount necessary to delay the onset of, inhibit the progression of, or halt altogether the particular condition being treated. Generally, a therapeutically effective amount will vary with the subject's age and condition, as well as the nature and extent of the disease in the subject, all of which can be determined by one of ordinary skill in the art. The dosage may be adjusted by the individual physician, particularly in the event of any complications being experienced.

As mentioned above, one aspect of the invention relates to nucleic acid sequences and their derivatives which code for an isolated peptide modulator or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrrolidone, 0.02% Bovine Serum Albumin, 25 mMNaH$_2$PO$_4$ (pH7), 0.5% SDS, 2 mM EDTA). SSC is 0.15 M Sodium Chloride/0.15 M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1×SSC/0.1×SDS at 65° C.

The present invention furthermore provides kits comprising the abovementioned pharmaceutical composition (in one or more containers) in at least one of the above formulations and an instruction manual or information brochure regarding instructions and/or information with respect to application of the pharmaceutical composition.

Those skilled in the field of the invention will appreciate that the invention described herein is susceptible to variations and modifications other than those specifically described. It is to be understood that the invention includes all such functional variations and modifications. The invention also includes all of the steps, features, compositions and compounds referred to or indicated in this specification, individually or collectively, and any and all combinations or any two or more of said steps or features. The present invention is not to be limited in scope by the specific embodiments described herein, which are intended for the purpose of exemplification only. Functionally-equivalent products, compositions and methods are clearly within the scope of the invention, as described herein. Furthermore, the present invention is performed without undue experimentation using, unless otherwise indicated, conventional techniques of molecular biology, microbiology, neurobiology, virology, recombinant DNA technology, peptide synthesis in solution, solid phase peptide synthesis, and immunology, or techniques cited herein.

BIBLIOGRAPHY

1. Abe, R. & Yamagishi, S. (2008) AGE-RAGE system and carcinogenesis. Current pharmaceutical design, 14: 940-945.
2. Ahmad, A., Bhattacharya, S., Sridhar, A., Iqbal, A. M. & Mariani, T. J. (2016) Recurrent copy number variants associated with bronchopulmonary dysplasia. Pediatric research, 79, 940-945.
3. Aho, V., Ollila, H. M., Rantanen, V., Kronholm, E., Surakka, I., van Leeuwen, W. M. A., Lehto, M., Matikainen, S., Ripatti, S., Härmä, M., Sallinen, M., Salomaa, V., Jauhiainen, M., Alenius, H., Paunio, T. & Porkka-Heiskanen, T. (2013) Partial Sleep Restriction Activates Immune Response-Related Gene Expression Pathways: Experimental and Epidemiological Studies in Humans. PLOS ONE, 8, e77184.
4. Alexander, S., Mathie, A. & Peter, J. (2011) Guide to Receptors and Channels (GRAC), 5th edition. Br. J. Pharmacol., 164, S1-S324.
5. Allen, S. et al. Chemokine: Receptor Structure, Interactions and Antagonism. Annual Review Immunology, 2007, 25: 787-820.
6. Allende, M. L., Bektas, M., Lee, B. G., Bonifacino, E., Kang, J., Tuymetova, G., Chen, W., Saba, J. D. & Proia, R. L. (2011) Sphingosine-1-phosphate lyase deficiency produces a pro-inflammatory response while impairing neutrophil trafficking. Journal of Biological Chemistry, 286, 7348-7358.
7. An, S., Bleu, T., Hallmark, O. G. & Goetzl, E. J. (1998) Characterization of a novel subtype of human G protein-coupled receptor for lysophosphatidic acid. Journal of Biological Chemistry, 273, 7906-7910.
8. Anders H J et al. (2010) Questions about Chemokine and Chemokine Receptor Antagonism in Renal Inflammation, Nephron Exp Nephrol, 114: e33-e38.
9. Angelopoulou, E., Piperi, C., Adamopoulos, C. & Papavassiliou, A. G. (2016) Pivotal role of high-mobility group box 1 (HMGB1) signalling pathways in glioma development and progression. Journal of molecular medicine, doi: 10.1007/s00109-016-1435-y
10. Antoniak, S., Owens, A. P., Baunacke, M., Williams, J. C., Lee, R. D., Weithäuser, A., Sheridan, P. A., Malz, R., Luyendyk, J. P. & Esserman, D. A. (2013) PAR-1 contributes to the innate immune response during viral infection. The Journal of clinical investigation, 123, 1310-1322.
11. Arita, M., Ohira, T., Sun, Y.-P., Elangovan, S., Chiang, N. & Serhan, C. N. (2007) Resolvin E1 selectively interacts with leukotriene B4 receptor BLT1 and ChemR23 to regulate inflammation. The Journal of Immunology, 178, 3912-3917.
12. Awojoodu, A. O., Ogle, M. E., Sefcik, L. S., Bowers, D. T., Martin, K., Brayman, K. L., Lynch, K. R., Peirce-Cottler, S. M. & Botchwey, E. (2013) Sphingosine 1-phosphate receptor 3 regulates recruitment of anti-inflammatory monocytes to microvessels during implant arteriogenesis. Proceedings of the National Academy of Sciences, 110, 13785-13790.
13. Ayer, L. M., Wilson, S. M., Traves, S. L., Proud, D. & Giembycz, M. A. (2008) 4, 5-Dihydro-1H-imidazol-2-yl)-[4-(4-isopropoxy-benzyl)-phenyl]-amine (RO1138452) is a selective, pseudo-irreversible orthosteric antagonist at the prostacyclin (IP)-receptor expressed by human airway epithelial cells: IP-receptor-mediated inhibition of CXCL9 and CXCL10 release. Journal of Pharmacology and Experimental Therapeutics, 324, 815-826.
14. Babusyte, A., Kotthoff, M., Fiedler, J. & Krautwurst, D. (2013) Biogenic amines activate blood leukocytes via trace amine-associated receptors TAAR1 and TAAR2. Journal of leukocyte biology, 93, 387-394.
15. Bader, M., Alenina, N., Andrade-Navarro, M. A. & Santos, R. A. (2014) MAS and its related G protein-coupled receptors, Mrgprs. Pharmacol. Rev., 66, 1080-1105.
16. Ballatore C., Huryn D. M. and Smith A. B. Carboxylic Acid (Bio)Isosteres in Drug Design. ChemMedChem, 2013, 8: 385-395.
17. Ballinger, M. L., et al. Glycated and carboxy-methylated proteins do not directly activate human vascular smooth muscle cells. Kidney Int, 2005, 68: 2756-2765.
18. Bandyopadhyay, S., Jeong, K. H., Hansen, J. T., Vassilev, P. M., Brown, E. M. & Chattopadhyay, N. (2007) Calcium-sensing receptor stimulates secretion of an interferon-γ-induced monokine (CXCL10) and monocyte chemoattractant protein—3 in immortalized GnRH neurons. Journal of neuroscience research, 85, 882-895.
19. Barile, G. R. & Schmidt, A. M. (2007) RAGE and its ligands in retinal disease. Current molecular medicine, 7: 758-765.
20. Baroni, A., Perfetto, B., Canozo, N., Braca, A., Farina, E., Melito, A., De Maria, S. & Cartenì, M. (2008) Bombesin: A possible role in wound repair. Peptides, 29, 1157-1166.
21. Bathgate, R., Halls, M., Van Der Westhuizen, E., Callander, G., Kocan, M. & Summers, R. (2013) Relaxin family peptides and their receptors. Physiological reviews, 93, 405-480.
22. Batkulwar K B, Bansode S B, Patil G V, Godbole R K, Kazi R S, Chinnathambi S, Shanmugam D, Kulkarni M J (2015) Investigation of phosphoproteome in RAGE signalling. Proteomics, 15, 245-259.
23. Beaulieu, J. M. & Gainetdinov, R. R. (2011) The physiology, signalling, and pharmacology of dopamine receptors. Pharmacol Rev, 63, 182-217.
24. Benigni A, Corna D, Zoja C, et al. (2009) Disruption of the angiotensin II type 1 receptor promotes longevity in mice. J Clin Invest, 119: 524-530.
25. Benigni, A., Cassis, P. and Remuzzi, G. (2010) Angiotensin II revisited: new roles in inflammation, immunology and aging. EMBO Mol Med, 2: 247-257.
26. Benya, R. V., Matkowskyj, K. A., Danilkovich, A. & Hecht, G. (1998) Galanin Causes Cl— Secretion in the Human Colon: Potential Significance of Inflammation-Associated NF-κB Activation on Galanin-1 Receptor Expression and Function. Annals of the New York Academy of Sciences, 863, 64-77.
27. Bernardi, S., Candido, R., Toffoli, B., Carretta, R. & Fabris, B. (2011) Prevention of accelerated atherosclerosis by AT1 receptor blockade in experimental renal failure. Nephrology, dialysis, transplantation: official publication of the European Dialysis and Transplant Association—European Renal Association, 26: 832-838.
28. Bhave, G., Karim, F., Carlton, S. & Gereau Iv, R. (2001) Peripheral group I metabotropic glutamate receptors modulate nociception in mice. Nature neuroscience, 4, 417-423.
29. Bierhaus, A., et al. (2001) Diabetes-associated sustained activation of the transcription factor nuclear factor-kappaB. Diabetes, 50: 2792-2808.
30. Billings, E. A., Lee, C. S., Owen, K. A., D'Souza, R. S., Ravichandran, K. S. & Casanova, J. E. (2016) The adhesion GPCR BAI1 mediates macrophage ROS production and microbicidal activity against Gram-negative bacteria. Sci. Signal., 9, ra14-ra14.
31. Blaes, N. & Girolami, J.-P. (2013) Targeting the 'Janus face' of the B2-bradykinin receptor. Expert Opinion on Therapeutic Targets, 17, 1145-1166.
32. Body, J.-J., Glibert, F., Nejai, S., Fernandez, G., Van Langendonck, A. & Borkowski, A. (1990) Calcitonin Receptors on Circulating Normal Human Lymphocytes*. The Journal of Clinical Endocrinology & Metabolism, 71, 675-681.
33. Boie, Y., N. Sawyer, D. M. Slipetz, K. M. Metters, and M. Abramovitz. Molecular cloning and characterization of the human prostanoid DP receptor. J Biol Chem, 1995, 270:18910-6.
34. Boie, Y., T. H. Rushmore, A. Darmon-Goodwin, R. Grygorczyk, D. M. Slipetz, and K. M. Metters. Cloning and expression of a cDNA for the human prostanoid IP receptor. J Biol Chem, 1994, 269:12173-8.
35. Boisvert, W. A. (2004) Modulation of atherogenesis by chemokines. Trends in Cardiovascular Medicine, 14: 161-165.
36. Bossard, C., Souazé, F., Jarry, A., Bezieau, S., Mosnier, J.-F., Forgez, P. & Laboisse, C. L. (2007) Over-expression of neurotensin high-affinity receptor 1 (NTS1) in relation with its ligand neurotensin (NT) and nuclear β-catenin in inflammatory bowel disease-related oncogenesis. Peptides, 28, 2030-2035.
37. Boulay, F., M. Tardif, L. Brouchon, and P. Vignais. The human N-formylpeptide receptor: characterization of two cDNA isolates and evidence for a new subfamily of G-protein-coupled receptors. Biochemistry, 1990, 29:11123-33.
38. Boxall, S., Berthele, A., Laurie, D., Sommer, B., Zieglgänsberger, W., Urban, L. & Tölle, T. (1997) Enhanced expression of metabotropic glutamate receptor 3 messenger RNA in the rat spinal cord during ultraviolet irradiation induced peripheral inflammation. Neuroscience, 82, 591-602.
39. Boyd, J. H., Holmes, C. L., Wang, Y., Roberts, H. & Walley, K. R. (2008) Vasopressin decreases sepsis-induced pulmonary inflammation through the V2R. Resuscitation, 79, 325-331.
40. Braley A., Kwak T., Jules J., Harja E., Landgraf R., Hudson B. I. (2016) Regulation of Receptor for Advanced Glycation End Products (RAGE) Ectodomain Shedding and Its Role in Cell Function. J Biol Chem. 291, 12057-73.
41. Bräuner-Osborne, H., Jensen, A. A., Sheppard, P. O., Brodin, B., Krogsgaard-Larsen, P. & O'Hara, P. (2001) Cloning and characterization of a human orphan family C G-protein coupled receptor GPRC5D. Biochimica et Biophysica Acta (BBA)-Gene Structure and Expression, 1518, 237-248.
42. Breyer, R. M., C. K. Bagdassarian, S. A. Myers, and M. D. Breyer. Prostanoid receptors: subtypes and signalling. Annu Rev Pharmacol Toxicol, 2001, 41:661-90.
43. Brezillon, S., Lannoy, V., Franssen, J.-D., Le Poul, E., Dupriez, V., Lucchetti, J., Detheux, M. & Parmentier, M. (2003) Identification of natural ligands for the orphan G protein-coupled receptors GPR7 and GPR8. Journal of Biological Chemistry, 278, 776-783.
44. Briscoe, C. P., Tadayyon, M., Andrews, J. L., Benson, W. G., Chambers, J. K., Eilert, M. M., Ellis, C., Elshourbagy, N. A., Goetz, A. S. & Minnick, D. T. (2003) The orphan 44. G protein-coupled receptor GPR40 is activated by medium and long chain fatty acids. Journal of Biological chemistry, 278, 11303-11311.
45. Brothers, S. P. & Wahlestedt, C. (2010) Therapeutic potential of neuropeptide Y (NPY) receptor ligands. EMBO Mol Med, 2, 429-439.
46. Brown, A. J., Goldsworthy, S. M., Barnes, A. A., Eilert, M. M., Tcheang, L., Daniels, D., Muir, A. I., Wigglesworth, M. J., Kinghorn, I. & Fraser, N. J. (2003) The Orphan G protein-coupled receptors GPR41 and GPR43 are activated by propionate and other short chain carboxylic acids. Journal of Biological Chemistry, 278, 11312-11319.
47. Bucher, M., Hobbhahn, J., Taeger, K. & Kurtz, A. (2002) Cytokine-mediated downregulation of vasopressin V1A receptors during acute endotoxemia in rats. American Journal of Physiology-Regulatory, Integrative and Comparative Physiology, 282, R979-R984.
48. Buler, M., Aatsinki, S.-M., Skoumal, R., Komka, Z., Tóth, M., Kerkelä, R., Georgiadi, A., Kersten, S. & Hakkola, J. (2012) Energy-sensing Factors Coactivator Peroxisome Proliferator-activated Receptor γ Coactivator 1-α (PGC-1α) and AMP-activated Protein Kinase Control Expression of Inflammatory Mediators in Liver INDUCTION OF INTERLEUKIN 1 RECEPTOR ANTAGONIST. Journal of Biological Chemistry, 287, 1847-1860.
49. Burgess, G. M., M. N. Perkins, H. P. Rang, E. A. Campbell, M. C. Brown, and P. Mcintyre. Bradyzide, a potent non-peptide B(2) bradykinin receptor antagonist with long-lasting oral activity in animal models of inflammatory hyperalgesia. Br J Pharmacol, 2000, 129:77-86.
50. Cai, Z., et al. Role of RAGE in Alzheimer's Disease. Cellular and molecular neurobiology, 2016, 36: 483-495.
51. Calderón-Garcidueñas, L., Kavanaugh, M., Block, M., D'Angiulli, A., Delgado-Chávez, R., Torres-Jardón, R., González-Maciel, A., Reynoso-Robles, R., Osnaya, N. & Villarreal-Calderon, R. (2012) Neuroinflammation, hyperphosphorylated tau, diffuse amyloid plaques, and down-regulation of the cellular prion protein in air pollution exposed children and young adults. Journal of Alzheimer's Disease, 28, 93-107.
52. Calonge, M., de Salamanca, A. E., Siemasko, K. F., Diebold, Y., Gao, J., Juárez-Campo, M. & Stern, M. E. (2005) Variation in the Expression of Inflammatory Markers and Neuroreceptors in Human Conjunctival Epithelial Cells. The Ocular Surface, 3, S-145-S-148.
53. Caminschi, I., Vandenabeele, S., Sofi, M., Mcknight, A. J., Ward, N., Brodnicki, T. C., Toy, T., Lahoud, M., Maraskovsky, E. & Shortman, K. (2006) Gene structure and transcript analysis of the human and mouse EGF-TM7 molecule, FIRE: Full Length Research Paper. DNA Sequence, 17, 8-14.
54. Candido, R., et al. (2002) Prevention of accelerated atherosclerosis by angiotensin-converting enzyme inhibition in diabetic apolipoprotein E-deficient mice. Circulation, 106: 246-253.
55. Candido, R., et al. (2004) Irbesartan but not amlodipine suppresses diabetes-associated atherosclerosis. Circulation, 109: 1536-1542.
56. Cani, P. D., Possemiers, S., Van de Wiele, T., Guiot, Y., Everard, A., Rottier, O., Geurts, L., Naslain, D., Neyrinck, A. & Lambert, D. M. (2009) Changes in gut microbiota control inflammation in obese mice through a mechanism involving GLP-2-driven improvement of gut permeability. Gut, 58, 1091-1103.
57. Cantagrel, V., Lossi, A., Boulanger, S., Depetris, D., Mattei, M., Gecz, J., Schwartz, C., Van Maldergem, L. & Villard, L. (2004) Disruption of a new X linked gene highly expressed in brain in a family with two mentally retarded males. Journal of medical genetics, 41, 736-742.
58. Cantarella, G., Scollo, M., Lempereur, L., Saccani-Jotti, G., Basile, F. & Bernardini, R. (2011) Endocannabinoids inhibit release of nerve growth factor by inflammation-activated mast cells. Biochemical pharmacology, 82, 380-388.
59. Capra, V., Ravasi, S., Accomazzo, M. R., Citro, S., Grimoldi, M., Abbracchio, M. P. & Rovati, G. E. (2005) CysLT1 receptor is a target for extracellular nucleotide-induced heterologous desensitization: a possible feedback mechanism in inflammation. Journal of Cell Science, 118, 5625-5636.
60. Caronti, B., Calderaro, C., Passarelli, F., Palladini, G. & Pontieri, F. E. (1998) Dopamine receptor mRNAs in the rat lymphocytes. Life sciences, 62, 1919-1925.
61. Carrillo-Vico, A., GARCÍA, S., Calvo, J. R. & Guerrero, J. M. (2003) Melatonin counteracts the inhibitory effect of PGE2 on IL-2 production in human lymphocytes via its mt1 membrane receptor. The FASEB Journal, 17, 755-757.
62. Caruso, C., Durand, D., Schioth, H. B., Rey, R., Seilicovich, A. & Lasaga, M. (2007) Activation of melanocortin 4 receptors reduces the inflammatory response and prevents apoptosis induced by lipopolysaccharide and interferon-gamma in astrocytes. Endocrinology, 148, 4918-4926.
63. Charo, I. F. & Ransohoff, R. M. (2006) The many roles of chemokines and chemokine receptors in inflammation. N Engl J Med, 354, 610-621.
64. Chen, A., Dong, L., Leffler, N. R., Asch, A. S., Witte, O. N. & Yang, L. V. (2011) Activation of GPR4 by acidosis increases endothelial cell adhesion through the cAMP/Epac pathway. PloS one, 6, e27586.
65. Chen, H. F., Jeung, E. B., Stephenson, M. & Leung, P. C. (1999) Human peripheral blood mononuclear cells express gonadotropin-releasing hormone (GnRH), GnRH receptor, and interleukin-2 receptor gamma-chain messenger ribonucleic acids that are regulated by GnRH in vitro. The Journal of clinical endocrinology and metabolism, 84, 743-750.
66. Chen, H. F., Jeung, E. B., Stephenson, M. & Leung, P. C. (1999) Human peripheral blood mononuclear cells express gonadotropin-releasing hormone (GnRH), GnRH receptor, and interleukin-2 receptor gamma-chain messenger ribonucleic acids that are regulated by GnRH in vitro. The Journal of clinical endocrinology and metabolism, 84, 743-750.
67. Chen, T.-Y., Hwang, T.-L., Lin, C.-Y., Lin, T.-N., Lai, H.-Y., Tsai, W.-P. & Lin, H.-H. (2011) EMR2 receptor ligation modulates cytokine secretion profiles and cell survival of lipopolysaccharide-treated neutrophils. Chang Gung Med J, 34, 468-477.
68. Chen, Y., Corriden, R., Inoue, Y., Yip, L., Hashiguchi, N., Zinkernagel, A., Nizet, V., Insel, P. A. & Junger, W. G. (2006) ATP release guides neutrophil chemotaxis via P2Y2 and A3 receptors. Science, 314, 1792-1795.
69. Chen, Z. J. & Minneman, K. P. (2005) Recent progress in alpha1-adrenergic receptor research. Acta Pharmacol Sin, 26, 1281-1287.
70. Chhajlani, V. (1996) Distribution of cDNA for melanocortin receptor subtypes in human tissues. Biochemistry and molecular biology international, 38, 73-80.
71. Chhuon, C., Pranke, I., Borot, F., Tondelier, D., Lipecka, J., Fritsch, J., Chanson, M., Edelman, A., Ollero, M. &

Guerrera, I. (2016) Changes in lipid raft proteome upon TNF-α stimulation of cystic fibrosis cells. Journal of Proteomics, 145, 246-253.
72. Chuah, Y. K., Basir, R., Talib, H., Tie, T. H. & Nordin, N. Receptor for advanced glycation end products and its involvement in inflammatory diseases. International journal of inflammation, 2013, 2013: 403460.
73. Consortium, I.G.o.A.S. (2013) Identification of multiple risk variants for ankylosing spondylitis through high-density genotyping of immune-related loci. Nature genetics, 45, 730-738.
74. Cook, I. H., Evans, J., Maldonado-Pérez, D., Critchley, H. O., Sales, K. J. & Jabbour, H. N. (2010) Prokineticin (PROK1) modulates interleukin (IL)-11 expression via prokineticin receptor 1 (PROKR1) and the calcineurin/NFAT signalling pathway. Molecular human reproduction, 16, 158-169.
75. Costa, A., Toschi, A., Murfuni, I., et al. Local Overexpression of Via-Vasopressin Receptor Enhances Regeneration in Tumor Necrosis Factor-Induced Muscle Atrophy. BioMed Research International, 2014, Article ID 235426, doi: 10.1155/2014/235426.
76. Cuddihy, R. M., Dutton, C. M. & Bahn, R. S. (1995) A polymorphism in the extracellular domain of the thyrotropin receptor is highly associated with autoimmune thyroid disease in females. Thyroid, 5, 89-95.
77. Cunningham, M. A., E. Rondeau, X. Chen, S. R. Coughlin, S. R. Holdsworth, and P. G. Tipping. Protease-activated receptor 1 mediates thrombin-dependent, cell-mediated renal inflammation in crescentic glomerulonephritis. J Exp Med, 2000, 191:455-62.
78. Czepielewski, R. S., Porto, B. N., Rizzo, L. B., Roesler, R., Abujamra, A. L., Pinto, L. G., Schwartsmann, G., de Queiroz Cunha, F. & Bonorino, C. (2012) Gastrin-releasing peptide receptor (GRPR) mediates chemotaxis in neutrophils. Proceedings of the National Academy of Sciences, 109, 547-552.
79. Czerwinski, M., Kern, J., Grodecka, M., Paprocka, M., Krop-Watorek, A. & Wasniowska, K. (2007) Mutational analysis of the N-glycosylation sites of Duffy antigen/receptor for chemokines. Biochem Biophys Res Commun, 356, 816-821.
80. D'Andrea, G., Terrazzino, S., Fortin, D., Farruggio, A., Rinaldi, L. & Leon, A. (2003) HPLC electrochemical detection of trace amines in human plasma and platelets and expression of mRNA transcripts of trace amine receptors in circulating leukocytes. Neuroscience letters, 346, 89-92.
81. D'Amato, M., Bruce, S., Bresso, F., Zucchelli, M., Ezer, S., Pulkkinen, V., Lindgren, C., Astegiano, M., Rizzetto, M. & Gionchetti, P. (2007) Neuropeptide s receptor 1 gene polymorphism is associated with susceptibility to inflammatory bowel disease. Gastroenterology, 133, 808-817.
82. D'Andrea, G., D'Arrigo, A., Facchinetti, F., Del Giudice, E., Colavito, D., Bernardini, D. & Leon, A. (2012) Octopamine, unlike other trace amines, inhibits responses of astroglia-enriched cultures to lipopolysaccharide via a β-adrenoreceptor-mediated mechanism. Neuroscience letters, 517, 36-40.
83. da Silveira, K. D., Coelho, F. M., Vieira, A. T., Sachs, D., Barroso, L. C., Costa, V. V., Bretas, T. L. B., Bader, M., de Sousa, L. P. & da Silva, T. A. (2010) Anti-inflammatory effects of the activation of the angiotensin-(1-7) receptor, MAS, in experimental models of arthritis. The Journal of Immunology, 185, 5569-5576.
84. Daffu, G., et al. Radical roles for RAGE in the pathogenesis of oxidative stress in cardiovascular diseases and beyond. International journal of molecular sciences, 2013, 14: 19891-19910.
85. Daugherty, A., Manning, M. W. & Cassis, L. A. (2000) Angiotensin II promotes atherosclerotic lesions and aneurysms in apolipoprotein E-deficient mice. J Clin Invest, 105: 1605-1612.
86. Davidson, C., Asaduzzaman, M., Arizmendi, N., Polley, D., Wu, Y., Gordon, J., Hollenberg, M., Cameron, L. & Vliagoftis, H. (2013) Proteinase-activated receptor-2 activation participates in allergic sensitization to house dust mite allergens in a murine model. Clinical & Experimental Allergy, 43, 1274-1285.
87. Dawson, J., Miltz, W., Mir, A. K., & Wiessner, C. (2003) Targeting monocyte chemoattractant protein-1 signalling in disease. Expert Opin Ther Targets, 7: 35-48.
88. De Martino, M. C., Hofland, L. J. & Lamberts, S. W. (2010) Somatostatin and somatostatin receptors: from basic concepts to clinical applications. Prog Brain Res, 182, 255-280.
89. Deng, J., Fujimoto, J., Ye, X.-F., Men, T.-Y., Van Pelt, C. S., Chen, Y.-L., Lin, X.-F., Kadara, H., Tao, Q. & Lotan, D. (2010) Knockout of the tumor suppressor gene Gprc5a in mice leads to NF-κB activation in airway epithelium and promotes lung inflammation and tumorigenesis. Cancer prevention research, 3, 424-437.
90. Dijksterhuis, J., Petersen, J. & Schulte, G. (2014) WNT/Frizzled signalling: receptor-ligand selectivity with focus on FZD-G protein signalling and its physiological relevance: IUPHAR Review 3. British journal of pharmacology, 171, 1195-1209.
91. Dixit, V. D., Schaffer, E. M., Pyle, R. S., Collins, G. D., Sakthivel, S. K., Palaniappan, R., Lillard, J. W. & Taub, D. D. (2004) Ghrelin inhibits leptin- and activation-induced proinflammatory cytokine expression by human monocytes and T cells. The Journal of clinical investigation, 114, 57-66.
92. Doi, Y., T. Minami, M. Nishizawa, T. Mabuchi, H. Mori, and S. Ito. Central nociceptive role of prostacyclin (IP) receptor induced by peripheral inflammation. Neuroreport, 2002, 13:93-6.
93. Donoghue, M., et al. A novel angiotensin-converting enzyme-related carboxypeptidase (ACE2) converts angiotensin I to angiotensin 1-9. Circulation research, 2000, 87: E1-9.
94. Dorsch, M., Qiu, Y., Soler, D., Frank, N., Duong, T., Goodearl, A., O'Neil, S., Lora, J. & Fraser, C. C. (2005) PK1/EG-VEGF induces monocyte differentiation and activation. Journal of Leukocyte Biology, 78, 426-434.
95. Drazen, D. L. & Nelson, R. J. (2001) Melatonin receptor subtype MT2 (Mel 1b) and not mt1 (Mel 1a) is associated with melatonin-induced enhancement of cell-mediated and humoral immunity. Neuroendocrinology, 74, 178-184.
96. Duchene, J., and A. Ahluwalia. The kinin B(1) receptor and inflammation: new therapeutic target for cardiovascular disease. Curr Opin Pharmacol, 2009, 9:125-31.
97. Duffy, R. A. Potential therapeutic targets for neurokinin-1 receptor antagonists. Expert Opin Emerg Drugs, 2004, 9:9-21.
98. Ehrenfeld, P., Millan, C., Matus, C., Figueroa, J., Burgos, R., Nualart, F., Bhoola, K. & Figueroa, C. (2006) Activation of kinin B1 receptors induces chemotaxis of human neutrophils. Journal of leukocyte biology, 80, 117-124.
99: Ekholm, M., Kahan, T., Jorneskog, G., Broijersen, A. & Wallen, N. H. (2009) Angiotensin II infusion in man is 100. Elliott, S. E., Parchim, N. F., Kellems, R. E., Xia, Y., Soffici, A. R. & Daugherty, P. S. (2016) A pre-eclampsia-associated Epstein-Barr virus antibody cross-reacts with placental GPR50. Clinical Immunology, 168, 64-71.
101. Elsasser, T. H. & Kahl, S. (2002) Adrenomedullin has multiple roles in disease stress: development and remission of the inflammatory response. Microscopy research and technique, 57, 120-129.
102. Engel, K. M., Schrock, K., Teupser, D., Holdt, L. M., Tonjes, A., Kern, M., Dietrich, K., Kovacs, P., Krügel, U. & Scheidt, H. A. (2011) Reduced food intake and body weight in mice deficient for the G protein-coupled receptor GPR82. PLOS One, 6, e29400.
103. English, D., A. T. Kovala, Z. Welch, K. A. Harvey, R. A. Siddiqui, and D. N. Brindley. Induction of endothelial cell chemotaxis by sphingosine 1-phosphate and stabilization of endothelial monolayer barrier function by lysophosphatidic acid, potential mediators of hematopoietic angiogenesis. J Hemather Stem Cell Res, 1999, 8:627-34.
104. Evankovich, J., Lear, T., Mckelvey, A., Dunn, S., Londino, J., Liu, Y., Chen, B. B., Mallampalli, R. K. (2017) Receptor for advanced glycation end products is targeted by FBXO10 for ubiquitination and degradation. FASEB J. doi: 10.1096/fj.201700031R.
105. Fallarino, F., Volpi, C., Fazio, F., Notartomaso, S., Vacca, C., Busceti, C., Bicciato, S., Battaglia, G., Bruno, V. & Puccetti, P. (2010) Metabotropic glutamate receptor-4 modulates adaptive immunity and restrains neuroinflammation. Nature medicine, 16, 897-902.
106. Farzan, M., Choe, H., Martin, K., Marcon, L., Hofmann, W., Karlsson, G., Sun, Y., Barrett, P., Marchand, N. & Sullivan, N. (1997) Two orphan seven-transmembrane segment receptors which are expressed in CD4-positive cells support simian immunodeficiency virus infection. The Journal of experimental medicine, 186, 405-411.
107. Feingold, E. A., Penny, L. A., Nienhuis, A. W. & Forget, B. G. (1999) An olfactory receptor gene is located in the extended human β-globin gene cluster and is expressed in erythroid cells. Genomics, 61, 15-23.
108. Ferrario, C. M. & Strawn, W. B. (2006) Role of the renin-angiotensin-aldosterone system and proinflammatory mediators in cardiovascular disease. Am J Cardiol, 98: 121-128.
109. Ferré, S., Baler, R., Bouvier, M., Caron, M. G., Devi, L. A., Durroux, T., Fuxe, K., George, S. R., Javitch, J. A., Lohse, M. J., Mackie, K., Milligan, G., Pfleger, K. D. G., Pin, J. P., Volkow, N., Waldhoer, M., Woods, A. S. and Franco R. (2009) Building a new conceptual framework for receptor heteromers. Nat Chem Biol, 5: 131-134.
110. Ferreira, M., Barcelos, L. S., Campos, P. P., Vasconcelos, A. C., Teixeira, M. M. & Andrade, S. P. (2004) Sponge-induced angiogenesis and inflammation in PAF receptor-deficient mice (PAFR-KO). British journal of pharmacology, 141, 1185-1192.
111. Ferrier L, Serradeil-Le Gal C, Schulte A M, Vasina V, Gaultier E, Schroedel S, Ursino M G, Chaumaz G, Pascal M, De Ponti F, Bueno L. Proinflammatory role of vasopressin through V1b receptors in hapten-induced experimental colitis in rodents: implication in IBD. Am J Physiol Gastrointest Liver Physiol, 2010, 299: G1298-307.
112. Finch, A. M., Sarramegna, V. & Graham, R. M. (2006) Ligand Binding, Activation, and Agonist Trafficking. In Perez, D. M. (ed) The Adrenergic Receptors: In the 21st Century. Humana Press, Totowa, NJ, pp. 25-85.
113. Fischer, A., Schmid, B., Ellinghaus, D., Nothnagel, M., Gaede, K. I., Schürmann, M., Lipinski, S., Rosenstiel, P., Zissel, G. & Höhne, K. (2012) A novel sarcoidosis risk locus for Europeans on chromosome 11q13. 1. American journal of respiratory and critical care medicine, 186, 877-885.
114. Flegel, C., Manteniotis, S., Osthold, S., Hatt, H. & Gisselmann, G. (2013) Expression Profile of Ectopic Olfactory Receptors Determined by Deep Sequencing. PLOS ONE, 8, e55368.
115. Fleischmann, A., Läderach, U., Friess, H., Buechler, M. W. & Reubi, J. C. (2000) Bombesin receptors in distinct tissue compartments of human pancreatic diseases. Laboratory investigation, 80, 1807-1817.
116. Fornari, T. A., Donate, P. B., Macedo, C., Sakamoto-Hojo, E. T., Donadi, E. A. & Passos, G. A. (2011) Development of type 1 diabetes mellitus in nonobese diabetic mice follows changes in thymocyte and peripheral T lymphocyte transcriptional activity. Clinical and Developmental Immunology, 2011.
117. Foster, H. R., Fuerst, E., Branchett, W., Lee, T. H., Cousins, D. J. & Woszczek, G. (2016) Leukotriene E4 is a full functional agonist for human cysteinyl leukotriene type 1 receptor-dependent gene expression. Scientific reports, 6.
118. Frasch, S. C., Berry, K. Z., Fernandez-Boyanapalli, R., Jin, H.-S., Leslie, C., Henson, P. M., Murphy, R. C. & Bratton, D. L. (2008) NADPH oxidase-dependent generation of lysophosphatidylserine enhances clearance of activated and dying neutrophils via G2A. Journal of Biological Chemistry, 283, 33736-33749.
119. Fredholm, B. B., AP, I. J., Jacobson, K. A., Linden, J. & Muller, C. E. (2011) International Union of Basic and Clinical Pharmacology. LXXXI. Nomenclature and classification of adenosine receptors—an update. Pharmacol Rev, 63, 1-34.
120. Freire-Garabal, M., Nunez, M., Balboa, J., López-Delgado, P., Gallego, R., García-Caballero, T., Fernández-Roel, M., Brenlla, J. & Rey-Méndez, M. (2003) Serotonin upregulates the activity of phagocytosis through 5-HT1A receptors. British journal of pharmacology, 139, 457-463.
121. Fujita, T., Matsuoka, T., Honda, T., Kabashima, K., Hirata, T. & Narumiya, S. (2011) A GPR40 agonist GW9508 suppresses CCL5, CCL17, and CXCL10 induction in keratinocytes and attenuates cutaneous immune inflammation. Journal of Investigative Dermatology, 131, 1660-1667.
122. Fujita, T., Tozaki-Saitoh, H. & Inoue, K. (2009) P2Y1 receptor signalling enhances neuroprotection by astrocytes against oxidative stress via IL-6 release in hippocampal cultures. Glia, 57, 244-257.
123. Fukami K, Ueda S, Yamagishi S, Kato S, Inagaki Y, Takeuchi M, Motomiya Y, Bucala R, Iida S, Tamaki K, Imaizumi T, Cooper M E, Okuda S. (2004) AGEs activate mesangial TGF-β-Smad signalling via an angiotensin II type 1 receptor interaction. Kidney Int, 66: 2137-2147.
124. Fukami, K., Taguchi, K., Yamagishi, S. & Okuda, S. Receptor for advanced glycation endproducts and progressive kidney disease. Current opinion in nephrology and hypertension, 2015, 24: 54-60.
125. Galiègue, S., Mary, S., Marchand, J., Dussossoy, D., Carrière, D., Carayon, P., Bouaboula, M., Shire, D., Le Fur, G. & Casellas, P. (1995) Expression of Central and Peripheral Cannabinoid Receptors in Human Immune Tissues and Leukocyte Subpopulations. European Journal of Biochemistry, 232, 54-61.

126. Galle, J., Sittig, D., Hanisch, I., Wobus, M., Wandel, E., Loeffler, M. & Aust, G. (2006) Individual cell-based models of tumor-environment interactions: Multiple effects of CD97 on tumor invasion. Am J Pathol, 169, 1802-1811.

127. Gantz, I., Muraoka, A., Yang, Y.-K., Samuelson, L. C., Zimmerman, E. M., Cook, H. & Yamada, T. (1997) Cloning and chromosomal localization of a gene (GPR18) encoding a novel seven transmembrane receptor highly expressed in spleen and testis. Genomics, 42, 462-466.

128. Gao, Z.-G., Ding, Y. & Jacobson, K. A. (2010) P2Y 13 receptor is responsible for ADP-mediated degranulation in RBL-2H3 rat mast cells. Pharmacological research, 62, 500-505.

129. Garcia-Vivas, J. M., Galaviz-Hernandez, C., Fernandez-Retana, J., Pedroza-Torres, A., Perez-Plasencia, C., Lopez-Camarillo, C. & Marchat, L. A. (2016) Transcriptomic Profiling of Adipose Tissue in Obese Women in Response to Acupuncture Catgut Embedding Therapy with Moxibustion. The Journal of Alternative and Complementary Medicine, 22, 658-668.

130. Garcia, J. G., A. Siflinger-Birnboim, R. Bizios, P. J. Del Vecchio, J. W. Fenton, 2nd, and A. B. Malik. Thrombin-induced increase in albumin permeability across the endothelium. J Cell Physiol, 1986, 128:96-104.

131. Garg, D. & Merhi, Z. Advanced Glycation End Products: Link between Diet and Ovulatory Dysfunction in PCOS? Nutrients, 2015, 7: 10129-10144.

132. Gatto, D., Wood, K. & Brink, R. (2011) EBl2 operates independently of but in cooperation with CXCR5 and CCR7 to direct B cell migration and organization in follicles and the germinal center. The Journal of Immunology, 187, 4621-4628.

133 Gaveriaux, C., Peluso, J., Simonin, F., Laforet, J. & Kieffer, B. (1995) Identification of kappa- and delta-opioid receptor transcripts in immune cells. FEBS Lett, 369, 272-276.

134. Gazel, A., Rosdy, M., Bertino, B., Tornier, C., Sahuc, F. & Blumenberg, M. (2006) A characteristic subset of psoriasis-associated genes is induced by oncostatin-M in reconstituted epidermis. Journal of investigative dermatology, 126, 2647-2657.

135. Gervais, F. G., Cruz, R. P., Chateauneuf, A., Gale, S., Sawyer, N., Nantel, F., Metters, K. M. & O'Neill, G. P. (2001) Selective modulation of chemokinesis, degranulation, and apoptosis in eosinophils through the PGD 2 receptors CRTH2 and DP. Journal of Allergy and Clinical Immunology, 108, 982-988.

136. Getting, S. J., Gibbs, L., Clark, A. J., Flower, R. J. & Perretti, M. (1999) POMC gene-derived peptides activate melanocortin type 3 receptor on murine macrophages, suppress cytokine release, and inhibit neutrophil migration in acute experimental inflammation. The Journal of Immunology, 162, 7446-7453.

137. Giannini, E., Lattanzi, R., Nicotra, A., Campese, A. F., Grazioli, P., Screpanti, I., Balboni, G., Salvadori, S., Sacerdote, P. & Negri, L. (2009) The chemokine Bv8/prokineticin 2 is up-regulated in inflammatory granulocytes and modulates inflammatory pain. Proceedings of the National Academy of Sciences, 106, 14646-14651.

138. Goldin, A., Beckman, J. A., Schmidt, A. M., and CreAGER, M. A. (2006) Advanced glycation end products: sparking the development of diabetic vascular injury Circulation, 114: 597-605.

139. Grafe, M., et al. (1997) Angiotensin II-induced leukocyte adhesion on human coronary endothelial cells is mediated by E-selectin. Circ Res, 81: 804-811.

140. Granados-Soto, V., Argüelles, C. F., Rocha-González, H. I., Godínez-Chaparro, B., Flores-Murrieta, F. J. & Villalón, C. M. (2010) The role of peripheral 5-HT1A, 5-HT1B, 5-HT1D, 5-HT1E and 5-HT1F serotonergic receptors in the reduction of nociception in rats. Neuroscience, 165, 561-568.

141. Grantham, R. (1974) Amino acid difference formula to help explain protein evolution. Science, 185: 862-864.

142. Grässel, S., Opolka, A., Anders, S., Straub, R. H., Grifka, J., Luger, T. A. & Böhm, M. (2009) The melanocortin system in articular chondrocytes: Melanocortin receptors, pro-opiomelanocortin, precursor proteases, and a regulatory effect of α-melanocyte-stimulating hormone on proinflammatory cytokines and extracellular matrix components. Arthritis & Rheumatism, 60, 3017-3027.

143. Greene T. W. et al. Protective groups in organic synthesis, 1991, Wiley, New York.

144. Gregory, M. A., Phang, T. L., Neviani, P., Alvarez-Calderon, F., Eide, C. A., O'Hare, T., Zaberezhnyy, V., Williams, R. T., Druker, B. J. & Perrotti, D. (2010) Wnt/Ca 2+/NFAT signalling maintains survival of Ph+ leukemia cells upon inhibition of Bcr-Abl. Cancer cell, 18, 74-87.

145. Guénard, F., Lamontagne, M., Bossé, Y., Deshaies, Y., Cianflone, K., Kral, J. G., Marceau, P. & Vohl, M.-C. (2015) Influences of Gestational Obesity on Associations between Genotypes and Gene Expression Levels in Offspring following Maternal Gastrointestinal Bypass Surgery for Obesity. PloS one, 10, e0117011.

146. Gugliucci, A. & Menini, T. The axis AGE-RAGE-soluble RAGE and oxidative stress in chronic kidney disease. Advances in experimental medicine and biology, 2014, 824: 191-208.

147. Guo, W. A., Knight, P. R. & Raghavendran, K. The receptor for advanced glycation end products and acute lung injury/acute respiratory distress syndrome. Intensive care medicine¬¬, 2012, 38: 1588-1598.

148. Haga, K., Kruse, A. C., Asada, H., Yurugi-Kobayashi, T., Shiroishi, M., Zhang, C., Weis, W. I., Okada, T., Kobilka, B. K., Haga, T. & Kobayashi, T. (2012) Structure of the human M2 muscarinic acetylcholine receptor bound to an antagonist. Nature, 482, 547-551.

149. Hagner, S., Stahl, U., Knoblauch, B., McGregor, G. & Lang, R. (2002) Calcitonin receptor-like receptor: identification and distribution in human peripheral tissues. Cell and tissue research, 310, 41-50.

150. Han, Y. T., et al. Fine tuning of 4,6-bisphenyl-2-(3-alkoxyanilino)pyrimidine focusing on the activity-sensitive aminoalkoxy moiety for a therapeutically useful inhibitor of receptor for advanced glycation end products (RAGE). Bioorganic & medicinal chemistry, 2015, 23: 579-587.

151. Han, Y. T., et al. Ligand-based design, synthesis, and biological evaluation of 2-aminopyrimidines, a novel series of receptor for advanced glycation end products (RAGE) inhibitors. Journal of medicinal chemistry, 2012, 55: 9120-9135.

152. Han, Y. T., et al. Pyrazole-5-carboxamides, novel inhibitors of receptor for advanced glycation end products (RAGE). European journal of medicinal chemistry, 2014, 79: 128-142.

153. Handley, D. A., C. M. Arbeeny, M. L. Lee, R. G. Van Valen, and R. N. Saunders. Effect of platelet activating 154. Hansen, W., Westendorf, A., Toepfer, T., Mauel, S., Geffers, R., Gruber, A. & Buer, J. (2010) Inflammation in vivo is modulated by GPR83 isoform-4 but not GPR83 isoform-1 expression in regulatory T cells. Genes and immunity, 11, 357-361.

155. Hanson, M. A., Roth, C. B., Jo, E., Griffith, M. T., Scott, F. L., Reinhart, G., Desale, H., Clemons, B., Cahalan, S. M., Schuerer, S. C., Sanna, M. G., Han, G. W., Kuhn, P., Rosen, H. & Stevens, R. C. (2012) Crystal structure of a lipid G protein-coupled receptor. Science, 335, 851-855.

156. Hartmann, K., Henz, B. M., Krüger-Krasagakes, S., Köhl, J., Burger, R., Guhl, S., Haase, I., Lippert, U. & Zuberbier, T. (1997) C3a and C5a stimulate chemotaxis of human mast cells. Blood, 89, 2863-2870.

157. Hartmeyer, M., Scholzen, T., Becher, E., Bhardwaj, R., Schwarz, T. & Luger, T. (1997) Human dermal microvascular endothelial cells express the melanocortin receptor type 1 and produce increased levels of IL-8 upon stimulation with alpha-melanocyte-stimulating hormone. The Journal of Immunology, 159, 1930-1937.

158. Harvey, R. C., Mullighan, C. G., Wang, X., Dobbin, K. K., Davidson, G. S., Bedrick, E. J., Chen, I.-M., Atlas, S. R., Kang, H. & Ar, K. (2010) Identification of novel cluster groups in pediatric high-risk B-precursor acute lymphoblastic leukemia with gene expression profiling: correlation with genome-wide DNA copy number alterations, clinical characteristics, and outcome. Blood, 116, 4874-4884.

159. Hata, A. N., and R. M. Breyer. Pharmacology and signalling of prostaglandin receptors: multiple roles in inflammation and immune modulation. Pharmacol Ther, 2004, 103:147-66.

160. Haworth, O., Cernadas, M. & Levy, B. D. (2011) NK cells are effectors for resolvin E1 in the timely resolution of allergic airway inflammation. The Journal of Immunology, 186, 6129-6135.

161. Hess B, Kutzner C, Van Der Spoel D, Lindahl E. GROMACS 4: Algorithms for highly efficient, load-balanced, and scalable molecular simulation. J Chem Theory Comput, 2008, 4: 435.

162. Heublein, S., Lenhard, M., Vrekoussis, T., Schoepfer, J., Kuhn, C., Friese, K., Makrigiannakis, A., Mayr, D. & Jeschke, U. (2012) The G-protein-coupled estrogen receptor (GPER) is expressed in normal human ovaries and is upregulated in ovarian endometriosis and pelvic inflammatory disease involving the ovary. Reproductive Sciences, 19, 1197-1204.

163. Hill, J., Duckworth, M., Murdock, P., Rennie, G., Sabido-David, C., Ames, R. S., Szekeres, P., Wilson, S., Bergsma, D. J. & Gloger, I. S. (2001) Molecular cloning and functional characterization of MCH2, a novel human MCH receptor. Journal of Biological Chemistry, 276, 20125-20129.

164. Hohenhaus, D. M., Schaale, K., Le Cao, K.-A., Seow, V., Iyer, A., Fairlie, D. P. & Sweet, M. J. (2013) An mRNA atlas of G protein-coupled receptor expression during primary human monocyte/macrophage differentiation and lipopolysaccharide-mediated activation identifies targetable candidate regulators of inflammation. Immunobiology, 218, 1345-1353.

165. Hollenberg, A. N. (2008) The role of the thyrotropin-releasing hormone (TRH) neuron as a metabolic sensor. Thyroid, 18, 131-139.

166. Hong, K. W., Shin, M. S., Ahn, Y. B., Lee, H. J. & Kim, H. D. (2015) Genomewide association study on chronic periodontitis in Korean population: results from the Yangpyeong health cohort. Journal of clinical pe riodontology, 42, 703-710.

167. Hoque, R., Farooq, A., Ghani, A., Gorelick, F. & Mehal, W. Z. (2014) Lactate reduces liver and pancreatic injury in Toll-like receptor- and inflammasome-mediated inflammation via GPR81-mediated suppression of innate immunity. Gastroenterology, 146, 1763-1774.

168. Horinouchi, T., Terada, K., Higashi, T. & Miwa, S. (2013) Endothelin receptor signalling: new insight into its regulatory mechanisms. J Pharmacol Sci, 123, 85-101.

169. Horne, K. & Woolley, I. J. (2009) Shedding light on DARC: the role of the Duffy antigen/receptor for chemokines in inflammation, infection and malignancy. Inflamm Res, 58, 431-435.167. Horton, J., Yamamoto, S. & Bryant-Greenwood, G. (2012) Relaxin augments the inflammatory IL6 response in the choriodecidua. Placenta, 33, 399-407.

170. Hsu, S. Y., Nakabayashi, K., Nishi, S., Kumagai, J., Kudo, M., Sherwood, O. D. & Hsueh, A. J. (2002) Activation of orphan receptors by the hormone relaxin. Science, 295, 671-674.

171. Ichimonji, I., Tomura, H., Mogi, C., Sato, K., Aoki, H., Hisada, T., Dobashi, K., Ishizuka, T., Mori, M. & Okajima, F. (2010) Extracellular acidification stimulates IL-6 production and Ca2+ mobilization through proton-sensing OGR1 receptors in human airway smooth muscle cells. American Journal of Physiology-Lung Cellular and Molecular Physiology, 299, L567-L577.

172. Ignatov, A., Robert, J., Gregory-Evans, C. & Schaller, H. (2006) RANTES stimulates Ca2+ mobilization and inositol trisphosphate ($IP_3$) formation in cells transfected with G protein-coupled receptor 75. British journal of pharmacology, 149, 490-497.

173. Improta, G., Carpino, F., Petrozza, V., Guglietta, A., Tabacco, A. & Broccardo, M. (2003) Central effects of selective NK 1 and NK 3 tachykinin receptor agonists on two models of experimentally-induced colitis in rats. Peptides, 24, 903-911.

174. Inbe, H., Watanabe, S., Miyawaki, M., Tanabe, E. & Encinas, J. A. (2004) Identification and characterization of a cell-surface receptor, P2Y15, for AMP and adenosine. Journal of Biological Chemistry, 279, 19790-19799.

175. Irukayama-Tomobe, Y., Tanaka, H., Yokomizo, T., Hashidate-Yoshida, T., Yanagisawa, M. & Sakurai, T. (2009) Aromatic D-amino acids act as chemoattractant factors for human leukocytes through a G protein-coupled receptor, GPR109B. Proceedings of the National Academy of Sciences, 106, 3930-3934.

176. İşeri, S. Ö., Şener, G., Sağlam, B., Gedik, N., Ercan, F. & Yeğen, B. ç. (2005) Oxytocin ameliorates oxidative colonic inflammation by a neutrophil-dependent mechanism. Peptides, 26, 483-491.

177. Ishihara, H., Connolly, A. J., Zeng, D., Kahn, M. L., Zheng, Y. W., Timmons, C., Tram, T. & Coughlin, S. R. (1997) Protease-activated receptor 3 is a second thrombin receptor in humans.

178. Ito, Y., Banno, R., Shibata, M., Adachi, K., Hagimoto, S., Hagiwara, D., Ozawa, Y., Goto, M., Suga, H. & Sugimura, Y. (2013) GABA type B receptor signalling in proopiomelanocortin neurons protects against obesity, insulin resistance, and hypothalamic inflammation in male mice on a high-fat diet. The Journal of Neuroscience, 33, 17166-17173.

179. Iwasa, T., Matsuzaki, T., Tungalagsuvd, A., Munkhzaya, M., Kawami, T., Niki, H., Kato, T., Kuwahara, A., Uemura, H., Yasui, T. & Irahara, M. (2014)

179. ...Hypothalamic Kiss 1 and RFRP gene expressions are changed by a high dose of lipopolysaccharide in female rats. Hormones and Behavior, 66, 309-316.
180. Izeboud, C. A., Vermeulen, R. M., Zwart, A., Voss, H.-P., van Miert, A. S. J. P. A. M. & Witkamp, R. F. (2000) Stereoselectivity at the β2-adrenoceptor on macrophages is a major determinant of the anti-inflammatory effects of ß2-agonists. Naunyn-Schmiedeberg's Archives of Pharmacology, 362, 184-189.
181. Jacoby, D. S., and Rader, D. J. (2003) Renin-angiotensin system and atherothrombotic disease: from genes to treatment. Arch Intern Med, 163: 1155-64.
182. Jaeger, W. C., Armstrong, S. P., Hill, S. J. and Pfleger, K. D. G., Biophysical detection of diversity and bias in GPCR function. Front Endocrinol, 2014, 5: 26.
183. Jaffre, F., Bonnin, P., Callebert, J., Debbabi, H., Setola, V., Doly, S., Monassier, L., Mettauer, B., Blaxall, B. C. & Launay, J.-M. (2009) Serotonin and angiotensin receptors in cardiac fibroblasts coregulate adrenergic-dependent cardiac hypertrophy. Circulation research, 104, 113-123.
184. Jahnsen, J., Falch, J., Mowinckel, P. & Aadland, E. (2002) Vitamin D status, parathyroid hormone and bone mineral density in patients with inflammatory bowel disease. Scandinavian journal of gastroenterology, 37, 192-199.
185. Jenne, C. N., Enders, A., Rivera, R., Watson, S. R., Bankovich, A. J., Pereira, J. P., Xu, Y., Roots, C. M., Beilke, J. N. & Banerjee, A. (2009) T-bet-dependent S1P5 expression in NK cells promotes egress from lymph nodes and bone marrow. The Journal of experimental medicine, 206, 2469-2481.
186. Jia, R.-Z., Zhang, X., Hu, P., Liu, X.-M., Hua, X.-D., Wang, X. & Ding, H.-J. (2012) Screening for differential methylation status in human placenta in preeclampsia using a CpG island plus promoter microarray. International journal of molecular medicine, 30, 133.
187. Jimenez-Andrade, J. M., Zhou, S., Du, J., Yamani, A., Grady, J. J., Castañeda-Hernandez, G. & Carlton, S. M. (2004) Pro-nociceptive role of peripheral galanin in inflammatory pain. Pain, 110, 10-21.
188. Johns, D. G., Ao, Z., Naselsky, D., Herold, C. L., Maniscalco, K., Sarov-Blat, L., Steplewski, K., Aiyar, N. & Douglas, S. A. (2004) Urotensin-II-mediated cardiomyocyte hypertrophy: effect of receptor antagonism and role of inflammatory mediators. Naunyn-Schmiedeberg's archives of pharmacology, 370, 238-250.
189. Jossart, C., Mulumba, M., Granata, R., Gallo, D., Ghigo, E., Marleau, S., Servant, M. J. & Ong, H. (2013) Pyroglutamylated RF-amide peptide (QRFP) gene is regulated by metabolic endotoxemia. Molecular Endocrinology, 28, 65-79.
190. Jules J, Maiguel D, Hudson B I, Alternative Splicing of the RAGE Cytoplasmic Domain Regulates Cell Signalling and Function. PLOS ONE, 2013, 8: e78267.
191. Jurisic, G., Sundberg, J., Bleich, A., Leiter, E., Broman, K., Buechler, G., Alley, L., Vestweber, D. & Detmar, M. (2010) Quantitative lymphatic vessel trait analysis suggests Vcam1 as candidate modifier gene of inflammatory bowel disease. Genes and immunity, 11, 219-231.
192. Kabashima, K., Saji, T., Murata, T., Nagamachi, M., Matsuoka, T., Segi, E., Tsuboi, K., Sugimoto, Y., Kobayashi, T. & Miyachi, Y. (2002) The prostaglandin receptor EP4 suppresses colitis, mucosal damage and CD4 cell activation in the gut. The Journal of clinical investigation, 109, 883-893.
193. Kable, J. W., Murrin, L. C. & Bylund, D. B. (2000) In vivo gene modification elucidates subtype-specific functions of alpha(2)-adrenergic receptors. J Pharmacol Exp Ther, 293, 1-7.
194. Kahn, M. L., Y. W. Zheng, W. Huang, V. Bigornia, D. Zeng, and S. Moff. A dual thrombin receptor system for platelet activation. Nature, 1998, 394:690-4.
195. Kalbe, B., Knobloch, J., Schulz, V. M., Wecker, C., Schlimm, M., Scholz, P., Jansen, F., Stoelben, E., Philippou, S., Hecker, E., Lübbert, H., Koch, A., Hatt, H. & Osterloh, S. (2016) Olfactory Receptors Modulate Physiological Processes in Human Airway Smooth Muscle Cells. Frontiers in Physiology, 7.
196. Kaminski, N. E. Immune regulation by cannabinoid compounds through the inhibition of the cyclic AMP signalling cascade and altered gene expression. Biochem Pharmacol, 1996, 52:1133-40.
197. Kanazawa, M., Watanabe, S., Tana, C., Komuro, H., Aoki, M. & Fukudo, S. (2011) Effect of 5-HT4 receptor agonist mosapride citrate on rectosigmoid sensorimotor function in patients with irritable bowel syndrome. Neurogastroenterology & Motility, 23, 754-e332.
198. Kang, Y. S et al. (2010) CCR2 antagonism improves insulin resistance, lipid metabolism, and diabetic nephropathy in type 2 diabetic mice. Kidney International, 78: 883-894.
199. Kawamata, Y., Fujii, R., Hosoya, M., Harada, M., Yoshida, H., Miwa, M., Fukusumi, S., Habata, Y., Itoh, T. & Shintani, Y. (2003) AG protein-coupled receptor responsive to bile acids. Journal of Biological Chemistry, 278, 9435-9440.
200. Kazemian, P., Kazemi-Bajestani, S. M., Alherbish, A., Steed, J. & Oudit, G. Y. (2012) The use of ω-3 polyunsaturated fatty acids in heart failure: a preferential role in patients with diabetes. Cardiovascular drugs and therapy, 26, 311-320.
201. Keermann, M., Köks, S., Reimann, E., Prans, E., Abram, K. & Kingo, K. (2015) Transcriptional landscape of psoriasis identifies the involvement of IL36 and IL36RN. BMC genomics, 16, 1.
202. Khasar, S. G., M. S. Gold, and J. D. Levine. A tetrodotoxin-resistant sodium current mediates inflammatory pain in the rat. Neurosci Lett, 1998, 256:17-20.
203. Kim, S. V., Xiang, W. V., Kwak, C., Yang, Y., Lin, X. W., Ota, M., Sarpel, U., Rifkin, D. B., Xu, R. & Littman, D. R. (2013) GPR15-mediated homing controls immune homeostasis in the large intestine mucosa. Science, 340, 1456-1459.
204. Kim, Y.-J., Sano, T., Nabetani, T., Asano, Y. & Hirabayashi, Y. (2012) GPRC5B activates obesity-associated inflammatory signalling in adipocytes. Sci. Signal., 5, ra85-ra85.
205. Kitagawa K et al. (2004) Blockade of CCR2 Ameliorates Progressive Fibrosis in Kidney, American Journal of Pathology, 165: 237-246.
206. Knowles, J. W., et al. (2000) Enhanced atherosclerosis and kidney dysfunction in eNOS(−/−) ApoE(−/−) mice are ameliorated by enalapril treatment. J Clin Invest, 105: 451-458.
207. Kodera, R., Shikata, K., Kataoka, H., Takatsuka, T., Miyamoto, S., Sasaki, M., Kajitani, N., Nishishita, S., Sarai, K. & Hirota, D. (2011) Glucagon-like peptide-1 receptor agonist ameliorates renal injury through its anti-inflammatory action without lowering blood glucose level in a rat model of type 1 diabetes. Diabetologia, 54, 965-978.

208. Kononikhin, A., Fedorchenko, K. Y., Ryabokon, A., Starodubtseva, N., Popov, I., Zavialova, M., Anaev, E., Chuchalin, A., Varfolomeev, S. & Nikolaev, E. (2016) Proteomic analysis of exhaled breath condensate for diagnostics of respiratory system diseases. Biochemistry (Moscow) Supplement Series B: Biomedical Chemistry, 10, 230-234.

209. Kottyan, L. C., Collier, A. R., Cao, K. H., Niese, K. A., Hedgebeth, M., Radu, C. G., Witte, O. N., Hershey, G. K. K., Rothenberg, M. E. & Zimmermann, N. (2009) Eosinophil viability is increased by acidic pH in a cAMP- and GPR65-dependent manner. Blood, 114, 2774-2782.

210. Krishnamoorthy, S., Recchiuti, A., Chiang, N., Fredman, G. & Serhan, C. N. (2012) Resolvin D1 receptor stereoselectivity and regulation of inflammation and pro-resolving microRNAs. The American journal of pathology, 180, 2018-2027.

211. Krishnamoorthy, S., Recchiuti, A., Chiang, N., Yacoubian, S., Lee, C.-H., Yang, R., Petasis, N. A. & Serhan, C. N. (2010) Resolvin D1 binds human phagocytes with evidence for proresolving receptors. Proceedings of the National Academy of Sciences, 107, 1660-1665.

212. Kruse, A. C., Ring, A. M., Manglik, A., Hu, J., Hu, K., Eitel, K., Hubner, H., Pardon, E., Valant, C., Sexton, P. M., Christopoulos, A., Felder, C. C., Gmeiner, P., Steyaert, J., Weis, W. I., Garcia, K. C., Wess, J. & Kobilka, B. K. (2013) Activation and allosteric modulation of a muscarinic acetylcholine receptor. Nature, 504, 101-106.

213. Kuduk, S. D., and M. G. Bock. Bradykinin B1 receptor antagonists as novel analgesics: a retrospective of selected medicinal chemistry developments. Curr Top Med Chem, 2008, 8:1420-30.

214. Kufareva, I., Salanga, C. L. & Handel, T. M. (2015) Chemokine and chemokine receptor structure and interactions: implications for therapeutic strategies. Immunol Cell Biol, 93, 372-383.

215. Kunikata, T., Yamane, H., Segi, E., Matsuoka, T., Sugimoto, Y., Tanaka, S., Tanaka, H., Nagai, H., Ichikawa, A. & Narumiya, S. (2005) Suppression of allergic inflammation by the prostaglandin E receptor subtype EP3. Nature immunology, 6, 524-531.

216. Kupp, L. I., Kosco, M. H., Schenkein, H. A. & Tew, J. G. (1991) Chemotaxis of germinal centers B cells in response to C5a. European journal of immunology, 21, 2697-2701.

217. Kwon, J. Y., Park, M. K., Seo, Y. R. & Song, J.-J. (2014) Genomic-based identification of novel potential biomarkers and molecular signalling networks in response to diesel exhaust particles in human middle ear epithelial cells. Molecular & Cellular Toxicology, 10, 95-105.

218. Lafrance, M., Roussy, G., Belleville, K., Maeno, H., Beaudet, N., Wada, K. & Sarret, P. (2010) Involvement of NTS2 receptors in stress-induced analgesia. Neuroscience, 166, 639-652.

219. Laird, J. M., Olivar, T., Lopez-Garcia, J. A., Maggi, C. A. & Cervero, F. (2001) Responses of rat spinal neurons to distension of inflamed colon: role of tachykinin NK2 receptors. Neuropharmacology, 40, 696-701.

220. Lamas, O., Martínez, J. A. & Marti, A. (2003) Effects of a β3-adrenergic agonist on the immune response in diet-induced (cafeteria) obese animals. Journal of Physiology and Biochemistry, 59, 183-191.

221. Lattin, J. E., Schroder, K., Su, A. I., Walker, J. R., Zhang, J., Wiltshire, T., Saijo, K., Glass, C. K., Hume, D. A. & Kellie, S. (2008) Expression analysis of G Protein-Coupled Receptors in mouse macrophages. Immunome research, 4, 1.

222. Laukova, M., Vargovic, P., Krizanova, O. & Kvetnansky, R. (2010) Repeated Stress Down-Regulates β2- and α2C-Adrenergic Receptors and Up-Regulates Gene Expression of IL-6 in the Rat Spleen. Cellular and Molecular Neurobiology, 30, 1077-1087.

223. Lazennec, G. & Richmond, A. (2010) Chemokines and chemokine receptors: new insights into cancer-related inflammation. Trends in molecular medicine, 16, 133-144.

224. Leeb-Lundberg, L. M., Marceau, F., Muller-Esterl, W., Pettibone, D. J. & Zuraw, B. L. (2005) International union of pharmacology. XLV. Classification of the kinin receptor family: from molecular mechanisms to pathophysiological consequences. Pharmacol Rev, 57, 27-77.

225. Le Poul, E., Loison, C., Struyf, S., Springael, J.-Y., Lannoy, V., Decobecq, M.-E., Brezillon, S., Dupriez, V., Vassart, G. & Van Damme, J. (2003) Functional characterization of human receptors for short chain fatty acids and their role in polymorphonuclear cell activation. Journal of Biological Chemistry, 278, 25481-25489.

226. Le, Y., Gong, W., Li, B., Dunlop, N. M., Shen, W., Su, S. B., Richard, D. Y. & Wang, J. M. (1999) Utilization of two seven-transmembrane, G protein-coupled receptors, formyl peptide receptor-like 1 and formyl peptide receptor, by the synthetic hexapeptide WKYMVm for human phagocyte activation. The Journal of Immunology, 163, 6777-6784.

227. Leclerc E, Fritz G, Weibel M, Heizmann C W, Galichet A. (2007) S100B and S100A6 differentially modulate cell survival by interacting with distinct RAGE (receptor for advanced glycation end products) immunoglobulin domains. J Biol Chem, 282: 31317-31331.

228. Leclerc, E. & Vetter, S. W. (2015) The role of S100 proteins and their receptor RAGE in pancreatic cancer. Biochimica et biophysica acta, 1852: 2706-2711.

229. Lee, B.-C., Cheng, T., Adams, G. B., Attar, E. C., Miura, N., Lee, S. B., Saito, Y., Olszak, I., Dombkowski, D. & Olson, D. P. (2003) P2Y-like receptor, GPR105 (P2Y14), identifies and mediates chemotaxis of bone-marrowhematopoietic stem cells. Genes & development, 17, 1592-1604.

230. Lee, B.-Y., Cho, S., Shin, D. H. & Kim, H. (2011) Genome-wide association study of copy number variations associated with pulmonary function measures in Korea Associated Resource (KARE) cohorts. Genomics, 97, 101-105.

231. Lee, J. E., Hong, E. J., Nam, H. Y., Kim, J. W., Han, B. G. & Jeon, J. P. (2011) MicroRNA signatures associated with immortalization of EBV-transformed lymphoblastoid cell lines and their clinical traits. Cell proliferation, 44, 59-66.

232. Lee, M. A., Bohm, M., Paul, M., and Ganten, D. (1993) Tissue renin-angiotensin systems. Their role in cardiovascular disease. Circulation, 87: IV7-13.

233. Leeb-Lundberg, L. M., F. Marceau, W. Muller-Esterl, D. J. Pettibone, and B. L. Zuraw. (2005) International Union of Pharmacology. XLV. Classification of the kinin receptor family: from molecular mechanisms to pathophysiological consequences. Pharmacol Rev, 57:27-77.

234. Levite, M., Chowers, Y., Ganor, Y., Besser, M., Hershkovits, R. & Cahalon, L. (2001) Dopamine interacts directly with its D3 and D2 receptors on normal human T cells, and activates β1 integrin function. European journal of immunology, 31, 3504-3512.

235. Li C., Pazgier M., Li J., Li C., Liu M., Zou G., Li Z., Chen J., Tarasov S. G., Lu W. Y., Lu W. Limitations of peptide retro-inverso isomerization in molecular mimicry. J Biol Chem, 2010, 285: 19572-19581.
236. Li X. C., and Zhuo J. L. (2008) Nuclear factor-kappaB as a hormonal intracellular signalling molecule: focus on angiotensin II-induced cardiovascular and renal injury. Current opinion in nephrology and hypertension. 17: 37-43
237. Li, X. & Tai, H. H. (2013) Activation of thromboxane A2 receptor (TP) increases the expression of monocyte chemoattractant protein-1 (MCP-1)/chemokine (C-C motif) ligand 2 (CCL2) and recruits macrophages to promote invasion of lung cancer cells. PLOS One, 8, e54073.
238. Liang, M., Niu, J., Zhang, L., Deng, H., Ma, J., Zhou, W., Duan, D., Zhou, Y., Xu, H. & Chen, L. (2016) Gene expression profiling reveals different molecular patterns in G-protein coupled receptor signalling pathways between early- and late-onset preeclampsia. Placenta, 40, 52-59.
239. Lin, C.-I., Chen, C.-N., Lin, P.-W., Chang, K.-J., Hsieh, F.-J. & Lee, H. (2007) Lysophosphatidic acid regulates inflammation-related genes in human endothelial cells through LPA 1 and LPA 3. Biochemical and biophysical research communications, 363, 1001-1008.
240. Lin, E.-J. D., Sainsbury, A., Lee, N. J., Boey, D., Couzens, M., Enriquez, R., Slack, K., Bland, R., During, M. J. & Herzog, H. (2006) Combined deletion of Y1, Y2, and Y4 receptors prevents hypothalamic neuropeptide Y overexpression-induced hyperinsulinemia despite persistence of hyperphagia and obesity. Endocrinology, 147, 5094-5101.
241. Lin, H. H., Faunce, D. E., Stacey, M., Terajewicz, A., Nakamura, T., Zhang-Hoover, J., Kerley, M., Mucenski, M. L., Gordon, S. & Stein-Streilein, J. (2005) The macrophage F4/80 receptor is required for the induction of antigen-specific efferent regulatory T cells in peripheral tolerance. J Exp Med, 201, 1615-1625.
242. Ling, P., Ngo, K., Nguyen, S., Thurmond, R. L., Edwards, J. P., Karlsson, L. & Fung-Leung, W. P. (2004) Histamine H4 receptor mediates eosinophil chemotaxis with cell shape change and adhesion molecule upregulation. British journal of pharmacology, 142, 161-171.
243. Liu, C., Kuei, C., Sutton, S., Chen, J., Bonaventure, P., Wu, J., Nepomuceno, D., Kamme, F., Tran, D.-T. & Zhu, J. (2005) INSL5 is a high affinity specific agonist for GPCR142 (GPR100). Journal of Biological Chemistry, 280, 292-300.
244. Liu, J., Escher, A., Improved assay sensitivity of an engineered secreted *Renilla* luciferase, Gene, 1999, 237 (1): 153-9.
245. Liu, S., Qian, Y., Li, L., Wei, G., Guan, Y., Pan, H., Guan, X., Zhang, L., Lu, X. & Zhao, Y. (2013) Lgr4 gene deficiency increases susceptibility and severity of dextran sodium sulfate-induced inflammatory bowel disease in mice. Journal of Biological Chemistry, 288, 8794-8803.
246. Liu, W., Wacker, D., Gati, C., Han, G. W., James, D., Wang, D., Nelson, G., Weierstall, U., Katritch, V., Barty, A., Zatsepin, N. A., Li, D., Messerschmidt, M., Boutet, S., Williams, G. J., Koglin, J. E., Seibert, M. M., Wang, C., Shah, S. T., Basu, S., Fromme, R., Kupitz, C., Rendek, K. N., Grotjohann, I., Fromme, P., Kirian, R. A., Beyerlein, K. R., White, T. A., Chapman, H. N., Caffrey, M., Spence, J. C., Stevens, R. C. & Cherezov, V. (2013) Serial femtosecond crystallography of G protein-coupled receptors. Science, 342, 1521-1524.
247. Logsdon, C. D., Fuentes, M. K., Huang, E. H. & Arumugam, T. (2007) RAGE and RAGE ligands in cancer. Current molecular medicine, 7: 777-789.
248. Lu, D., Zhao, Y., Tawatao, R., Cottam, H. B., Sen, M., Leoni, L. M., Kipps, T. J., Corr, M. & Carson, D. A. (2004) Activation of the Wnt signalling pathway in chronic lymphocytic leukemia. Proceedings of the National Academy of Sciences of the United States of America, 101, 3118-3123.
249. Lu, M. C., Lai, N. S., Yu, H. C., Huang, H. B., Hsieh, S. C. & Yu, C. L. (2010) Anti-citrullinated protein antibodies bind surface-expressed citrullinated Grp78 on monocyte/macrophages and stimulate tumor necrosis factor a production. Arthritis & Rheumatism, 62, 1213-1223.
250. Lundequist, A. & Boyce, J. A. (2011) LPA5 is abundantly expressed by human mast cells and important for lysophosphatidic acid induced MIP-1B release. PLOS One, 6, e18192.
251. Ma, T. K., Kam, K. K., Yan, B. P., Lam, Y. Y., Renin-angiotensin-aldosterone system blockade for cardiovascular diseases: current status, Br J Pharmacol, 2010, 160: 1273-1292.
252. Maekawa, A., Balestrieri, B., Austen, K. F. & Kanaoka, Y. (2009) GPR17 is a negative regulator of the cysteinyl leukotriene 1 receptor response to leukotriene D4. Proceedings of the National Academy of Sciences, 106, 11685-11690.
253. Malik, P., Chaudhry, N., Mittal, R. & Mukherjee, T. K. (2015) Role of receptor for advanced glycation end products in the complication and progression of various types of cancers. Biochimica et biophysica acta, 1850: 1898-1904.
254. Malki, A., Fiedler, J., Fricke, K., Ballweg, I., Pfaffl, M. W. & Krautwurst, D. (2015) Class I odorant receptors, TAS1R and TAS2R taste receptors, are markers for subpopulations of circulating leukocytes. Journal of leukocyte biology, 97, 533-545.
255. Malki, A., Fiedler, J., Fricke, K., Ballweg, 1., Pfaffl, M. W. & Krautwurst, D. (2015) Class I odorant receptors, TAS1R and TAS2R taste receptors, are markers for subpopulations of circulating leukocytes. Journal of leukocyte biology, 97, 533-545.
256. Malki, A., Fiedler, J., Fricke, K., Ballweg, I., Pfaffl, M. W. & Krautwurst, D. (2015) Class I odorant receptors, TAS1R and TAS2R taste receptors, are markers for subpopulations of circulating leukocytes. Journal of leukocyte biology, 97, 533-545.
257. Manigrasso, M. B., et al. (2016) Small Molecule Inhibition of Ligand-Stimulated RAGE-DIAPH1 Signal Transduction. Scientific reports, 6: 22450.
258. Manning, M., Stoev, S., Chini, B., Durroux, T., Mouillac, B. & Guillon, G. (2008) Peptide and non-peptide agonists and antagonists for the vasopressin and oxytocin V1a, V1b, V2 and OT receptors: research tools and potential therapeutic agents. Prog Brain Res, 170, 473-512.
259. Mao, Y., Zhang, M., Tuma, R. F. & Kunapuli, S. P. (2010) Deficiency of PAR4 attenuates cerebral ischemia/reperfusion injury in mice. Journal of Cerebral Blood Flow & Metabolism, 30, 1044-1052.
260. Marazziti, D., Ori, M., Nardini, M., Rossi, A., Nardi, I. & Cassano, G. B. (2001) mRNA expression of serotonin receptors of type 2C and 5A in human resting lymphocytes. Neuropsychobiology, 43, 123-126.
261. Marinakis, E., Bagkos, G., Piperi, C., Roussou, P. & Diamanti-Kandarakis, E. (2014) Critical role of RAGE in lung physiology and tumorigenesis: a potential target of therapeutic intervention? Clinical chemistry and laboratory medicine, 52: 189-200.

262. Martinez, C., Abad, C., Delgado, M., Arranz, A., Juarranz, M. G., Rodriguez-Henche, N., Brabet, P., Leceta, J. & Gomariz, R. P. (2002) Anti-inflammatory role in septic shock of pituitary adenylate cyclase-activating polypeptide receptor. Proceedings of the National Academy of Sciences, 99, 1053-1058.

263. Martinez, F. O., Gordon, S., Locati, M. & Mantovani, A. (2006) Transcriptional profiling of the human monocyte-to-macrophage differentiation and polarization: new molecules and patterns of gene expression. The Journal of Immunology, 177, 7303-7311.

264. Marvar, P. J., et al. (2010) Central and peripheral mechanisms of T-lymphocyte activation and vascular inflammation produced by angiotensin II-induced hypertension. Circ Res, 107: 263-270.

265. Mas, V., Maluf, D., Archer, K. J., Potter, A., Suh, J., Gehrau, R., Descalzi, V. & Villamil, F. (2011) Transcriptome at the time of hepatitis C virus recurrence may predict the severity of fibrosis progression after liver transplantation. Liver Transplantation, 17, 824-835.

266. Maslowski, K. M., Vieira, A. T., Ng, A., Kranich, J., Sierro, F., Yu, D., Schilter, H. C., Rolph, M. S., Mackay, F. & Artis, D. (2009) Regulation of inflammatory responses by gut microbiota and chemoattractant receptor GPR43. Nature, 461, 1282-1286.

267. Masters, S. L., Dunne, A., Subramanian, S. L., Hull, R. L., Tannahill, G. M., Sharp, F. A., Becker, C., Franchi, L., Yoshihara, E. & Chen, Z. (2010) Activation of the NLRP3 inflammasome by islet amyloid polypeptide provides a mechanism for enhanced IL-1 [beta] in type 2 diabetes. Nature immunology, 11, 897-904.

268. Matavelli, L. C., Huang, J. & Siragy, H. M. (2011) Angiotensin AT2 receptor stimulation inhibits early renal inflammation in renovascular hypertension. Hypertension, 57, 308-313.

269. Matloubian, M., Lo, C. G., Cinamon, G., Lesneski, M. J., Xu, Y., Brinkmann, V., Allende, M. L., Proia, R. L. & Cyster, J. G. (2004) Lymphocyte egress from thymus and peripheral lymphoid organs is dependent on S1P receptor 1. Nature, 427, 355-360.

270. Matsumoto, M., Saito, T., Takasaki, J., Kamohara, M., Sugimoto, T., Kobayashi, M., Tadokoro, M., Matsumoto, S.-i., Ohishi, T. & Furuichi, K. (2000) An evolutionarily conserved G-protein coupled receptor family, SREB, expressed in the central nervous system. Biochemical and biophysical research communications, 272, 576-582.

271. Matsumura, T., Oyama, M., Kozuka-Hata, H., Ishikawa, K., Inoue, T., Muta, T., Semba, K. & Inoue, J.-i. (2010) Identification of BCAP-L as a negative regulator of the TLR signalling-induced production of IL-6 and IL-10 in macrophages by tyrosine phosphoproteomics. Biochemical and Biophysical Research Communications, 400, 265-270.

272. Matsuoka, T., M. Hirata, H. Tanaka, Y. Takahashi, T. Murata, and K. Kabashima. Prostaglandin D2 as a mediator of allergic asthma. Science, 2000, 287:2013-7.

273. Matteucci, C., Minutolo, A., Sinibaldi-Vallebona, P., Palamara, A. T., Rasi, G., Mastino, A. & Garaci, E. (2010) Transcription profile of human lymphocytes following in vitro treatment with thymosin alpha-1. Annals of the New York Academy of Sciences, 1194, 6-19.

274. McPherson, J. A., Barringhaus, K. G., Bishop, G. G., Sanders, J. M., Rieger, J. M., Hesselbacher, S. E., Gimple, L. W., Powers, E. R., Macdonald, T. & Sullivan, G. (2001) Adenosine A2A receptor stimulation reduces inflammation and neointimal growth in a murine carotid ligation model. Arteriosclerosis, Thrombosis, and Vascular Biology, 21, 791-796.

275. McQuiston, T., Luberto, C. & Del Poeta, M. (2011) Role of sphingosine-1-phosphate (S1P) and S1P receptor 2 in the phagocytosis of *Cryptococcus neoformans* by alveolar macrophages. Microbiology, 157, 1416-1427.

276. McVerry, B. J., X. Peng, P. M. Hassoun, S. Sammani, B. A. Simon, and J. G. Garcia. Sphingosine 1-phosphate reduces vascular leak in murine and canine models of acute lung injury. Am J Respir Crit Care Med, 2004, 170:987-93.

277. Mehta, D., M. Konstantoulaki, G. U. Ahmmed, and A. B. Malik. Sphingosine 1-phosphate-induced mobilization of intracellular Ca2+ mediates rac activation and adherens junction assembly in endothelial cells. J Biol Chem, 2005, 280:17320-8.

278. Mellado, M., Fernández-Agulló, T., Rodríguez-Frade, J. M., García San Frutos, M., de la Peña, P., Martínez-A, C. & Montoya, E. (1999) Expression analysis of the thyrotropin-releasing hormone receptor (TRHR) in the immune system using agonist anti-TRHR monoclonal antibodies. FEBS Letters, 451, 308-314.

279. Michel, M. C., Beck-Sickinger, A., Cox, H., Doods, H. N., Herzog, H., Larhammar, D., Quirion, R., Schwartz, T. & Westfall, T. (1998) XVI. International Union of Pharmacology recommendations for the nomenclature of neuropeptide Y, peptide YY, and pancreatic polypeptide receptors. Pharmacol Rev, 50, 143-150.

280. Minami, T., H. Nakano, T. Kobayashi, Y. Sugimoto, F. Ushikubi, and A. Ichikawa. Characterization of EP receptor subtypes responsible for prostaglandin E2-induced pain responses by use of EP1 and EP3 receptor knockout mice. Br J Pharmacol, 2001, 133:438-44.

281. Mitić, K., Stanojević, S., Kuštrimović, N., Vujić, V. & Dimitrijević, M. (2011) Neuropeptide Y modulates functions of inflammatory cells in the rat: Distinct role for Y1, Y2 and Y5 receptors. Peptides, 32, 1626-1633.

282. Mitsuhashi, M., Mitsuhashi, T. & Payan, D. (1989) Multiple signalling pathways of histamine H2 receptors. Identification of an H2 receptor-dependent Ca2+ mobilization pathway in human HL-60 promyelocytic leukemia cells. Journal of Biological Chemistry, 264, 18356-18362.

283. Mo, J., Yang, A., Chen, Z., Shao, T., Zhang, Y. & Chen, Q. (2013) Neuronostatin ameliorates sodium taurocholate-induced acute pancreatitis in rats. Digestive diseases and sciences, 58, 2903-2907.

284. Moore, D. J., Chambers, J. K., Wahlin, J.-P., Tan, K. B., Moore, G. B., Jenkins, O., Emson, P. C. & Murdock, P. R. (2001) Expression pattern of human P2Y receptor subtypes: a quantitative reverse transcription-polymerase chain reaction study. Biochimica et Biophysica Acta (BBA)-Gene Structure and Expression, 1521, 107-119.

285. Moriyama, M., Sato, T., Inoue, H., Fukuyama, S., Teranishi, H., Kangawa, K., Kano, T., Yoshimura, A. & Kojima, M. (2005) The neuropeptide neuromedin U promotes inflammation by direct activation of mast cells. The Journal of experimental medicine, 202, 217-224.

286. Morooka H, Iwanaga Y, Tamaki Y, Takase T, Akahoshi Y, Nakano Y, Fujiki H, Miyazaki S. Chronic administration of oral vasopressin type 2 receptor antagonist tolvaptan exerts both myocardial and renal protective effects in rats with hypertensive heart failure. Circ Heart Fail, 2012, 5: 484-92.

287. Muir, A. I., Chamberlain, L., Elshourbagy, N. A., Michalovich, D., Moore, D. J., Calamari, A., Szekeres, P.

287. G., Sarau, H. M., Chambers, J. K. & Murdock, P. (2001) AXOR12, a novel human G protein-coupled receptor, activated by the peptide KiSS-1. Journal of Biological Chemistry, 276, 28969-28975.

288. Murata, T., F. Ushikubi, T. Matsuoka, M. Hirata, A. Yamasaki, and Y. Sugimoto. Altered pain perception and inflammatory response in mice lacking prostacyclin receptor. Nature, 1997, 388:678-82.

289. Murphy, P. M., M. Baggiolini, I. F. Charo, C. A. Hebert, R. Horuk, and K. Matsushima. (2000) International Union of Pharmacology. XXII. Nomenclature for chemokine receptors. Pharmacol Rev, 52:145-76.

290. Mustafa, S., Ayoub, M. A. and Pfleger, K. D. G., (2010) Uncovering GPCR heteromer-biased ligands. Drug Discov Today Technol, 7: e77-e85.

291. Mustafa, S., See, H. B., Seeber, R. M., Armstrong, S. P., White, C. W., Ventura, S., Ayoub, M. A., and Pfleger, K. D., Identification and profiling of novel alpha1A-adrenoceptor-CXC chemokine receptor 2 heteromer, J Biol Chem, 2012, 287: 12952-65.

292. Nagamachi, M., Sakata, D., Kabashima, K., Furuyashiki, T., Murata, T., Segi-Nishida, E., Soontrapa, K., Matsuoka, T., Miyachi, Y. & Narumiya, S. (2007) Facilitation of Th1-mediated immune response by prostaglandin E receptor EP1. The Journal of experimental medicine, 204, 2865-2874.

293. Neeper, M., Schmidt, A. M., Brett, J. , Yan, S. D., Wang, F., Pan, Y. C., Elliston, K., Stern, D., Shaw, A., Cloning and expression of a cell surface receptor for advanced glycosylation end products of proteins, J Biol Chem, 1992, 268:21, 14998-5004.

294. Nemeth, Z. H., Lutz, C. S., Csoka, B., Deitch, E. A., Leibovich, S. J., Gause, W. C., Tone, M., Pacher, P., Vizi, E. S. & Haskó, G. (2005) Adenosine augments IL-10 production by macrophages through an A2B receptor-mediated posttranscriptional mechanism. The Journal of Immunology, 175, 8260-8270.

295. Neumann, J., Schaale, K., Farhat, K., Endermann, T., Ulmer, A. J., Ehlers, S. & Reiling, N. (2010) Frizzled1 is a marker of inflammatory macrophages, and its ligand Wnt3a is involved in reprogramming *Mycobacterium tuberculosis*-infected macrophages. The FASEB Journal, 24, 4599-4612.

296. Nichols, D. E. & Nichols, C. D. (2008) Serotonin receptors. Chem Rev, 108, 1614-1641.

297. Nie, Y., Ma, R. C., Chan, J. C., Xu, H. & Xu, G. (2012) Glucose-dependent insulinotropic peptide impairs insulin signalling via inducing adipocyte inflammation in glucose-dependent insulinotropic peptide receptor-overexpressing adipocytes. The FASEB Journal, 26, 2383-2393.

298. Niedernberg, A., Tunaru, S., Blaukat, A., Ardati, A. & Kostenis, E. (2003) Sphingosine 1-phosphate and dioleoylphosphatidic acid are low affinity agonists for the orphan receptor GPR63. Cellular Signalling, 15, 435-446.

299. Nijmeijer, S., Vischer, H. F. & Leurs, R. (2016) Adhesion GPCRs in immunology. Biochemical pharmacology.

300. Nishio, R., Matsumori, A., Shioi, T., Wang, W., Yamada, T., Ono, K. & Sasayama, S. (1998) Denopamine, a 31-adrenergic agonist, prolongs survival in a murine model of congestive heart failure induced by viral myocarditis: suppression of tumor necrosis factor-α production in the heart. Journal of the American College of Cardiology, 32, 808-815.

301. Obinata, H. and Hla, T., Sphingosine 1-phosphate in coagulation and inflammation, Semin Immunopathol, 2012, 34: 73-91.

302. Ohshima, S., Yamaguchi, N., Nishioka, K., Mima, T., Ishii, T., Umeshita-Sasai, M., Kobayashi, H., Shimizu, M., Katada, Y. & Wakitani, S. (2002) Enhanced local production of osteopontin in rheumatoid joints. The Journal of Rheumatology, 29, 2061-2067.

303. Okamoto, K., Imbe, H., Morikawa, Y., Itoh, M., Sekimoto, M., Nemoto, K. & Senba, E. (2002) 5-HT2A receptor subtype in the peripheral branch of sensory fibers is involved in the potentiation of inflammatory pain in rats. Pain, 99, 133-143.

304. Osborn, O., McNelis, J., Sanchez-Alavez, M., Talukdar, S., Lu, M., Li, P., Thiede, L., Morinaga, H., Kim, J. J. & Heinrichsdorff, J. (2012) G protein-coupled receptor 21 deletion improves insulin sensitivity in diet-induced obese mice. The Journal of clinical investigation, 122, 2444-2453.

305. Othman, M. A., Grygalewicz, B., Pienkowska-Grela, B., Rincic, M., Rittscher, K., Melo, J. B., Carreira, I. M., Meyer, B., Marzena, W. & Liehr, T. (2015) Novel Cryptic Rearrangements in Adult B-Cell Precursor Acute Lymphoblastic Leukemia Involving the MLL Gene. Journal of Histochemistry & Cytochemistry, 0022155415576201.

306. Ott, C., et al. Role of advanced glycation end products in cellular signalling. Redox biology, 2014, 2: 411-429.

307. Paavonen, A., Watson, A. M., Li J., Paavonen, K., Koitka, A., Calkin, A. C., Barit, D., Coughlan, M. T., Drew, B. G., Lancaster, G. I., Thomas, M., Forbes, J. M., Nawroth, P. P., Bierhaus A., Cooper M. E., and Jandeleit-Dahm K. A. Receptor for advanced glycation end products (RAGE) deficiency attenuates the development of atherosclerosis in diabetes, Diabetes. 2008, 57: 2461-9.

308. Panula, P., Chazot, P. L., Cowart, M., Gutzmer, R., Leurs, R., Liu, W. L., Stark, H., Thurmond, R. L. & Haas, H. L. (2015) International Union of Basic and Clinical Pharmacology. XCVIII. Histamine Receptors. Pharmacol Rev, 67, 601-655.

309. Park J et al. (2008) MCP-1/CCR2 system is involved in high glucose-induced fibronectin and type IV collagen expression in cultured mesangial cells, Am J Physiol Renal Physiol, 295: F749-F757.

310. Park, L., et al. (1998) Suppression of accelerated diabetic atherosclerosis by the soluble receptor for advanced glycation endproducts. Nature medicine, 4: 1025-1031.

311. Parker, H., Habib, A., Rogers, G., Gribble, F. & Reimann, F. (2009) Nutrient-dependent secretion of glucose-dependent insulinotropic polypeptide from primary murine K cells. Diabetologia, 52, 289-298.

312. Pasternack, S. M., von Kügelgen, I., Al Aboud, K., Lee, Y.-A., Rüschendorf, F., Voss, K., Hillmer, A. M., Molderings, G. J., Franz, T. & Ramirez, A. (2008) G protein-coupled receptor P2Y5 and its ligand LPA are involved in maintenance of human hair growth. Nature genetics, 40, 329-334.

313. Patel, Y. C. (1999) Somatostatin and its receptor family. Front Neuroendocrinol, 20, 157-198.

314. Peluso, J., LaForge, K. S., Matthes, H. W., Kreek, M. J., Kieffer, B. L. & Gavériaux-Ruff, C. (1998) Distribution of nociceptin/orphanin FQ receptor transcript in human central nervous system and immune cells. Journal of neuroimmunology, 81, 184-192.

315. Peng, Y.-M., van de Garde, M. D., Cheng, K.-F., Baars, P. A., Remmerswaal, E. B., van Lier, R. A., Mackay, C. R., Lin, H.-H. & Hamann, J. (2011) Specific expression of GPR56 by human cytotoxic lymphocytes. Journal of leukocyte biology, 90, 735-740.

316. Perret, G., Valensi, P., Hugues, J. N., Vassy, R. & Uzzan, B. (1988) Use of a pharmacokinetic model to characterize the thyrotropin (TSH) and prolactin (PRL) response to thyrotropin-releasing hormone (THR) in man. Methods and findings in experimental and clinical pharmacology, 10, 387-391.

317. Petersen, H. & Myren, J. (1974) Secretin dose-response in health and chronic pancreatic inflammatory disease. Scandinavian journal of gastroenterology, 10, 851-861.

318. Pfleger, K. D. & Eidne, K. A. (2006) Illuminating insights into protein-protein interactions using bioluminescence resonance energy transfer (BRET). Nat Methods 3, 165-174.

319. Piirainen, H., Ashok, Y., Nanekar, R. T. & Jaakola, V. P. (2011) Structural features of adenosine receptors: from crystal to function. Biochim Biophys Acta, 1808, 1233-1244.

320. Pillai, S. G., Cousens, D. J., Barnes, A. A., Buckley, P. T., Chiano, M. N., Hosking, L. K., Cameron, L.-A., Fling, M. E., Foley, J. J. & Green, A. (2004) A coding polymorphism in the CYSLT2 receptor with reduced affinity to LTD4 is associated with asthma. Pharmacogenetics and Genomics, 14, 627-633.

321. Piomelli, D., A. Giuffrida, A. Calignano, and F. Rodriguez de Fonseca. The endocannabinoid system as a target for therapeutic drugs. Trends Pharmacol Sci, 2000, 21:218-24.

322. Poloso, N. J., Urquhart, P., Nicolaou, A., Wang, J. & Woodward, D. F. (2013) PGE 2 differentially regulates monocyte-derived dendritic cell cytokine responses depending on receptor usage (EP 2/EP 4). Molecular immunology, 54, 284-295.

323. Powell, W. S. & Rokach, J. (2013) The eosinophil chemoattractant 5-oxo-ETE and the OXE receptor. Progress in lipid research, 52, 651-665.

324. Putranto E W, Murata H, Yamamoto K, Kataoka K, Yamada H, Futami J, Sakaguchi M, Huh N H (2013) Inhibition of RAGE signalling through the intracellular delivery of inhibitor peptides by PEI cationization. Int J Mol Med., 32, 938-944.

325. Qin, L., Kufareva, I., Holden, L. G., Wang, C., Zheng, Y., Zhao, C., Fenalti, G., Wu, H., Han, G. W., Cherezov, V., Abagyan, R., Stevens, R. C. & Handel, T. M. (2015) Structural biology. Crystal structure of the chemokine receptor CXCR4 in complex with a viral chemokine. Science, 347, 1117-1122.

326. Qu, L., Fan, N., Ma, C., Wang, T., Han, L., Fu, K., Wang, Y., Shimada, S. G., Dong, X. & LaMotte, R. H. (2014) Enhanced excitability of MRGPRA3- and MRGPRD-positive nociceptors in a model of inflammatory itch and pain. Brain, 137, 1039-1050.

327. Quigley, D. A., To, M. D., Perez-Losada, J., Pelorosso, F. G., Mao, J.-H., Nagase, H., Ginzinger, D. G. & Balmain, A. (2009) Genetic architecture of mouse skin inflammation and tumour susceptibility. Nature, 458, 505-508.

328. Raether H. Surface plasmons on smooth and rough surfaces and on gratings, in Series Springer Tracts in Modern Physics, 1988, Springer-Verlag Berlin Heidelberg.

329. Rai V, Maldonado A Y, Burz D S, Reverdatto S, Schmidt A M and Shekhtman A; Signal Transduction in Receptor for Advanced Glycation End Products (RAGE), J Biol Chem, 2012, 287: 5133-44.

330. Rajagopalan, S., Kurz, S., Munzel, T., Tarpey, M., Freeman, B. A., Griendling, K. K. and Harrison, D. G., (1996) Angiotensin II-mediated hypertension in the rat increases vascular superoxide production via membrane NADH/NADPH oxidase activation. Contribution to alterations of vasomotor tone, J Clin Invest., 97: 1916-23.

331. Ramasamy R, Shekhtman A, Schmidt A M, The multiple faces of RAGE-opportunities for therapeutic intervention in aging and chronic disease. Expert Opin Ther Targets, 2016, 20: 431-446.

332. Ramasamy, R. & Schmidt, A. M. Receptor for advanced glycation end products (RAGE) and implications for the pathophysiology of heart failure. Current heart failure reports, 2012, 9: 107-116.

333. Rao V et al. (2006) Role for Macrophage Metalloelastase in Glomerular Basement Membrane Damage Associated with Alport Syndrome, American Journal of Pathology, 169: 32-46.

334. Rao, S., Garrett-Sinha, L. A., Yoon, J. & Simon, M. C. (1999) The Ets Factors P U. 1 and Spi-B Regulate the Transcriptionin Vivo of P2Y10, a Lymphoid Restricted Heptahelical Receptor. Journal of Biological Chemistry, 274, 34245-34252.

335. Ray, R., Juranek, J. K. & Rai, V. RAGE axis in neuroinflammation, neurodegeneration and its emerging role in the pathogenesis of amyotrophic lateral sclerosis. Neuroscience and biobehavioral reviews, 2016, 62: 48-55.

336. Rebeck, G. W., Maynard, K. I., Hyman, B. T. & Moskowitz, M. A. (1994) Selective 5-HT1D alpha serotonin receptor gene expression in trigeminal ganglia: implications for antimigraine drug development. Proceedings of the National Academy of Sciences, 91, 3666-3669.

337. Rees, S., den Daas, I., Foord, S., Goodson, S., Bull, D., Kilpatrick, G. & Lee, M. (1994) Cloning and characterisation of the human 5-HT5A serotonin receptor. FEBS letters, 355, 242-246.

338. Robinson, L. J., Tourkova, I., Wang, Y., Sharrow, A. C., Landau, M. S., Yaroslavskiy, B. B., Sun, L., Zaidi, M. & Blair, H. C. (2010) FSH-receptor isoforms and FSH-dependent gene transcription in human monocytes and osteoclasts. Biochemical and biophysical research communications, 394, 12-17.

339. Rollins, B. J. (1996) Monocyte chemoattractant protein 1: a potential regulator of monocyte recruitment in inflammatory disease. Mol. Med. Today, 2: 198-204.

340. Rompler, H., Schulz, A., Pitra, C., Coop, G., Przeworski, M., Paabo, S. & Schoneberg, T. (2005) The rise and fall of the chemoattractant receptor GPR33. Journal of Biological Chemistry.

341. Rosen, H., Gonzalez-Cabrera, P. J., Sanna, M. G. & Brown, S. (2009) Sphingosine 1-phosphate receptor signalling. Annu Rev Biochem, 78, 743-768.

342. Rossi, L., Lemoli, R. M. & Goodell, M. A. (2013) Gpr171, a putative P2Y-like receptor, negatively regulates myeloid differentiation in murine hematopoietic progenitors. Experimental hematology, 41, 102-112.

343. Roy A, Kucukural A, Zhang Y. I-TASSER: a unified platform for automated protein structure and function prediction. Nature Protocols, 2010, 5: 725-738.

344. Rubic, T., Lametschwandtner, G., Jost, S., Hinteregger, S., Kund, J., Carballido-Perrig, N., Schwärzler, C., Junt, T., Voshol, H. & Meingassner, J. G. (2008) Triggering the succinate receptor GPR91 on dendritic cells enhances immunity. Nature immunology, 9, 1261-1269.

345. Russo, I. & Frangogiannis, N. G. Diabetes-associated cardiac fibrosis: Cellular effectors, molecular mechanisms and therapeutic opportunities. Journal of molecular and cellular cardiology, 2016, 90: 84-93.

346. Saban, R., Saban, M. R., Nguyen, N.-B., Lu, B., Gerard, C., Gerard, N. P. & Hammond, T. G. (2000) Neurokinin-1 (NK-1) receptor is required in antigen-induced cystitis. The American journal of pathology, 156, 775-780.
347. Sakaguchi M, Murata H, Yamamoto K, Ono T, Sakaguchi Y, Motoyama A, Hibino T, Kataoka K, Huh N H. (2011) TIRAP, an adaptor protein for TLR2/4, transduces a signal from RAGE phosphorylated upon ligand binding. PLOS One, 6: e23132.
348. Sakamoto, Y., Inoue, H., Kawakami, S., Miyawaki, K., Miyamoto, T., Mizuta, K. & Itakura, M. (2006) Expression and distribution of Gpr119 in the pancreatic islets of mice and rats: predominant localization in pancreatic polypeptide-secreting PP-cells. Biochemical and biophysical research communications, 351, 474-480.
349. Salmon, A.-M., Damaj, M. I., Marubio, L. M., Epping-Jordan, M. P., Merlo-Pich, E. & Changeux, J.-P. (2001) Altered neuroadaptation in opiate dependence and neurogenic inflammatory nociception in aCGRP-deficient mice. Nature neuroscience, 4, 357-358.
350. Sampaio, A. L., Rae, G. A. & Maria das Graças, M. (2004) Effects of endothelin ETA receptor antagonism on granulocyte and lymphocyte accumulation in LPS-induced inflammation. Journal of leukocyte biology, 76, 210-216.
351. Sarkar, C., Das, S., Chakroborty, D., Chowdhury, U. R., Basu, B., Dasgupta, P. S. & Basu, S. (2006) Cutting edge: stimulation of dopamine D4 receptors induce T cell quiescence by up-regulating Krüppel-like factor-2 expression through Inhibition of ERK1/ERK2 phosphorylation. The Journal of Immunology, 177, 7525-7529.
352. Sasaki, Y., Hoshi, M., Akazawa, C., Nakamura, Y., Tsuzuki, H., Inoue, K. & Kohsaka, S. (2003) Selective expression of Gi/o-coupled ATP receptor P2Y12 in microglia in rat brain. Glia, 44, 242-250.
353. Sato, K. Z., Fujii, T., Watanabe, Y., Yamada, S., Ando, T., Kazuko, F. & Kawashima, K. (1999) Diversity of mRNA expression for muscarinic acetylcholine receptor subtypes and neuronal nicotinic acetylcholine receptor subunits in human mononuclear leukocytes and leukemic cell lines. Neuroscience letters, 266, 17-20.
354. Satoh, A., Shimosegawa, T., Satoh, K., Ito, H., Kohno, Y., Masamune, A., Fujita, M. & Toyota, T. (2000) Activation of adenosine A1-receptor pathway induces edema formation in the pancreas of rats. Gastroenterology, 119, 829-836.
355. Schaub, A., Futterer, A. & Pfeffer, K. (2001) PUMA-G, an IFN-gamma-inducible gene in macrophages is a novel member of the seven transmembrane spanning receptor superfamily. Eur J Immunol, 31, 3714-3725.
356. Schiffmann, E., Corcoran, B. A. & Wahl, S. M. (1975) N-formylmethionyl peptides as chemoattractants for leucocytes. Proceedings of the National Academy of Sciences, 72, 1059-1062.
357. Schmidhuber, S. M., Rauch, I., Kofler, B. & Brain, S. D. (2009) Evidence that the modulatory effect of galanin on inflammatory edema formation is mediated by the galanin receptor 3 in the murine microvasculature. Journal of molecular neuroscience: MN, 37, 177-181.
358. Schmidt, A. M., Yan, S. D., Wautier, J. L. & Stern, D. (1999) Activation of receptor for advanced glycation end products: a mechanism for chronic vascular dysfunction in diabetic vasculopathy and atherosclerosis. Circ Res, 84: 489-497.
359. Schmitz, F., Schrader, H., Otte, J.-M., Schmitz, H., Stüber, E., Herzig, K.-H. & Schmidt, W. E. (2001) Identification of CCK-B/gastrin receptor splice variants in human peripheral blood mononuclear cells. Regulatory peptides, 101, 25-33.
360. Schuelert, N. & McDougall, J. J. (2011) The abnormal cannabidiol analogue O-1602 reduces nociception in a rat model of acute arthritis via the putative cannabinoid receptor GPR55. Neuroscience letters, 500, 72-76.
361. Schwarze, S. R., Hruska, K. A., Dowdy, S. F. (2000) Protein transduction: unrestricted delivery into all cells? Trends Cell Biol, 10: 290-295.
362. Shen, Z.-J., Hu, J., Esnault, S., Dozmorov, I. & Malter, J. S. (2015) RNA Seq profiling reveals a novel expression pattern of TGF-β target genes in human blood eosinophils. Immunology letters, 167, 1-10.
363. Shen. J., Huang. Y. M., Wang. M., et al. (2016) Renin-angiotensin system blockade for the risk of cancer and death. J Renin Angiotensin Aldosterone Syst. 8, 17(3).
364. Shihoya, W., Nishizawa, T., Okuta, A., Tani, K., Dohmae, N., Fujiyoshi, Y., Nureki, O. & Doi, T. (2016) Activation mechanism of endothelin ETB receptor by endothelin-1. Nature, 537, 363-368.
365. Sima, C., Cheng, Q., Rautava, J., Levesque, C., Sherman, P. & Glogauer, M. (2015) Identification of quantitative trait loci influencing inflammation-mediated alveolar bone loss: insights into polygenic inheritance of host—biofilm disequilibria in periodontitis. Journal of periodontal research.
366. Sjolander S and Urbaniczky C. Integrated fluid handling system for biomolecular interaction analysis. Anal. Chem., 1991, 63: 2338-2345.
367. Sohn, S.-H., Chung, H.-S., Ko, E., Jeong, H.-j., Kim, S.-H., Jeong, J.-H., Kim, Y., Shin, M., Hong, M. & Bae, H. (2009) The genome-wide expression profile of Nelumbinis semen on lipopolysaccharide-stimulated BV-2 microglial cells. Biological and Pharmaceutical Bulletin, 32, 1012-1020.
368. Solinski, H. J., Petermann, F., Rothe, K., Boekhoff, I., Gudermann, T. & Breit, A. (2013) Human Mas-Related G Protein-Coupled Receptors-X1 Induce Chemokine Receptor 2 Expression in Rat Dorsal Root Ganglia Neurons and Release of Chemokine Ligand 2 from the Human LAD-2 Mast Cell Line. PLOS ONE, 8, e58756.
369. Sonobe, Y., Nakane, H., Watanabe, T. & Nakano, K. (2004) Regulation of Con A-dependent cytokine production from CD4+ and CD8+ T lymphocytes by autosecretion of histamine. Inflammation Research, 53, 87-92.
370. Sonoda, N., Katabuchi, H., Tashiro, H., Ohba, T., Nishimura, R., Minegishi, T. & Okamura, H. (2005) Expression of variant luteinizing hormone/chorionic gonadotropin receptors and degradation of chorionic gonadotropin in human chorionic villous macrophages. Placenta, 26, 298-307.
371. Soro-Paavonen, A., Watson, AM., Thomas, M. C., et al. (2008) Receptor for advanced glycation end products (RAGE) deficiency attenuates the development of atherosclerosis in diabetes, Diabetes, 57:2461-2469.
372. Souza, D. G., Lomez, E. S. L., Pinho, V., Pesquero, J. B., Bader, M., Pesquero, J. L. & Teixeira, M. M. (2004) Role of Bradykinin B2 and B1 Receptors in the Local, Remote, and Systemic Inflammatory Responses That Follow Intestinal Ischemia and Reperfusion Injury. The Journal of Immunology, 172, 2542-2548.
373. Sparvero, L. J., et al. (2009) RAGE (Receptor for Advanced Glycation Endproducts), RAGE ligands, and their role in cancer and inflammation. Journal of translational medicine, 7: 17.

374. Stacey, M., Lin, H.-H., Hilyard, K. L., Gordon, S. & McKnight, A. J. (2001) Human epidermal growth factor (EGF) module-containing mucin-like hormone receptor 3 is a new member of the EGF-TM7 family that recognizes a ligand on human macrophages and activated neutrophils. Journal of Biological Chemistry, 276, 18863-18870.

375. Stefulj, J., Jernej, B., Cicin-Sain, L., Rinner, I. & Schauenstein, K. (2000) mRNA expression of serotonin receptors in cells of the immune tissues of the rat. Brain, behavior, and immunity, 14, 219-224.

376. Stockhammer, O. W., Rauwerda, H., Wittink, F. R., Breit, T. M., Meijer, A. H. & Spaink, H. P. (2010) Transcriptome analysis of Traf6 function in the innate immune response of zebrafish embryos. Molecular immunology, 48, 179-190.

377. Stoddart L A, Johnstone E K M, Wheal A J, Goulding J, Robers M B, Machleidt T, Wood K V, Hill S J and Pfleger K D G. Application of BRET to monitor ligand binding to GPCRs. Nat Methods, 2015, 12: 661-663.

378. Su P. C., Berger B. W. (2013) A novel assay for assessing juxtamembrane and transmembrane domain interactions important for receptor heterodimerization. J Mol Biol. 425, 4652-4658.

379. Subramanian, H., Gupta, K., Guo, Q., Price, R. & Ali, H. (2011) Mas-related Gene X2 (MrgX2) Is a Novel G Protein-coupled Receptor for the Antimicrobial Peptide LL-37 in Human Mast Cells RESISTANCE TO RECEPTOR PHOSPHORYLATION, DESENSITIZATION, AND INTERNALIZATION. Journal of Biological Chemistry, 286, 44739-44749.

380. Sugimoto, T., Saito, M., Mochizuki, S., Watanabe, Y., Hashimoto, S. & Kawashima, H. (1994) Molecular cloning and functional expression of a cDNA encoding the human V1b vasopressin receptor. Journal of Biological Chemistry, 269, 27088-27092.

381. Sugimoto, Y. & Narumiya, S. (2007) Prostaglandin E receptors. J Biol Chem, 282, 11613-11617.

382. Sugo, T., Tachimoto, H., Chikatsu, T., Murakami, Y., Kikukawa, Y., Sato, S., Kikuchi, K., Nagi, T., Harada, M. & Ogi, K. (2006) Identification of a lysophosphatidylserine receptor on mast cells. Biochemical and biophysical research communications, 341, 1078-1087.

383. Sukkar, M. B., et al. RAGE: a new frontier in chronic airways disease. British Journal of Pharmacology, 2012, 167: 1161-1176.

384. Sunuwar, L., Medini, M., Cohen, L., Sekler, I. & Hershfinkel, M. (2016) The zinc sensing receptor, ZnR/GPR39, triggers metabotropic calcium signalling in colonocytes and regulates occludin recovery in experimental colitis. Phil. Trans. R. Soc. B, 371, 20150420.

385. Suzuki, T., Won, K.-J., Horiguchi, K., Kinoshita, K., Hori, M., Torihashi, S., Momotani, E., Itoh, K., Hirayama, K. & Ward, S. M. (2004) Muscularis inflammation and the loss of interstitial cells of Cajal in the endothelin ETB receptor null rat. American Journal of Physiology-Gastrointestinal and Liver Physiology, 287, G638-G646.

386. Swan, C., Duroudier, N. P., Campbell, E., Zaitoun, A., Hastings, M., Dukes, G. E., Cox, J., Kelly, F. M., Wilde, J. & Lennon, M. G. (2013) Identifying and testing candidate genetic polymorphisms in the irritable bowel syndrome (IBS): association with TNFSF15 and TNFα. Gut, 62, 985-994.

387. Swaney, J., Chapman, C., Correa, L., Stebbins, K., Bundey, R., Prodanovich, P., Fagan, P., Baccei, C., Santini, A. & Hutchinson, J. (2010) A novel, orally active LPA1 receptor antagonist inhibits lung fibrosis in the mouse bleomycin model. British journal of pharmacology, 160, 1699-1713.

388. Szabo, A., Stolz, L. and Granzow, R. Surface plasmon resonance and its use in biomolecular interaction analysis (BIA). Curr Opin Struct Biol, 1995, 5: 699-705.

389. Taguchi, A., et al. (2000) Blockade of RAGE-amphoterin signalling suppresses tumour growth and metastases. Nature, 405: 354-360.

390. Takayama, K., Yuhki, K., Ono, K., Fujino, T., Hara, A., Yamada, T., Kuriyama, S., Karibe, H., Okada, Y., Takahata, O., Taniguchi, T., Iijima, T., Iwasaki, H., Narumiya, S. & Ushikubi, F. (2005) Thromboxane A2 and prostaglandin F2alpha mediate inflammatory tachycardia. Nat Med, 11, 562-566.

391. Takenouchi, R., Inoue, K., Kambe, Y. & Miyata, A. (2012)N-arachidonoyl glycine induces macrophage apoptosis via GPR18. Biochemical and biophysical research communications, 418, 366-371.

392. Tan, Q., Zhu, Y., Li, J., Chen, Z., Han, G. W., Kufareva, I., Li, T., Ma, L., Fenalti, G., Li, J., Zhang, W., Xie, X., Yang, H., Jiang, H., Cherezov, V., Liu, H., Stevens, R. C., Zhao, Q. & Wu, B. (2013) Structure of the CCR5 chemokine receptor-HIV entry inhibitor maraviroc complex. Science, 341, 1387-1390.

393. Taniyama, Y., Suzuki, T., Mikami, Y., Moriya, T., Satomi, S. & Sasano, H. (2005) Systemic distribution of somatostatin receptor subtypes in human: an immunohistochemical study. Endocrine journal, 52, 605-611.

394. Taquet, N., Philippe, C., Reimund, J.-M. & Muller, C. D. (2012) Inflammatory Bowel Disease G-Protein Coupled Receptors (GPCRs) Expression Profiling with Microfluidic Cards.

395. Taub, D. D., Eisenstein, T. K., Geller, E. B., Adler, M. W. & Rogers, T. J. (1991) Immunomodulatory activity of mu- and kappa-selective opioid agonists. Proceedings of the National Academy of Sciences, 88, 360-364.

396. Tayebati, S., Bronzetti, E., Morra Di Cella, S., Mulatero, P., Ricci, A., Rossodivita, I., Schena, M., Schiavone, D., Veglio, F. & Amenta, F. (2000) In situ hybridization and immunocytochemistry of alpha1-adrenoceptors in human peripheral blood lymphocytes. Journal of autonomic pharmacology, 20, 305-312.

397. Ter Beek, W. P., Muller, E. S., Van Den Berg, M., Meijer, M. J., Biemond, 1. & Lamers, C. B. (2008) Motilin receptor expression in smooth muscle, myenteric plexus, and mucosa of human inflamed and noninflamed intestine. Inflammatory bowel diseases, 14, 612-619.

398. Tesch, G. H. (2008) MCP-1/CCL2: a new diagnostic marker and therapeutic target for progressive renal injury in diabetic nephropathy. Am J Physiol Renal Physiol, 294: 697-701.

399. Teuscher, C., Subramanian, M., Noubade, R., Gao, J. F., Offner, H., Zachary, J. F. & Blankenhorn, E. P. (2007) Central histamine H3 receptor signalling negatively regulates susceptibility to autoimmune inflammatory disease of the CNS. Proceedings of the National Academy of Sciences, 104, 10146-10151.

400. Thal, D. M., Sun, B., Feng, D., Nawaratne, V., Leach, K., Felder, C. C., Bures, M. G., Evans, D. A., Weis, W. I., Bachhawat, P., Kobilka, T. S., Sexton, P. M., Kobilka, B. K. & Christopoulos, A. (2016) Crystal structures of the M1 and M4 muscarinic acetylcholine receptors. Nature, 531, 335-340.

401. Theodoropoulou, M. & Stalla, G. K. (2013) Somatostatin receptors: from signalling to clinical practice. Front Neuroendocrinol, 34, 228-252.

402. Thoene-Reineke, C., Rumschussel, K., Schmerbach, K. et al., Prevention and intervention studies with telmisartan, ramipril and their combination in different rat stroke models. PloS One, 2011, 6: e23646.

403. Thomas, M. C., Pickering, R. J., Tsorotes, D., Koitka, A., Sheehy, K., Bernardi, S., Toffoli B., Nguyen-Huu, T. P., Head, G. A., Fu, Y., Chin-Dusting, J., Cooper, M. E., Tikellis C. (2010) Genetic Ace2 deficiency accentuates vascular inflammation and atherosclerosis in the ApoE knockout mouse. Circulation Research, 107: 888-97.

404. Thomas, M. C., Tikellis, C., Burns, W. M., et al., Interactions between renin angiotensin system and advanced glycation in the kidney, Journal of the American Society of Nephrology, 2005, 16: 2976-2984.

405. Thompson, S. W., A. Dray, and L. Urban. Injury-induced plasticity of spinal reflex activity: NK1 neurokinin receptor activation and enhanced A- and C-fiber mediated responses in the rat spinal cord in vitro. J Neurosci, 1994, 14:3672-87.

406. Tichelaar, J. W., Wesselkamper, S. C., Chowdhury, S., Yin, H., Berclaz, P.-Y., Sartor, M. A., Leikauf, G. D. & Whitsett, J. A. (2007) Duration-dependent cytoprotective versus inflammatory effects of lung epithelial fibroblast growth factor-7 expression. Experimental lung research, 33, 385-417.

407. Tikellis, C, Wookey, P. J., Candido, R., Thomas, M. C. (2004) Improved islet morphology after blockade of the renin-angiotensin system in the ZDF rat, Diabetes, 53: 989-997.

408. Tikellis, C., Pickering, R. J., Tsorotes, D., Huet, O., Chin-Dusting, J., Cooper, M. E., and Thomas, M. C. (2012) Activation of the Renin-Angiotensin system mediates the effects of dietary salt intake on atherogenesis in the apolipoprotein E knockout mouse, Hypertension, 60: 98-105.

409. Tiruppathi, C., R. D. Minshall, B. C. Paria, S. M. Vogel, and A. B. Malik. Role of Ca2+signalling in the regulation of endothelial permeability. Vascul Pharmacol, 2002, 39:173-85.

410. Tiulpakov A, White C W, Abhayawardana R S, See H B, Chan A S, Seeber R M, Heng J I, Dedov I, Pavlos N J, Pfleger K D G, Mutations of vasopressin receptor 2 including novel L312S have differential effects on trafficking, Mol Endocrinol, 2016, 30: 889-904.

411. Tong, L., Lan, W., Lim, R. R. & Chaurasia, S. S. S100A proteins as molecular targets in the ocular surface inflammatory diseases. The ocular surface, 2014, 12: 23-31.

412. Torres, R., S. D. Croll, J. Vercollone, J. Reinhardt, J. Griffiths, and S. Zabski. Mice genetically deficient in neuromedin U receptor 2, but not neuromedin U receptor 1, have impaired nociceptive responses. Pain, 2007, 130: 267-78.

413. Tsatsanis, C., Androulidaki, A., Dermitzaki, E., Gravanis, A. & Margioris, A. N. (2007) Corticotropin releasing factor receptor 1 (CRF1) and CRF2 agonists exert an anti-inflammatory effect during the early phase of inflammation suppressing LPS-induced TNFα release from macrophages via induction of COX-2 and PGE2. Journal of cellular physiology, 210, 774-783.

414. Uhlén, M., FAGERberg, L., Hallström, B. M., Lindskog, C., Oksvold, P., Mardinoglu, A., Sivertsson, Å., Kampf, C., Sjöstedt, E. & Asplund, A. (2015) Tissue-based map of the human proteome. Science, 347, 1260419.

415. Uhlén, M., FAGERberg, L., Hallström, B. M., Lindskog, C., Oksvold, P., Mardinoglu, A., Sivertsson, Å., Kampf, C., Sjöstedt, E. & Asplund, A. (2015) Tissue-based map of the human proteome. Science, 347, 1260419.

416. Vaughan, K. R., Stokes, L., Prince, L. R., Marriott, H. M., Meis, S., Kassack, M. U., Bingle, C. D., Sabroe, I., Surprenant, A. & Whyte, M. K. (2007) Inhibition of neutrophil apoptosis by ATP is mediated by the P2Y11 receptor. The Journal of Immunology, 179, 8544-8553.

417. Venkataraman, C. & Kuo, F. (2005) The G-protein coupled receptor, GPR84 regulates IL-4 production by T lymphocytes in response to CD3 crosslinking. Immunology letters, 101, 144-153.

418. Voice, J. K., Grinninger, C., Kong, Y., Bangale, Y., Paul, S. & Goetzl, E. J. (2003) Roles of vasoactive intestinal peptide (VIP) in the expression of different immune phenotypes by wild-type mice and T cell-targeted type II VIP receptor transgenic mice. The Journal of Immunology, 170, 308-314.

419. Volpi, C., Fazio, F. & Fallarino, F. (2012) Targeting metabotropic glutamate receptors in neuroimmune communication. Neuropharmacology, 63, 501-506.

420. Volz, H. C., Kaya, Z., Katus, H. A. & Andrassy, M. (2010) The role of HMGB1/RAGE in inflammatory cardiomyopathy. Seminars in thrombosis and hemostasis, 36: 185-194.

421. Vu, T. K., D. T. Hung, V. I. Wheaton, and S. R. Coughlin. Molecular cloning of a functional thrombin receptor reveals a novel proteolytic mechanism of receptor activation. Cell, 1991, 64:1057-68.

422. Wacker, D., Wang, C., Katritch, V., Han, G. W., Huang, X. P., Vardy, E., McCorvy, J. D., Jiang, Y., Chu, M., Siu, F. Y., Liu, W., Xu, H. E., Cherezov, V., Roth, B. L. & Stevens, R. C. (2013) Structural features for functional selectivity at serotonin receptors. Science, 340, 615-619.

423. Wada, N., Hashinaga, T., Otabe, S., Yuan, X., Kurita, Y., Kakino, S., Ohoki, T., Nakayama, H., Fukutani, T. & Tajiri, Y. (2013) Selective modulation of Wnt ligands and their receptors in adipose tissue by chronic hyperadiponectinemia. PloS one, 8, e67712.

424. Wan, W., et al. The Emerging Role of HMGB1 in Neuropathic Pain: A Potential Therapeutic Target for Neuroinflammation. Journal of immunology research, 2016, 2016: 6430423.

425. Wang, D. B., Dayton, R. D., Zweig, R. M. & Klein, R. L. (2010) Transcriptome analysis of a tau overexpression model in rats implicates an early pro-inflammatory response. Experimental neurology, 224, 197-206.

426. Wang, J., Simonavicius, N., Wu, X., Swaminath, G., Reagan, J., Tian, H. & Ling, L. (2006) Kynurenic acid as a ligand for orphan G protein-coupled receptor GPR35. Journal of Biological Chemistry, 281, 22021-22028.

427. Warny, M., Aboudola, S., Robson, S. C., Sevigny, J., Communi, D., Soltoff, S. P. & Kelly, C. P. (2001) P2Y6 nucleotide receptor mediates monocyte interleukin-8 production in response to UDP or lipopolysaccharide. Journal of Biological Chemistry, 276, 26051-26056.

428. Watanabe, T., Tomioka, N. H., Doshi, M., Watanabe, S., Tsuchiya, M. & Hosoyamada, M. (2013) Macrophage migration inhibitory factor is a possible candidate for the induction of microalbuminuria in diabetic db/db mice. Biological and Pharmaceutical Bulletin, 36, 741-747.

429. Waters, K. M., Tan, R., Genetos, D. C., Verma, S., Yellowley, C. E. & Karin, N. J. (2007) DNA microarray analysis reveals a role for lysophosphatidic acid in the regulation of anti-inflammatory genes in MC3T3-E1 cells. Bone, 41, 833-841.

430. Wellendorph, P. & Bräuner-Osborne, H. (2004) Molecular cloning, expression, and sequence analysis of GPRC6A, a novel family C G-protein-coupled receptor. Gene, 335, 37-46.

431. Wensman, H., Kamgari, N., Johansson, A., Grujic, M., Calounova, G., Lundequist, A., Rönnberg, E. & Pejler, G. (2012) Tumor-mast cell interactions: Induction of pro-tumorigenic genes and anti-tumorigenic 4-1BB in MCs in response to Lewis Lung Carcinoma. Molecular immunology, 50, 210-219.

432. Wess, J., Eglen, R. M. & Gautam, D. (2007) Muscarinic acetylcholine receptors: mutant mice provide new insights for drug development. Nat Rev Drug Discov, 6, 721-733.

433. White, J. F., Noinaj, N., Shibata, Y., Love, J., Kloss, B., Xu, F., Gvozdenovic-Jeremic, J., Shah, P., Shiloach, J., Tate, C. G. & Grisshammer, R. (2012) Structure of the agonist-bound neurotensin receptor. Nature, 490, 508-513.

434. White, J. H., Chiano, M., Wigglesworth, M., Geske, R., Riley, J., White, N., Hall, S., Zhu, G., Maurio, F. & Savage, T. (2008) Identification of a novel asthma susceptibility gene on chromosome 1qter and its functional evaluation. Human molecular genetics, 17, 1890-1903.

435. Wright, D. H., Ford-Hutchinson, A. W., Chadee, K. & Metters, K. M. (2000) The human prostanoid DP receptor stimulates mucin secretion in LS174T cells. British journal of pharmacology, 131, 1537-1545.

436. Wu, B., Chien, E. Y., Mol, C. D., Fenalti, G., Liu, W., Katritch, V., Abagyan, R., Brooun, A., Wells, P., Bi, F. C., Hamel, D. J., Kuhn, P., Handel, T. M., Cherezov, V. & Stevens, R. C. (2010) Structures of the CXCR4 chemokine GPCR with small-molecule and cyclic peptide antagonists. Science, 330, 1066-1071.

437. Wu, Q.-L., Zierold, C. & Ranheim, E. A. (2009) Dysregulation of Frizzled 6 is a critical component of B-cell leukemogenesis in a mouse model of chronic lymphocytic leukemia. Blood, 113, 3031-3039.

438. Xia, W., Han, J., Huang, G. & Ying, W. Inflammation in ischaemic brain injury: current advances and future perspectives. Clinical and experimental pharmacology & physiology, 2010, 37: 253-258.

439. Xie, J., Mendez, J. D., Mendez-Valenzuela, V. & Aguilar-Hernandez, M. M. Cellular signalling of the receptor for advanced glycation end products (RAGE). Cellular signalling, 2013, 25: 2185-2197.

440. Xiong, X., White, R. E., Xu, L., Yang, L., Sun, X., Zou, B., Pascual, C., Sakurai, T., Giffard, R. G. & Xie, X. S. (2013) Mitigation of murine focal cerebral ischemia by the hypocretin/orexin system is associated with reduced inflammation. Stroke, 44, 764-770.

441. Xue J., Manigrasso M., Scalabrin M., Rai V., Reverdatto S., Burz D. S., Fabris D., Schmidt A. M., Shekhtman A. (2016) Change in the Molecular Dimension of a RAGE-Ligand Complex Triggers RAGE Signaling. Structure. 24, 1509-22.

442. Yadav, M., Huang, M.-C. & Goetzl, E. J. (2011) VPAC1 (vasoactive intestinal peptide (VIP) receptor type 1) G protein-coupled receptor mediation of VIP enhancement of murine experimental colitis. Cellular immunology, 267, 124-132.

443. Yamagishi, S. & Matsui, T. Role of receptor for advanced glycation end products (RAGE) in liver disease. European journal of medical research, 2015, 20: 15.

444. Yan, S. F., Ramasamy, R., Schmidt, A. M., The RAGE axis: A fundamental mechanism signalling danger to the vulnerable vasculature. Circ Res, 2010, 106: 842-853.

445. Yang J, Yan R, Roy A, Xu D, Poisson J, Zhang Y. The I-TASSER Suite: Protein structure and function prediction, Nature Methods, 2015, 12: 7-8.

446. Yang, D., Chen, Q., Gertz, B., He, R., Phulsuksombati, M., Ye, R. D. & Oppenheim, J. J. (2002) Human dendritic cells express functional formyl peptide receptor-like-2 (FPRL2) throughout maturation. J Leukoc Biol, 72, 598-607.

447. Yang, H.-Y. & Iadarola, M. (2003) Activation of spinal neuropeptide FF and the neuropeptide FF receptor 2 during inflammatory hyperalgesia in rats. Neuroscience, 118, 179-187.

448. Ye, R. D., F. Boulay, J. M. Wang, C. Dahlgren, C. Gerard, and M. Parmentier. International Union of Basic and Clinical Pharmacology. LXXIII. Nomenclature for the formyl peptide receptor (FPR) family. Pharmacol Rev, 2009, 61:119-61.

449. Yi, T., Lee, D.-S., Jeon, M.-S., Kwon, S. W. & Song, S. U. (2012) Gene expression profile reveals that STAT2 is involved in the immunosuppressive function of human bone marrow-derived mesenchymal stem cells. Gene, 497, 131-139.

450. Yin, J., Babaoglu, K., Brautigam, C. A.; Clark, L., Shao, Z., Scheuermann, T. H., Harrell, C. M., Gotter, A. L., Roecker, A. J., Winrow, C. J., Renger, J. J., Coleman, P. J. & Rosenbaum, D. M. (2016) Structure and ligand-binding mechanism of the human OX1 and OX2 orexin receptors. Nat Struct Mol Biol, 23, 293-299.

451. Yin, J., Mobarec, J. C., Kolb, P. & Rosenbaum, D. M. (2015) Crystal structure of the human OX2 orexin receptor bound to the insomnia drug suvorexant. Nature, 519, 247-250.

452. Yin, X., Cheng, H., Lin, Y., Fan, X., Cui, Y., Zhou, F., Shen, C., Zuo, X., Zheng, X. & Zhang, W. (2014) Five regulatory genes detected by matching signatures of eQTL and GWAS in psoriasis. Journal of dermatological science, 76, 139-142.

453. Yokomizo, T., Kato, K., Terawaki, K., Izumi, T. & Shimizu, T. (2000) A Second Leukotriene B4 Receptor, Blt2 A New Therapeutic Target in Inflammation and Immunological Disorders. The Journal of experimental medicine, 192, 421-432.

454. Yost, C. C., A. S. Weyrich, and G. A. Zimmerman. The platelet activating factor (PAF) signalling cascade in systemic inflammatory responses. Biochimie, 2010, 92:692-7.

455. You, J., Nguyen, A. V., Albers, C. G., Lin, F. & Holcombe, R. F. (2008) Wnt pathway-related gene expression in inflammatory bowel disease. Digestive diseases and sciences, 53, 1013-1019.

456. Zammataro, M., Chiechio, S., Montana, M. C., Traficante, A., Copani, A., Nicoletti, F. & Gereau, R. W. (2011) mGlu2 metabotropic glutamate receptors restrain inflammatory pain and mediate the analgesic activity of dual mGlu2/mGlu3 receptor agonists. Molecular pain, 7, 1.

457. Zeng, H., A. GrAGERov, J. G. Hohmann, M. N. Pavlova, B. A. Schimpf, and H. Xu. Neuromedin U receptor 2-deficient mice display differential responses in sensory perception, stress, and feeding. Mol Cell Biol, 2006, 26:9352-63.

458. Zhang Y. I-TASSER server for protein 3D structure prediction. BMC Bioinformatics, 2008, 9: 40.

459. Zhang, F., Wu, R., Qiang, X., Zhou, M. & Wang, P. (2010a) Antagonism of α2A-adrenoceptor: a novel approach to inhibit inflammatory responses in sepsis. Journal of Molecular Medicine, 88, 289-296.

460. Zhang, H., Unal, H., Gati, C., Won Han, G., Liu, W., Zatsepin, N. A., James, D., Want, D., Nelson, G., Weierstall, U., Sawaya, M. R., Xu, Q., Messerschmidt, M., Williams, G. J., Boutet, S., Yefanov, O. M., White, T. A., Wang, C., Ishchenko, A., Tirupula, K. C., Desnoyer, et al., Structure of the Angiotensin Receptor Revealed by Serial Femtosecond Crystallography, Cell, 2015, 161: 4, 833-844.

461. Zhang, X., Schmudde, I., Laumonnier, Y., Pandey, M., Clark, J., König, P., Gerard, N., Gerard, C., Wills-Karp, M. & Köhl, J. (2010b) A critical role for C5L2 in the pathogenesis of experimental allergic asthma. Journal of immunology (Baltimore, Md.: 1950), 185, 6741.

462. Zhao, W., Ho, L., Varghese, M., Yemul, S., Dams-O'Connor, K., Gordon, W., Knable, L., Freire, D., Haroutunian, V. & Pasinetti, G. M. (2013) Decreased level of olfactory receptors in blood cells following traumatic brain injury and potential association with tauopathy. Journal of Alzheimer's Disease, 34, 417-429.

463. Zhao, Z., Lee, C. C., Baldini, A. & Caskey, C. T. (1995) A Human Homologue of the *Drosophila* Polarity Gene frizzled Has Been Identified and Mapped to 17q21.1. Genomics, 27, 370-373.

464. Zheng, Y., Qin, L., Zacarias, N. V., de Vries, H., Han, G. W., Gustavsson, M., Dabros, M., Zhao, C., Cherney, R. J., Carter, P., Stamos, D., Abagyan, R., Cherezov, V., Stevens, R. C., AP, I. J., Heitman, L. H., Tebben, A., Kufareva, I. & Handel, T. M. (2016) Structure of CC chemokine receptor 2 with orthosteric and allosteric antagonists. Nature, 540, 458-461.

465. Zhong, H., Shlykov, S. G., Molina, J. G., Sanborn, B. M., Jacobson, M. A., Tilley, S. L. & Blackburn, M. R. (2003) Activation of murine lung mast cells by the adenosine A3 receptor. The Journal of Immunology, 171, 338-345.

466. Zhou, N., Fan, X., Mukhtar, M., Fang, J., Patel, C. A., DuBois, G. C. & Pomerantz, R. J. (2003) Cell-cell fusion and internalization of the CNS-based, HIV-1 co-receptor, APJ. Virology, 307, 22-36.

467. Zhou, Z., et al. Receptor for AGE (RAGE) mediates neointimal formation in response to arterial injury. Circulation, 2003, 107: 2238-2243.

468. Zhu, P., Sun, W., Zhang, C., Song, Z. & Lin, S. (2016) The role of neuropeptide Y in the pathophysiology of atherosclerotic cardiovascular disease. International Journal of Cardiology, 220, 235-241.

469. Ziogas, D. C., Gras-Miralles, B., Mustafa, S., Geiger, B. M., Najarian, R. M., Nagel, J. M., Flier, S. N., Popov, Y., Tseng, Y.-H. & Kokkotou, E. (2013) Anti-melanin-concentrating hormone treatment attenuates chronic experimental colitis and fibrosis. American Journal of Physiology-Gastrointestinal and Liver Physiology, 304, G876-G884.

470. Zlotnik, A., and O. Yoshie. (2000) Chemokines: a new classification system and their role in immunity. Immunity, 12:121-7.

---

The invention claimed is:

1. An isolated or purified peptide that inhibits RAGE ligand-independent signaling, the peptide comprising an amino acid sequence at least 90% identical to a fragment of residues 22 to 404 of wild-type RAGE as set forth in SEQ ID NO: 14, wherein the peptide comprises:
   (i) a C-terminus of residue 390 and a contiguous sequence to at least residue 379, wherein residue 379 is Q or a conservative amino acid substitution thereof;
   (ii) a N-terminus of residue 380 and a contiguous sequence to at least residue 391, wherein residue 391 is S or a conservative amino acid substitution thereof; or
   (iii) a contiguous sequence including at least both residues 379 and 391, wherein the residue at 379 is not Q or a conservative amino acid substitution thereof, or the residue at 391 is not S or a conservative amino acid substitution thereof.

2. The isolated or purified peptide according to claim 1, wherein the isolated or purified peptide is a medicament.

3. The isolated or purified peptide according to claim 1, wherein the isolated or purified peptide treats, prevents, or manages a RAGE-related disorder in a patient in need of such treatment when administered to the patient.

4. The isolated or purified peptide according to claim 1, wherein the peptide comprises a C-terminus of residue 390 and a contiguous sequence of wild-type RAGE as set forth in SEQ ID NO: 14 to at least residue 379, wherein residue 379 is Q.

5. The isolated or purified peptide according to claim 1, wherein the peptide sequence is as set forth in SEQ ID NO: 5, 6, 8, 9 or 10.

6. The isolated or purified peptide according to claim 1, wherein the peptide sequence is as set forth in SEQ ID NO: 5, 6 or 8.

7. The isolated or purified peptide according to claim 1, wherein the peptide comprises a C-terminus of residue 390 and a contiguous sequence of wild-type RAGE as set forth in SEQ ID NO: 14 to at least residue 379, wherein residue 379 is a conservative amino acid substitution selected from the group consisting of: K, R, D, N and E.

8. The isolated or purified peptide according to claim 7, wherein the conservative amino acid substitution is K.

9. The isolated or purified peptide according to claim 1, wherein the peptide sequence is as set forth in SEQ ID NO: 11, 12 or 13.

10. The isolated or purified peptide according to claim 1, wherein the peptide sequence is as set forth in SEQ ID NO: 11.

11. The isolated or purified peptide according to claim 1, wherein the peptide:
    lacks the residue(s) at 366, 367 or both 366 and 367; or
    comprises the residue(s) at 366, 367 or both 366 and 367, wherein one or both of the residues have a non-conservative amino acid substitution that prevents binding to diaphanous-1.

12. The isolated or purified peptide according to claim 11, wherein the non-conservative amino acid substitution is A.

13. The isolated or purified peptide according to claim 1, wherein the peptide comprises a contiguous sequence of wild-type RAGE as set forth in SEQ ID NO: 14 including at least both residues 379 and 391, wherein the residue at 379 is Q or a conservative amino acid substitution and the residue at 391 is selected from the group consisting of: A, C, E, Y, V, R, N, K, H, G, F and D.

14. The isolated or purified peptide according to claim 1, wherein the peptide comprises a contiguous sequence of wild-type RAGE as set forth in SEQ ID NO: 14 including at least both residues 379 and 391, wherein the residue at 379 is Q or a conservative amino acid substitution and the residue at 391 is E.

15. The isolated or purified peptide according to claim 1, wherein the peptide comprises a contiguous sequence of wild-type RAGE as set forth in SEQ ID NO: 14 including at least both residues 379 and 391, wherein the residue at 379 is Q or a conservative amino acid substitution and the residue at 391 is A.

16. The isolated or purified peptide according to claim 1, wherein the peptide sequence is as set forth in SEQ ID NO: 2.

17. The isolated or purified peptide according to claim 1, wherein the peptide sequence is as set forth in SEQ ID NO: 7.

18. The isolated or purified peptide according to claim 1, wherein the peptide comprises a contiguous sequence of wild-type RAGE as set forth in SEQ ID NO: 14 including at least both residues 379 and 391, wherein the residue at 379 is A and the residue at 391 is S or a conservative amino acid substitution.

19. The isolated or purified peptide according to claim 1, wherein the peptide comprises a N-terminus of residue 380 and a contiguous sequence of wild-type RAGE as set forth in SEQ ID NO: 14 to at least residue 391, wherein residue 391 is S.

20. The isolated or purified peptide according to claim 1, wherein the peptide comprises a N-terminus of residue 380 and a contiguous sequence of wild-type RAGE as set forth in SEQ ID NO: 14 to at least residue 391, wherein residue 391 is a conservative amino acid substitution selected from the group consisting of: W, T, M, Q and I.

21. The isolated or purified peptide according to claim 1, wherein the fragment is of residues 362 to 404 of wild-type RAGE as set forth in SEQ ID NO: 14.

22. A fusion polypeptide comprising a peptide according to claim 1.

23. An isolated nucleic acid comprising a nucleotide sequence encoding for a peptide or fusion polypeptide according to claim 1.

24. A pharmaceutical composition comprising a therapeutically effective amount of an isolated or purified peptide according to claim 1 and with one or more excipients.

25. The isolated or purified peptide according to claim 1, wherein residue 388 is leucine or a conservative substitution thereof.

26. The isolated or purified peptide according to claim 1, wherein residue 388 is leucine.

* * * * *